United States Patent
Foreman et al.

(10) Patent No.: US 11,291,731 B2
(45) Date of Patent: *Apr. 5, 2022

(54) SILICON BASED DRUG CONJUGATES AND METHODS OF USING SAME

(71) Applicant: BlinkBio, Inc., Jupiter, FL (US)

(72) Inventors: Kenneth W. Foreman, Syosset, NY (US); Hanh N. Nguyen, Jupiter, FL (US); Leslie O. Ofori, Jupiter, FL (US); Jutta Wanner, Palm Beach, FL (US); Douglas S. Werner, West Palm Beach, FL (US)

(73) Assignee: BlinkBio, Inc., Jupiter, FL (US)

( * ) Notice: Subject to any disclaimer, the term of this patent is extended or adjusted under 35 U.S.C. 154(b) by 20 days.

This patent is subject to a terminal disclaimer.

(21) Appl. No.: 15/889,638

(22) Filed: Feb. 6, 2018

(65) Prior Publication Data

US 2019/0290771 A1    Sep. 26, 2019

Related U.S. Application Data

(63) Continuation of application No. 15/477,721, filed on Apr. 3, 2017, now Pat. No. 9,931,407, which is a continuation of application No. PCT/US2016/032177, filed on May 12, 2016.

(60) Provisional application No. 62/173,002, filed on Jun. 9, 2015, provisional application No. 62/160,575, filed on May 12, 2015.

(51) Int. Cl.
| | | |
|---|---|---|
| *A61K 38/07* | (2006.01) | |
| *A61K 47/54* | (2017.01) | |
| *C08G 77/452* | (2006.01) | |
| *C09D 183/08* | (2006.01) | |
| *A61K 47/64* | (2017.01) | |
| *A61K 47/65* | (2017.01) | |
| *A61K 47/68* | (2017.01) | |
| *A61K 31/475* | (2006.01) | |
| *C08G 77/28* | (2006.01) | |

(52) U.S. Cl.
CPC ............ *A61K 47/54* (2017.08); *A61K 31/475* (2013.01); *A61K 38/07* (2013.01); *A61K 47/545* (2017.08); *A61K 47/641* (2017.08); *A61K 47/645* (2017.08); *A61K 47/65* (2017.08); *A61K 47/6885* (2017.08); *A61K 47/6889* (2017.08); *C08G 77/452* (2013.01); *C09D 183/08* (2013.01); *C08G 77/28* (2013.01)

(58) Field of Classification Search
None
See application file for complete search history.

(56) References Cited

U.S. PATENT DOCUMENTS

| | | |
|---|---|---|
| 6,326,011 B1 | 12/2001 | Miyazawa et al. |
| 7,687,496 B2 | 3/2010 | Narkunan et al. |
| 8,575,188 B2 | 11/2013 | Cai et al. |
| 9,931,407 B2 | 4/2018 | Foreman et al. |
| 10,064,880 B2 | 9/2018 | Nguyen et al. |
| 10,293,053 B2 | 5/2019 | Nguyen et al. |
| 10,716,801 B2 | 7/2020 | Nguyen et al. |
| 2004/0161403 A1 | 8/2004 | Zhao et al. |
| 2009/0149399 A1 | 6/2009 | Tung |
| 2010/0159446 A1 | 6/2010 | Haff et al. |
| 2011/0263688 A1 | 10/2011 | Barany et al. |
| 2012/0045396 A1 | 2/2012 | Godin-Vilentchouk et al. |
| 2012/0295874 A1 | 11/2012 | Barany et al. |
| 2013/0296285 A1 | 11/2013 | Alferiev et al. |
| 2014/0161729 A1 | 6/2014 | Barany et al. |
| 2014/0163229 A1 | 6/2014 | Barany et al. |
| 2014/0193437 A1 | 7/2014 | Lin et al. |
| 2014/0194383 A1 | 7/2014 | Barany et al. |
| 2014/0243286 A1 | 8/2014 | Arnold et al. |
| 2014/0243321 A1 | 8/2014 | Arnold et al. |
| 2014/0243322 A1 | 8/2014 | Arnold et al. |
| 2014/0274951 A1 | 9/2014 | Guzzo et al. |
| 2014/0296181 A1 | 10/2014 | Arnold et al. |
| 2015/0080570 A1 | 3/2015 | Arnold et al. |
| 2015/0087043 A1 | 3/2015 | Arnold et al. |
| 2015/0105553 A1 | 4/2015 | Barany et al. |
| 2017/0080001 A1 | 3/2017 | Barany et al. |
| 2021/0161921 A1 | 6/2021 | Nguyen et al. |

FOREIGN PATENT DOCUMENTS

| | | |
|---|---|---|
| WO | WO-2009051580 A1 | 4/2009 |
| WO | WO-2009126290 A2 | 10/2009 |

OTHER PUBLICATIONS

International Search Report and Written Opinion for International Application No. PCT/US2016/032177, dated Aug. 18, 2016.
U.S. Appl. No. 16/037,447, "Silanol Based Therapeutic Payloads," filed Jul. 17, 2018.
Morris et al. "Folate mediated L-arginine modified oligo (alkylaminosiloxane) graft poly (ethyleneimine) for tumor targeted gene delivery," Biomaterials, 2011, 32(11):3030-3041.
U.S. Appl. No. 15/992,264/ U.S. Pat. No. 10,064,880, Silanol Based Therapeutic Payloads, filed Mar. 15, 2018/ Sep. 4, 2018.
U.S. Appl. No. 16/037,447/ U.S. Pat. No. 10,716,801, Silanol Based Therapeutic Payloads, filed Jul. 17, 2018/ Jul. 21, 2020.
U.S. Appl. No. 16/223,613/ U.S. Pat. No. 10,293,053, Silanol Based Therapeutic Payloads, filed Dec. 18, 2018/ May 21, 2019.

(Continued)

*Primary Examiner* — Thomas S Heard
(74) *Attorney, Agent, or Firm* — Goodwin Procter LLP

(57) ABSTRACT

Described herein are silicon based conjugates capable of delivering one or more payload moieties to a target cell or tissue. Contemplated conjugates may include a silicon-heteroatom core, one or more optional catalytic moieties, a targeting moiety that permits accumulation of the conjugate within a target cell or tissue, one or more payload moieties (e.g., a therapeutic agent or imaging agent), and two or more non-interfering moieties covalently bound to the silicon-heteroatom core.

11 Claims, 51 Drawing Sheets

Specification includes a Sequence Listing.

(56) References Cited

OTHER PUBLICATIONS

U.S. Appl. No. 16/914,977, Silanol Based Therapeutic Payloads, filed Jun. 29, 2020.
U.S. Appl. No. 15/447,721/ U.S. Pat. No. 9,931,407, Silicon Based Drug Conjugates and Methods of Using Same, filed Apr. 3, 2017/ Apr. 3, 2018.

CHLOROTOXIN IMAGE TAKEN
FR. *TOXIN* 2012, 4, 1082

FIG. 2 (Cont.)

ALKOXYALKYL-ARYL:

$R^1 = R^2 = $ Me, Et, i-Pr, t-Bu $R^1 + R^2 = $ ⟨cyclic⟩$_n$  n=1,2,3

$R^1 = $ Me, $R^2 = $ Et; $R^1 = $ Me, $R^2 = $ i-Pr; $R^1 = $ Et, $R^2 = $ i-Pr

ALKOXYALKYL-ALKYL:

$R^1 = R^2 = $ Me, Et, i-Pr, t-Bu $R^1 + R^2 = $ ⟨cyclic⟩$_n$  n=1,2,3

$R^1 = $ Me, $R^2 = $ Et; $R^1 = $ Me, $R^2 = $ i-Pr; $R^1 = $ Et, $R^2 = $ i-Pr

LIGAND: FOLIC ACID n=1,2,3

$R^1, R^2$ = INDEPENDENTLY SELECTED: Me, i-Pr, t-Bu, (CH2)n-CARBOXYLIC ACID, (CH2)n-AMINO ACID, (CH2)n-AMINE (OPTIONALLY FURTHER SUBSTITUTED)

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: PhPro

<400> SEQUENCE: 1

Pro Pro Pro Pro
1

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Lys Glu Glu Glu Lys Lys Glu Glu Glu Lys Lys Glu Glu Glu Lys
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Thr Phe Phe Tyr Gly Gly Ser Arg Gly Lys Arg Asn Asn Phe Lys Thr
1               5                   10                  15

Glu Glu Tyr
```

SILICON BASED DRUG CONJUGATES AND METHODS OF USING SAME

CROSS REFERENCE TO RELATED APPLICATIONS

This application is a continuation of U.S. patent application Ser. No. 15/477,721, filed Apr. 3, 2017, which is a continuation of International Patent Application serial number PCT/US2016/032177, filed May 12, 2016, which claims the benefit of, and priority to, U.S. provisional application Ser. No. 62/173,002, filed Jun. 9, 2015, and 62/160,575, filed May 12, 2015, the contents of each of which is hereby incorporated by reference herein in its entirety.

SEQUENCE LISTING

The instant application contains a Sequence Listing which has been filed electronically in ASCII format and is hereby incorporated by reference in its entirety. Said ASCII copy, created on Jun. 4, 2019, is named COF-033C1_SL.txt and is 1,236 bytes in size.

BACKGROUND

Devices and methods for delivery of desired components to a site of interest remain a growing need. A variety of methods and routes of administration have been developed to deliver pharmaceuticals or diagnostics, such as small molecular drugs, imaging agents and/or other biologically active compounds (e.g., peptides, hormones, proteins, and enzymes) and many routes of administration are known for delivering desired pharmaceuticals to a patient. As greater knowledge is learned regarding toxicity of drugs and the ability to elicit specific responses by delivery of a pharmaceutical only to a specific portion of the body, controlled release of pharmaceuticals after their administration has become a highly important area of research.

The therapeutic efficacy of active agents is often limited by the inability to selectively deliver the drugs to the cell. For example, most of the currently available anticancer drugs are highly cytotoxic, and can kill normal cells along with cancerous cells. Thus, when high doses of drugs are used, there can be severe side effects. As a result, most of the currently used anticancer drugs have a rather limited therapeutic index. Such a limit on dosage prevents the complete eradication of cancer cells in a patient, and can lead to recurrence of the cancer in many patients. The limit in dosage can also predispose the recurring cancer to drug resistance, thus worsening the prognosis for the patient. Likewise, the ability to observe selective uptake can lead to selective diagnostics. For example, there is ongoing need for visualizing the delivery of anticancer agents to tumors via various imaging techniques just as much as there is a need for delivering a cocktail of anticancer agents specifically to those tumors.

More generally, technologies which can specifically deliver drugs to affected tissues in diseases involving viral, bacterial, inflammatory, metabolic, and neurologic imbalances represent an important therapeutic breakthrough. Often, therapeutics for these diseases very strictly requires a large therapeutic window to be considered for clinical study. Introduction of moieties which deliver these therapeutics directly and specifically to the diseased tissues or to the disease-causing agents lowers the specificity requirements of the therapeutic itself.

On the surface, antibodies appear to be an ideal coupling partner for therapeutics, helping to deliver them to very specific tissues. However, most antibody-drug conjugates suffer from some drawbacks. In one case, reliable engineering of the attachments is challenging, with only statistical distributions of drugs on the antibody frequently occurring. The potential for cleavage away from the intended target remains with the linker chemistries employed. In another case, the drug is too well attached to the antibody and has trouble either cleaving from the antibody or in escaping from the endosome or lysosome once it is cleaved. The end result is either unwanted systemic toxicity or a lack of efficacy. In addition, the drug or payload may not be cleaved or released in a uniform manner, thereby resulting in a non-uniform distribution of the drug or payload. A technology is sorely needed which allows clean delivery of a uniformly modified antibody to a diseased tissue whereupon the drug is released and permeates the endosome to reach its therapeutic target. Accordingly, there is an ongoing need for new therapeutic approaches that permit the selective delivery of active agents to diseased cells, thereby providing improved therapeutic indices.

SUMMARY

Described herein are silicon based conjugates capable of delivering one or more payload moieties to a target cell or tissue. Contemplated conjugates may include a silicon based construct comprising a silicon-heteroatom core having two or more non-interfering moieties each covalently bound to the silicon-heteroatom and an optional catalytic moiety covalently bound directly or indirectly to the silicon-heteroatom core. Contemplated conjugates may also include one or more targeting moieties that permit accumulation of the conjugate within a target cell or tissue, one or more payload moieties (e.g., a therapeutic agent, diagnostic, or imaging agent), and two or more non-interfering moieties covalently bound to the silicon-heteroatom core.

In another embodiment a pharmaceutically acceptable drug conjugate is provided, comprising: a biological sequence selected from the group consisting of an antibody, antibody fragment, protein, or polypeptide, at least one therapeutic agent covalently attached to the biological sequence by a spacer containing a cleavable Si-heteroatom moiety (e.g., a siloxane or silylether moiety). In some embodiments, such a drug conjugate (e.g., an antibody drug conjugate) is substantially stable in aqueous solution having a pH between 7 and 7.5 and/or hydrolytically cleaves in aqueous solution having a pH less than 7 or greater than 7.5 to release the therapeutic agent.

BRIEF DESCRIPTION OF THE FIGURES

FIG. 2 discloses SEQ ID NOS 3 and 3, respectively, in order of appearance.

DETAILED DESCRIPTION

Figure 1:
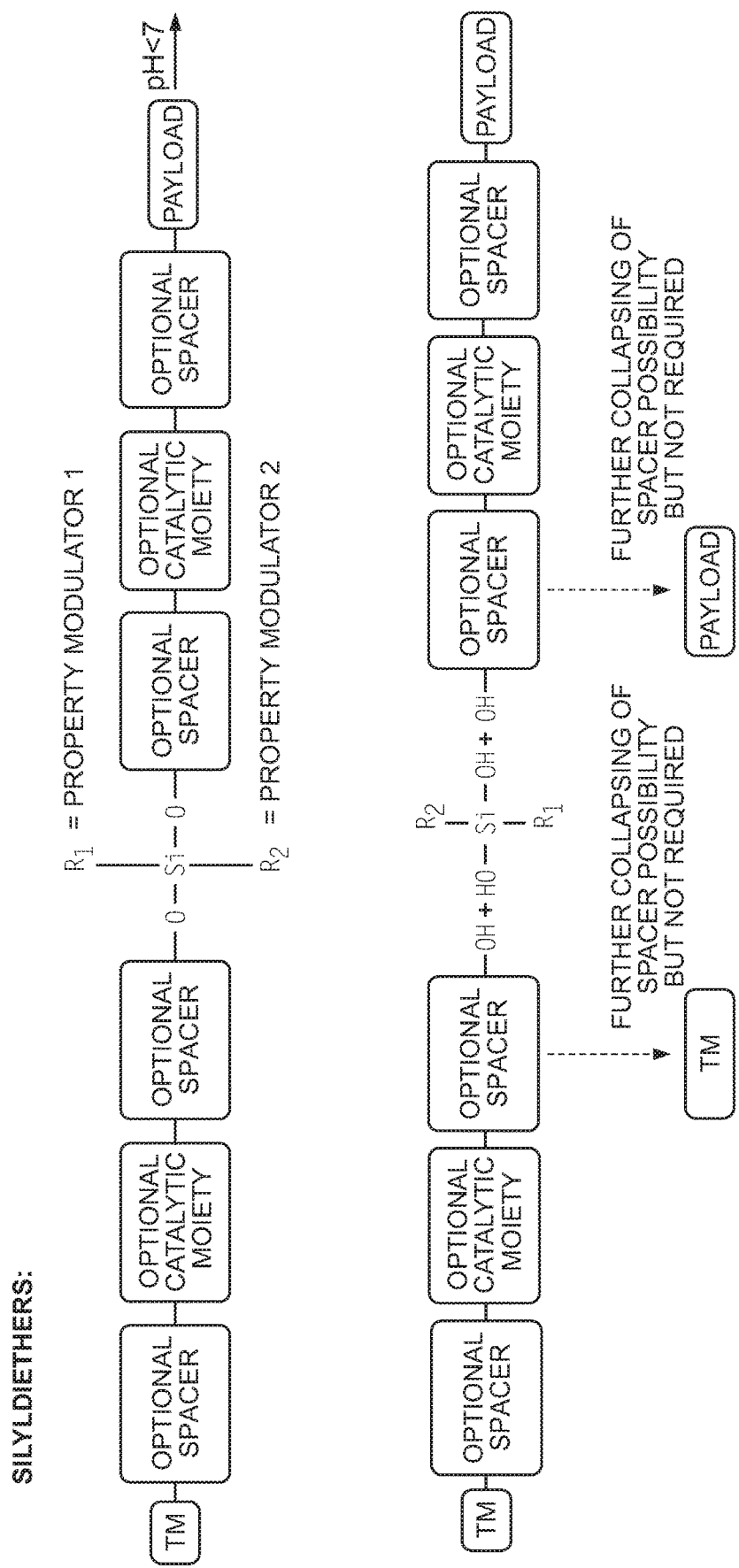
FIG. 1 shows hydrolysis reaction schemes for three embodiments of contemplated conjugates illustrating release of a payload. "TM" is a targeting moiety.
Figure 1:
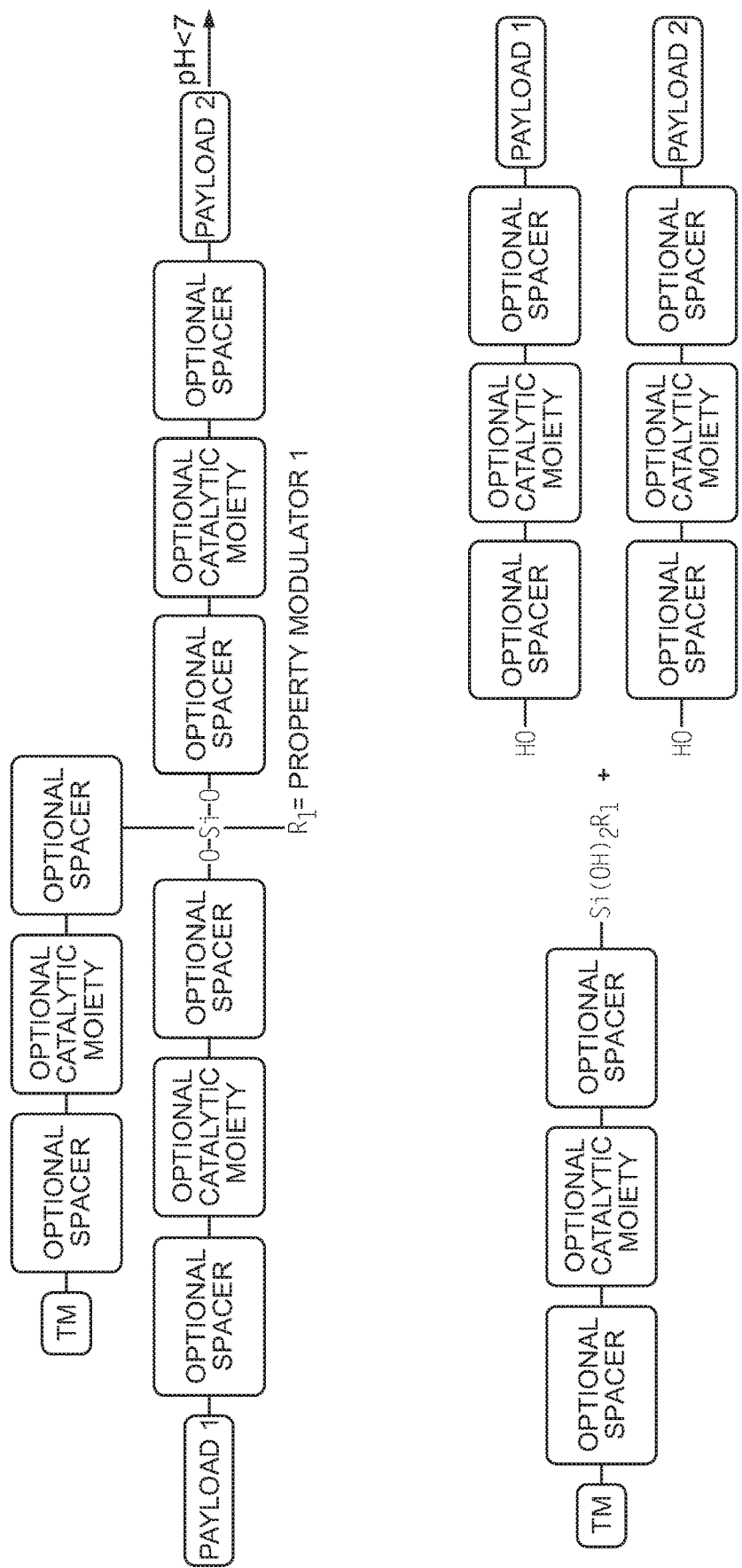
Figure 1:
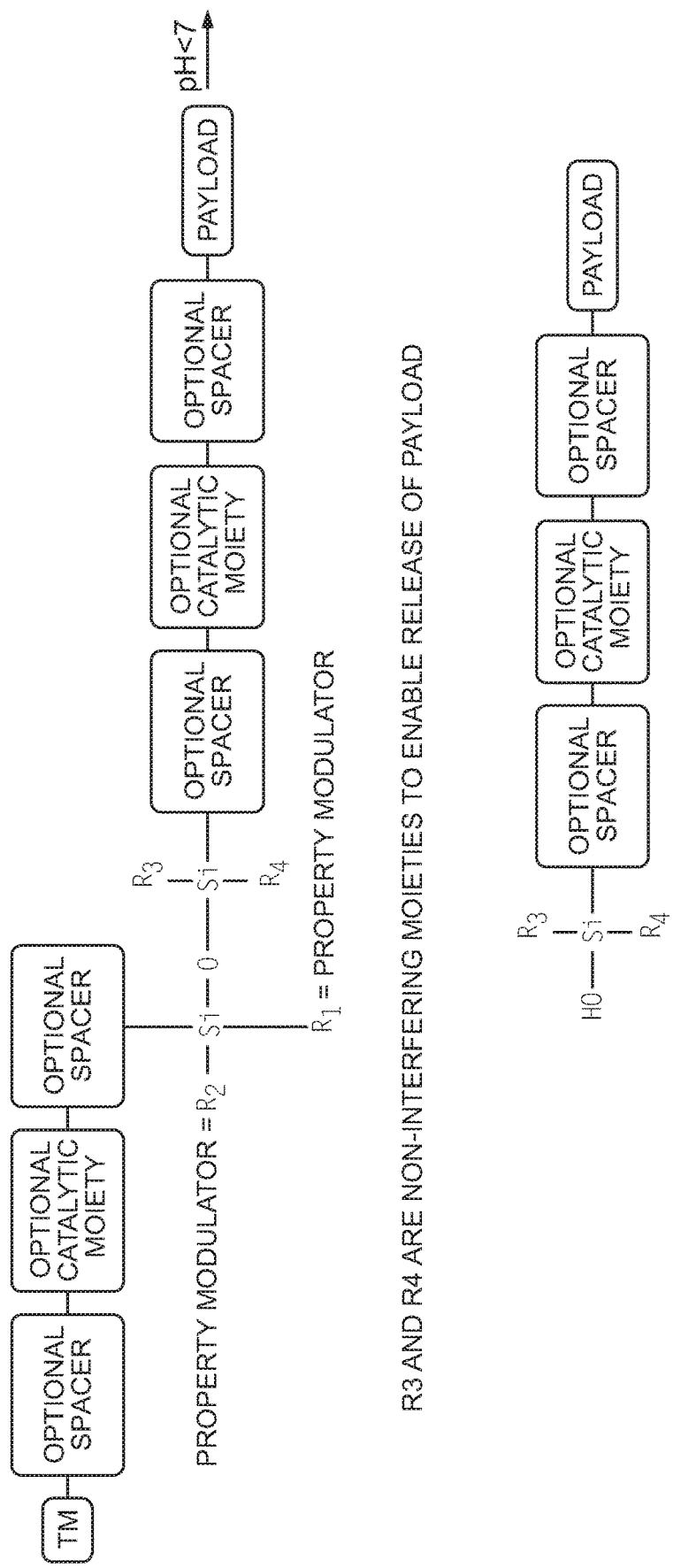
Figure 1:
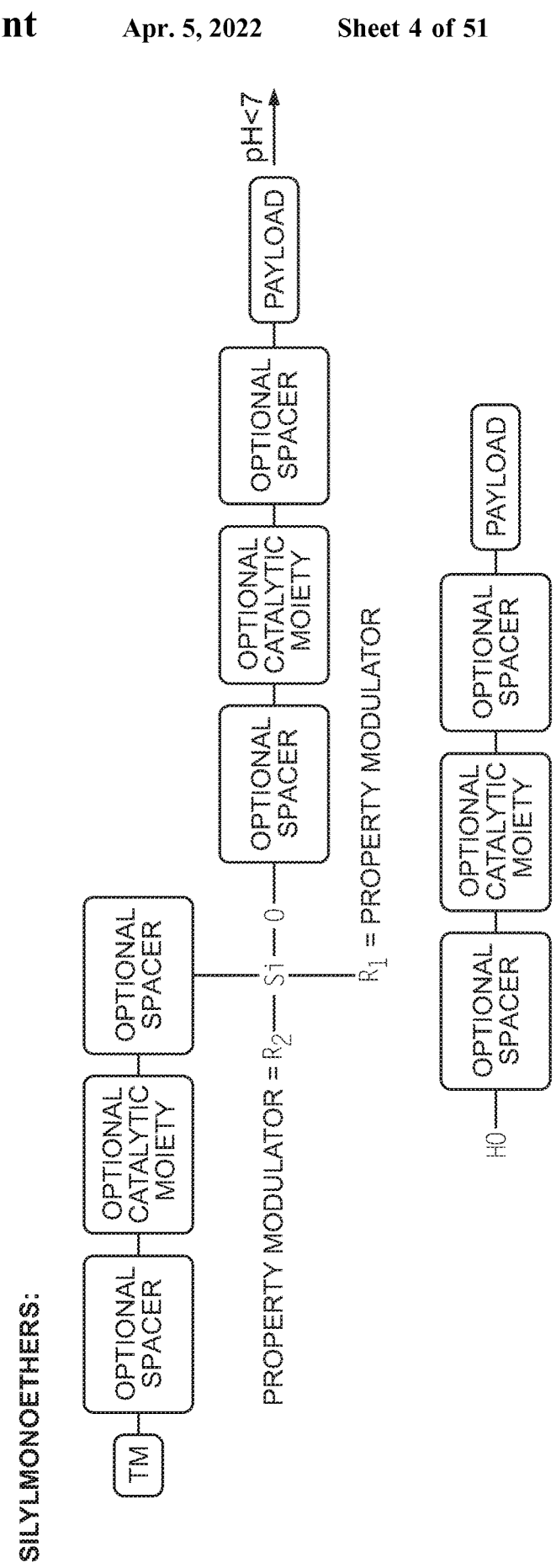
Figure 2:
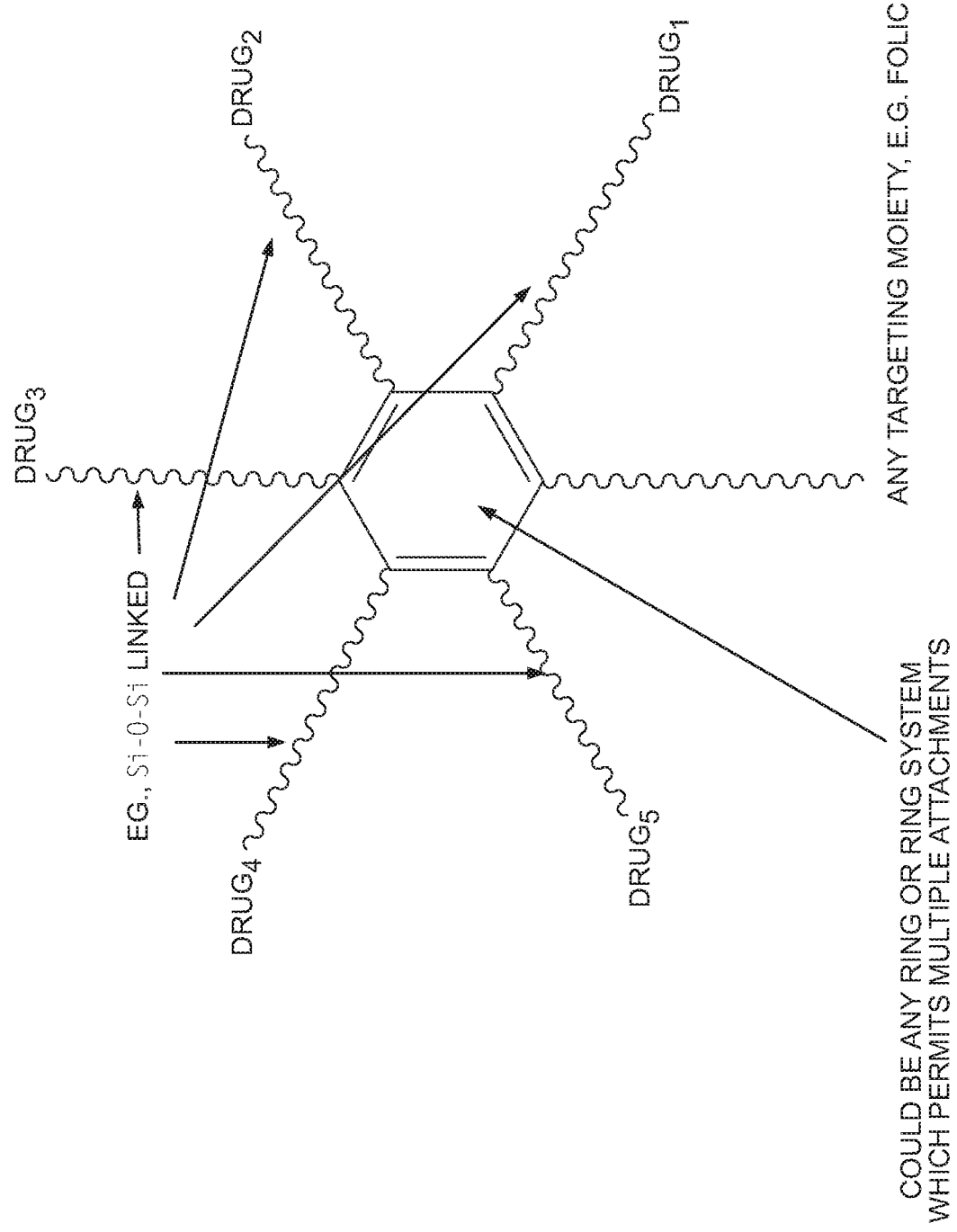
FIG. 2 shows contemplated conjugates containing a scaffold to which a targeting moiety (e.g., a ligand, or an endocytosis agent) and a plurality of payloads (e.g., drugs) are attached. A ligand when shown could be a folic acid, RGD or RGD derivatives, DUPA or DUPA derivatives, an angiopeptide, hyaluronic acid, mannose, or chlorotoxin.
Figure 2:
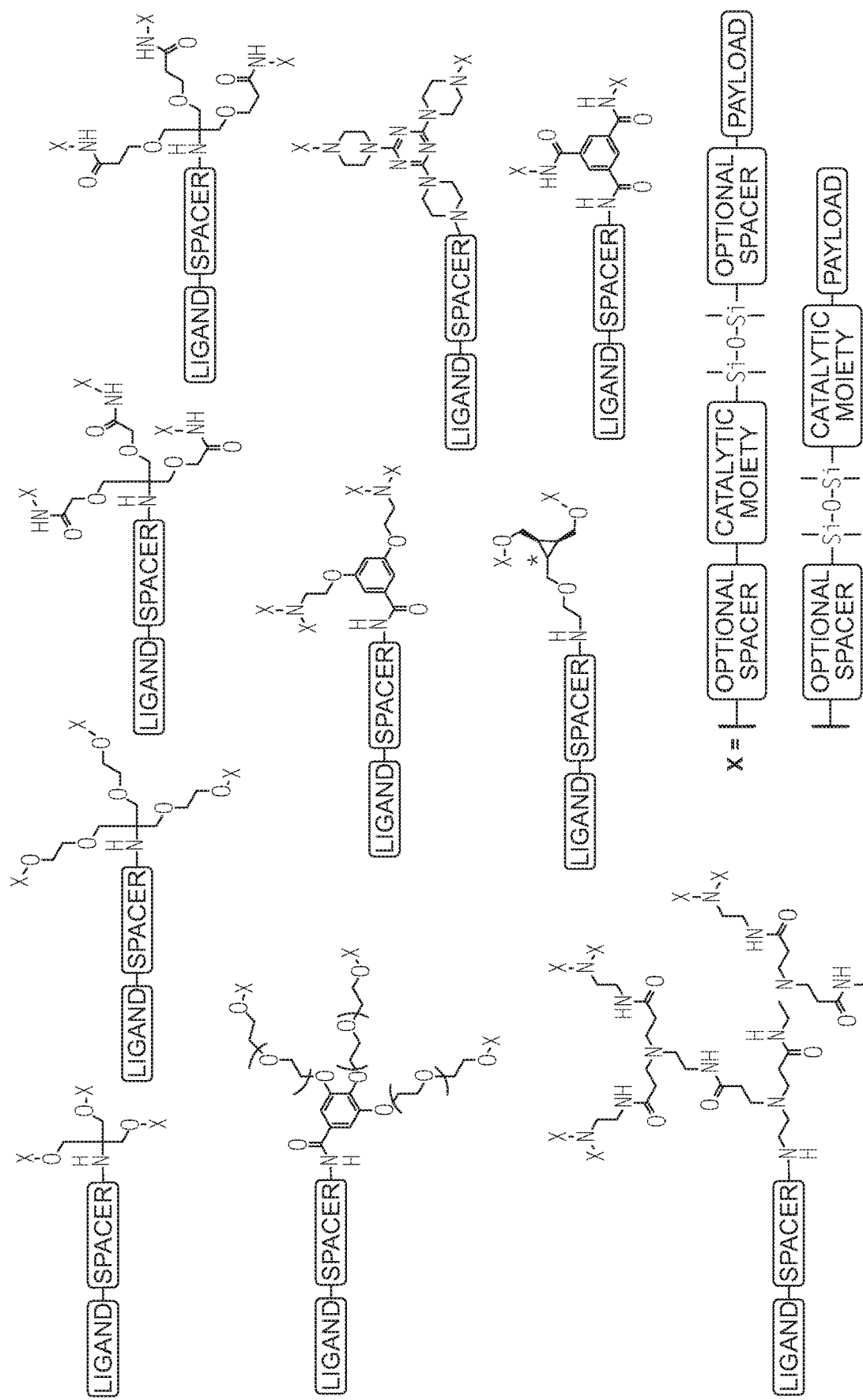
Figure 2:
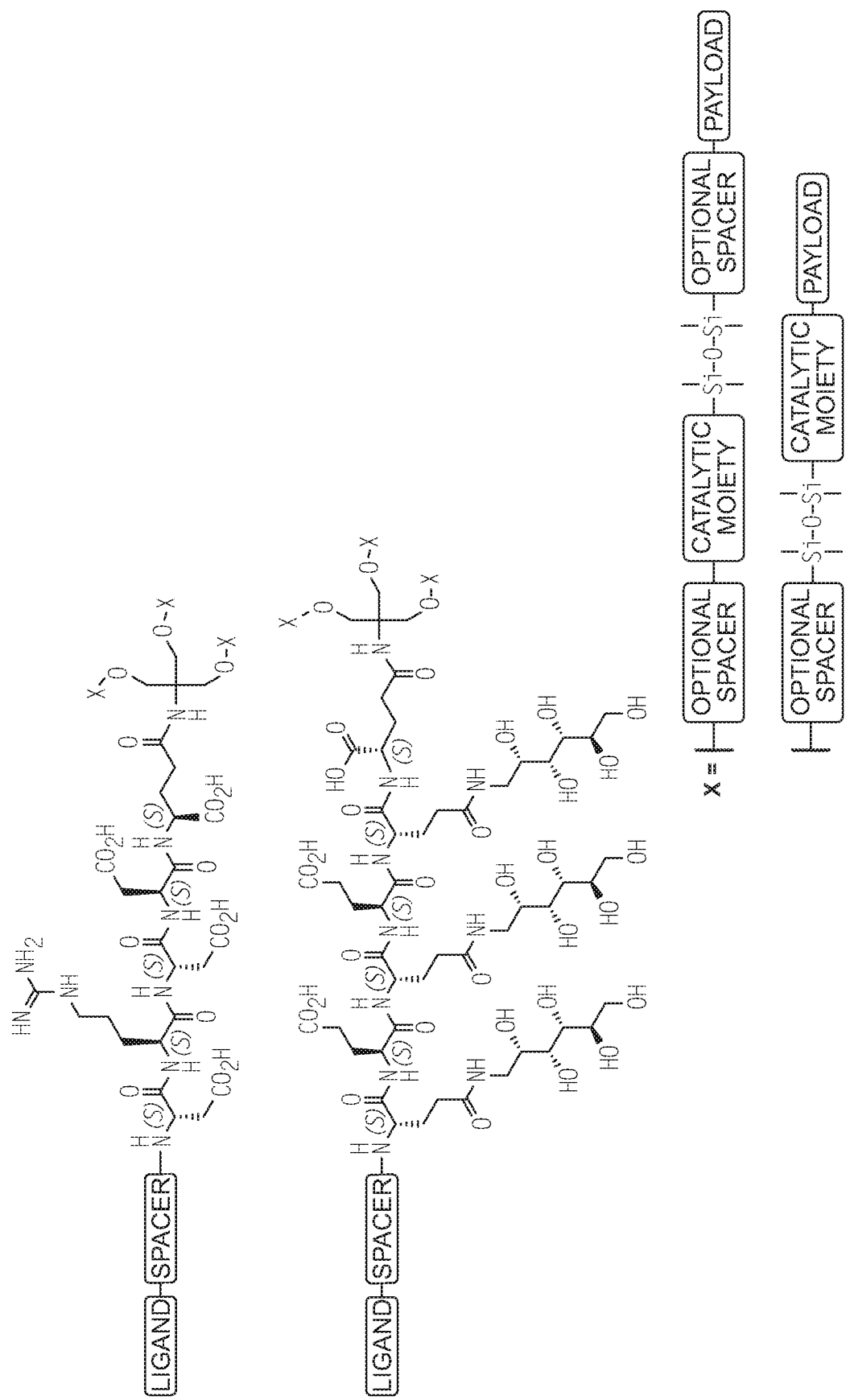
Figure 2:
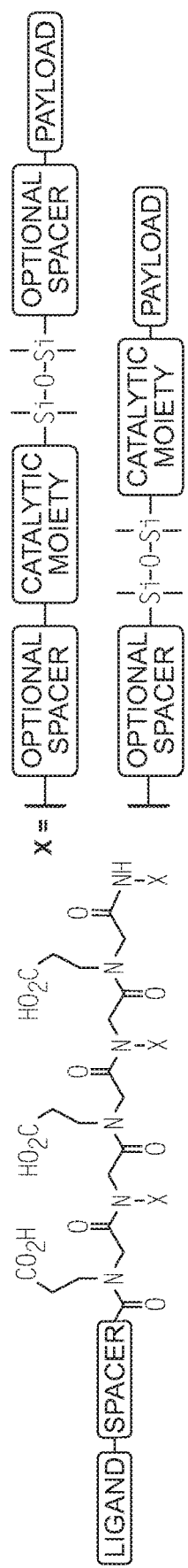
Figure 2:
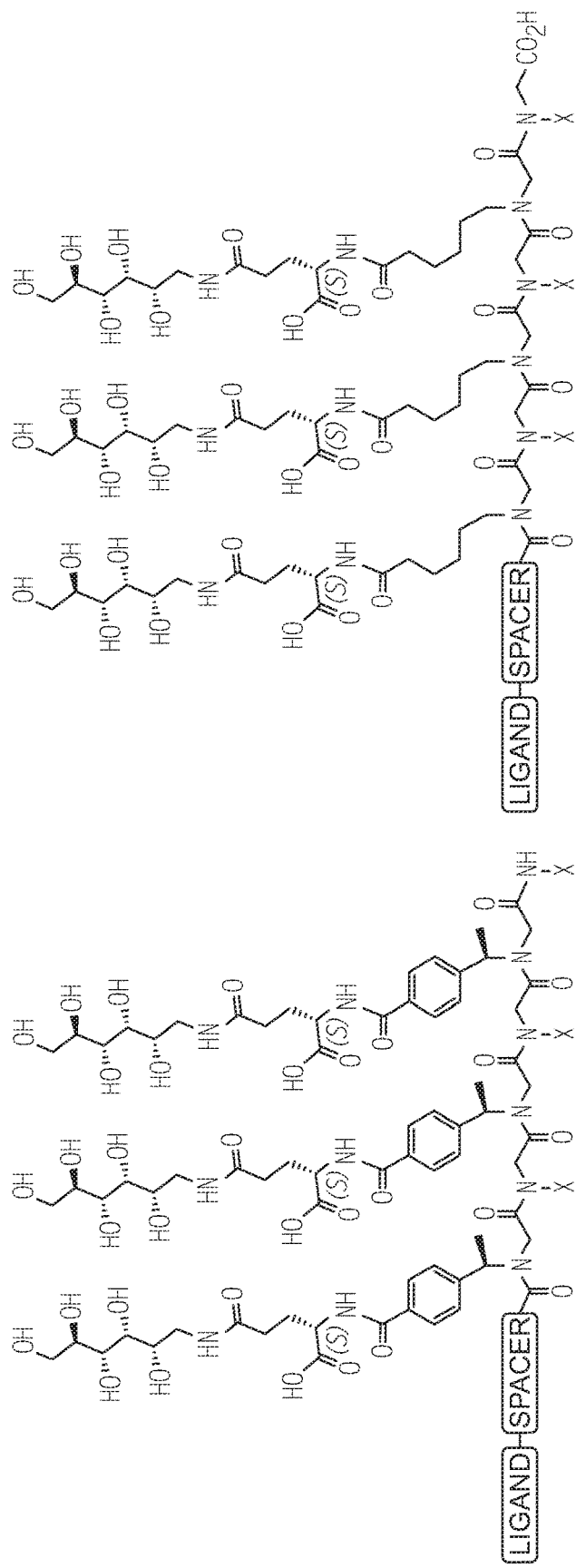
Figure 2:
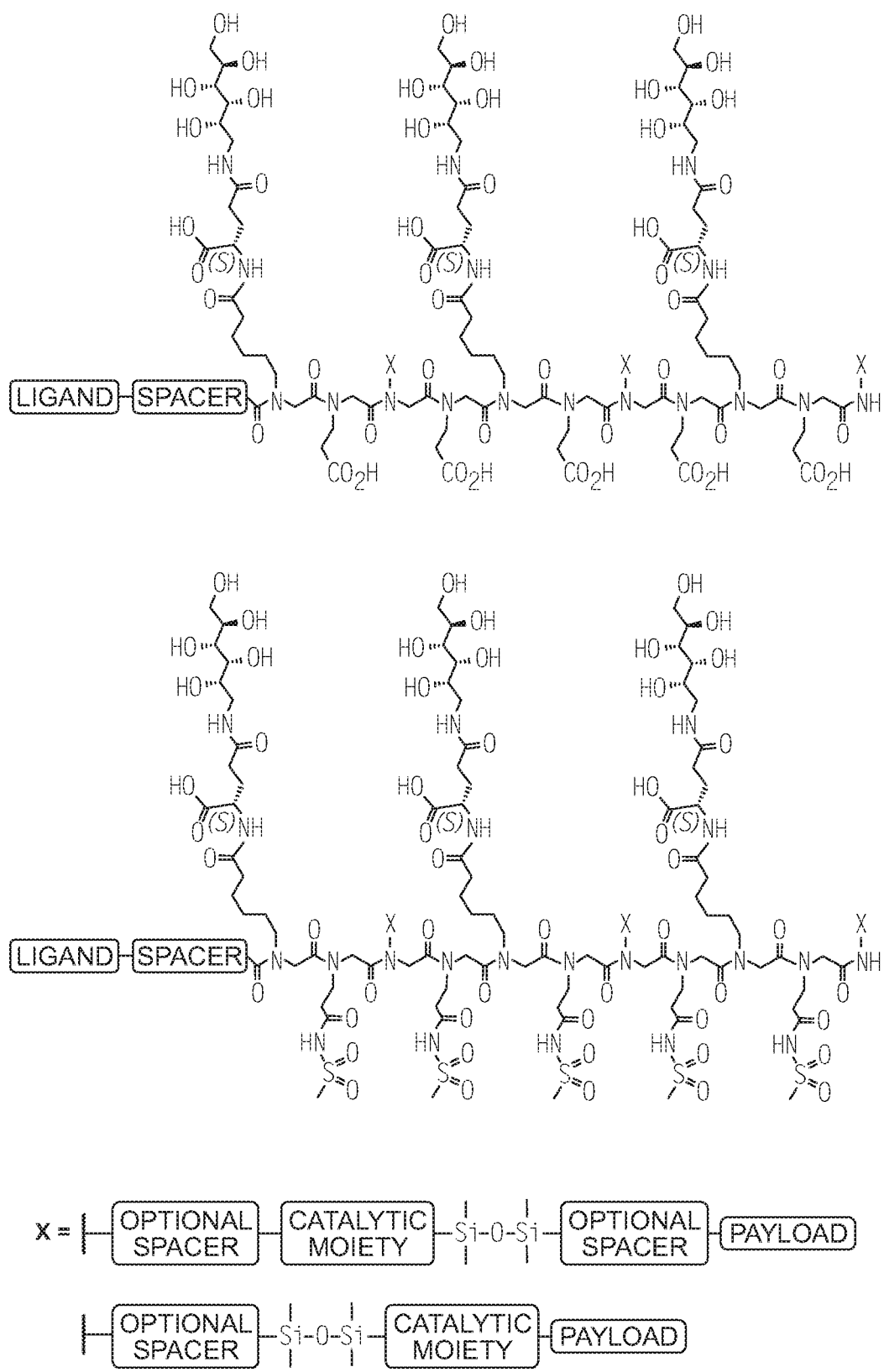
Figure 2:
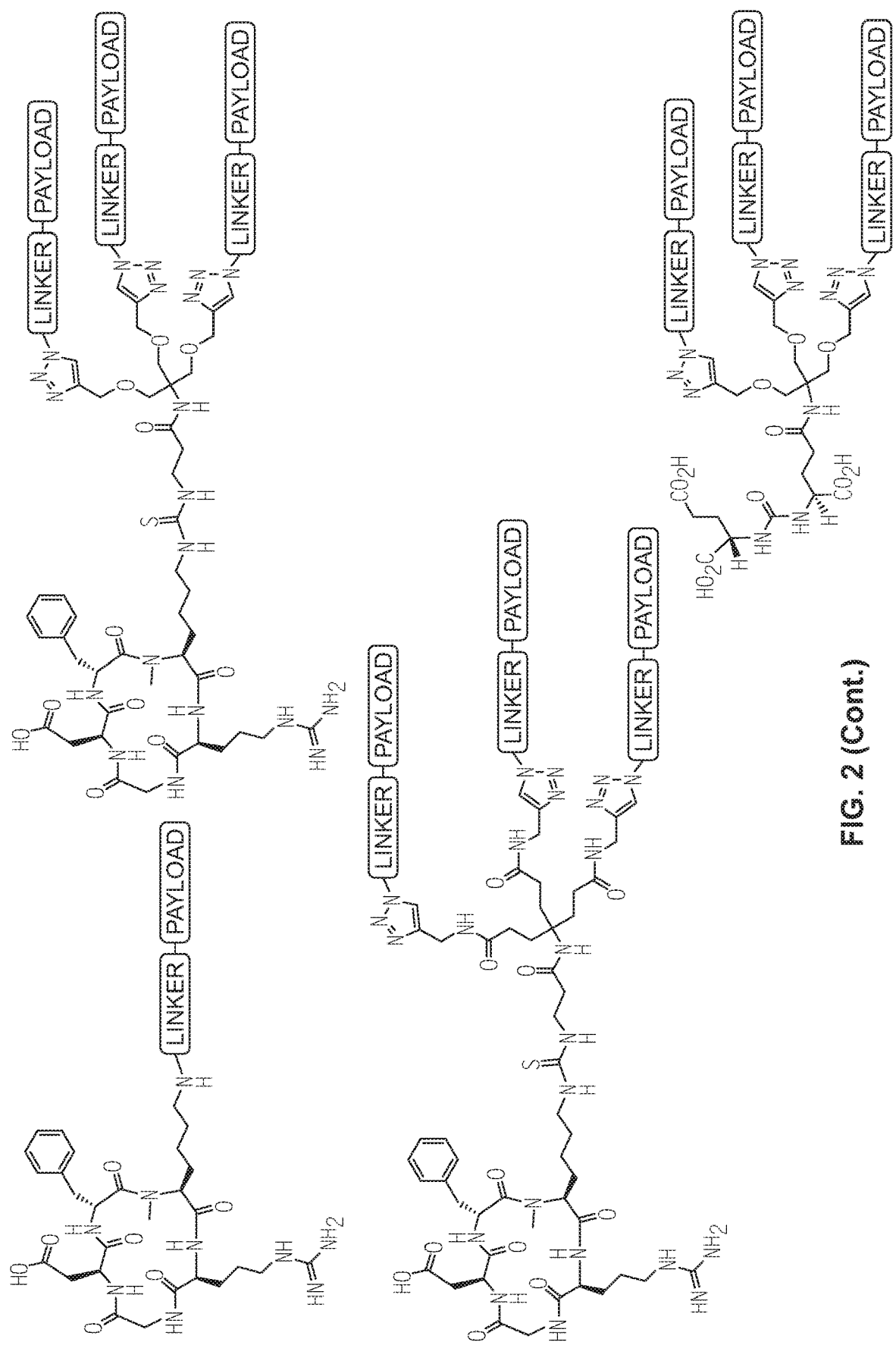
Figure 2:
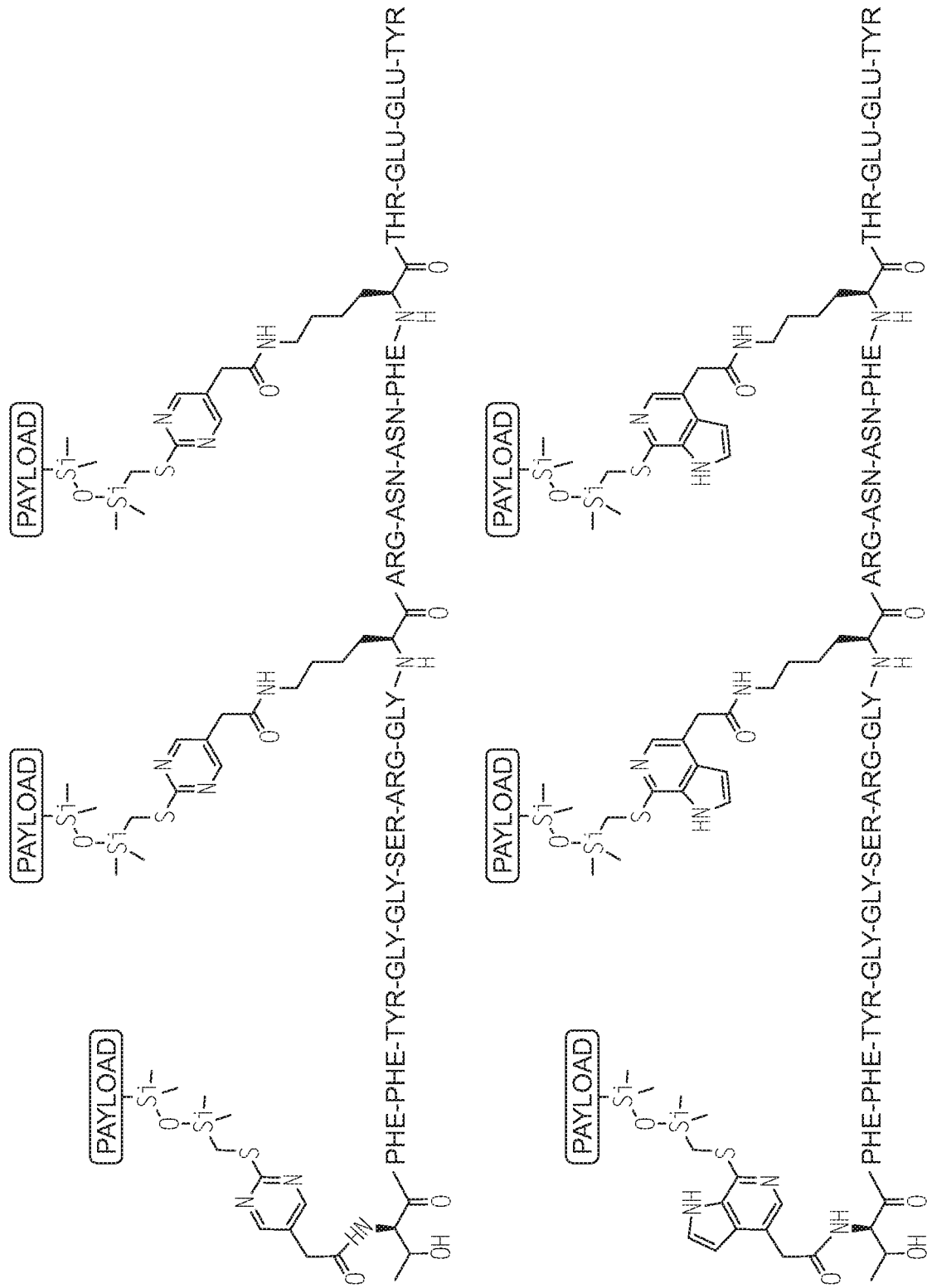
Figure 2:
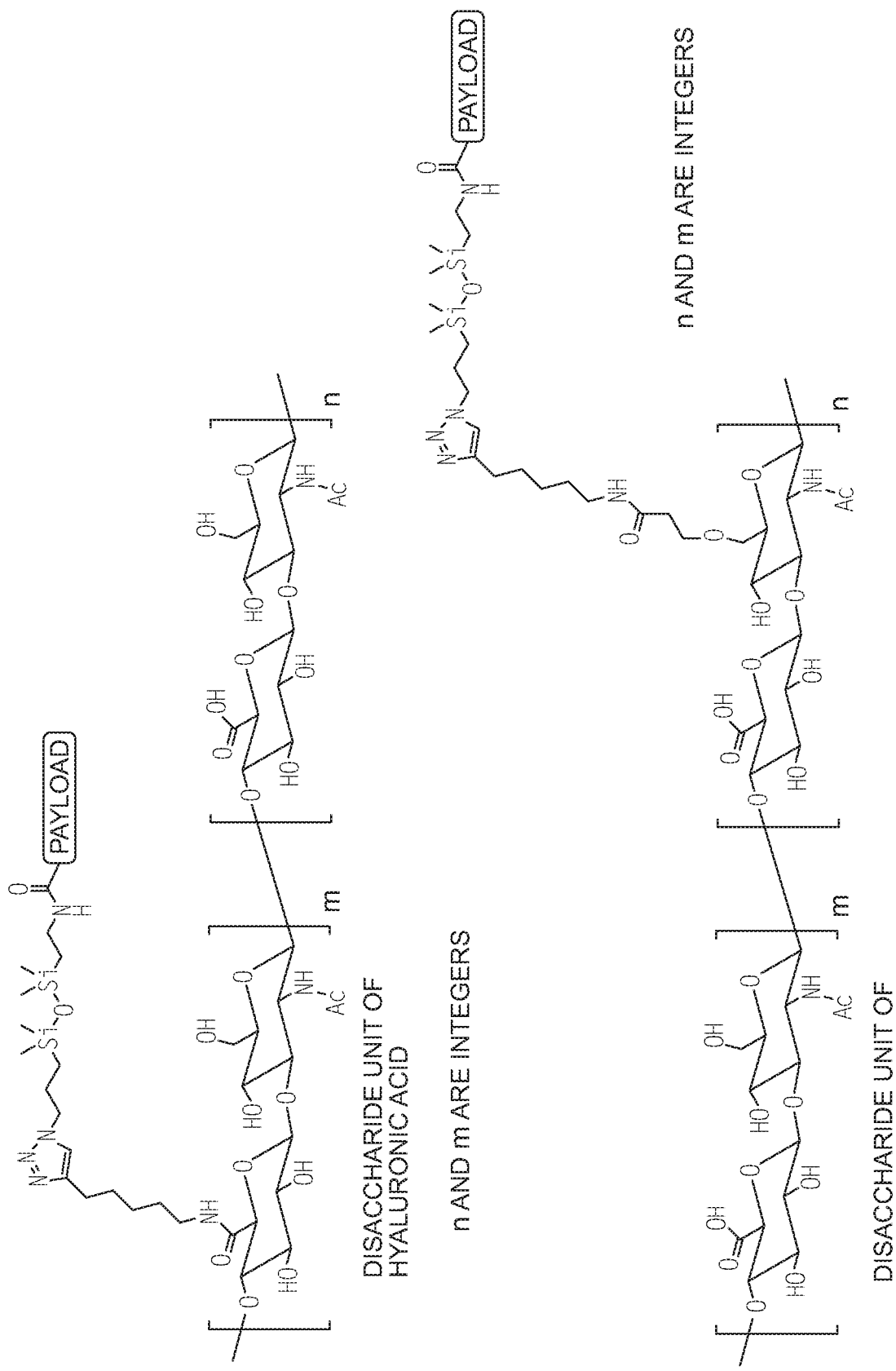
Figure 2:
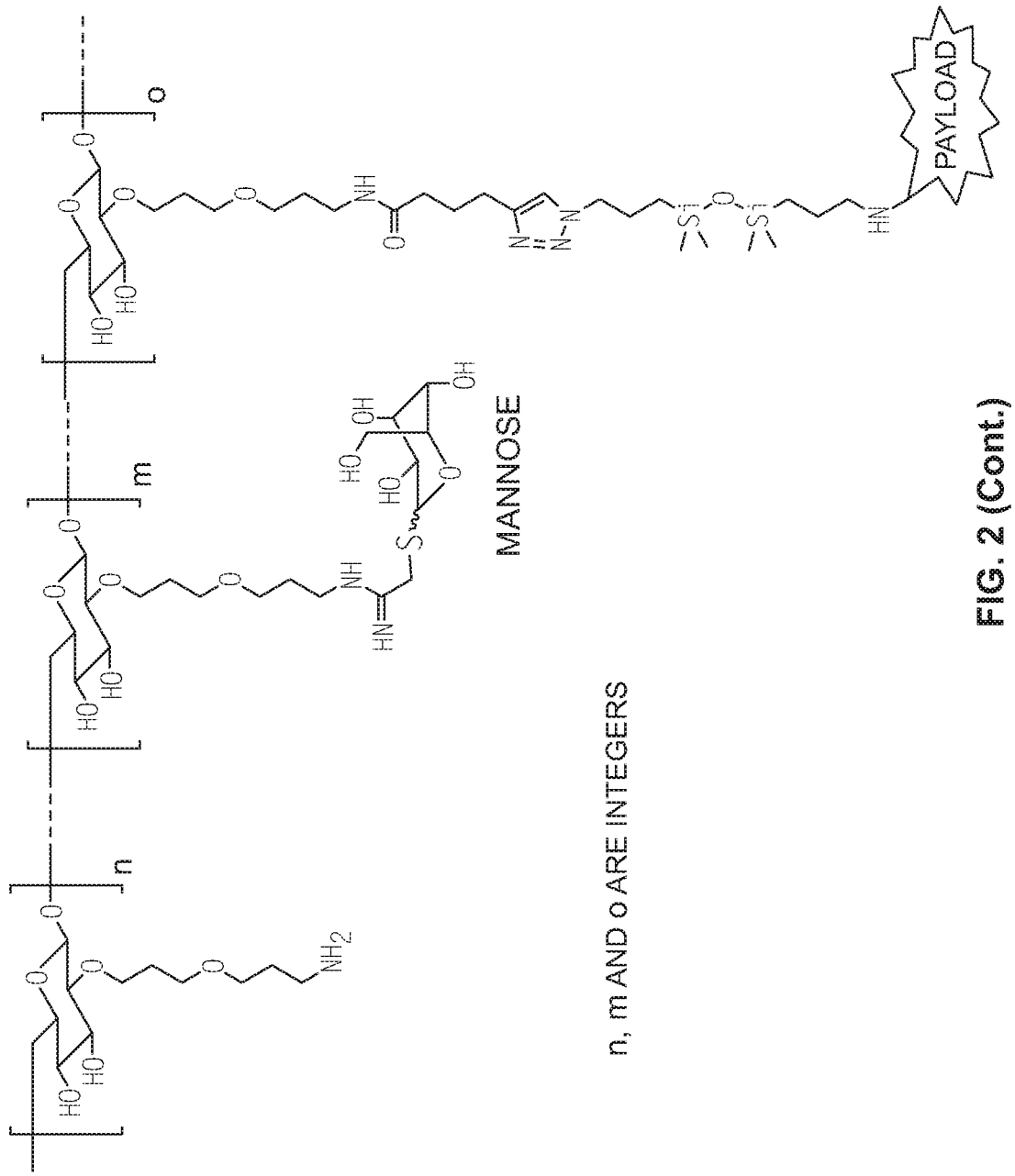
Figure 2:
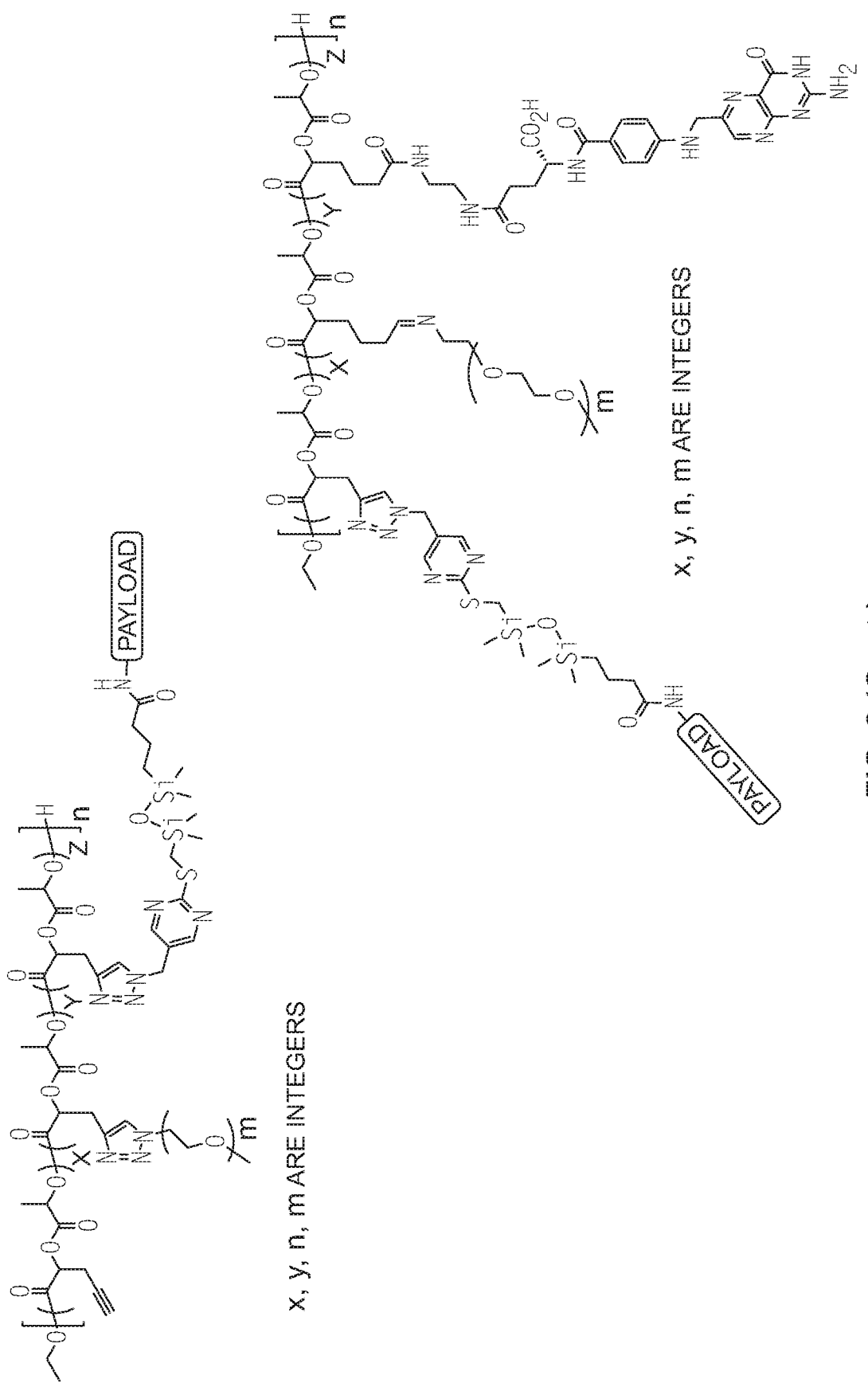
Figure 2:
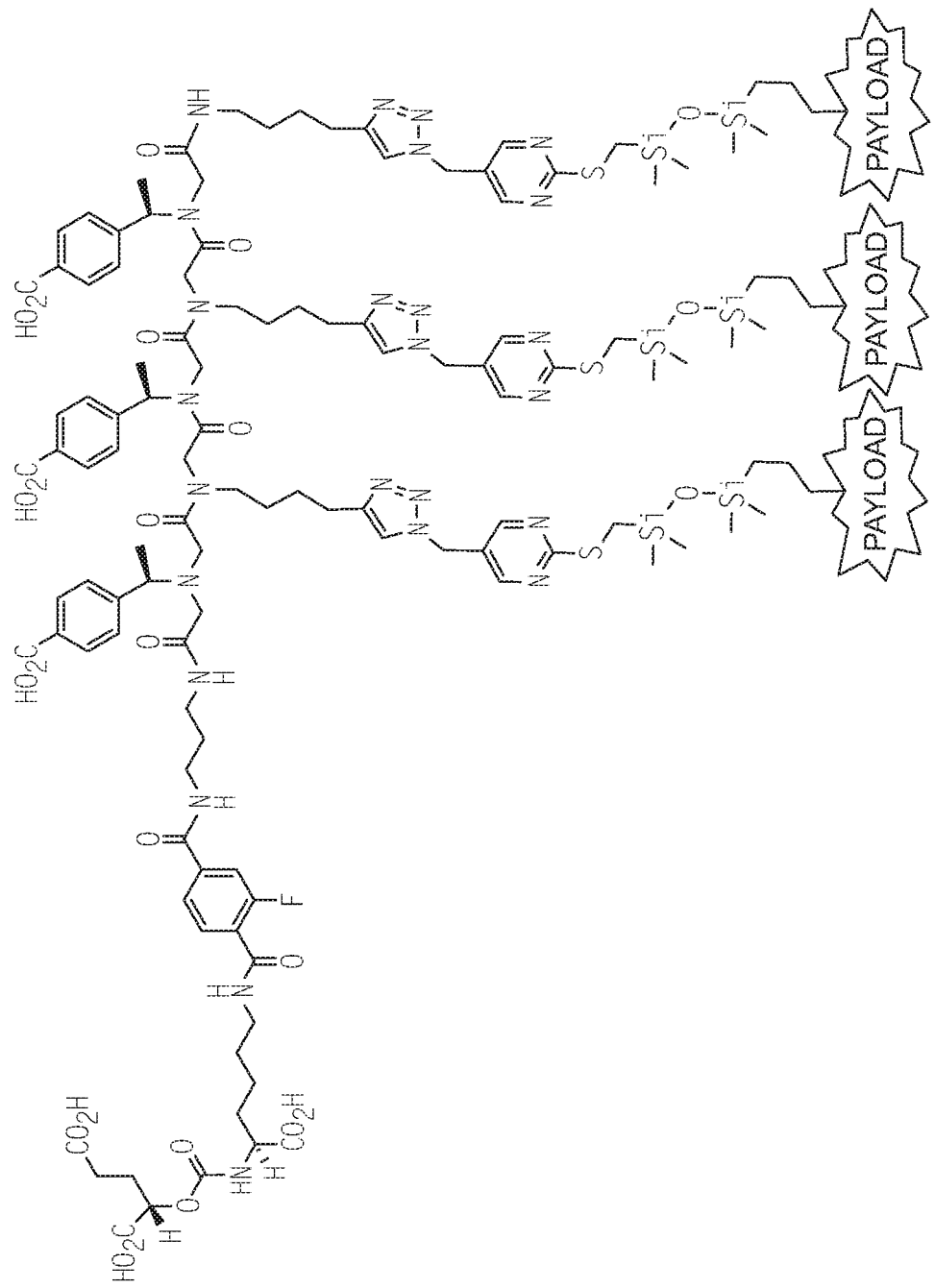

Described herein are silicon based conjugates capable of delivering one or more payload moieties to a target cell or tissue. Contemplated conjugates may include a silicon based construct comprising a silicon-heteroatom core having two or more non-interfering moieties each covalently bound to the silicon-heteroatom and an optional catalytic moiety covalently bound directly or indirectly to the silicon-heteroatom core. Contemplated conjugates may also include one or more targeting moieties that permit accumulation of the conjugate within a target cell or tissue, one or more payload moieties (e.g., a therapeutic agent, diagnostic, or imaging agent), and two or more non-interfering moieties covalently bound to the silicon-heteroatom core. Also described are methods of making the compositions and methods of administering the conjugates.

For example, provided herein is a silicon based conjugate capable of delivering one or more payload moieties to a target cell or tissue, wherein the silicon based conjugate comprises:
a) a silicon based construct comprising:
a silicon-heteroatom core having two or more non-interfering moieties each covalently bound to the silicon-heteroatom core such that the presence of the two or more non-interfering moieties provides that the conjugate is covalently stable; and
an optional catalytic moiety covalently bound directly or indirectly to the silicon-heteroatom core;
b) one or more targeting moieties L, that permits accumulation of the conjugate within a target cell or tissue, wherein L for each occurrence is covalently bound directly or indirectly to the silicon based construct; and
one or more payload moieties P, wherein P for each occurrence is covalently bound directly or indirectly to the silicon based construct;
c) wherein the optional catalytic moiety can transfer a proton to the silicon-heteroatom core, and provides pH-dependent payload release of the payload P in vivo or in vitro;
or pharmaceutically acceptable salts, cocrystals, stereoisomers, metabolites, tautomers, solvates, and hydrates thereof.

In some embodiments, a disclosed silicon based conjugate may include two or more non-interfering moieties which each may be the same or different, and which each may be independently selected to minimize untargeted cellular uptake of the conjugate and/or, for example, to optimize cleavage of the payload P such that P is released into the target cell or tissue.

In certain embodiments, a disclosed silicon based conjugate may have a silicon-heteroatom core that may be, for example, a siloxane represented by:

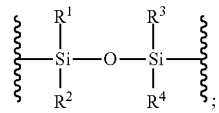

wherein $R^1$, $R^2$, $R^3$ and $R^4$ are each the non-interfering moiety. In certain embodiments, $R^1$, $R^2$, $R^3$ and $R^4$ may each be independently selected, for example, from $C_{1-4}$alkyl.

In an embodiment, a disclosed silicon based conjugate may have a silicon based construct is represented by:

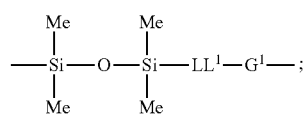

wherein $G^1$ is a catalytic moiety and $LL^1$ is the optional linker moiety linking the silicon-heteroatom core to the catalytic moiety. In an embodiment, $G^1$ may be, for example, a heteroaryl. In some embodiments, a disclosed catalytic moiety or moieties may be selected to cleave a Si—O bond of the silicon-heteroatom core such that the payload moiety, P, is released into the target cell or tissue.

Figure 9:
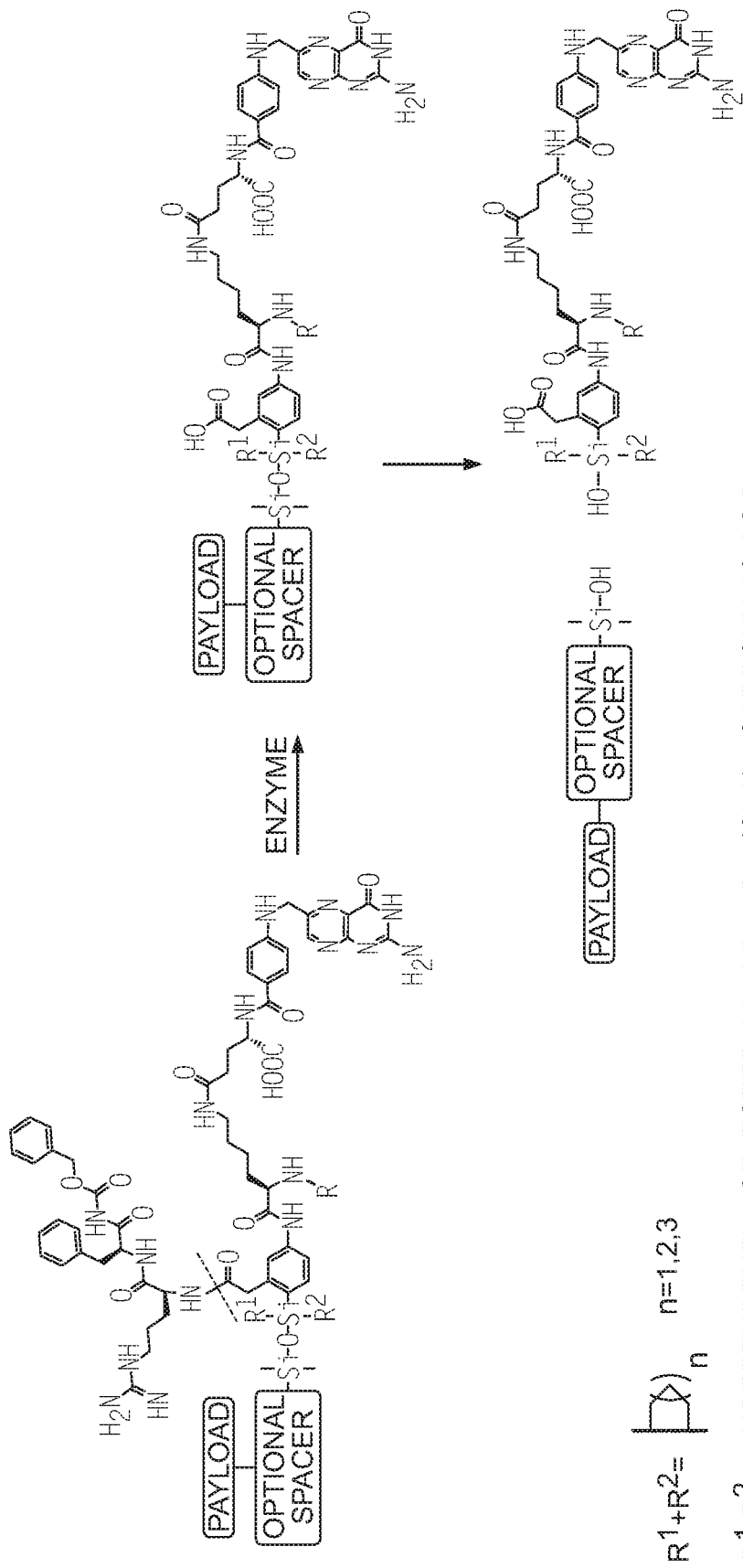
FIGS. 9, 10, and 11 show various mechanisms and end products of an initial non-pH dependent protease enzyme cleavage, followed by pH-dependent release of a payload.
Figure 10:
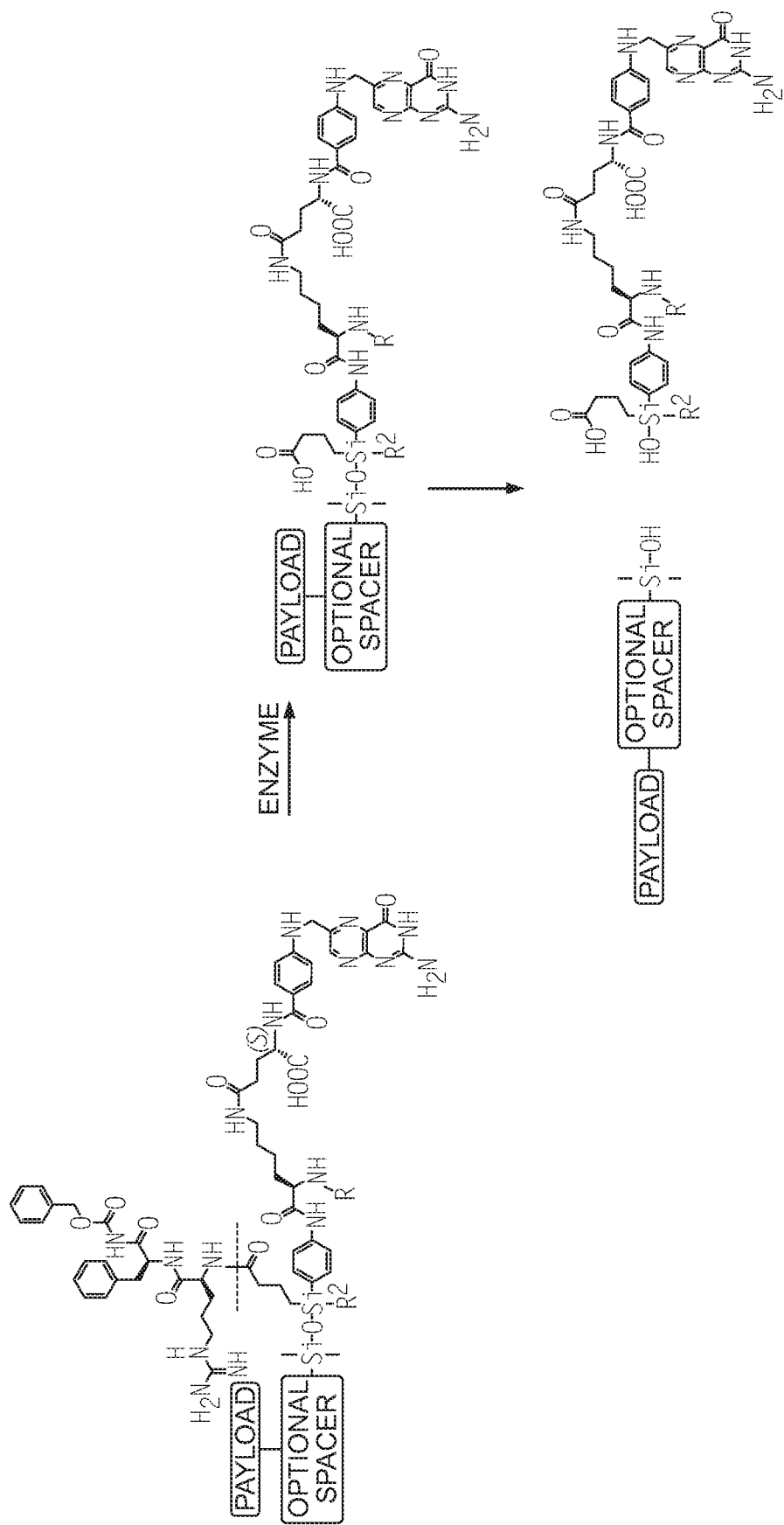
Figure 11:
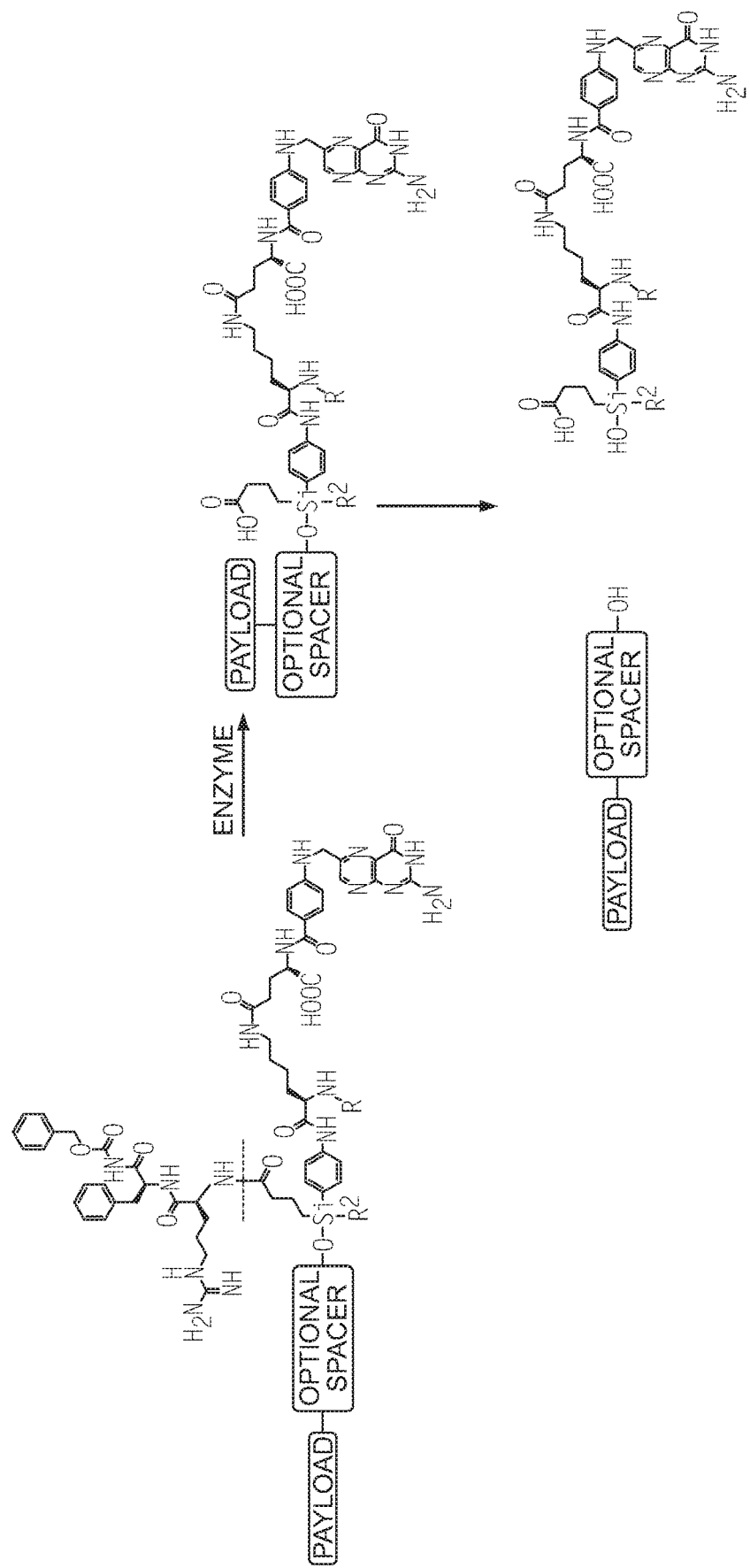

Silicon based conjugates contemplated herein may be substantially stable in an aqueous solution having a pH of between e.g., about 7 and about 7.5 at 25° C., and also hydrolytically cleaves in aqueous solution having a pH less than about 7 or greater than about 7.5 to release the payload moiety from the conjugate, e.g., upon administration to a patient, the payload P may be cleaved from the conjugate and e.g., released, delivered or available to a target cell, tissue, or molecular target. For example, contemplated conjugates may be stable in certain aqueous solutions (e.g., an in vitro solution or an in vivo solution at 25° C. or 37° C. (for example, serum, plasma, whole blood, and/or cytosol)) at a certain pH, and may then be capable of releasing the payload e.g., at a specific site in vivo. Alternatively, contemplated conjugates may be capable of releasing the payload in an initially pH independent manner, e.g., by reductive or hydrolytic cleavage. For example, conjugates may release the payload(s) enzymatically (e.g. in vivo) as shown in e.g., FIGS. 9-11.

Figure 3A:
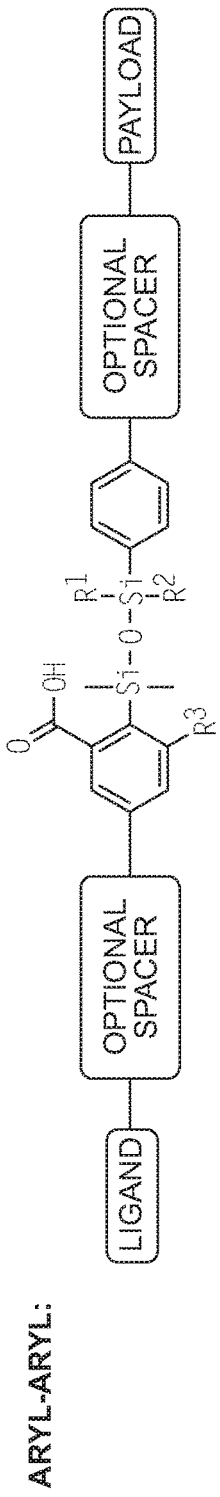
FIGS. 3A and 3B show various non-limiting embodiments for siloxane configurations, with exemplary non-interfering moieties $R^1$ and $R^2$, catalytic moiety, and exemplary divalent spacers between a payload and a targeting moiety (Ligand).
Figure 3A:
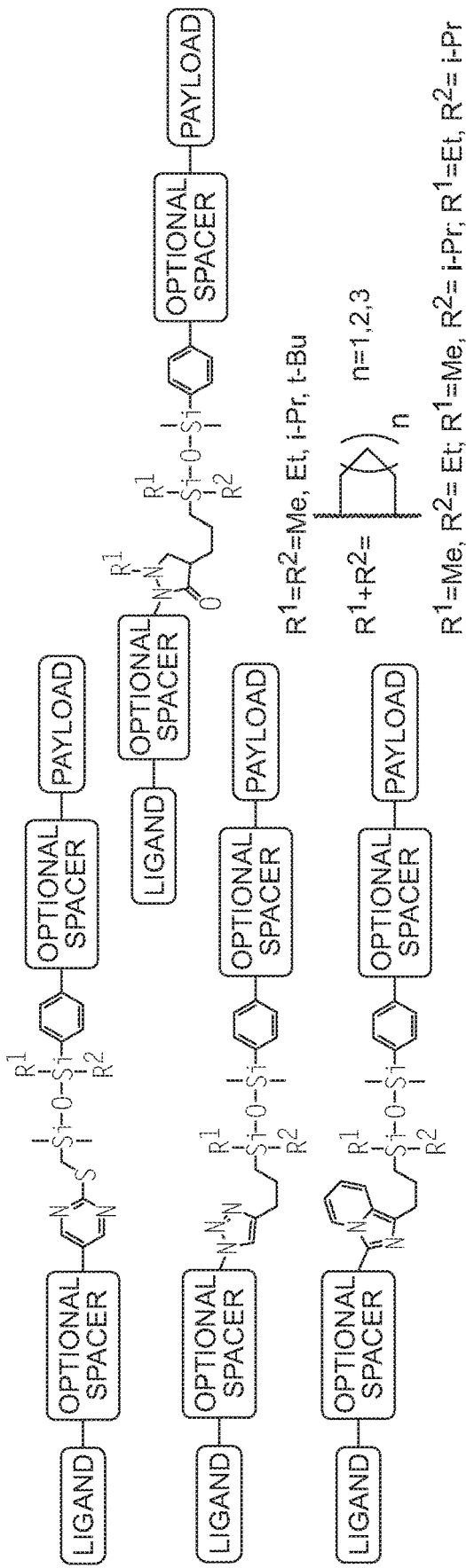
Figure 3A:
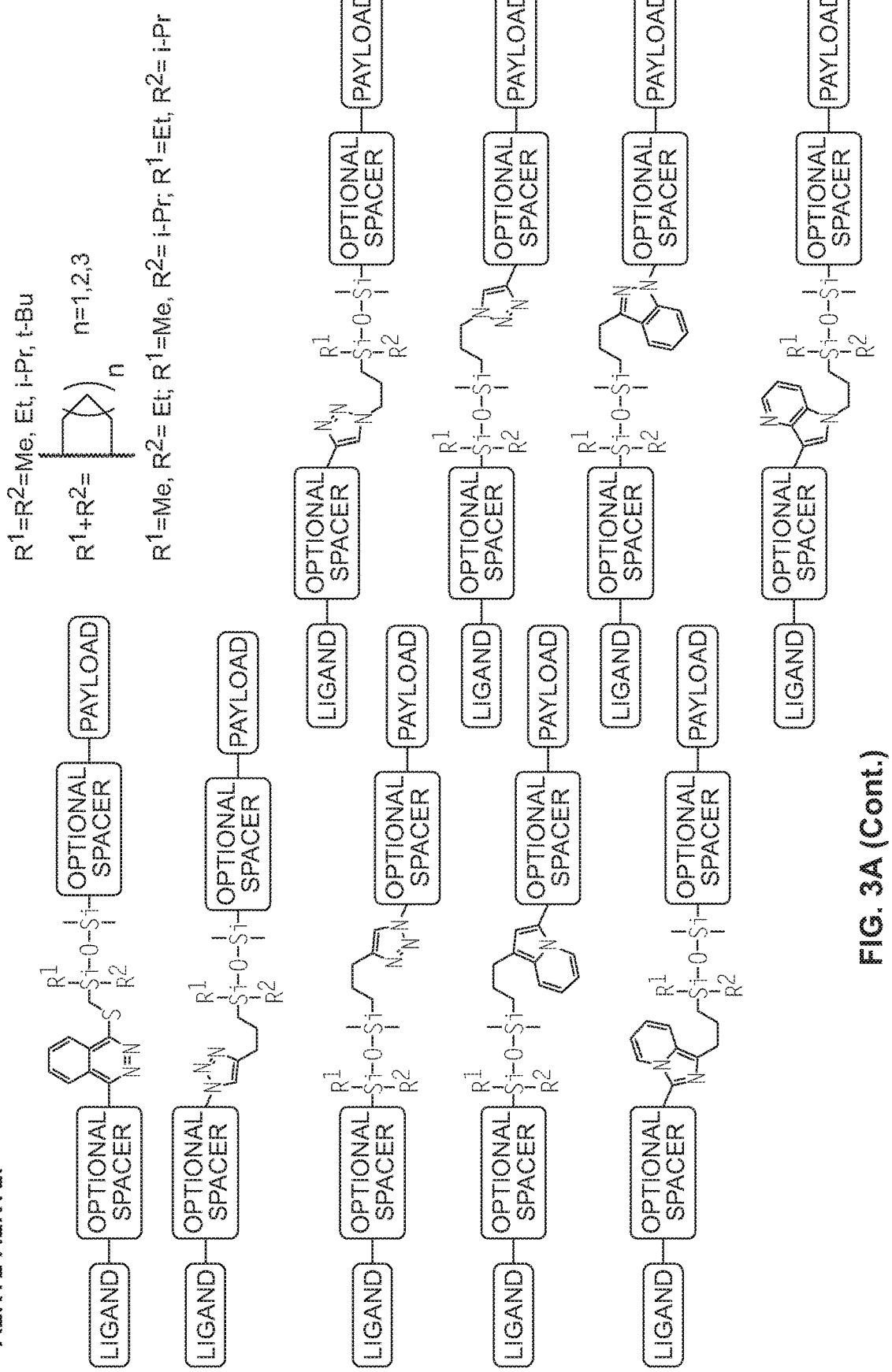
Figure 3A:
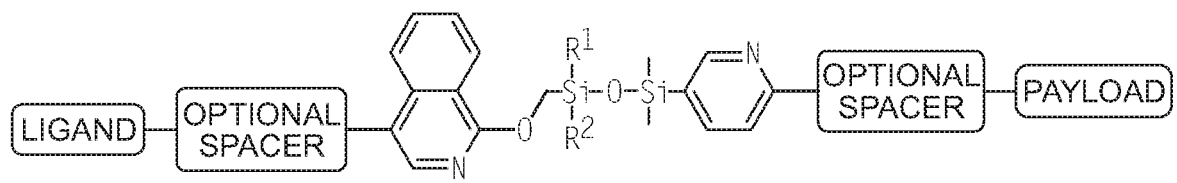
Figure 3A:
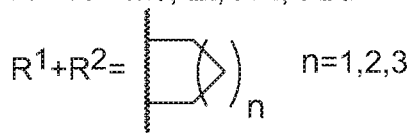
Figure 3A:
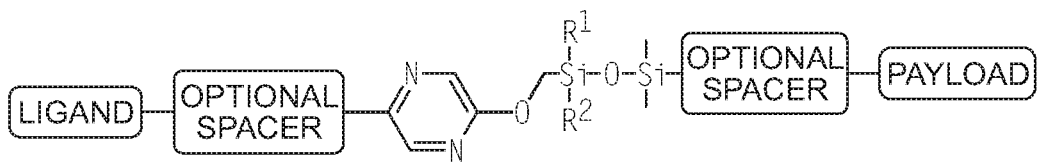
Figure 3A:
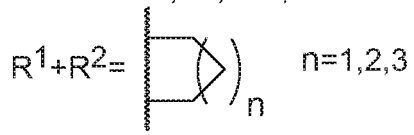
Figure 3B:
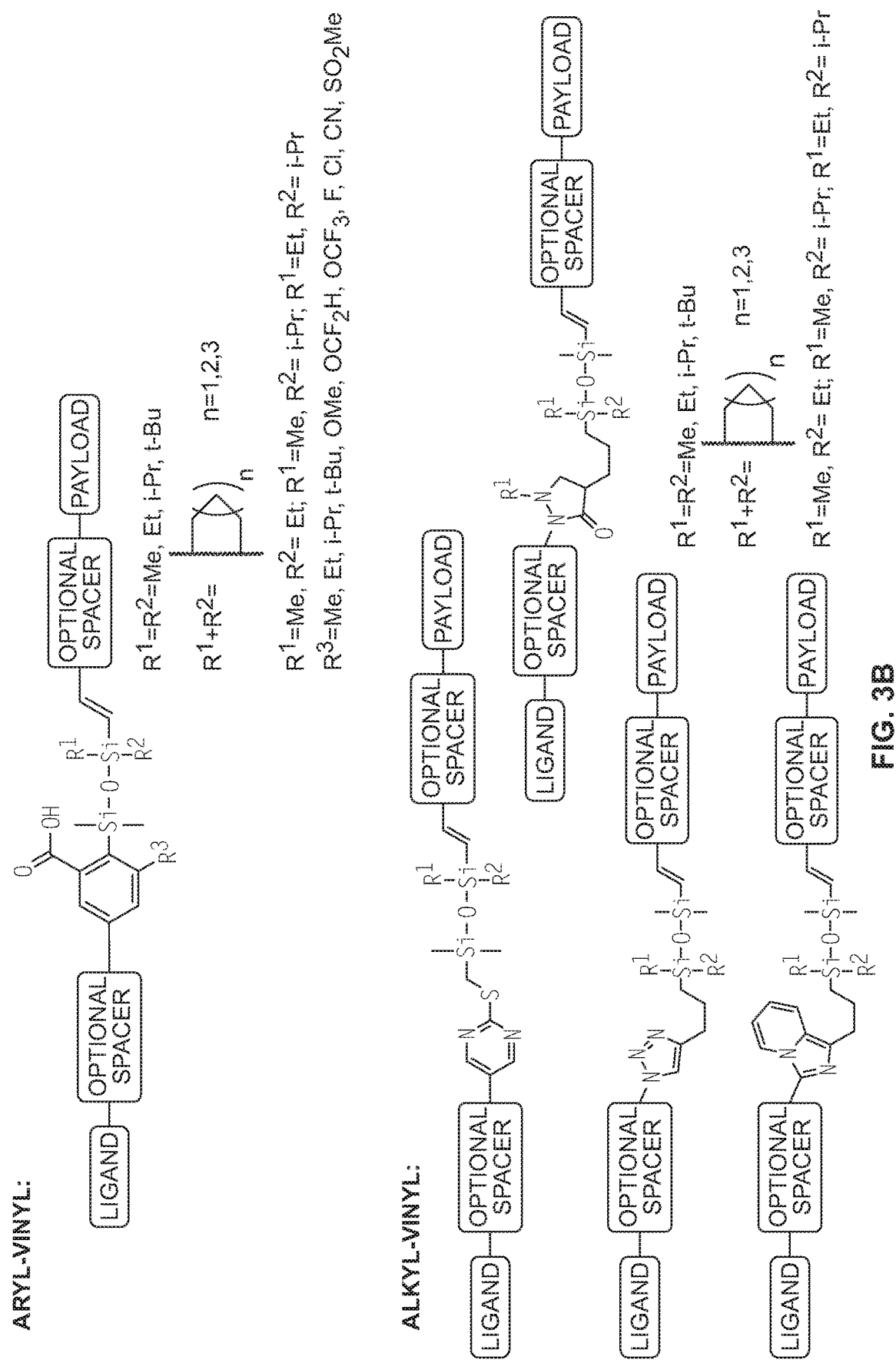
Figure 4:
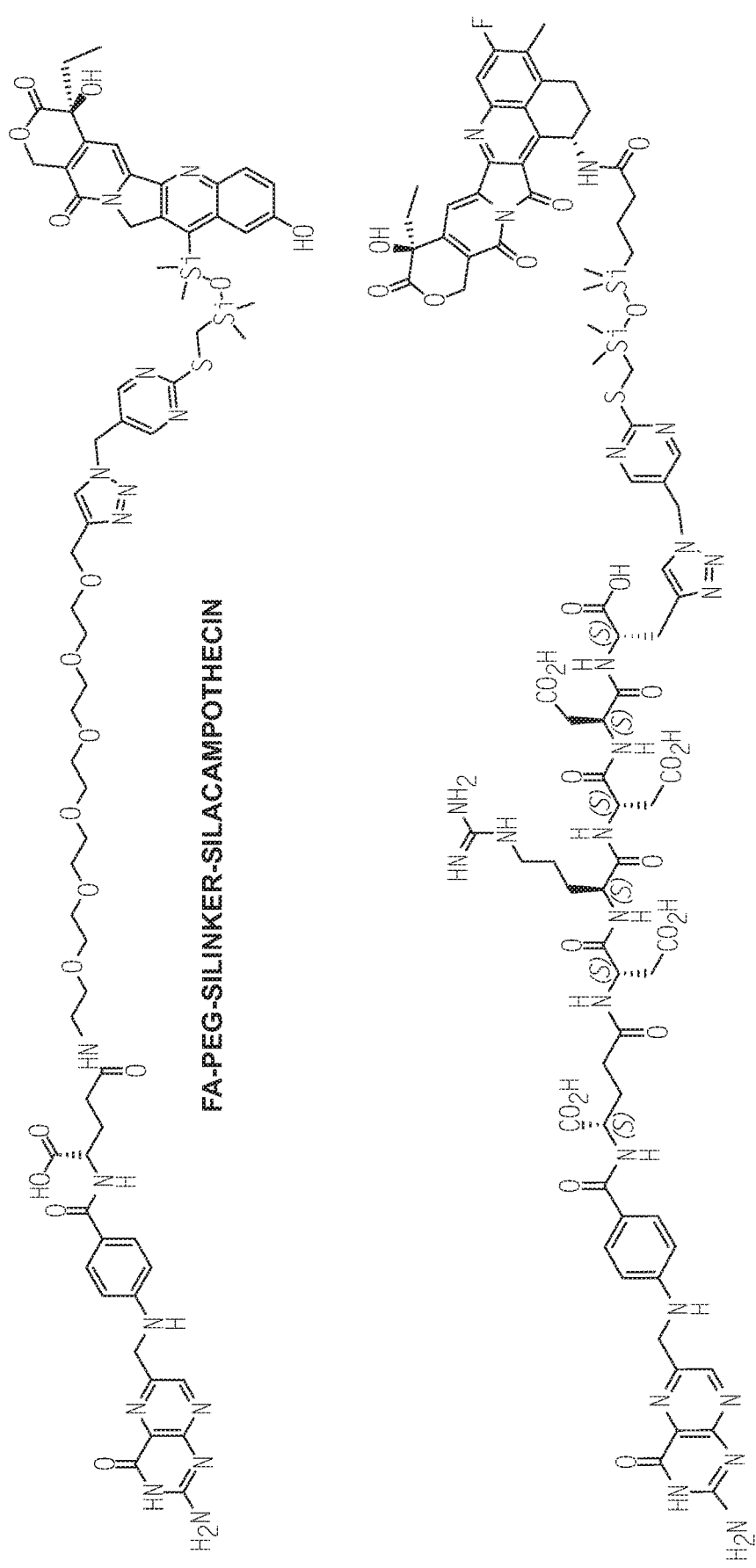
FIG. 4 shows contemplated conjugates containing the folic acid (targeting moiety), a spacer (PEG units or peptides), a catalytic unit (thiopyrimidine), a disilylether linker, and a payload (sila-camptothecin).
Figure 5:
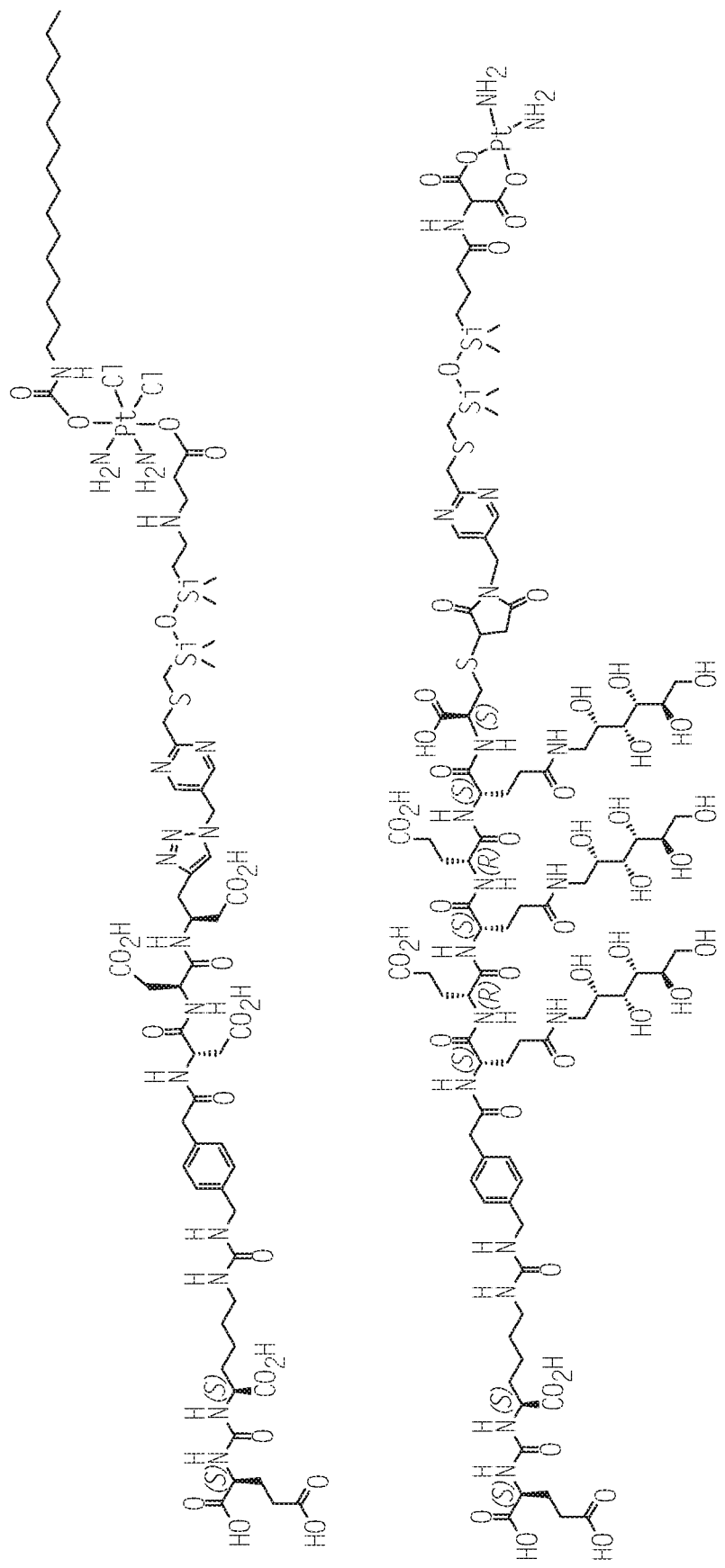
FIG. 5 shows contemplated conjugates containing a platinum(II)-based or platinum(IV)-based payload.
Figure 5:
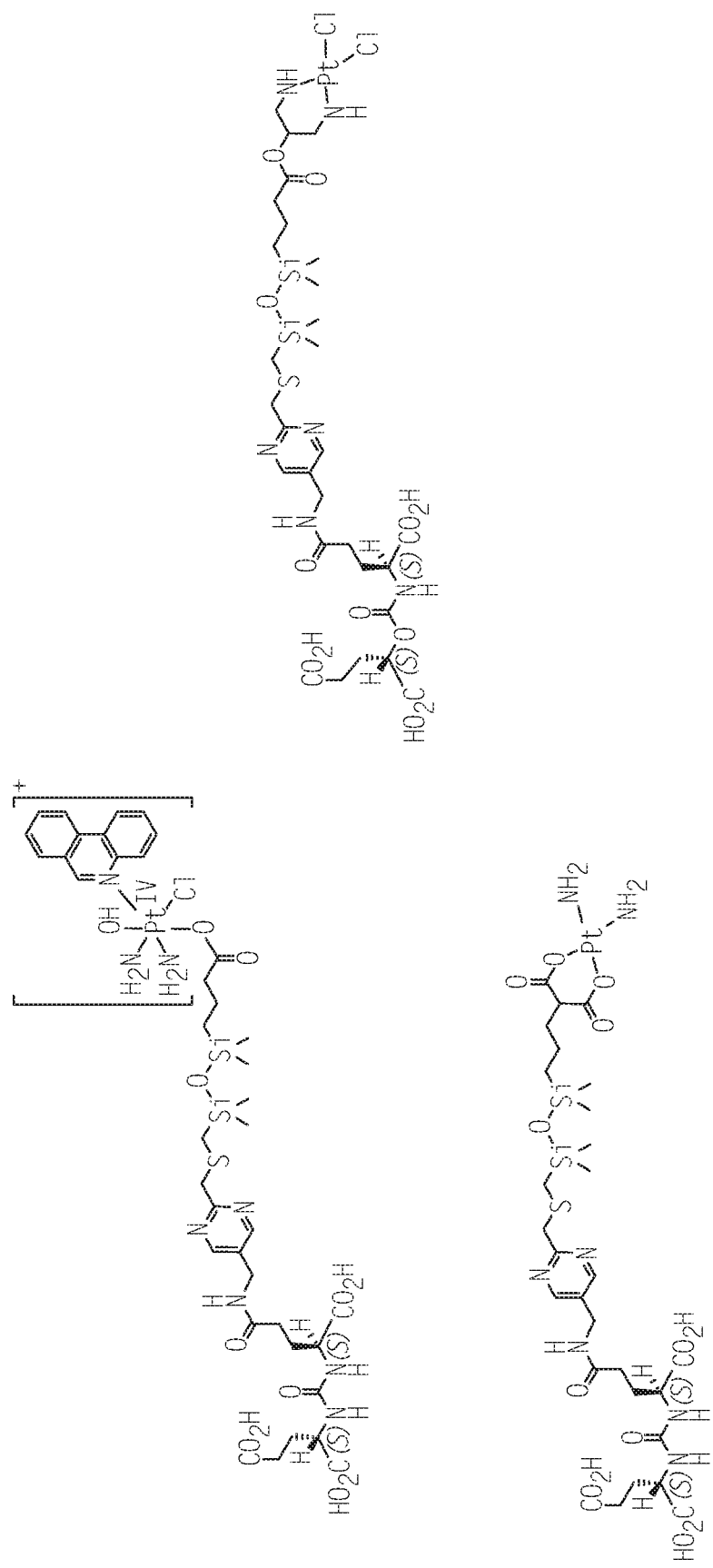
Figure 6:
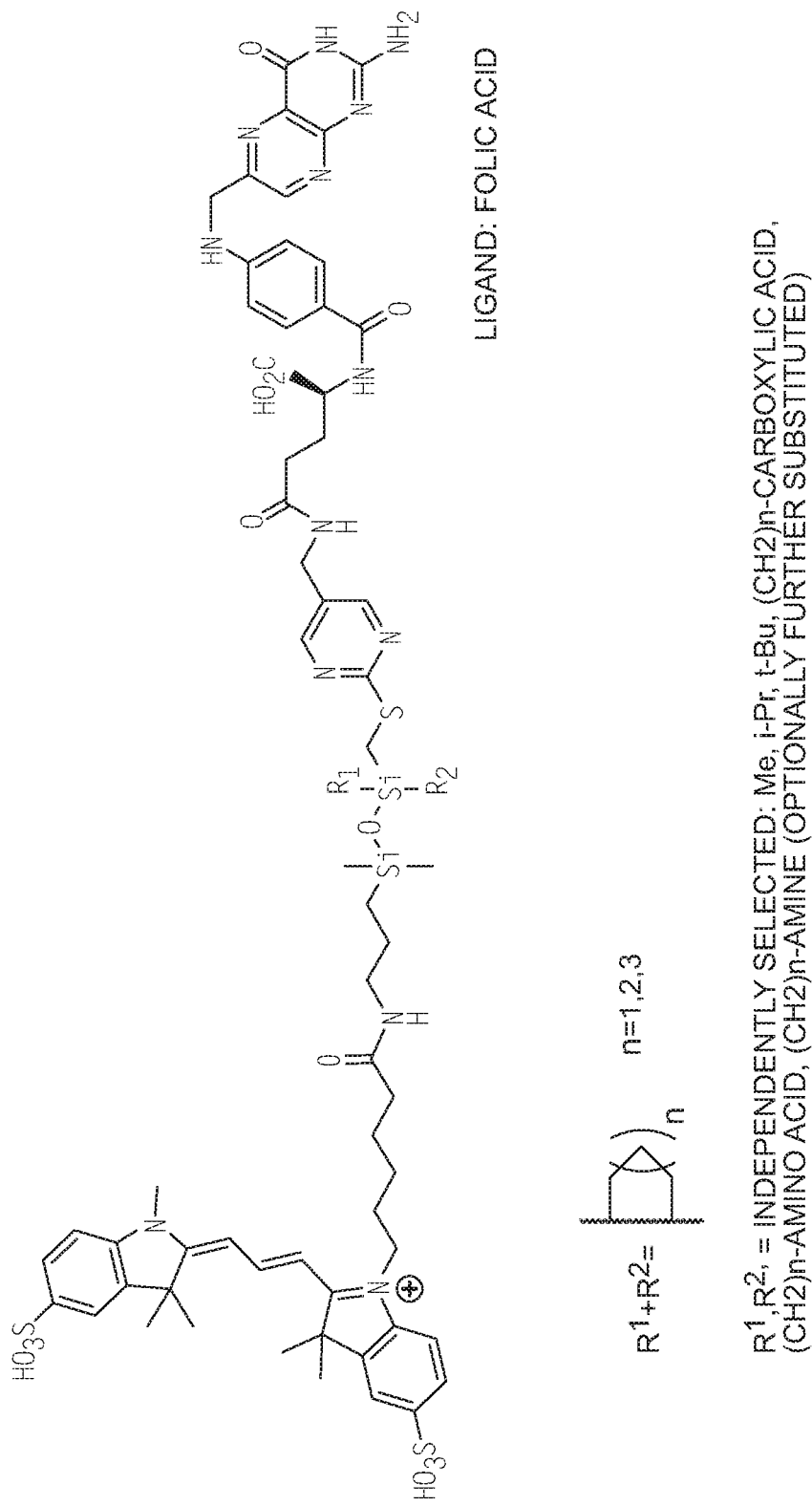
FIG. 6 shows a contemplated fluorophore-folic acid conjugate.
Figure 7:
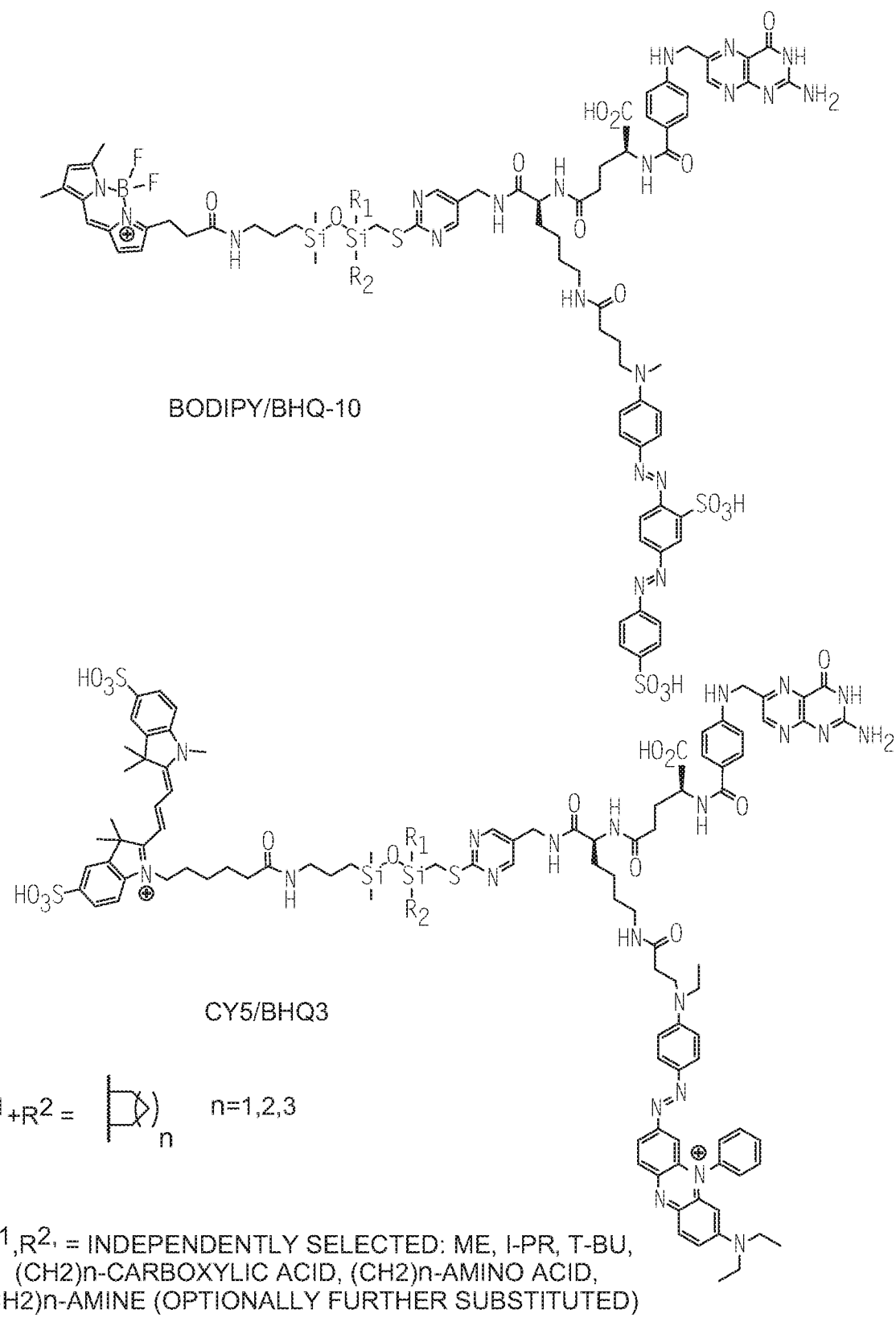
FIG. 7 shows contemplated fluorophore/quencher-folic acid conjugates.
Figure 8:
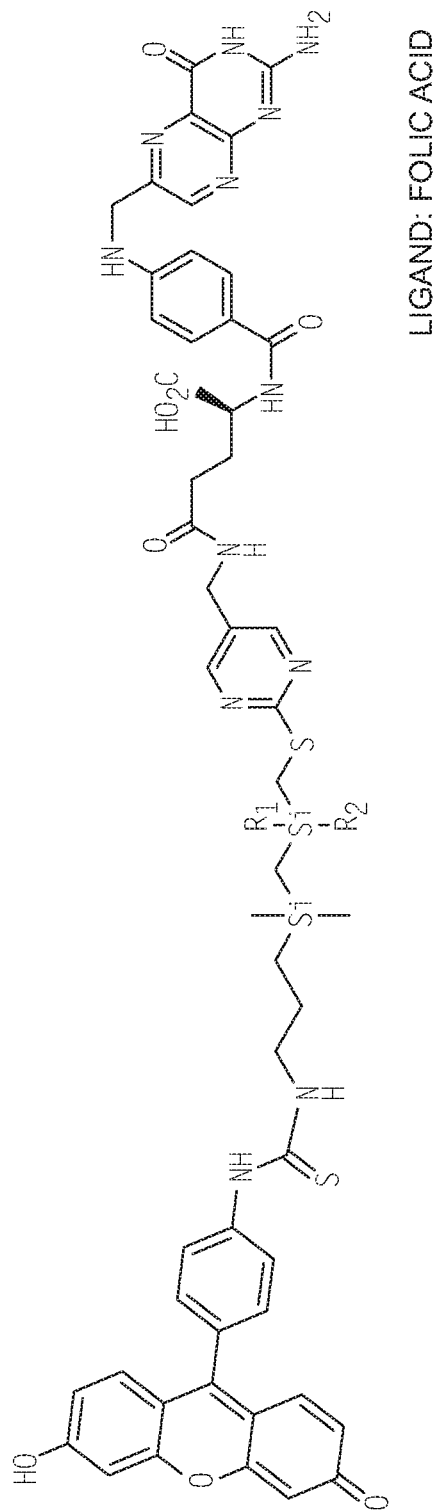
FIG. 8 shows another contemplated fluorophore-folic acid conjugate using fluorescein as the fluorophore.
Figure 8:
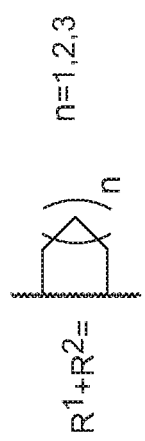
Figure 16:
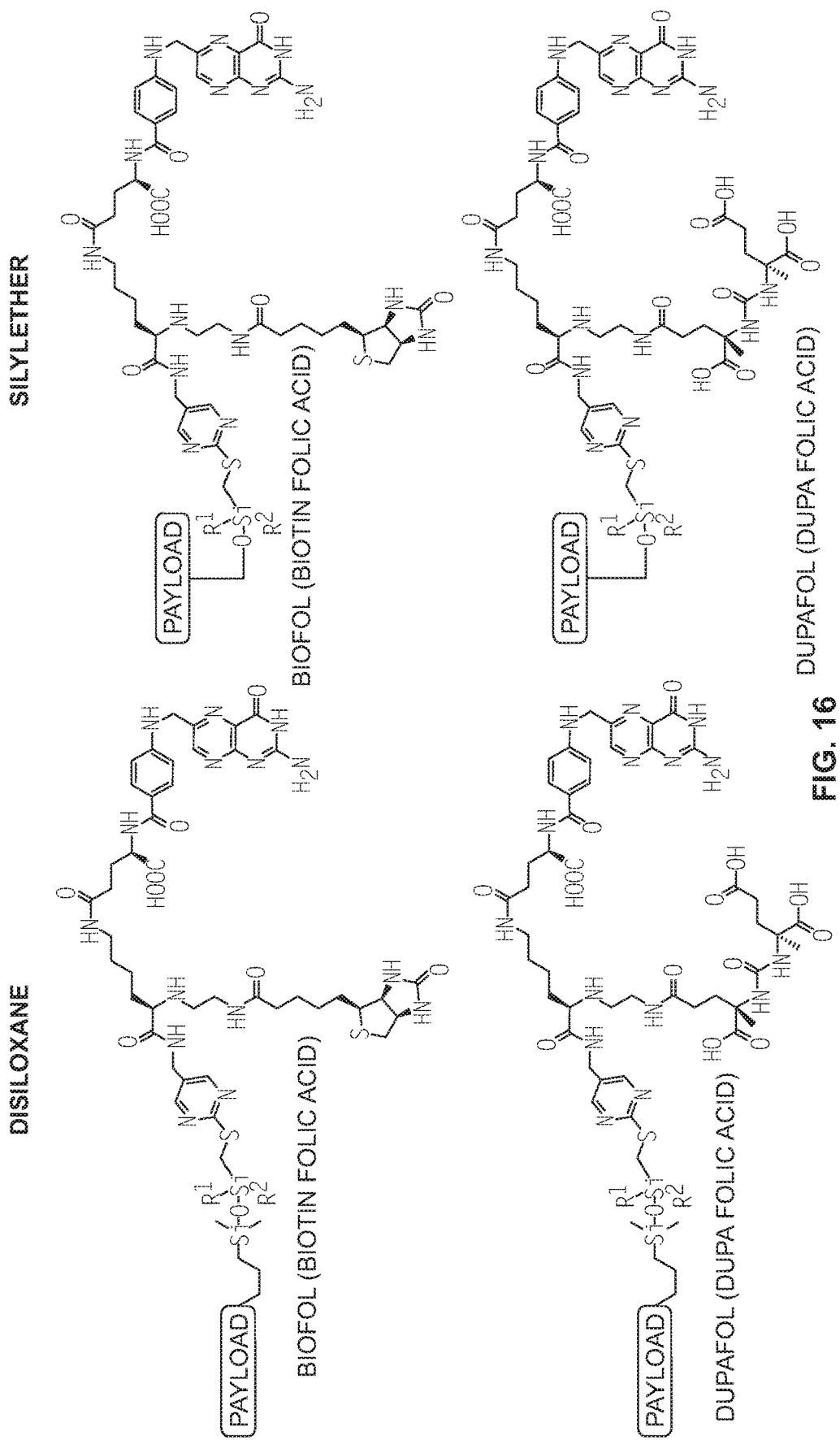
FIG. 16 shows contemplated disilylether and silylether conjugates comprising two targeting moieties and a payload.
Figure 16:
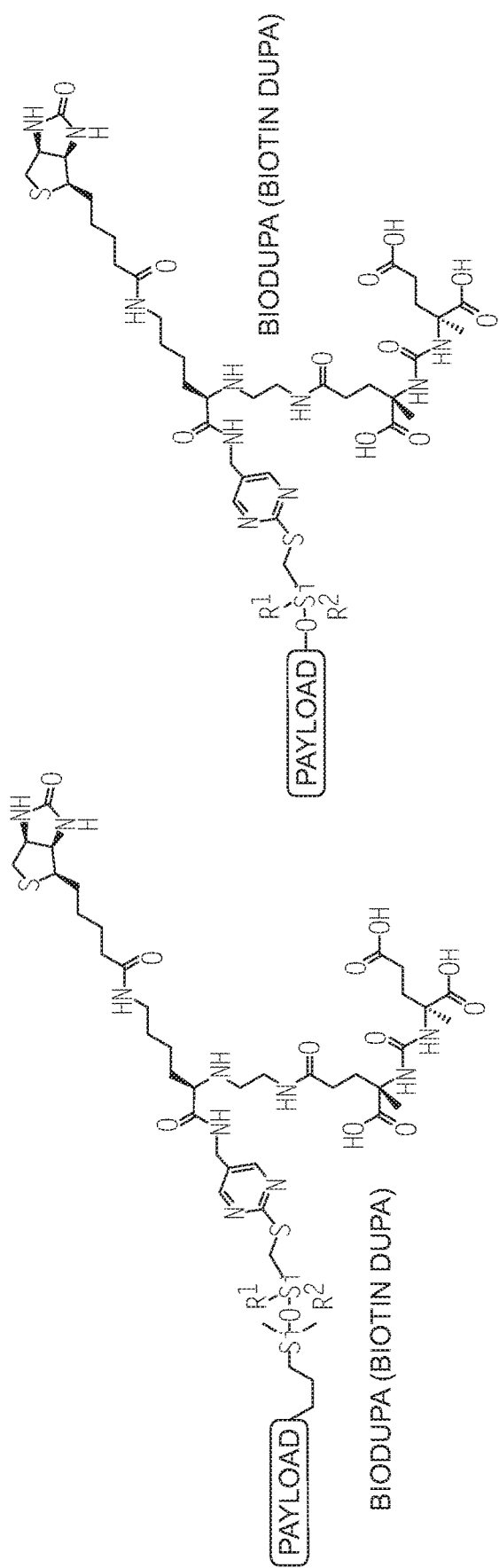
Figure 17:
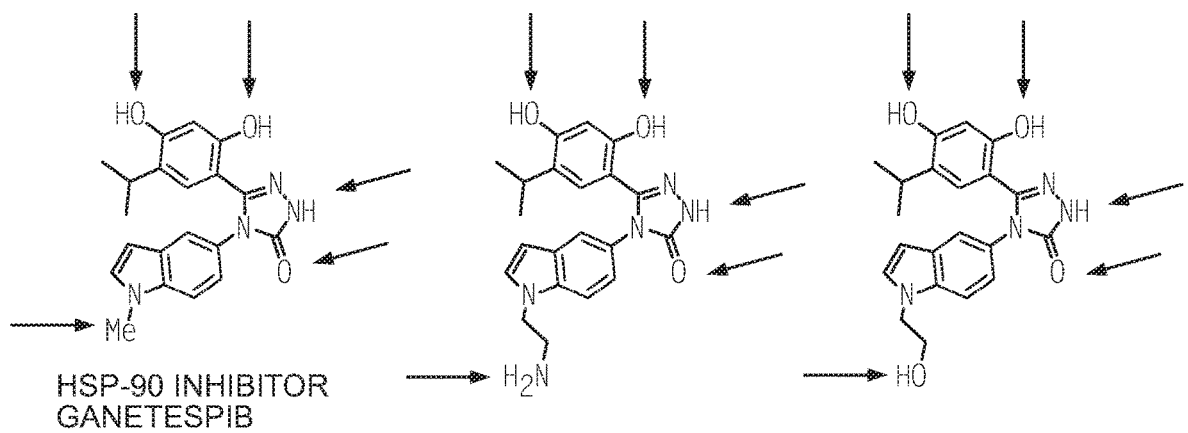
FIG. 17 shows various points for attaching connectors on HSP-90 (heat shock protein 90) inhibitor ganetespib or its derivatives.
Figure 17:
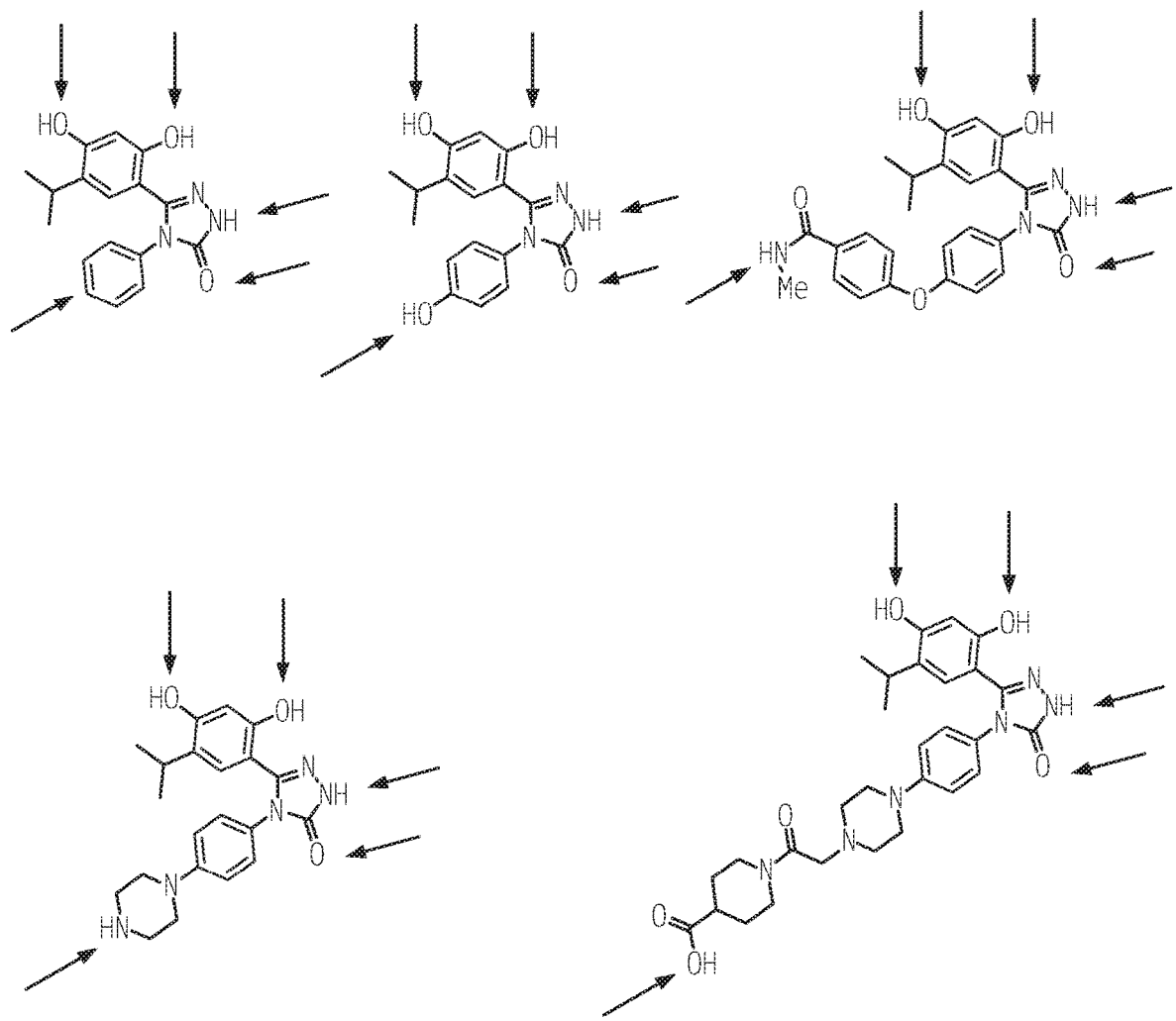
Figure 18:
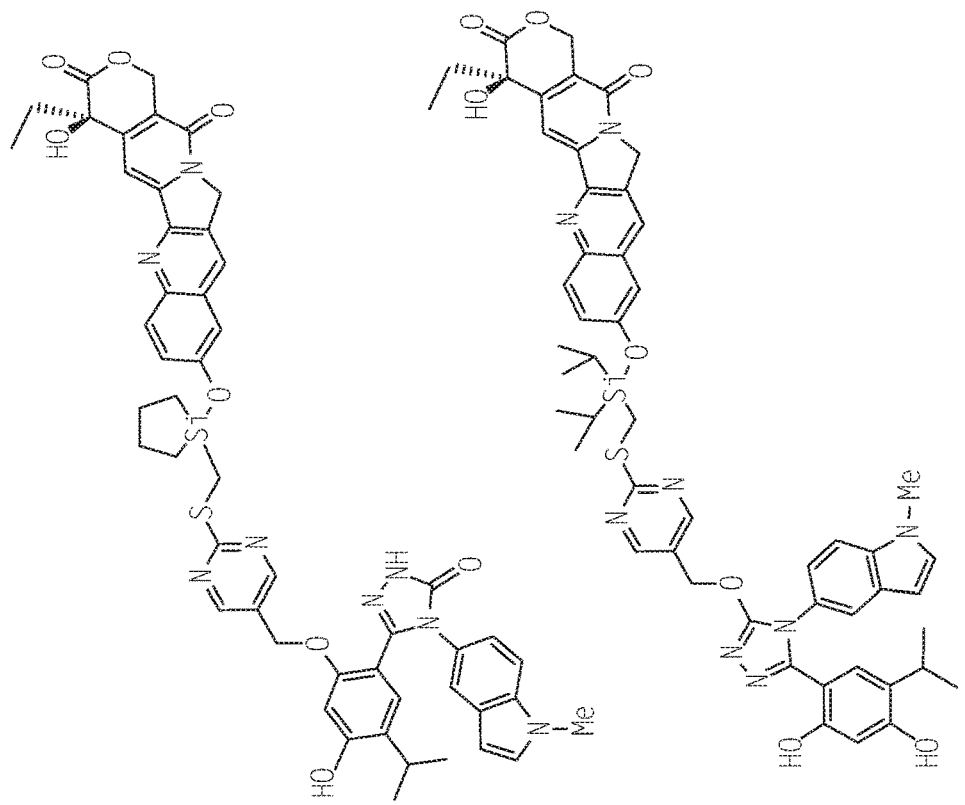
FIG. 18 shows contemplated HSP-90 ganetespib analogs with camptothecin silicon-containing conjugates.
Figure 18:
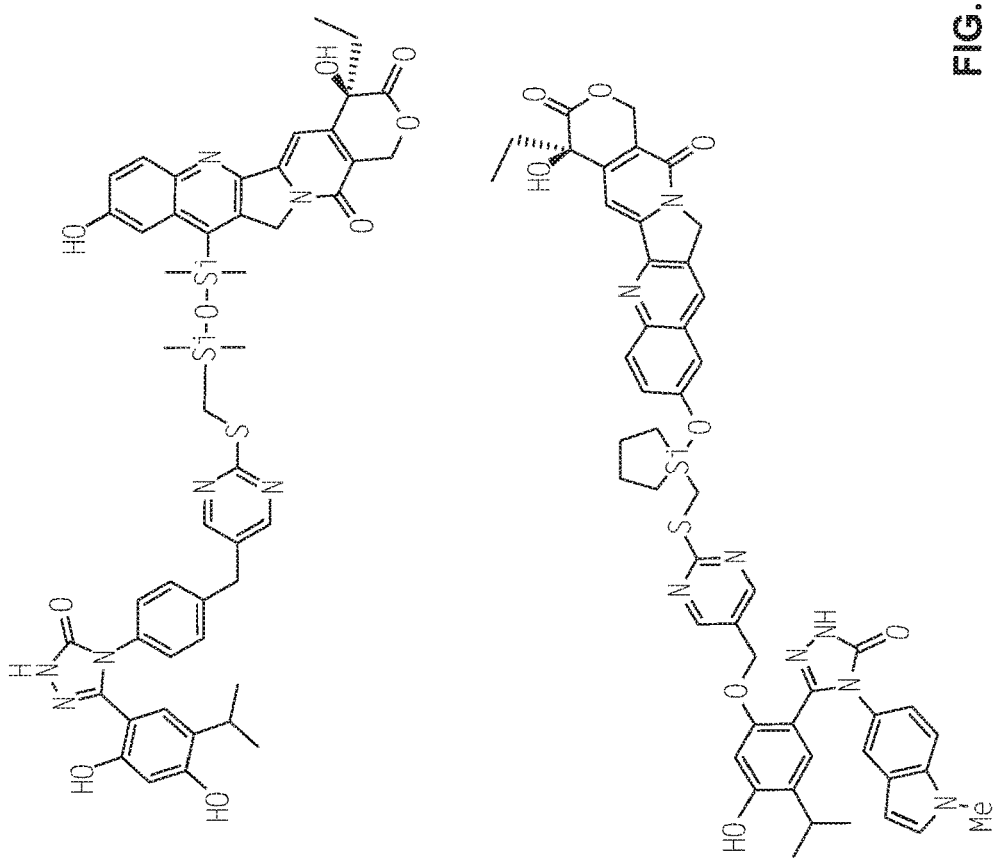
Figure 19:
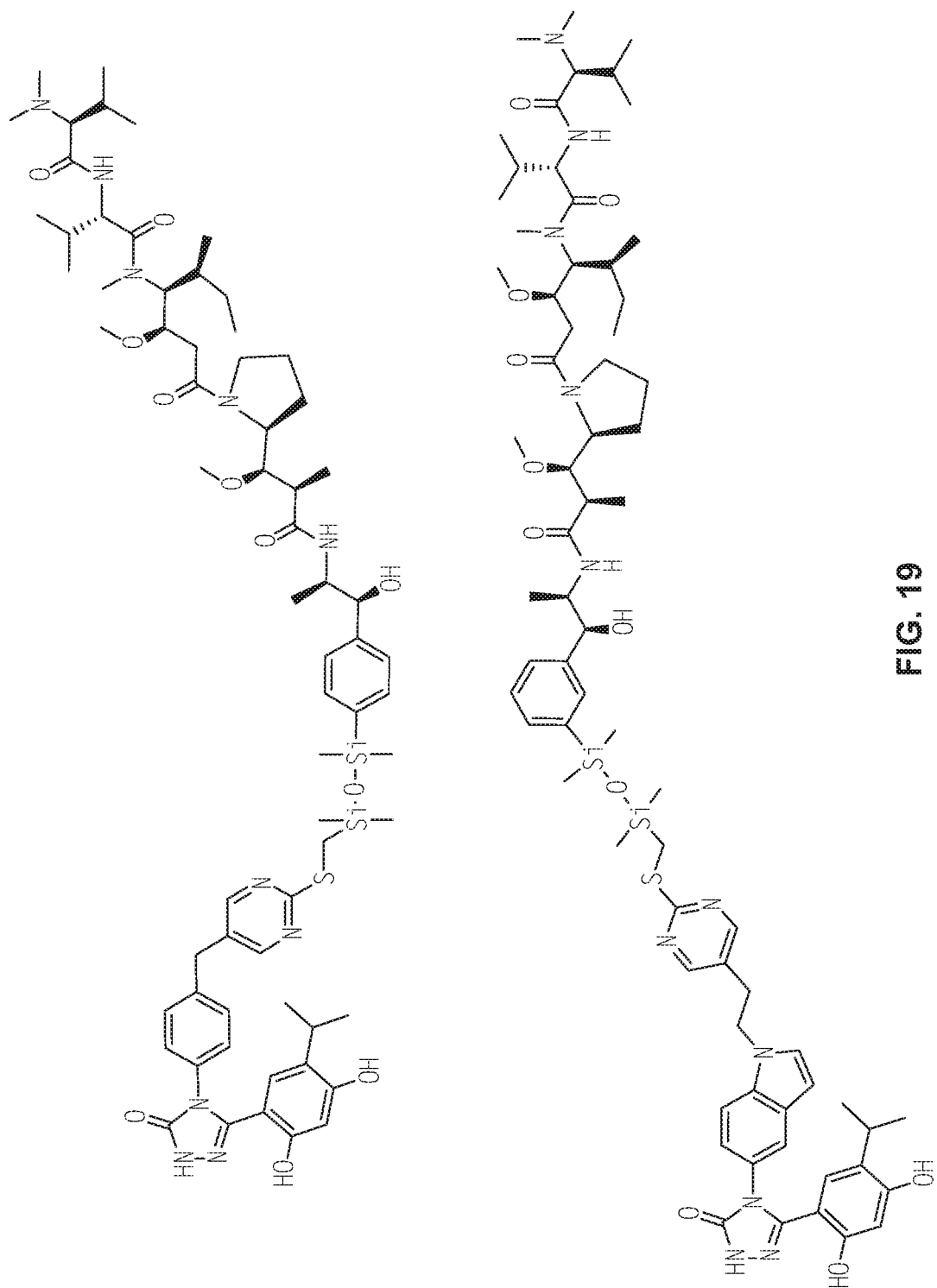
FIG. 19 shows contemplated HSP-90 ganetespib analogs with auristatin F silicon-containing conjugates.
Figure 20:
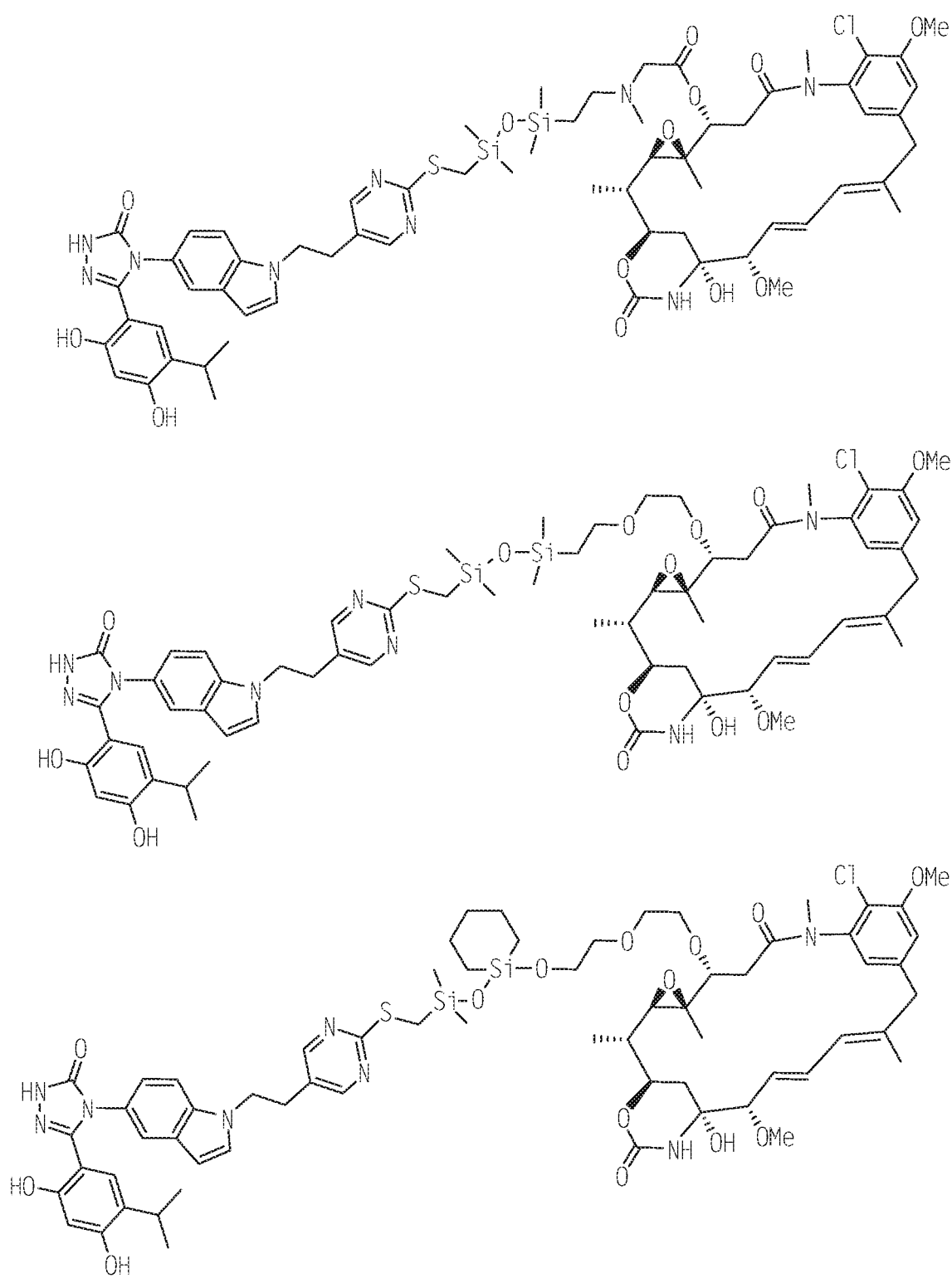
FIG. 20 shows contemplated HSP-90 ganetespib analogs with DM1 silicon-containing conjugates.
Figure 21:
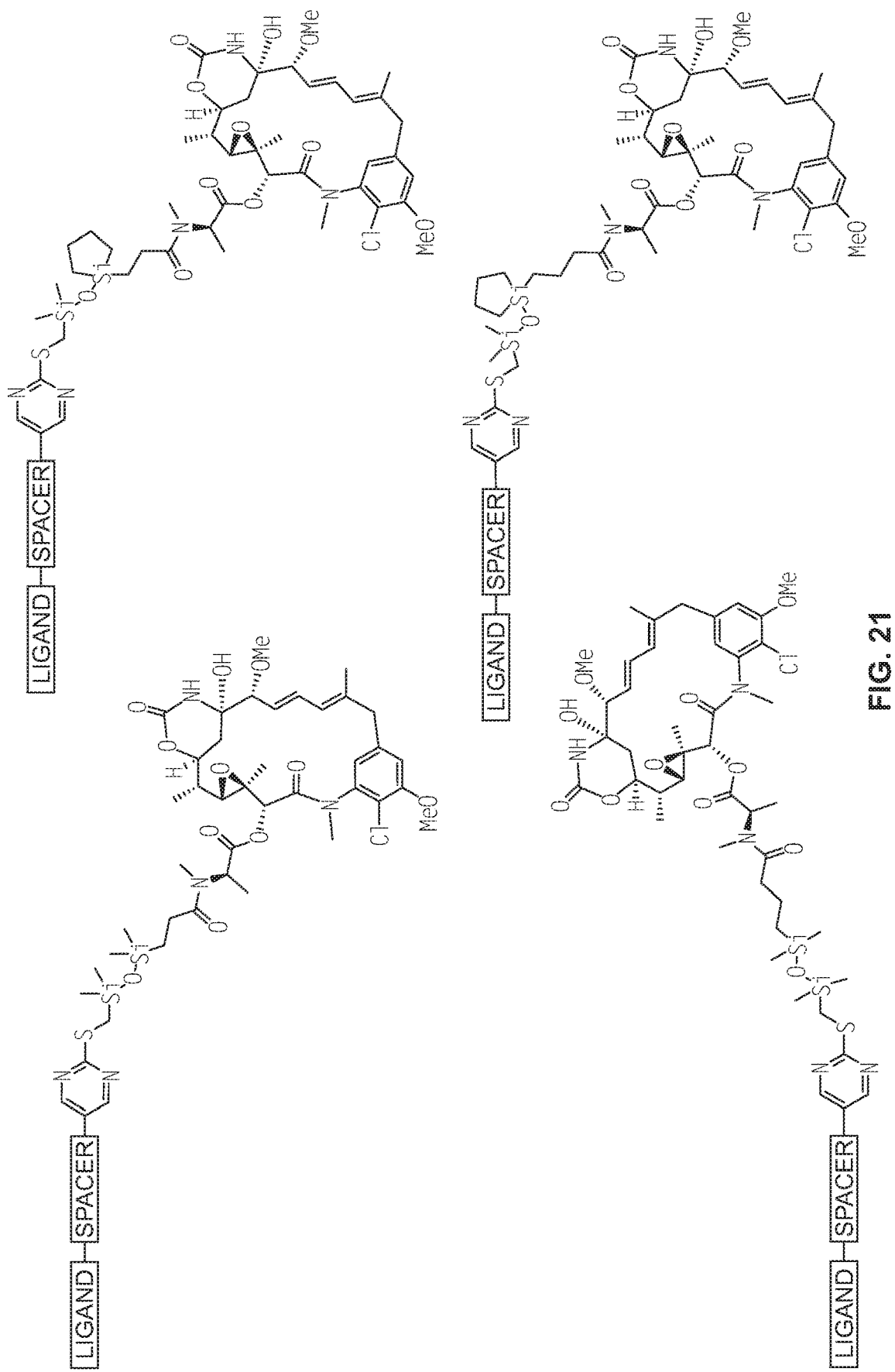
FIG. 21 shows contemplated maytansine payload moieties modified with silicon-containing spacers.
Figure 21:
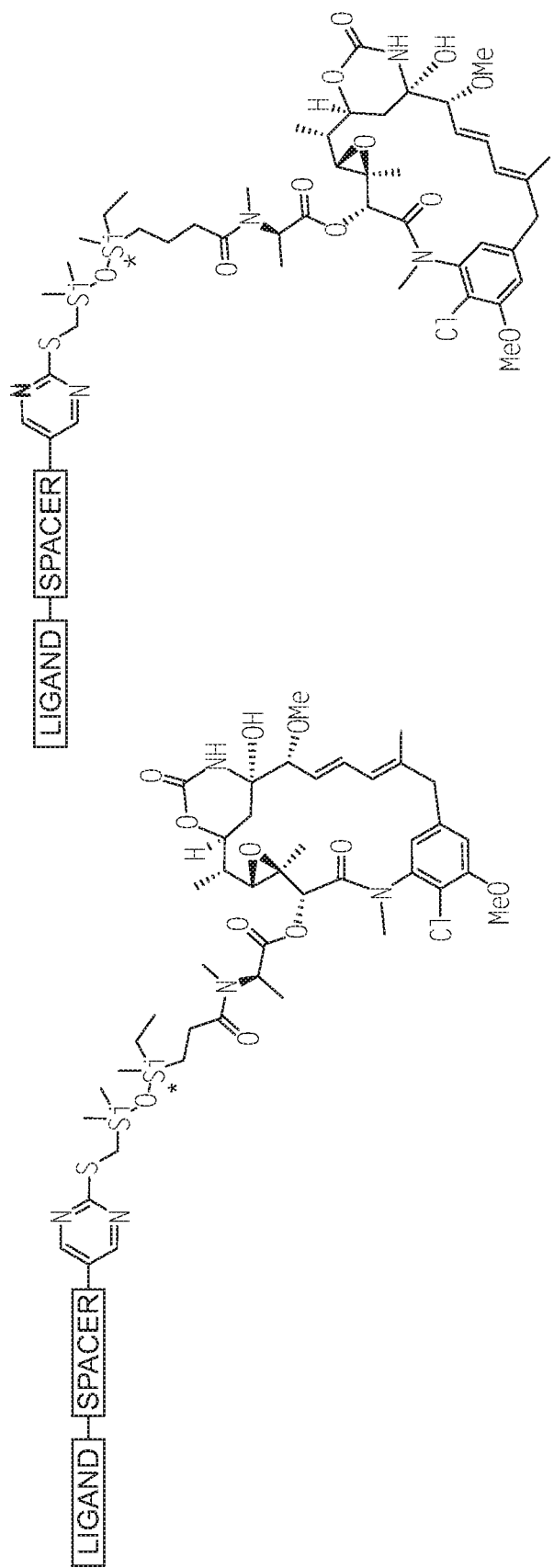
Figure 22:
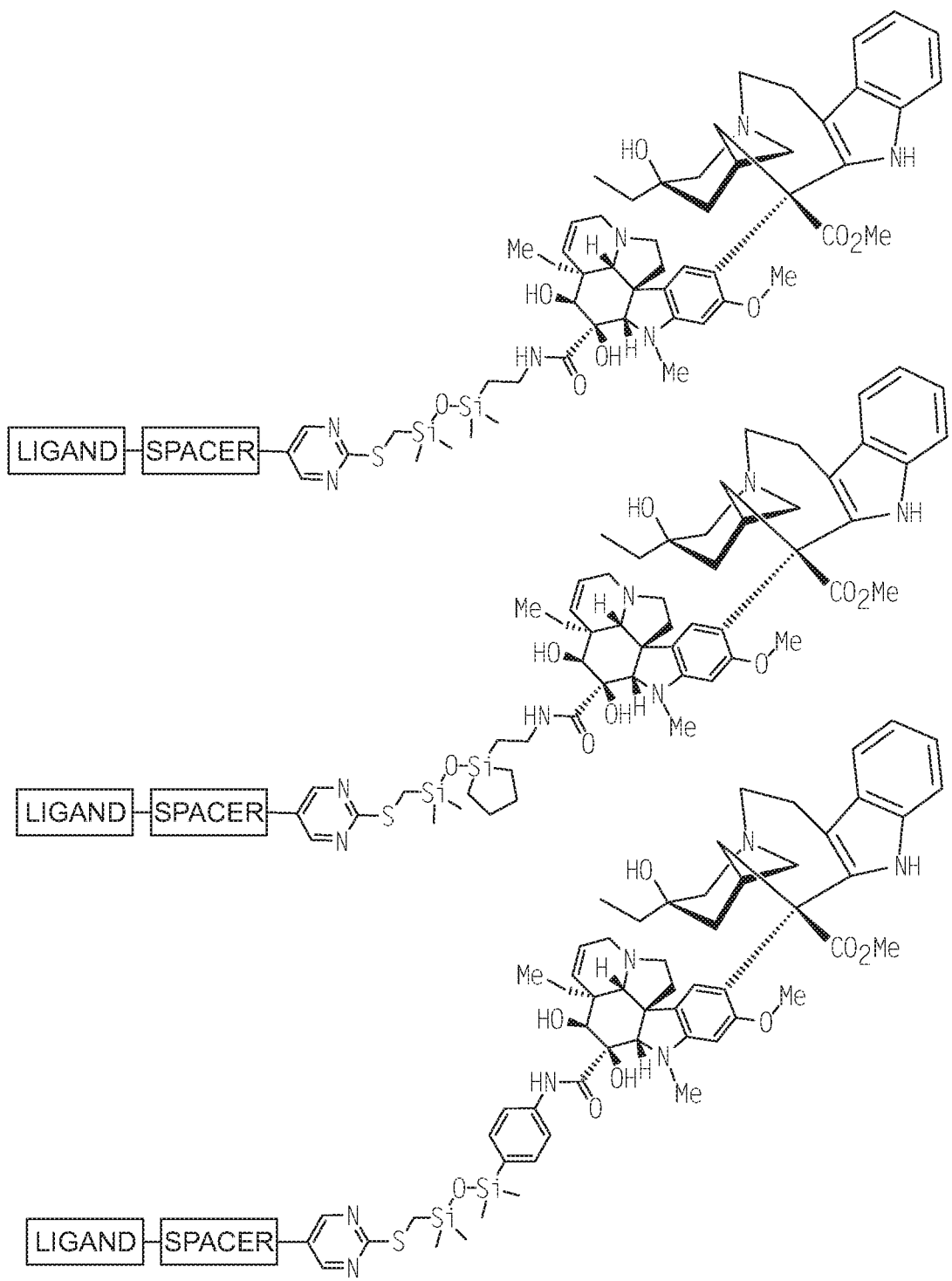
FIG. 22 shows contemplated deacetyl vinblastine payload moieties modified with silicon-containing spacers.
Figure 23:
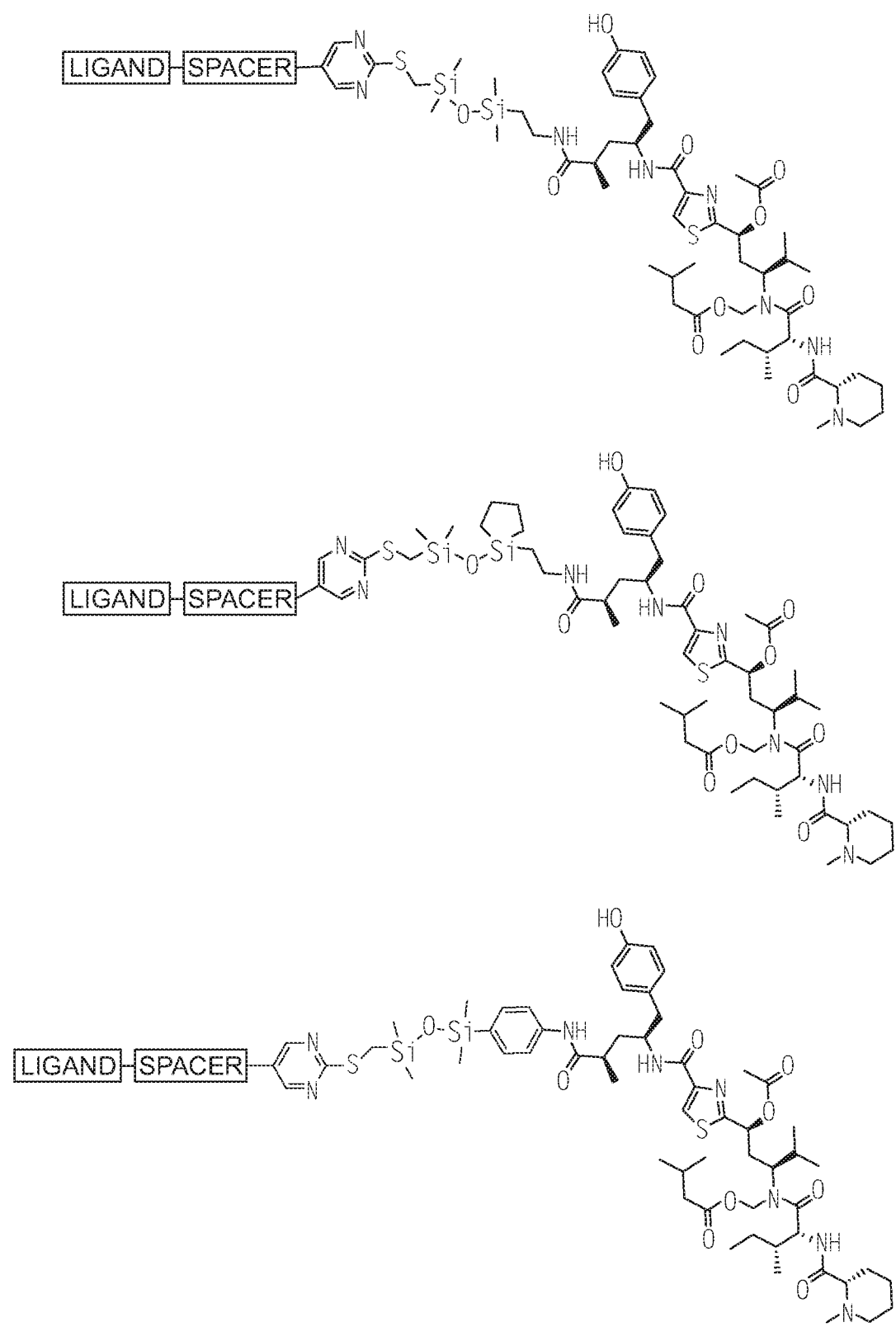
FIG. 23 shows contemplated tubulysin payload moieties modified with silicon-containing spacers.
Figure 24:
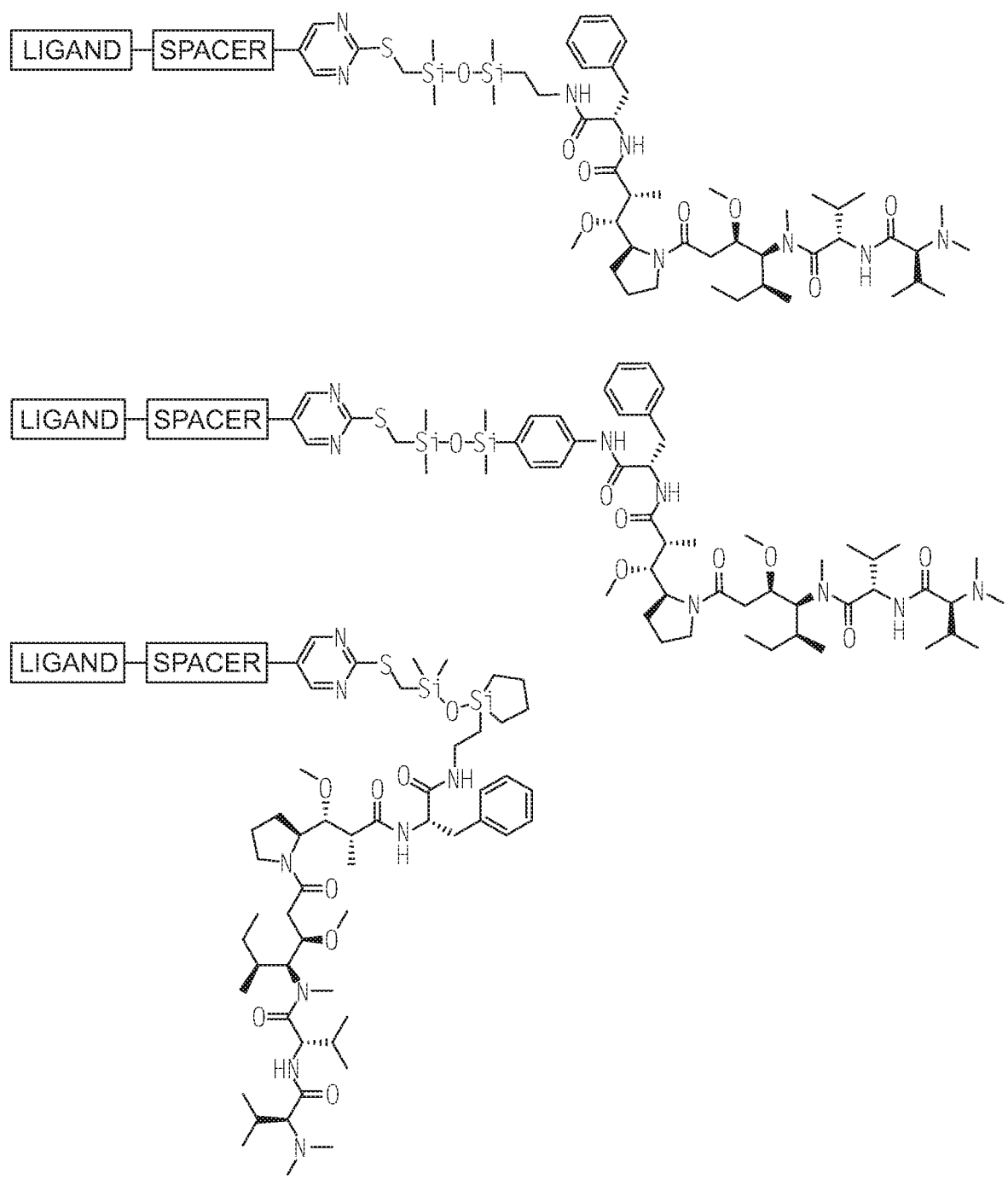
FIG. 24 shows contemplated auristatin payload moieties modified with silicon-containing spacers.
Figure 24:
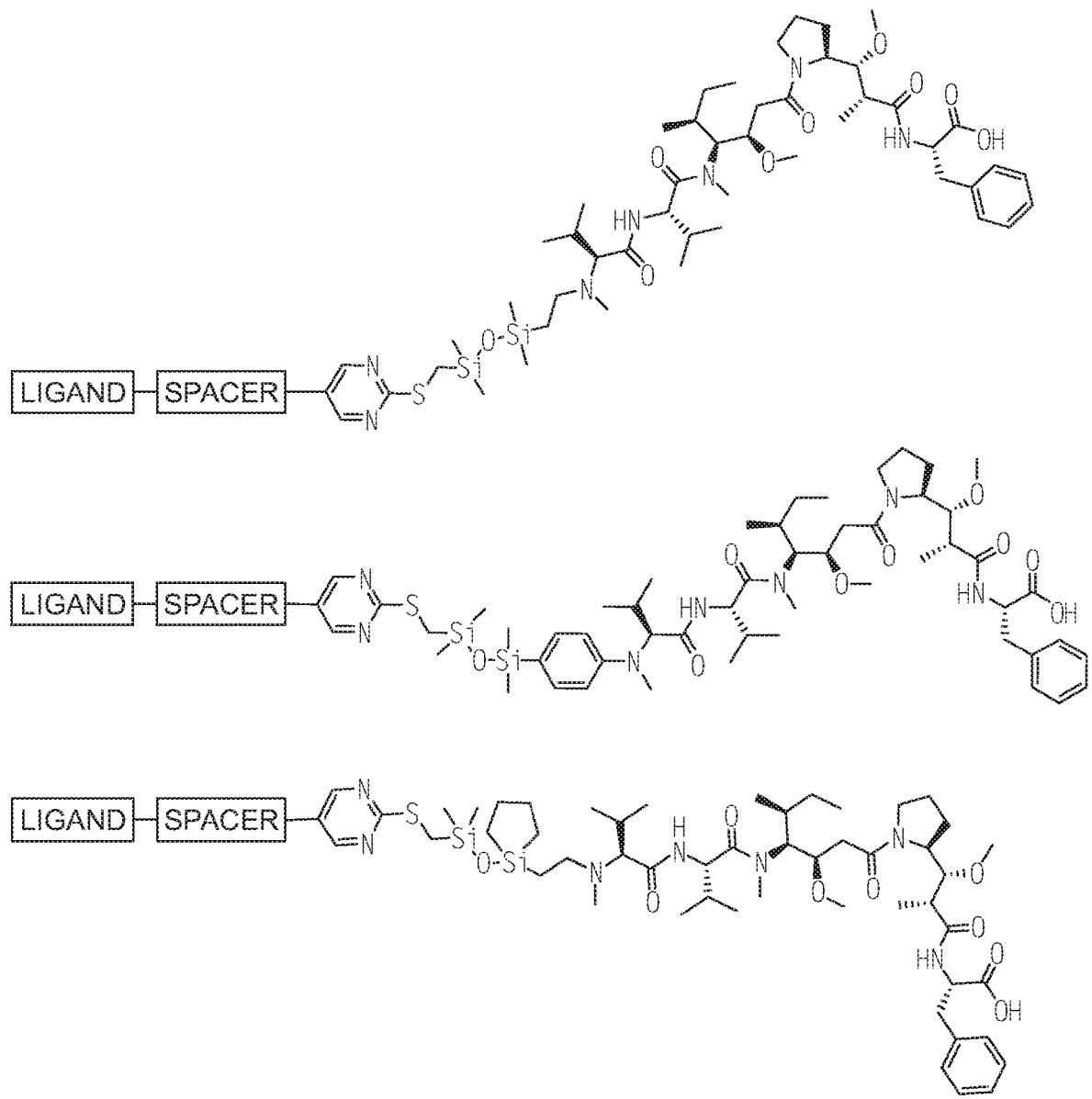

Contemplated silicon based conjugates may include at least one targeting moiety L (e.g., may include one, two, three or more moieties), which may be covalently bound for each occurrence to the Si-heteroatom core (e.g., the siloxane or silylether core through a divalent spacer moiety Y, or may be directly bonded to e.g. a heteroatom of the silicon-heteroatom core and/or to a Si atom itself. The payload moieties, P, may be, for each occurrence, covalently bound to the Si-heteroatom core (e.g., siloxane or silylether core) through a divalent spacer moiety Y or directly to e.g., a heteroatom of the silicon-heteroatom core and/or to a Si atom itself. Exemplary conjugates with one targeting moiety are shown in FIGS. 3A-3B, and exemplary bis-targeting moiety conjugates are shown in FIG. 16.

Divalent spacers (e.g., a moiety Y), when present on the conjugate, may be selected, for example to maximize targeting moiety L's affinity to a target cell and/or tissue and in certain embodiments may be selected to optimize length, rigidity and/or flexibility, or to optimize in vivo parameters and physicochemical properties (such as solubility) of the drug conjugate. The divalent spacer moiety may contain a pH-sensitive catalytic moiety which enables the pH-dependent hydrolysis. Exemplary spacers may include aliphatic and aromatic moieties or a combination of both and, for example, may be separately alkylene, alkoxyalkyl, aryl, biaryl, heteroaryl, and vinyl moieties (e.g., are each independently selected for each occurrence from the group consisting of: a bond, $C_{1-6}$alkyl, phenyl, heteroaryl, $C_{1-6}$alkyoxy, and $C_{1-6}$alkyoxy-$C_{1-6}$alkyl, and optionally substituted, by e.g., a substituent selected from the group consisting of halogen, $C_{1-6}$alkyl and $C_{1-6}$alkyoxy) for each occurrence, as shown in e.g., FIGS. 3A and 3B. Exemplary spacers may also include peptidic units with natural and non-natural amino acids, or carbohydrates. In a certain embodiment, a spacer is self-immolating and may result in pH dependent cleavage and/or reductive cleavage. Specific exemplary conjugates with self-immolating spaces are shown in e.g., FIG. 15. Exemplary spacers may include an adaptor moiety which enables the addition of multiple payloads (e.g., either the same or different payloads). Exemplary catalytic moieties may include, but are not limited to, monocyclic or bicyclic heteroaryl systems, for example, optionally substituted pyrroles, furans, thiophenes, imidazoles, pyrazoles, oxazoles, isoxazoles, thiazoles, isothiazoles, pyridines, pyrimidines, triazoles, tetrazoles, etc.

Conjugates can include one, two or more non-interfering moieties (e.g., R moieties), each covalently bound to the silicon-heteroatom core, such that the presence of the two or more non-interfering moieties provides stability and optionally is selected to optimize the hydrolysis profile, e.g., that the conjugate is covalently stable and may also optimize the release profile of the payload. The non-interfering moieties each may be the same or different, and each may be independently selected to minimize untargeted cellular uptake of the conjugate and/or optimize the timing of cleavage of the connection to the payload P such that P is selectively released into the target cell or tissue. For example, one or more non-interfering moieties may be selected to optimize Si—O bond cleavage such that P is released into the target cell or tissue. Exemplary disclosed conjugates with e.g., a siloxane or a silylether core and the release of payload under certain pH conditions is shown in FIG. 1, with non-interfering moieties represented by $R^1$, $R^2$, $R^3$, and $R^4$.

Conjugates disclosed herein may include targeting moieties (e.g., one, two or three) that each selectively binds or recognizes at least one of cell surface receptors, transporters, and antigens that are overexpressed in a disease state. For example, a targeting moiety may be capable of binding to at least one of: a cell surface receptor, a cognate ligand of a cell surface receptor, an antigen or a cell wall (e.g., a bacterial cell wall).

For example, targeting moieties may include one or more ligands that selectively bind or recognize at least one of Folate Receptors, prostate specific membrane antigen (PSMA), surface antigen in leukemia SAIL, intergrin $\alpha_v\beta_3$, asialoglycoprotein receptor, hydroxyapatite, delta-like protein-3 DLL3 receptor, receptor dystroglycan, cholescystokinin receptors, somatostatin receptor, onco fetal antigens, receptor tyrosine kinases, GPCRs, GPCRmAB targets, sigma-receptor, transferrin receptor, mannose receptor vitamin receptors, Trop-2, Notch receptor, CD33, CD44, and CD206. For example, a targeting moiety may be selected from the group consisting of: folic acid its derivatives, DUPA its derivatives, RGD and its derivatives, GPCR mABs, transferrin, G11 and analogs thereof which target EGFR, carbohydrates, aptamers, somatostatin analogs, and extracellular ligands that induce receptor internalization upon binding. For example, targeting moieties may be selected from the group consisting of: small molecules, peptides, peptidomimetics, aptamers, antibodies, and carbohydrates and derivatives thereof. A targeting moiety in certain embodiments is a protein (e.g., an antibody or antibody fragment), nucleic acid, lipid, oligomer, glycopeptide, polysaccharide, polymer (e.g., a dendrimer), nanoparticle, or any combination thereof. For example, a viral coat protein is contemplated, as e.g., a cognate ligand of certain cell surface receptors.

Silicon based conjugates disclosed herein may include one, two, or more payloads that may be a therapeutic or diagnostic agent, e.g., may each selected from the group consisting of: antigens, proteins, cytotoxic agents, metabolic modulators, anti-inflammatory agents, anti-viral agents, pathway modulators, synthetic lethal combinations, siRNA, mRNA, miRNA, endosomal escape enhancers, and imaging agents. For example, each payload may be selected from the group consisting of: check-point inhibitors, kinase inhibitors, proteasome inhibitors, topoisomerase inhibitors, tubulin inhibitors, rapamycin analogs, auristatin F analogs, maytansinoid analogs, duocarmycin analogs, calicheamicin analogs, DM4 analogs, PET tracers, radioactive tracers and fluorophores, photosensitizers, and radiosensitizers, for example, selected from camptothecin analogs, doxorubicin analogs, vinca alkaloid analogs, taxane analogs (docetaxel, paclitaxel), rapamycin analogs, platinum based chemotherapeutics, and tubulysin analogs. The payload moiety of a contemplated conjugate, in some cases, may be a molecule that is, e.g., modulating cellular pathways by binding to a biomolecule, such as, for example, a protein or a specific protein domain, a component of a biological cell such as ribosome (composed of proteins and nucleic acids), or an enzyme active site. In some embodiments, the payload moiety may be a diagnostic agent.

In an embodiment, provided herein is a silicon based conjugate represented by the formula:

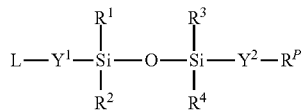

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;
P is a payload moiety or payload cassette;
$R^P$ is P, H, or $R^5$;
$Y^1$ is represented by the formula:

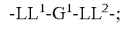

$Y^2$ is represented by the formula:

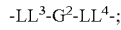

$G^1$ and $G^2$ are each optional catalytic moieties each independently selected from the group consisting of -heteroaryl-, —O-heteroaryl-, —$NR^a$-heteroaryl-, —$S(O)_w$-heteroaryl-(wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl-(wherein w is 0, 1, or 2), —$NR^a$—$SO_2$-phenyl-, —$SO_2$—$NR^a$-phenyl-, —C(O)—$C_{0-6}$alkyl-, —$NR^a$—C(O)—$C_{0-6}$alkyl-, —$NR^a$—$C_{0-6}$alkyl-; wherein -heteroaryl-, —O-heteroaryl-, —$NR^a$-heteroaryl-, —$S(O)_w$-heteroaryl-(wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—$NR^aR^b$, —$NR^a$—C(O)—$C_{1-6}$alkyl, —C(O)—$NR^a$—$SO_2$—$C_{1-6}$alkyl, —$SO_3H$, —$SO_2$—$NR^aR^b$, —$NR^a$—$SO_2$—$C_{1-6}$alkyl, and —$SO_2$—$NR^a$—$C_{1-6}$alkyl;

$LL^1$, $LL^2$, $LL^3$ and $LL^4$ are spacer moieties each independently selected from the group consisting of a bond, and $C_{1-20}$alkylene, wherein one, two, three or four methylene units of $C_{1-20}$alkylene are optionally and independently replaced by $C_{3-8}$cycloalkylene, $C_{2-10}$alkenylene $C_{2-10}$alkynylene, aryl, heteroaryl, amino acids, polypeptides, —$NR^{1Y}$—, —$N(R^{1Y})C(O)$—, —$C(O)N(R^{1Y})$—, —O—, —C(O)—, —OC(O)—, —C(O)O—, —S—, —SO—, —$SO_2$—, —C(═S)—, —C(═$NR^{1Y}$)—, —$NR^{1Y}$—$C_{1-15}$alkyl-$NR^{1Y}$—C(O)—; —($CH_2$—$CH_2$—O)$_s$—, —(O—$CH_2$—$CH_2$)$_s$—, —$NR^{1Y}$—($CH_2$—$CH_2$—O)$_s$—$C_{1-6}$alkyl-$NR^{1Y}$—C(O)—; —(O—$CH_2$—$CH_2$)$_s$—$NR^{1Y}$—C(O)—; —S—$C_{0-6}$alkyl-; —$NR^{1Y}$—$C_{1-6}$ alkyl-; —$N(C_{1-3}$alkyl)-$C_{1-6}$alkyl-NH—C(O)—; —NH—$C_{1-6}$alkyl-N($C_{1-3}$alkyl)-C(O)—; —$SO_2$—$NR^{1Y}$—$C_{0-6}$alkyl-; —N($R^{1Y}$)$SO_2$—$C_{0-6}$alkyl-; —$SO_2$-heterocyclyl-$C_{0-6}$alkyl-; -heterocyclyl-C(O)—; -heterocyclyl-$C_{0-6}$alkyl-$NR^{1Y}$—C(O)—; —$NR^{1Y}$—$C_{0-6}$alkylene-heterocyclyl-C(O)—; —O—$C_{1-6}$alkylene-C(O)—; —O—$C_{1-15}$alkylene-$NR^{1Y}$—C(O)—; —O—$C_{1-15}$alkylene-C(O)—$NR^{1Y}$—; —O—$C_{1-6}$alkylene-; a natural or unnatural amino acid; a natural or unnatural oligopeptide; a natural or unnatural polypeptide; photocleavable motifs; carbohydrates, and a self-immolating connector; wherein $LL^1$, $LL^2$, $LL^3$ and $LL^4$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;

s is an integer from 1-15;

$R^1$, $R^2$, $R^3$, $R^4$ are selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$alkyl, —O—C(O)—$C_{1-6}$alkyl, —NHC(O)$C_{1-6}$alkyl, —C(O)$NH_2$, —C(O)NH$C_{1-6}$alkyl, —C(O)N($C_{1-6}$alkyl)$_2$, —NHC(O)$CF_3$, —C(O)—$NR^a$—$SO_2$—$C_{1-6}$alkyl, —$SO_3H$, —$SO_2$—$NR^aR^b$, —$NR^a$—$SO_2$—$C_{1-6}$alkyl, and —$SO_2$—$NR^a$—$C_{1-6}$alkyl, amidine, guanidine, urea, sulfonamide, acylsulfonamide, sulfonyl amide, $C_{1-6}$alkyl, heteroaryl, and phenyl;

$R^5$ is selected independently for each occurrence from the group consisting of H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)$NH_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

or any pairwise combination of $Y^1$, $Y^2$, $R^1$, $R^2$, $R^3$, and $R^4$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $R^1$ and $R^2$, together with the silicon to which they are attached, form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

or $Y^1$ and $R^1$, together with the atoms to which they are attached, form a 4-8 membered heterocyclic ring, optionally containing one or more additional heteroatoms selected from O, S, or N; wherein the 4-8 membered heterocyclic ring is optionally substituted;

or $Y^1$ and $R^1$, and $R^1$ and $R^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted;

or $Y^1$, $R^1$, and $R^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted; and wherein the silicon based conjugate is substantially stable in aqueous solution having a pH of between 7 and 7.5 and hydrolytically cleaves in aqueous solution having a pH less than 7 or greater than 7.5 to release the payload moiety or payload cassette from the conjugate.

For example, a contemplated silicon based conjugate disclosed herein may be represented by the formula:

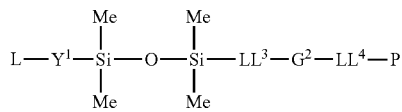

wherein $G^2$ is a heteroaryl.

Figure 25:
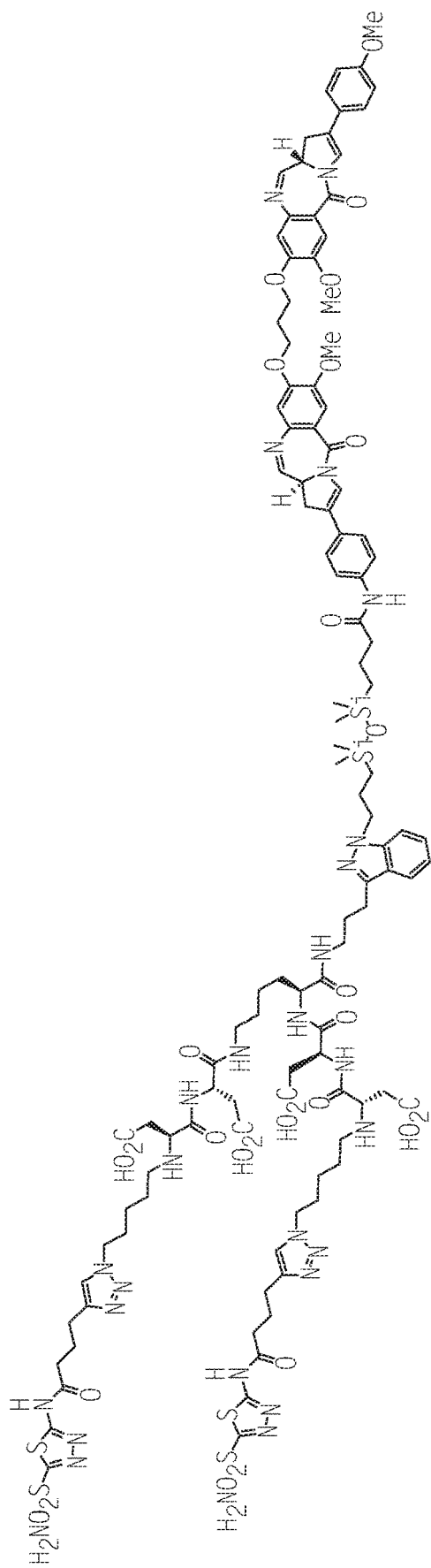
FIG. 25 shows contemplated pyrrolobenzodiazepine (PDB) payload moieties modified with silicon-containing spacers.
Figure 25:
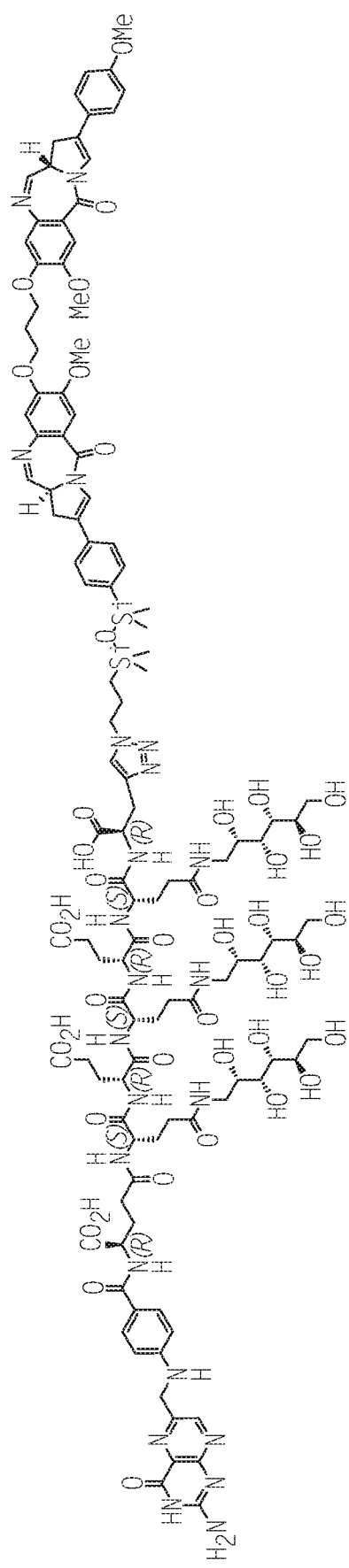

FIG. 25 shows a contemplated silicon based conjugate in which the silicon-heteroatom core is, for example, a siloxane (e.g., —Si—O—Si—).

Figure 26:
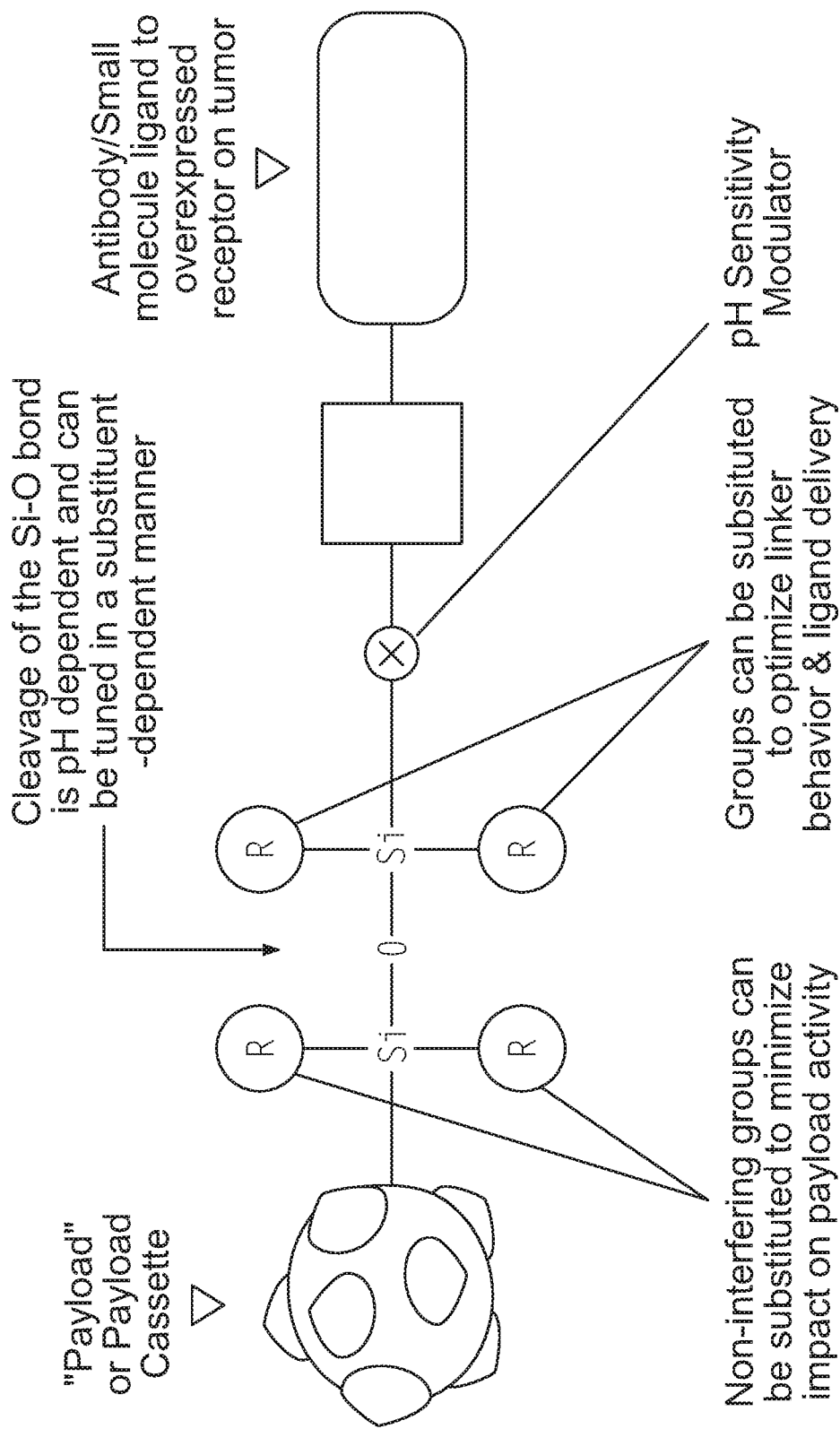
FIG. 26 shows a contemplated silicon based conjugate in which the silicon-heteroatom core is a siloxane (e.g., —Si—O—Si—).
Figure 27:
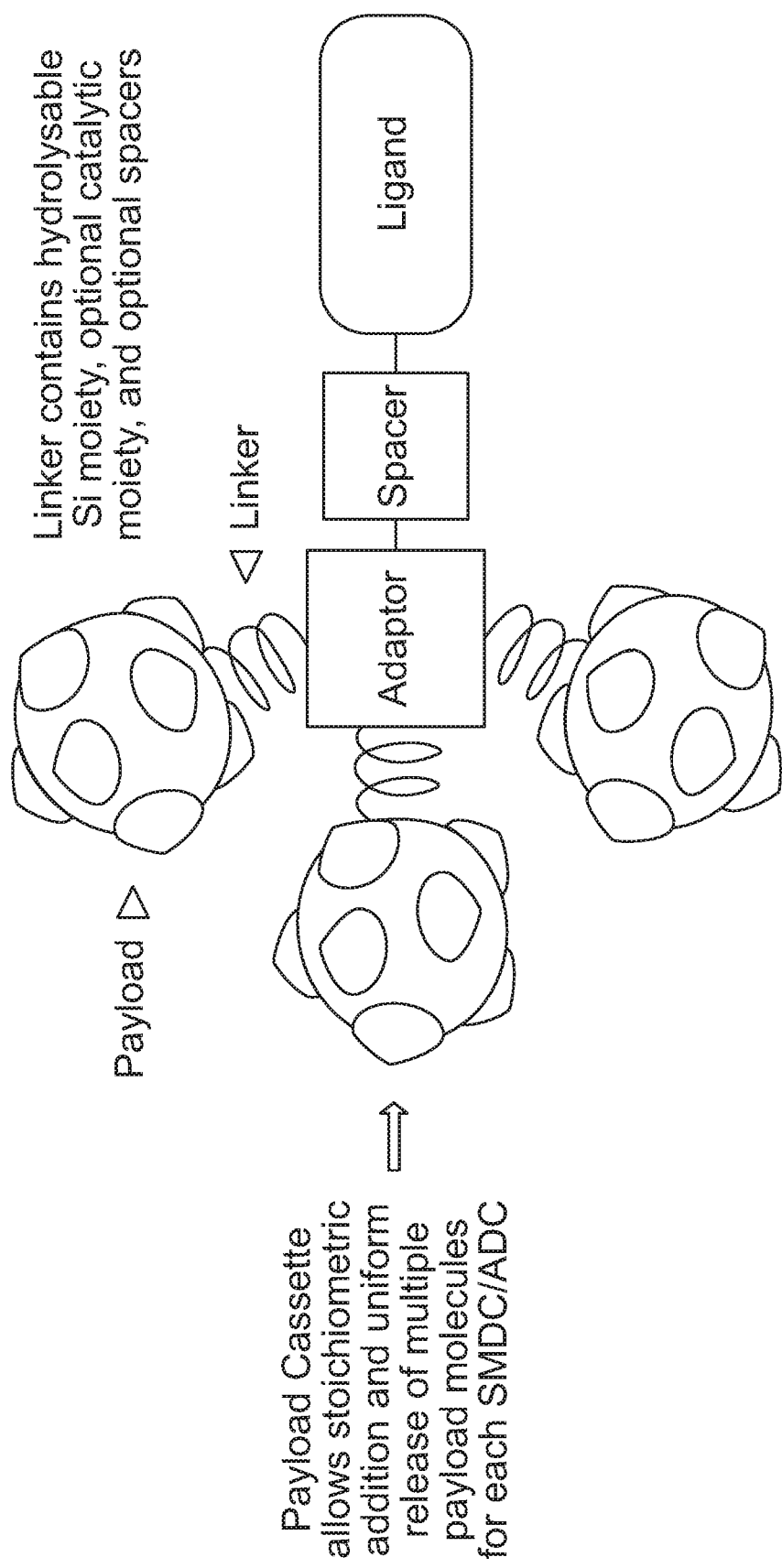
FIG. 27 shows a contemplated silicon based conjugate having multiple payload moieties in a payload cassette construct.

Also provided herein is a silicon based conjugate capable of delivering and/or releasing multiple payload moieties, or for example a payload cassette, to a target cell or tissue. For example, the payload may be a payload cassette. For example, a disclosed payload cassette may allow stoichiometric addition and uniform release of multiple payload moieties for each silicon based conjugate. In some embodiments, a payload cassette may include a branched or linear adaptor moiety having multiple points of attachment to which multiple payload moieties are directly or indirectly covalently bound. FIG. 26 shows a contemplated silicon based conjugate having, for example, multiple payload moieties in a payload cassette construct.

For example, provided herein is a silicon based conjugate having the formula:

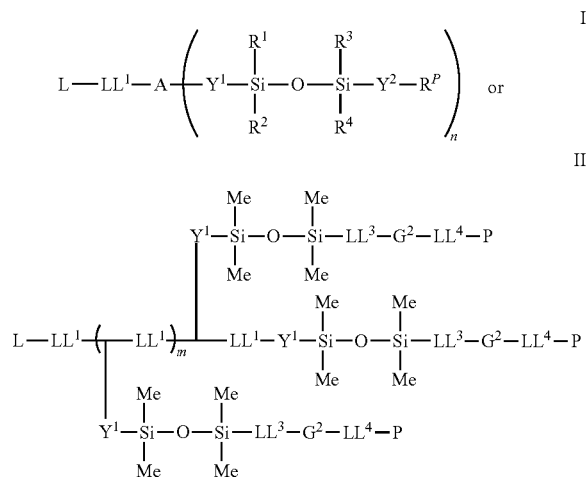

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;

A is an adaptor moiety selected from the group consisting of a carbon atom, a nitrogen atom, $C_{3-6}$cycloalkyl, $C_{3-6}$cycloalkenyl, phenyl, aryl, biaryl, heteroaryl, heterobiaryl, and mono or bicyclic heterocyclyl;

P is a payload moiety;

$R^P$ is P, H, or $R^5$;

$Y^1$ is represented by the formula:

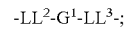

$Y^2$ is represented by the formula:

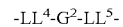

n is an integer from 2 to 15;

m is an integer from 1 to 12;

$G^1$ and $G^2$ are each optional catalytic moieties each independently selected for each occurrence from the group consisting of -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, —C(O)—$C_{0-6}$alkyl-, —C(O)—O—$C_{0-6}$alkyl-, —O—C(O)—$C_{0-6}$alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O— heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, $S(O)_w$-phenyl (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—O—$C_{1-6}$alkyl, —C(O)—$NR^aR^b$, —$NR^a$—C (O)—$C_{1-6}$alkyl, —C(O)—$NR^a$—$SO_2$—$C_{1-6}$alkyl, —$SO_3$H, —$SO_2$—$NR^aR^b$, —$NR^a$—$SO_2$—$C_{1-6}$alkyl, and —$SO_2$—$NR^a$—$C_{1-6}$alkyl;

$LL^2$, $LL^3$, $LL^4$ and $LL^5$ are spacer moieties each independently selected for each occurrence from the group consisting of a bond and $C_{1-20}$alkylene, wherein one, two, three or four methylene units of $C_{1-20}$alkylene are optionally and independently replaced by $C_{3-8}$cycloalkylene, $C_{2-10}$alkenylene $C_{2-10}$alkynylene, aryl, heteroaryl, amino acids, polypeptides, —$NR^{1Y}$—, —$N(R^{1Y})C(O)$—, —$C(O)N(R^{1Y})$—, —O—, —C(O)—, —OC(O)—, —C(O)O—, —S—, —SO—, —$SO_2$—, —C(=S)—, —C(=$NR^{1Y}$)—, —$NR^{1Y}$—$C_{1-15}$alkyl-$NR^{1Y}$—C(O)—; —($CH_2$—$CH_2$—O)$_s$—, —(O—$CH_2$—$CH_2$)$_s$—, —$NR^{1Y}$—($CH_2$—$CH_2$—O)$_s$—$C_{1-6}$alkyl-$NR^{1Y}$—C(O)—; —(O—$CH_2$—$CH_2$)$_s$—$NR^{1Y}$—C(O)—; —S—$C_{0-6}$alkyl-; —$NR^{1Y}$—$C_{1-6}$alkyl-; —N($C_{1-3}$alkyl)-$C_{1-6}$alkyl-NH—C(O)—; —NH—$C_{1-6}$alkyl-N($C_{1-3}$alkyl)-C(O)—; —$SO_2$—$NR^{1Y}$—$C_{0-6}$alkyl-; —N($R^{1Y}$)$SO_2$—$C_{0-6}$alkyl-; —$SO_2$-heterocyclyl-$C_{0-6}$alkyl-; -heterocyclyl-C(O)—; -heterocyclyl-$C_{0-6}$alkyl-$NR^{1Y}$—C(O)—; —$NR^{1Y}$—$C_{0-6}$alkylene-heterocyclyl-C(O)—; —O—$C_{1-6}$alkylene-C(O)—; —O—$C_{1-15}$alkylene-$NR^{1Y}$—C(O)—; —O—$C_{1-15}$alkylene-C(O)—$NR^{1Y}$—; —O—$C_{1-6}$alkylene-; a natural or unnatural amino acid; a natural or unnatural oligopeptide; a natural or unnatural polypeptide; photocleavable motifs; carbohydrates, and a self-immolating connector; wherein $LL^1$, $LL^2$, $LL^3$, $LL^4$ and $LL^5$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;

s is an integer from 1-15;

$R^1$, $R^2$, $R^3$, $R^4$ are selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —NHC(O)$C_{1-6}$alkyl, —C(O)$NH_2$, —C(O)NH$C_{1-6}$alkyl, —C(O)N($C_{1-6}$alkyl)$_2$, —NHC(O)$CF_3$, —C(O)—$NR^a$—$SO_2$—$C_{1-6}$alkyl, —$SO_3$H, —$SO_2$—$NR^aR^b$, —$NR^a$—$SO_2$— $C_{1-6}$alkyl, and —$SO_2$—$NR^a$—$C_{1-6}$alkyl, amidine, guanidine, urea, sulfonamide, acylsulfonamide, sulfonyl amide, $C_{1-6}$alkyl, heteroaryl, and phenyl;

$R^5$ is selected independently for each occurrence from the group consisting of H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)$NH_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

or any pairwise combination of $Y^1$, $Y^2$, $R^1$, $R^2$, $R^3$, and $R^4$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $R^1$ and $R^2$, together with the silicon to which they are attached, form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

or $Y^1$ and $R^1$, together with the atoms to which they are attached, form a 4-8 membered heterocyclic ring, optionally containing one or more additional heteroatoms selected from O, S, or N; wherein the 4-8 membered heterocyclic ring is optionally substituted;

or $Y^1$ and $R^1$, and $R^1$ and $R^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted;

or $Y^1$, $R^1$, and $R^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted; and wherein the silicon based conjugate is substantially stable in aqueous solution having a pH of between 7 and 7.5 and hydrolytically cleaves in aqueous solution having a pH less than 7 or greater than 7.5 to release the payload moiety from the conjugate.

In certain embodiments, A may be a carbon atom. In certain embodiments, n may be 3. In certain embodiments, A may be phenyl. In certain embodiments, n may be 4-15.

For example, a disclosed silicon based conjugate may be branched or linear and may be represented by the formula:

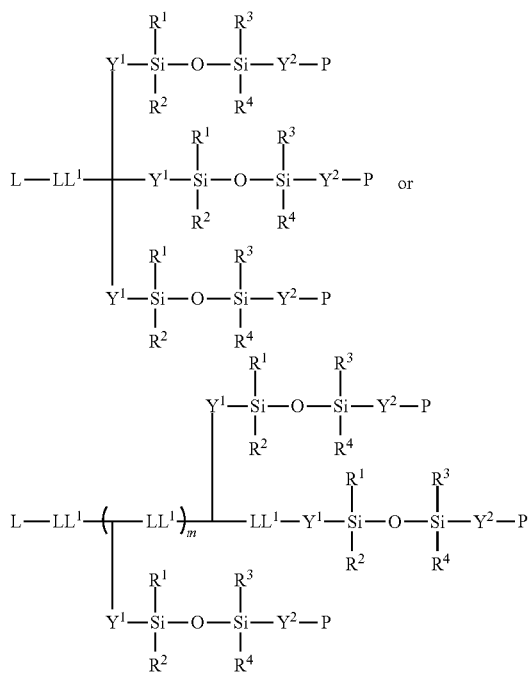

wherein m is an integer from 1 to 12.

For example, a disclosed silicon based conjugate may be represented by the formula:

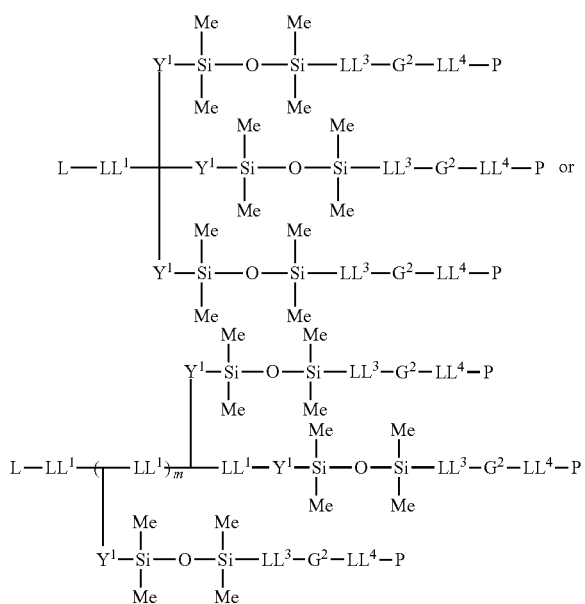

wherein $G^2$ is a heteroaryl and m is an integer from 1 to 12.

In an embodiment, a disclosed silicon based conjugate may have multiple payloads which may be different. For example, if two or more payload moieties are present on the conjugate, the payload moieties may be different. For example, if three payload moieties are present on the conjugate, the three payload moieties may be different.

In an embodiment, a disclosed silicon based conjugate may have multiple payloads which may be the same. For example, if two or more payload moieties are present on the conjugate, the payload moieties may be the same. For example, if three payload moieties are present on the conjugate, the three payload moieties may be the same.

In an embodiment, payload moieties of a disclosed silicon based conjugate may be selected independently for each occurrence to provide a synthetic lethal drug combination capable of effecting death of a target cell having one or more gene mutations but not of a cell in which the one or more gene mutations are absent. In another embodiment, payload moieties of a disclosed silicon based conjugate may be selected independently for each occurrence to provide a synthetic lethal drug combination capable of effecting death of a diseased target tissue comprised of cells having one or more gene mutations, but not of a tissue comprised of cells in which the one or more gene mutations are absent. Without being limited by theory, use of a disclosed silicon based conjugate in a synthetic lethal approach may be advantageous in cases in which the combination of a mutation and the action of a payload moiety causes lethality, whereas the mutation or the action of a payload moiety alone are non-lethal. For example, synthetic lethality may arise when a combination of mutations in one, two or more genes leads to cell death, whereas a mutation in only one of these genes does not, and by itself is said to be viable. For example, use of a disclosed silicon based conjugate in a synthetic lethal approach to, e.g., cancer therapy may provide a means of developing therapies that reduce off-target effects of chemotherapies and chemopreventative drugs. For example, a disclosed silicon based conjugate that target synthetic lethal partners of mutations in, e.g., cancer cells, may not be toxic to normal cells, which may avoid off-target side effects of chemotherapeutics. For example, one or more mutations may be associated with a cancer selected from the group consisting of, e.g., renal carcinoma (e.g., VHL clear cell renal carcinoma), mutant KRAS cancers, and breast cancer (e.g., triple negative breast cancer).

Also provided herein is a silicon based conjugate having multiple targeting moieties, for example, to increase avidity by increasing the number of targeting moieties for binding to a cell surface receptor. In certain embodiments, a disclosed silicon based conjugate may have, for example, 2 to about 30 targeting moieties. In an embodiment, each targeting moiety may be connected to a spacer or an adaptor via covalent bonds. Exemplary spacers and adaptors to which a therapeutic moiety may be attached include, but are not limited to, peptides, peptoids, PEGs, oligosaccharides, polymers, and oligomers. A spacer or adaptor to a targeting moiety is bound may have configurations such as, for example, oligomeric comb polymer, dendrimer, or dendrimer wedge. In certain embodiments, the multiple targeting moieties may be mixed in different combinations to bind to target the heterogeneity of a tumor cell surface receptors, tumor microenvironment, and/or organ tissues. In some embodiments, the multiple targeting moieties may be combined with endosomal disrupting agents, cell penetrating peptides (CPP), hydrophilic groups, albumin, etc.

In an embodiment, a disclosed silicon based conjugate having multiple targeting moieties may target a cell, tissue and/or organ including, but not limited to, for example, those of the kidney, brain, liver, bone, lung, bladder, intestine, cancer, joint, synovial fluid, macrophages, dendritic cells, Th cells, lymphatic system, eye, thymus, dorsal root ganglion (DRG), and muscular system.

In an embodiment, a disclosed silicon based conjugate may have multiple targeting moieties which may be different. For example, if two or more targeting moieties are present on the conjugate, the targeting moieties may be different. For example, if three targeting moieties are present on the conjugate, the three targeting moieties may be different.

In an embodiment, a disclosed silicon based conjugate may have targeting moieties which may be the same. For example, if two or more targeting moieties are present on the conjugate, the targeting moieties may be the same. For example, if three targeting moieties are present on the conjugate, the three targeting moieties may be the same.

For example, a disclosed silicon based conjugate may be represented by the formula:

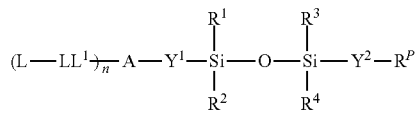

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;

A is an adaptor moiety selected from the group consisting of a carbon atom, a nitrogen atom, $C_{3-6}$cycloalkyl, $C_{3-6}$cycloalkenyl, phenyl, aryl, biaryl, heteroaryl, heterobiaryl, and mono or bicyclic heterocyclyl;

P is a payload moiety;

$R^P$ is P, H, or $R^5$;

$Y^1$ is represented by the formula:

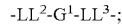

$Y^2$ is represented by the formula:

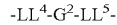

n is an integer from 2 to 15;

$G^1$ and $G^2$ are each optional catalytic moieties each independently selected from the group consisting of a bond, -heteroaryl-, —O-heteroaryl-, —$NR^a$-heteroaryl-, —S(O)$_w$-heteroaryl- (wherein w is 0, 1, or 2), —$NR^a$—SO$_2$-heteroaryl-, —SO$_2$—$NR^a$-heteroaryl-, -phenyl-, —O-phenyl-, —$NR^a$-phenyl-, —S(O)$_w$-phenyl- (wherein w is 0, 1, or 2), —$NR^a$—SO$_2$-phenyl-, —SO$_2$—$NR^a$-phenyl-, —C(O)—$C_{0-6}$alkyl-, —C(O)—O—$C_{0-6}$alkyl-, —O—C(O)—$C_{0-6}$alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —S(O)$_w$-heteroaryl- (wherein w is 0, 1, or 2), —$NR^a$—SO$_2$-heteroaryl-, —SO$_2$—$NR^a$-heteroaryl-, -phenyl-, —O-phenyl-, —$NR^a$-phenyl-, —S(O)$_w$-phenyl- (wherein w is 0, 1, or 2), —$NR^a$—SO$_2$-phenyl-, —SO$_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—O—$C_{1-6}$alkyl, —C(O)—$NR^aR^b$, —$NR^a$—C(O)—$C_{1-6}$alkyl, —C(O)—$NR^a$—SO$_2$—$C_{1-6}$alkyl, —SO$_3$H, —SO$_2$—$NR^aR^b$, —$NR^a$—SO$_2$—$C_{1-6}$alkyl, and —SO$_2$—$NR^a$—$C_{1-6}$alkyl;

$LL^1$, $LL^2$, $LL^3$, $LL^4$ and $LL^5$ are spacer moieties each independently selected for each occurrence from the group consisting of a bond and $C_{1-20}$alkylene, wherein one, two, three or four methylene units of $C_{1-20}$alkylene are optionally and independently replaced by $C_{3-8}$cycloalkylene, $C_{2-10}$alkenylene $C_{2-10}$alkynylene, aryl, heteroaryl, amino acids, polypeptides, —$NR^{1Y}$—, —$N(R^{1Y})$C(O)—, —C(O)$N(R^{1Y})$—, —O—, —C(O)—, —OC(O)—, —C(O)O—, —S—, —SO—, —SO$_2$—, —C(=S)—, —C(=$NR^{1Y}$)—, —$NR^{1Y}$—$C_{1-15}$alkyl-$NR^{1Y}$—C(O)—; —(CH$_2$—CH$_2$—O)$_s$—, —(O—CH$_2$—CH$_2$)$_s$—, —$NR^{1Y}$—(CH$_2$—CH$_2$—O)$_s$—$C_{1-6}$alkyl-$NR^{1Y}$—C(O)—; —(O—CH$_2$—CH$_2$)$_s$—$NR^{1Y}$—C(O)—; —S—$C_{0-6}$alkyl-; —$NR^{1Y}$—$C_{1-6}$ alkyl-; —N($C_{1-3}$alkyl)-$C_{1-6}$alkyl-NH—C(O)—; —NH—$C_{1-6}$alkyl-N($C_{1-3}$alkyl)-C(O)—; —SO$_2$—$NR^{1Y}$—$C_{0-6}$alkyl-; —N($R^{1Y}$)SO$_2$—$C_{0-6}$alkyl-; —SO$_2$-heterocyclyl-$C_{0-6}$alkyl-; -heterocyclyl-C(O)—; -heterocyclyl-$C_m$alkyl-$NR^{1Y}$—C(O)—; —$NR^{1Y}$—$C_{0-6}$alkylene-heterocyclyl-C(O)—; —O—$C_{1-6}$alkylene-C(O)—; —O—$C_{1-15}$alkylene-$NR^{1Y}$—C(O)—; —O—$C_{1-15}$alkylene-C(O)—$NR^{1Y}$—; —O—$C_{1-6}$alkylene-; a natural or unnatural amino acid; a natural or unnatural oligopeptide; a natural or unnatural polypeptide; photocleavable motifs; carbohydrates, and a self-immolating connector; wherein $LL^1$, $LL^2$, $LL^3$, $LL^4$ and $LL^5$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;

s is an integer from 1-15;

$R^1$, $R^2$, $R^3$, $R^4$ are selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$alkyl, —O—C(O)—$C_{1-6}$alkyl, —NHC(O)$C_{1-6}$alkyl, —C(O)NH$_2$, —C(O)NH$C_{1-6}$alkyl, —C(O)N($C_{1-6}$alkyl)$_2$, —NHC(O)CF$_3$, —C(O)—$NR^a$—SO$_2$—$C_{1-6}$alkyl, —SO$_3$H, —SO$_2$—$NR^aR^b$, —$NR^a$—SO$_2$—$C_{1-6}$alkyl, and —SO$_2$—$NR^a$—$C_{1-6}$alkyl, amidine, guanidine, urea, sulfonamide, acylsulfonamide, sulfonyl amide, $C_{1-6}$alkyl, heteroaryl, and phenyl;

$R^5$ is selected independently for each occurrence from the group consisting of H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)NH$_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

or any pairwise combination of $Y^1$, $Y^2$, $R^1$, $R^2$, $R^3$, and $R^4$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $R^1$ and $R^2$, together with the silicon to which they are attached, form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

or $Y^1$ and $R^1$, together with the atoms to which they are attached, form a 4-8 membered heterocyclic ring, optionally containing one or more additional heteroatoms selected from O, S, or N; wherein the 4-8 membered heterocyclic ring is optionally substituted;

or $Y^1$ and $R^1$, and $R^1$ and $R^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted;

or $Y^1$, $R^1$, and $R^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted; and wherein the silicon based conjugate is substantially stable in aqueous solution having a pH of between 7 and 7.5 and is hydrolytically cleaves in aqueous solution having a pH less than 7 or greater than 7.5 to release the payload moiety from the conjugate.

In certain embodiments, A may be a carbon atom. In certain embodiments, n may be 3. In certain embodiments, A may be phenyl. In certain embodiments, n may be 4-15.

For example, a disclosed silicon based conjugate may be represented by the formula:

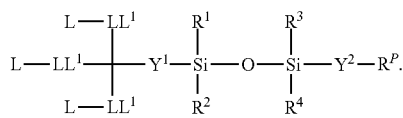

For example, a disclosed silicon based conjugate may be represented by the formula:

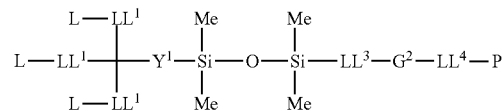

wherein $G^2$ is a heteroaryl.

In an embodiment, a disclosed silicon based conjugate may be represented by the formula:

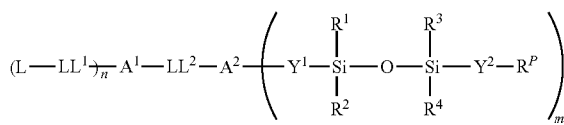

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;

$A^1$ and $A^2$ are each adaptor moieties each independently selected from the group consisting of a carbon atom, a nitrogen atom, $C_{3-6}$cycloalkyl, $C_{3-6}$cycloalkenyl, phenyl, aryl, biaryl, heteroaryl, heterobiaryl, and mono or bicyclic heterocyclyl;

P is a payload moiety;

$R^P$ is P, H, or $R^5$;

$Y^1$ is represented by the formula:

$LL^2$-$G^1$-$LL^3$-;

$Y^2$ is represented by the formula:

-$LL^4$-$G^2$-$LL^5$- n is an integer from 2 to 15;

m is an integer from 2 to 15;

$G^1$ and $G^2$ are each optional catalytic moieties each independently selected for each occurrence from the group consisting of a bond, -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, —O—C(O)—$C_{0-6}$ alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkoxy, —COOH, —C(O)—$NR^aR^b$, —$NR^a$—C(O)—$C_{1-6}$alkyl, —C(O)—$NR^a$—$SO_2$—$C_{1-6}$alkyl, —$SO_3H$, —$SO_2$—$NR^aR^b$, —$NR^a$—$SO_2$— $C_{1-6}$alkyl, and —$SO_2$—$NR^a$—$C_{1-6}$alkyl;

$LL^1$, $LL^2$, $LL^3$, $LL^4$ and $LL^5$ are spacer moieties each independently selected for each occurrence from the group consisting of a bond and $C_{1-20}$alkylene, wherein one, two, three or four methylene units of $C_{1-20}$alkylene are optionally and independently replaced by $C_{3-8}$cycloalkylene, $C_{2-10}$alkenylene $C_{2-10}$alkynylene, aryl, heteroaryl, amino acids, polypeptides, —N($R^{1Y}$)C(O)—, —C(O)N($R^{1Y}$)—, —O—, —C(O)—, —OC(O)—, —C(O)O—, —S—, —SO—, —SO$_2$—, —C(=S)—, —C(=N$R^{1Y}$)—, —N$R^{1Y}$—C$_{1-15}$alkyl-N$R^{1Y}$—C(O)—; —(CH$_2$—CH$_2$—O)$_s$—, —(O—CH$_2$—CH$_2$)$_s$—, —N$R^{1Y}$—(CH$_2$—CH$_2$—O)$_s$—C$_{1-6}$alkyl-N$R^{1Y}$—C(O)—; —(O—CH$_2$—CH$_2$)$_s$—N$R^{1Y}$—C(O)—; —N$R^{1Y}$—C$_{1-6}$alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—N$R^{1Y}$—C$_{0-6}$alkyl-; —N($R^{1Y}$)SO$_2$—C$_{0-6}$alkyl-; —SO$_2$-heterocyclyl-C$_{0-6}$alkyl-; -heterocyclyl-C(O)—; -heterocyclyl-C$_{0-6}$alkyl-N$R^{1Y}$—C(O)—; —N$R^{1Y}$—C$_{0-6}$alkylene-heterocyclyl-C(O)—; —O—C$_{1-6}$alkylene-C(O)—; —O—C$_{1-15}$alkylene-N$R^{1Y}$—C(O)—; —O—C$_{1-15}$alkylene-C(O)—N$R^{1Y}$—; —O—C$_{1-6}$alkylene-; a natural or unnatural amino acid; a natural or unnatural oligopeptide; a natural or unnatural polypeptide; photocleavable motifs; carbohydrates, and a self-immolating connector; wherein $LL^1$, $LL^2$, $LL^3$, $LL^4$ and $LL^5$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;

s is an integer from 1-15;

$R^1$, $R^2$, $R^3$, $R^4$ are selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-N$R^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH(C$_{1-6}$alkyl), —N(C$_{1-6}$alkyl)$_2$, oxo, —COOH, —C(O)O—C$_{1-6}$alkyl, —O—C(O)—C$_{1-6}$alkyl, —NHC(O)C$_{1-6}$alkyl, —C(O)NH$_2$, —C(O)NHC$_{1-6}$alkyl, —C(O)N(C$_{1-6}$alkyl)$_2$, —NHC(O)CF$_3$, —C(O)—N$R^a$—SO$_2$—C$_{1-6}$alkyl, —SO$_3$H, —SO$_2$—N$R^aR^b$, —N$R^a$—SO$_2$—C$_{1-6}$alkyl, and —SO$_2$—N$R^a$—C$_{1-6}$alkyl, amidine, guanidine, urea, sulfonamide, acylsulfonamide, sulfonyl amide, C$_{1-6}$alkyl, heteroaryl, and phenyl;

$R^5$ is selected independently for each occurrence from the group consisting of H, —OH, $OR^a$, $C_{1-6}$alkyl, —O—C$_{1-6}$alkyl, $C_{2-6}$alkenyl, $C_{2-6}$alkynyl, $C_{3-6}$cycloalkyl, —C$_{1-6}$alkyl-N$R^aR^b$, α- or β-amino acid, heterocyclyl, phenyl, naphthalene, and heteroaryl; wherein C$_{1-6}$alkyl, C$_{2-6}$alkenyl, C$_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH(C$_{1-6}$alkyl), —N(C$_{1-6}$alkyl)$_2$, oxo, —COOH, —C(O)O—C$_{1-6}$, —C(O)NH$_2$, —C(O)NHC$_{1-6}$alkyl, —C(O)N(C$_{1-6}$alkyl)$_2$, amidine, guanidine, urea, sulfonamide, acylsulfonamide, sulfonyl amide, C$_{1-6}$alkyl, heteroaryl, and phenyl;

or any pairwise combination of $Y^1$, $Y^2$, $R^1$, $R^2$, $R^3$, and $R^4$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $R^1$ and $R^2$, together with the silicon to which they are attached, form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

or $Y^1$ and $R^1$, together with the atoms to which they are attached, form a 4-8 membered heterocyclic ring, optionally containing one or more additional heteroatoms selected from O, S, or N; wherein the 4-8 membered heterocyclic ring is optionally substituted;

or $Y^1$ and $R^1$, and $R^1$ and $R^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted;

or $Y^1$, $R^1$, and $R^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted; and wherein the silicon based conjugate is substantially stable in aqueous solution having a pH of between 7 and 7.5 and is hydrolytically cleaves in aqueous solution having a pH less than 7 or greater than 7.5 to release the payload moiety from the conjugate.

In certain embodiments, $A^1$ and $A^2$ each may be a carbon atom. In certain embodiments, m and n each may be 3.

For example, a disclosed silicon based conjugate may be represented by the formula:

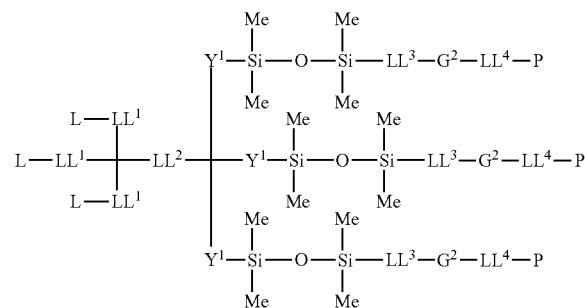

wherein $G^2$ is a heteroaryl.

In certain embodiments, a disclosed silicon based conjugate may be assembled through synthetic transformations well known to one skilled in the art. For example, a payload moiety may be attached to a divalent spacer moiety, and/or a targeting moiety may be attached to a divalent spacer moiety, synthetic transformations well known to one skilled in the art of organic synthesis. Exemplary transformations may include, but are not limited to, amide bond formation, conjugate addition of a nucleophile onto a succinimide or maleimide, "click" type reaction (i.e., an azide-alkyne cycloaddition, Huisgen cycloaddition), aldehyde/ketone condensation, oximes (aldoxime, ketoxime), imine (aldimine, ketimine, sulfinyl imine), hydrazone (acyl hydrazone, carboxyl hydrazone, semi-carbazone), ketal/acetal, orthoester, reductive amination, pyrazole formation (1,3-dicarbonyl+ hydrazine), Pictet-Spengler (hydrazino & hydroxyl/alkoxyamino), strain-promoted alkyne-nitrone cycloaddition, photoinduced tetrazole-alkene cycloaddition, Staudinger ligation, Diels-Alder, Michael addition (thiol+α,β-unsaturated carbonyl), Caddick Michael addition/elimination (thiol+α,β-unsaturated bromo-carbonyl), amide, carbamate, acylsulfonamide, sulfonylamide, thiourea, urea, metal-catalyzed coupling reactions (Pd, Rh, Ru, Re, Cu, Mn, Fe, etc.), or additions to squaric acid ester amides. In an embodiment, a silicon based conjugate is provided that is represented by formula A or B:

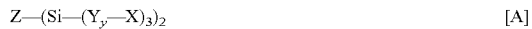

wherein
- y, for each occurrence of Y, is 0 or 1;
- q is 0, 1, 2, 3, or 4;
- t is (4-q);
- Z is an optionally substituted heteroatom;
- Y is a divalent spacer moiety; which may optionally include a catalytic moiety G;
- X is independently selected for each occurrence from P, a payload moiety; L, a targeting moiety, and R, such that at least one P and one L is present;
- R, for each occurrence, may the same or different and is a non-interfering moiety; and
- G is an optional catalytic moiety selected from the group consisting of -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl-(wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkyl, C$_{1-6}$alkoxy, —COOH, —C(O)—O—C$_{1-6}$alkyl, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl.

In an embodiment, a silicon based conjugate is provided that is an acid- or base-cleavable silylether conjugate having the formula:

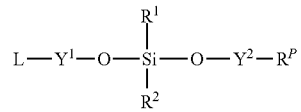

and pharmaceutically acceptable salts, cocrystals, stereoisomers, metabolites, tautomers, solvates, and hydrates thereof, wherein:
- L is a targeting moiety that permits selective accumulation of the conjugate within a target cell or tissue;
- P is a payload moiety or payload cassette;
- R$^P$ is H, P, or R$^3$;
- Y$^1$ is represented by the formula:

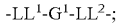

- Y$^2$ is represented by the formula:

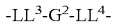

- G$^1$ and G$^2$ are each optional catalytic moieties each independently selected from the group consisting of -heteroaryl-, —O-heteroaryl-, —NR$^a$-heteroaryl-, —S(O)$_w$-heteroaryl-(wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl-(wherein w is 0, 1, or 2), —NR$^a$—SO$_2$-phenyl-, —SO$_2$—NR$^a$-phenyl-, —C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$— heteroaryl-, —S(O)$_w$-heteroaryl-(wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkyl, C$_{1-6}$alkoxy, —COOH, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl;
- LL$^1$, LL$^2$, LL$^3$ and LL$^4$ are spacer moieties each independently selected from the group consisting of a bond, and C$_{1-20}$alkylene, wherein one, two, three or four methylene units of C$_{1-20}$alkylene are optionally and independently replaced by C$_{3-8}$cycloalkylene, C$_{2-10}$alkenylene C$_{2-10}$alkynylene, aryl, heteroaryl, amino acids, polypeptides, —NR$^{1Y}$—, —N(R$^{1Y}$)C(O)—, —C(O)N(R$^{1Y}$)—, —O—, —C(O)—, —OC(O)—, —C(O)O—, —S—, —SO—, —SO$_2$—, —C(=S)—, —C(=NR$^{1Y}$)—, —NR$^{1Y}$—C$_{1-15}$alkyl-NR$^{1Y}$—C(O)—; —(CH$_2$—CH$_2$—O)$_s$—, —(O—CH$_2$—CH$_2$)$_s$—, —NR$^{1Y}$—(CH$_2$—CH$_2$—O)$_s$—C$_{1-6}$alkyl-NR$^{1Y}$—C(O)—; —(O—CH$_2$—CH$_2$)$_s$—NR$^{1Y}$—C(O)—; —NR$^{1Y}$—C$_{1-6}$ alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—NR$^{1Y}$—C$_{0-6}$alkyl-; —N(R$^{1Y}$)SO$_2$—C$_{0-6}$alkyl-; —SO$_2$-heterocyclyl-C$_{0-6}$alkyl-; -heterocyclyl-C(O)—; -heterocyclyl-C$_{0-6}$alkyl-NR$^{1Y}$—C(O)—; —NR$^{1Y}$—C$_{0-6}$alkylene-heterocyclyl-C(O)—; —O—C$_{1-6}$alkylene-C(O)—; —O—C$_{1-15}$alkylene-NR$^{1Y}$—C(O)—; —O—C$_{1-15}$alkylene-C(O)—NR$^{1Y}$—; —O—C$_{1-6}$alkylene-; a natural or unnatural amino acid; a natural or unnatural oligopeptide; a natural or unnatural polypeptide; photocleavable motifs; carbohydrates, and a self-immolating connector; wherein LL$^1$, LL$^2$, LL$^3$ and LL$^4$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide; and s is an integer from 1-15;

$R^1$ and $R^2$ are selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$ alkenyl, $C_{2-6}$ alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)NH$_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

$R^3$ is selected independently for each occurrence from the group consisting of H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)NH$_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

or any pairwise combination of $Y^1$, $Y^2$, $R^1$, and $R^2$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $R^1$ and $R^2$, together with the silicon to which they are attached, form a 4-8 membered heterocyclic ring, optionally containing one or more additional heteroatoms selected from O, S, or N; wherein the 4-8 membered heterocyclic ring is optionally substituted;

or any two or more substituents covalently bonded to the Si may together optionally form a 4-8 membered heterocyclic ring, optionally containing one or more additional heteroatoms selected from O, S, or N; wherein the 4-8 membered heterocyclic ring is optionally substituted; provided that all attached P can be released from the conjugate under conditions suitable for selective release into a targeted cell or tissue;

or $Y^1$ and $R^1$, or $Y^1$ and $R^2$, together with the atoms to which they are attached, form a 4-8 membered heterocyclic ring, optionally containing one or more additional heteroatoms selected from O, S, or N; wherein the 4-8 membered heterocyclic ring is optionally substituted;

or $Y^1$ and $R^1$, and $R^1$ and $R^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted;

or $Y^1$, $R^1$, and $R^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

$R^a$ and $R^b$ are independently selected, for each occurrence, from the group consisting of hydrogen, $C_{1-6}$alkyl, $C_{2-6}$alkenyl, heteroaryl, and phenyl; wherein $C_{1-6}$alkyl, $C_{2-6}$alkenyl, heteroaryl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted;

wherein the silylether is substantially stable in aqueous solution having a pH of between 7 and 7.5 and hydrolytically cleaves in aqueous solution having a pH less than 7 or greater than 7.5 to release the payload moiety or payload cassette from the conjugate.

For example, provided herein is an acid- or base-cleavable silylether conjugate selected from the group consisting of:

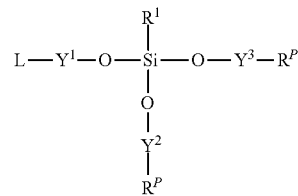

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;

P is a payload moiety or payload cassette;

$R^P$ is P or $R^3$;

$Y^1$ is represented by the formula:

-LL$^1$-G$^1$-LL$^2$-;

$Y^2$ is represented by the formula:

-LL$^3$-G$^2$-LL$^4$-;

$Y^3$ is represented by the formula:

-LL$^5$-G$^3$-LL$^6$-

$G^1$, $G^2$ and $G^3$ are each optional catalytic moieties each independently selected from the group consisting of -heteroaryl-, —O-heteroaryl-, —$NR^a$-heteroaryl-, —S(O)$_w$-heteroaryl-(wherein w is 0, 1, or 2), —$NR^a$—SO$_2$-heteroaryl-, —SO$_2$—$NR^a$-heteroaryl-, -phenyl-, —O-phenyl-, —$NR^a$-phenyl-, —S(O)$_w$-phenyl- (wherein w is 0, 1, or 2), —$NR^a$—SO$_2$-phenyl-, —SO$_2$—$NR^a$-phenyl-, —C(O)—$C_{0-6}$alkyl-, —C(O)—

O—$C_{0-6}$alkyl-, —O—C(O)—$C_{0-6}$alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—O—$C_{1-6}$alkyl, —C(O)—$NR^aR^b$, —$NR^a$—C(O)—$C_{1-6}$alkyl, —C(O)—$NR^a$—$SO_2$—$C_{1-6}$alkyl, —$SO_3H$, —$SO_2$—$NR^aR^b$, —$NR^a$—$SO_2$— $C_{1-6}$alkyl, and —$SO_2$—$NR^a$—$C_{1-6}$alkyl;

$LL^1$, $LL^2$, $LL^3$, $LL^4$, $LL^5$ and $LL^6$ are spacer moieties each independently selected from the group consisting of a bond, and $C_{1-20}$alkylene, wherein one, two, three or four methylene units of $C_{1-20}$alkylene are optionally and independently replaced by $C_{3-8}$cycloalkylene, $C_{2-10}$alkenylene $C_{2-10}$alkynylene, aryl, heteroaryl, amino acids, polypeptides, —$NR^{1Y}$—, —$N(R^{1Y})C(O)$—, —$C(O)N(R^{1Y})$—, —O—, —C(O)—, —OC(O)—, —C(O)O—, —S—, —SO—, —$SO_2$—, —C(=S)—, —C(=$NR^{1Y}$)—, —$NR^{1Y}$—$C_{1-15}$alkyl-$NR^{1Y}$—C(O)—; —$(CH_2$—$CH_2$—O$)_s$—, —(O—$CH_2$—$CH_2)_s$—, —$NR^{1Y}$—$(CH_2$—$CH_2$—O$)_s$—$C_{1-6}$alkyl-$NR^{1Y}$—C(O)—; —(O—$CH_2$—$CH_2)_s$—$NR^{1Y}$—C(O)—; —S—$C_{0-6}$alkyl-; —$NR^{1Y}$—$C_{1-6}$ alkyl-; —N($C_{1-3}$ alkyl)-$C_{1-6}$alkyl-NH—C(O)—; —NH—$C_{1-6}$alkyl-N($C_{1-3}$ alkyl)-C(O)—; —$SO_2$—$NR^{1Y}$—$C_{0-6}$alkyl-; —N($R^{1Y}$)$SO_2$—$C_{0-6}$alkyl-; —$SO_2$-heterocyclyl-$C_{0-6}$alkyl-; -heterocyclyl-C(O)—; -heterocyclyl-$C_m$alkyl-$NR^{1Y}$—C(O)—; —$NR^{1Y}$—$C_{0-6}$alkylene-heterocyclyl-C(O)—; —O—$C_{1-6}$alkylene-C(O)—; —O—$C_{1-15}$alkylene-$NR^{1Y}$—C(O)—; —O—$C_{1-15}$alkylene-C(O)—$NR^{1Y}$—; —O—$C_{1-6}$alkylene-; a natural or unnatural amino acid; a natural or unnatural oligopeptide; a natural or unnatural polypeptide; photocleavable motifs; carbohydrates, and a self-immolating connector; wherein $LL^1$, $LL^2$, $LL^3$, $LL^4$, $LL^5$ and $LL^6$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic; and s is an integer from 1-15;

$R^1$ is selected independently for each occurrence from the group consisting of —$Y^1$-L, —$Y^1$—P, H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$ alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid, and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)$NH_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

or any pairwise combination of $Y^1$, $Y^2$, $Y^3$ and $R^1$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or $Y^1$ and $R^1$, together with the atoms to which they are attached, form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

$R^3$ is selected independently for each occurrence from the group consisting of H, —OH, $OR^a$, $C_{1-6}$alkyl, —O—$C_{1-6}$alkyl, $C_{2-6}$alkenyl, $C_{2-6}$alkynyl, $C_{3-6}$cycloalkyl, —$C_{1-6}$alkyl-$NR^aR^b$, α- or β-amino acid, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, amino acid and heteroaryl are optionally substituted by one or more substituents selected from the group consisting of halogen, cyano, hydroxyl, amino, —NH($C_{1-6}$alkyl), —N($C_{1-6}$alkyl)$_2$, oxo, —COOH, —C(O)O—$C_{1-6}$, —C(O)$NH_2$, —C(O)NH$C_{1-6}$alkyl, —C(O)N($C_{1-6}$alkyl)$_2$, amidine, guanidine, urea, sulfonamide, acylsulfonamide, sulfonyl amide, $C_{1-6}$alkyl, heteroaryl, and phenyl;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted by one or more substituents;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted;

wherein the silylether is substantially stable in aqueous solution having a pH of between 7 and 7.5 and hydrolytically cleaves in aqueous solution having a pH less than 7 or greater than 7.5 to release the payload moiety or payload cassette from the conjugate.

Also provided herein, in an embodiment, is a cleavable silylether conjugate selected from the group consisting of:

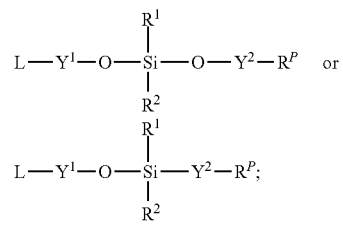

and pharmaceutically acceptable salts, cocrystals, stereoisomers, metabolites, tautomers, solvates, and hydrates thereof, wherein:

L is a targeting moiety that permits selective accumulation of the conjugate within a target cell or tissue;

P is a payload moiety or payload cassette;

$R^P$ is H, P, or $R^3$;

$Y^1$ is represented by the formula:

-$LL^1$-$G^1$-$LL^2$-;

$Y^2$ is represented by the formula:

-$LL^3$-$G^2$-$LL^4$-;

$G^1$ and $G^2$ are each optional catalytic moieties each independently selected from the group consisting of -heteroaryl-, —O-heteroaryl-, —NR$^a$-heteroaryl-, —S(O)$_w$-heteroaryl-(wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl-(wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$-heteroaryl-, —S(O)$_w$-heteroaryl-(wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkyl, C$_{1-6}$alkoxy, —COOH, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$ alkyl;

LL$^1$, LL$^2$, LL$^3$ and LL$^4$ are spacer moieties each independently selected from the group consisting of a bond, and C$_{1-20}$alkylene, wherein one, two, three or four methylene units of C$_{1-20}$alkylene are optionally and independently replaced by C$_{3-8}$cycloalkylene, C$_{2-10}$alkenylene C$_{2-10}$alkynylene, aryl, heteroaryl, amino acids, polypeptides, —NR$^{1Y}$—, —N(R$^{1Y}$)C(O)—, —C(O)N(R$^{1Y}$)—, —O—, —C(O)—, —OC(O)—, —C(O)O—, —S—, —SO—, —SO$_2$—, —C(=S)—, —C(=NR$^{1Y}$)—, —NR$^{1Y}$—C$_{1-15}$alkyl-NR$^{1Y}$—C(O)—; —(CH$_2$—CH$_2$—O)$_s$—, —(O—CH$_2$—CH$_2$)$_s$—, —NR$^{1Y}$—(CH$_2$—CH$_2$—O)$_s$—C$_{1-6}$alkyl-NR$^{1Y}$—C(O)—; —(O—CH$_2$—CH$_2$)$_s$—NR$^{1Y}$—C(O)—; —NR$^{1Y}$—C$_{1-6}$ alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—NR$^{1Y}$—C$_{0-6}$alkyl-; —N(R$^{1Y}$)SO$_2$—C$_{0-6}$alkyl-; —SO$_2$-heterocyclyl-C$_{0-6}$alkyl-; -heterocyclyl-C(O)—; -heterocyclyl-C$_{0-6}$alkyl-NR$^{1Y}$—C(O)—; —NR$^{1Y}$—C$_{0-6}$alkylene-heterocyclyl-C(O)—; —O—C$_{1-6}$alkylene-C(O)—; —O—C$_{1-15}$alkylene-NR$^{1Y}$—C(O)—; —O—C$_{1-15}$alkylene-C(O)—NR$^{1Y}$—; —O—C$_{1-6}$alkylene-; a natural or unnatural amino acid; a natural or unnatural oligopeptide; a natural or unnatural polypeptide; photocleavable motifs; carbohydrates, and a self-immolating connector; wherein LL$^1$, LL$^2$, LL$^3$ and LL$^4$ are optionally substituted;

wherein, independently for each occurrence, R$^{1Y}$ is selected from the group consisting of H, C$_{1-6}$ alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic; and s is an integer from 1-15;

R$^1$ and R$^2$ are selected independently for each occurrence from the group consisting of —Y$^1$-L, Y$^1$—P, H, —OH, OR$^a$, C$_{1-6}$ alkyl, —O—C$_{1-6}$ alkyl, C$_{2-6}$alkenyl, C$_{2-6}$alkynyl, C$_{3-6}$cycloalkyl, —C$_{1-6}$alkyl-NR$^a$R$^b$, α- or β-amino acid, heterocyclyl, phenyl, naphthalene, and heteroaryl; wherein C$_{1-6}$alkyl, C$_{2-6}$alkenyl, C$_{3-6}$cycloalkyl, R$^a$, R$^b$, heterocyclyl, phenyl, naphthalene, amino acid, and heteroaryl are optionally substituted by one or more substituents selected from the group consisting of halogen, cyano, hydroxyl, amino, —NH(C$_{1-6}$alkyl), —N(C$_{1-6}$alkyl)$_2$, oxo, —COOH, —C(O)O—C$_{1-6}$, —C(O)NH$_2$, —C(O)NHC$_{1-6}$alkyl, —C(O)N(C$_{1-6}$alkyl)$_2$, amidine, guanidine, urea, sulfonamide, acylsulfonamide, sulfonyl amide, heteroaryl, and phenyl;

R$^3$ is selected independently for each occurrence from the group consisting of H, —OH, OR$^a$, C$_{1-6}$alkyl, —O—C$_{1-6}$alkyl, C$_{2-6}$alkenyl, C$_{2-6}$alkynyl, C$_{3-6}$cycloalkyl, C$_{1-6}$alkyl NR$^a$R$^b$, α- or β-amino acid, heterocyclyl, phenyl, naphthalene, and heteroaryl; wherein C$_{1-6}$alkyl, C$_{2-6}$alkenyl, C$_{3-6}$cycloalkyl, R$^a$, R$^b$, heterocyclyl, phenyl, naphthalene, amino acid and heteroaryl are optionally substituted by one or more substituents selected from the group consisting of halogen, cyano, hydroxyl, amino, —NH(C$_{1-6}$alkyl), —N(C$_{1-6}$alkyl)$_2$, oxo, —COOH, —C(O)O—C$_{1-6}$, —C(O)NH$_2$, —C(O)NHC$_{1-6}$alkyl, —C(O)N(C$_{1-6}$alkyl)$_2$, amidine, guanidine, urea, sulfonamide, acylsulfonamide, sulfonyl amide, C$_{1-6}$alkyl, heteroaryl, and phenyl;

or any pairwise combination of Y$^1$, Y$^2$, R$^1$, and R$^2$ may, independently, together with the atoms to which they are attached, each form a 4-10 membered heterocyclic ring, optionally containing one or more additional heteroatoms selected from O, S, or N; wherein the 4-10 membered heterocyclic ring is optionally substituted; each ring formed may optionally be fused to another through a single shared atom or single shared bond;

or R$^1$ and R$^2$, together with the silicon to which they are attached, form a 4-8 membered heterocyclic ring, optionally containing one or more additional heteroatoms selected from O, S, or N; wherein the 4-8 membered heterocyclic ring is optionally substituted;

or Y$^1$ and R$^1$, together with the atoms to which they are attached, form a 4-8 membered heterocyclic ring, optionally containing one or more additional heteroatoms selected from O, S, or N; wherein the 4-8 membered heterocyclic ring is optionally substituted;

or Y$^1$ and R$^1$, and R$^1$ and R$^2$, together with the atoms to which they are attached, form a 7-11 membered bicyclic heterocyclic ring, optionally containing one or more additional heteroatoms selected from O, S, or N; wherein the 7-11 membered bicyclic heterocyclic ring is optionally substituted by one or more substituents selected from the group consisting of halogen, cyano, oxo, amino, and hydroxyl;

or Y$^1$, R$^1$, and R$^2$, together with the atoms to which they are attached, form an 11-15 membered tricyclic heterocyclic ring, optionally containing one or more additional heteroatoms selected from O, S, or N; wherein the 11-15 membered tricyclic heterocyclic ring is optionally substituted;

R$^a$ and R$^b$ are independently selected, for each occurrence, from the group consisting of hydrogen, C$_{1-6}$alkyl, C$_{2-6}$alkenyl, and phenyl; wherein C$_{1-6}$alkyl, C$_{2-6}$alkenyl, and phenyl may be optionally substituted;

or R$^a$ and R$^b$, together with the nitrogen to which they are attached, form a 4-7 membered heterocyclic ring, optionally containing an additional heteroatom selected from O, S, or N; wherein the 4-7 membered heterocyclic ring is optionally substituted;

wherein the silylether is substantially stable in aqueous solution having a pH of at least 7 and hydrolytically cleaves in aqueous solution having a pH less than 7 to release the payload moiety or payload cassette from the conjugate.

In certain embodiments, a payload may be capable of binding an intracellular biomolecular target.

Exemplary silicon based conjugates may be selected from the group consisting of:

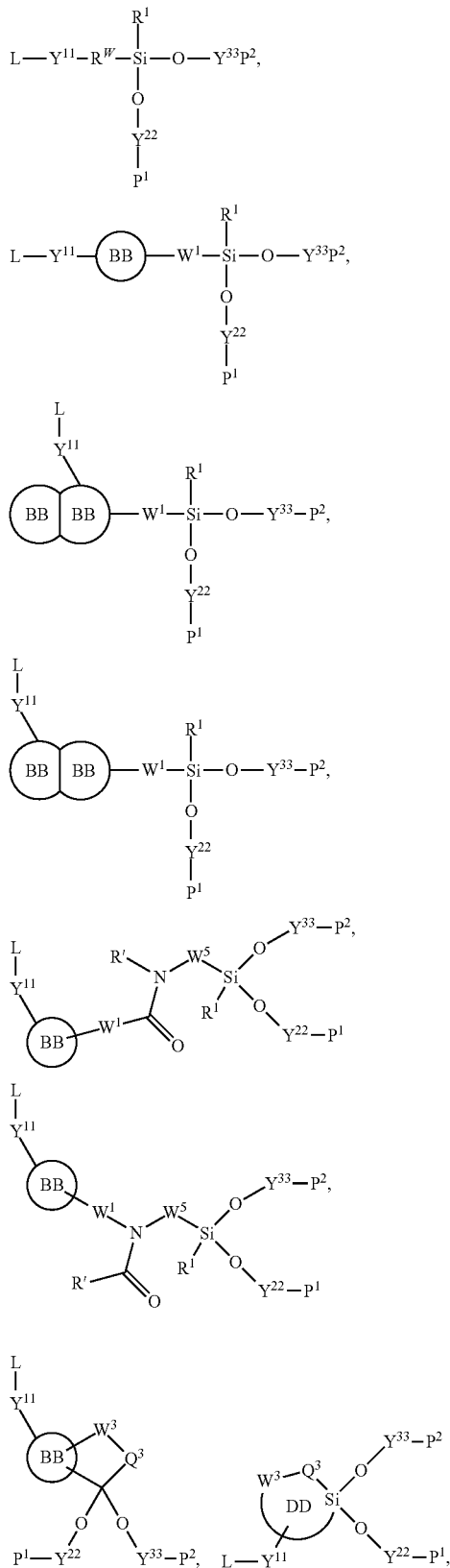

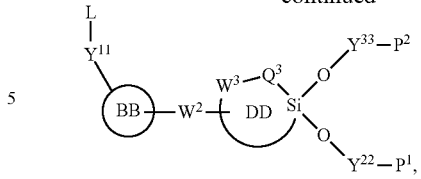

and pharmaceutically acceptable salts, cocrystals, stereoisomers, metabolites, tautomers, solvates, and hydrates thereof, wherein:

L is, for each example, a moiety capable of binding to a cell surface receptor;

$Y^{11}$, $Y^{22}$ and $Y^{33}$ are each independently a bond or spacer;

$P^1$ is a first payload moiety;

$P^2$ is a second payload moiety;

$Y^{11}$, $Y^{22}$ and $Y^{33}$ are each independently selected from the group consisting of a bond, $C_{1-20}$alkylene, wherein one, two, or three or four methylene units of the hydrocarbon chain are optionally and independently replaced by $C_{3-8}$cycloalkylene, $C_{2-10}$alkenylene, $C_{2-10}$alkynylene, amino acids, polypeptides, —N($R^{1Y}$)C(O)—, —C(O)N($R^{1Y}$)—, —O—, —C(O)—, —OC(O)—, —C(O)O—, —SO—, —SO$_2$—, —C(=S)—, —C(=N$R^{1Y}$)—, phenyl, naphthyl, or a mono or bicyclic heterocycle ring; —NR$^{1Y}$—C$_{1-15}$alkyl-NR$^{1Y}$—C(O)—; —(CH$_2$—CH$_2$—O)$_s$—; —(O—CH$_2$—CH$_2$)$_s$—; —NR$^{1Y}$—(CH$_2$—CH$_2$—O)$_s$—C$_{1-6}$alkyl-NR$^{1Y}$—C(O)—; —(O—CH$_2$—CH$_2$)$_s$—NR$^{1Y}$—C(O)—; —S—C$_{0-6}$alkyl-; —NR$^{1Y}$—C$_{1-6}$alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—NR$^{1Y}$—C$_{0-6}$alkyl-; —N(R$^{1Y}$)SO$_2$—C$_{0-6}$alkyl-, —SO$_2$-heterocyclyl-C$_{0-6}$alkyl-; -heterocyclyl-C(O)—; -heterocyclyl-C$_m$alkyl-NR$^{1Y}$—C(O)—; —NR$^{1Y}$—C$_{0-6}$alkylene-heterocyclene-C(O)—; —O—C$_{1-6}$alkylene-C(O)—; —O—C$_{1-15}$alkylene-NR$^{1Y}$—C(O)—; —O—C$_{1-15}$alkylene-C(O)—NR$^{1Y}$—; —O—C$_{1-6}$alkylene-; a natural or unnatural amino acid; a natural or unnatural oligopeptide; a natural or unnatural polypeptide; photocleavable motifs; and a self-immolating connector; wherein $Y^{11}$ and $Y^{22}$ and $Y^{33}$ are optionally substituted;

wherein, independently for each occurrence, $R^{1Y}$ is selected from the group consisting of H, $C_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic; and s is an integer from 1-15;

$R^1$ is selected independently for each occurrence from the group consisting of H, $Y^{11}$—P, $Y^{11}$-L, —OH, $C_{1-6}$alkyl, —O—C$_{1-6}$alkyl, $C_{2-6}$alkenyl, $C_{3-6}$cycloalkyl, —C$_{1-6}$alkyl-NR$^a$R$^b$, heterocyclyl, phenyl, naphthalene, and heteroaryl; wherein $C_{1-6}$alkyl, $C_{2-6}$alkenyl, $C_{3-6}$cycloalkyl, R$^a$, R$^b$, heterocyclyl, phenyl, naphthalene, and heteroaryl, are optionally substituted by one or more substituents selected from the group consisting of halogen, cyano, hydroxyl, amino, $C_{1-6}$alkyl, heteroaryl, and phenyl;

R$^a$ and R$^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted by one or more substituents selected from the group consisting of halogen, cyano, oxo, and hydroxyl; or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted by one or more substituents selected from the group consisting of halogen, cyano, oxo, amino, and hydroxyl;

$R^W$ is selected from the group consisting of a bond, —$C_{1-4}$alkyl-, —O—$C_{1-4}$alkyl-, —$N(R^a)$—$C_{1-4}$alkyl-, —$C_{1-4}$alkyl-C(O)—, —C(O)$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, $R^a$, $R^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—$NR^aR^b$, halogen, cyano, hydroxyl, cycloalkyl, heterocyclic, phenyl, heteroaryl, $R^a$ and $R^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^1$, independently for each occurrence, is selected from the group consisting of a bond, —$C_{1-4}$alkylene-, —O—$C_{1-4}$alkylene-, —$C_{1-4}$alkylene-C(O)—, —C(O)—$C_{1-4}$alkylene-, —$C_{1-4}$alkylene-$N(R^a)$—, —$N(R^a)$—$C_{1-4}$alkylene-, —$C_{1-4}$alkylene-O—C(O)—, —C(O)—O—$C_{1-4}$alkylene-, —$NR^a$—C(O)—, —$C_{2-6}$alkenylene-, —$C_{2-6}$alkynylene-, —$C_{3-6}$cycloalkylene-, -phenylene-, -heteroarylene-, and heterocyclene; wherein $C_{1-4}$alkylene, $C_{2-6}$alkenylene, $C_{2-6}$alkynylene, $C_{3-6}$cycloalkylene, R', phenylene, heterocyclene, and heteroarylene are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^2$, independently for each occurrence, is (a) absent; or (b) selected from the group consisting of —$C_{1-4}$alkylene-, —O—$C_{1-4}$alkylene-, —S—$C_{1-4}$alkylene-, —C(O)—, —C(O)—$C_{1-4}$alkylene-, —N(R')—$C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three, or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—$N(R')_2$, —$N(R')_2$, halogen, hydroxyl, nitro, and cyano;

$W^3$, independently for each occurrence, is selected from the group consisting of —$C_{1-4}$alkylene-, —O—$C_{1-4}$alkylene-, —S—$C_{1-4}$alkylene, —S(O)—, —C(O)—, —C(O)—$C_{1-4}$alkylene-, —N(R')—$C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—$N(R')_2$, —$N(R')_2$, halogen, hydroxyl, nitro, and cyano;

$W^5$ is selected from the group consisting of —$C_{1-4}$alkylene-, —$C_{1-4}$alkylene-N(R')—, —C(O)$C_{1-4}$alkylene-, —C(O)—O—$C_{1-4}$alkylene-, —$C_{2-6}$alkenylene-, —$C_{2-6}$alkynylene-, —$C_{3-6}$cycloalkylene-, -heterocyclene-, -phenylene-, and heteroarylene; wherein $C_{1-4}$alkylene, $C_{2-6}$alkenylene, $C_{2-6}$alkynylene, $C_{3-6}$cycloalkylene, heterocyclene, phenylene, and heteroarylene are optionally substituted by one, two, three or more substituents selected from the group consisting of $C_{1-4}$alkyl, $C_{1-4}$alkoxy, —C(O)$C_{1-4}$alkyl, —C(O)—$N(R')_2$, —$N(R')_2$, halogen, hydroxyl, nitro, and cyano;

wherein $R^W$, $W^1$, $W^2$, $W^3$, $W^5$ and $Y^{11}$, $Y^{22}$ and $Y^{33}$ may optionally contain a catalytic moiety G selected from the group consisting of -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkoxy, —COOH, —C(O)—$NR^aR^b$, —$NR^a$—C(O)—$C_{1-6}$alkyl, —C(O)—$NR^a$—$SO_2$—$C_{1-6}$alkyl, —$SO_3H$, —$SO_2$—$NR^aR^b$, —$NR^a$—$SO_2$—$C_{1-6}$alkyl, and —$SO_2$—$NR^a$—$C_{1-6}$alkyl;

$Q^3$ is independently selected, for each occurrence, from the group consisting of a bond, $R^W$, —N(R')—, —O—, —S—, and

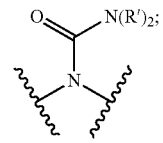

BB, independently for each occurrence, is a 4-8 membered cycloalkyl, heterocyclic, phenyl, naphthyl, or heteroaryl moiety, wherein the cycloalkyl, heterocyclic, phenyl, naphthyl, or heteroaryl moiety is optionally substituted with one, two, three or more groups represented by $R^{BB}$; wherein $R^1$, independently for each occurrence, may be optionally bonded to BB;

DD is a 4-8 membered heterocyclic ring, wherein the heterocyclic ring is optionally substituted with one, two, three or more groups represented by $R^{BB}$;

each $R^{BB}$ is independently selected, for each occurrence, from the group consisting of hydrogen, halogen, nitro, cyano, hydroxyl, amino, thio, oxo, —COOH, —CONHR', substituted or unsubstituted aliphatic, substituted or unsubstituted heteroaliphatic, —$C_{1-4}$alkyl, —O—$C_{1-4}$alkyl, —$N(R^a)$—$C_{1-4}$alkyl, —C(O)$C_{1-4}$alkyl, —C(O)—$NR^aR^b$, —$C_{2-6}$alkenyl, —$C_{2-6}$alkynyl, —$C_{3-6}$cycloalkyl, heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl, phenoxy, heterocyclyl, and heteroaryl are optionally substituted by one, two, three or more substituents selected from the group consisting of C$_{1-4}$alkyl, C$_{1-4}$alkoxy, —C(O)C$_{1-4}$alkyl, —C(O)—NR$^a$R$^b$, halogen, cyano, hydroxyl, cycloalkyl, heterocyclic, phenyl, or heteroaryl; or two R$^{BB}$ together with the atoms to which they are attached form a fused 5- or 6-membered cycloalkyl or heterocyclic bicyclic ring system; and R' is independently selected, for each occurrence, from the group consisting of hydrogen, substituted or unsubstituted aliphatic, and substituted or unsubstituted heteroaliphatic.

In another embodiment, provided herein are drug conjugates represented by:

L-Y$^1$-Q-Y$^2$—P and pharmaceutically acceptable salts, cocrystals, stereoisomers, metabolites, tautomers, solvates, and hydrates thereof, wherein:

L is a moiety capable of binding to a cell surface receptor;
Y$^1$ and Y$^2$ are each independently a bond or spacer;
P is a payload moiety; and
Q is a siloxane comprising:
a first group selected from the group consisting of:

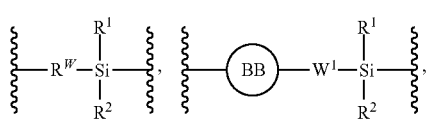

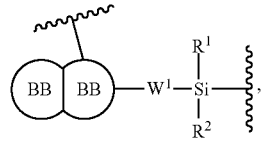

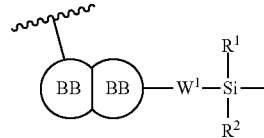

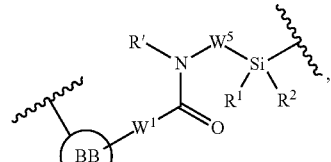

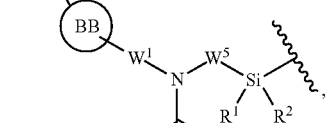

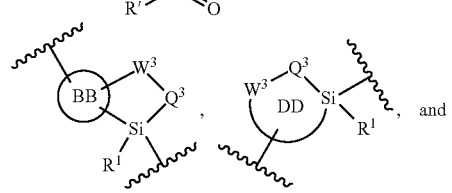

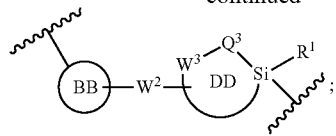

and
a second group selected from the group consisting of:

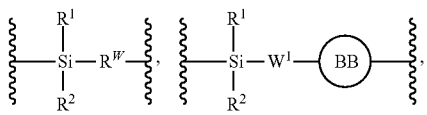

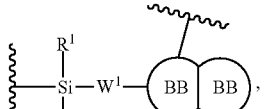

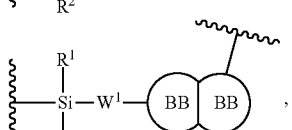

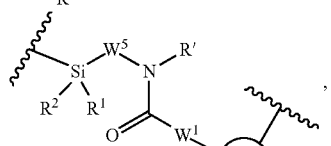

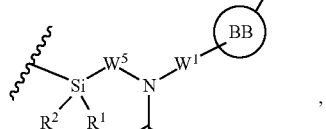

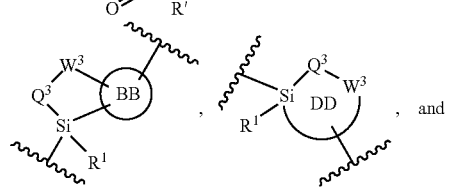

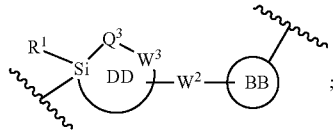

wherein the Si of the first group and the Si of the second group are connected by an oxygen atom;
wherein:
R$^1$ and R$^2$ are selected independently for each occurrence from the group consisting of L, H, P, —OH, C$_{1-6}$alkyl, —O—C$_{1-6}$alkyl, C$_{2-6}$alkenyl, C$_{3-6}$cycloalkyl, —C$_{1-6}$alkyl-NR$^a$R$^b$, heterocyclyl, phenyl, naphthalene, and heteroaryl; wherein C$_{1-6}$alkyl, C$_{2-6}$alkenyl, C$_{3-6}$cycloalkyl, R$^a$, R$^b$, heterocyclyl, phenyl, naphthalene, and heteroaryl, are optionally substituted by one or more substituents selected from the group consisting of halogen, cyano, hydroxyl, amino, C$_{1-6}$alkyl, heteroaryl, and phenyl; or R$^1$ and R², together with the silicon to which they are attached, may form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted by one or more substituents selected from the group consisting of halogen, cyano, oxo, and hydroxyl; or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted by one or more substituents selected from the group consisting of halogen, cyano, oxo, amino, and hydroxyl;

$R^W$ is selected from the group consisting of a bond, —$C_{1-4}$alkyl-, —O—$C_{1-4}$alkyl-, —N($R^a$)—$C_{1-4}$alkyl-, —$C_{1-4}$alkyl-C(O)—, —(O)$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, $R^a$, $R^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—$NR^aR^b$, halogen, cyano, hydroxyl, cycloalkyl, heterocyclic, phenyl, heteroaryl, $R^a$ and $R^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^1$, independently for each occurrence, is selected from the group consisting of a bond, —$C_{1-4}$alkylene-, —O—$C_{1-4}$alkylene-, —$C_{1-4}$alkylene-C(O)—, —C(O)—$C_{1-4}$alkylene-, —$C_{1-4}$alkylene-N($R^a$)—, —N($R^a$)—$C_{1-4}$alkylene-, —$C_{1-4}$alkylene-O—C(O)—, —C(O)—O—$C_{1-4}$alkylene-, —$NR^a$—C(O)—, —$C_{2-6}$alkenylene-, —$C_{2-6}$alkynylene-, —$C_{3-6}$cycloalkylene-, -phenylene-, -heteroarylene-, and heterocyclene; wherein $C_{1-4}$alkylene, $C_{2-6}$alkenylene, $C_{2-6}$alkynylene, $C_{3-6}$cycloalkylene, R', phenylene, heterocyclene, and heteroarylene are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_{1-4}$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^2$, independently for each occurrence, is (a) absent; or (b) selected from the group consisting of —$C_{1-4}$alkylene-, —O—$C_{1-4}$alkylene-, —S—$C_{1-4}$alkylene, —C(O)—, —C(O)—$C_{1-4}$alkylene-, —N(R')—$C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three, or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—N(R')$_2$, —N(R')$_2$, halogen, hydroxyl, nitro, and cyano;

$W^3$, independently for each occurrence, is selected from the group consisting of —$C_{1-4}$alkylene-, —O—$C_{1-4}$alkylene-, —S—$C_{1-4}$alkylene, —S(O)—, —C(O)—, —C(O)—$C_{1-4}$alkylene-, —N(R') $C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three, or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—N(R')$_2$, —N(R')$_2$, halogen, hydroxyl, nitro, and cyano;

$W^5$ is selected from the group consisting of —$C_{1-4}$alkylene-, —$C_{1-4}$alkylene-N(R')—, —C(O)$C_{1-4}$alkylene-, —C(O)—O—$C_{1-4}$alkylene-, —$C_{2-6}$alkenylene-, —$C_{2-6}$alkynylene-, —$C_{3-6}$cycloalkylene-, -heterocyclene-, -phenylene-, and heteroarylene; wherein $C_{1-4}$alkylene, $C_{2-6}$alkenylene, $C_{2-6}$alkynylene, $C_{3-6}$cycloalkylene, heterocyclene, phenylene, and heteroarylene are optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—N(R')$_2$, —N(R')$_2$, halogen, hydroxyl, nitro, and cyano;

wherein $R^W$, $W^1$, $W^2$, $W^3$, $W^5Y^1$ and $Y^2$ may optionally contain a catalytic moiety G selected from the group consisting of -heteroaryl-, —O-heteroaryl-, —$NR^a$-heteroaryl-, —S(O)$_w$-heteroaryl- (wherein w is 0, 1, or 2), —$NR^a$—SO$_2$-heteroaryl-, —SO$_2$—$NR^a$-heteroaryl-, -phenyl-, —O-phenyl-, —$NR^a$-phenyl-, —S(O)$_w$-phenyl- (wherein w is 0, 1, or 2), —$NR^a$—SO$_2$-phenyl-, —SO$_2$—$NR^a$-phenyl-, —C(O)$C_{0-6}$alkyl, —C(O)—O—$C_{0-6}$alkyl-, —O—C(O)—$C_{0-6}$alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —S(O)$_w$-heteroaryl-(wherein w is 0, 1, or 2), —$NR^a$—SO$_2$-heteroaryl-, —SO$_2$—$NR^a$-heteroaryl-, -phenyl-, —O-phenyl-, —$NR^a$-phenyl-, —S(O)$_w$-phenyl- (wherein w is 0, 1, or 2), —$NR^a$—SO$_2$-phenyl-, —SO$_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—O—$C_{1-6}$alkyl, —C(O)—$NR^aR^b$, —$NR^a$—C(O)—$C_{1-6}$alkyl, —C(O)—$NR^a$—SO$_2$—$C_{1-6}$alkyl, —SO$_3$H, —SO$_2$—$NR^aR^b$, —$NR^a$—SO$_2$—$C_{1-6}$alkyl, and —SO$_2$—$NR^a$—$C_{1-6}$ alkyl;

$Q^3$ is independently selected, for each occurrence, from the group consisting of a bond, $R^W$, —N(R')—, —O—, —S—, and

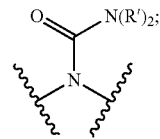

R' is independently selected, for each occurrence, from the group consisting of hydrogen, substituted or unsubstituted aliphatic, and substituted or unsubstituted heteroaliphatic;

BB, independently for each occurrence, is a 4-8 membered cycloalkyl, heterocyclic, phenyl, naphthyl, or heteroaryl moiety, wherein the cycloalkyl, heterocyclic, phenyl, naphthyl, or heteroaryl moiety is optionally substituted with one, two, three or more groups represented by $R^{BB}$; wherein $R^1$, independently for each occurrence, may be optionally bonded to BB; and DD is a 4-8 membered heterocyclic ring, wherein the heterocyclic ring is optionally substituted with one, two, three or more groups represented by $R^{BB}$;

each $R^{BB}$ is independently selected, for each occurrence, from the group consisting of hydrogen, halogen, nitro, cyano, hydroxyl, amino, thio, oxo, —COOH, —CONHR', substituted or unsubstituted aliphatic, substituted or unsubstituted heteroaliphatic, —$C_{1-4}$alkyl, —O—$C_{1-4}$alkyl, —N($R^a$)—$C_{1-4}$ alkyl, —C(O)$C_{1-4}$ alkyl, —C(O)—O—$C_{1-4}$alkyl, —C(O)—$NR^aR^b$, —$C_{2-6}$alkenyl, —$C_{2-6}$alkynyl, —$C_{3-6}$cycloalkyl, heterocyclic, phenyl, phenoxy, heteroaryl, —$C_{1-4}$alkylene-phenyl, —$C_{1-4}$alkylene-heteroaryl, —$C_{1-4}$alkylene-heterocyclyl, —$C_{2-6}$alkenylene-phenyl, —$C_{2-6}$alkenylene-heteroaryl, —$C_{2-6}$alkenylene-heterocyclyl, —$C_{2-6}$alkynyl-phenyl, —$C_{2-6}$alkynyl-heteroaryl, —$C_{2-6}$alkynyl-heterocyclyl; wherein $C_{1-4}$alkyl, $C_{2-6}$alkenyl, $C_{2-6}$alkynyl, $C_{3-6}$cycloalkyl, phenyl, phenoxy, heterocyclyl, and heteroaryl are optionally substituted by one, two, three or more substituents selected from the group consisting of $C_1$ alkyl, $C_{1-4}$alkoxy, —C(O)$C_{1-4}$alkyl, —C(O)—O—$C_{1-4}$alkyl, —C(O)—$NR^aR^b$, halogen, cyano, hydroxyl, cycloalkyl, heterocyclic, phenyl, or heteroaryl; or two $R^{BB}$ together with the atoms to which they are attached form a fused 5- or 6-membered cycloalkyl or heterocyclic bicyclic ring system.

Provided herein, in an embodiment, are drug conjugates represented by:

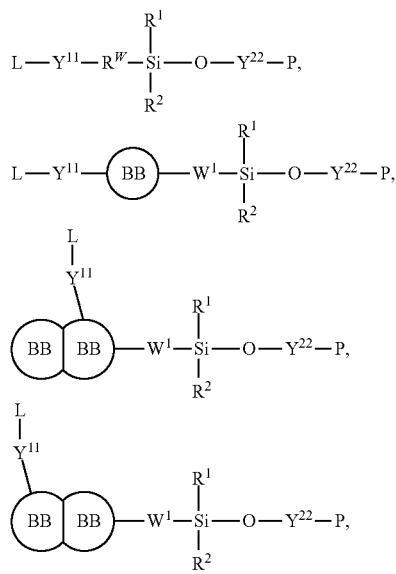

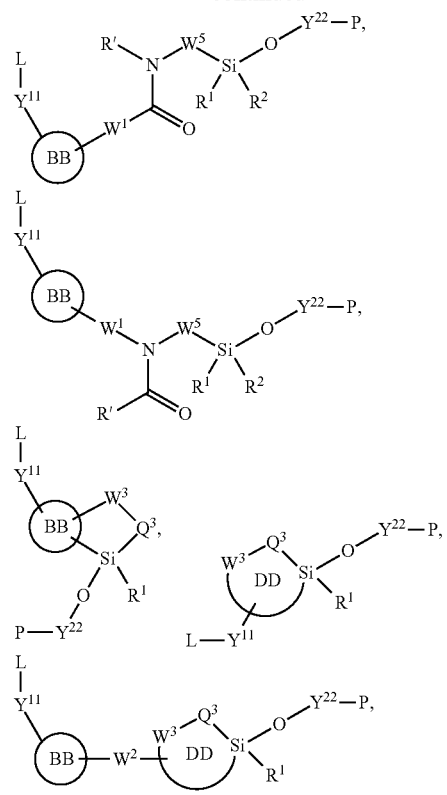

and pharmaceutically acceptable salts, cocrystals, stereoisomers, metabolites, tautomers, solvates, and hydrates thereof, wherein:

L is a moiety capable of binding to a cell surface receptor;
$Y^1$ and $Y^2$ are each independently a bond or spacer;
P is a payload moiety;
$R^1$ and $R^2$ are selected independently for each occurrence from the group consisting of L, P, H, —OH, $C_{1-6}$alkyl, —O—$C_{1-6}$ alkyl, $C_{2-6}$alkenyl, $C_{3-6}$cycloalkyl, —$C_{1-6}$alkyl-$NR^aR_b$, heterocyclyl, phenyl, naphthalene, and heteroaryl; wherein $C_{1-6}$alkyl, $C_{2-6}$alkenyl, $C_{3-6}$cycloalkyl, $R^a$, $R^b$, heterocyclyl, phenyl, naphthalene, and heteroaryl, are optionally substituted by one or more substituents selected from the group consisting of halogen, cyano, hydroxyl, amino, $C_{1-6}$alkyl, heteroaryl, and phenyl; or $R^1$ and $R^2$, together with the silicon to which they are attached, may form a 4-8 membered heterocyclic ring, optionally containing one or more additional heteroatoms selected from O, S, or N; wherein the 4-8 membered heterocyclic ring is optionally substituted by one or more substituents selected from the group consisting of halogen, cyano, oxo, amino, and hydroxyl;

$R^a$ and $R^b$ are independently selected, for each occurrence, from the group consisting of hydrogen, $C_{1-6}$alkyl, $C_{2-6}$alkenyl, and phenyl; wherein $C_{1-6}$alkyl, $C_{2-6}$alkenyl, and phenyl may be optionally substituted by one or more substituents selected from the group consisting of halogen, cyano, oxo, and hydroxyl; or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted by one or more substituents selected from the group consisting of halogen, cyano, oxo, amino, and hydroxyl;

$R^W$ is selected from the group consisting of a bond, —$C_{1-4}$alkyl-, —O—$C_{1-4}$alkyl-, —$C_{1-4}$alkyl-C(O)—, —C(O)$C_{1-4}$alkyl-, —$C_{1-4}$alkyl-O—C(O)—, —C(O)—O—$C_{1-4}$alkyl-, —$NR^a$—C(O)—, —$C_{2-6}$alkenyl-, —$C_{2-6}$alkynyl-, —$C_{3-6}$cycloalkyl-, -phenyl-, -heteroaryl-, and -heterocyclic-; wherein $C_{1-4}$alkyl, $R^a$, $R^b$, $C_{2-6}$alkenyl, $C_{2-6}$alkynyl, $C_{3-6}$cycloalkyl, phenyl and heteroaryl may be optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—$NR^aR^b$, halogen, cyano, hydroxyl, cycloalkyl, heterocyclic, phenyl, heteroaryl, $R^a$ and $R^b$, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^1$, independently for each occurrence, is selected from the group consisting of a bond, —$C_{1-4}$alkylene-, —O—$C_{1-4}$alkylene-, —$C_{1-4}$alkylene-C(O)—, —C(O)—$C_{1-4}$alkylene-, —$C_{1-4}$alkylene-$N(R^a)$—, —$N(R^a)$—$C_{1-4}$alkylene-, —$C_{1-4}$alkylene-O—C(O)—, —C(O)—O—$C_{1-4}$alkylene-, —$NR^a$—C(O)—, —$C_{2-6}$alkenylene-, —$C_{2-6}$alkynylene-, —$C_{3-6}$cycloalkylene-, -phenylene-, -heteroarylene-, and heterocyclene; wherein $C_{1-4}$alkylene, $C_{2-6}$alkenylene, $C_{2-6}$alkynylene, $C_{3-6}$cycloalkylene, R', phenylene, heterocyclene, and heteroarylene are optionally substituted independently, for each occurrence, with one, two, three or more substituents selected from the group consisting of $C_{1-4}$alkyl, $C_{2-6}$alkenyl, $C_{2-6}$alkynyl, $C_{1-4}$alkoxy, —C(O)$C_{1-6}$alkyl, —C(O)—O—$C_1$alkyl, cycloalkyl, heterocyclic, phenyl, heteroaryl, halogen, hydroxyl, nitro sulfoxide, sulfone, sulfonamide and cyano, wherein the cycloalkyl, heterocyclic, phenyl, or heteroaryl moiety is optionally substituted with one, two, three or more substituents selected from halogen, amino, cyano, hydroxyl, $C_{1-6}$alkyl, phenyl, heteroaryl, and amino;

$W^2$, independently for each occurrence, is (a) absent; or (b) selected from the group consisting of —$C_{1-4}$alkylene-, —O—$C_{1-4}$alkylene-, —S—$C_{1-4}$alkylene-, —C(O)—, —C(O)—$C_{1-4}$alkylene-, —N(R')—$C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three, or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—$N(R')_2$, —$N(R')_2$, halogen, hydroxyl, nitro, and cyano;

$W^3$, independently for each occurrence, is selected from the group consisting of —$C_{1-4}$alkylene-, —O—$C_{1-4}$alkylene-, —S—$C_{1-4}$alkylene, —S(O)—, —C(O)—, —C(O)—$C_{1-4}$alkylene-, —N(R')—$C_{1-4}$alkylene-, —C(O)—O—$C_{1-4}$alkylene-, and —$C_{2-6}$alkenylene-; wherein $C_{1-4}$alkylene and $C_{2-6}$alkenylene are optionally substituted, independently for each occurrence, with one, two, three, or more substituents selected from the group consisting of $C_{1-4}$alkyl, $C_{1-4}$alkoxy, —C(O)$C_{1-6}$alkyl, —C(O)—O—$C_{1-4}$alkyl, —C(O)—$N(R')_2$, —$N(R')_2$, halogen, hydroxyl, nitro, and cyano;

$W^5$ is selected from the group consisting of —$C_{1-4}$alkylene-, —$C_{1-4}$alkylene-N(R')—, —C(O)$C_{1-4}$alkylene-, —C(O)—O—$C_{1-4}$alkylene-, —$C_{2-6}$alkenylene-, —$C_{2-6}$alkynylene-, —$C_{3-6}$cycloalkylene-, -heterocyclene-, -phenylene-, and heteroarylene; wherein $C_{1-4}$alkylene, $C_{2-6}$alkenylene, $C_{2-6}$alkynylene, $C_{3-6}$cycloalkylene, heterocyclene, phenylene, and heteroarylene are optionally substituted by one, two, three or more substituents selected from the group consisting of $C_{1-4}$alkyl, $C_{1-4}$alkoxy, —C(O)$C_{1-4}$alkyl, —C(O)—O—$C_{1-4}$alkyl, —C(O)—$N(R')_2$, —$N(R')_2$, halogen, hydroxyl, nitro, and cyano;

wherein $R^W$, $W^1$, $W^2$, $W^3$, $W^5$ and $Y^{22}$ may optionally contain a catalytic moiety G selected from the group consisting of -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, —C(O)—$C_{0-6}$alkyl-, —C(O)—O—$C_{0-6}$alkyl-, —O—C(O)—$C_{0-6}$alkyl-, —$NR^a$—C(O)—$C_{0-6}$alkyl-, —C(O)—$NR^a$—$C_{0-6}$alkyl-, and —$NR^a$—$C_{0-6}$alkyl-; wherein -heteroaryl-, —O-heteroaryl-, —$NR^a$-heteroaryl-, —$S(O)_w$-heteroaryl- (wherein w is 0, 1, or 2), —$NR^a$—$SO_2$-heteroaryl-, —$SO_2$—$NR^a$-heteroaryl-, -phenyl-, —O-phenyl-, —$NR^a$-phenyl-, —$S(O)_w$-phenyl- (wherein w is 0, 1, or 2), —$NR^a$—$SO_2$-phenyl-, —$SO_2$—$NR^a$-phenyl-, may optionally be substituted by one or more substituents selected from the group consisting of halogen, hydroxyl, cyano, $C_{1-6}$alkyl, $C_{1-6}$alkoxy, —COOH, —C(O)—O—$C_{1-6}$alkyl, —C(O)—$NR^aR^b$, —$NR^a$—C(O)—$C_{1-6}$alkyl, —C(O)—$NR^a$—$SO_2$—$C_{1-6}$alkyl, —$SO_3H$, —$SO_2$—$NR^aR^b$, —$NR^a$—$SO_2$—$C_{1-6}$alkyl, and —$SO_2$—$NR^a$—$C_{1-6}$alkyl;

$Q^3$ is independently selected, for each occurrence, from the group consisting of a bond, $R^W$, —N(R')—, —O—, —S—, and

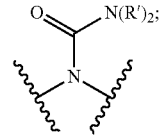

R' is independently selected, for each occurrence, from the group consisting of hydrogen, substituted or unsubstituted aliphatic, and substituted or unsubstituted heteroaliphatic;

BB, independently for each occurrence, is a 4-8 membered cycloalkyl, heterocyclic, phenyl, naphthyl, or heteroaryl moiety, wherein the cycloalkyl, heterocyclic, phenyl, naphthyl, or heteroaryl moiety is optionally substituted with one, two, three or more groups represented by $R^{BB}$; wherein $R^1$, independently for each occurrence, may be optionally bonded to BB; and DD is a 4-8 membered heterocyclic ring, wherein the heterocyclic ring is optionally substituted with one, two, three or more groups represented by $R^{BB}$;

each $R^{BB}$ is independently selected, for each occurrence, from the group consisting of hydrogen, halogen, nitro, cyano, hydroxyl, amino, thio, oxo, —COOH, —CONHR', substituted or unsubstituted aliphatic, substituted or unsubstituted heteroaliphatic, —$C_{1-4}$alkyl, —O—$C_{1-4}$alkyl, —$N(R')$—$C_{1-4}$alkyl, —C(O)$C_{1-4}$alkyl, —C(O)—O—$C_{1-4}$alkyl, —C(O)—$NR^aR^b$, —$C_{2-6}$alkenyl, —$C_{2-6}$alkynyl, —$C_{3-6}$cycloalkyl, heterocyclic, phenyl, phenoxy, heteroaryl, —$C_{1-4}$alkylene-phenyl, —C$_{1-4}$alkylene-heteroaryl, —C$_{1-4}$alkylene-heterocyclyl, —C$_{2-6}$alkenylene-phenyl, —C$_{2-6}$alkenylene-heteroaryl, —C$_{2-6}$alkenylene-heterocyclyl, —C$_{2-6}$alkynyl-phenyl, —C$_{2-6}$alkynyl-heteroaryl, —C$_{2-6}$alkynyl-heterocyclyl; wherein C$_{1-4}$alkyl, C$_{2-6}$alkenyl, C$_{2-6}$alkynyl, C$_{3-6}$cycloalkyl, phenyl, phenoxy, heterocyclyl, and heteroaryl are optionally substituted by one, two, three or more substituents selected from the group consisting of C$_{1-4}$alkyl, C$_{1-4}$alkoxy, —C(O)C$_{1-4}$alkyl, —C(O)—O—C$_{1-4}$alkyl, —C(O)—NR$^a$R$^b$, halogen, cyano, hydroxyl, cycloalkyl, heterocyclic, phenyl, or heteroaryl; or two R$^{BB}$ together with the atoms to which they are attached form a fused 5- or 6-membered cycloalkyl or heterocyclic bicyclic ring system.

Scaffold Based Conjugates

In another embodiment, a pharmaceutically acceptable drug delivery conjugate is provided, comprising a scaffold having a plurality of covalently bonded moieties each selected from the group consisting of:

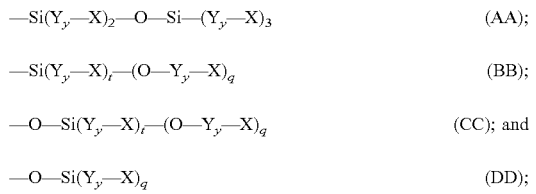

wherein y, for each occurrence of Y, is 0 or 1;

q, for each occurrence, is 0, 1, 2, or 3;

t is (3-q);

Y is a divalent spacer moiety; wherein Y may optionally contain a catalytic moiety G selected from the group consisting of -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$—S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkoxy, —COOH, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl;

X is independently selected for each occurrence from P, a payload moiety or payload cassette; L, a targeting moiety, and R, such that at least one P and one L is present; and R, for each occurrence, may the same or different and is a non-interfering moiety. A scaffold may be any system that provides multiple attachments to each Si moiety (AA), (BB), (CC) or (DD), can be selected for example, from a ring system, a polymer, a dendrimer, a protein, a nanoparticle, and viral capsid. Such a multi targeting-moiety/payload conjugate may facilitate e.g., more than one therapeutic to a patient and/or cellular or molecular target. In some embodiments, one or more of the covalently bound Si moieties and/or payload moieties is cleavable, e.g., acid- or base-cleavable, and/or the conjugate is substantially stable in aqueous solution having a pH of between 7 and 7.5 and/or hydrolytically cleaves in aqueous solution having a pH less than 7 or greater than 7.5 to release one or more of the payload moieties.

Antibody-Drug Conjugates

In an embodiment, a pharmaceutically acceptable drug conjugate is provided, comprising: a biological sequence selected from the group consisting of an antibody, antibody fragment, protein, or polypeptide, at least one therapeutic agent covalently attached to the biological sequence by a connector containing a cleavable Si-heteroatom moiety (e.g., a siloxane or silylether moiety). In some embodiments, the drug conjugate is substantially stable in aqueous solution having a pH between 7 and 7.5 and/or hydrolytically cleaves in aqueous solution having a pH less than 7 or greater than 7.5 at 25° C. or 37° C. to release the therapeutic agent. For instance, in some embodiments, an aqueous solution having a pH of between about 7 and about 7.5 may be selected from the group consisting of serum, plasma, whole blood, or a cytosol. In certain embodiments, an aqueous solution having a pH less than about 7 or greater than about 7.5 may be selected from the group consisting of bile fluids, an endosome, a lysosome, or a tumor or inflammatory microenvironment.

For example, a drug conjugate provided that includes an antibody (e.g., a monoclonal antibody), covalently bonded through a natural or unnatural amino acid to a silylether or siloxane moiety; an optional divalent spacer moiety covalently bound to one or more of a silylether or siloxane moiety; and one or more payload moieties covalently bound to a divalent spacer moiety or to a silylether or siloxane moiety.

For example, provided herein is an antibody drug conjugate represented by:

antibody-[spacer]-([Si-moiety]-[spacer]-payload)$_n$,
 wherein
 n is 1, 2, or more; and
 [Si moiety] is selected from a silylether or siloxane moiety, and is covalently bound to the antibody for each occurrence directly or indirectly from an oxygen or silicon atom on the Si moiety to natural or unnatural amino acid present on the antibody;
 where one or more [spacer] moieties, for each occurrence, may be present or absent. For example, the antibody or antibody fragment may have an amino acid sequence containing one or two non-naturally occurring amino acids. In some embodiments an acid- or base-cleavable connector or spacer is attached to the antibody using a bioorthogonal moiety.

For example, provided here in is a drug -antibody conjugate, represented by:

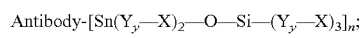

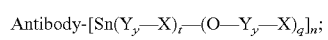

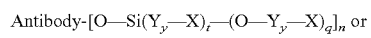

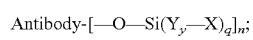

wherein y, for each occurrence of Y, is 0 or 1;

q, for each occurrence, is 0, 1, 2, or 3;

t is (3-q);

n is 1, 2, or more;

Y is the divalent spacer moiety; wherein Y may optionally contain a catalytic moiety G selected from the group consisting of a bond, -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkoxy, —COOH, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl;

X is independently selected for each occurrence from P, a payload moiety; L, a targeting moiety, and R, such that at least one P is present; and R, for each occurrence, may the same or different and is a non-interfering moiety.

Figure 12:
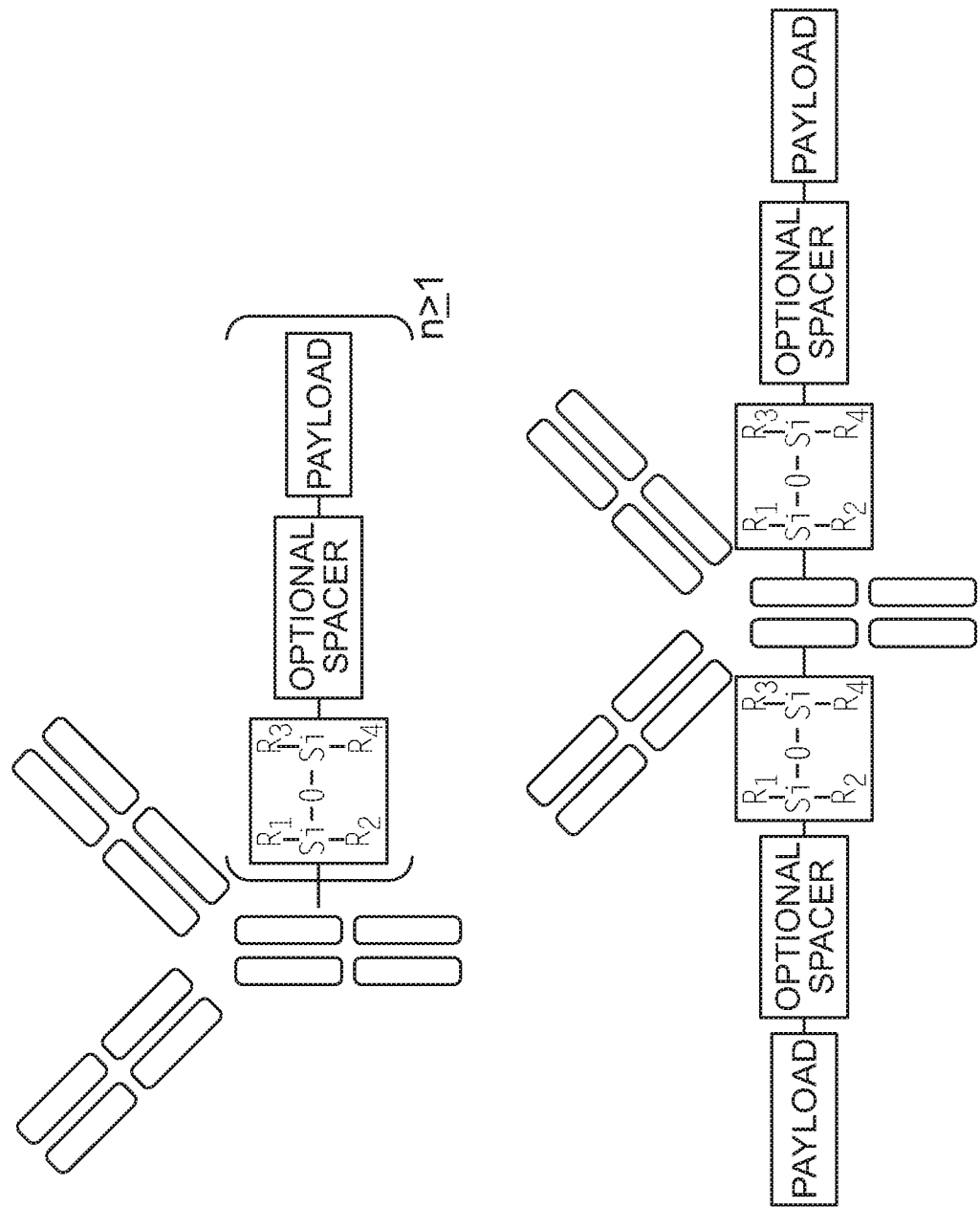
FIGS. 12 and 13 show exemplary silicon based mAb-drug conjugates.

FIG. 12 shows an exemplary and pictorial heterogeneous or homogeneous siloxane mAb-drug conjugate. For example, the siloxane or silylether moiety can be either incorporated via unnatural silanolic-amino acids engineered into the mAb, or attached to naturally occurring amino acids such as lysine, cysteine, or threonine via appropriate linker chemistries (amides, disulfides, esters). Exemplary engineered incorporation of silanol amino acids are exemplified here in an embodiment with n=2 attachments. In some embodiments, a contemplated mAb-drug conjugate will have substantially identical/reproducible numbers of payloads per mAb.

Figure 13:
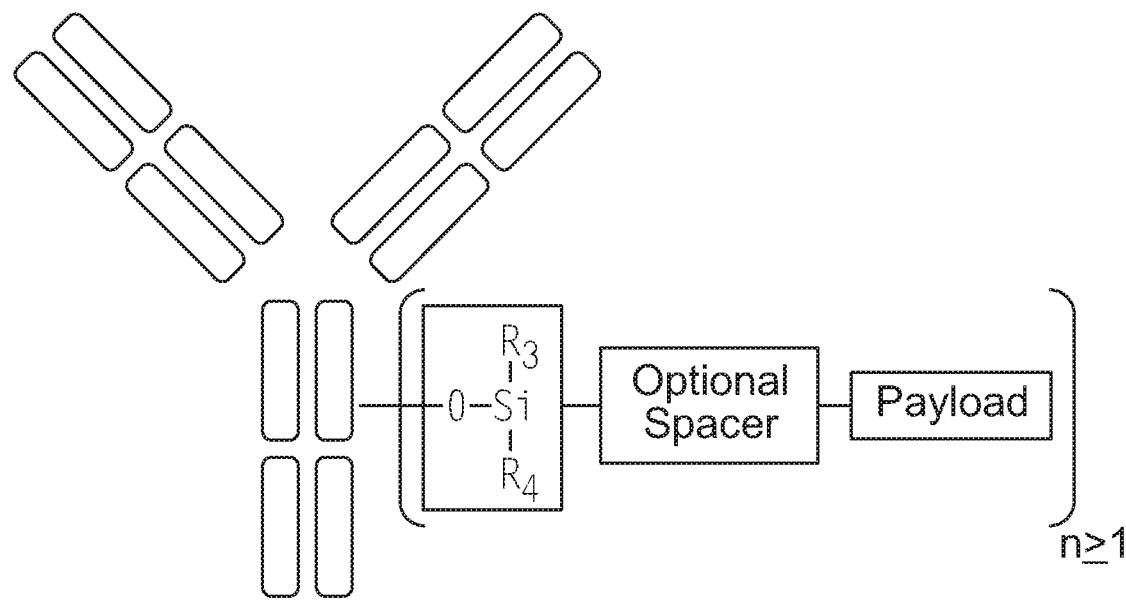
Figure 13:
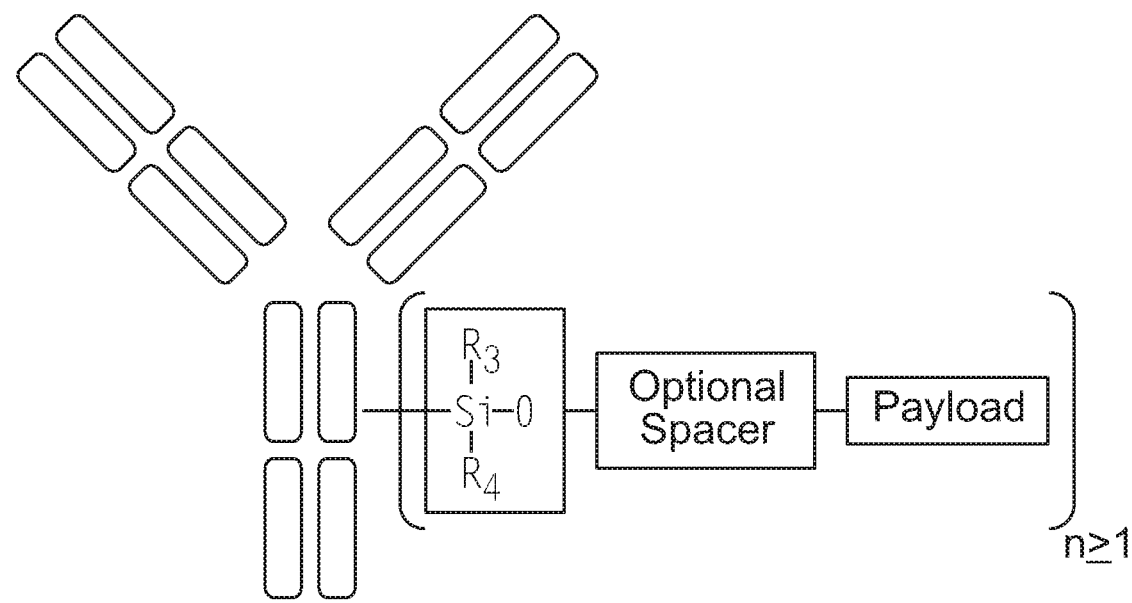

FIG. 13 shows an exemplary and pictorial heterogeneous or homogeneous silyl ether mAb-drug conjugate embodiment. For example, the silylether moiety can be attached to naturally occurring amino acids such as threonine and tyrosine using appropriate chemistries or the silylether moiety can be either incorporated via unnatural silanolic-amino acids engineered into the mAb, or, properly substituted silanols (e.g. Ar—SiR3, R4OH) attached to naturally occurring amino acids such as lysine, cysteine, threonine via appropriate linker chemistries (amides, disulfides, esters).

Figure 14:
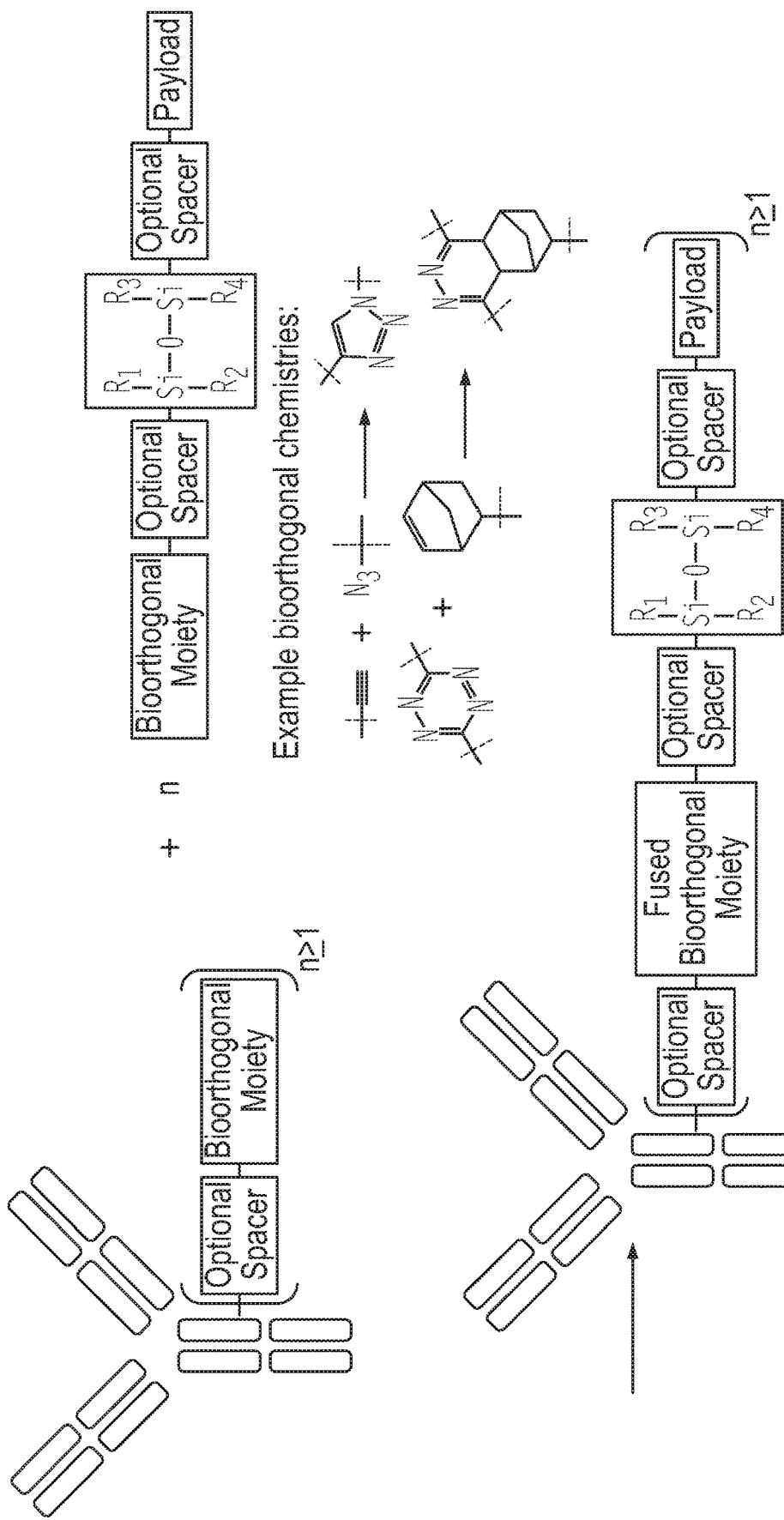
FIG. 14 indicates an exemplary route to preparation of a disclosed homogenous siloxane/silylether mAb-drug conjugates.
Figure 15A:
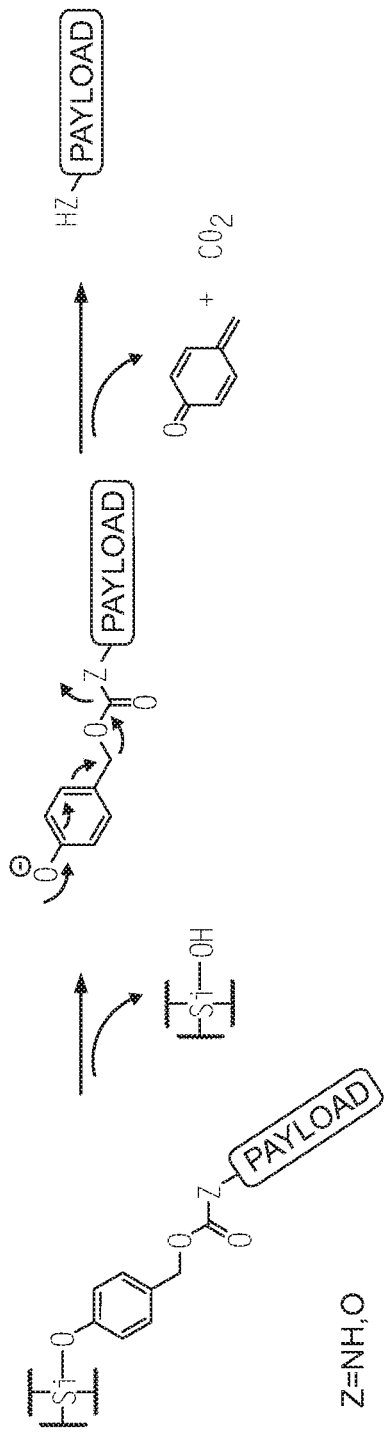
FIGS. 15A, 15B and 15C describe exemplary routes of payload cleavage for certain disclosed conjugates having a self-immolating spacer.
Figure 15A:
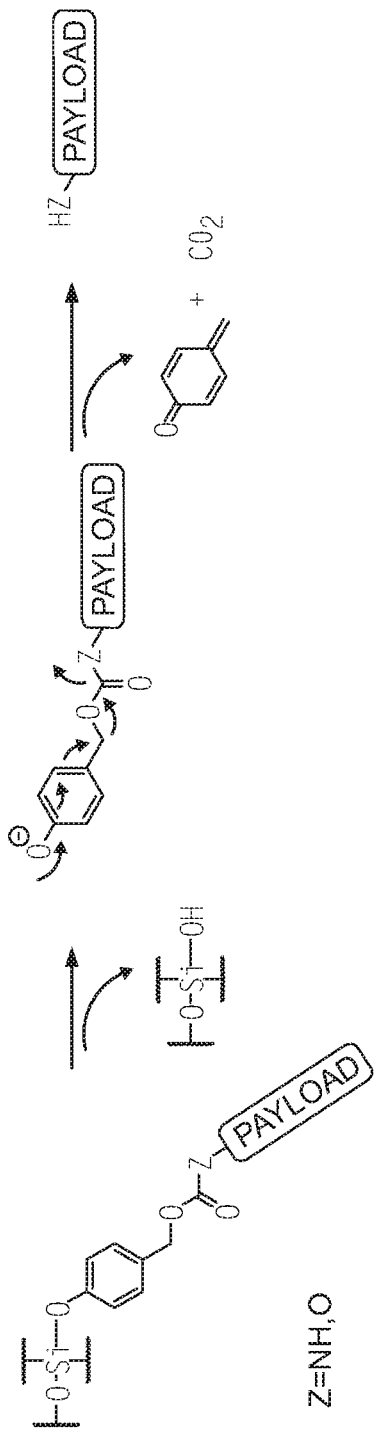
Figure 15B:
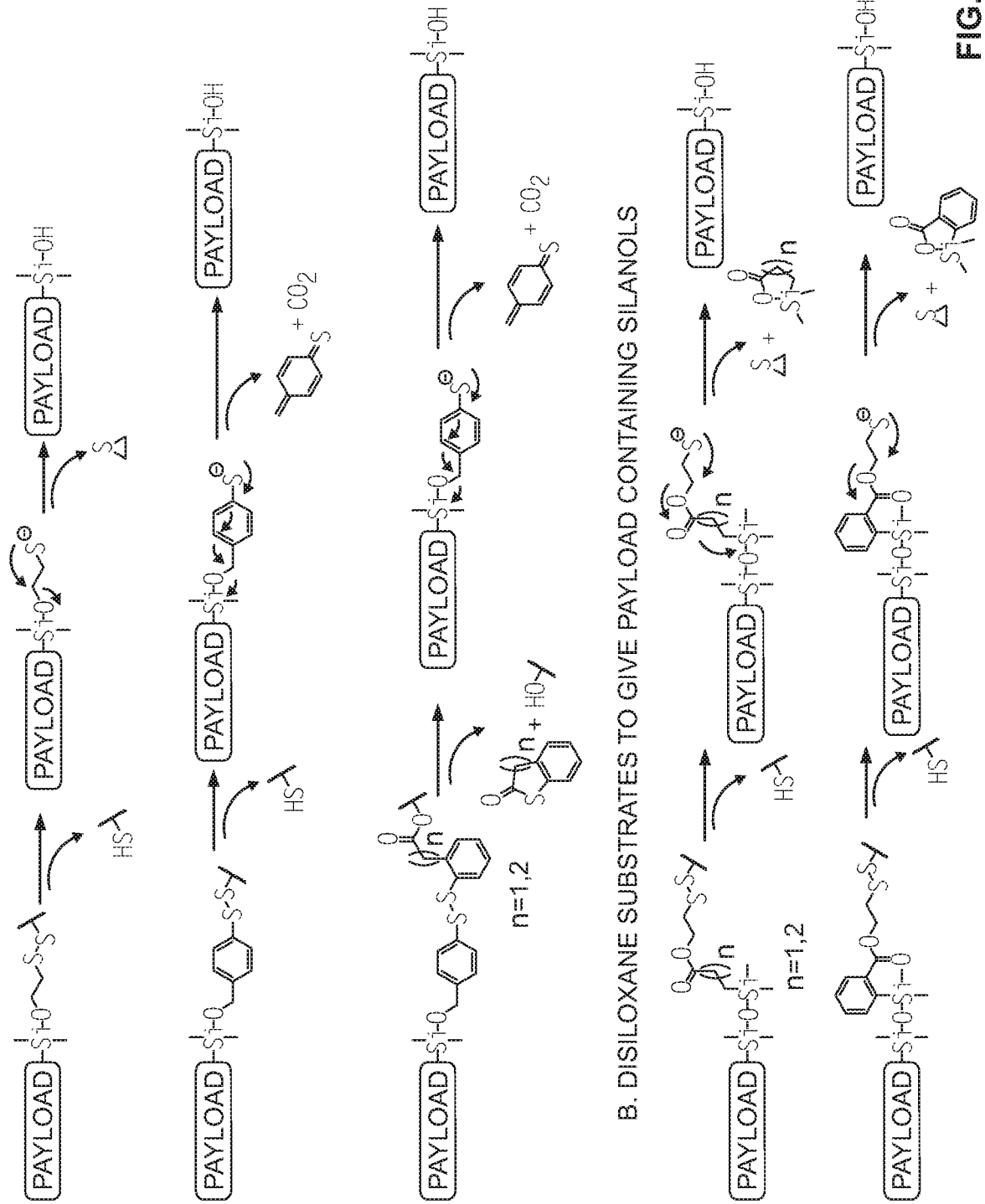
Figure 15C:
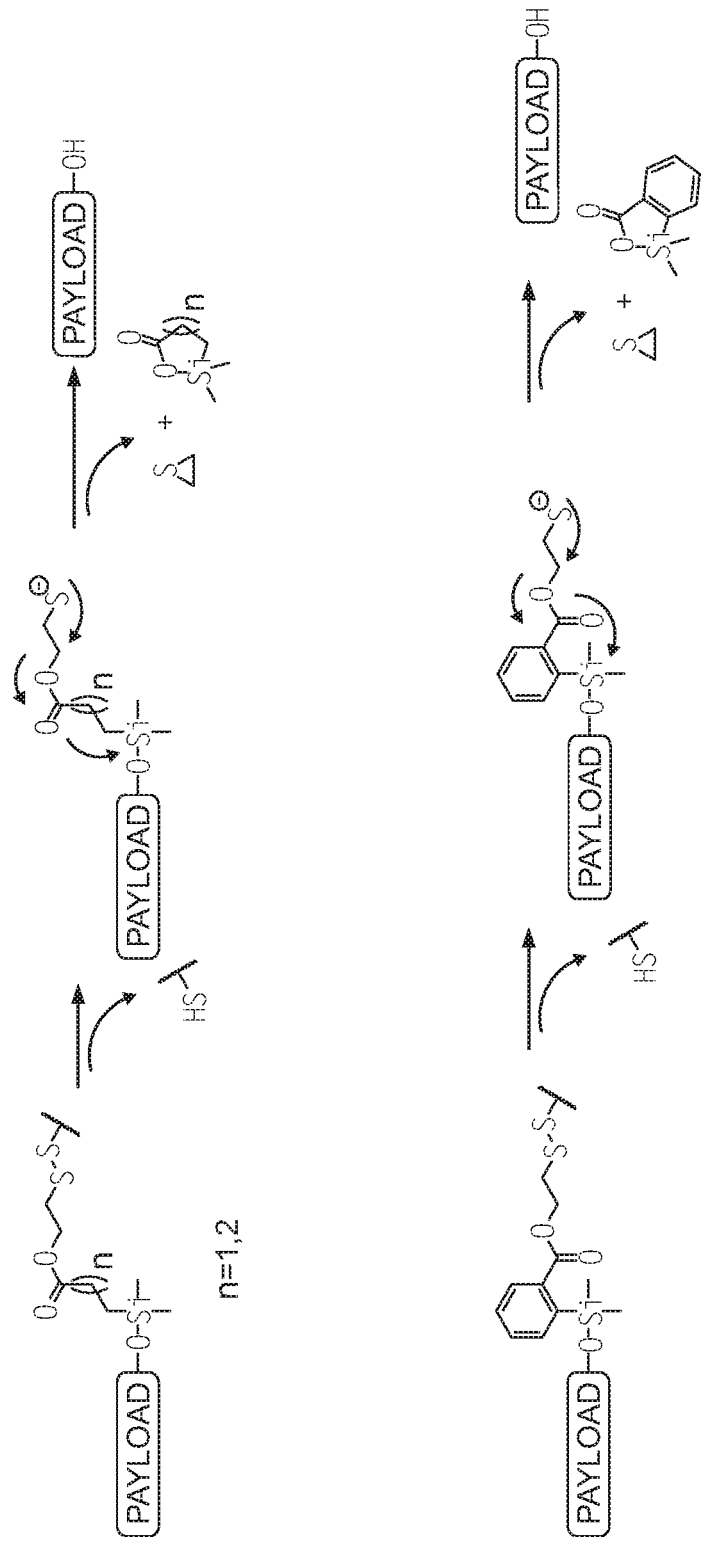

FIG. 14 pictorially indicates a disclosed embodiment and route to homogeneous silicon mAb-drug conjugates. For example, unnatural amino acids bearing irreversible bioorthogonal moieties may be used; once the protein is synthesized, a silanol may be incorporated viable irreversible coupling to the bioorthogonal moiety.

Therapeutic Payloads

In various embodiments, the payload may be a therapeutic moiety. The therapeutic moiety can be, for example, a cytotoxic moiety. A cytotoxic moiety can be analogs of SN-38, bendamustine, a VDA, doxorubicin, pemetrexed, vorinostat, lenalidomide, irinotecan, ganetespib, docetaxel, 17-AAG, 5-FU, abiraterone, crizotinib, KW-2189, BUMB2, DC1, CC-1065, adozelesin, or (a) fragment(s) thereof.

In various embodiments, the payload may be selected from an antifolate or fragments thereof (e.g., temozolomide, mitozolomide, nitrogen mustards, estramustine, or chloromethine).

In various embodiments, the payload may be selected from: peptidyl-prolyl isomerase ligands, e.g., FK506 (tacrolimus); rapamycin, cyclosporin A; steroid hormone receptor ligands, e.g., naturally occurring steroid hormones, such as estrogen, progestin, testosterone, as well as synthetic derivatives and mimetics thereof; small molecules that bind to cytoskeletal proteins, e.g., antimitotic agents, such as taxanes, colchicine, colcemid, nocadozole, vinblastine, and vincristine, actin binding agents, such as cytochalasin, latrunculin, halloidin; lenalidomide, pomalidomide, camptothecins including SN-38, topotecan, combretastatins, capecitabine, gemcitabine, vinca alkaloids, platinum-containing compounds, metformin, HDAC inhibitors (e.g., suberoylanilidehydroxamic acid (SAHA)), thymidylate synthase inhibitors such as methotrexate, pemetrexed, and raltitrexed; nitrogen mustards such as bendamustine and melphalan; 5-fluorouracil (5-FU) and its derivatives; and agents used in ADC drugs, such as vedotin and DM1.

In various embodiments, the payload may be selected from: central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs), analgesics (morphine and derivatives, oripavine derivatives, morphinan derivatives, phenylpiperidines, 2,6-methane-3-benzazocaine derivatives, diphenylpropylamines and isosteres, salicylates, 7-aminophenol derivatives, 5-pyrazolone derivatives, arylacetic acid derivatives, fenamates and isosteres) and antiemetics (anticholinergics, antihistamines, antidopaminergics); central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics; psychopharmacological/psychotropics, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives), antidepressants (tricyclic compounds, MAO inhibitors).

In various embodiments, the payload may be selected from: respiratory tract drugs, e.g., central antitussives (opium alkaloids and their derivatives); immunosuppressive agents; pharmacodynamic agents, such as peripheral nervous system drugs, e.g., local anesthetics (ester derivatives, amide derivatives); drugs acting at synaptic or neuroeffector junctional sites, e.g., cholinergic agents, cholinergic blocking agents, neuromuscular blocking agents, adrenergic agents, antiadrenergic agents; smooth muscle active drugs, e.g., spasmolytics (anticholinergics, musculotropic spasmolytics), vasodilators, smooth muscle stimulants; histamines and antihistamines, e.g., histamine and derivative thereof (betazole), antihistamines (Hi-antagonists, H2-antagonists), histamine metabolism drugs; cardiovascular drugs, e.g., cardiotonics (plant extracts, butenolides, pentadienolids, alkaloids from erythrophleum species, ionophores, -adrenoceptor stimulants), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemo styptics; chemo therapeutic agents, such as anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, and cytostatics, i.e., antineoplastic agents or cytotoxic drugs, such as alkylating agents, e.g., mechlorethamine hydrochloride (nitrogen mustard, mustargen, HN2), cyclophosphamide (Cytovan, Endoxana), ifosfamide (IFEX), chlorambucil (Leukeran), Melphalan (phenylalanine mustard, L-sarcolysin, Alkeran, L-PAM), busulfan (Myleran), Thiotepa (triethylenethiophosphoramide), carmustine (BiCNU, BCNU), lomustine (CeeNU, CCNU), streptozocin (Zanosar); plant alkaloids, e.g., vincristine (Oncovin), vinblastine (Velban, Velbe), paclitaxel (Taxol); antimetabolites, e.g., methotrexate (MTX), mercaptopurine (Purinethol, 6-MP), thioguanine (6-TG), fluorouracil (5-FU), cytarabine (Cytosar-U, Ara-C), azacitidine (Mylosar, 5-AZA); antibiotics, e.g., dactinomycin (Actinomycin D, Cosmegen), doxorubicin (Adriamycin), daunorubicin (duanomycin, Cerubidine), idarubicin (Idamycin), bleomycin (Blenoxane), picamycin (Mithramycin, Mithracin), mitomycin (Mutamycin), and other anticellular proliferative agents, e.g., hydroxyurea (Hydrea), procarbazine (Mutalane), dacarbazine (DTIC-Dome), cisplatin (Platinol) carboplatin (Paraplatin), asparaginase (Elspar), etoposide (VePesid, VP-16-213), amsarcrine (AMSA, m-AMSA), mitotane (Lysodren), or mitoxantrone (Novatrone).

In various embodiments, the payload may be selected from: anti-inflammatory agents; antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; β-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin; polypeptides, e.g., amphomycin, bacitracin, capreomycin; tetracyclines, e.g., apicycline, chlortetracycline, clomocycline; synthetic antibacterial agents, such as 2,4-diaminopyrimidines, nitrofurans, quinolones and analogs thereof, sulfonamides, or sulfones.

In various embodiments, the payload may be selected from: antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, thiocarbamates, e.g., tolciclate, triazoles, e.g., fluconazole, itraconazole, or terconazole.

In various embodiments, the payload may be selected from: anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, or diethylcarbamazine.

In various embodiments, the payload may be selected from: antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, or dibasic sodium arsenate.

In various embodiments, the payload may be selected from: antiprotozoan agents, such as: acranil, tinidazole, ipronidazole, ethylstibamine, pentamidine, acetarsone, aminitrozole, anisomycin, nifuratel, tinidazole, benzidazole, or suramin.

In various embodiments, the payload may be selected from: docetaxel or paclitaxel; BEZ235; temsirolimus; PLX4032; cisplatin; AZD8055; and crizotinib.

In various embodiments, the payload may be a topotecan or irinotecan.

In various embodiments the payload may be selected from siRNA, mRNA or miRNA optionally in combination with endosomal escape enhancers.

In various embodiments the payload may be selected from antigens.

Methods

In some embodiments, contemplated conjugates may be administered to a patient in need thereof a therapeutically effective amount of the one or more payloads. In some embodiments, a payload moiety may have a molecular weight between 50 Da and 2000 Da, in some embodiments between 50 Da and 1500 Da, in some embodiments, between 50 Da and 1000 Da, and in some embodiments, between 50 Da and 500 Da. In certain embodiments, a targeting moiety may have a molecular weight of less than 2000 Da, in some embodiments, less than 1000 Da, and in some embodiments less than 500 Da.

Disclosed conjugates may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound may be administered orally, subcutaneously, topically, parenterally, by inhalation spray or rectally in dosage unit formulations containing conventional non-toxic pharmaceutically acceptable carriers, adjuvants, and vehicles. Parenteral administration may include subcutaneous injections, intravenous or intramuscular injections, or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a partial or total alleviation of symptoms, is achieved.

In another aspect, conjugates disclosed here may be formulated together with a pharmaceutically acceptable carrier provided. In particular, the present disclosure provides conjugates disclosed herein formulated together with one or more pharmaceutically acceptable carriers. These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral, i.v., or subcutaneous administration.

Exemplary pharmaceutical compositions may be used in the form of a pharmaceutical preparation, for example, in solid, semisolid, spray-dried, dispersion, or liquid form, which contains one or more of the compounds, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, enteral pharmaceutical formulations including a disclosed conjugate, an enteric material, and a pharmaceutically acceptable carrier or excipient thereof are provided. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methacrylate-methylmethacrylate-chlorotrimethylammonium ethyl acrylate copolymer, natural resins such as zein, shellac and copal collophorium, and several commercially available enteric dispersion systems (e. g., Eudragit L30D55, Eudragit FS30D, Eudragit L100, Eudragit 5100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that may be used.

Also contemplated herein are methods and compositions that include additional active agents, or administering additional active agents.

Certain terms employed in the specification, examples, and appended claims are collected here. These definitions should be read in light of the entirety of the disclosure and understood as by a person of skill in the art. Unless defined otherwise, all technical and scientific terms used herein have the same meaning as commonly understood by a person of ordinary skill in the art.

Definitions

In some embodiments, the compounds, as described herein, may be substituted with any number of substituents or functional moieties. In general, the term "substituted" whether preceded by the term "optionally" or not, and substituents contained in formulas, refer to the replacement of hydrogen radicals in a given structure with the radical of a specified substituent.

In some instances, when more than one position in any given structure may be substituted with more than one substituent selected from a specified group, the substituent may be either the same or different at every position.

As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. In some embodiments, heteroatoms such as nitrogen may have hydrogen substituents and/or any permissible substituents of organic compounds described herein which satisfy the valencies of the heteroatoms. Non-limiting examples of substituents include acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Furthermore, the compounds described herein are not intended to be limited in any manner by the permissible substituents of organic compounds. In some embodiments, combinations of substituents and variables described herein may be preferably those that result in the formation of stable compounds. The term "stable," as used herein, refers to compounds which possess stability sufficient to allow manufacture and which maintain the integrity of the compound for a sufficient period of time to be detected and preferably for a sufficient period of time to be useful for the purposes detailed herein.

The term "acyl," as used herein, refers to a moiety that includes a carbonyl group. In some embodiments, an acyl group may have a general formula selected from —C(O)R$_x$; —CO$_2$(R$_x$); —C(O)N(R$_x$)$_2$; —OC(O)R$_x$; —OCO$_2$R$_x$; and —OC(O)N(R$_x$)$_2$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties.

The term "heteroaliphatic," as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to acyl; aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —SCN; —SR$_x$; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —OR$_x$, —C(O)R$_x$; —CO$_2$(R$_x$); —C(O)N(R$_x$)$_2$; —OC(O)R$_x$; —OCO$_2$R$_x$; —OC(O)N(R$_x$)$_2$; —N(R$_x$)$_2$; —SOR$_x$; —S(O)$_2$R$_x$; —NR$_x$C(O)R$_x$; or —C(R$_x$)$_3$; wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

In general, the terms "aryl" and "heteroaryl," as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substituents, i.e., the substituents recited for aliphatic moieties, or for other moieties as disclosed herein, resulting in the formation of a stable compound. In certain embodiments, aryl refers to a mono- or bicyclic carbocyclic ring system having one or two aromatic rings including, but not limited to, phenyl, naphthyl, tetrahydronaphthyl, indanyl, indenyl, and the like. In certain embodiments, the term heteroaryl, as used herein, refers to a cyclic aromatic radical having from five to ten ring atoms of which one ring atom is selected from the group consisting of S, O, and N; zero, one, or two ring atoms are additional heteroatoms independently selected from the group consisting of S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like. In certain embodiments, any of the above aryl or heteroaryl rings may be fused to a heterocyclic ring.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; cycloalkoxy; heterocyclylalkoxy; heterocyclyloxy; heterocyclyloxyalkyl; alkenyloxy; alkynyloxy; aryloxy; heteroalkoxy; heteroaryloxy; alkylthio; arylthio; heteroalkylthio; heteroarylthio; oxo; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, hydrogen, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heterocyclic," as used herein, refers to an aromatic or non-aromatic, partially unsaturated or fully saturated, 3- to 10-membered ring system, which includes single rings of 3 to 8 atoms in size and bi- and tri-cyclic ring systems which may include aromatic five- or six-membered aryl or aromatic heterocyclic groups fused to a non-aromatic ring. These heterocyclic rings include those having from one to three heteroatoms independently selected from the group consisting of oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from the group consisting of O, S, and N (wherein the nitrogen and sulfur heteroatoms may be optionally oxidized), including, but not limited to, a bi- or tri-cyclic group, comprising fused six-membered rings having between one and three heteroatoms independently selected from the group consisting of the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring.

The term "alkenyl" as used herein refers to an unsaturated straight or branched hydrocarbon having at least one carbon-carbon double bond, such as a straight or branched group of 2-6 or 3-4 carbon atoms, referred to herein for example as C$_{2-6}$alkenyl, and C$_{3-4}$alkenyl, respectively. Exemplary alkenyl groups include, but are not limited to, vinyl, allyl, butenyl, pentenyl, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as C$_{3-6}$alkenyloxy. Exemplary "alkenyloxy" groups include, but are not limited to allyloxy, butenyloxy, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as C$_{1-6}$alkoxy, and C$_2$-C$_6$alkoxy, respectively. Exemplary alkoxy groups include, but are not limited to methoxy, ethoxy, isopropoxy, etc.

The term "alkoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as C$_{1-6}$alkoxycarbonyl. Exemplary alkoxycarbonyl groups include, but are not limited to, methoxycarbonyl, ethoxycarbonyl, t-butoxycarbonyl, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, for example, such as a straight or branched group of 1-6, 1-4, or 1-3 carbon atoms, referred to herein as C$_{1-6}$alkyl, C$_{1-4}$alkyl, and C$_{1-3}$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as C$_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as C$_{2-6}$alkynyl, and C$_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "carboxylic acid" as used herein refers to a group of formula —CO$_2$H.

The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as C$_{3-6}$cycloalkyl or C$_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" as used herein refer to F, Cl, Br, or I.

The term "heterocyclylalkoxy" as used herein refers to a heterocyclyl-alkyl-O— group.

The term "heterocyclyloxyalkyl" refers to a heterocyclyl-O-alkyl- group.

The term "heterocyclyloxy" refers to a heterocyclyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

The term "connector" as used herein to refers to an atom or a collection of atoms optionally used to link interconnecting moieties, such as a disclosed linker and a pharmacophore. Contemplated connectors are generally hydrolytically stable.

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic, or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal, or human that is being sought by the researcher, veterinarian, medical doctor, or other clinician. The compounds are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers, atropisomers, or diastereomers. The term "stereoisomers" when used herein consist of all geometric isomers, enantiomers or diastereomers. These compounds may be designated by the symbols "R" or "S," depending on the configuration of substituents around the stereogenic carbon atom. Various stereoisomers of these compounds and mixtures thereof are encompassed by this disclosure. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers, atropisomers, or diastereomers. The enantiomers and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. Various stereoisomers of these compounds and mixtures thereof are encompassed by this disclosure.

Individual enantiomers and diastereomers of the compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like. In one embodiment, the compound is amorphous. In one embodiment, the compound is a polymorph. In another embodiment, the compound is in a crystalline form.

Also embraced are isotopically labeled compounds which are identical to those recited herein, except that one or more atoms are replaced by an atom having an atomic mass or mass number different from the atomic mass or mass number usually found in nature. Examples of isotopes that can be incorporated into the compounds include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, $^{10}$B, and $^{36}$Cl, respectively. For example, a compound may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood, or liver). Prodrugs are well known in the art (for example, see Rautio, Kumpulainen, et al, Nature Reviews Drug Discovery 2008, 7, 255). For example, if a compound or a pharmaceutically acceptable salt, hydrate, or solvate of the compound contains a carboxylic acid functional group, a prodrug can comprise an ester formed by the replacement of the hydrogen atom of the acid group with a group such as $(C_{1-8})$alkyl, $(C_{2-12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$alkylcarbamoyl-$(C_1$-$C_2)$alkyl and piperidino-, pyrrolidino- or morpholino$(C_2$-$C_3)$alkyl.

Similarly, if a compound contains an alcohol functional group, a prodrug can be formed by the replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl$(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1$-$C_6)$alkyl)$_2$ or glycosyl (the radical resulting from the removal of a hydroxyl group of the hemiacetal form of a carbohydrate).

If a compound incorporates an amine functional group, a prodrug can be formed, for example, by creation of an amide or carbamate, an N-acyloxyalkyl derivative, an (oxodioxolenyl)methyl derivative, an N-Mannich base, imine, or enamine. In addition, a secondary amine can be metabolically cleaved to generate a bioactive primary amine, or a tertiary amine can be metabolically cleaved to generate a bioactive primary or secondary amine. For examples, see Simplício et al., *Molecules* 2008, 13, 519 and references therein.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Liquid Chromatography Mass Spectrometry (LCMS) was performed on a Waters Acquity UPLC/SQD2 mass spectrometer under the following parameters: Column: ACE Excel 2 SuperC18; Length:100 mm; Diameter: 2.1 mm; pore size: 2.0 µm; Column temp: 40° C., Sample temp: 25° C. or 37° C. Gradient elution methods and mobile phase eluents are shown below.

| polar_3min_0_1500 (0.8 mL/min flow) | | |
|---|---|---|
| Time (min) | Solvent A (%) | Solvent B (%) |
| 0 | 95 | 5 |
| 0.2 | 95 | 5 |
| 1.50 | 10 | 90 |
| 2.00 | 10 | 90 |
| 2.20 | 95 | 5 |
| 3.00 | 95 | 5 |

| non_polar_3min (0.8 mL/min flow) | | |
|---|---|---|
| Time (min) | Solvent A (%) | Solvent B (%) |
| 0 | 85 | 15 |
| 0.2 | 85 | 15 |
| 1.60 | 1 | 99 |
| 2.20 | 1 | 99 |
| 2.80 | 85 | 15 |
| 3.00 | 85 | 15 |

Acidic mobile phase eluents were Solvent A (0.1% formic acid in water, pH=2.6) and Solvent B (0.1% formic acid in acetonitrile, pH=2.6).

Basic mobile phase eluents were Solvent A (0.1% NH$_4$OH in water, pH=10.63) and Solvent B (100% acetonitrile).

Neutral mobile phase eluents were Solvent A (5 mM ammonium formate in water, pH=7.7) and Solvent B (100% acetonitrile).

Slightly acidic mobile phase eluents were Solvent A (10 mM ammonium acetate in water, pH=6.33) and Solvent B (100% acetonitrile).

Preparative High-performance liquid chromatography (HPLC) was performed on a Waters 2489 HPLC equipped with a UV/Vis detector, 2545 Binary Gradient Module, and Waters Fraction Collector III using ChromScope software and under the following conditions: Preparative column: XBridge Prep C18 5 mm; OBD 19×250 mm column; Column temp: 25° C.; Sample temp: 25° C. Neutral mobile phase eluents were Solvent A (10 mM Ammonium bicarbonate in water, 5% acetonitrile, pH=7.4, degassed) and Solvent B (100% acetonitrile, degassed). Gradient elution methods and mobile phase eluents are shown below.

| Preparative HPLC gradient 1 | | | |
|---|---|---|---|
| Time (min) | Flow (mL/min) | Solvent A (%) | Solvent B (%) |
| Initial | 18 | 95 | 5 |
| 5 | 18 | 90 | 10 |
| 20 | 18 | 40 | 60 |
| 25 | 18 | 20 | 80 |
| 30 | 18 | 10 | 90 |
| 35 | 18 | 5 | 95 |
| 40 | 18 | 95 | 5 |

| Preparative HPLC gradient 2 | | | |
|---|---|---|---|
| Time (min) | Flow (mL/min) | Solvent A (%) | Solvent B (%) |
| Initial | 20 | 80 | 20 |
| 2 | 20 | 60 | 40 |
| 5 | 20 | 50 | 50 |
| 10 | 20 | 40 | 60 |
| 20 | 20 | 20 | 80 |
| 35 | 20 | 20 | 80 |
| 45 | 20 | 20 | 80 |
| 50 | 20 | 15 | 85 |
| 60 | 20 | 5 | 95 |
| 65 | 20 | 5 | 95 |
| 80 | 20 | 5 | 95 |
| 100 | 20 | 90 | 10 |

| Preparative HPLC gradient 3 | | | |
|---|---|---|---|
| Time (min) | Flow (mL/min) | Solvent A (%) | Solvent B (%) |
| Initial | 18 | 95 | 5 |
| 5 | 18 | 90 | 10 |
| 20 | 18 | 70 | 30 |
| 30 | 18 | 50 | 50 |
| 40 | 18 | 40 | 60 |
| 45 | 18 | 20 | 80 |
| 50 | 18 | 10 | 90 |
| 55 | 18 | 5 | 95 |
| 60 | 18 | 95 | 5 |

| Preparative HPLC gradient 4 | | | |
|---|---|---|---|
| Time (min) | Flow (mL/min) | Solvent A (%) | Solvent B (%) |
| Initial | 18 | 95 | 5 |
| 5 | 18 | 90 | 10 |
| 10 | 18 | 80 | 20 |
| 20 | 18 | 70 | 30 |
| 30 | 18 | 60 | 40 |
| 40 | 18 | 50 | 50 |
| 45 | 18 | 70 | 30 |
| 50 | 18 | 5 | 95 |
| 55 | 18 | 95 | 5 |

Example 1 and Example 6

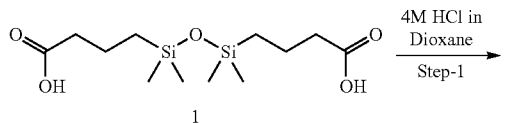

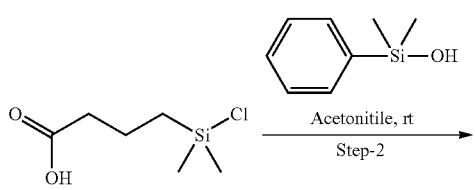

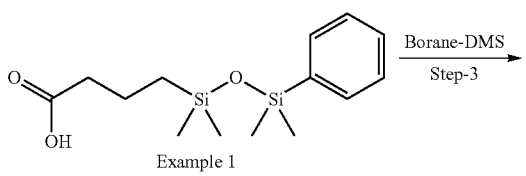

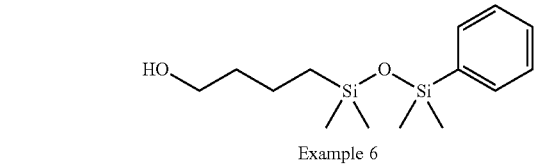

4-(1,1,3,3-Tetramethyl-3-phenyldisiloxanyl)butan-1-ol [Example 6]

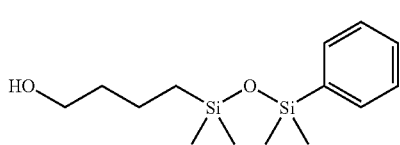 [SMILES: C[Si](C)(CCCCO)O[Si](C)(C)c1ccccc1]

A solution of 4-(1,1,3,3-tetramethyl-3-phenyldisiloxanyl) butanoic acid (1 g, 3.37 mmol) in THF (20 mL) was charged with borane-DMS (0.96 mL, 10.1 mmol) dropwise at room temperature under nitrogen atmosphere and stirred further for 1 h. The reaction mixture was concentrated in vacuo resulting in the crude compound which was purified by column chromatography on silica gel eluting with 10-15% ethyl acetate in n-hexane to afford 805 mg, 85% yield of the title compound as colorless oil. $^1$H NMR (400 MHz, DMSO-$d_6$) δ=7.49 (d, J=3.42 Hz, 2H), 7.28-7.40 (m, 3H), 4.24 (t, J=4.40 Hz, 1H), 3.31 (d, J=5.38 Hz, 2H), 1.21-1.44 (m, 4H), 0.43-0.51 (m, 2H), 0.26 (s, 6H), 0.00 (s, 6H). $^1$H NMR (400 MHz, CDCl$_3$) δ=7.54 (d, J=3.42 Hz, 2H), 7.35-7.40 (m, 3H), 3.17 (q, J=6.68 Hz, 2H), 1.94 (s, 3H), 1.43-1.52 (m, 2H), 0.47-0.55 (m, 2H), 0.33 (s, 6H), 0.07 (s, 6H); MS (ES$^+$): m/z=263.91 [M−18]; LCMS: $t_R$=3.71 min.

4-(1,1,3,3-Tetramethyl-3-phenyldisiloxanyl)butanoic Acid [Example 1]

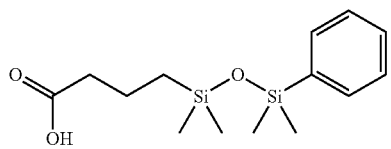 [SMILES: C[Si](C)(CCCC(=O)O)O[Si](C)(C)c1ccccc1]

A solution of 4-(chlorodimethylsilyl)butanoic acid (2.3 g, 12.7 mmol) in acetonitrile (115 mL) was charged with dimethyl(phenyl)silanol (969 mg, 6.36 mmol) and stirred at room temperature for 2 h. The reaction mixture was concentrated in vacuo, dissolved in diethyl ether (40 mL) and concentrated resulting in the crude compound which was purified by column chromatography on silica gel eluting with 40-70% ethyl acetate in n-hexane to afford 900 mg, 24% yield, of the title compound as colorless oil. $^1$H NMR (400 MHz, DMSO-$d_6$) δ=11.91 (br. s, 1H), 7.46-7.51 (m, 2H), 7.28-7.37 (m, 3H), 2.15 (t, J=7.09 Hz, 2H), 1.42-1.53 (m, 2H), 0.44-0.52 (m, 2H), 0.25 (s, 6H), −0.03 (s, 6H). $^1$H NMR (400 MHz, CDCl$_3$) δ=7.54 (d, J=3.42 Hz, 2H), 7.33-7.41 (m, 3H), 2.35 (t, J=7.34 Hz, 2H), 1.66 (td, J=7.70, 15.90 Hz, 2H), 0.54-0.63 (m, 2H), 0.32 (s, 6H), 0.07 (s, 6H); MS (ES+): m/z=295.00 [M−H]; LCMS: $t_R$=2.13 min.

4-(Chlorodimethylsilyl)butanoic Acid (2)

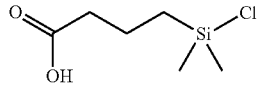

A solution of 4,4'-(1,1,3,3-tetramethyldisiloxane-1,3-diyl) dibutyric acid (2 g, 6.52 mmol) in 4M HCl in dioxane (60 mL) was stirred at room temperature for 2 h. The reaction mixture was concentrated in vacuo resulting in 2.35 g of crude compound as colorless oil. The crude compound was used in the next step without further purification. $^1$H NMR (400 MHz, DMSO-$d_6$) δ=2.22 (t, J=7.09 Hz, 2H), 1.50-1.55 (m, 2H), 0.45-0.56 (m, 2H), 0.05 (s, 6H).

Example 2 and Example 3

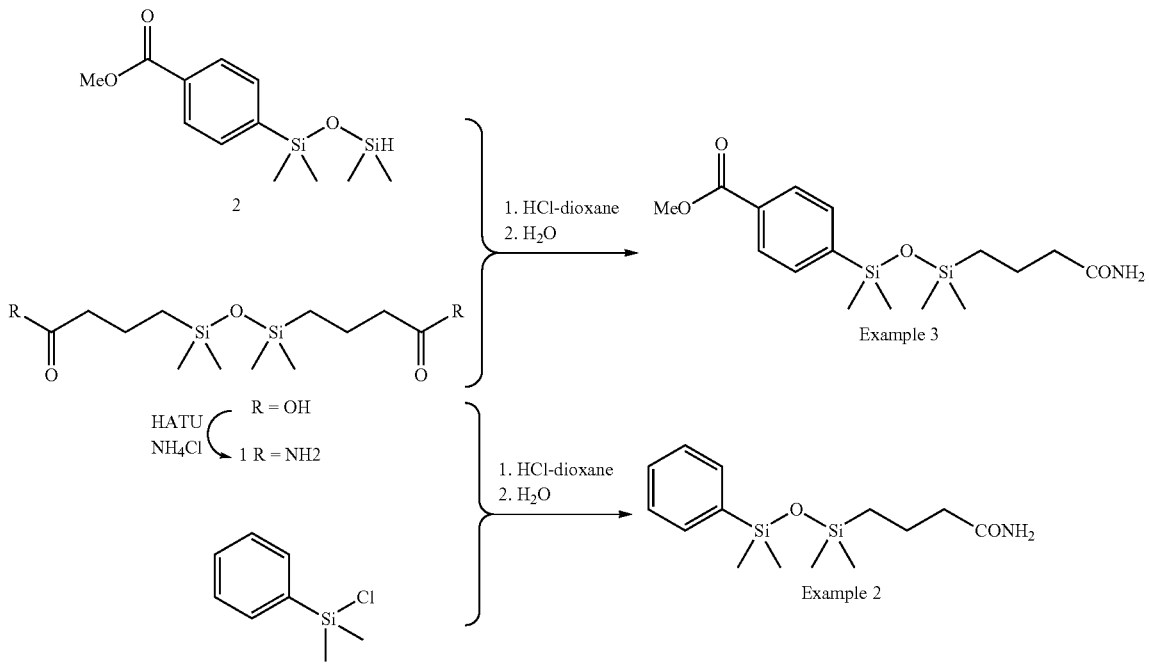

4-(1,1,3,3-tetramethyl-3-phenyldisiloxanyl)butanamide [Example 2]

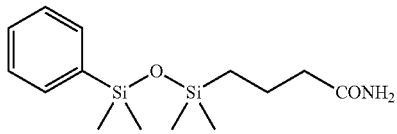 [SMILES: C[Si](C)(CCCC(N)=O)O[Si](C)(C)c1ccccc1]

A solution of HCl-dioxane (5N, 5 mL) was added to a solution of compound 1 (3.0 g, 9.8 mmol) in dioxane (7 mL) at room temperature. The reaction mixture was stirred for 2 h. The solvent was removed under reduced pressure. The residue was azeotroped with ACN (5 mL×2) to remove the excessive acid, and then dissolved in ACN (4 mL), chlorodimethylphenylsilane (5.0 g, 29.4 mmol) and H$_2$O (0.5 mL) were added in sequence. The reaction mixture was stirred at room temperature for 2 h, then concentrated. The crude product was purified by prep-HPLC to afford 350 mg, 10% yield of the title compound. $^1$H NMR (400 MHz, DMSO-d6): δ 7.45-7.50 (m, 2H), 7.32-7.40 (m, 3H), 7.16 (bs, 1H), 6.65 (bs, 1H), 1.98 (t, J=8.2 Hz, 2H), 1.45 (m, 2H), 0.45 (m, 2H), 0.25 (s, 6H), 0.00 (s, 6H). ESI for C$_{14}$H$_{25}$NO$_2$Si$_2$. Found 296.33 [M+H]$^+$.

4,4'-(1,1,3,3-tetramethyldisiloxane-1,3-diyl)dibutanamide (1)

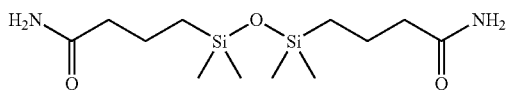 [SMILES: C[Si](C)(CCCC(N)=O)O[Si](C)(C)CCCC(N)=O]

HATU (9.3 g, 29.8 mmol) was added to a solution of 1,3-bis(3-carboxypropyl)tetramethyldisiloxane (3.06 g, 9.8 mmol) and ammonium chloride (1.3 g, 29.8 mmol) in DMF (50 mL) at room temperature. The pH was adjusted to 8-9 with DIPEA (3-5 mL), then the reaction mixture was stirred at room temperature for 12 h, then quenched with water (200 mL). The mixture was stirred for 3 h, then filtrated. The solid was collected, washed with water (20 mL×5), dried, and concentrated to dryness. The crude product was purified by column chromatography on silica gel (DCM:MeOH=20:1 to 10:1) to afford 5.1 g, ~100% yield of the title compound.

Methyl 4-(3-(4-amino-4-oxobutyl)-1,1,3,3-tetramethyldisiloxanyl)benzoate [Example 3]

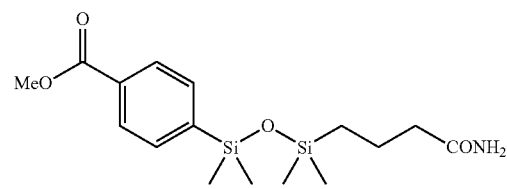 [SMILES: COC(=O)c1ccc([Si](C)(C)O[Si](C)(C)CCCC(N)=O)cc1]

A solution of HCl-dioxane (5N, 10 mL) was added to a mixture of compound 2 (3.0 g, 11.2 mmol) and 1,3-bis(3-carboxypropyl)tetramethyl disiloxane (3.4 g, 11 mmol) in dioxane (5 mL) at room temperature. The reaction mixture was stirred for 2 h. The solvent was removed under reduced pressure then the residue was dissolved in MeCN (10 mL), followed by the addition of H$_2$O (~0.5 mL). The mixture was stirred for 3 h. The solvent was concentrated in vacuo and the crude product was purified by prep-HPLC to afford 500 mg, 12% yield of the title compound. $^1$H NMR (400 MHz, DMSO-d6): δ 7.90 (d, J=8.4 Hz, 2H), 7.63 (d, J=8.4

Hz, 2H), 7.17 (bs, 1H), 6.65 (bs, 1H), 3.81 (s, 3H), 1.94 (m, 2H), 1.45 (m, 2H), 0.45 (m, 2H), 0.25 (s, 6H), 0.00 (s, 6H). ESI for C$_{16}$H$_{27}$NO$_4$Si$_2$. Found 354.73 [M+H]$^+$.

Example 4 and Example 18

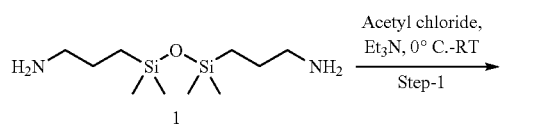

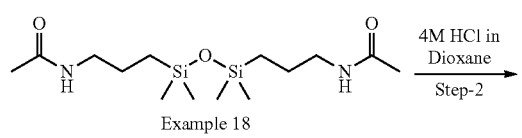

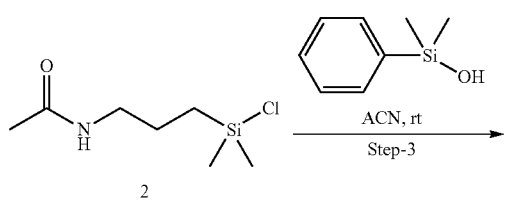

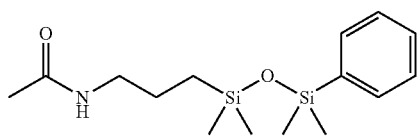 [SMILES: CC(=O)NCCC[Si](C)(C)O[Si](C)(C)c1ccccc1]

N-(3-(1,1,3,3-Tetramethyl-3-phenyldisiloxanyl)propyl)acetamide [Example 4]

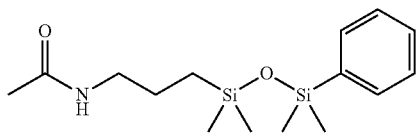

A solution of N-(3-(chlorodimethylsilyl)propyl)acetamide (3 g, 15.4 mmol) in acetonitrile (150 mL) was charged with dimethyl(phenyl)silanol (1.17 g, 7.74 mmol) and stirred at room temperature for 2 h. The reaction mixture was concentrated in vacuo, dissolved in diethyl ether and concentrated resulting in the crude compound which was purified by column chromatography on silica gel eluting with 40-70% ethyl acetate in n-hexane to afford 2 g, 42% yield of the title compound as colorless oil. $^1$H NMR (400 MHz, DMSO-d$_6$) δ=7.74 (br. s, 1H), 7.46-7.51 (m, 2H), 7.31-7.37 (m, 3H), 2.92 (q, J=6.68 Hz, 2H), 1.73 (s, 3H), 1.34 (td, J=7.70, 15.90 Hz, 2H), 0.41-0.48 (m, 2H), 0.26 (s, 6H), 0.00 (s, 6H), $^1$H NMR (400 MHz, CDCl$_3$) δ=7.54 (d, J=3.42 Hz, 2H), 7.35-7.40 (m, 3H), 3.17 (q, J=6.68 Hz, 2H), 1.94 (s, 3H), 1.43-1.52 (m, 2H), 0.47-0.55 (m, 2H), 0.33 (s, 6H), 0.07 (s, 6H); MS (ES+): m/z=310.00 [M+H]$^+$; LCMS: t$_R$=3.08 min.

N-(3-(Chlorodimethylsilyl)propyl)acetamide (2)

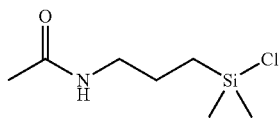

A solution of N,N-((1,1,3,3-tetramethyldisiloxane-1,3-diyl)bis(propane-3,1-diyl))diacetamide (2.6 g, 7.81 mmol) in dioxane: HCl (4M, 78 mL) was stirred at room temperature for 2 h. The reaction mixture was concentrated in vacuo resulting in 3.02 g of crude compound as colorless oil. The crude compound was used in the next step without further purification. $^1$H NMR (400 MHz, DMSO-d$_6$) δ=7.89 (br. s, 1H), 2.99 (d, J=5.38 Hz, 2H), 1.80 (s, 3H), 1.39 (td, J=7.83, 15.65 Hz, 2H), 0.44-0.50 (m, 2H), 0.05 (s, 6H).

N,N'-((1,1,3,3-Tetramethyldisiloxane-1,3-diyl)bis(propane-3,1-diyl))diacetamide [Example 18]

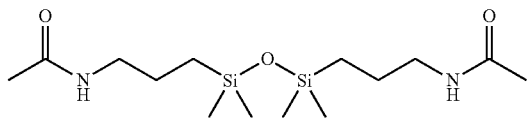 [SMILES: CC(=O)NCCC[Si](C)(C)O[Si](C)(C)CCCNC(C)=O]

A solution of 3,3'-(1,1,3,3-tetramethyldisiloxane-1,3-diyl)bis(propan-1-amine) (2 g, 8.04 mmol) in diethyl ether (100 mL) at 0° C. was charged with triethyl amine (2.8 mL, 20.1 mmol) and acetyl chloride (1.4 mL, 19.2 mmol) and stirred at room temperature for 1 h. The solid precipitated was filtered, washed with diethyl ether and the filtrate was concentrated in vacuo resulting in 2.67 g of the title compound as colorless oil. The crude compound was used in the next step without further purification. $^1$H NMR (400 MHz, DMSO-d$_6$) δ=7.77 (br. s, 2H), 2.94 (d, J=6.36 Hz, 4H), 1.69-1.83 (m, 6H), 1.35 (d, J=6.85 Hz, 4H), 0.36-0.50 (m, 4H), 0.00 (s, 12H), $^1$H NMR (400 MHz, CDCl$_3$) δ=6.04 (br. s, 1H), 3.21 (q, J=6.68 Hz, 4H), 1.93-2.07 (m, 6H), 1.53 (td, J=7.83, 15.65 Hz, 4H), 0.46-0.55 (m, 4H), 0.05 (s, 12H); MS (ESMS+): m/z=355.05 [M+Na]$^+$; ESMS: t$_R$=0.13 min, m/z=377.00 [M+2Na]$^+$; ESMS: t$_R$=0.15 min; MS (ES$^+$): m/z=333.00 [M+H]$^+$; LCMS: t$_R$=2.07 min.

Synthetic Scheme: Example 5 and Example 91

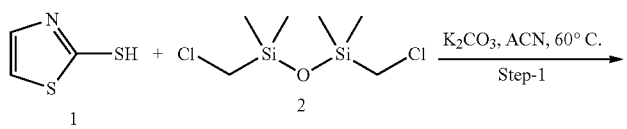

-continued

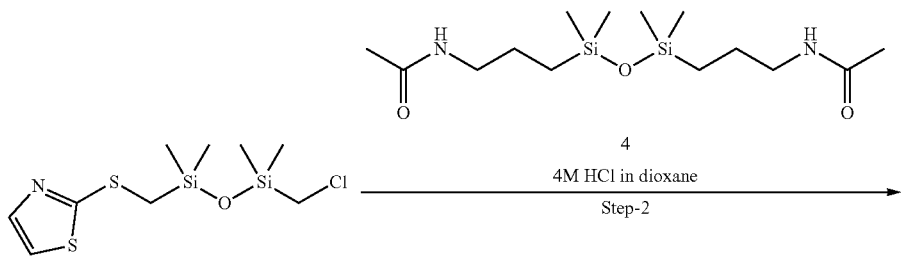

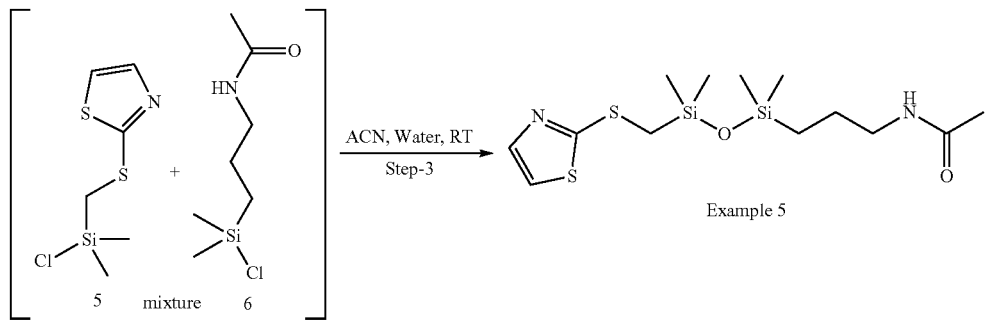

N-(3-(1,1,3,3-Tetramethyl-3-((thiazol-2-ylthio)methyl)disiloxanyl)propyl)acetamide [Example 5]

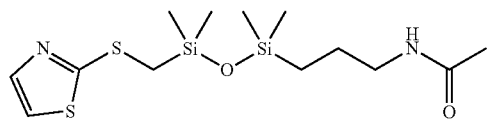 [SMILES: CC(=O)NCCC[Si](C)(C)O[Si](C)(C)CSc1nccs1]

A solution of 2-(((3-(chloromethyl)-1,1,3,3-tetramethyldisiloxanyl)methyl)thio)thiazole (1 g, 3.210 mmol) and N,N'-((1,1,3,3-tetramethyldisiloxane-1,3-diyl)bis(propane-3,1-diyl))diacetamide (1.03 g, 3.210 mmol) in 4M HCl in dioxane (20 mL) was stirred at room temperature for 1 h. The reaction mixture was concentrated in vacuo resulting in the crude intermediate 5 and 6. The mixture of intermediate 5 and 6 was dissolved in acetonitrile (20 mL) and followed by addition of water (0.23 mL, 12.86 mmol), DIPEA (3.34 mL, 19.29 mmol) and stirred at room temperature for 1 h. The reaction mixture was concentrated in vacuo resulting in the crude compound which was purified by Combi Flash chromatography on silica gel eluting with 0-10% methanol in DCM to afford 535 mg, 46% yield, of the title compound as colorless oil. $^1$H NMR (400 MHz, DMSO-$d_6$) δ=7.76 (br. s, 1H), 7.66 (d, J=3.42 Hz, 1H), 7.60 (d, J=3.42 Hz, 1H), 2.96 (q, J=6.52 Hz, 2H), 1.75 (s, 3H), 1.32-1.42 (m, 2H), 0.44-0.50 (m, 2H), 0.17 (s, 6H), 0.05 (s, 6H) 2H protons merged in solvent peak. $^1$H NMR (400 MHz, CDCl$_3$) δ=7.64 (d, J=2.45 Hz, 1H), 7.20 (d, J=2.93 Hz, 1H), 3.22 (q, J=6.68 Hz, 2H), 2.50 (s, 2H), 1.96 (s, 3H), 1.60-1.65 (m, 2H), 0.51-0.59 (m, 2H), 0.23 (s, 6H), 0.10 (s, 6H), MS (ES$^+$): m/z=363.05 [M+H]$^+$; LCMS: $t_R$=3.16 min.

2-(((3-(Chloromethyl)-1,1,3,3-tetramethyldisiloxanyl)methyl)thio)thiazole [Example 91]

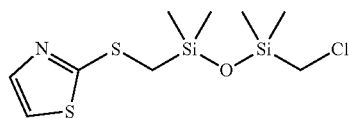 [SMILES: C[Si](C)(CCl)O[Si](C)(C)CSc1nccs1]

A solution of thiazole-2-thiol (2 g, 17.09 mmol) in acetonitrile (50 mL) was added potassium carbonate (4.7 g, 34.18 mmol) and 1,3-bis(chloromethyl)-1,1,3,3-tetramethyldisiloxane (5.92 g, 25.64 mmol) at room temperature. The reaction mixture was further heated to 60° C. and stirred for 1 h. The reaction mixture was concentrated in vacuo resulting in the crude compound which was purified by Combi Flash chromatography on silica gel eluting with 10-20% ethyl acetate in n-hexane to afford 3.4 g, 65% yield, of the title compound as colorless oil. $^1$H NMR (400 MHz, DMSO-$d_6$) δ=7.68 (d, J=3.42 Hz, 1H), 7.61 (d, J=3.42 Hz, 1H), 2.87 (s, 2H), 2.53 (s, 2H), 0.21 (s, 6H), 0.17 (s, 6H); MS (ES$^+$): m/z=312.00 [M+H]$^+$; LCMS: $t_R$=4.15 min.

Example 7, Example 22, Example 23, and Example 25

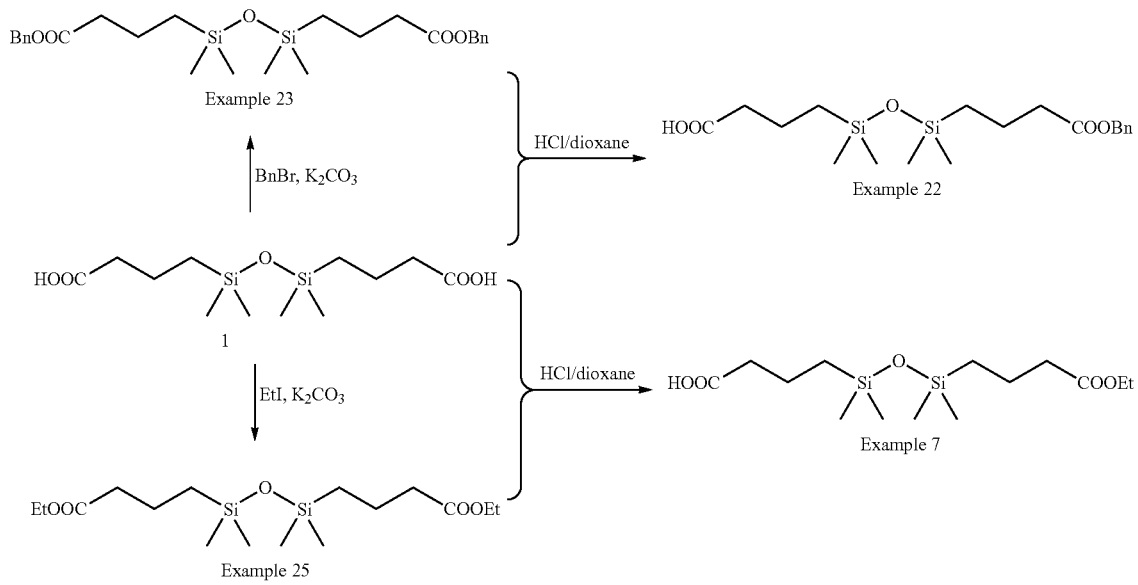

4-(3-(4-ethoxy-4-oxobutyl)-1,1,3,3-tetramethyldisiloxanyl)butanoic acid [Example 7]

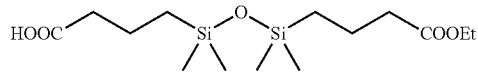 [SMILES: CCOC(=O)CCC[Si](C)(C)O[Si](C)(C)CCCC(=O)O]

A solution of HCl-dioxane (5N, 5 mL) was added to a mixture of compound 1 (1.6 g, 5.5 mmol) and Example 25 (2.01 g, 5.5 mmol) in dioxane (5 mL) at room temperature. The mixture was stirred for 2 h. The solvent was removed under reduced pressure, and the residue was azeotroped with ACN (5 mL×2) to remove the excessive acid, then dissolved in ACN (4 mL), followed by the addition of 5 drops of water (ca. 0.2 mL). The mixture was stirred for 0.5 h. The reaction was complete by LC-MS analysis. The resulting mixture was eluted with EtOAc (50 mL), then washed with brine (30 mL×3), dried and concentrated to dryness. The residue was purified by column chromatography on silica gel (hexane:EtOAc=10:1 to 5:1) to afford the desired compound (750 mg, 41% yield). $^1$H NMR (400 MHz, CDCl$_3$): δ 4.07 (m, 2H), 2.30 (m, 2H), 2.26 (m, 2H), 1.57-1.63 (m, 4H), 1.19 (m, 3H), 0.45-0.53 (m, 4H), 0.01-0.09 (m, 12H). ESI for C$_{14}$H$_{30}$O$_5$Si$_2$. Found 357.32 [M+Na]$^+$

4-(3-(4-(benzyloxy)-4-oxobutyl)-1,1,3,3-tetramethyldisiloxanyl)butanoicacid [Example 22]

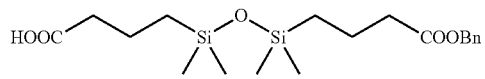

Compound Example 22 (890 mg, 55% yield) was prepared from compound 1 and Example 23 following the same procedure for Example 6. $^1$H NMR (300 MHz, CDCl3): δ 7.36 (m, 5H), 5.14 (s, 2H), 2.36-2.43 (m, 4H), 1.64-1.69 (m, 4H), 0.52-0.59 (m, 4H), 0.04-0.09 (m, 12H). ESI for C19H32O5Si2. Found 395.5 [M−H]−

Dibenzyl 4,4'-(1,1,3,3-tetramethyldisiloxane-1,3-diyl)dibutyrate [Example 23]

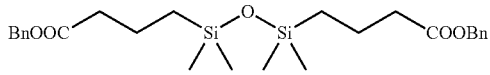

To a solution of compound 1 (2.01 g, 6.5 mmol) in ACN (20 mL) was added K$_2$CO$_3$ (1.80 g, 13 mmol) at room temperature. The mixture was heated to reflux at 60° C. for 1 h. BnBr (2.20 g, 13 mmol) was added to the mixture and refluxed for another 1 h. Solid was filtered after the reaction was cooled to room temperature. The filtrate was diluted with EtOAc (50 mL), washed with brine (50 mL×2) and dried over anhydrous Na$_2$SO$_4$. The solvent was removed under reduced pressure. Crude product was purified by column chromatography on silica gel (hexane:EtOAc=100:1 to 80:1) to afford the desired product (2.41 g, 75% yield). $^1$H NMR (400 MHz, CDCl$_3$): δ 7.30 (m, 10H), 5.07 (s, 4H), 2.33 (m, 4H), 1.62 (m, 4H), 0.48 (m, 4H), 0.01 (m, 12H). ESI for C$_{26}$H$_{38}$O$_5$Si$_2$. Found 509.5 [M+Na]$^+$

Diethyl 4,4'-(1,1,3,3-tetramethyldisiloxane-1,3-diyl)dibutyrate [Example 25]

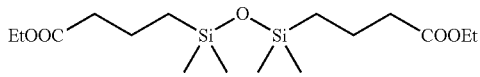

To a solution of compound 1 (4.00 g, 13 mmol) in ACN (40 mL) was added K2CO3 (3.62 g, 26 mmol) at room temperature. The mixture was heated under reflux at 60° C. and stirred for 1 h. The mixture was cooled to 40° C., and iodoethane (4.10 g, 26 mmol) was added carefully. The reaction mixture was further heated under reflux and stirred for 2 h. The reaction mixture was cooled to room temperature and then filtered to remove the solid. The filtrate was concentrated to dryness. The residue was purified by column chromatography on silica gel (hexane:EtOAc=80:1) to afford the desired product (600 mg, 12% yield). $^1$H NMR (400 MHz, CDCl$_3$): δ 4.06 (m, 4H), 2.26 (m, 4H), 1.59 (m, 4H), 1.20 (m, 4H), 0.89 (m, 12H). ESI for C$_{16}$H$_{34}$O$_5$Si$_2$. Found 385.29 [M+Na]$^+$ Example 8

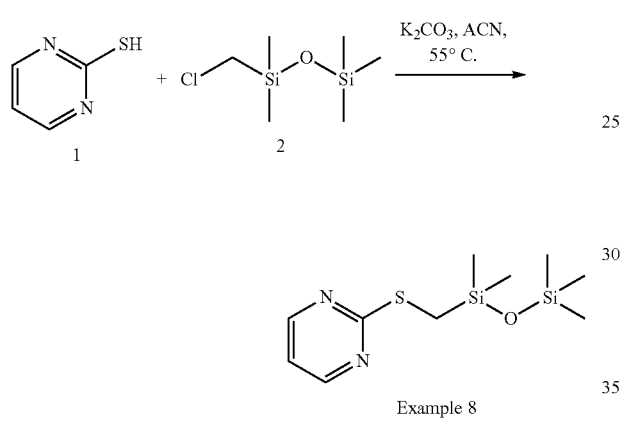

Example 8

2-(((1,1,3,3,3-Pentamethyldisiloxanyl)methyl)thio) pyrimidine [Example 8]

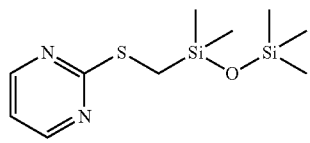 [SMILES: C[Si](C)(C)O[Si](C)(C)CSc1ncccn1]

A solution of pyrimidine-2-thiol (2 g, 17.8 mmol) in acetonitrile (60 mL) was charged with potassium carbonate (3.69 g, 26.7 mmol) and 1-(chloromethyl)-1,1,3,3,3-pentamethyldisiloxane 2 (3.86 g, 19.6 mmol) at room temperature and was further heated to 55° C. for 3 h. The reaction mixture was concentrated in vacuo, diluted with diethyl ether and stirred for 15 min. The solid precipitated was filtered and the filtrate was concentrated in vacuo resulting in the crude compound which was purified by column chromatography on silica gel eluting with 0-5% ethyl acetate in n-hexane to afford 3 g, 62% yield, of the title compound as a colorless oil. $^1$H NMR (400 MHz, DMSO-d$_6$) δ=8.55 (d, J=4.89 Hz, 2H), 7.12 (t, J=4.65 Hz, 1H), 2.31 (s, 2H), 0.09 (s, 6H), 0.00 (s, 9H); MS (ES$^+$): m/z=273.05 [M+H]$^+$; LCMS: $t_R$=3.46 min.

Example 9

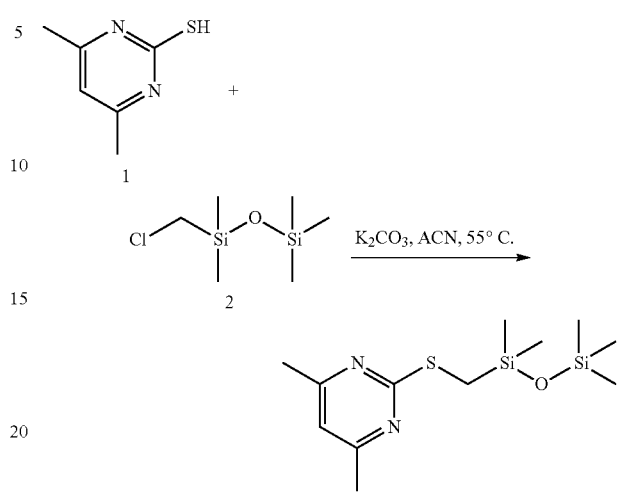

Example 9

2 4,6-Dimethyl-2-(((1,1,3,3,3-pentamethyldisiloxanyl)methyl)thio)pyrimidine [Example 9]

A solution of 4,6-dimethylpyrimidine-2-thiol (2 g, 14.2 mmol) in acetonitrile (60 mL) was charged with potassium carbonate (2.95 g, 21.3 mmol) and 1-(chloromethyl)-1,1,3,3,3-pentamethyldisiloxane 2 (3.08 g, 15.6 mmol) at room temperature and was further heated to 55° C. for 3 h. The reaction mixture was concentrated in vacuo, diluted with diethyl ether and stirred for 15 min. The solid precipitated was filtered and the filtrate was concentrated in vacuo resulting in the crude compound which was purified by column chromatography on silica gel eluting with 0-5% ethyl acetate in n-hexane to afford 3.5 g, 82% yield, of the title compound as a colorless oil. $^1$H NMR (400 MHz, DMSO-d$_6$) δ=6.85 (s, 1H), 2.26 (s, 8H), 0.07 (s, 6H), 0.00 (s, 9H); MS (ES$^+$): m/z=301.05 [M+H]$^+$; LCMS: $t_R$=3.81 min.

Example 10

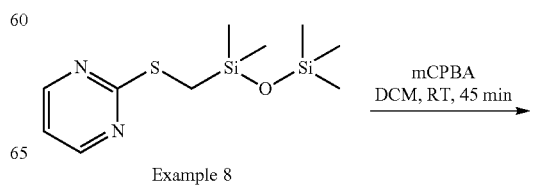

Example 8

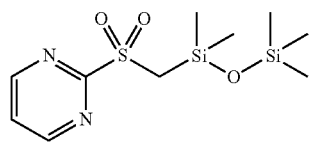

Example 10

Example 11

2-(((1,1,3,3,3-Pentamethyldisiloxanyl)methyl)sulfonyl)pyrimidine [Example 10]

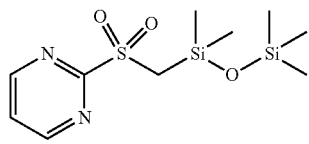 [SMILES: C[Si](C)(C)O[Si](C)(C)CS(=O)(=O)c1ncccn1]

A solution of 2-(((1,1,3,3,3-pentamethyldisiloxanyl) methyl)thio)pyrimidine (2 g, 17.8 mmol) in DCM (30 mL) was charged with 3-chlorobenzoperoxoic acid (3.86 g, 19.6 mmol) in lots over a period of 15 min at room temperature and further stirred for 30 min. The reaction mixture was washed with saturated sodium bicarbonate solution and the organic layer was separated. The separated organic layers were dried over anhydrous $Na_2SO_4$, filtered and concentrated in vacuo resulting in the crude compound which was purified by column chromatography on silica gel eluting with 20-50% ethyl acetate in n-hexane to afford 1.4 g, 84% yield, of the title compound as a colorless oil. $^1$H NMR (400 MHz, DMSO-$d_6$) δ=9.01 (d, J=4.40 Hz, 2H), 7.76 (t, J=4.89 Hz, 1H), 3.26 (s, 3H), 0.22 (s, 6H), 0.00 (s, 9H).
$^1$H NMR (400 MHz, CDCl$_3$) δ=8.94 (d, J=4.40 Hz, 2H), 7.52 (t, J=4.40 Hz, 1H), 3.21 (s, 2H), 0.42 (s, 6H), 0.11 (s, 9H); MS (ES$^+$): m/z=305.00 [M+H]$^+$; LCMS: $t_R$=3.17 min.

Example 11

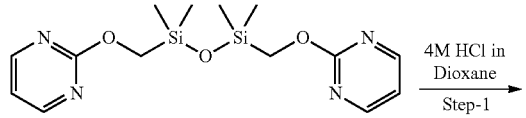

2-((1,1,3,3,3-Pentamethyldisiloxanyl)methoxy)pyrimidine [Example 11]

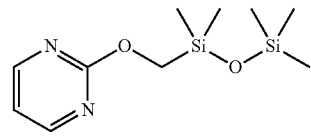 [SMILES: C[Si](C)(C)O[Si](C)(C)COc1ncccn1]

A solution of triethyl amine (0.18 mL, 1.28 mmol) and trimethylsilanol (154 mg, 1.71 mmol) was charged with 2-((chlorodimethylsilyl)methoxy)pyrimidine (173 mg, 0.85 mmol) in acetonitrile (3 mL) and stirred at room temperature for 2 h. The reaction mixture was concentrated in vacuo, dissolved in diethyl ether and concentrated resulting in the crude compound which was purified by column chromatography on silica gel eluting with 5-15% ethyl acetate in n-hexane to afford 150 mg, 68% yield, of the title compound as a colorless oil. $^1$H NMR (400 MHz, DMSO-$d_6$) δ=8.53 (d, J=4.40 Hz, 2H), 7.05 (t, J=4.89 Hz, 1H), 3.93 (s, 2H), 0.11 (s, 6H), 0.00 (s, 9H); MS (ES$^+$): m/z=257.08 [M+H]$^+$; LCMS: $t_R$=3.55 min.

2-((Chlorodimethylsilyl)methoxy)pyrimidine (1)

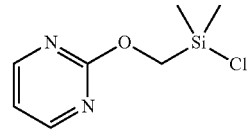

A solution of 1,1,3,3-tetramethyl-1,3-bis((pyrimidin-2-yloxy)methyl)disiloxane (300 mg, 0.85 mmol) in dioxane: HCl (4M, 3 mL) was stirred at room temperature for 2 h. The reaction mixture was concentrated in vacuo resulting in 173 mg of crude compound as colorless oil. The crude compound was used in the next step without further purification. $^1$H NMR (400 MHz, DMSO-$d_6$) δ=8.80 (d, J=4.89 Hz, 1H), 7.53-7.59 (m, 1H), 7.38 (d, J=5.38 Hz, 1H), 2.48 (br. s, 2H), 0.34 (s, 3H), 0.24 (s, 3H); MS (ES$^+$): m/z=289.03 [M+ACN+2Na]$^+$; LCMS: $t_R$=3.76 min.

Example 12, Example 13, and Example 14

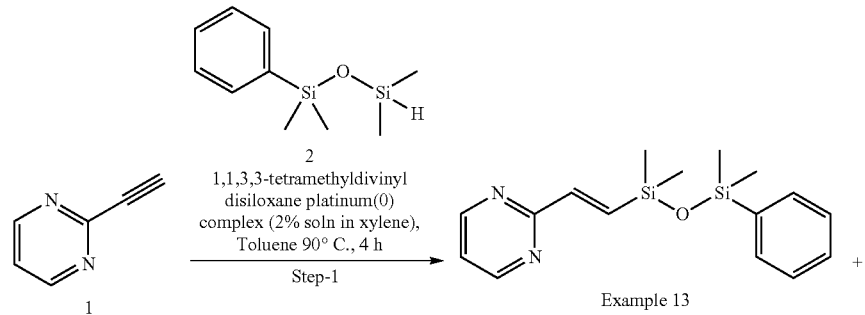

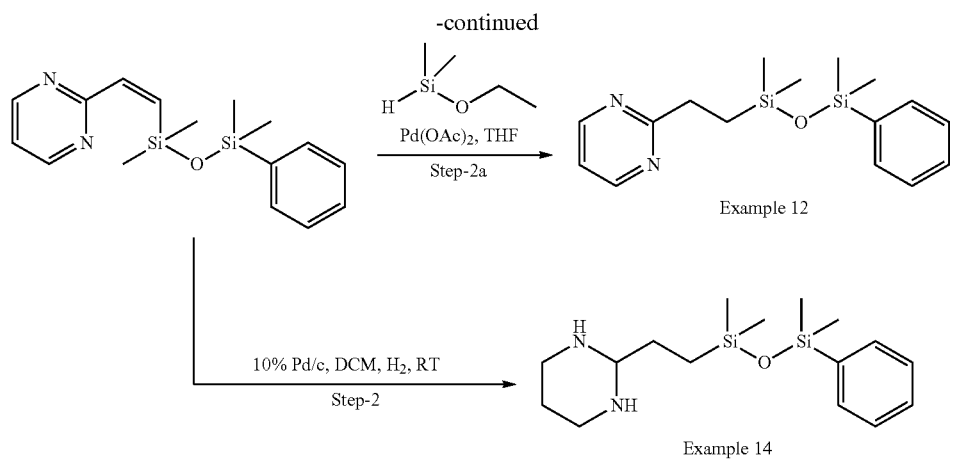

Example 12

Example 14

2-(2-(1,1,3,3-Tetramethyl-3-phenyldisiloxanyl)ethyl) pyrimidine [Example 12]

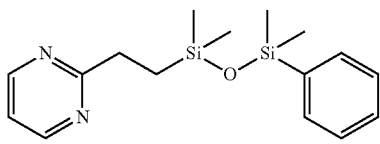 [SMILES: C[Si](C)(CCc1ncccn1)O[Si](C)(C)c1ccccc1]

A mixture of (E)-2-(2-(1,1,3,3-tetramethyl-3-phenyldisiloxanyl)vinyl)pyrimidine and (Z)-2-(2-(1,1,3,3-tetramethyl-3-phenyldisiloxanyl)vinyl)pyrimidine (400 mg, 1.27 mmol) in THF (4 mL) was charged with ethoxydimethylsilane (397 mg, 3.81 mmol), palladium acetate (28 mg, 0.13 mmol) and under argon atmosphere at room temperature for 30 min. The reaction mixture was concentrated in vacuo resulting in the crude compound which was purified by column chromatography on silica gel eluting with 0-35% ethyl acetate in n-hexane to afford 350 mg, 87% yield, of the title compound as a colorless oil. $^1$H NMR (400 MHz, DMSO-$d_6$) δ=8.65 (d, J=4.89 Hz, 2H), 7.46-7.50 (m, 2H), 7.31-7.35 (m, 3H), 7.25 (t, J=4.89 Hz, 1H), 2.80-2.85 (m, 2H), 0.95-1.00 (m, 2H), 0.25 (s, 6H), 0.00 (s, 6H); MS (ES$^+$): m/z=317.05 [M+H]$^+$; LCMS: $t_R$=3.79 min.

(E)-2-(2-(1,1,3,3-Tetramethyl-3-phenyldisiloxanyl)vinyl)pyrimidine [Example 13]

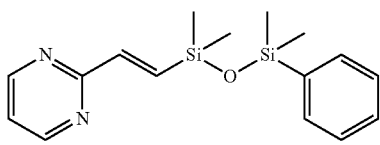 [SMILES: C[Si](C)(/C=C/c1ncccn1)O[Si](C)(C)c1ccccc1]

A solution of 2-ethynylpyrimidine (2 g, 19.2 mmol) in toluene (20 mL) was charged with 1,1,3,3-tetramethyl-1-phenyldisiloxane (4.04 g, 19.2 mmol) was purged with argon for 30 min. To the resulting solution was added 2% solution of 1,1,3,3-tetramethyldivinyl disiloxane platinum (0) complex in xylene (23 mL, 0.96 mmol) and stirred at room temperature for 2 h. The reaction mixture was heated to 90° C. for 4 h. The reaction mixture was concentrated in vacuo resulting in the crude compound which was purified by column chromatography on silica gel eluting with 0-10% ethyl acetate in n-hexane to afford 2.71 g, 45% yield, of a colorless oil of the title compound as a mixture of cis & trans. $^1$H NMR (400 MHz, DMSO-$d_6$) δ=8.80 (br. s, 2H), 7.55 (br. s, 2H), 7.26-7.43 (m, 5H), 6.99 (d, J=19.07 Hz, 1H), 0.34 (br. s, 6H), 0.24 (br. s, 6H); MS (ES$^+$): m/z=315.12 [M+H]$^+$; LCMS: $t_R$=3.81 min.

2-(2-(1,1,3,3-Tetramethyl-3-phenyldisiloxanyl)ethyl) hexahydropyrimidine [Example 14]

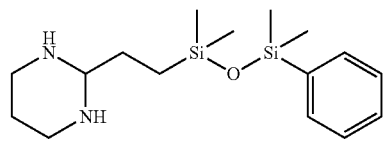 [SMILES: C[Si](C)(CCC1NCCCN1)O[Si](C)(C)c1ccccc1]

A mixture of (E)-2-(2-(1,1,3,3-tetramethyl-3-phenyldisiloxanyl)vinyl)pyrimidine and (Z)-2-(2-(1,1,3,3-tetramethyl-3-phenyldisiloxanyl)vinyl)pyrimidine (300 mg, 0.95 mmol) in DCM (6 mL) was charged with 10% Pd/C (30 mg, 10% w/w) and under argon atmosphere at room temperature. The resulting solution was stirred under hydrogen atmosphere at room temperature for 6 h. The reaction mixture was filtered through a pad of Celite and the filtrate was concentrated in vacuo resulting in the crude compound which was purified by column chromatography on silica gel eluting with 0-35% ethyl acetate in n-hexane to afford 261 mg, 85% yield, of the title compound as white semi solid. $^1$H NMR (400 MHz, DMSO-$d_6$) δ=9.47 (br. s, 2H), 7.49 (dd, J=1.96, 6.85 Hz, 2H), 7.32-7.39 (m, 3H), 3.23 (t, J=5.62 Hz, 4H), 2.30 (dd, J=4.65, 8.56 Hz, 2H), 1.73-1.81 (m, 2H), 1.15-1.25 (m, 1H), 0.78-0.86 (m, 2H), 0.28 (s, 6H), 0.05 (s, 6H); MS (ES$^+$): m/z=322.10 [M+]; LCMS: $t_R$=2.32 min.

Example 15, Example 16, and Example 17

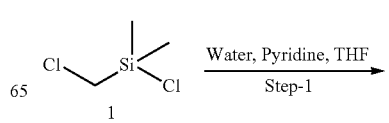

-continued

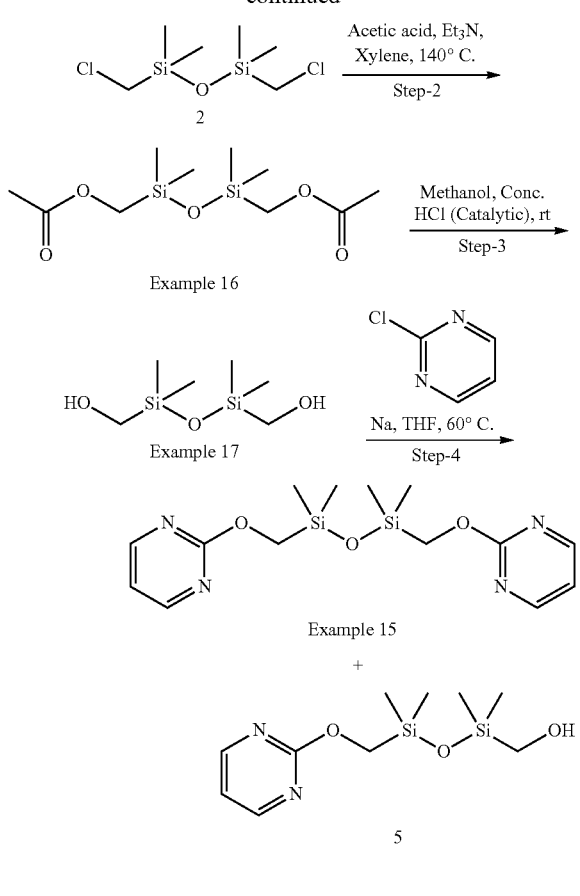

1,1,3,3-Tetramethyl-1,3-bis((pyrimidin-2-yloxy)methyl)disiloxane [Example 15]

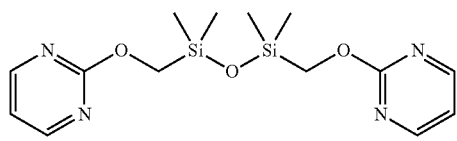 [SMILES: C[Si](C)(COc1ncccn1)O[Si](C)(C)COc1ncccn1]

A solution of (1,1,3,3-tetramethyldisiloxane-1,3-diyl)dimethanol (1 g, 5.14 mmol) and 2-chloropyrimidine (1.17 g, 10.2 mmol) in THF (10 mL) was charged with sodium (236 mg, 10.2 mmol) at room temperature and heated to 60° C. for 30 min. The reaction mixture was diluted with diethyl ether and filtered through a pad of Celite and the filtrate was concentrated in vacuo resulting in the crude compound (mixture of PLF-B-65 and Int-5) which was purified and separated by column chromatography on silica gel followed by reverse phase Combi flash column chromatography to afford 625 mg, 35% yield, of the title compound as a white solid. $^1$H NMR (400 MHz, DMSO-$d_6$) δ=8.54-8.59 (m, 4H), 7.08 (d, J=1.96 Hz, 2H), 3.97 (d, J=1.47 Hz, 4H), 0.15 (d, J=1.96 Hz, 12H), $^1$H NMR (400 MHz, CDCl$_3$) δ=8.50 (d, J=2.45 Hz, 4H), 6.87-6.91 (m, 2H), 4.03 (s, 4H), 0.24 (s, 12H); MS (ES$^+$): m/z=351.10 [M+H]$^+$; LCMS: $t_R$=3.12 min.

(1,1,3,3-Tetramethyldisiloxane-1,3-diyl)dimethanol [Example 17]

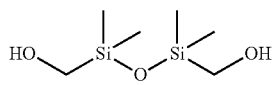

A solution of (1,1,3,3-tetramethyldisiloxane-1,3-diyl)bis(methylene) diacetate (12 g, 43.1 mmol) in methanol (480 mL) was charged with conc. HCl (1.2 mL) at room temperature and stirred for 24 h. The reaction mixture was stirred with solid sodium bicarbonate and concentrated in vacuo and the residue was stirred in ether, filtered. The filtrate was concentrated in vacuo resulting in the crude compound which was purified by column chromatography on silica gel eluting with 0-5% methanol in DCM to afford 7.5 g, 90% yield of the title compound as a colorless oil. $^1$H NMR (400 MHz, DMSO-$d_6$) δ=3.99-4.05 (m, 2H), 3.01 (s, 4H), 0.00 (s, 12H), $^1$H NMR (400 MHz, CDCl$_3$) δ=3.34 (s, 4H), 0.15 (s, 12H); MS (ES$^+$): m/z=195.00 [M+]; LCMS: $t_R$=1.60 min.

(1,1,3,3-Tetramethyldisiloxane-1,3-diyl)bis(methylene) diacetate [Example 17]

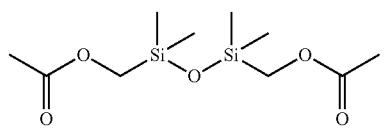 [SMILES: CC(=O)OC[Si](C)(C)O[Si](C)(C)COC(C)=O]

A solution of acetic acid (6.9 mL, 121.1 mmol) in xylene (140 mL) was charged with triethyl amine (16.9 mL, 121.1 mmol), 1,3-bis(chloromethyl)-1,1,3,3-tetramethyldisiloxane (14 g, 60.5 mmol) at room temperature and heated to 140° C. for 14 h. The reaction mixture was concentrated in vacuo, diluted with diethyl ether and the solid precipitated was filtered. The filtrate was concentrated in vacuo, resulting in the crude compound which was purified by column chromatography on silica gel eluting with 5-15% ethyl acetate in n-hexane to afford 12.6 g, 75% yield, of the title compound as colorless oil. $^1$H NMR (400 MHz, DMSO-$d_6$) δ=3.60 (s, 4H), 1.94 (s, 6H), 0.06 (s, 12H); $^1$H NMR (400 MHz, CDCl$_3$) δ=3.71 (s, 4H), 2.06 (s, 6H), 0.16 (s, 12H).

1,3-Bis(chloromethyl)-1,1,3,3-tetramethyldisiloxane (2)

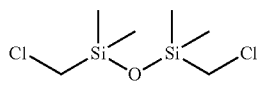

A solution of ice cold pyridine (12.4 mL, 139.7 mmol) and H$_2$O (1.25 mL, 69.8 mmol) in THF (600 mL) was charged with chloro(chloromethyl)dimethylsilane (20 g, 139.7 mmol) dropwise and stirred at room temperature for 1 h. The solid precipitated was filtered and the filtrate was concentrated in vacuo to afford 14.4 g of the title compound as colourless oil. The crude compound was used in the next step without further purification or analysis.

Example 19

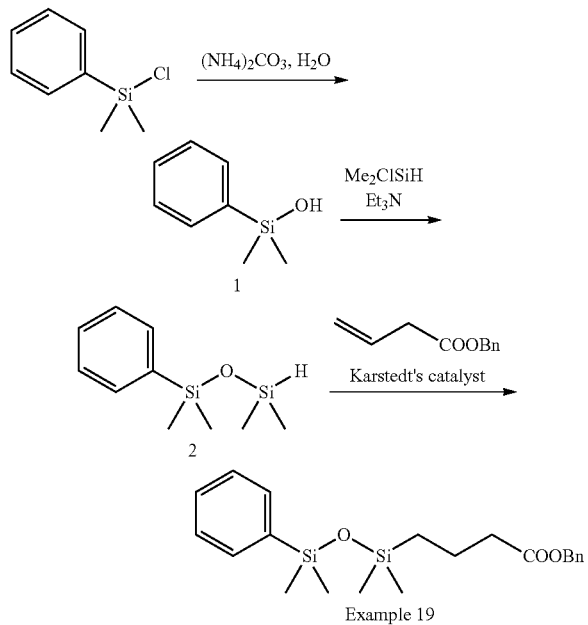

Benzyl 4-(1,1,3,3-tetramethyl-3-phenyldisiloxanyl)butanoate [Example 19]

A catalytic quantity of Karstedt's catalyst (platinum-divinyltetramethyldisiloxane complex, in xylene, Pt ~2%, 10 mg) was added to a solution of compound 2 (2.1 g, 10 mmol) and benzyl 2-(benzyloxycarbonylamino)acrylate (1.7 g, 10 mmol) in dry toluene (5 mL). The reaction mixture was stirred for 2 h at 70° C. under nitrogen atmosphere. The solvent was removed under reduced pressure and the residue was further purified by flash column chromatography on silica gel (hexane:EtOAc=50:1) to afford the desired product (2.7 g, 70.0% yield) as an oil. $^1$H NMR (400 MHz, CDCl$_3$): δ 7.45-7.50 (m, 2H), 7.20-7.40 (m, 9H), 5.06 (s, 2H), 2.28 (t, J=7.6 Hz, 2H), 1.60 (m, 2H), 0.50 (m, 2H), 0.00 (m, 6H).

Dimethyl(phenyl)silanol (1)

Chlorodimethyl(phenyl)silane (5.0 g, 29 mmol) was added dropwise to a rapidly stirred suspension of ammonium carbonate (5.7 g, 59.3 mmol) in ether (50 mL) and saturated NaCl aqueous (20 mL) over 5 min at room temperature. The reaction mixture was stirred for further 10 min, then separated. And the aqueous layer was re-extracted with ether (10 mL×3). The combined organic layers were dried over Na$_2$SO$_4$, filtered and concentrated to afford 1 (4.5 g, ~100% yield), which was used for next step without further purification.

1,1,3,3-tetramethyl-1-phenyldisiloxane (2)

Chlorodimethylsilane (2.8 g, 29 mmol) was added to a stirred solution of compound 1 (4.5 g, 29 mmol) and triethylamine (5.9 g, 58 mmol) in DCM (20 mL) at room temperature. The reaction mixture was stirred for 30 min. The mixture was washed with saturated NaCl aqueous (10 mL×2). The organic layer was dried over anhydrous Na$_2$SO$_4$, filtered and concentrated to afford 2 (3.5 g, 57.6% yield), which was used for next step without further purification.

Example 20

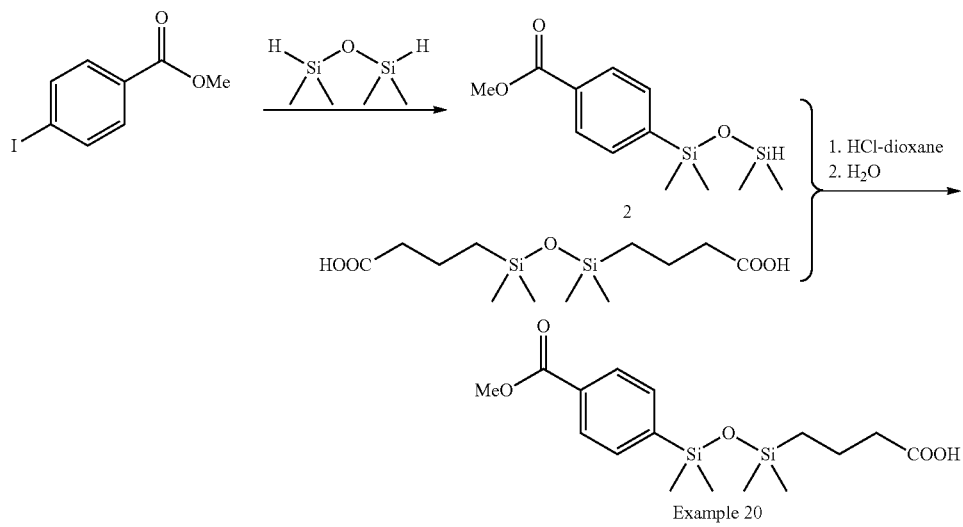

4-(3-(4-(methoxycarbonyl)phenyl)-1,1,3,3-tetramethyldisiloxanyl)butanoic Acid [Example 20]

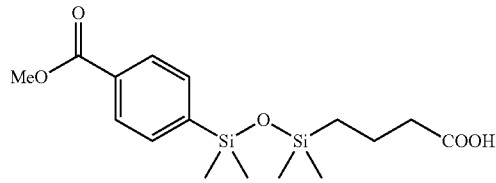 [SMILES: COC(=O)c1ccc([Si](C)(C)O[Si](C)(C)CCCC(=O)O)cc1]

A solution of HCl-dioxane (5N, 10 mL) was added to a mixture of compound 3 (2.6 g, 9 mmol) and 1,3-bis(3-carboxypropyl)tetramethyldisiloxane (3.4 g, 11 mmol) in dioxane (5 mL) at room temperature. The reaction mixture was stirred for 2 h. The solvent was removed under reduced pressure. The residue was dissolved in ACN (10 mL), followed by the addition of H$_2$O (~0.5 mL). The mixture was stirred for 3 h. The solvent was removed by rotary evaporation. The crude product was purified by column chromatography on silica gel (hexane:EtOAc=20:1) to afford the desired (3.0 g, 88.3% yield). $^1$H NMR (400 MHz, CDCl$_3$): δ 7.93 (d, J=8.4 Hz, 2H), 7.53 (d, J=8.4 Hz, 2H), 3.85 (s, 3H), 2.28 (t, 2H), 1.58 (m, 2H), 0.51 (m, 2H), 0.35 (s, 6H), 0.04 (s, 6H). ESI for C$_{16}$H$_{26}$O$_5$Si$_2$. Found 353.29 [M−H]$^-$.

Methyl 4-[dimethylsilyloxy(dimethyl)silyl]benzoate (2)

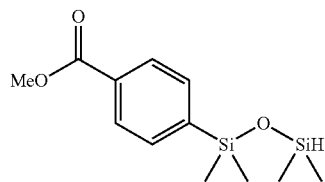

DIEA (2.95 g, 23 mmol) was added to a solution of methyl 4-iodobenzoate (3.0 g, 11 mmol) in dry toluene (15 mL), followed by the addition of Pd(P(tBu)$_3$)$_2$ (291 mg, 0.57 mmol) and 1,1,3,3-tetramethyldisiloxane (2.3 g, 17 mmol) at 0° C. under nitrogen atmosphere. The reaction mixture was stirred for 2 h, then quenched with water (20 mL). The organic phase was separated and washed with brine (20 mL), dried over anhydrous Na$_2$SO$_4$, concentrated to dryness to afford compound 1 (2.6 g, 88.1% yield), which was used for next step without further purification.

Example 21

Benzyl 4-(3-(3-(((benzyloxy)carbonyl)amino)propyl)-1,1,3,3-tetramethyldisiloxanyl)butanoate [Example 21]

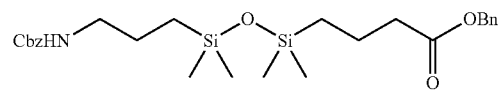

Pt(0) (Karstedt's Catalyst, 15 mg) was added to a mixture of compound 1 (1.9 g, 10.0 mmol) and dimethylsilyloxy(dimethyl)silane (1.3 g, 10.0 mmol) in toluene (5 mL) at room temperature under nitrogen atmosphere. Benzyl but-3-enoate (1.8 g, 10.0 mmol) was subsequently added to the mixture. The reaction mixture was heated to 80° C. and stirred for 2 h. The reaction was judged to be complete by GC-MS analysis, then concentrated. The crude product was purified by column chromatography on silica gel (hexane:EtOAc=40:1) to afford the desired product (1.2 g, 64.5% yield). $^1$H NMR (300 MHz, CDCl$_3$): δ 7.33-7.38 (m, 10H), 5.12-5.14 (m, 4H), 4.93 (s, 1H), 3.17 (m, 2H), 2.40 (m, 2H), 1.68 (m, 3H), 1.52 (m, 2H), 0.95 (d, J=7.5 Hz, 1H), 0.51-0.57 (m, 4H), 0.05-0.13 (m, 12H). ESI for C$_{26}$H$_{39}$NO$_5$Si$_2$. Found 502.5 [M+H]$^+$.

Benzyl allylcarbamate (1)

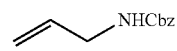

Cbz-OSu (13.7 g, 58.8 mmol) was added to a suspension of allylamine (2.7 g, 54 mmol) and Na$_2$CO$_3$ (12.5 g, 118 mmol) in acetonitrile (50 mL) and H$_2$O (100 mL) at room temperature. The reaction mixture was stirred for 2 h, then diluted with H$_2$O (100 mL). The mixture was extracted with EtOAc (100 mL×3). The combined organic layers were dried over Na$_2$SO$_4$, concentrated to afford compound 1 (9.1 g, 88.2% yield).

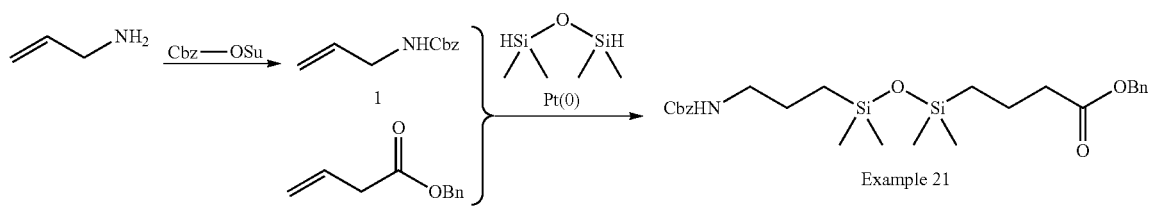

Example 21

Example 24

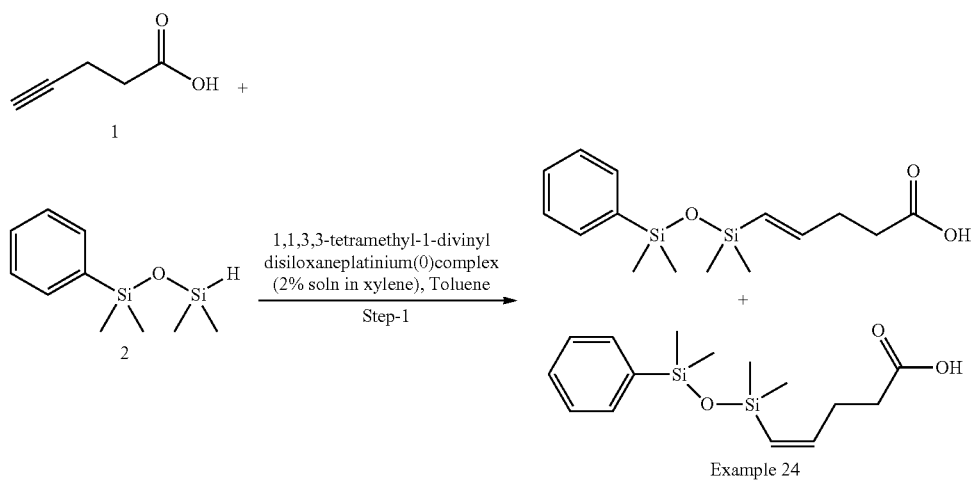

(E) and (Z)-5-(1,1,3,3-Tetramethyl-3-phenyldisiloxanyl)pent-4-enoic Acid [Example 24]

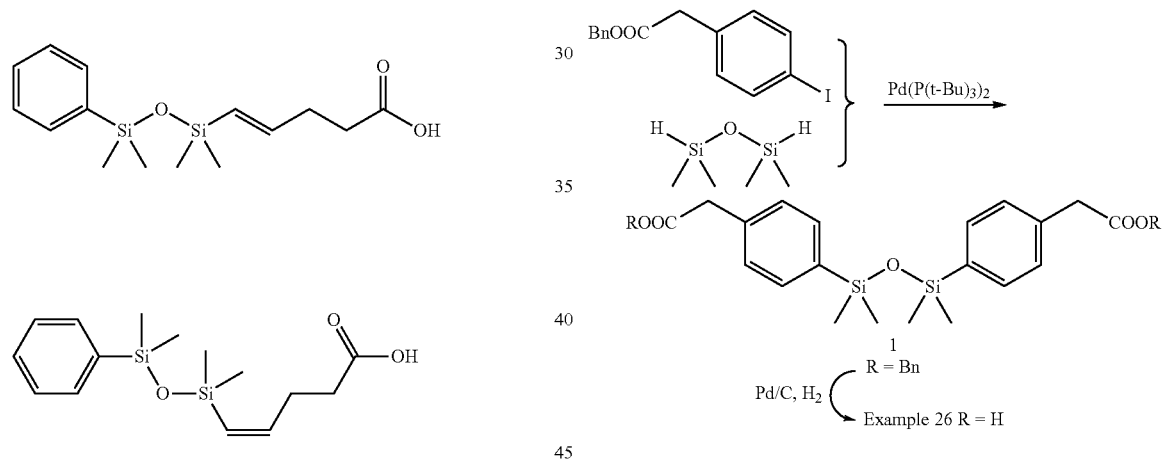

A solution of pent-4-ynoic acid (1 g, 10.19 mmol) in toluene (10 mL) was charged with 1,1,3,3-tetramethyl-1-phenyldisiloxane (2.14 g, 10.19 mmol) and purged with argon at room temperature for 30 min. To the resulting solution was added and 2% solution of 1,1,3,3-tetramethyl-1-divinyldisiloxane platinum(0) complex in xylene (12.1 mL, 0.51 mmol) and stirred at room temperature for 1 h. The reaction mixture was concentrated in vacuo resulting in the crude compound which was purified by column chromatography on silica gel eluting with 5-20% ethyl acetate in n-hexane to afford 2.5 g (80% yield), trans-cis isomers of the title compound as a colorless oil. $^1$H NMR (400 MHz, DMSO-$d_6$) δ=11.97 (br. s, 2H), 7.26-7.49 (m, 10H), 6.02 (d, J=18.59 Hz, 2H), 5.46-5.58 (m, 2H), 2.22 (d, J=15.65 Hz, 8H), 0.20 and 0.22 (2s, 12H), 0.01 and 0.03 (2s, 12H), $^1$H NMR (400 MHz, CDCl$_3$) δ 7.33-7.59 (m, 10H), 6.09 (d, J=19.07 Hz, 2H), 5.55-5.72 (m, 2H), 2.45 (d, J=14.67 Hz, 8H), 0.34 and 0.32 (2s, 12H), 0.15 and 0.13 (2s, 12H); MS (ES$^+$): m/z=291.00 [M−18]$^+$; LCMS: $t_R$=3.42 min.

Example 26

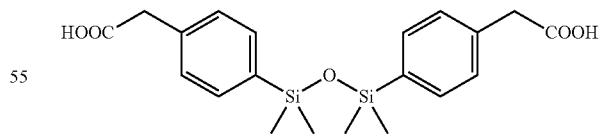

2,2'-((1,1,3,3-tetramethyldisiloxane-1,3-diyl)bis(4,1-phenylene))diacetic Acid [Example 26]

Compound 1 (900 mg, 1.5 mmol) was dissolved in methanol (20 mL) at room temperature, followed by the addition of Pd/C (10%, 500 mg). The reaction was stirred for 5 h under H$_2$. The mixture was filtered, and the filtrate was concentrated to dryness to afford the desired product (403 mg, 66.8% yield). $^1$H NMR (400 MHz, DMSO): δ 7.46 (d, J=8.0 Hz, 4H), 7.25 (d, J=8.0 Hz, 4H), 3.56 (s, 4H), 0.30 (s, 12H). ESI for C$_{20}$H$_{26}$O$_5$Si$_2$. Found 401.47 [M−H]$^−$.

83
Dibenzyl 2,2'-((1,1,3,3-tetramethyldisiloxane-1,3-diyl)bis(4,1-phenylene))diacetate (1)

84
4-Methyl-2-(((1,1,3,3,3-pentamethyldisiloxanyl)methyl)thio)pyrimidine [Example 27]

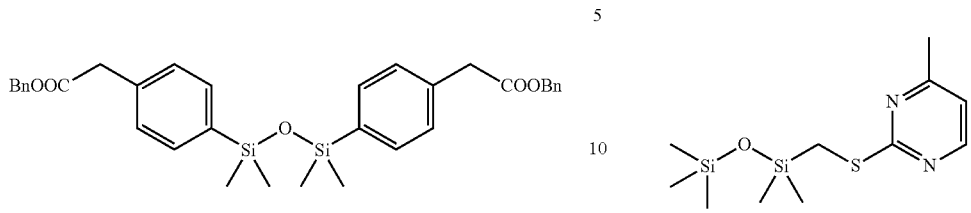

Compound benzyl 2-(4-iodophenyl)acetate (1.15 g, 3 mmol) was added to a solution of 1,1,3,3-tetramethyldisiloxane (225 mg, 1.5 mmol) in THF (40 mL) under nitrogen atmosphere. Pd(P(t-Bu)$_3$)$_2$ (4 mg) was subsequently added to the mixture, followed by the addition of DIEA (800 mg, 6.5 mmol). The reaction mixture was stirred at room temperature for 2.5 h. The mixture was concentrated to dryness, and the residue was purified by prep-HPLC to afford 1 (975 mg, 65% yield).

Example 27, Example 28, Example 29, Example 30 and Example 31

K$_2$CO$_3$ (4.3 g, 31 mmol) was added to a solution of 4-methylpyrimidine-2-thiol (2.5 g, 15.4 mmol) and 18-crown-6 (0.21 g, 0.8 mmol) in toluene (50 mL). The mixture was stirred at 120° C. for 1 h. Then chloromethylpentamethyldisiloxane (3.0 g, 15.2 mmol) and NaI (0.12 g, 0.8 mmol) were added. The mixture was stirred at 120° C. for another 4 h. After cooled to room temperature, the solid was filtered. The filtrate was concentrated to dryness. The residue was purified by flash column chromatography on silica gel (EtOAc/hexane=1:50 to 1:30) to afford the desired product (3.1 g, 68.2% yield). $^1$H NMR (400 MHz, CDCl$_3$): δ 8.24-8.25 (d, J=5.2 Hz, 1H), 6.68-6.70 (d, J=5.2 Hz, 1H),

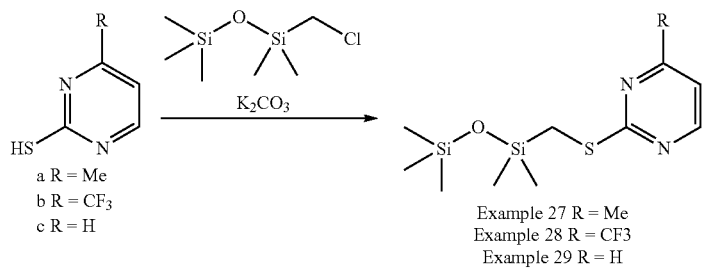

a R = Me
b R = CF$_3$
c R = H

Example 27 R = Me
Example 28 R = CF3
Example 29 R = H

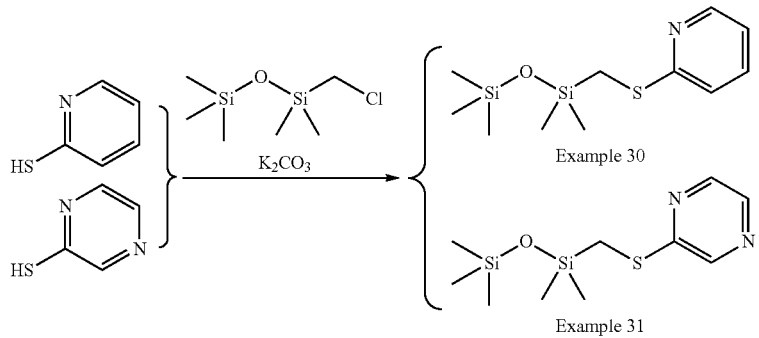

2.33 (s, 3H), 2.31 (s, 2H), 0.10 (s, 6H), 0.00 (s, 9H). ESI for C₁₁H₂₂N₂OSSi₂. Found 287.63 [M+H]⁺.

2-(((1,1,3,3,3-pentamethyldisiloxanyl)methyl)thio)-4-(trifluoromethyl)pyrimidine [Example 28]

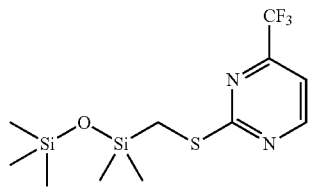 [SMILES: C[Si](C)(C)O[Si](C)(C)CSc1nccc(C(F)(F)F)n1]

Example 28 (1.6 g, 75.3% yield) was prepared from 4-(trifluoromethyl) pyrimidine-2-thiol following the same procedure for synthesizing Example 27. ¹H NMR (400 MHz, CDCl₃): δ 8.62-8.64 (d, J=4.8 Hz, 1H), 7.14-7.15 (d, J=4.8 Hz, 1H), 2.34 (s, 2H), 0.10 (s, 6H), 0.00 (s, 9H). ESI for C₁₁H₁₉F₃N₂OSSi₂. Found 341.41 [M+H]⁺.

2-(((1,1,3,3,3-pentamethyldisiloxanyl)methyl)thio) pyrimidine [Example 29]

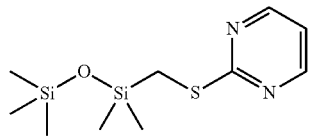 [SMILES: C[Si](C)(C)O[Si](C)(C)CSc1ncccn1]

Example 29 (5.6 g, 78.8% yield) was prepared from pyrimidine-2-thiol following the same procedure for compound Example 27. ¹H NMR (400 MHz, CDCl₃): δ 8.42 (s, 1H), 8.41 (s, 1H), 6.83-6.86 (t, 1H), 2.31 (s, 2H), 0.10 (s, 6H), 0.00 (s, 9H). ESI for C₁₀H₂₀N₂OSSi₂. Found 273.58 [M+H]⁺.

2-(((1,1,3,3,3-pentamethyldisiloxanyl)methyl)thio) pyridine [Example 30]

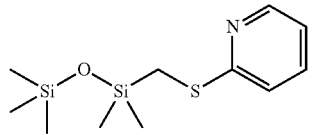 [SMILES: C[Si](C)(C)O[Si](C)(C)CSc1ccccn1]

Example 30 (1.6 g, 75.6% yield) was prepared from pyridine-2-thiol following the same procedure for compound Example 27. ¹H NMR (400 MHz, CDCl₃): δ 8.31 (m, 1H), 7.34-7.38 (m, 1H), 7.10-7.16 (m, 1H), 6.83-6.87 (m, 1H), 2.28 (s, 2H), 0.10 (s, 6H), 0.00 (s, 9H). ESI for C₁₁H₂₁NOSSi₂. Found 272.2 [M+H]⁺.

2-(((1,1,3,3,3-pentamethyldisiloxanyl)methyl)thio) pyrazine [Example 31]

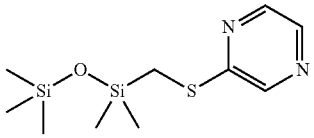 [SMILES: C[Si](C)(C)O[Si](C)(C)CSc1cnccn1]

Example 31 (3.5 g, 75.3% yield) was prepared from pyrazine-2-thiol following the same procedure for compound Example 27. ¹H NMR (400 MHz, CDCl₃): δ 8.39-8.40 (d, J=2.4 Hz, 1H), 8.25-8.26 (m, 1H), 8.07-8.08 (d, J=2.4 Hz, 1H), 2.26 (s, 2H), 0.10 (s, 6H), 0.00 (s, 9H). ESI for C₁₀H₂₀N₂OSSi₂. Found 273.65 [M+H]⁺.

Example 32

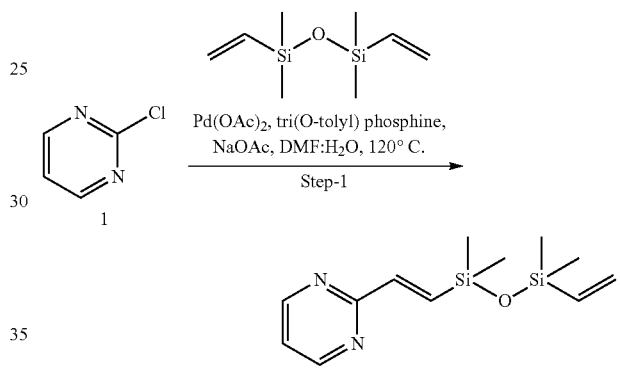

Example 32

(E)-2-(2-(1,1,3,3-Tetramethyl-3-vinyldisiloxanyl) vinyl)pyrimidine [Example 32]

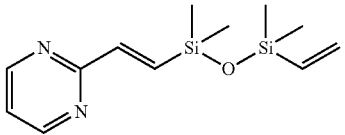 [SMILES: C=C[Si](C)(C)O[Si](C)(C)/C=C/c1ncccn1]

A solution of 2-chloropyrimidine (10 g, 87.3 mmol) in DMF (200 mL) was charged with 1,1,3,3-tetramethyl-1,3-divinyldisiloxane (24.4 g, 131.0 mmol), palladium acetate (1.96 g, 8.73 mmol), tri(O-tolyl) phosphine (5.3 g, 17.4 mmol) and solution of sodium acetate (21.4 g, 262.0 mmol) in H₂O (10 mL) at room temperature and heated to 120° C. for 14 h. The reaction mixture was diluted with H₂O and DCM, the emulsion formed was filtered through a pad of Celite. The separated organic layer was washed with H₂O and dried over anhydrous Na₂SO₄, filtered and concentrated in vacuo resulting in the crude compound which was purified by column chromatography on silica gel followed by combiflash column chromatography to afford 3.40 g, 15% yield, of the title compound as a colorless oil. ¹H NMR (400 MHz, DMSO-d₆) δ=8.80 (d, J=4.89 Hz, 2H), 7.38 (t, J=4.89 Hz, 1H), 7.30 (d, J=19.07 Hz, 1H), 6.98 (d, J=18.59 Hz, 1H), 6.10-6.17 (m, 1H), 5.97 (dd, J=3.91, 14.67 Hz, 1H), 5.73-5.81 (m, 1H), 0.24 (s, 6H), 0.16 (s, 6H), ¹H NMR (400 MHz, CDCl₃) δ=8.60-8.77 (m, 2H), 7.38 (d, J=19.07 Hz, 1H), 7.12 (d, J=8.80 Hz, 2H), 6.09-6.22 (m, 1H), 5.95 (d, J=14.18 Hz, 1H), 5.71-5.79 (m, 1H), 0.26 (s, 6H), 0.18 (s, 6H); MS (ES⁺): m/z=265.07 [M+H]⁺; LCMS: t_R=3.72 min.

Example 33 and Example 34

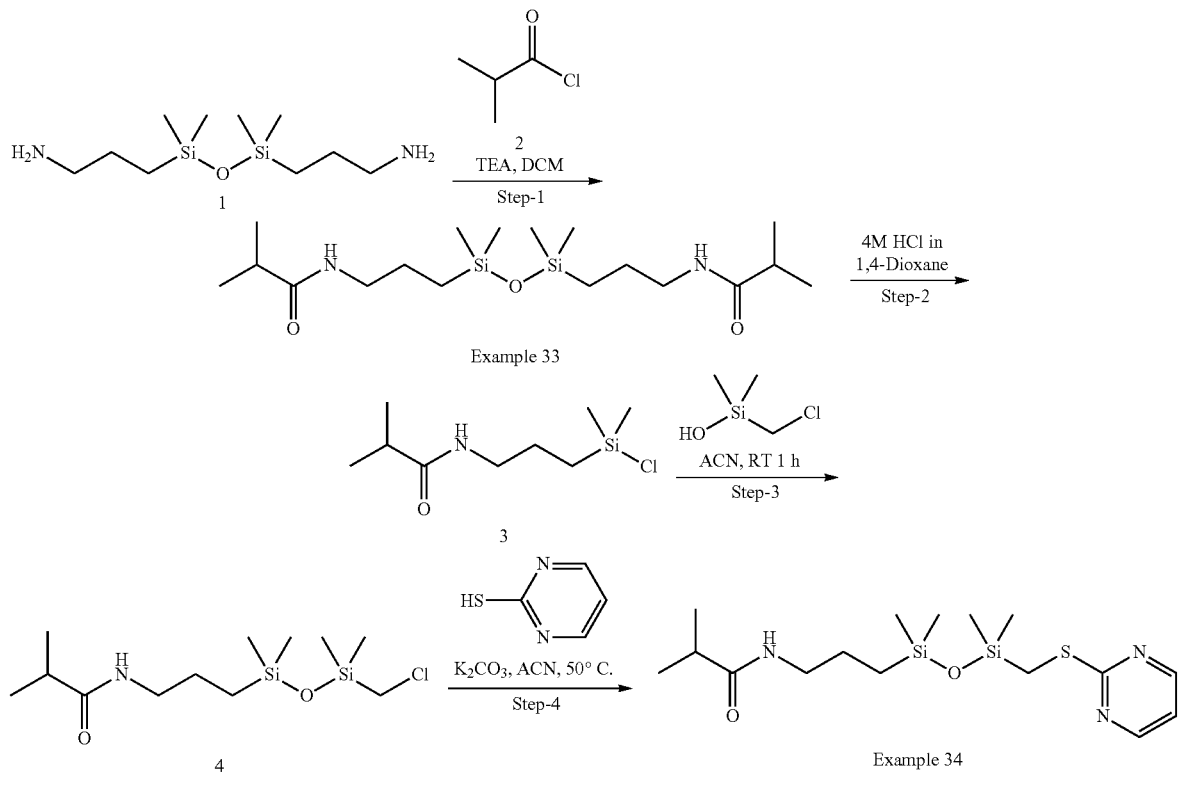

N-(3-(1,1,3,3-Tetramethyl-3-((pyrimidin-2-ylthio)methyl)disiloxanyl)propyl) isobutyramide [Example 34]

A solution of pyrimidine-2-thiol (91 mg, 0.81 mmol) in acetonitrile (10 mL) was charged with potassium carbonate (111 mg, 0.81 mmol) and N-(3-(3-(chloromethyl)-1,1,3,3-tetramethyldisiloxanyl)propyl)isobutyramide (250 mg, 0.81 mmol) at room temperature and was further heated to 50° C. for 3 h. The reaction mixture was concentrated in vacuo resulting in the crude compound which was purified by column chromatography on silica gel eluting with 20-40% ethyl acetate in n-hexane to afford 280 mg, 90% yield, of as colorless oil. ¹H NMR (400 MHz, DMSO-d₆) δ=8.57 (d, J=4.89 Hz, 2H), 7.62 (br. s, 1H), 7.14 (t, J=4.89 Hz, 1H), 2.89-2.97 (m, 2H), 2.32 (s, 2H), 2.20-2.29 (m, 1H), 1.33 (td, J=7.70, 15.90 Hz, 2H), 0.92 (d, J=6.85 Hz, 6H), 0.39-0.47 (m, 2H), 0.11 (s, 6H), 0.050 (s, 6H).

¹H NMR (400 MHz, CDCl₃) δ=8.51 (d, J=3.91 Hz, 2H), 6.95 (br. s, 1H), 3.22 (d, J=6.36 Hz, 2H), 2.42 (s, 2H), 2.27-2.37 (m, 1H), 1.54 (d, J=7.34 Hz, 2H), 1.15 (d, J=6.36 Hz, 6H), 0.50-0.58 (m, 2H), 0.21 (s, 6H), 0.09 (s, 6H); MS (ES⁺): m/z=385.85 [M+H]⁺; LCMS: t_R=3.43 min.

N-(3-(3-(Chloromethyl)-1,1,3,3-tetramethyldisiloxanyl)propyl)isobutyramide (4)

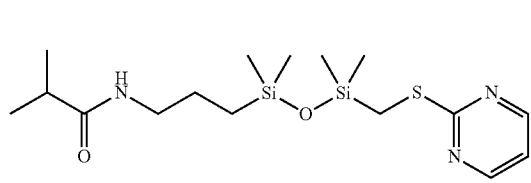

A solution of N-(3-(chlorodimethylsilyl)propyl)isobutyramide (569 mg, 2.57 mmol) in acetonitrile (10 mL) was charged with (chloromethyl)dimethylsilanol (319 mg, 2.57 mmol) and stirred at room temperature for 1 h. The reaction mixture was concentrated in vacuo, dissolved in diethyl ether and concentrated resulting in the crude compound which was purified by column chromatography on silica gel eluting with 10-40% ethyl acetate in n-hexane to afford 557 mg, 70% yield, of the title compound as a colorless oil. ¹H NMR (400 MHz, DMSO-d₆) δ=7.62 (br. s, 1H), 2.88-2.96 (m, 2H), 2.78 (s, 2H), 2.21-2.29 (m, 1H), 1.27-1.36 (m, 2H), 0.91 (d, J=6.85 Hz, 6H), 0.39-0.46 (m, 2H), 0.09 (s, 6H), 0.00 (s, 6H).

N-(3-(Chlorodimethylsilyl)propyl)isobutyramide (3)

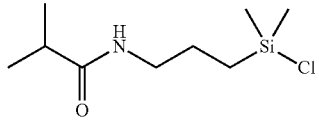

A solution of N,N'-((1,1,3,3-tetramethyldisiloxane-1,3-diyl)bis(propane-3,1-diyl))bis(2-methylpropanamide) (1 g, 2.57 mmol) in dioxane: HCl (4M, 10 mL) was stirred at room temperature for 1 h. The reaction mixture was concentrated in vacuo resulting in 569 mg of the title compound as a colorless oil. The crude compound was used in the next step without further purification and analysis.

N,N'-((1,1,3,3-Tetramethyldisiloxane-1,3-diyl)bis(propane-3,1-diyl))bis(2-methylpropanamide) [Example 33]

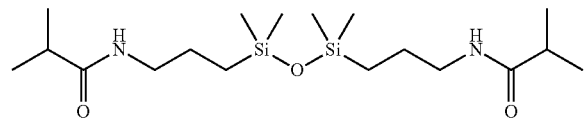 [SMILES: CC(C)C(=O)NCCC[Si](C)(C)O[Si](C)(C)CCCNC(=O)C(C)C]

A solution of 3,3'-(1,1,3,3-tetramethyldisiloxane-1,3-diyl)bis(propan-1-amine) (1 g, 4.03 mmol) in DCM (10 mL) at 0° C. was charged with triethyl amine (1.4 mL, 10.0 mmol) and isobutyryl chloride (0.92 mL, 8.80 mmol) and stirred at room temperature for 1 h. The solid precipitated was filtered, washed with diethyl ether and the filtrate was concentrated in vacuo resulting in the crude compound which was purified by column chromatography on silica gel eluting with 10-40% ethyl acetate in n-hexane to afford 1.25 g, 80% yield, of the title compound as a white solid. $^1$H NMR (400 MHz, DMSO-$d_6$) δ=7.66 (br. s, 2H), 2.95 (d, J=6.36 Hz, 4H), 2.29 (t, J=6.60 Hz, 2H), 1.31-1.40 (m, 4H), 0.95 (d, J=6.85 Hz, 12H), 0.38-0.47 (m, 4H), 0.00 (s, 12H); MS-ELSD (ES$^+$): m/z=411.00 [M+Na]$^+$; LCMS: $t_R$=2.72 min.

Example 35

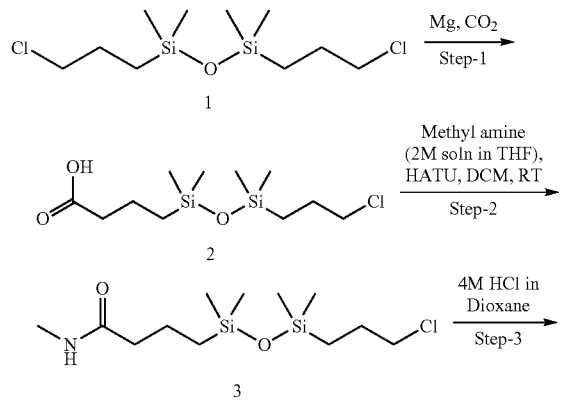

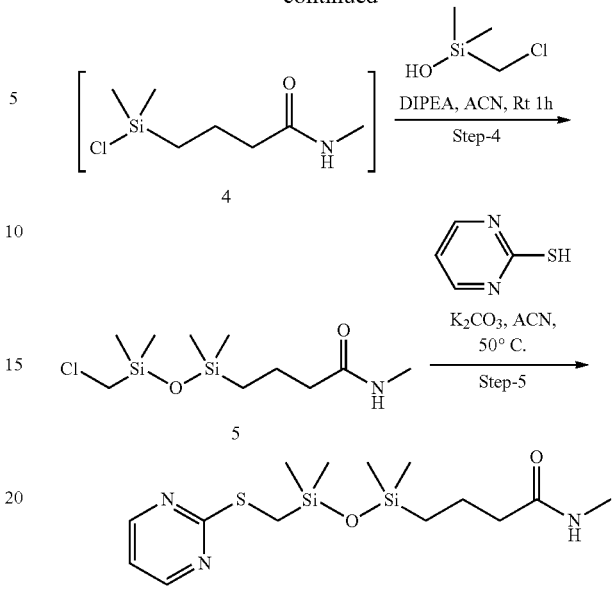

Example 35

N-Methyl-4-(1,1,3,3-tetramethyl-3-((pyrimidin-2-ylthio)methyl)disiloxanyl)butanamide [Example 35]

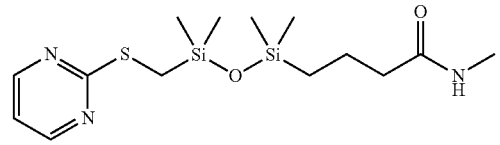 [SMILES: CNC(=O)CCC[Si](C)(C)O[Si](C)(C)CSc1ncccn1]

A solution of 4-(3-(chloromethyl)-1,1,3,3-tetramethyldisiloxanyl)-N-methylbutanamide (200 mg, 0.71 mmol) in acetonitrile (10 mL) was charged with potassium carbonate (147 mg, 1.06 mmol) and pyrimidine-2-thiol (79 mg, 0.71 mmol) at room temperature and heated to 50° C. for 2 h. The reaction mixture was concentrated in vacuo, diluted with ethyl acetate and stirred for 15 min. The solid was filtered and the filtrate was concentrated in vacuo resulting in the crude compound which was purified by column chromatography on silica gel eluting with 40-50% ethyl acetate in n-hexane to afford 58 mg, 23% yield, of the title compound as a colorless oil. $^1$H NMR (400 MHz, DMSO-$d_6$) δ=8.57 (d, J=4.89 Hz, 2H), 7.61 (br. s, 1H), 7.14 (t, J=4.89 Hz, 1H), 2.49 (d, J=4.40 Hz, 2H), 2.33 (s, 2H), 1.99 (t, J=7.34 Hz, 2H), 1.41-1.50 (m, 3H), 0.39-0.46 (m, 2H), 0.11 (s, 6H), 0.00 (s, 6H); MS (ESMS): m/z=380.00 [M+Na]$^+$.

4-(3-(Chloromethyl)-1,1,3,3-tetramethyldisiloxanyl)-N-methylbutanamide (5)

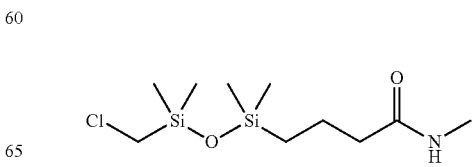

A solution of 4-(3-(3-chloropropyl)-1,1,3,3-tetramethyldisiloxanyl)-N-methylbutanamide (450 mg, 1.45 mmol) in dioxane: HCl (4M, 10 mL) was stirred at room temperature for 1 h. The reaction mixture was concentrated in vacuo resulting in the crude chloro intermediate which was used further without purification. The crude intermediate was dissolved in acetonitrile (10 mL) followed by addition of DIPEA (0.5 mL, 2.91 mmol) and (chloromethyl)dimethylsilanol (361 mg, 2.91 mmol) and stirred at room temperature for 1 h. The reaction mixture was concentrated in vacuo resulting in the crude compound which was purified by column chromatography on silica gel eluting with 30-60% ethyl acetate in n-hexane to afford 204 mg, 50% yield, of the title compound as a colorless oil. $^1$H NMR (400 MHz, DMSO-$d_6$) δ=7.66 (br. s, 1H), 2.54 (d, J=4.40 Hz, 3H), 2.05 (t, J=7.34 Hz, 2H), 1.66-1.76 (m, 1H), 1.46-1.56 (m, 2H), 0.56-0.63 (m, 1H), 0.43-0.51 (m, 2H), 0.15 (s, 3H), 0.06 (s, 6H), 0.04 (s, 3H).

4-(3-(3-Chloropropyl)-1,1,3,3-tetramethyldisiloxanyl)-N-methylbutanamide (3)

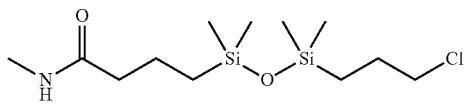 [SMILES: CNC(=O)CCC[Si](C)(C)O[Si](C)(C)CCCCl]

A solution of 4-(3-(3-chloropropyl)-1,1,3,3-tetramethyldisiloxanyl)butanoic acid (750 mg, 2.53 mmol) in dichloromethane (10 mL) was charged with potassium carbonate (699 mg, 5.06 mmol), HATU (1.24 g, 3.29 mmol), 2M solution of methyl amine in THF (2.5 mL, 5.06 mmol) and stirred at room temperature for 3 h. The reaction mixture was concentrated in vacuo resulting in the crude compound which was purified by column chromatography on silica gel eluting with 30-60% ethyl acetate in n-hexane to afford 469 mg, 60% yield, of the title compound as a colorless oil. $^1$H NMR (400 MHz, DMSO-$d_6$) δ=7.62 (br. s, 1H), 3.56 (t, J=5.96 Hz, 2H), 2.51 (br. s, 3H), 2.01 (t, J=6.68 Hz, 2H), 1.68 (d, J=6.68 Hz, 2H), 1.47 (d, J=6.68 Hz, 2H), 0.57 (d, J=8.11 Hz, 2H), 0.43 (d, J=7.63 Hz, 2H), 0.01 (br. s, 12H).

4-(3-(3-Chloropropyl)-1,1,3,3-tetramethyldisiloxanyl)butanoic Acid (2)

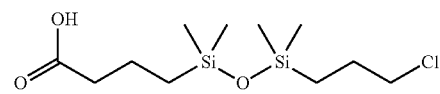 [SMILES: C[Si](C)(CCCCl)O[Si](C)(C)CCCC(=O)O]

A solution of magnesium (183 mg, 7.65 mmol) in THF (10 mL) was added a pinch of iodine and 1,3-bis(3-chloropropyl)-1,1,3,3-tetramethyldisiloxane (1 g, 3.48 mmol) dropwise at room temperature and further heated to 60° C. for 2 h. The resulting solution was slowly cooled to −78° C. and charged with dry ice. The reaction mixture was warmed to room temperature and quenched with dilute hydrochloric acid solution and extracted with ethyl acetate (3×25 mL). The combined organic layers were dried over anhydrous Na$_2$SO$_4$, filtered and concentrated in vacuo resulting in the crude compound which was purified by column chromatography on silica gel eluting with 40-50% ethyl acetate in n-hexane to afford 772 mg, 75% yield, of the title compound as a colorless oil. $^1$H NMR (400 MHz, DMSO-$d_6$) δ=11.95 (br. s, 1H), 3.52-3.66 (m, 3H), 2.21 (t, J=6.44 Hz, 2H), 1.53 (d, J=6.68 Hz, 2H), 0.47-0.63 (m, 5H), 0.04 (br. s, 12H).

Example 36

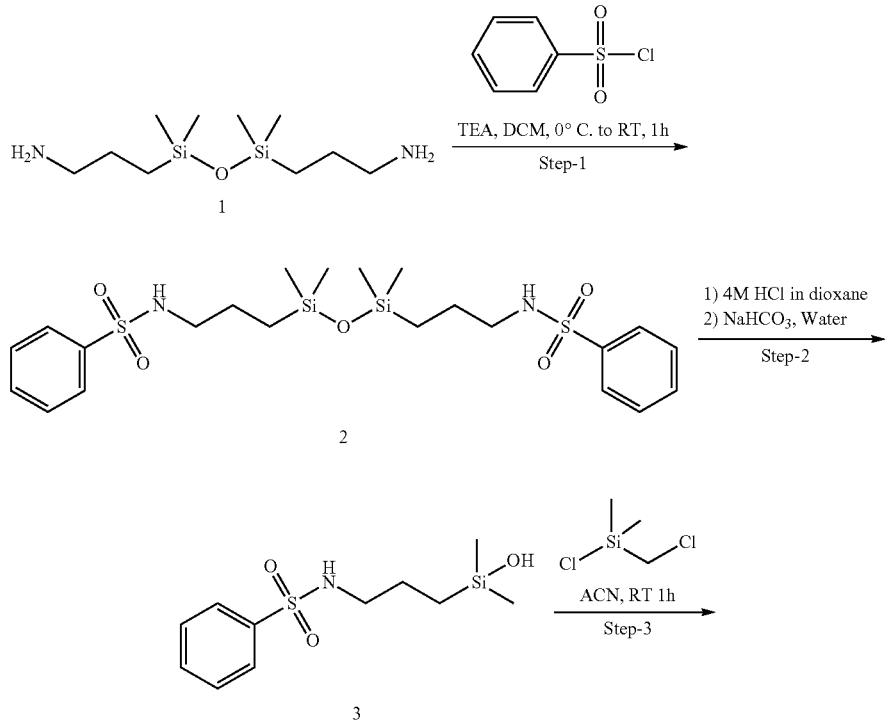

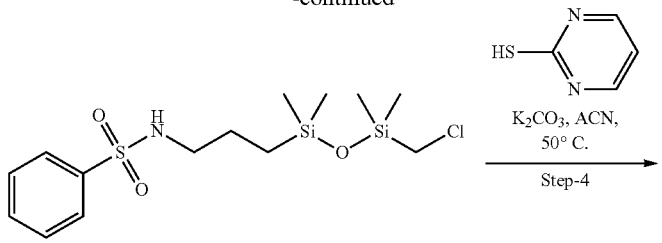

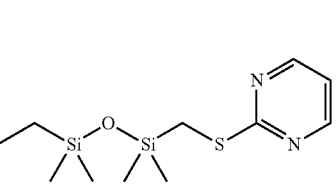

Example 36

N-(3-(1,1,3,3-Tetramethyl-3-((pyrimidin-2-ylthio)methyl)disiloxanyl)propyl) benzenesulfonamide [Example 36]

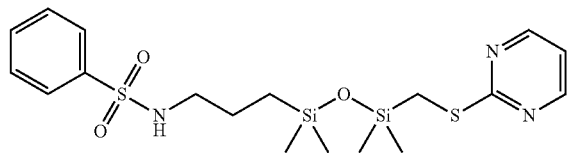 [SMILES: C[Si](C)(CCCNS(=O)(=O)c1ccccc1)O[Si](C)(C)CSc1ncccn1]

A solution of N-(3-(3-(chloromethyl)-1,1,3,3-tetramethyldisiloxanyl)propyl) benzenesulfonamide (600 mg, 1.57 mmol) in acetonitrile (10 mL) was charged with potassium carbonate (326 mg, 2.36 mmol) and pyrimidine-2-thiol (177 mg, 1.57 mmol) at room temperature and heated to 50° C. for 3 h. The reaction mixture was concentrated in vacuo, diluted with ethyl acetate and stirred for 15 min. The solid precipitated was filtered and the filtrate was concentrated in vacuo resulting in the crude compound which was purified by column chromatography on silica gel eluting with 20-40% ethyl acetate in n-hexane to afford 359 mg, 50% yield, of the title compound as a colorless oil. $^1$H NMR (400 MHz, DMSO-$d_6$) δ=8.63 (d, J=4.89 Hz, 2H), 7.79 (d, J=6.85 Hz, 2H), 7.55-7.66 (m, 4H), 7.20 (t, J=4.89 Hz, 1H), 2.67-2.75 (m, 2H), 2.36 (s, 2H), 1.36 (td, J=7.83, 15.65 Hz, 2H), 0.38-0.48 (m, 2H), 0.14 (s, 6H), 0.00 (s, 6H); MS (ELSD): m/z=411.00[M+Na]$^+$; LCMS: $t_R$=2.72 min.

N-(3-(3-(Chloromethyl)-1,1,3,3-tetramethyldisiloxanyl)propyl)benzenesulfonamide (4)

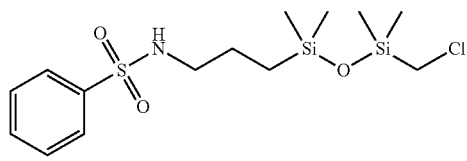 [SMILES: C[Si](C)(CCl)O[Si](C)(C)CCCNS(=O)(=O)c1ccccc1]

A solution of N-(3-(hydroxydimethylsilyl)propyl)benzenesulfonamide (600 mg, 2.19 mmol) in acetonitrile (10 mL) was charged with chloro(chloromethyl)dimethylsilane (312 mg, 2.19 mmol) and stirred at room temperature for 1 h. The reaction mixture was concentrated in vacuo resulting in the crude compound which was purified by column chromatography on silica gel eluting with 15-25% ethyl acetate in n-hexane to afford 626 mg, 75% yield, of the title compound as a colorless oil. $^1$H NMR (400 MHz, DMSO-$d_6$) δ=7.78 (d, J=6.20 Hz, 2H), 7.60 (d, J=6.20 Hz, 4H), 2.81 (br. s, 2H), 2.71 (d, J=5.72 Hz, 2H), 1.35 (br. s, 2H), 0.43 (d, J=7.15 Hz, 2H), 0.11 (br. s, 6H), 0.00 (br. s, 6H).

N-(3-(Hydroxydimethylsilyl)propyl)benzenesulfonamide (3)

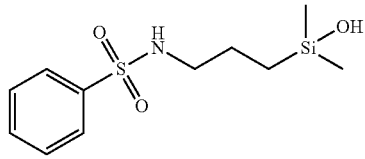 [SMILES: C[Si](C)(O)CCCNS(=O)(=O)c1ccccc1]

A solution of N,N-((1,1,3,3-tetramethyldisiloxane-1,3-diyl)bis(propane-3,1-diyl)) dibenzenesulfonamide (1 g, 1.89 mmol) in 4M HCl in dioxane (10 mL) was stirred at room temperature for 30 min. The reaction mixture was concentrated in vacuo resulting in the crude chloro intermediate which was used in further without purification. To the crude intermediate was added aqueous sodium bicarbonate solution (20 mL) and stirred at room temperature for 30 min. The reaction mixture was extracted with ethyl acetate (3×25 mL) and the combined organic layers were dried over anhydrous Na$_2$SO$_4$, filtered and concentrated in vacuo resulting in the crude compound which was purified by column chromatography on silica gel eluting with 20-40% ethyl acetate in n-hexane to afford 672 mg, 65% yield, of the title compound as a colorless oil. $^1$H NMR (400 MHz, DMSO-$d_6$) δ=7.85 (d, J=6.68 Hz, 2H), 7.67 (d, J=7.15 Hz, 4H), 5.36 (br. s, 1H), 2.77 (d, J=6.20 Hz, 2H), 1.43 (br. s, 2H), 0.45 (d, J=7.15 Hz, 2H), 0.00 (br. s, 6H).

N,N'-((1,1,3,3-Tetramethyldisiloxane-1,3-diyl)bis(propane-3,1-diyl)) dibenzenesulfonamide (2)

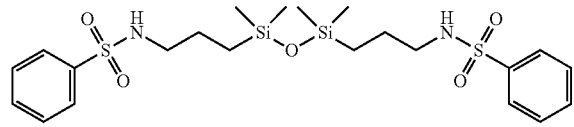 [SMILES: C[Si](C)(CCCNS(=O)(=O)c1ccccc1)O[Si](C)(C)CCCNS(=O)(=O)c1ccccc1]

A solution of 3 3,3'-(1,1,3,3-tetramethyldisiloxane-1,3-diyl)bis(propan-1-amine) (1 g, 4.03 mmol) in dichloromethane (50 mL) at 0° C. was charged with triethyl amine (1.4 mL, 10.08 mmol) and benzenesulfonyl chloride (1.56 g, 8.87 mmol) and stirred at room temperature for 1 h. The reaction mixture was concentrated in vacuo, diluted with diethyl ether and stirred for 15 min. The solid was filtered and the filtrate was concentrated in vacuo resulting in the crude compound which was purified by column chromatography on silica gel eluting with 15-25% ethyl acetate in n-hexane to afford 1.89 g, 89% yield, of the title compound as a white solid. $^1$H NMR (400 MHz, DMSO-$d_6$) δ=7.85 (d, J=7.34 Hz, 4H), 7.62-7.72 (m, 8H), 2.76 (q, J=6.68 Hz, 4H), 1.38 (td, J=7.83, 15.65 Hz, 4H), 0.39-0.47 (m, 4H), 0.00 (s, 12H).

Example 37, Example 38, Example 39, and Example 40

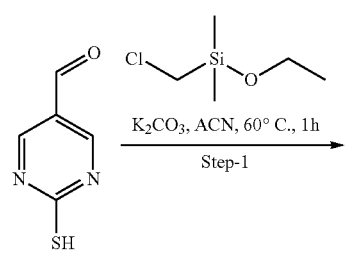

K$_2$CO$_3$, ACN, 60° C., 1h
Step-1

Int-4 aldehyde

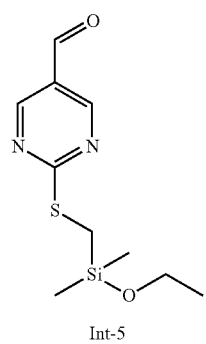

+

Int-5

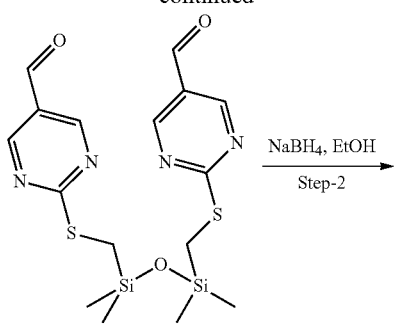

NaBH$_4$, EtOH
Step-2

Example 37

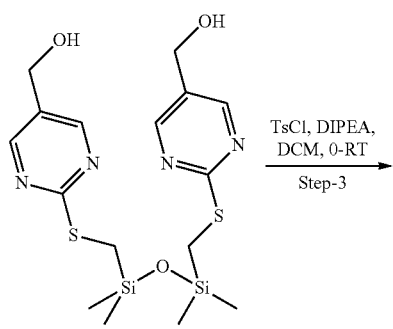

TsCl, DIPEA, DCM, 0-RT
Step-3

Example 38

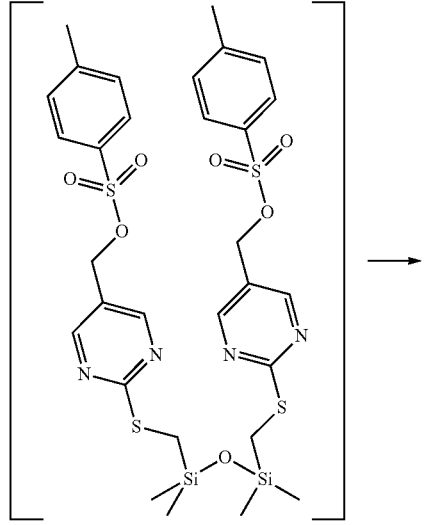

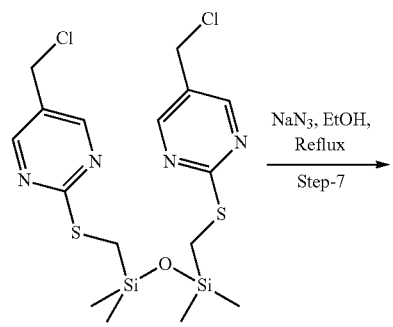

NaN$_3$, EtOH, Reflux
Step-7

Example 39

1,3-Bis(((5-(chloromethyl)pyrimidin-2-yl)thio)methyl)-1,1,3,3-tetramethyldisiloxane [Example 39]

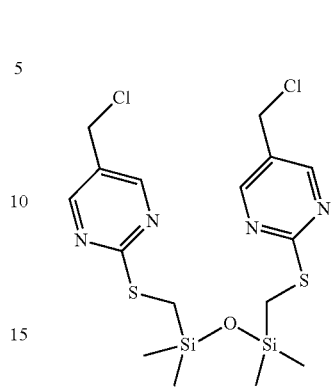

A solution of ((((1,1,3,3-tetramethyldisiloxane-1,3-diyl)bis(methylene))bis(sulfanediyl))bis(pyrimidine-2,5-diyl)) dimethanol (15 g, 33.93 mmol) in DCM (200 mL) was cooled to 0° C. and charged with DIPEA (17.7 mL, 101.8 mmol) and tosyl chloride (14.2 g, 67.87 mmol) under a nitrogen atmosphere and stirred at room temperature for 5 h. The reaction mixture was concentrated in vacuo resulting in crude compound which was purified by column chromatography on silica gel eluting with 30-70% ethyl acetate in n-hexane to afford 8.12 g, 50% yield, of the title compound as an off white solid. $^1$H NMR (400 MHz, DMSO-d$_6$) δ=8.69 (s, 4H), 4.77 (s, 4H), 2.41 (s, 4H), 0.18 (s, 12H); MS (ES$^+$): m/z=248.95 monomer [M+H]$^+$, 231.00 monomer [M−18]$^+$; LCMS: t$_R$=2.62/3.82 min.

((((1,1,3,3-tetramethyldisiloxane-1,3-diyl)bis(methylene))bis(sulfanediyl))bis(pyrimidine-2,5-diyl)) dimethanol [Example 38]

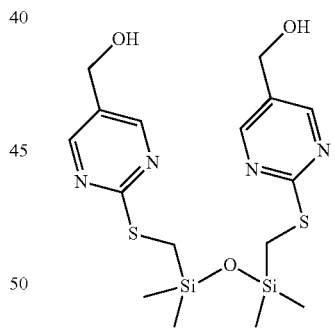

A solution of 2,2'-(((1,1,3,3-tetramethyldisiloxane-1,3-diyl)bis(methylene)) bis(sulfanediyl)) bis(pyrimidine-5-carbaldehyde) (22 g, 50.22 mmol) in ethanol (150 mL) was cooled to 0° C. and charged with sodium borohydride (1.89 g, 50.22 mmol) then stirred at room temperature for 1 h. The reaction mixture was concentrated in vacuo resulting in the crude compound which was purified by silica gel column chromatography on silica gel eluting with 40-100% ethyl acetate to afford 15.54, 70% yield, of the title compound as a white solid. $^1$H NMR (400 MHz, DMSO-d$_6$) δ=8.54 (s, 4H), 5.34 (t, J=5.55 Hz, 2H), 4.46 (d, J=5.31 Hz, 4H), 2.40 (s, 4H), 0.18 (s, 12H); MS (ES$^+$): m/z=443.20 [M+H]$^+$/465.25 [M+Na]$^+$; LCMS: t$_R$=1.99/2.81 min.

-continued

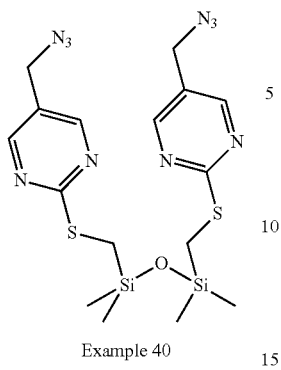

Example 40

1,3-Bis(((5-(azidomethyl)pyrimidin-2-yl)thio)methyl)-1,1,3,3-tetramethyldisiloxane [Example 40]

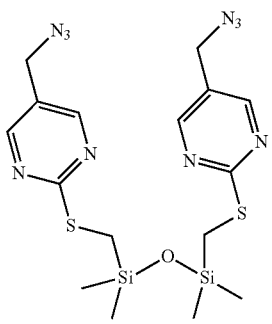 [SMILES: C[Si](C)(CSc1ncc(CN=[N+]=[N-])cn1)O[Si](C)(C)CSc1ncc(CN=[N+]=[N-])cn1]

A solution of 1,3-bis(((5-(chloromethyl)pyrimidin-2-yl)thio)methyl)-1,1,3,3-tetramethyldisiloxane (1 g, 3.267 mmol) in ethanol (50 mL) was added sodium azide (1.84 g, 6.535 mmol) and heated to reflux for 2 h. The reaction mixture was concentrated in vacuo resulting in crude residue which was stirred in diethyl ether. The suspension was filtered and the filtrate was concentrated in vacuo resulting in the crude compound which was purified by column chromatography on silica gel eluting with ethyl acetate in n-hexane to afford 1.1 g, 90% yield, of the title compound as an off white solid. $^1$H NMR (400 MHz, DMSO-d$_6$) δ=8.65 (s, 4H), 4.49 (s, 4H), 2.41 (s, 4H), 0.18 (s, 12H); MS (ES$^+$): m/z=256.00/256.05 monomer [M+H]$^+$; LCMS: t$_R$=2.54/3.74 min.

2,2'-(((1,1,3,3-tetramethyldisiloxane-1,3-diyl)bis(methylene))bis(sulfanediyl)) bis(pyrimidine-5-carbaldehyde) [Example 37]

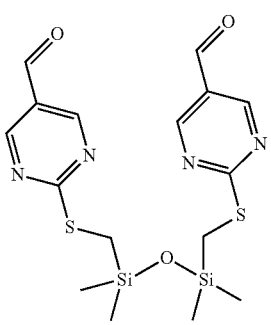 [SMILES: C[Si](C)(CSc1ncc(C=O)cn1)O[Si](C)(C)CSc1ncc(C=O)cn1]

A solution of 2-mercaptopyrimidine-5-carbaldehyde (34.5 g, 246.4 mmol) in acetonitrile (100 mL) was added potassium carbonate (102 g, 739.2 mmol) and (chloromethyl)(ethoxy)dimethylsilane (37.6 g, 246.4 mmol) and stirred at 60° C. for 1 h. The reaction mixture was concentrated in vacuo resulting in the crude compound which was purified by column chromatography on silica gel eluting with 20-50% ethyl acetate in n-hexane to afford 22.11 g, 35% yield of the title compound as an off white solid. $^1$H NMR (400 MHz, DMSO-$d_6$) δ=9.93 (s, 2H), 8.94 (s, 4H), 2.43 (s, 4H), 0.14 (s, 12H); MS (ES$^+$): m/z=229.00 monomer [M+H]$^+$; LCMS: $t_R$=3.52 min.

Int-4 Aldehyde

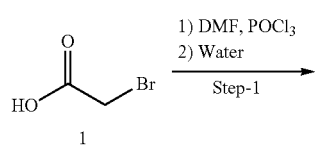

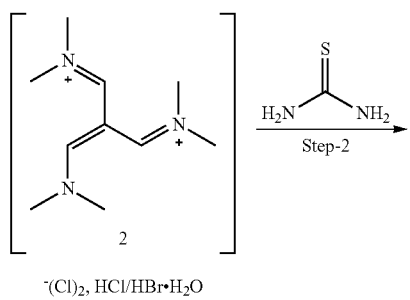

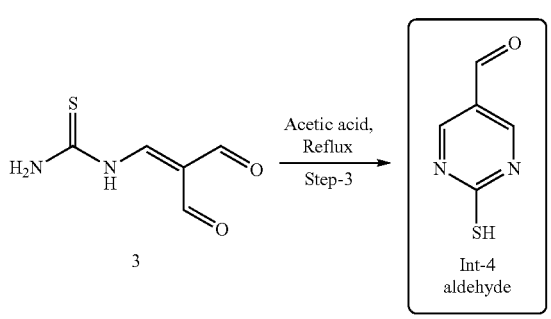

In-4 aldehyde (2-mercaptopyrimidine-5-carbaldehyde) was prepared according to a literature preparation: *Organic Letters* 2014, 16, 1282-1285, 2014. $^1$H NMR (400 MHz, DMSO-$d_6$) δ=14.33 (br. s, 1H), 9.76 (s, 1H), 8.70 (br. s, 2H), 3.33 (br. s, 1H).

Example 41 and Example 42

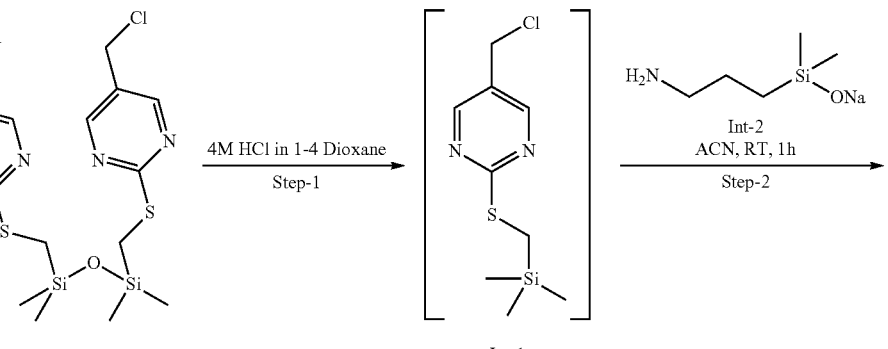

-continued
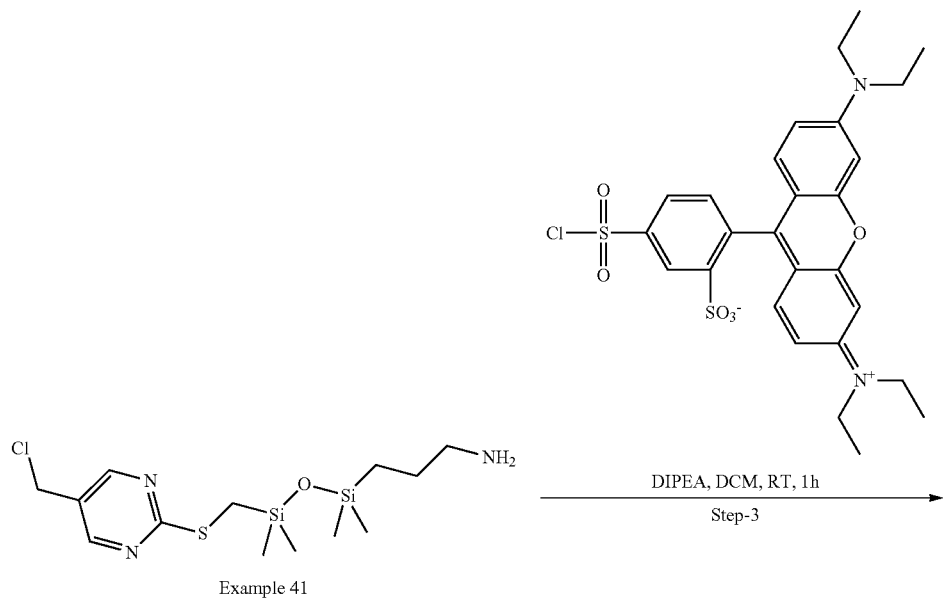
Example 41
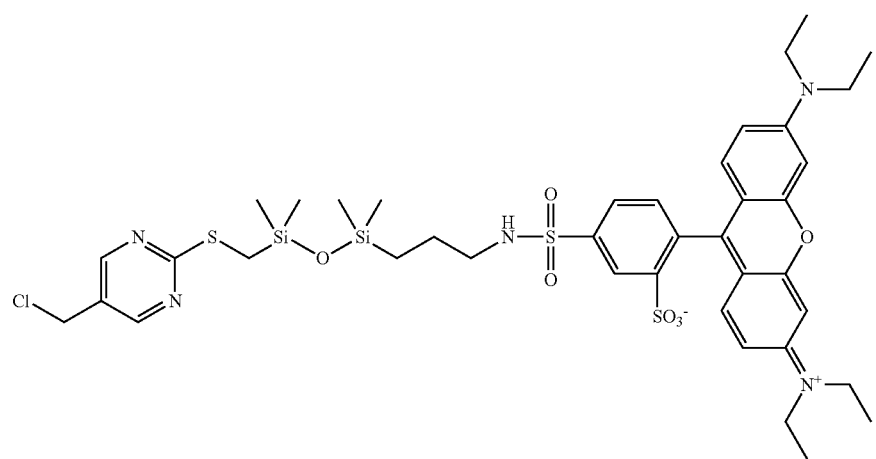
Example 42

5-(N-(3-(3-(((5-(Chloromethyl)pyrimidin-2-yl)thio)methyl)-1,1,3,3-tetramethyldisiloxanyl)propyl) sulfamoyl)-2-(6-(diethylamino)-3-(diethyliminio)-3H-xanthen-9-yl)benzenesulfonate [Example 42]

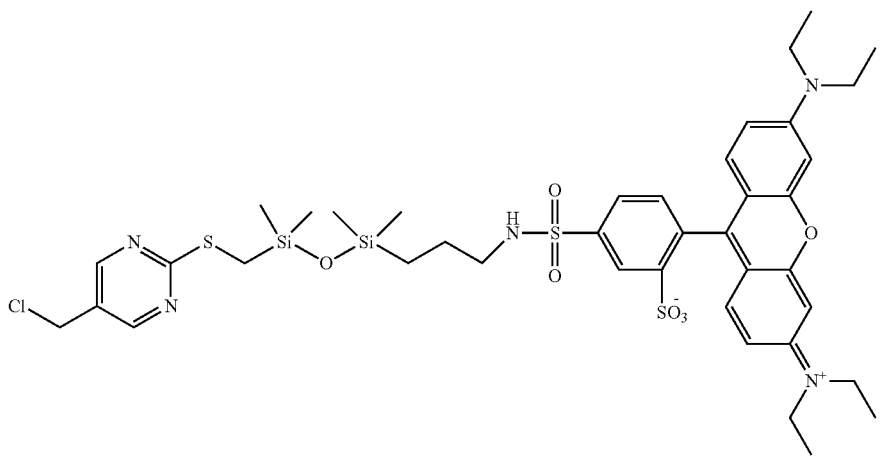

A solution of 3-(3-(((5-(chloromethyl)pyrimidin-2-yl)thio)methyl)-1,1,3,3-tetramethyldisiloxanyl)propan-1-amine (40 mg, 0.109 mmol) in DCM (5 mL) was added DIPEA (28 mg, 0.20 mmol) and 5-(chlorosulfonyl)-2-(6-(diethylamino)-3-(diethyliminio)-3H-xanthen-9-yl)benzenesulfonate (63 mg, 0.101 mmol) at room temperature and stirred for 1 h. The completion of reaction was monitored by LCMS. The reaction mixture was concentrated in vacuo resulting in the crude compound which was purified by silica gel column chromatography eluting with 0-10% methanol in DCM to afford 29 mg, 30% yield, of the title compound as violet solid. $^1$H NMR (400 MHz, DMSO-$d_6$) δ=8.65 (s, 2H), 8.37-8.38 (m, 1H), 7.87-7.91 (m, 2H), 7.42 (d, J=7.83 Hz, 1H), 6.94-6.98 (m, 3H), 6.90 (d, J=1.47 Hz, 2H), 4.73 (s, 2H), 3.55-3.67 (m, 8H), 2.75-2.83 (m, 1H), 2.36 (s, 2H), 1.44 (td, J=7.70, 15.90 Hz, 2H), 1.14-1.21 (m, 12H), 0.77-0.84 (m, 2H), 0.43-0.51 (m, 2H), 0.11-0.15 (m, 6H), 0.01-0.04 (m, 6H); MS (ES$^+$): m/z=904.55 [M+H]$^+$; LCMS: $t_R$=3.66 min.

3-(3-(((5-(Chloromethyl)pyrimidin-2-yl)thio)methyl)-1,1,3,3-tetramethyldisiloxanyl)propan-1-amine [Example 41]

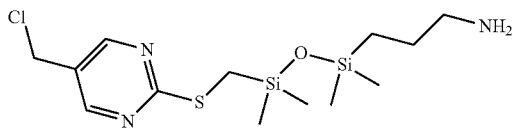 [SMILES: C[Si](C)(CCCN)O[Si](C)(C)CSc1ncc(CCl)cn1]

A solution of 1,3-bis(((5-(chloromethyl)pyrimidin-2-yl)thio)methyl)-1,1,3,3-tetramethyldisiloxane (1 g, 2.0 mmol) in 4M HCl in dioxane (20 mL) was stirred at room temperature for 1 h. The reaction mixture was concentrated in vacuo resulting in the crude reaction mixture. The crude was dissolved in acetonitrile (50 mL) and followed by addition of 75 mg and sodium (3-aminopropyl) dimethylsilanolate (638 mg, 2.0 mmol) and stirred at room temperature for 1 h.

The reaction mixture was concentrated in vacuo resulting in the crude compound which was purified by column chromatography on silica gel eluting with 0-10% methanol in DCM to afford 500 mg, 35% yield, of the title compound as colourless oil. $^1$H NMR (400 MHz, DMSO-$d_6$) δ=8.69 (s, 1H), 7.77 (br. s, 1H), 4.76 (s, 2H), 3.34 (br. s, 2H), 2.89-3.03 (m, 2H), 2.66-2.79 (m, 1H), 2.40 (d, J=3.91 Hz, 1H), 1.47-1.61 (m, 1H), 0.92-1.00 (m, 2H), 0.48-0.56 (m, 1H), 0.17 (d, J=2.45 Hz, 6H), 0.07 (d, J=4.89 Hz, 6H); MS (ES+): m/z=364.10[M+H]$^+$; LCMS: $t_R$=2.20 min.
Example 43
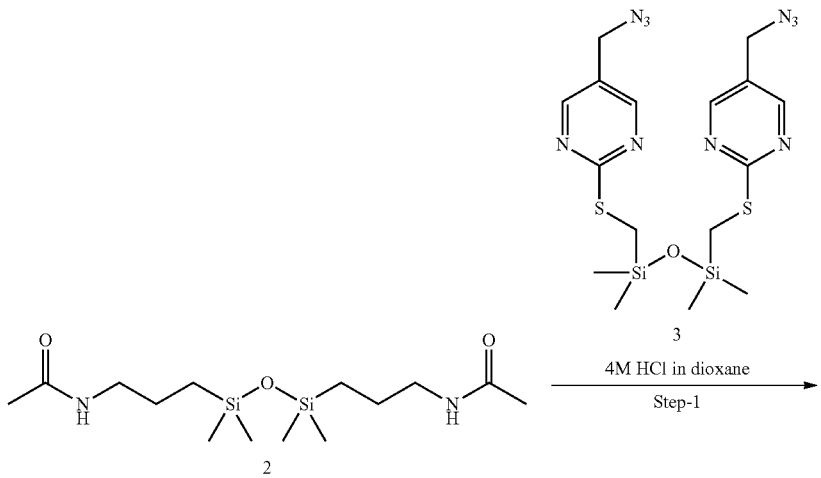
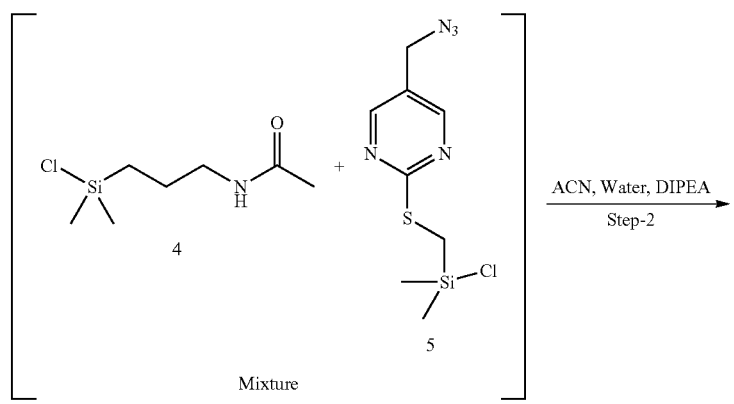
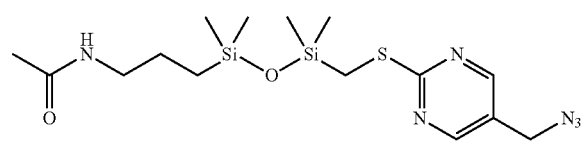
Example 43

N-(3-(3-(((5-(Azidomethyl)pyrimidin-2-yl)thio)methyl)-1,1,3,3-tetramethyldisiloxanyl) propyl) acetamide [Example 43]

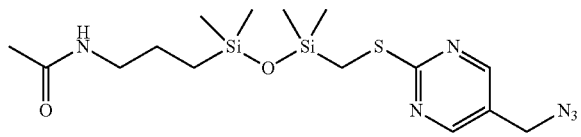 [SMILES: CC(=O)NCCC[Si](C)(C)O[Si](C)(C)CSc1ncc(CN=[N+]=[N-])cn1]

A solution of N,N'-((1,1,3,3-tetramethyldisiloxane-1,3-diyl)bis(propane-3,1-diyl))diacetamide (400 mg, 1.2 mmol) and 1,3-bis(((5-(azidomethyl)pyrimidin-2-yl)thio)methyl)-1,1,3,3-tetramethyldisiloxane (592 mg, 1.2 mmol) in 4M HCl in dioxane (10 mL) was stirred at room temperature for 1 h. The reaction mixture was concentrated in vacuo resulting in the crude mixture of 2-((3-(chlorodimethylsilyl)propyl)amino)-2-oxoethan-1-ylium (4) and 5-(azidomethyl)-2-(((chlorodimethylsilyl)methyl)thio)pyrimidine (5). The crude mixture was dissolved in acetonitrile (10 mL) and charged with water (43 mg, 2.4 mmol) followed by DIPEA (2.46 g, 7.2 mmol) and stirred at room temperature for 1 h. The reaction mixture was concentrated in vacuo resulting in the crude compound which was purified by column chromatography on silica gel eluting with 40-70% ethyl acetate in n-hexane to afford 280 mg, 73% yield, of the title compound as a colourless oil. $^1$H NMR (400 MHz, DMSO-$d_6$) δ=8.65 (s, 2H), 7.78 (br. s, 1H), 4.48 (s, 2H), 2.91-3.00 (m, 2H), 2.38 (s, 2H), 1.75 (s, 3H), 1.32-1.41 (m, 2H), 0.42-0.49 (m, 2H), 0.15 (s, 6H), 0.03 (s, 6H); MS (ES$^+$): m/z=413.09 [M+H]$^+$; LCMS: $t_R$=3.26 min.

Example 44 and Example 45

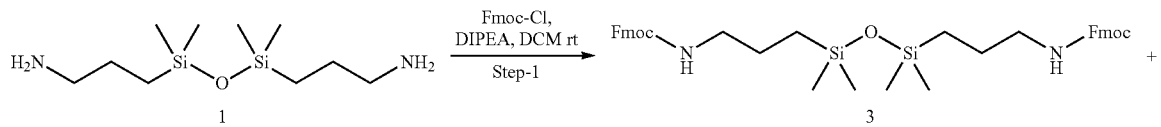

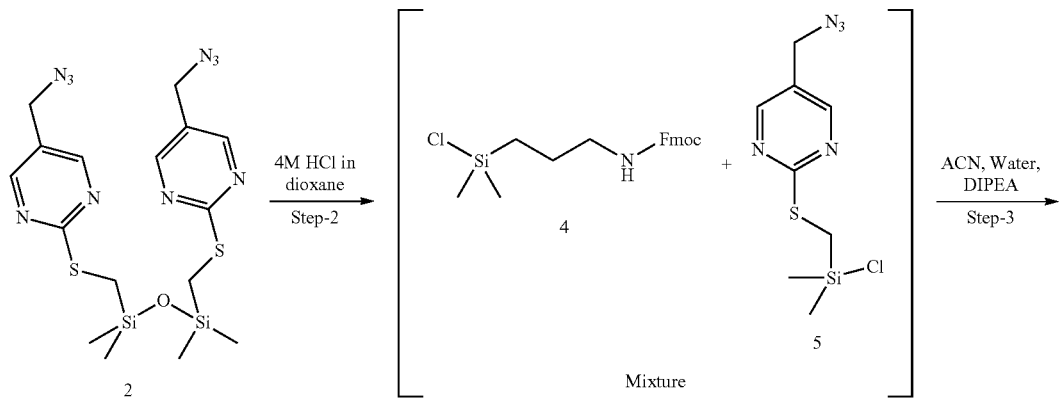

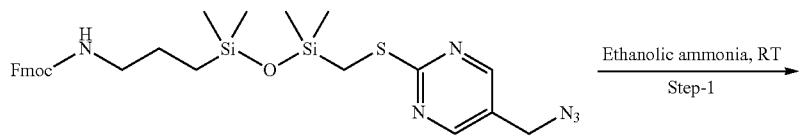

Example 45

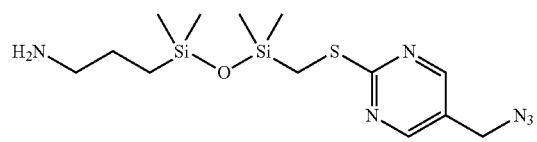

Example 44

3-(3-(((5-(Azidomethyl)pyrimidin-2-yl)thio)methyl)-1,1,3,3-tetramethyldisiloxanyl) propan-1-amine [Example 44]

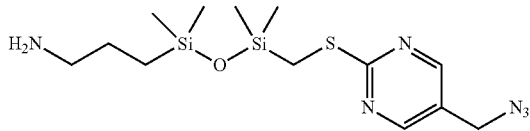 [SMILES: C[Si](C)(CCCN)O[Si](C)(C)CSc1ncc(CN=[N+]=[N-])cn1]

A solution of (9H-fluoren-9-yl)methyl(3-(3-(((5-(azidomethyl)pyrimidin-2-yl)thio)methyl)-1,1,3,3-tetramethyldisiloxanyl)propyl)carbamate (3.4 g, 5.734 mmol) was charged with ethanolic ammonia (40 mL) and stirred at room temperature for 15 h. The reaction mixture was concentrated in vacuo and the crude compound was purified by combiflash column chromatography eluting with 0-10% methanol saturated with ammonia in DCM to afford 1.10 g, 52% yield, of the title compound as a light brown oil. $^1$H NMR (400 MHz, DMSO-$d_6$) δ=8.67 (s, 2H), 4.51 (s, 2H), 2.45-2.52 (m, 4H), 2.39-2.43 (m, 2H), 1.31-1.41 (m, 2H), 0.46-0.53 (m, 2H), 0.18 (s, 6H), 0.06 (s, 6H); MS (ES$^+$): m/z=371.20 [M+H]$^+$; LCMS: $t_R$=2.23 min.

(9H-fluoren-9-yl)methyl(3-(3-(((5-(azidomethyl)pyrimidin-2-yl)thio)methyl)-1,1,3,3-tetramethyldisiloxanyl)propyl)carbamate [Example 45]

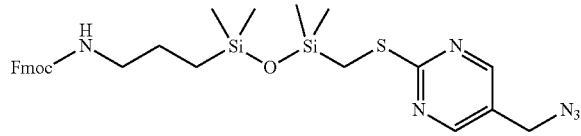

A solution of mixture 1,3-bis(((5-(azidomethyl)pyrimidin-2-yl)thio)methyl)-1,1,3,3tetramethyldisiloxane (2.50 g, 3.45 mmol) and bis((9H-fluoren-9-yl)methyl) ((1,1,3,3-tetramethyldisiloxane-1,3-diyl)bis(propane-3,1-diyl))dicarbamate (1.7 g, 3.45 mmol) were dissolved in 4M HCl in dioxane (30 mL) and stirred at room temperature for 1 h. The reaction mixture was concentrated in vacuo resulting in the crude mixture of 4 and 5. The mixture of 4 and 5 was dissolved in acetonitrile (30 mL) then charged with water (124 mg, 6.91 mmol), DIPEA (2.6 g, 20.7 mmol) and stirred at room temperature for 1 h. The reaction mixture was concentrated in vacuo resulting in the crude compound which was purified by column chromatography on silica gel eluting with 10-25% ethyl acetate in n-hexane to afford 3.40 g, 85% yield of the title compound as a colourless oil. $^1$H NMR (400 MHz, CDCl$_3$) δ=8.50 (s, 2H), 7.78-7.83 (m, 2H), 7.64 (d, J=7.34 Hz, 2H), 7.41-7.47 (m, 2H), 7.32-7.38 (m, 2H), 4.44 (d, J=6.85 Hz, 2H), 4.34 (s, 2H), 4.23-4.30 (m, 1H), 3.18-3.26 (m, 2H), 2.47 (s, 2H), 1.53-1.61 (m, 1H), 1.28-1.33 (m, 2H), 0.55-0.63 (m, 2H), 0.27 (s, 6H), 0.15 (s, 6H), MS (ES$^+$): m/z=593.35 [M+H]$^+$; LCMS: $t_R$=4.03 min.

Bis((9H-fluoren-9-yl)methyl)((1,1,3,3-tetramethyldisiloxane-1,3-diyl)bis(propane-3,1-diyl))dicarbamate (3)

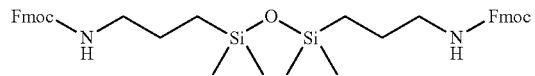

A solution of 3,3'-(1,1,3,3-tetramethyldisiloxane-1,3-diyl)bis(propan-1-amine) (3 g, 12 mmol) in DCM (60 mL) was charged with DIPEA (4.68 g, 36 mmol) and Fmoc-Cl (6.8 g, 26.6 mmol) and stirred at room temperature for 1 h. The reaction mixture was diluted with water and separated organic layer was dried over sodium sulphate. The organic layer was diluted with 10% methanol in DCM and concentrated in vacuo resulting in the crude compound. The crude compound was stirred in methanol, filtered and dried to afford 7.96 g, 95% yield of the title compound as a white solid. $^1$H NMR (400 MHz, DMSO-$d_6$) δ=7.89 (d, J=7.34 Hz, 4H), 7.68 (d, J=7.34 Hz, 4H), 7.38-7.44 (m, 4H), 7.32 (t, J=7.34 Hz, 4H), 4.29 (d, J=6.85 Hz, 4H), 4.21 (d, J=6.36 Hz, 2H), 4.04 (q, J=7.17 Hz, 2H), 2.95 (q, J=6.52 Hz, 4H), 1.41 (td, J=7.58, 15.16 Hz, 4H), 0.43-0.50 (m, 4H), 0.04 (s, 12H).

Example 46, Example 47, Example 48, and Example 49

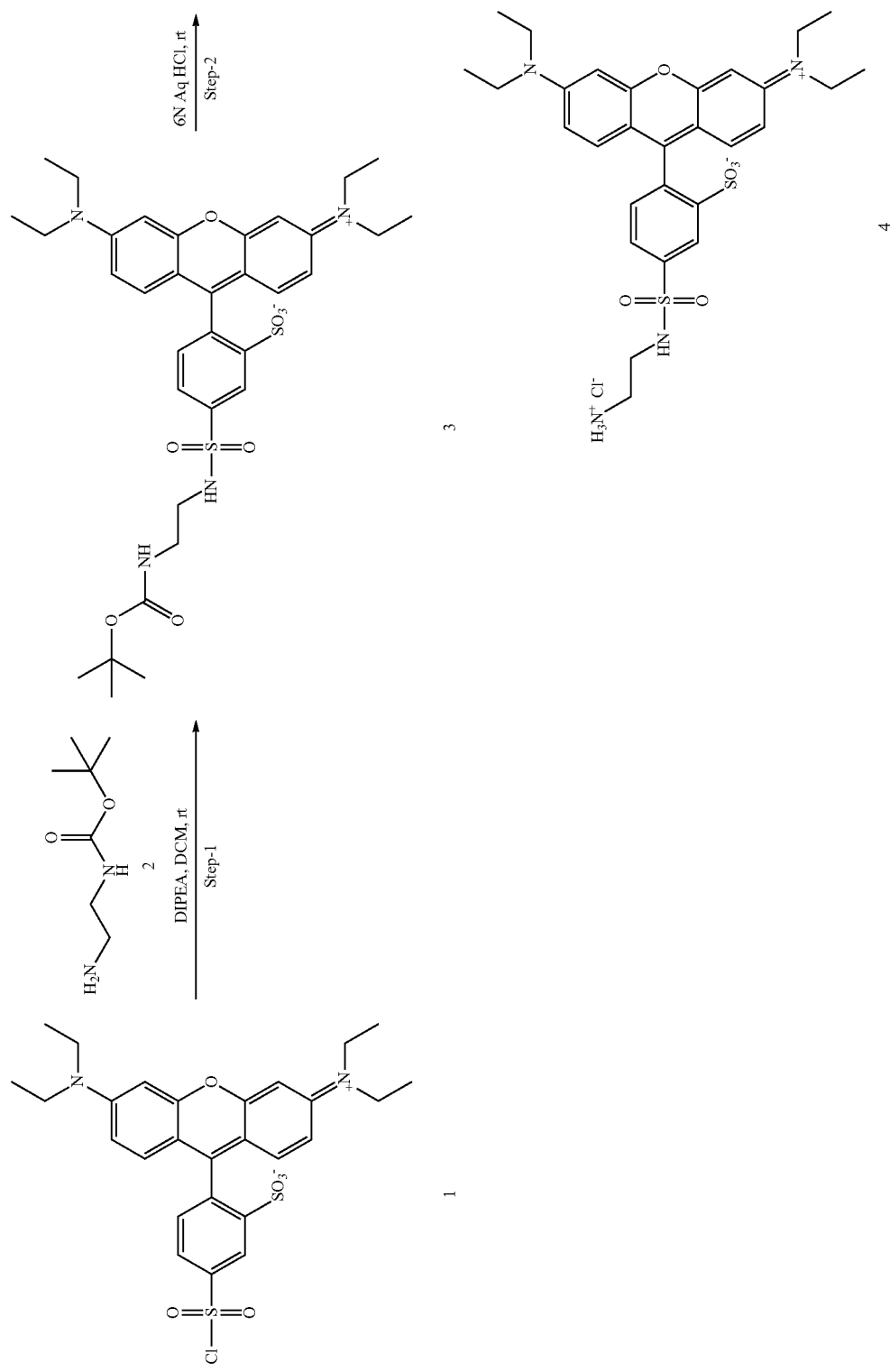

-continued
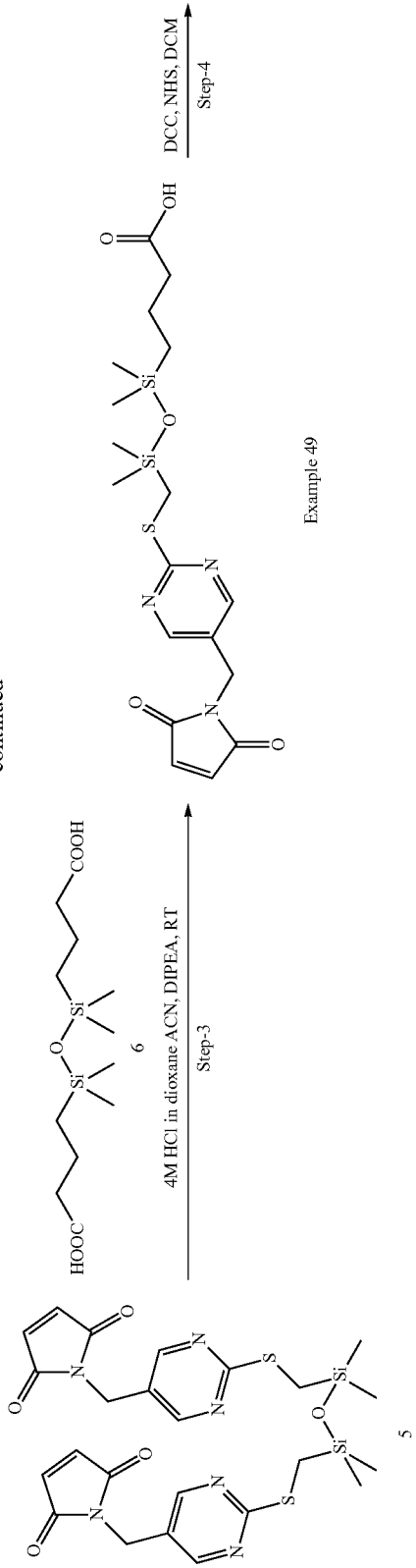
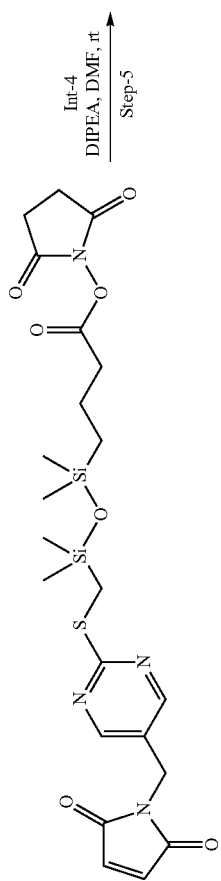
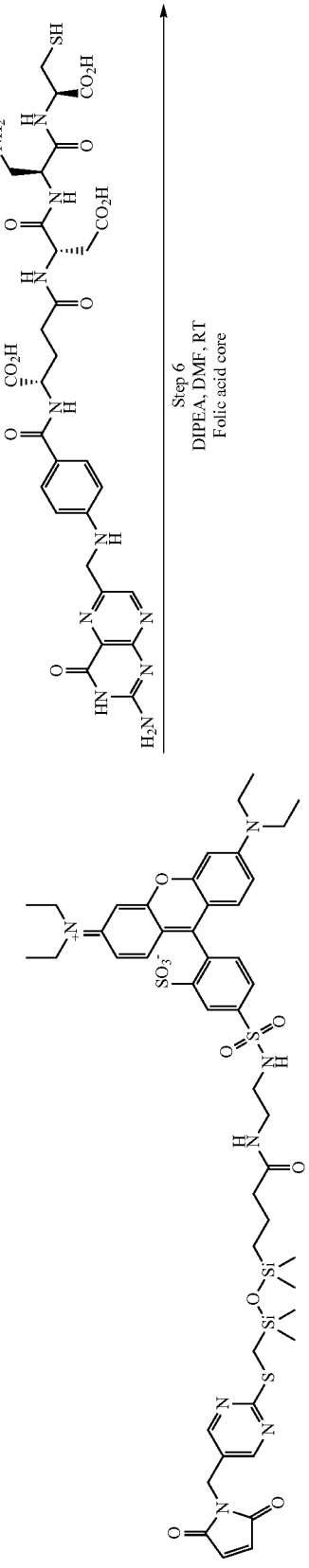

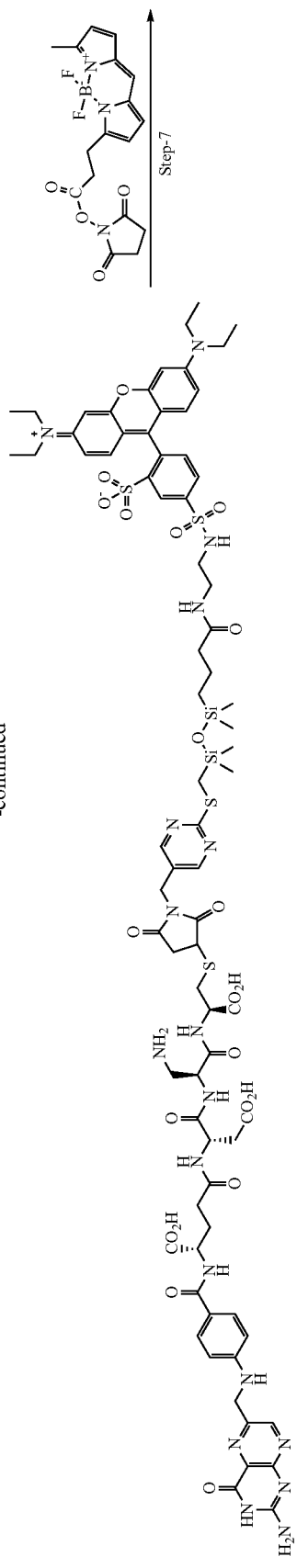
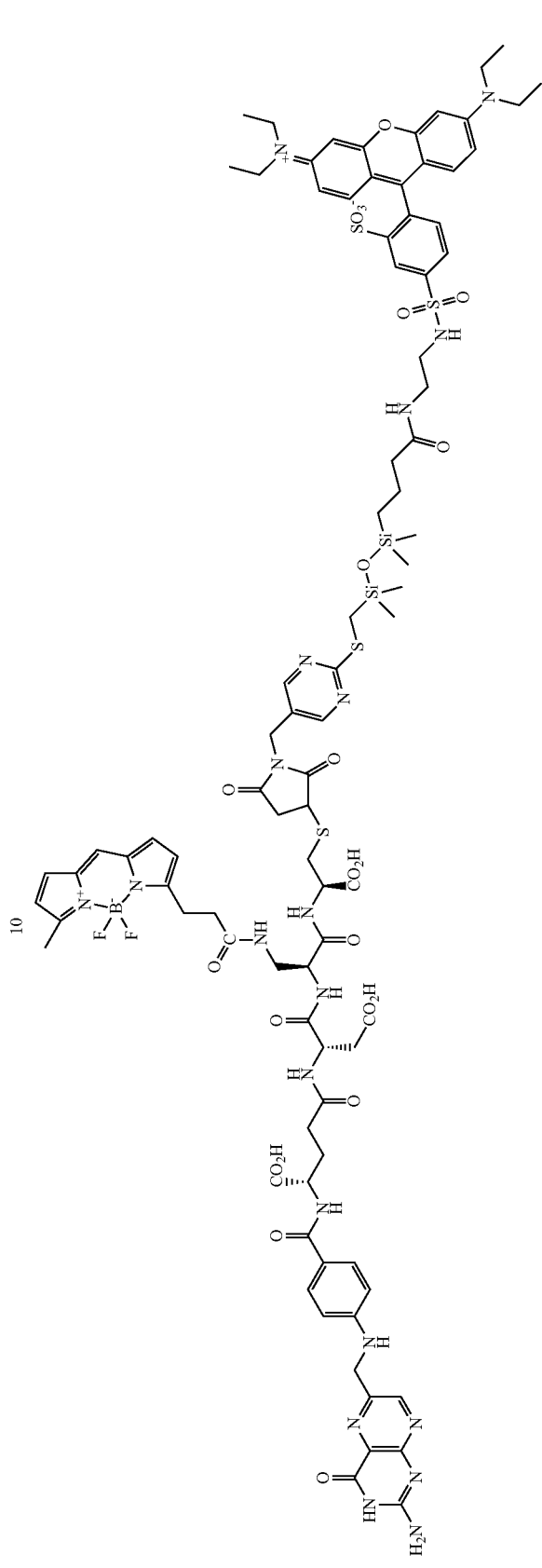
Example 46

5-(N-(2-(4-(3-(((5-((3-(((3S,8S,11S,14R)-1-(4-(((2-amino-4-oxo-3,4-dihydropteridin-6-yl)methyl)amino)phenyl)-3,14-dicarboxy-8-(carboxymethyl)-11-((3-(5,5-difluoro-7-methyl-5H-514,614-dipyrrolo[1,2-c:2',1'-f][1,3,2]diazaborinin-3-yl)propanamido)methyl)-1,6,9,12-tetraoxo-2,7,10,13-tetraazapentadecan-15-yl)thio)-2,5-dioxopyrrolidin-1-yl)methyl)pyrimidin-2-yl)thio)methyl)-1,1,3,3-tetramethyldisiloxanyl)butanamido)ethyl)sulfamoyl)-2-(6-(diethylamino)-3-(diethyliminio)-3H-xanthen-9-yl)benzenesulfonate [Example 46]

benzenesulfonate (68.8 mg, 0.0386 mmol) was charged 2,5-dioxopyrrolidin-1-yl difluoro-7-methyl-5H-514,614-dipyrrolo[1,2-c:2',1'-f][1,3,2]diazaborinin-3-yl)propanoate (18 mg, 0.0463 mmol) at room temperature and stirred for 2 h. The reaction mixture was concentrated in vacuo resulting in the crude compound which was purified by trituration in ethyl acetate to afford 30 mg, 38% yield of the title compound as a violet solid. $^1$H NMR (400 MHz, DMSO-$d_6$) δ=8.64 (br. s, 2H), 8.51 (br. s, 1H), 8.41 (br. s, 1H), 8.05-8.22 (m, 4H), 7.94 (d, J=8.31 Hz, 2H), 7.60-7.68 (m, 2H), 7.48 (d, J=7.83 Hz, 1H), 7.03 (d, J=8.80 Hz, 2H), 6.90-7.01 (m, 4H), 6.62 (d, J=7.83 Hz, 2H), 6.26-6.34 (m, 2H), 5.43 (br. s, 2H),

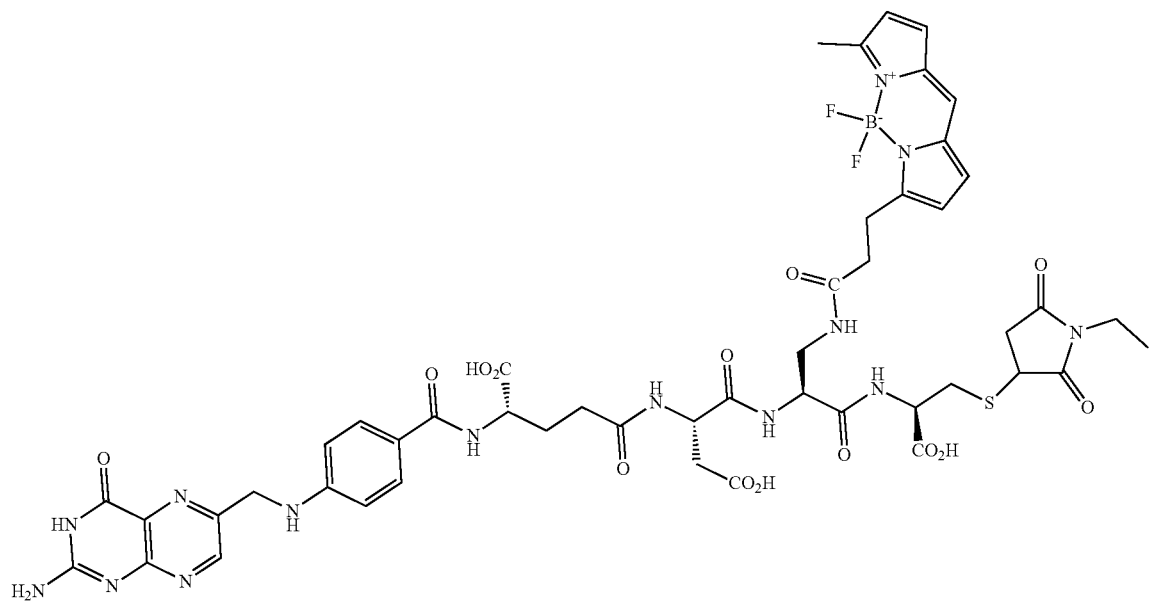

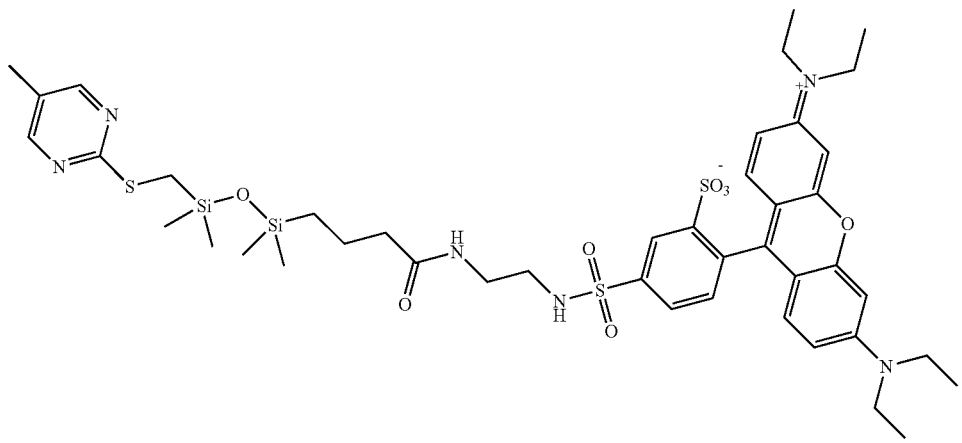

A solution of 5-(N-(2-(4-(3-(((5-((3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)methyl)pyrimidin-2-yl)thio)methyl)-1,1,3,3-tetramethyldisiloxanyl) butanamido) ethyl)sulfamoyl)-2-(6-(diethylamino)-3-(diethyliminio)-3H-xanthen-9-yl)

4.60 (br. s, 2H), 4.44-4.56 (m, 5H), 4.26 (br. s, 4H), 4.13 (br. s, 2H), 4.04 (d, J=7.34 Hz, 5H), 3.48-3.70 (m, 16H), 3.16 (d, J=8.80 Hz, 3H), 2.84-3.12 (m, 11H), 2.68 (br. s, 3H), 2.29-2.35 (m, 2H), 2.25 (br. s, 2H), 1.98-2.10 (m, 4H), 1.51 (br. s, 3H), 1.17-1.28 (m, 8H), 0.85 (d, J=6.36 Hz, 2H), 0.46 (d, J=8.31 Hz, 2H), 0.14 (s, 6H), 0.04 (s, 6H), MS (ES$^+$): m/z=1028 [M/2+H]$^+$; LCMS: $t_R$=2.97 min.

5-(N-(2-(4-(3-(((5-((3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)methyl)pyrimidin-2-yl)thio)methyl)-1,1,3,3-tetramethyldisiloxanyl)butanamido)ethyl)sulfamoyl)-2-(6-(diethylamino)-3-(diethyliminio)-3H-xanthen-9-yl)benzenesulfonate (10)

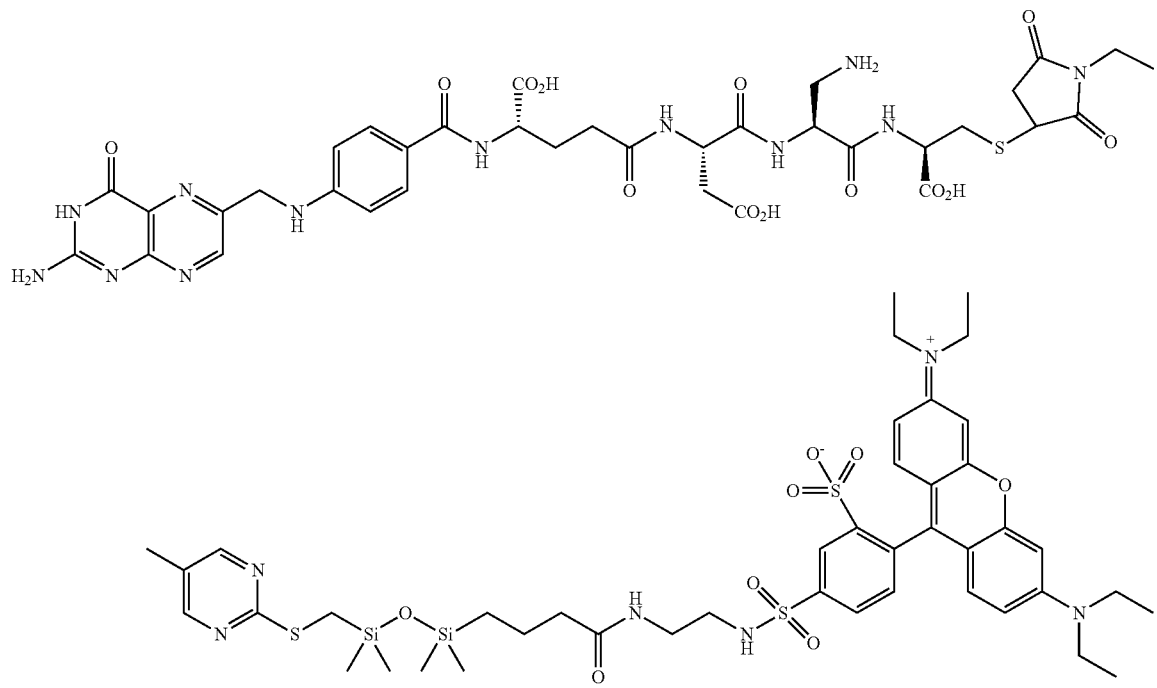

A solution of 2-(6-(diethylamino)-3-(diethyliminio)-3H-xanthen-9-yl)-5-(N-(2-(4-(3-(((5-((2,5-dioxo-2,5-dihydro-1H-pyrrol-1-yl)methyl)pyrimidin-2-yl)thio)methyl)-1,1,3,3-tetramethyldisiloxanyl)butanamido)ethyl)sulfamoyl)benzenesulfonate (40 mg, 0.0386 mmol) in DMF (1.5 mL) was charged with DIPEA (0.02 mL, 0.115 mmol) and N5-((S)-1-(((S)-3-amino-1-(((R)-1-carboxy-2-mercaptoethyl)amino)-1-oxopropan-2-yl)amino)-3-carboxy-1-oxopropan-2-yl)-N2-(4-(((2-amino-4-oxo-3,4-dihydropteridin-6-yl)methyl)amino)benzoyl)-L-glutamine (28.6 mg, 0.0385 mmol) and stirred at room temperature for 1 h. The crude reaction mixture was used directly in the next step without work-up or further purification. MS (ES+): m/z=891.48 [M/2+H]+; LCMS: $t_R$=2.39 min.

2-(6-(Diethylamino)-3-(diethyliminio)-3H-xanthen-9-yl)-5-(N-(2-(4-(3-(((5-((2,5-dioxo-2,5-dihydro-1H-pyrrol-1-yl)methyl)pyrimidin-2-yl)thio)methyl)-1,1,3,3-tetramethyl disiloxanyl)butanamido)ethyl)sulfamoyl)benzenesulfonate [Example 47]

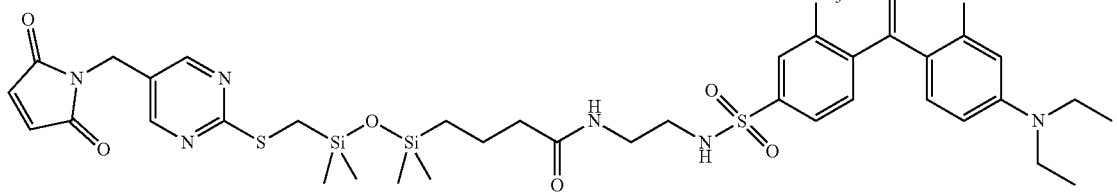

A solution of 2,5-dioxopyrrolidin-1-yl 4-(3-(((5-((2,5-dioxo-2,5-dihydro-1H-pyrrol-1-yl)methyl)pyrimidin-2-yl)thio)methyl)-1,1,3,3-tetramethyldisiloxanyl)butanoate (100 mg, 0.181 mmol) in DMF (2 mL) was charged with DIPEA (0.09 mL, 0.545 mmol) and 5-(N-(2-ammonioethyl)sulfamoyl)-2-(6-(diethylamino)-3-(diethyliminio)-3H-xanthen-9-yl)benzenesulfonate chloride (110 mg, 0.181 mmol) and stirred at room temperature for 4 h. The reaction mixture was concentrated in vacuo resulting in the crude compound which was purified by column chromatography on silica gel eluting with 0-10% methanol in DCM to afford 100 mg, 53% yield, of the title compound as violet solid. $^1$H NMR (400 MHz, DMSO-$d_6$) δ=8.49 (s, 2H), 8.38 (d, J=1.47 Hz, 1H), 7.98 (t, J=5.62 Hz, 1H), 7.89 (dd, J=1.47, 7.83 Hz, 1H), 7.83 (t, J=5.62 Hz, 1H), 7.44 (d, J=8.31 Hz, 1H), 6.94-7.04 (m, 6H), 6.91 (d, J=1.96 Hz, 2H), 4.55 (s, 2H), 3.56-3.67 (m, 8H), 3.07-3.14 (m, 3H), 2.82-2.91 (m, 3H), 2.57 (s, 2H), 2.27-2.34 (m, 3H), 2.03 (t, J=7.34 Hz, 3H), 1.47 (td, J=7.70, 15.90 Hz, 3H), 1.20-1.24 (m, 2H), 0.78-0.86 (m, 2H), 0.40-0.49 (m, 3H), 0.11 (s, 6H), −0.02 (s, 6H); MS (ES$^+$): m/z=1037.15 [M+H]$^+$; LCMS: $t_R$=3.29 min.

2,5-Dioxopyrrolidin-1-yl 4-(3-(((5-((2,5-dioxo-2,5-dihydro-1H-pyrrol-1-yl)methyl) pyrimidin-2-yl)thio)methyl)-1,1,3,3-tetramethyldisiloxanyl)butanoate [Example 49]

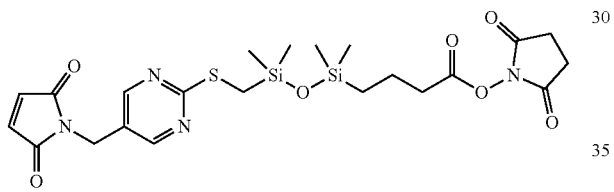

A solution of 4-(3-(((5-((2,5-dioxo-2,5-dihydro-1H-pyrrol-1-yl)methyl)pyrimidin-2-yl)thio)methyl)-1,1,3,3-tetramethyldisiloxanyl)butanoic acid (270 mg, 0.597 mmol) in DCM (5 mL) was charged with DCC (135 mg, 0.657 mmol) and N-hydroxysuccinimide (75 mg, 0.657 mmol) and stirred at room temperature for 15 h. The reaction mixture was concentrated in vacuo resulting in the crude compound which was purified by column chromatography on silica gel eluting with 0-5% methanol in DCM to afford 222 mg, 68% yield, of the title compound as a colourless oil. $^1$H NMR (400 MHz, DMSO-$d_6$) δ=8.50 (s, 2H), 7.03 (s, 2H), 4.55 (s, 2H), 2.78 (s, 4H), 2.60-2.66 (m, 2H), 2.35 (s, 2H), 1.59-1.68 (m, 2H), 0.56-0.62 (m, 2H), 0.14 (s, 6H), 0.03 (s, 6H); MS (ES$^+$): m/z=550.80 [M+H]$^+$; LCMS: $t_R$=3.39 min.

4-(3-(((5-((2,5-Dioxo-2,5-dihydro-1H-pyrrol-1-yl)methyl)pyrimidin-2-yl)thio)methyl)-1,1,3,3-tetramethyldisiloxanyl)butanoic Acid [Example 48]

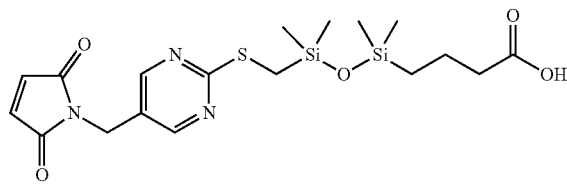 [SMILES: C[Si](C)(CCCC(=O)O)O[Si](C)(C)CSc1ncc(CN2C(=O)C=CC2=O)cn1]

A solution of 1,1'-(((((1,1,3,3-tetramethyldisiloxane-1,3-diyl)bis(methylene))bis(sulfanediyl))bis(pyrimidine-2,5-diyl))bis(methylene))bis(1H-pyrrole-2,5-dione) (400 mg, 0.666 mmol) and 4,4'-(1,1,3,3-tetramethyldisiloxane-1,3-diyl)dibutyric acid (203 mg, 0.666 mmol) was charged with 4M HCl in dioxane (10 mL) and stirred at room temperature for 1 h. The reaction mixture was concentrated in vacuo resulting in the crude intermediate. The crude intermediate was dissolved in acetonitrile (20 mL) and followed by addition of DIPEA (0.69 mL, 3.999 mmol) and water (20 mL) and stirred for 1 h at room temperature. The reaction mixture was concentrated in vacuo resulting in the crude compound which was purified by column chromatography on silica gel eluting with 0-5% methanol in DCM to afford 270 mg, 90% yield, of the title compound as a white solid. $^1$H NMR (400 MHz, DMSO-$d_6$) δ=11.93 (s, 1H), 8.53 (s, 2H), 7.06 (s, 2H), 4.58 (s, 2H), 2.37 (s, 2H), 2.20 (t, J=7.09 Hz, 2H), 1.47-1.59 (m, 2H), 0.47-0.56 (m, 2H), 0.17 (s, 6H), 0.05 (s, 6H); MS (ES$^+$): m/z=454.18 [M+H]$^+$; LCMS: $t_R$=3.26 min.

5-(N-(2-Ammonioethyl)sulfamoyl)-2-(6-(diethylamino)-3-(diethyliminio)-3H-xanthen-9-yl)benzenesulfonate Chloride (4)

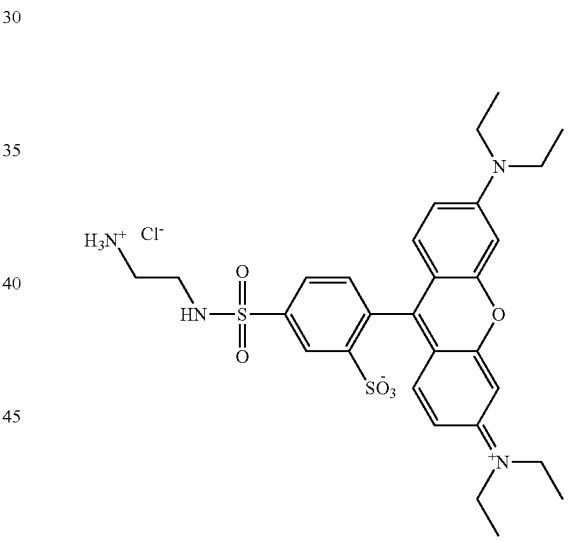

A solution of 5-(N-(2-((tert-butoxycarbonyl)amino)ethyl)sulfamoyl)-2-(6-(diethylamino)-3-(diethyliminio)-3H-xanthen-9-yl)benzenesulfonate (170 mg, 0.242 mmol) in 6N aqueous HCl (4 mL) was stirred at room temperature for 1 h. The reaction mixture was concentrated in vacuo to afford 116 mg, 80% yield, of the title compound as dark red solid. $^1$H NMR (400 MHz, DMSO-$d_6$) δ=8.45 (d, J=1.47 Hz, 1H), 8.26 (t, J=5.62 Hz, 1H), 7.96-7.99 (m, 1H), 7.92 (br. s, 2H), 7.53 (d, J=7.83 Hz, 1H), 7.01-7.06 (m, 2H), 6.94-6.99 (m, 3H), 4.00-4.07 (m, 1H), 3.59-3.72 (m, 7H), 3.39 (s, 2H), 3.06-3.13 (m, 2H), 2.95 (d, J=5.38 Hz, 2H), 1.15-1.26 (m, 12H); MS (ES$^+$): m/z=601.40 [M+H]$^+$; LCMS: $t_R$=1.99 min.

123

5-(N-(2-((tert-butoxycarbonyl)amino)ethyl)sulfamoyl)-2-(6-(diethylamino)-3-(diethyliminio)-3H-xanthen-9-yl)benzenesulfonate (3)

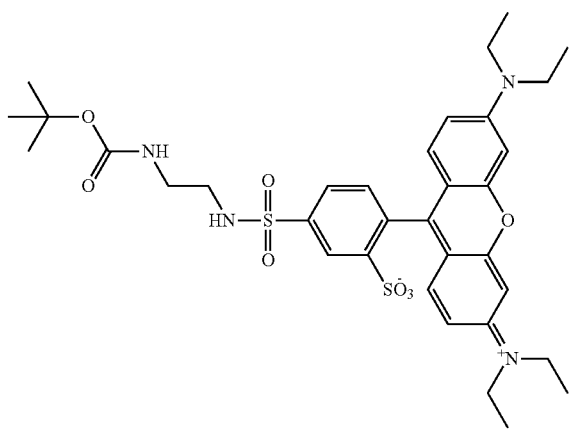

A solution of 5-(chlorosulfonyl)-2-(6-(diethylamino)-3-(diethyliminio)-3H-xanthen-9-yl)benzenesulfonate (170 mg, 0.242 mmol) in DMF (4 mL) was charged with DIPEA (0.18 mL, 1.03 mmol) and tert-butyl(2-aminoethyl)carbamate (55.4 mg, 0.346 mmol) was stirred at room temperature for 1 h. The reaction mixture was concentrated in vacuo resulting in the crude compound which was purified by column chromatography on silica gel eluting with 0-5% methanol in DCM to afford 179 mg, 74% yield, of the title compound as pink solid. $^1$H NMR (400 MHz, DMSO-$d_6$) δ=8.41 (s, 1H), 8.02 (t, J=5.87 Hz, 1H), 7.93 (d, J=7.83 Hz, 1H), 7.48 (d, J=7.83 Hz, 1H), 6.97-7.06 (m, 4H), 6.94 (s, 2H), 6.87 (br. s, 1H), 3.58-3.70 (m, 8H), 2.99-3.06 (m, 2H), 2.85-2.91 (m, 2H), 1.37 (s, 9H), 1.21 (t, J=6.85 Hz, 12H); MS (ES$^+$): m/z=701.35 [M+H]$^+$; LCMS: $t_R$=2.92 min.

Example 50

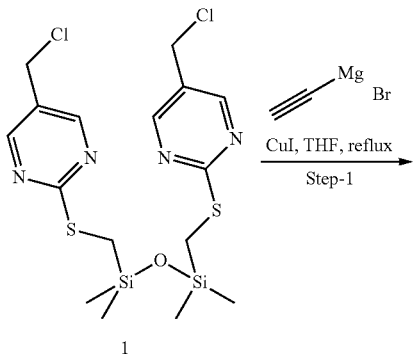

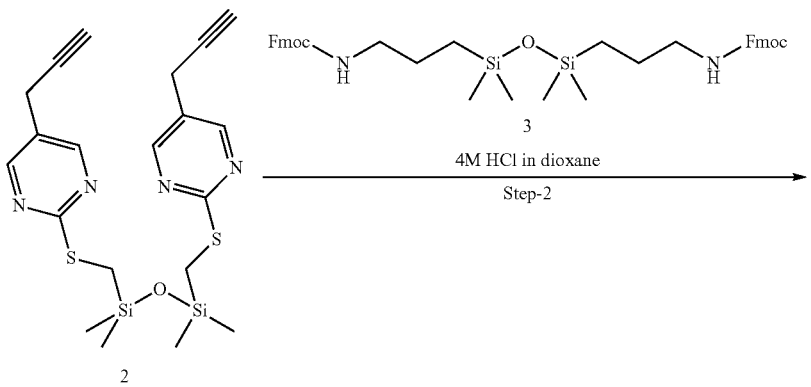

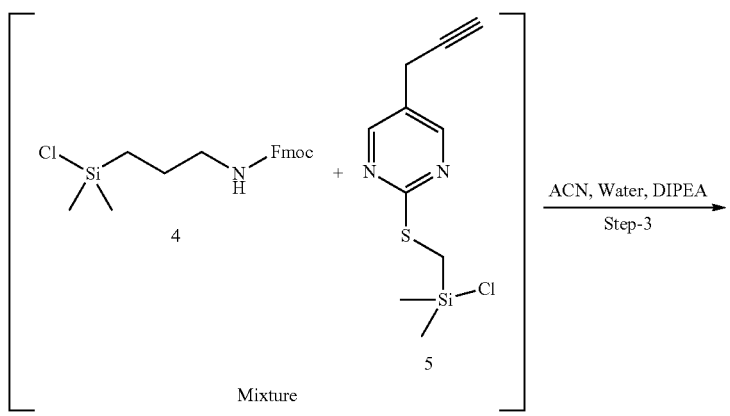

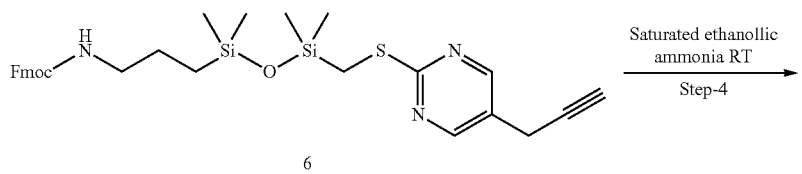

3-(1,1,3,3-Tetramethyl-3-(((5-(prop-2-yn-1-yl)pyrimidin-2-yl)thio)methyl)disiloxanyl)propan-1-amine [Example 50]

(9H-fluoren-9-yl)methyl(3-(1,1,3,3-tetramethyl-3-(((5-(prop-2-yn-1-yl)pyrimidin-2-yl)thio)methyl)disiloxanyl)propyl)carbamate (6)

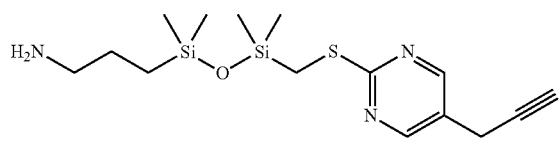 [SMILES: C#CCc1cnc(SC[Si](C)(C)O[Si](C)(C)CCCN)nc1]

A solution of (9H-fluoren-9-yl)methyl(3-(1,1,3,3-tetramethyl-3-(((5-(prop-2-yn-1-yl)pyrimidin-2-yl)thio)methyl)disiloxanyl)propyl)carbamate (2.50 g, 4.347 mmol) in saturated ethanolic ammonia (50 mL) was stirred at room temperature for 15 h. The reaction mixture was concentrated in vacuo and the crude compound was purified by combi-flash column chromatography eluting with 0-10% methanol saturated with ammonia in DCM to afford 250 mg, 16% yield, of the title compound as colorless oil. $^1$H NMR (400 MHz, DMSO-$d_6$) δ=8.52 (s, 2H), 6.36 (t, J=6.85 Hz, 1H), 5.39 (d, J=6.85 Hz, 2H), 2.46 (d, J=6.85 Hz, 2H), 2.38 (s, 2H), 1.66 (br. s, 2H), 1.29-1.38 (m, 2H), 0.44-0.51 (m, 2H), 0.16 (s, 6H), 0.05 (s, 6H); MS (ES$^+$): m/z=354.15 [M+H]$^+$; LCMS: $t_R$=2.33 min.

A solution of mixture of 1,1,3,3-tetramethyl-1,3-bis(((5-(prop-2-yn-1-yl)pyrimidin-2-yl)thio)methyl)disiloxane (2.48 g, 5.050 mmol) and bis((9H-fluoren-9-yl)methyl) ((1,1,3,3-tetramethyldisiloxane-1,3-diyl)bis(propane-3,1-diyl)) dicarbamate (3.50 g, 5.05 mmol) in 4M HCl in dioxane (35 mL) was stirred at room temperature for 1 h. The reaction mixture was concentrated in vacuo resulting in the crude intermediate 4 and 5. The mixture of 4 and 5 was dissolved in acetonitrile (350 mL) and followed by addition of water (0.90 mL, 5.05 mmol) and DIPEA (2.63 mL, 15.15 mmol) and stirred at room temperature for 1 h. The reaction mixture was concentrated in vacuo resulting in the crude compound which was purified by chromatography on silica gel eluting with 0-40% ethyl acetate in n-hexane to afford 2.50 g, 86% yield, of the title compound as a colorless oil. MS (ES$^+$): m/z=576.45 [M+H]$^+$; LCMS: $t_R$=3.98 min.

1,1,3,3-Tetramethyl-1,3-bis(((5-(prop-2-yn-1-yl)pyrimidin-2-yl)thio)methyl)disiloxane (2)

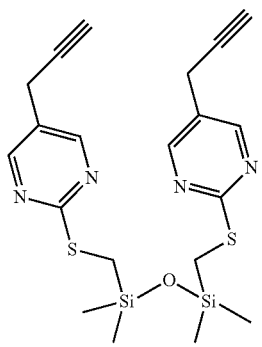 [SMILES: C#CCc1cnc(SC[Si](C)(C)O[Si](C)(C)CSc2ncc(CC#C)cn2)nc1]

A solution of 1,3-bis(((5-(chloromethyl)pyrimidin-2-yl)thio)methyl)-1,1,3,3-tetramethyldisiloxane (6 g, 12.52 mmol) in THF (200 mL) was added copper iodide (4.76 g, 25.05 mmol) and ethynylmagnesium bromide (9.6 g, 75.15 mmol) at room temperature. The reaction mixture was further heated to reflux at 70° C. and stirred for another 12 h. The reaction mixture was filtered, diluted with water (50 mL) and concentrated in vacuo resulting in the crude compound which was purified by column chromatography on silica gel eluting with 0-20% ethyl acetate in n-hexane to afford 3.70 g, 60% yield of the title compound as a white solid. $^1$H NMR (400 MHz, DMSO-$d_6$) δ=8.53 (s, 4H), 3.59 (d, J=2.45 Hz, 4H), 3.13 (t, J=2.45 Hz, 2H), 2.37 (s, 4H), 0.15 (s, 12H).

Example 51

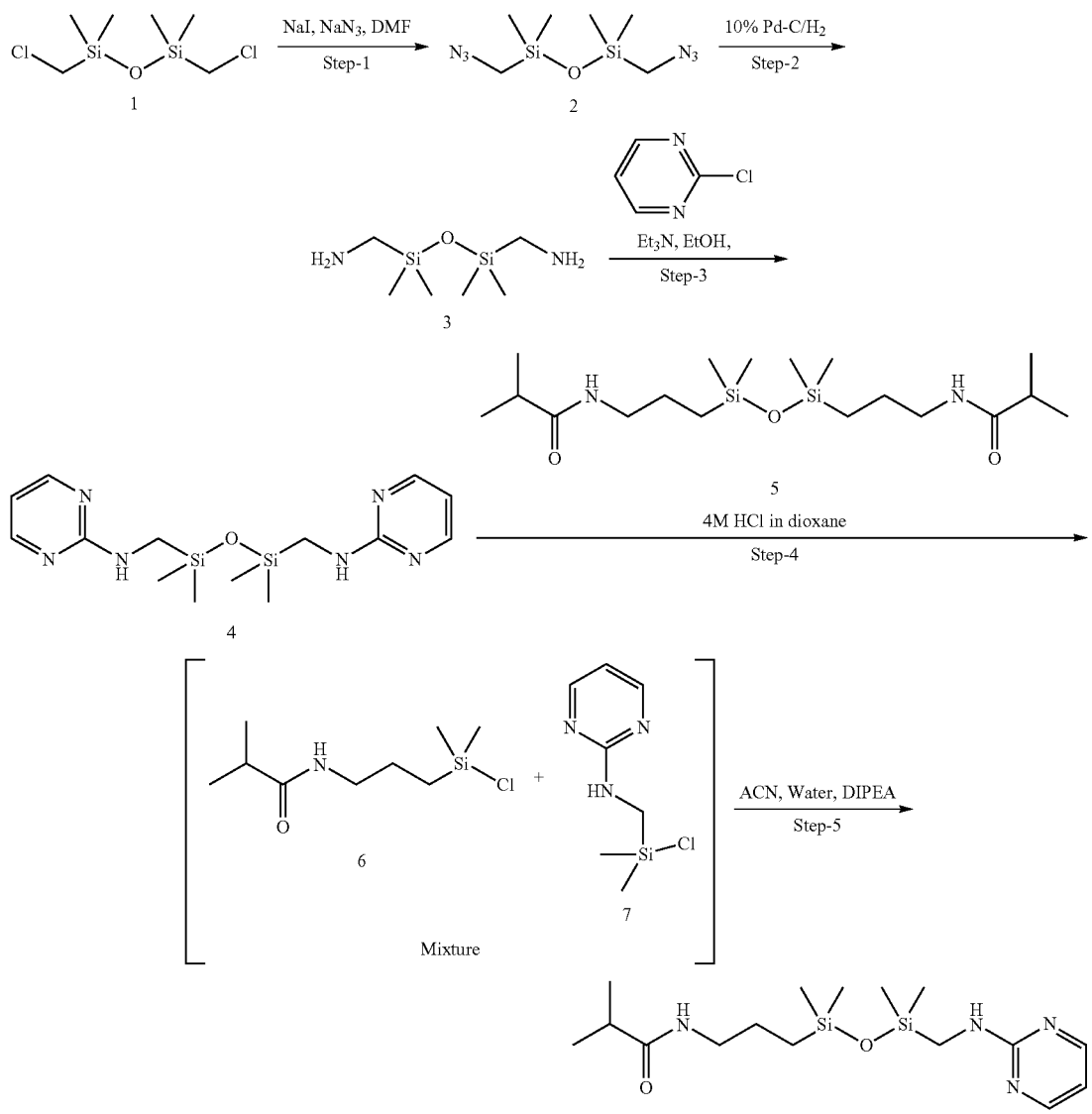

Example 51

N-(3-(1,1,3,3-tetramethyl-3-((pyrimidin-2-ylamino)methyl)disiloxanyl)propyl)isobutyramide [Example 51]

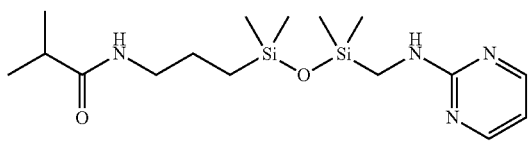 [SMILES: CC(C)C(=O)NCCC[Si](C)(C)O[Si](C)(C)CNc1ncccn1]

A solution of mixture of N,N'-((1,1,3,3-tetramethyldisiloxane-1,3-diyl)bis(methylene))bis(pyrimidin-2-amine) (500 mg, 1.436 mmol) and N,N'-((1,1,3,3-tetramethyldisiloxane-1,3-diyl)bis(propane-3,1-diyl))bis(2-methylpropanamide) (567 mg, 1.436 mmol) in 4M HCl in dioxane (15 mL) was stirred at room temperature for 1 h. The reaction mixture was concentrated in vacuo resulting in the crude intermediate 6 and 7. The mixture of 6 and 7 was dissolved in acetonitrile (50 mL) and followed by addition of water (0.051 mL, 2.80 mmol), DIPEA (2.2 g, 17.05 mmol) and stirred at room temperature for 1 h. The reaction mixture was concentrated in vacuo resulting in the crude compound which was purified by chromatography on silica with 0-30% ethyl acetate in n-hexane to afford 160 mg, 30% yield, of the title compound as colorless oil. $^1$H NMR (400 MHz, DMSO-$d_6$) δ=8.21 (d, J=4.40 Hz, 2H), 7.62-7.69 (m, 1H), 6.82 (t, J=5.14 Hz, 1H), 6.48 (t, J=4.89 Hz, 1H), 2.97 (q, J=6.85 Hz, 2H), 2.75 (d, J=5.38 Hz, 2H), 2.31 (quin, J=6.85 Hz, 1H), 1.32-1.42 (m, 2H), 0.97 (d, J=6.85 Hz, 6H), 0.40-0.48 (m, 2H), 0.11 (s, 6H), 0.01 (s, 6H); MS (ES$^+$): m/z=184.08 [M/2+H]$^+$; LCMS: $t_R$=1.42 min.

N,N'-((1,1,3,3-tetramethyldisiloxane-1,3-diyl)bis(methylene))bis(pyrimidin-2-amine) (4)

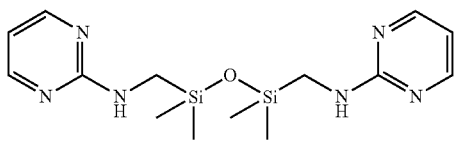 [SMILES: C[Si](C)(CNc1ncccn1)O[Si](C)(C)CNc1ncccn1]

A solution of (1,1,3,3-tetramethyldisiloxane-1,3-diyl)dimethanamine (3 g, 15.35 mmol) in ethanol (10 mL) was charged with triethyl amine (12.8 mL, 92.10 mmol) and 2-chloropyrimidine (3.5 g, 30.70 mmol) at room temperature. The reaction mixture was further heated to 60° C. for 2 h. The reaction mixture was concentrated in vacuo resulting in the crude compound which was purified by combi-flash column chromatography eluting with 0-10% methanol in DCM to afford 3.2 g, 60% yield of the title compound as colorless oil. MS (ES$^+$): m/z=184.00 [M/2+18]$^+$; LCMS: $t_R$=1.34 min.

(1,1,3,3-Tetramethyldisiloxane-1,3-diyl)dimethanamine (3)

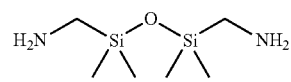

A solution of 1,3-bis(azidomethyl)-1,1,3,3-tetramethyldisiloxane (4.5 g, 18.41 mmol) in methanolic ammonia (150 mL) was charged with 10% Pd/C (450 mg, 10% by wt) under argon atmosphere. The reaction mixture was stirred under hydrogen atmosphere in autoclave at room temperature for 2 h. The reaction mixture was filtered through a pad of Celite and washed with methanol. The filtrate was concentrated in vacuo to afford 2.86 g, 90% yield, of the title compound as colorless oil. $^1$H NMR (400 MHz, DMSO-$d_6$) δ=2.48 (br. s, 4H), 2.01 (s, 2H), 0.06 (3, 12H).

1,3-Bis(azidomethyl)-1,1,3,3-tetramethyldisiloxane (2)

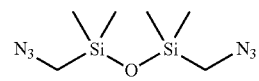

A solution of 1,3-bis(chloromethyl)-1,1,3,3-tetramethyldisiloxane (5 g, 21.64 mmol) in DMF (50 mL) was charged with sodium azide (3 g, 47.61 mmol) and sodium iodide (7 g, 47.61 mmol) at room temperature. The reaction mixture was further heated to 90° C. for 12 h. The reaction mixture was concentrated in vacuo and the residue was stirred in ether (50 mL) and filtered. The filtrate was concentrated in vacuo to afford 4.40 g, 85% yield, of the title compound as colorless oil. $^1$H NMR (400 MHz, DMSO-$d_6$) δ=2.76 (s, 4H), 0.09 (s, 12H).

Example 52 and Example 77

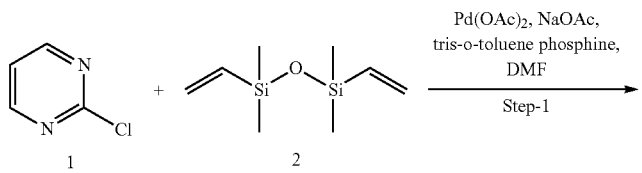

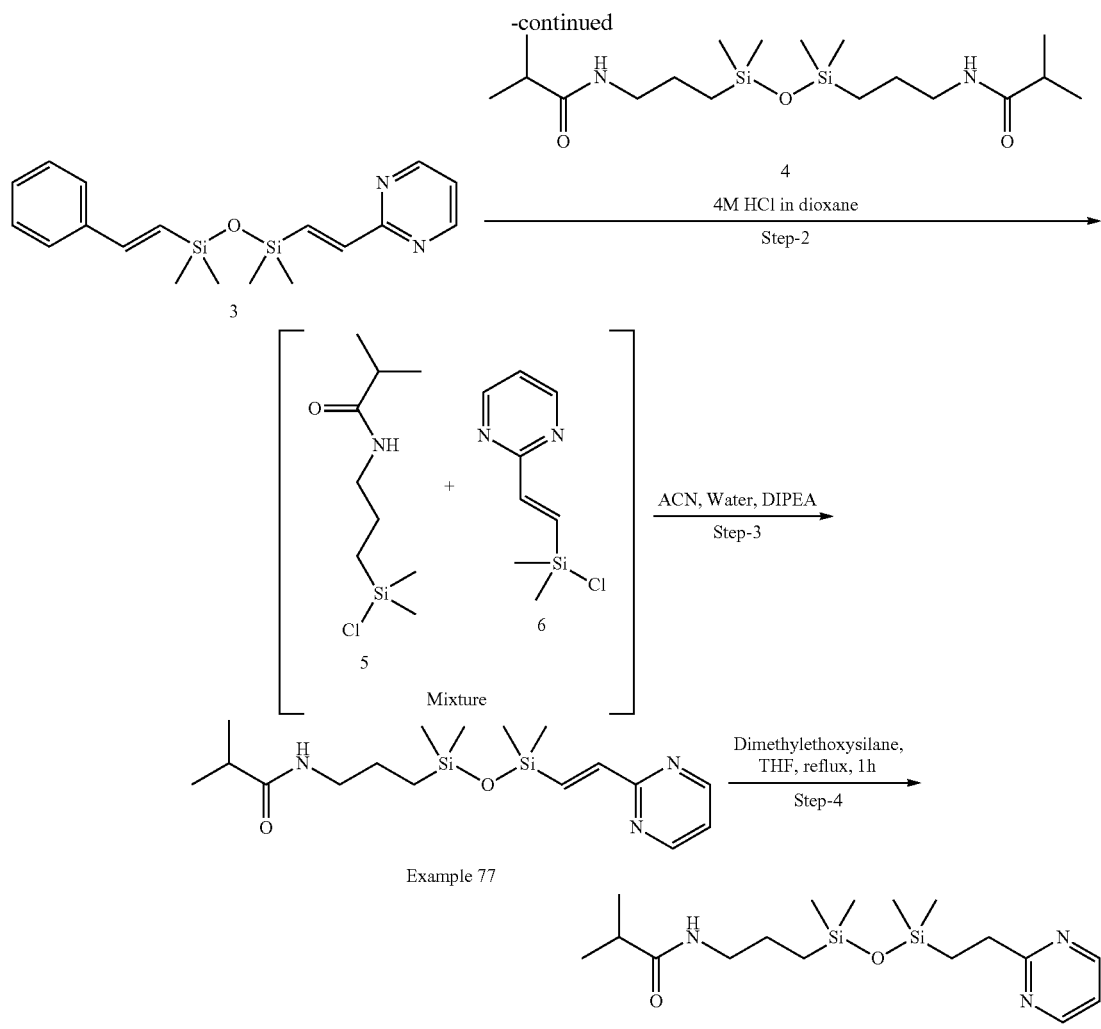

Example 77

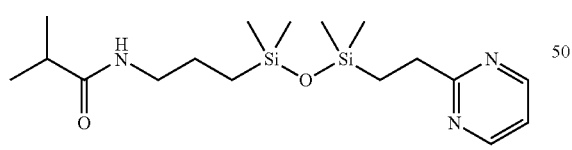

Example 52

N-(3-(1,1,3,3-Tetramethyl-3-(2-(pyrimidin-2-yl)ethyl)disiloxanyl)propyl)isobutyramide [Example 52]

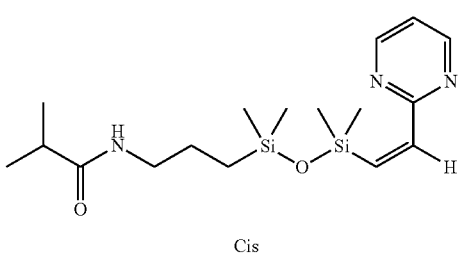

A solution of ((E)-N-(3-(1,1,3,3-tetramethyl-3-(2-(pyrimidin-2-yl)vinyl) disiloxanyl) propyl) isobutyramide (600 mg, 1.643 mmol) in THF (20 mL) was charged with Pd(OAc)₂ (73 mg, 0.328 mmol) and dimethyl ethoxy silane (512 mg, 4.931 mmol) and stirred at room temperature for 1 h. The reaction mixture was concentrated in vacuo and the crude compound was purified by Combi Flash chromatography on silica gel eluting with 0-10% methanol saturated with ammonia in DCM to afford 90 mg, 15% yield, of the title compound as a colorless oil. ¹H NMR (400 MHz, DMSO-d₆) δ=8.72 (d, J=4.89 Hz, 2H), 7.70 (br. s, 1H), 7.32 (t, J=4.89 Hz, 1H), 2.99 (q, J=6.52 Hz, 2H), 2.83-2.92 (m, 2H), 2.28-2.36 (m, 1H), 1.39 (td, J=7.83, 15.65 Hz, 2H), 0.95-1.04 (m, 8H), 0.44-0.50 (m, 2H), 0.05 (s, 12H); MS (ES⁺): m/z=182.95 monomer [M+H]⁺; LCMS: t$_R$=1.89/2.12 min.

(E)-N-(3-(1,1,3,3-Tetramethyl-3-(2-(pyrimidin-2-yl)vinyl) disiloxanyl) propyl) isobutyramide [Example 77]

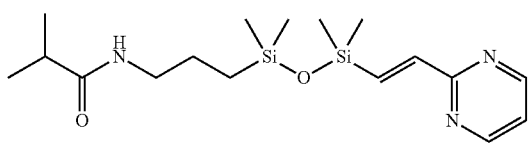 [SMILES: CC(C)C(=O)NCCC[Si](C)(C)O[Si](C)(C)CCc1ncccn1]

Trans

A solution of mixture of 1,1,3,3-tetramethyl-1,3-bis((E)-2-(pyrimidin-2-yl)vinyl)disiloxane (1 g, 2.923 mmol) and N,N'-((1,1,3,3-tetramethyldisiloxane-1,3-diyl)bis(propane-3,1-diyl))bis(2-methylpropanamide) (1.13 g, 2.923 mmol) in 4M HCl in dioxane (20 mL) was stirred at room temperature for 1 h. The reaction mixture was concentrated in vacuo resulting in the crude intermediate 5 and 6. The mixture of 5 and 6 was dissolved in acetonitrile (50 mL) and followed by addition of water (0.105 mL, 5.846 mmol) and DIPEA (3 mL, 17.54 mmol) and stirred at room temperature for 1 h. The reaction mixture was concentrated in vacuo resulting in the crude compound which was purified by Combi Flash chromatography on silica gel eluting with 0-10% ethyl acetate in n-hexane to afford 1.02 g, 48% yield, of the title compound (mixture of cis and trans) as a colorless oil. $^1$H NMR (400 MHz, DMSO-$d_6$) δ=(mixture of cis and trans) 8.81 (d, J=4.89 Hz, 2H), 8.77 (t, J=5.38 Hz, 2H), 7.68 (br. s, 2H), 7.39 (q, J=4.40 Hz, 4H), 7.27-7.36 (m, 1H), 6.96-7.06 (m, 1H), 4.02-4.12 (m, 1H), 3.44 (dt, J=3.42, 15.16 Hz, 2H), 3.08-3.19 (m, 2H), 3.00 (q, J=6.36 Hz, 4H), 2.32 (td, J=6.30, 13.33 Hz, 2H), 1.38-1.46 (m, 4H), 0.98 (s, 6H), 0.97 (s, 6H), 0.20-0.32 (m, 12H), 0.07-0.12 (m, 12H); MS (ES$^+$): m/z=366.15 [M+H]$^+$; LCMS: $t_R$=3.22/3.31 min.

1,1,3,3-Tetramethyl-1,3-bis((E)-2-(pyrimidin-2-yl)vinyl)disiloxane (3)

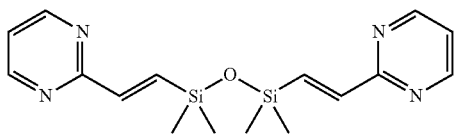 [SMILES: C[Si](C)(/C=C/c1ncccn1)O[Si](C)(C)/C=C/c1ncccn1]

A solution of 2-chloropyrimidine (5 g, 43.85 mmol) in DMF (95 mL) was added 1,1,3,3-tetramethyl-1,3-divinyldisiloxane (4.07 g, 21.92 mmol), sodium acetate (10.8 g, 131.5 mmol), palladium acetate (982 mg, 4.385 mmol) and tris-o-toluene phosphine (2.6 g, 8.771 mmol) at room temperature. The reaction mixture was further heated to reflux at 120° C. for 14 h and diluted with water and filtered through a pad of Celite. The separated organic layer was washed with water and separated. The organic layer was dried over Na$_2$SO$_4$, filtered and concentrated in vacuo resulting in the crude compound which was purified by combiflash column chromatography on silica gel eluting with 0-20% ethyl acetate in n-hexane to afford 3.15 g, 21% yield, of the title compound as colorless oil. MS (ES$^+$): m/z=342.55 [M+H]$^+$; LCMS: 181.08 (monomer); $t_R$=2.1 min.

Example 53

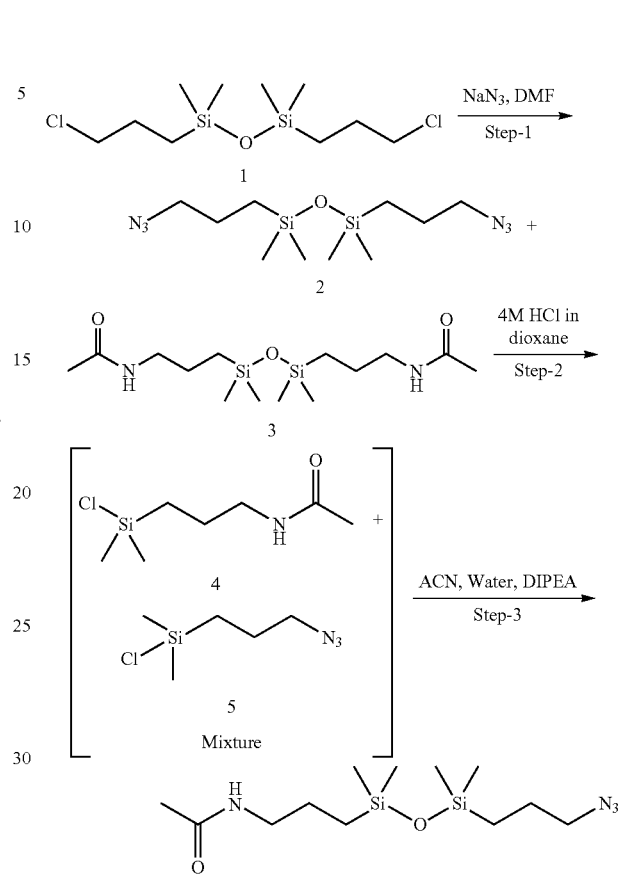

Example 53

N-(3-(3-(3-azidopropyl)-1,1,3,3-tetramethyldisiloxanyl)propyl)acetamide [Example 53]

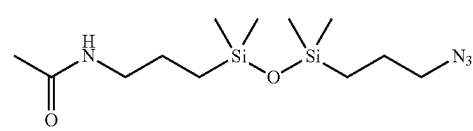 [SMILES: CC(=O)NCCC[Si](C)(C)O[Si](C)(C)CCCN=[N+]=[N-]]

A solution of mixture of 1,3-bis(3-azidopropyl)-1,1,3,3-tetramethyldisiloxane (361 mg, 1.2 mmol) and N,N'-((1,1,3,3-tetramethyldisiloxane-1,3-diyl)bis(propane-3,1-diyl))diacetamide (400 mg, 1.2 mmol) were dissolved in 4M HCl in dioxane (10 mL) and stirred at room temperature for 1 h. The reaction mixture was concentrated in vacuo resulting in the crude mixture of 4 and 5. The crude mixture was was charged with acetonitrile (10 mL) and water (43 mg, 2.4 mmol) followed by DIPEA (931 mg, 7.2 mmol) and stirred at room temperature for 1 h. The reaction mixture was concentrated in vacuo resulting in the crude compound which was purified by chromatography on silica gel chromatography eluting with 20-40% ethyl acetate in n-hexane to afford 280 mg, 73% yield, of the title compound as colorless oil. $^1$H NMR (400 MHz, DMSO-$d_6$) δ=7.80 (br. s, 1H), 3.28 (t, J=6.85 Hz, 2H), 2.93-3.01 (m, 2H), 1.76 (s, 3H), 1.49-1.58 (m, 2H), 1.32-1.41 (m, 2H), 0.50-0.55 (m, 2H), 0.42-0.49 (m, 2H), 0.05 (s, 6H), 0.03 (s, 6H); (ESMS): m/z=339.00 [M+Na]⁺ and 360.85 [M+ACN]⁺

1,3-Bis(3-azidopropyl)-1,1,3,3-tetramethyldisiloxane (2)

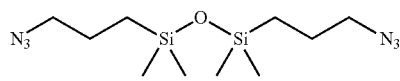 [SMILES: C[Si](C)(CCCN=[N+]=[N-])O[Si](C)(C)CCCN=[N+]=[N-]]

A solution of 1,3-bis(3-chloropropyl)-1,1,3,3-tetramethyldisiloxane (3 g, 10.4 mmol) in DMF (30 mL) was charged with sodium azide (1.49 g, 22.9 mmol) and stirred at 90° C. for 12 h. The reaction mixture was concentrated in vacuo and reaction mixture was dissolved in diethyl ether. The preciptate was filtered of through a fritted funnel and the filtrate was concentrated in vacuo to afford 2.80 g, 90% yield, of the title compound as colorless oil.

$^1$H NMR (400 MHz, DMSO-$d_6$) δ=3.28 (t, J=6.85 Hz, 4H), 1.49-1.59 (m, 4H), 0.49-0.57 (m, 4H), 0.06 (s, 12H).

Example 54

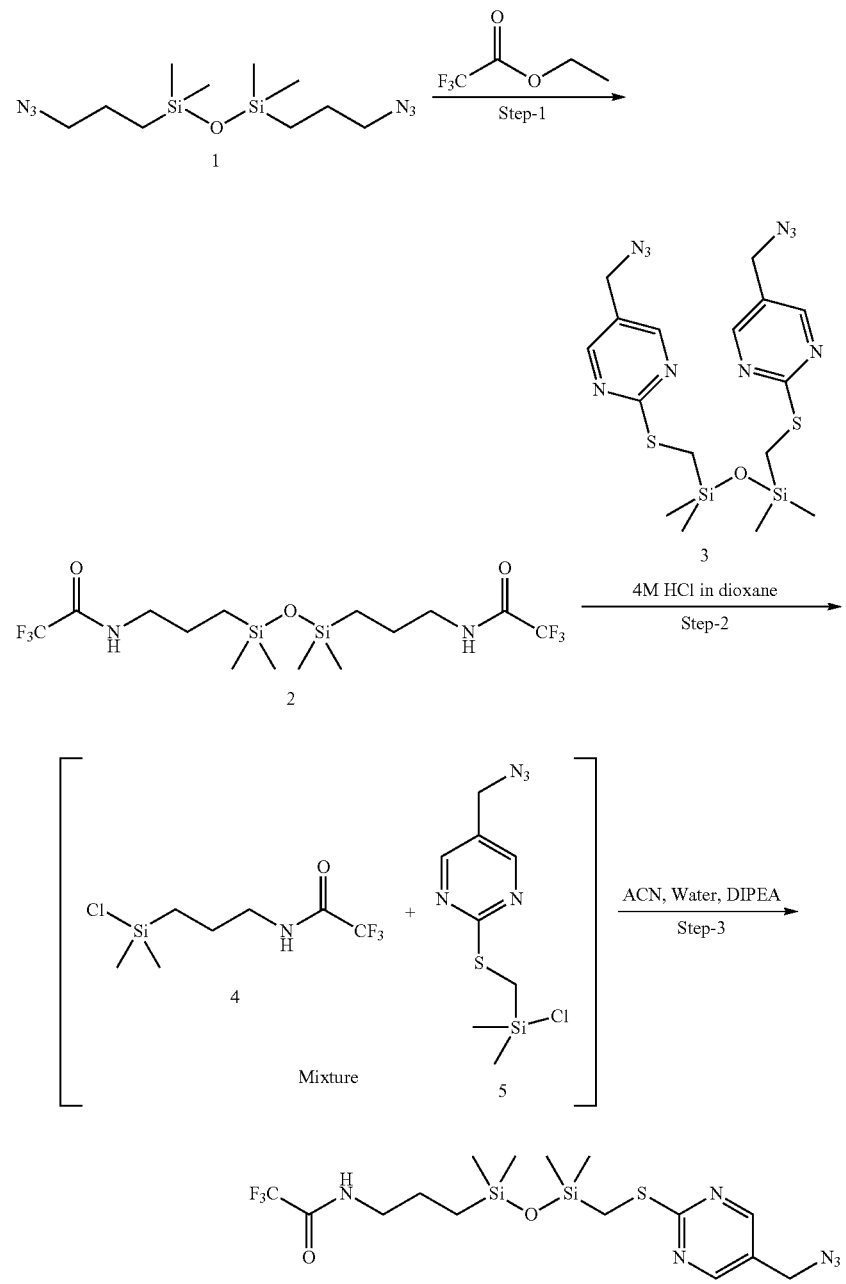

Example 54

N-(3-(3-(((5-(Azidomethyl)pyrimidin-2-yl)thio)methyl)-1,1,3,3-tetramethyldisiloxanyl)propyl)-2,2,2-trifluoroacetamide [Example 54]

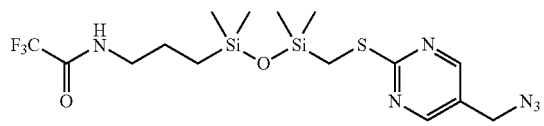 [SMILES: C[Si](C)(CCCNC(=O)C(F)(F)F)O[Si](C)(C)CSc1ncc(CN=[N+]=[N-])cn1]

A solution of N,N'-((1,1,3,3-tetramethyldisiloxane-1,3-diyl)bis(propane-3,1-diyl))bis(2,2,2-trifluoroacetamide) (447 mg, 0.9 mmol) and 1,3-bis(((5-(azidomethyl)pyrimidin-2-yl)thio)methyl)-1,1,3,3-tetramethyldisiloxane (400 mg, 0.9 mmol) was charged with 4M HCl in dioxane (10 mL) and stirred at room temperature for 1 h. The reaction mixture was concentrated in vacuo resulting in the crude mixture of 4 and 5 which was charged with acetonitrile (10 mL) and water (32 mg, 1.8 mmol), followed by DIPEA (703 mg, 5.45 mmol) and stirred at room temperature for 1 h. The reaction mixture was concentrated in vacuo resulting in the crude compound which was purified by chromatography on silica gel eluting with 0-40% ethyl acetate in n-hexane to afford 249 mg, 59% yield, of the title compound as colorless oil. $^1$H NMR (400 MHz, DMSO-$d_6$) δ=9.39 (br. s, 1H), 8.62-8.66 (m, 2H), 4.48 (s, 2H), 3.12 (q, J=6.85 Hz, 2H), 2.38 (s, 2H), 1.41-1.52 (m, 2H), 0.43-0.51 (m, 2H), 0.15 (s, 6H), 0.04 (s, 6H); MS (ES$^+$): m/z=467.14 [M+H]$^+$; LCMS: $t_R$=3.63 min.

N,N'-((1,1,3,3-Tetramethyldisiloxane-1,3-diyl)bis(propane-3,1-diyl))bis(2,2,2-trifluoroacetamide) (2)

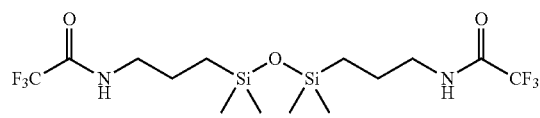 [SMILES: C[Si](C)(CCCNC(=O)C(F)(F)F)O[Si](C)(C)CCCNC(=O)C(F)(F)F]

A solution of 3,3'-(1,1,3,3-tetramethyldisiloxane-1,3-diyl)bis(propan-1-amine) (1 g, 4.03 mmol) was charged with ethyl 2,2,2-trifluoroacetate (1.70 g, 12.09 mmol) and stirred at room temperature for 1 h. The reaction mixture was concentrated in vacuo until dryness to afford 1.76 g, 80% yield, of the title compound as colorless oil. The crude compound was used directly for next step without further purification. $^1$H NMR (400 MHz, DMSO-$d_6$) δ=9.40 (br. s, 2H), 3.13 (q, J=6.85 Hz, 4H), 1.47 (td, J=7.83, 15.65 Hz, 4H), 0.42-0.50 (m, 4H), 0.03 (s, 12H).

Example 55

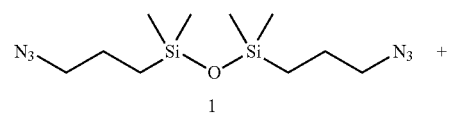

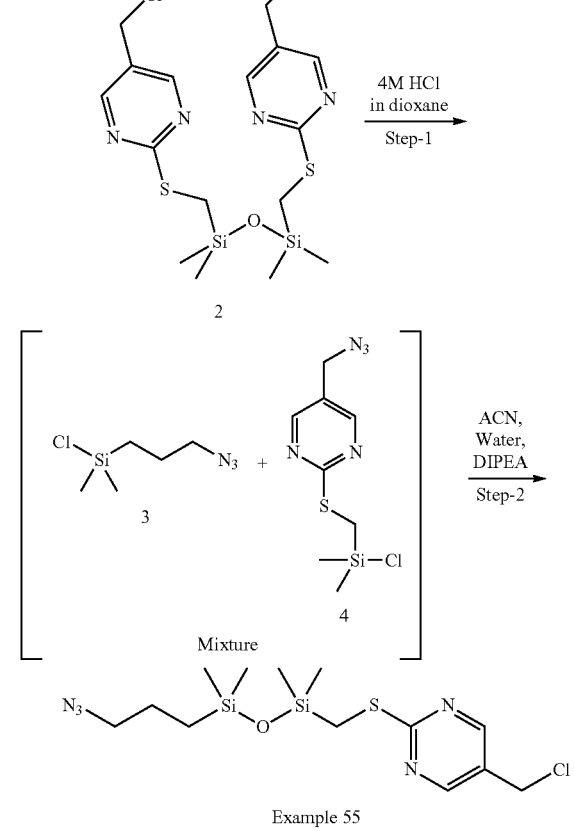

Example 55

2-(((3-(3-Azidopropyl)-1,1,3,3-tetramethyldisiloxanyl)methyl)thio)-5-(chloromethyl)pyrimidine [Example 55]

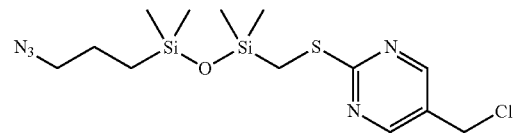 [SMILES: C[Si](C)(CCCN=[N+]=[N-])O[Si](C)(C)CSc1ncc(CCl)cn1]

A solution of mixture 1,3-bis(3-azidopropyl)-1,1,3,3-tetramethyldisiloxane (2.0 g, 6.66 mmol) and 1,3-bis(((5-(chloromethyl)pyrimidin-2-yl)thio)methyl)-1,1,3,3-tetramethyldisiloxane (3.19 g, 6.66 mmol) in 4M HCl in dioxane (50 mL) was stirred at room temperature for 1 h. The reaction mixture was concentrated in vacuo resulting in the crude mixture of 3 and 4 were charged with mixture acetonitrile (20 mL) and water (239 mg, 13.32 mmol), and DIPEA (10.3 g, 79.9 mmol) and stirred at room temperature for 1 h. The reaction mixture was concentrated in vacuo resulting in the crude compound which was purified by chromatography on silica gel eluting with 0-20% ethyl acetate in n-hexane to afford 3.40 g, 85% yield, of the title compound as a colorless oil. $^1$H NMR (400 MHz, DMSO-$d_6$) δ=8.64 (s, 2H), 4.71 (s, 2H), 3.20 (t, J=6.85 Hz, 2H), 2.34 (s, 2H), 1.42-1.52 (m, 2H), 0.44-0.50 (m, 2H), 0.11 (s, 6H), 0.00 (s, 6H); MS (ES$^+$): m/z=389.80 [M+H]$^+$; LCMS: $t_R$=4.11 min.

Example 56

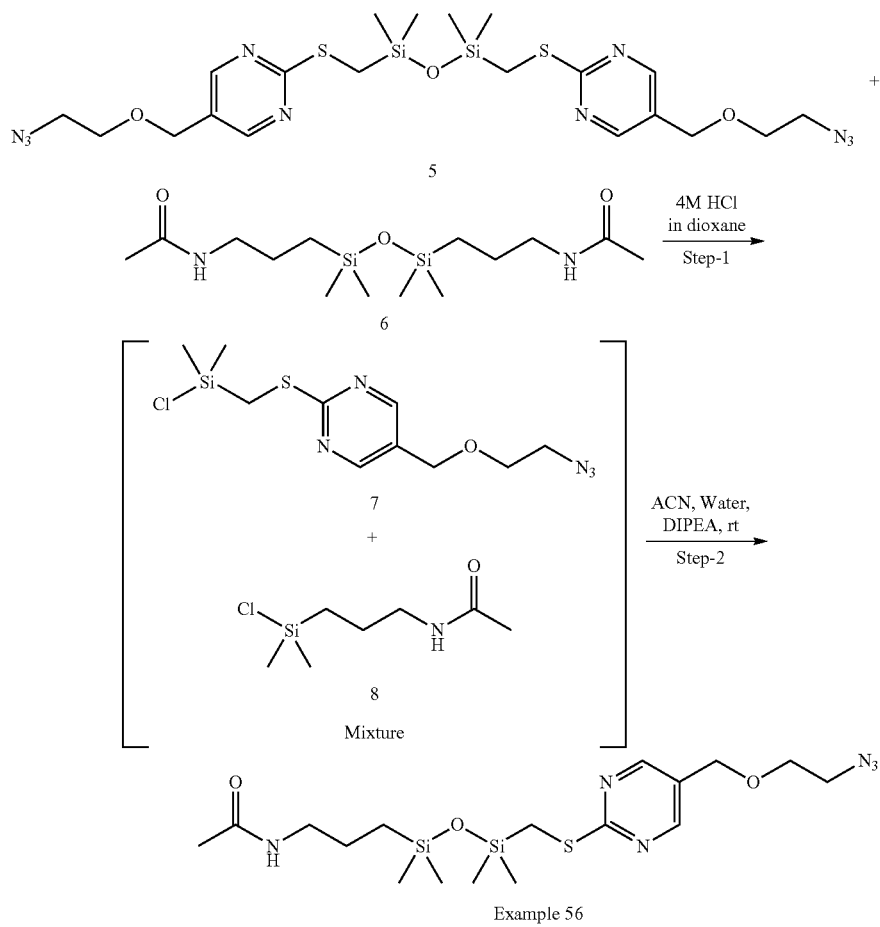

N-(3-(3-(((5-((2-Azidoethoxy)methyl)pyrimidin-2-yl)thio)methyl)-1,1,3,3-tetramethyldisiloxanyl)propyl)acetamide [Example 56]

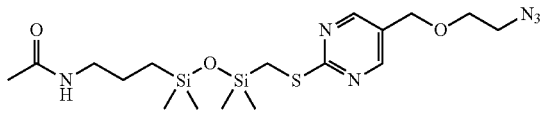 [SMILES: CC(=O)NCCC[Si](C)(C)O[Si](C)(C)CSc1ncc(COCCN=[N+]=[N-])cn1]

A solution of mixture of 1,3-bis(((5-((2-azidoethoxy)methyl)pyrimidin-2-yl)thio)methyl)-1,1,3,3-tetramethyldisiloxane (500 mg, 0.862 mmol) and N,N'-((1,1,3,3-tetramethyldisiloxane-1,3-diyl)bis(propane-3,1-diyl))diacetamide (286 mg, 0.862 mmol) dissolved in 4M HCl in dioxane (20 mL) was stirred at room temperature for 1 h. The reaction mixture was concentrated in vacuo resulting in the crude intermediate 7 and 8. The crude mixture of 7 and 8 was charged with acetonitrile (60 mL) and water (0.031 mL, 17.24 mmol) followed by DIPEA (0.89 mL, 51.72 mmol) and stirred at room temperature for 1 h. The reaction mixture was concentrated in vacuo resulting in the crude compound which was purified by chromatography on silica gel eluting with 0-70% ethyl acetate in n-hexane to afford 595 mg, 75% yield, of the title compound as a colorless oil. $^1$H NMR (400 MHz, DMSO-$d_6$) δ=8.58 (s, 2H), 7.77 (br. s, 1H), 4.51 (s, 2H), 3.64 (t, J=4.65 Hz, 2H), 3.42 (t, J=4.65 Hz, 2H), 2.95 (q, J=6.36 Hz, 2H), 2.35-2.40 (m, 2H), 1.73-1.78 (m, 3H), 1.31-1.41 (m, 2H), 0.42-0.50 (m, 2H), 0.15 (s, 6H), 0.04 (s, 6H); MS (ES$^+$): m/z=457.29 [M+H]$^+$; LCMS: $t_R$=3.25 min.

Example 57

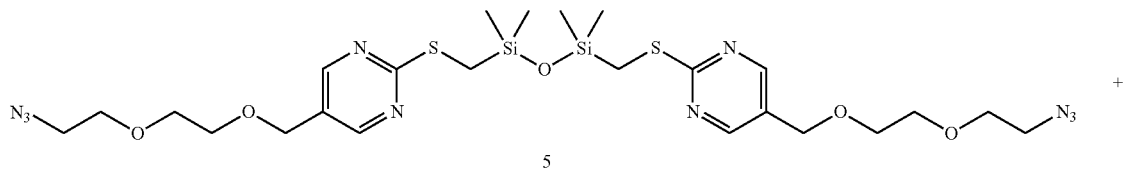

-continued

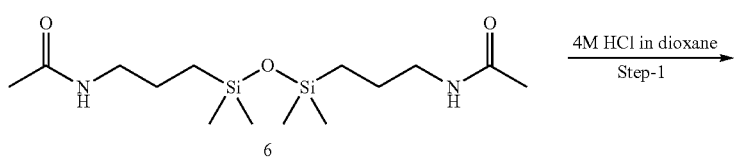

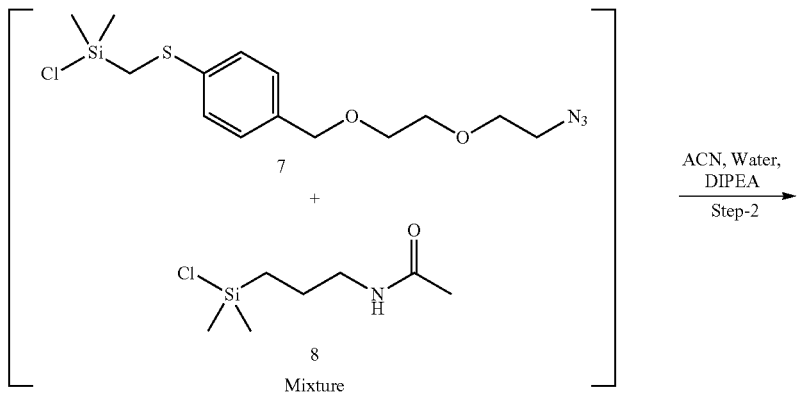

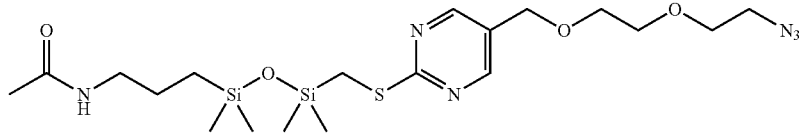 [SMILES: CC(=O)NCCC[Si](C)(C)O[Si](C)(C)CSc1ncc(COCCOCCN=[N+]=[N-])cn1]

Example 57

N-(3-(3-(((5-((2-(2-Azidoethoxy)ethoxy)methyl)pyrimidin-2-yl)thio)methyl)-1,1,3,3-tetramethyldisiloxanyl)propyl)acetamide [Example 57]

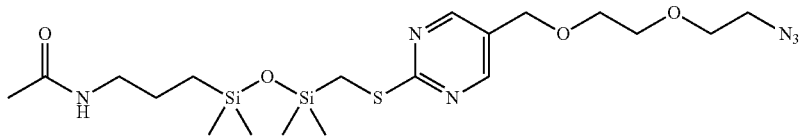

A solution of mixture of 1,3-bis(((5-((2-(2-azidoethoxy)ethoxy)methyl)pyrimidin-2-yl)thio)methyl)-1,1,3,3-tetramethyldisiloxane (500 mg, 0.748 mmol) and N,N'-((1,1,3,3-tetramethyldisiloxane-1,3-diyl)bis(propane-3,1-diyl))diacetamide (248 mg, 0.748 mmol) in 4M HCl in dioxane (20 mL) was stirred at room temperature for 1 h. The reaction mixture was concentrated in vacuo resulting in the crude intermediate 7 and 8. The mixture of intermediate 7 and 8 was charged with acetonitrile (60 mL) and water (0.026 mL, 1.497 mmol) followed by DIPEA (0.39 mL, 2.24 mmol) and stirred at room temperature for 1 h. The reaction mixture was concentrated in vacuo resulting in the crude compound which was purified by column chromatography on silica gel eluting with 0-10% methanol in DCM to afford 530 mg, 71% yield, of the title compound as a colorless oil. $^1$H NMR (400 MHz, DMSO-$d_6$) δ=8.60 (s, 2H), 7.79 (br. s, 1H), 4.49 (s, 2H), 3.62-3.57 (m, 6H), 3.37-3.42 (m, 2H), 2.93-3.02 (m, 2H), 2.40 (s, 2H), 1.78 (s, 3H), 1.35-1.45 (m, 2H), 0.45-0.53 (m, 2H), 0.18 (s, 6H), 0.07 (s, 6H); MS (ES$^+$): m/z=501.37 [M+H]$^+$; LCMS: $t_R$=3.21 min.

Example 58

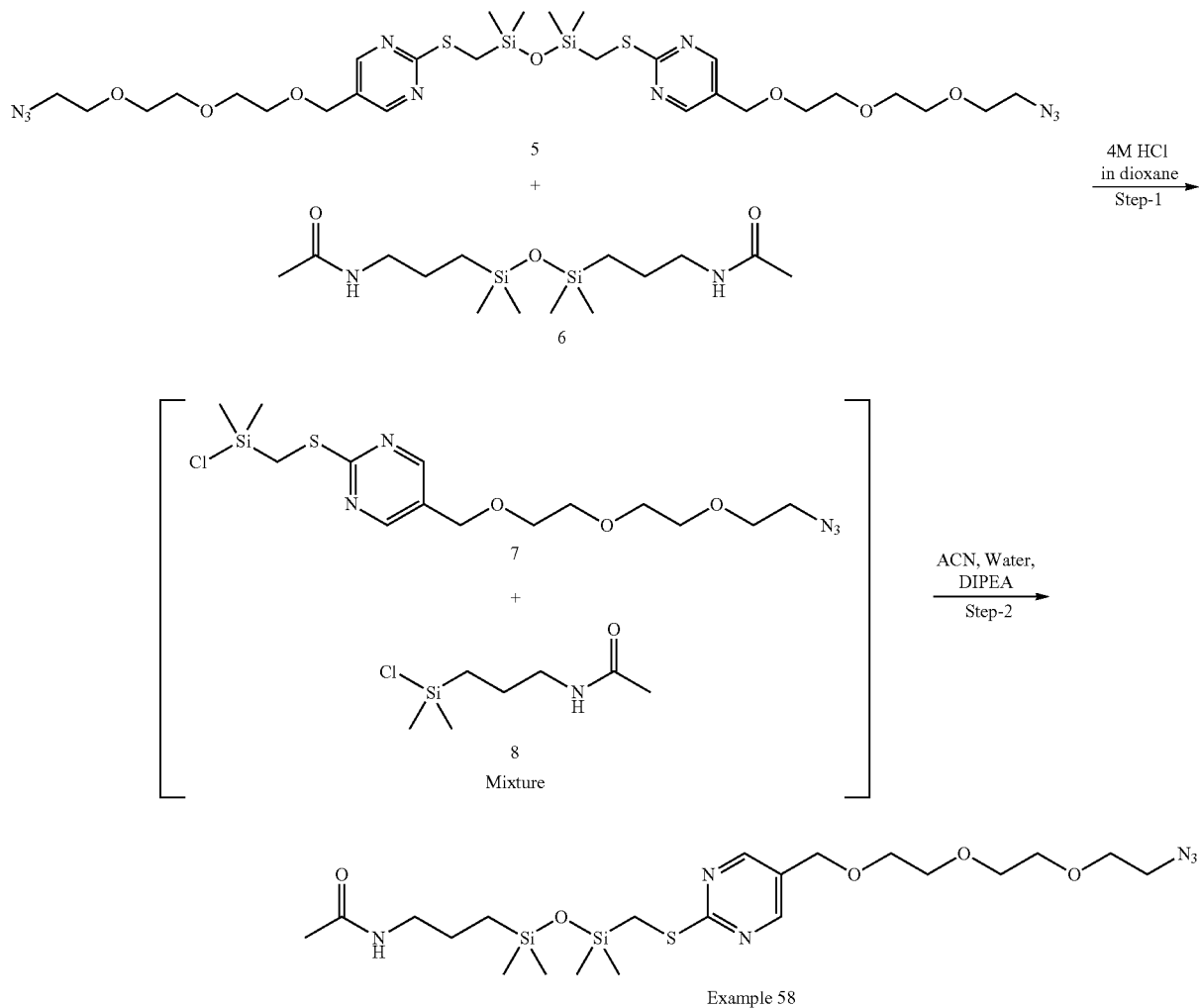

N-(3-(3-((5-((2-(2-(2-azidoethoxy)ethoxy)ethoxy)methyl)pyrimidin-2-yl)thio)methyl)-1,1,3,3-tetramethyldisiloxanyl)propyl)acetamide [Example 58]

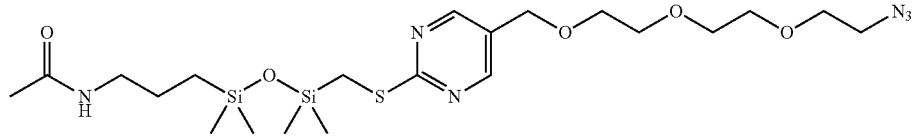 [SMILES: CC(=O)NCCC[Si](C)(C)O[Si](C)(C)CSc1ncc(COCCOCCOCCN=[N+]=[N-])cn1]

A solution of mixture of 1,3-bis(((5-((2-(2-(2-azidoethoxy)ethoxy)ethoxy)methyl)pyrimidin-2-yl)thio)methyl)-1,1,3,3-tetramethyldisiloxane (600 mg, 0.797 mmol) and N,N'-((1,1,3,3-tetramethyldisiloxane-1,3-diyl)bis(propane-3,1-diyl))diacetamide (263 mg, 0.797 mmol) dissolved in 4M HCl in dioxane (20 mL) was stirred at room temperature for 1 h. The reaction mixture was concentrated in vacuo resulting in the crude intermediate 7 and 8. The mixture of intermediate 7 and 8 was charged with acetonitrile (60 mL) and water (0.014 mL, 0.797 mmol) followed by DIPEA (306 mg, 2.393 mmol) and stirred at room temperature for 1 h. The reaction mixture was concentrated in vacuo resulting in the crude compound which was purified by column chromatography on silica gel eluting with 0-10% methanol in DCM to afford 430 mg, 50% yield, of the title compound as a colorless oil. $^1$H NMR (400 MHz, DMSO-$d_6$) δ=8.60 (s, 2H), 7.79 (s, 1H), 4.49 (s, 2H), 3.53-3.64 (m, 10H), 3.37-3.43 (m, 2H), 2.94-3.03 (m, 2H), 2.40 (s, 2H), 1.78 (s, 3H), 1.35-1.45 (m, 2H), 0.45-0.53 (m, 2H), 0.18 (s, 6H), 0.07 (s, 6H); MS (ES$^+$): m/z=545.30 [M+H]$^+$; LCMS: $t_R$=3.19 min.

Example 59

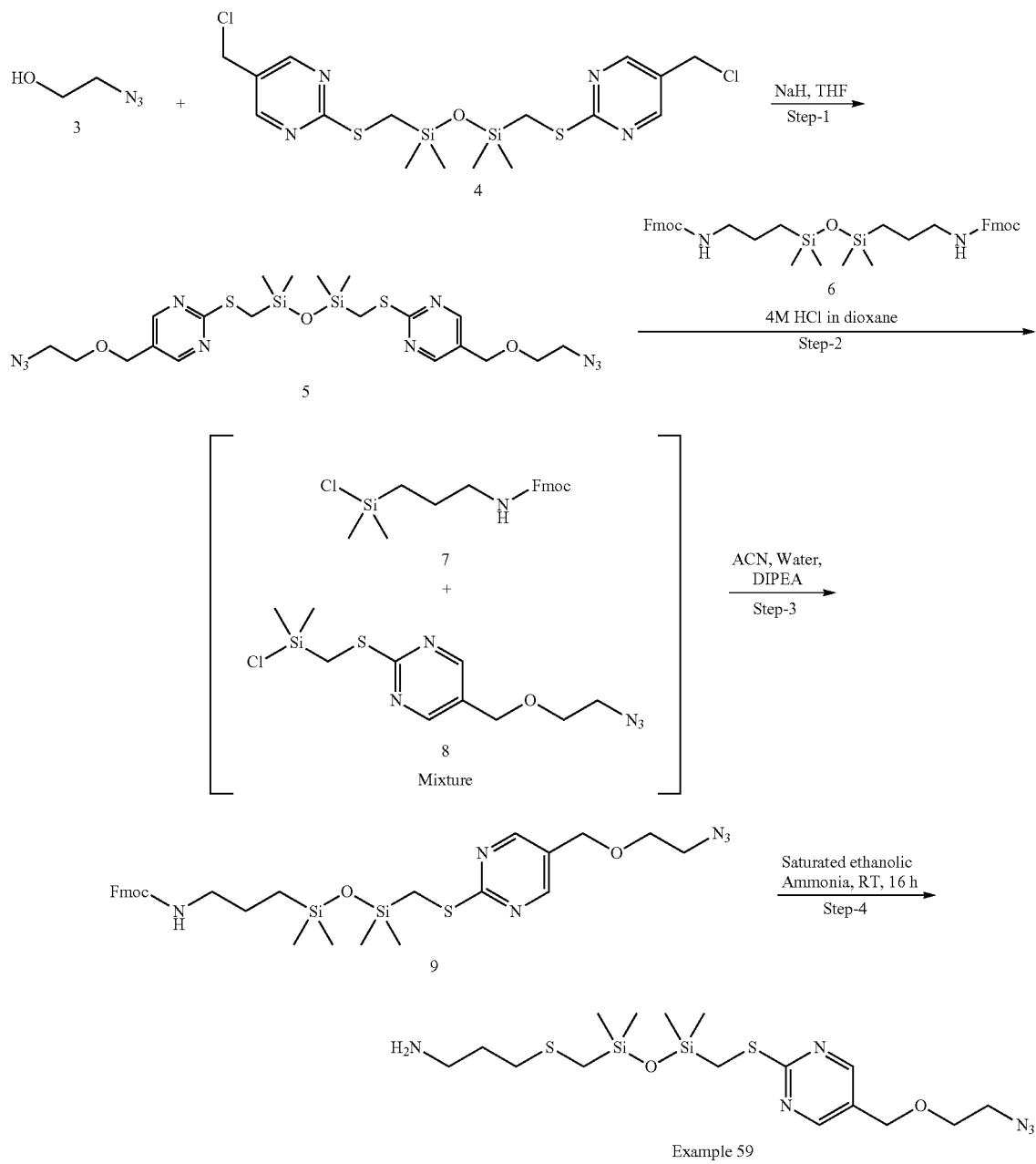

3-(3-(((5-((2-Azidoethoxy)methyl)pyrimidin-2-yl)thio)methyl)-1,1,3,3-tetramethyldisiloxanyl)propan-1-amine [Example 59]

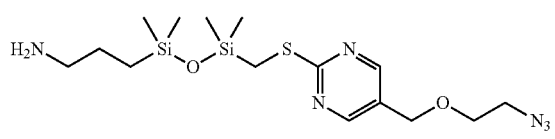 [SMILES: C[Si](C)(CCCN)O[Si](C)(C)CSc1ncc(COCCN=[N+]=[N-])cn1]

A solution of (9H-fluoren-9-yl)methyl(3-(3-(((5-((2-azidoethoxy)methyl)pyrimidin-2-yl)thio)methyl)-1,1,3,3-tetramethyldisiloxanyl)propyl)carbamate (4.4 g, 6.068 mmol) in saturated ethanolic ammonia (132 mL) was stirred at room temperature for 16 h. The reaction mixture was concentrated in vacuo and the crude compound was purified by column chromatography on silica gel eluting with 0-10% methanol saturated with ammonia in DCM to afford 1.1 g, 36% yield, of the title compound as a colorless oil. $^1$H NMR (400 MHz, DMSO-$d_6$) δ=8.62 (s, 2H), 4.54 (s, 2H), 3.64-3.69 (m, 2H), 3.43-3.47 (m, 2H), 2.46-2.50 (m, 2H), 2.40 (s, 2H), 1.73-2.25 (m, 2H), 1.30-1.41 (m, 2H), 0.46-0.54 (m, 2H), 0.18 (s, 6H), 0.07 (s, 6H); MS (ES$^+$): m/z=415.15 [M+H]$^+$; LCMS: $t_R$=2.31 min.

(9H-Fluoren-9-yl)methyl(3-(3-(((5-((2-azidoethoxy)methyl)pyrimidin-2-yl)thio)methyl)-1,1,3,3-tetramethyldisiloxanyl)propyl)carbamate (9)

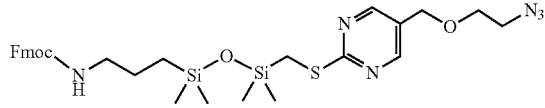

A solution of mixture of 1,3-bis(((5-((2-azidoethoxy)methyl)pyrimidin-2-yl)thio)methyl)-1,1,3,3-tetramethyldisiloxane (4.0 g, 6.896 mmol) and bis((9H-fluoren-9-yl)methyl) ((1,1,3,3-tetramethyldisiloxane-1,3-diyl)bis(propane-3,1-diyl))dicarbamate (4.7 g, 6.896 mmol) in 4M HCl in dioxane (100 mL) was stirred at room temperature for 1 h. The reaction mixture was concentrated in vacuo resulting in the crude intermediate 7 and 8. The mixture of intermediate 7 and 8 was dissolved in acetonitrile (300 mL) and followed by addition of water (0.25 mL, 13.79 mmol) and DIPEA (7.2 mL, 41.37 mmol) and stirred at room temperature for 1 h. The reaction mixture was concentrated in vacuo resulting in the crude compound which was purified by column chromatography on silica gel eluting with 0-70% ethyl acetate in n-hexane to afford 4.40 g, 50.6% yield, of the title compound as a colorless oil. $^1$H NMR (400 MHz, DMSO-$d_6$) δ=8.59 (s, 2H), 7.89 (d, J=7.34 Hz, 2H), 7.69 (d, J=7.34 Hz, 2H), 7.37-7.45 (m, 2H), 7.27-7.35 (m, 3H), 4.48-4.57 (m, 2H), 4.25-4.32 (m, 2H), 4.18-4.24 (m, 1H), 3.63-3.68 (m, 2H), 3.41-3.46 (m, 2H), 2.95 (q, J=6.36 Hz, 2H), 2.36-2.42 (m, 2H), 1.42 (td, J=7.46, 15.41 Hz, 2H), 0.44-0.52 (m, 2H), 0.17 (s, 6H), 0.06 (s, 6H); MS (ES$^+$): m/z=637.90 [M+H]$^+$; LCMS: $t_R$=4.00 min.

1,3-Bis(((5-((2-azidoethoxy)methyl)pyrimidin-2-yl)thio)methyl)-1,1,3,3-tetramethyldisiloxane (5)

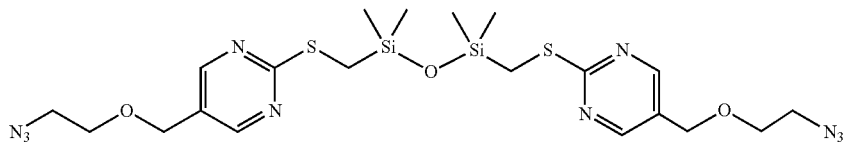 [SMILES: C[Si](C)(CSc1ncc(COCCN=[N+]=[N-])cn1)O[Si](C)(C)CSc1ncc(COCCN=[N+]=[N-])cn1]

A solution of 2-azidoethan-1-ol (2.40 g, 28.70 mmol) in THF (300 mL) at 0° C. was charged with sodium hydride (1.37 g, 34.44 mmol) and stirred at 0° C. for 30 min. The reaction mixture was then charged with 1,3-bis(((5-(chloromethyl)pyrimidin-2-yl)thio)methyl)-1,1,3,3-tetramethyldisiloxane (5.50 g, 11.48 mmol) and the resulting solution was stirred at 0° C. for another 1 h. The reaction mixture was concentrated in vacuo resulting in the crude compound which was purified by column chromatography on silica gel eluting with 0-100% ethyl acetate in n-hexane to afford 5.94 g, 60% yield, of the title compound as colorless oil.

$^1$H NMR (400 MHz, DMSO-$d_6$) δ=8.70 (s, 2H), 8.59 (s, 2H), 4.78 (s, 2H), 4.52 (s, 2H), 3.64-3.67 (m, 2H), 3.58 (br. s, 2H), 3.41-3.46 (m, 2H), 3.24-3.28 (m, 1H), 2.41 (d, J=2.93 Hz, 4H), 1.95-2.01 (m, 1H), 0.18 (s, 12H).

Example 60

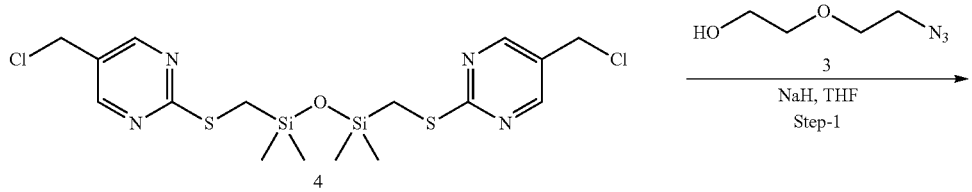

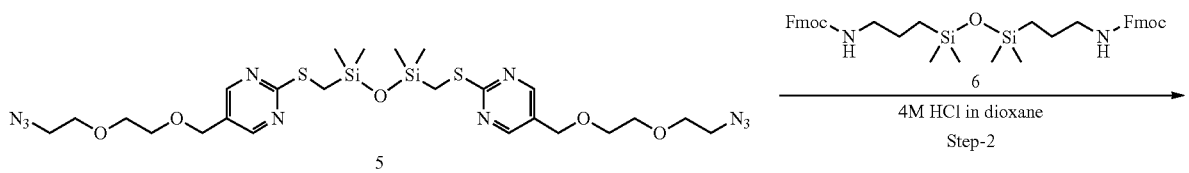

-continued

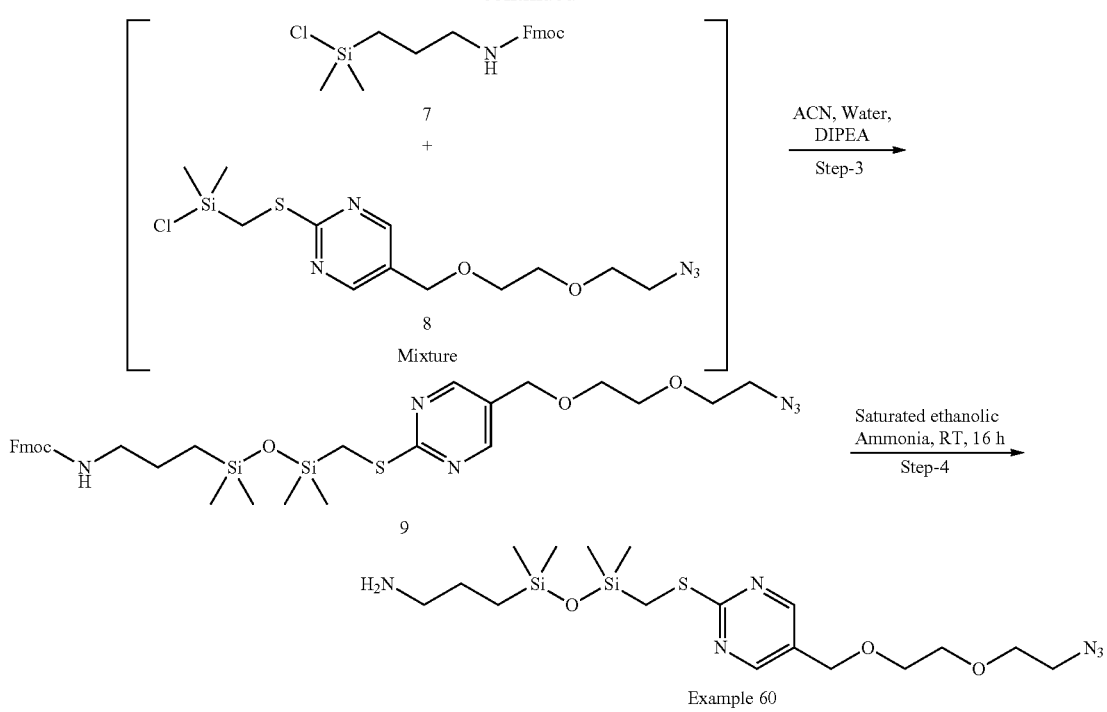

Example 60

3-(3-(((5-((2-(2-Azidoethoxy)ethoxy)methyl)pyrimidin-2-yl)thio)methyl)-1,1,3,3-tetramethyldisiloxanyl)propan-1-amine [Example 60]

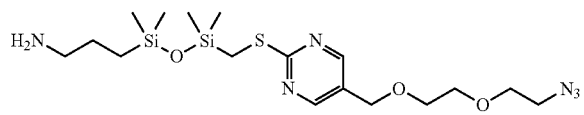 [SMILES: C[Si](C)(CCCN)O[Si](C)(C)CSc1ncc(COCCOCCN=[N+]=[N-])cn1]

A solution of (9H-fluoren-9-yl)methyl(3-(3-(((5-((2-(2-azidoethoxy)ethoxy)methyl) pyrimidin-2-yl) thio) methyl)-1,1,3,3-tetramethyldisiloxanyl)propyl)carbamate (3.80 g, 5.24 mmol) in saturated ethanolic ammonia (76 mL) was stirred at room temperature for 15 h. The reaction mixture was concentrated in vacuo and the crude compound was purified by column chromatography on silica gel eluting with 0-10% methanol saturated with ammonia in DCM to afford 950 mg, 39% yield, of the title compound as colorless oil. $^1$H NMR (400 MHz, DMSO-$d_6$) δ=8.60 (s, 2H), 4.50 (s, 2H), 3.59-3.64 (m, 6H), 3.37-3.43 (m, 2H), 2.46-2.50 (m, 2H), 2.40 (s, 2H), 1.76 (br. s, 2H), 1.32-1.41 (m, 2H), 0.47-0.53 (m, 2H), 0.18 (s, 6H), 0.07 (s, 6H); MS (ES$^+$): m/z=459.79 [M+H]$^+$; LCMS: $t_R$=2.23 min.

(9H-fluoren-9-yl)methyl(3-(3-(((5-((2-(2-azidoethoxy)ethoxy)methyl)pyrimidin-2-yl)thio)methyl)-1,1,3,3-tetramethyldisiloxanyl)propyl)carbamate (9)

A solution of mixture of 1,3-bis(((5-((2-(2-azidoethoxy)ethoxy)methyl)pyrimidin-2-yl)thio)methyl)-1,1,3,3-tetramethyldisiloxane (3.70 g, 5.538 mmol) and bis((9H-fluoren-9-yl)methyl) ((1,1,3,3-tetramethyldisiloxane-1,3-diyl)bis(propane-3,1-diyl))dicarbamate (3.80 g, 5.538 mmol) in 4M HCl in dioxane (100 mL) was stirred at room temperature for 1 h. The reaction mixture was concentrated in vacuo resulting in the crude intermediate 7 and 8. The mixture of intermediate 7 and 8 was dissolved in acetonitrile (300 mL) and followed by addition of water (0.199 mL, 11.07 mmol) and DIPEA (5.76 mL, 33.23 mmol) and stirred at room temperature for 1 h. The reaction mixture was concentrated in vacuo resulting in the crude compound which was purified by column chromatography on silica gel eluting with 0-10% methanol in DCM to afford 3.8 g, 50.6% yield, of the title compound as colorless oil. $^1$H NMR (400 MHz, DMSO-$d_6$) δ=8.57 (s, 2H), 7.89 (d, J=7.34 Hz, 2H), 7.69 (d, J=7.34 Hz, 2H), 7.39-7.45 (m, 2H), 7.25-7.35 (m, 3H), 4.48 (s, 2H), 4.29 (d, J=6.85 Hz, 2H), 4.17-4.24 (m, 1H), 3.57-3.63 (m, 6H), 3.35-3.41 (m, 2H), 2.95 (q, J=6.85 Hz, 2H), 2.39 (s, 2H), 1.42 (td, J=7.76, 15.28 Hz, 2H), 0.44-0.52 (m, 2H), 0.17 (s, 6H), 0.06 (s, 6H); MS (ES$^+$): m/z=681.48 [M+H]$^+$; LCMS: $t_R$=3.97 min.

1,3-Bis(((5-((2-(2-azidoethoxy)ethoxy)methyl)pyrimidin-2-yl)thio)methyl)-1,1,3,3-tetramethyldisiloxane (5)

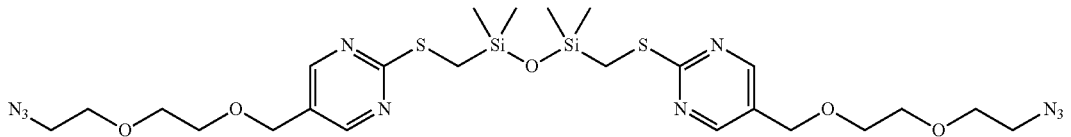 [SMILES: C[Si](C)(CSc1ncc(COCCOCCN=[N+]=[N-])cn1)O[Si](C)(C)CSc1ncc(COCCOCCN=[N+]=[N-])cn1]

A solution of 2-(2-azidoethoxy)ethan-1-ol (3.76 g, 28.70 mmol) in THF (300 mL) at 0° C. was charged with sodium hydride (1.37 g, 57.08 mmol) and stirred at 0° C. for 30 min. The cooled reaction mixture was then charged with 1,3-bis(((5-(chloromethyl)pyrimidin-2-yl)thio)methyl)-1,1,3,3-tetramethyldisiloxane (5.5 g, 11.40 mmol) and stirred at 0° C. for an additional 1 h. The reaction mixture was concentrated in vacuo resulting in the crude compound which was purified by column chromatography on silica gel eluting with 0-5% methanol in DCM to afford 4.4 g, 58% yield, of the title compound as a colorless oil. $^1$H NMR (400 MHz, DMSO-d$_6$) δ=8.55-8.60 (m, 4H), 4.60 (t, J=5.38 Hz, 4H), 4.48 (s, 4H), 3.44-3.53 (m, 12H), 2.40 (s, 2H), 2.35 (s, 2H), 0.18 (s, 6H), 0.13 (s, 6H); MS (ES$^+$): m/z=334.10 [M/2+H]$^+$; LCMS: t$_R$=2.65 min.

Example 61

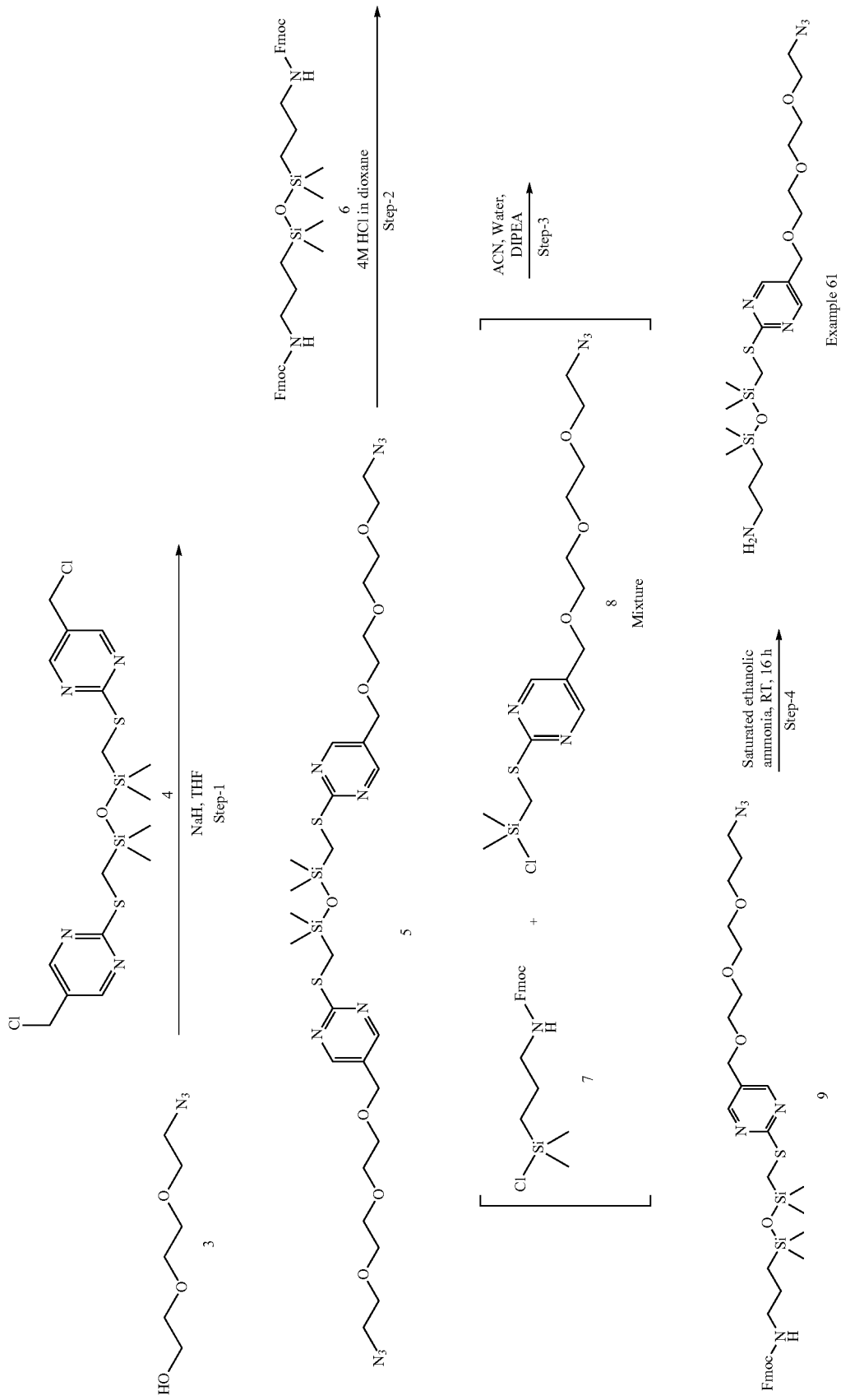

3-(3-(((5-((2-(2-(2-Azidoethoxy)ethoxy)ethoxy)methyl)pyrimidin-2-yl)thio)methyl)-1,1,3,3-tetramethyldisiloxanyl)propan-1-amine [Example 61]

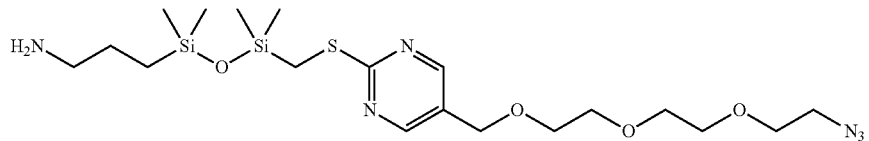 [SMILES: C[Si](C)(CCCN)O[Si](C)(C)CSc1ncc(COCCOCCOCCN=[N+]=[N-])cn1]

A solution of (9H-fluoren-9-yl)methyl(3-(3-(((5-((2-(2-(2-azidoethoxy)ethoxy)ethoxy) methyl) pyrimidin-2-yl)thio)methyl)-1,1,3,3-tetramethyldisiloxanyl)propyl)carbamate (3.69 g, 5.089 mmol) in saturated ethanolic ammonia (73.8 mL) was stirred at room temperature for 16 h. The reaction mixture was concentrated in vacuo and the crude compound was purified by column chromatography on silica gel eluting with 0-10% methanol in DCM to afford 1.1 g, 44% yield, of the title compound as a colorless oil. $^1$H NMR (400 MHz, DMSO-$d_6$) δ=8.60 (s, 2H), 4.49 (s, 2H), 3.53-3.63 (m, 10H), 3.36-3.42 (m, 2H), 2.47-2.50 (m, 2H), 2.40 (s, 2H), 1.77-1.93 (m, 2H), 1.31-1.40 (m, 2H), 0.47-0.53 (m, 2H), 0.18 (s, 6H), 0.07 (s, 6H); MS (ES$^+$): m/z=503.37 [M+H]$^+$; LCMS: $t_R$=2.21 min.

(9H-fluoren-9-yl)methyl(3-(3-(((5-((2-(2-(2-azidoethoxy)ethoxy) ethoxy) methyl)pyrimidin-2-yl)thio)methyl)-1,1,3,3-tetramethyldisiloxanyl)propyl)carbamate (9)

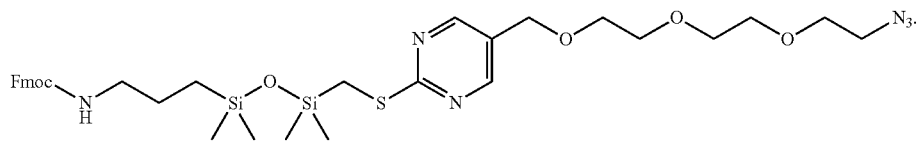

A solution of mixture of 1,3-bis(((5-((2-(2-(2-azidoethoxy)ethoxy)ethoxy)methyl)pyrimidin-2-yl)thio)methyl)-1,1,3,3-tetramethyldisiloxane (4.89 g, 6.459 mmol) and bis((9H-fluoren-9-yl)methyl) ((1,1,3,3-tetramethyldisiloxane-1,3-diyl)bis(propane-3,1-diyl))dicarbamate (4.30 g, 6.459 mmol) in 4M HCl in dioxane (50 mL) was stirred at room temperature for 1 h. The reaction mixture was concentrated in vacuo resulting in the crude intermediate 7 and 8. The mixture of intermediate 7 and 8 was dissolved in acetonitrile (150 mL) and followed by addition of water (0.114 mL, 6.459 mmol) and DIPEA (3.3 mL, 19.37 mmol) and stirred at room temperature for 1 h. The reaction mixture was concentrated in vacuo resulting in the crude compound which was purified by column chromatography on silica gel eluting with 70-100% ethyl acetate in n-hexane to afford 3.69 g, 82% yield, of the title compound as colorless oil. $^1$H NMR (400 MHz, DMSO-$d_6$) δ=8.56 (s, 2H), 7.88 (d, J=7.34 Hz, 2H), 7.67 (d, J=7.34 Hz, 2H), 7.36-7.43 (m, 2H), 7.31 (t, J=7.34 Hz, 2H), 7.27 (br. s, 1H), 4.45 (s, 2H), 4.27 (d, J=6.85 Hz, 2H), 4.20 (d, J=6.36 Hz, 1H), 3.51-3.60 (m, 10H), 3.34-3.39 (m, 2H), 2.90-2.98 (m, 2H), 2.38 (s, 2H), 1.34-1.45 (m, 2H), 0.43-0.50 (m, 2H), 0.15 (s, 6H), 0.05 (s, 6H); MS (ES$^+$): m/z=725.51 [M+H]$^+$; LCMS: $t_R$=3.97 min.

1,3-Bis(((5-((2-(2-(2-azidoethoxy)ethoxy)ethoxy)methyl)pyrimidin-2-yl)thio)methyl)-1,1,3,3-tetramethyldisiloxane (5)

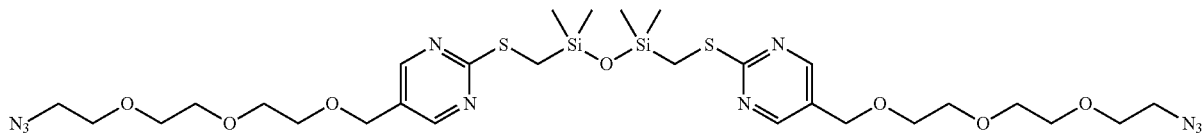 [SMILES: C[Si](C)(CSc1ncc(COCCOCCOCCN=[N+]=[N-])cn1)O[Si](C)(C)CSc1ncc(COCCOCCOCCN=[N+]=[N-])cn1]

A solution of 2-(2-(2-azidoethoxy)ethoxy)ethan-1-ol (2.3 g, 13.14 mmol) in THF (500 mL) was cooled to 0° C. and charged with sodium hydride (1.62 g, 39.42 mmol) and stirred at 0° C. for 30 min. The reaction was charged with 1,3-bis(((5-(chloromethyl)pyrimidin-2-yl)thio)methyl)-1,1,3,3-tetramethyldisiloxane (6.5 g, 13.14 mmol) and stirred at 0° C. for an additional 1 h. The reaction mixture was concentrated in vacuo resulting in the crude compound which was purified by column chromatography on silica gel eluting with 0-5% methanol in DCM to afford 5.94 g, 60% yield, of the title compound as a colorless oil. $^1$H NMR (400 MHz, DMSO-$d_6$) δ=8.57 (s, 4H), 4.57 (t, J=5.62 Hz, 2H), 4.47 (s, 4H), 3.46-3.63 (m, 22H), 2.41 (s, 4H), 0.18 (s, 12H); MS (ES$^+$): m/z=380.00 [M/2+H]$^+$; LCMS: $t_R$=3.66 min.

Example 62

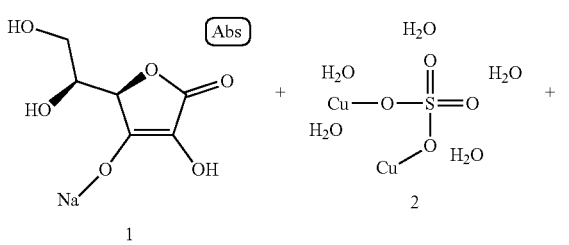

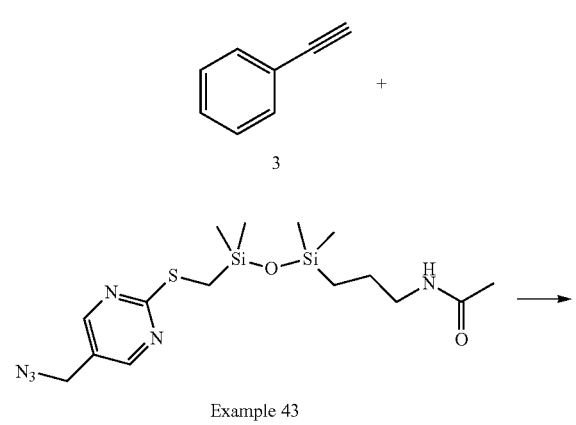

Example 62

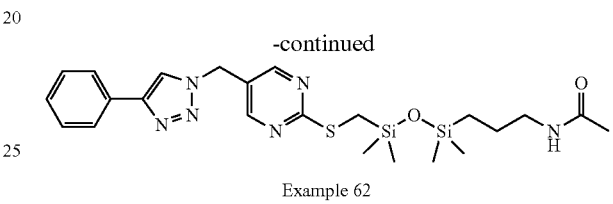

N-(3-(1,1,3,3-tetramethyl-3-(((5-((4-phenyl-1H-1,2,3-triazol-1-yl)methyl)pyrimidin-2-yl)thio)methyl)disiloxanyl)propyl)acetamide [Example 62]

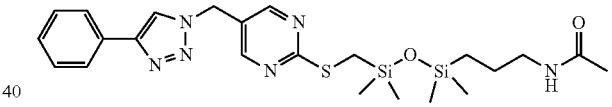

A solution of ethynylbenzene (14.85 mg, 0.145 mmol) and N-(3-(3-(((5-(azidomethyl) pyrimidin-2-yl)thio) methyl)-1,1,3,3-tetramethyldisiloxanyl)propyl)acetamide (Example 43, 50 mg, 0.121 mmol) were dissolved in DMF (121 µl). The reaction mixture was charged with sodium ascorbate (24.00 mg, 0.121 mmol) in water (121 µl) followed by the addition of copper sulfate pentahydrate (28.5 mg, 0.091 mmol) in water (121 µl). After 5 min the reaction was complete and the reaction was worked up. The reaction mixture was partitioned between DCM and water and separated. The aqueous was extracted with DCM (3×) and the combined DCM fractions were dried over Na$_2$SO$_4$, filtered and concentrated. The crude was purified by ISCO chromatography on silica gel [4 g cartridge, eluting with 0% of (10% NH$_4$OH in MeOH) in DCM to 8% of (10% NH$_4$OH in MeOH) in DCM] resulting in 17.3 mg, 27.7% yield of the title compound as a clear colorless oil. $^1$H NMR (CHLOROFORM-d, 400 MHz): δ (ppm) 8.55 (s, 2H), 7.79-7.83 (m, 2H), 7.78 (s, 1H), 7.40-7.46 (m, 2H), 7.31-7.38 (m, 1H), 5.54 (s, 2H), 3.16-3.23 (m, 2H), 2.96 (s, 1H), 2.89 (s, 1H), 2.41 (s, 2H), 1.97 (s, 3H), 1.66 (s, 2H), 1.45-1.55 (m, 2H), 1.26 (s, 4H), 0.48-0.55 (m, 2H), 0.21 (s, 6H), 0.08 (s, 6H), MS (ES+): m/z=515.34 [M+H]$^+$; LCMS: $t_R$=2.20 min [polar_3 min_1500].

Example 63
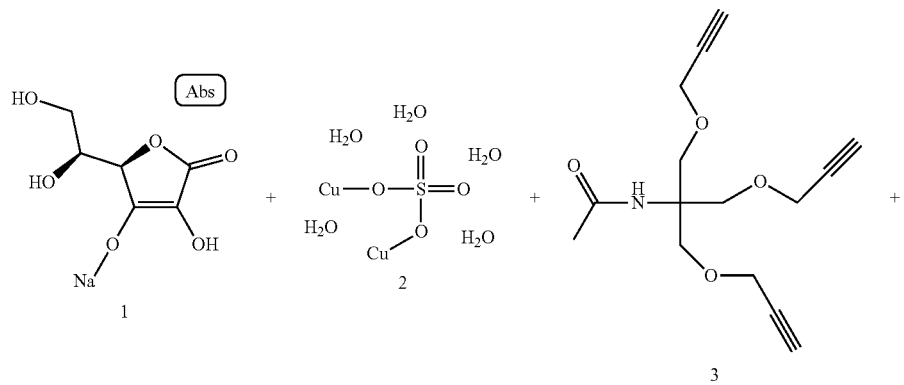
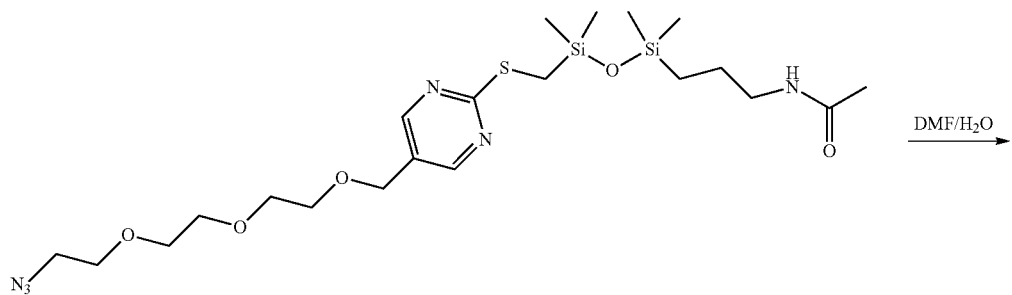
Example 58
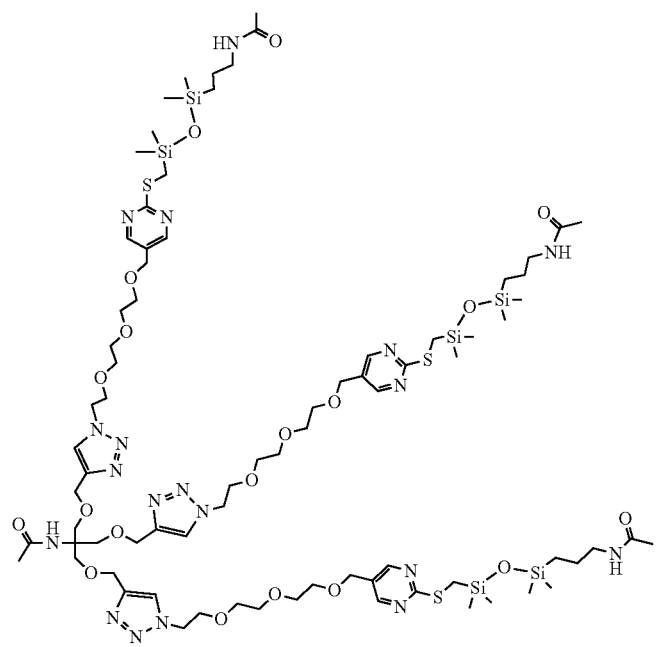
Example 63

Example 63

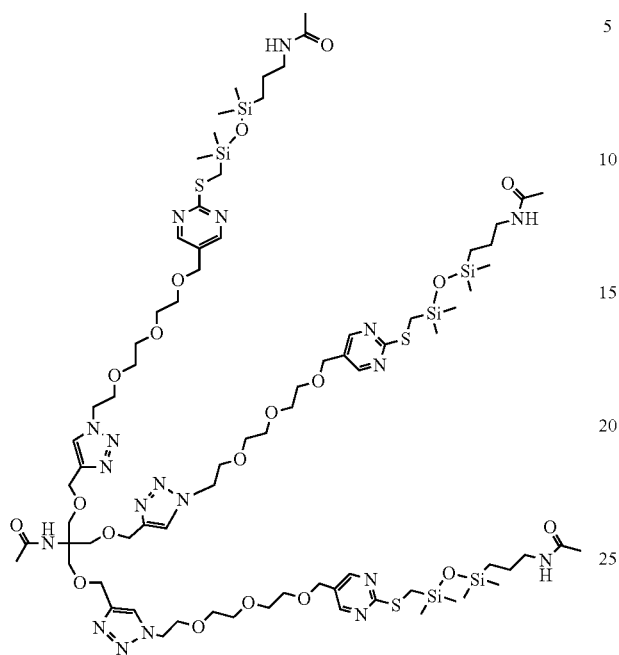

A solution of N-(1,3-bis(prop-2-yn-1-yloxy)-2-((prop-2-yn-1-yloxy)methyl)propan-2-yl)acetamide (10.00 mg, 0.036 mmol) and N-(3-(3-(((5-((2-(2-(2-azidoethoxy)ethoxy)ethoxy)methyl)pyrimidin-2-yl)thio)methyl)-1,1,3,3-tetramethyl disiloxanyl)propyl)acetamide [Example 58] (60.9 mg, 0.112 mmol) were dissolved in DMF (36.1 µl). The reaction mixture was charged with sodium ascorbate (7.14 mg, 0.036 mmol) in water (36.1 µl) followed by the addition of copper sulfate pentahydrate (8.47 mg, 0.027 mmol) in water (36.1 µl). After 15 min the reaction mixture was checked by LCMS and found to have a mass consistent with desired product. The reaction mixture was partitioned between DCM and water and separated. The aqueous was extracted with DCM (3×) and the combined fractions were dried over $Na_2SO_4$, filtered and concentrated in vacuo resulting in a crude which was purified by ISCO chromatography on silica gel [4 g cartridge, eluting with 0% of (10% $NH_4OH$ in MeOH) in DCM to 8% of (10% $NH_4OH$ in MeOH) in DCM] resulting in 11.000 mg, 15.96% yield of the title compound as a clear colorless oil.clear colorless oil. $^1$H NMR (CHLOROFORM-d, 400 MHz): δ (ppm) 8.50 (s, 6H), 7.71 (s, 3H), 6.28 (s, 1H), 5.73-5.86 (m, 3H), 4.57 (s, 6H), 4.54 (t, J=5.2 Hz, 6H), 4.50 (s, 6H), 3.86-3.90 (m, 6H), 3.81 (s, 6H), 3.63 (d, J=10.9 Hz, 23H), 3.18-3.25 (m, 6H), 2.41 (s, 6H), 1.97 (s, 9H), 1.93 (s, 3H), 1.77 (s, 8H), 1.48-1.57 (m, 6H), 0.50-0.57 (m, 6H), 0.21 (s, 18H), 0.09 (s, 18H), MS (ES+): m/z=1911.43, 1912.44, 1913.23 [M+H]$^+$; LCMS: $t_R$=2.31 min [polar_3 min_1500].

N-(1,3-bis(prop-2-yn-1-yloxy)-2-((prop-2-yn-1-yloxy)methyl)propan-2-yl)acetamide (3)

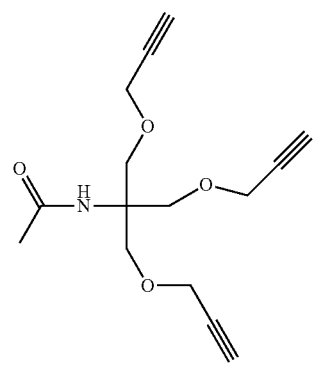 [SMILES: C#CCOCC(COCC#C)(COCC#C)NC(C)=O]

The title compound was prepared as described in the literature: *J. Org. Chem.*, 2008, 73, 5602-56-5

Example 64 and Example 80

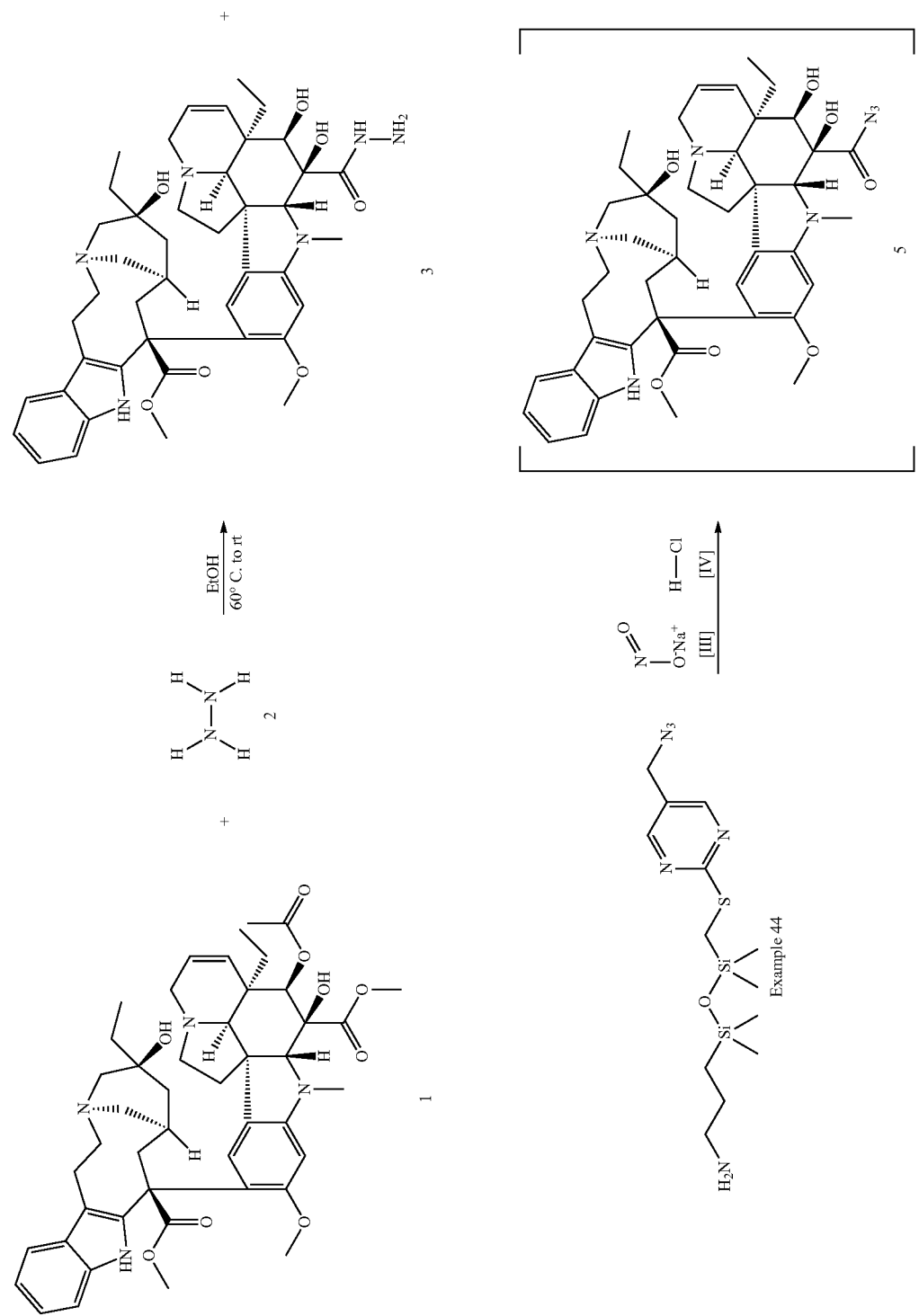

-continued
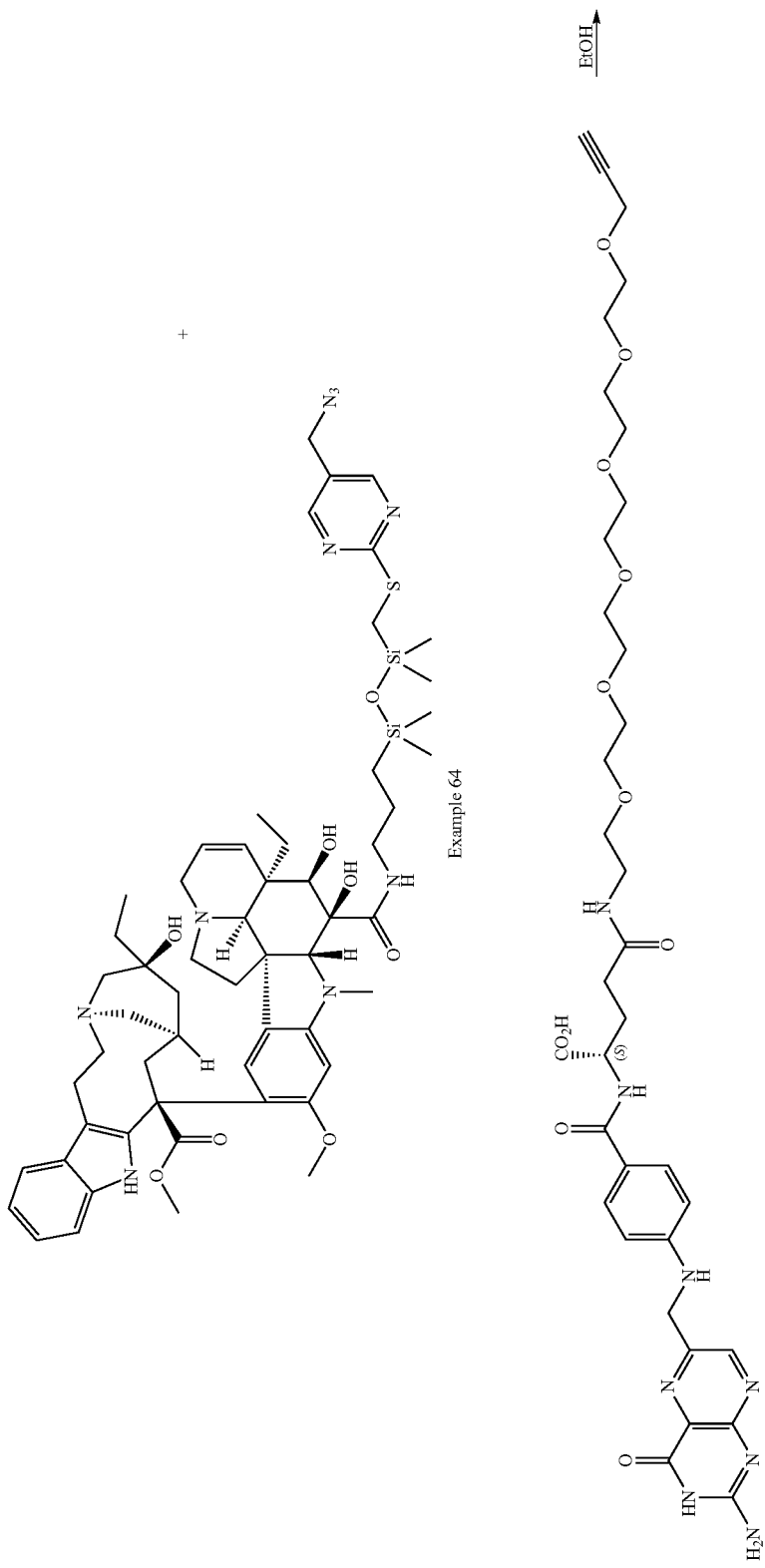

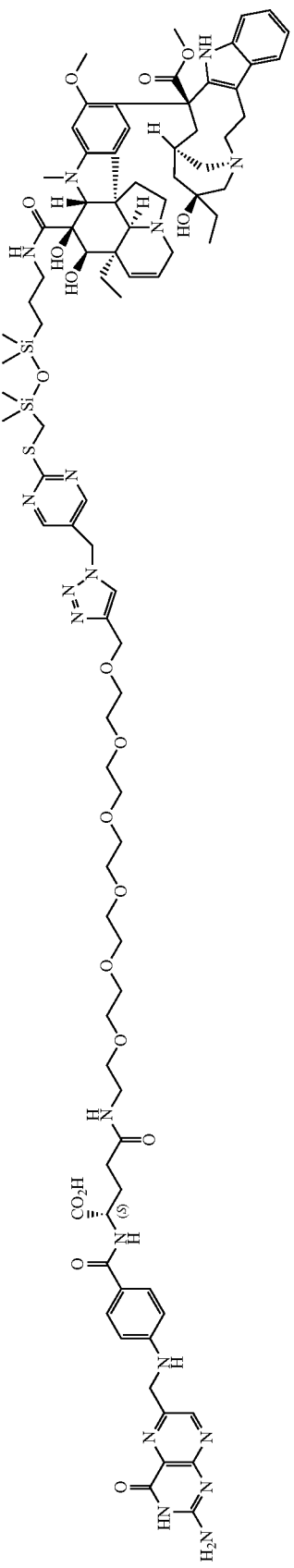
Example 80

(S)-24-(4-(((2-amino-4-oxo-3,4-dihydropteridin-6-yl)methyl)amino)benzamido)-1-(1-((2-(((3-(3-((3aR,3a1R,4R,5S,5aR,10bR)-3a-ethyl-9-((3S,5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl) methyl)thio) pyrimidin-5-yl)methyl)-1H-1,2,3-triazol-4-yl)-21-oxo-2,5,8,11,14,17-hexaoxa-20-azapentacosan-25-oic Acid [Example 80]

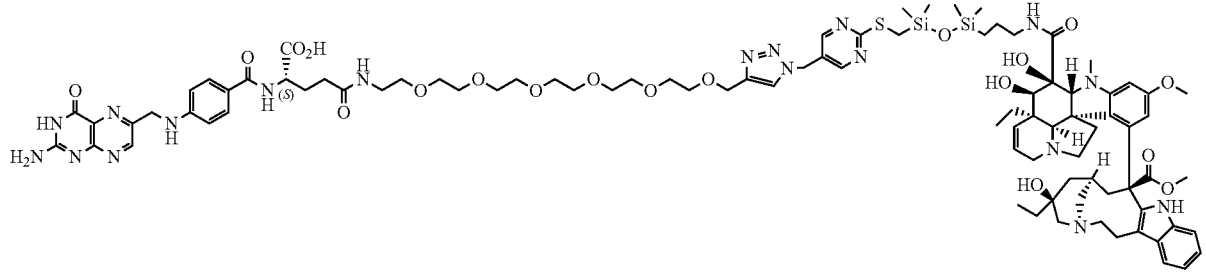

To an Eppendorf vial, DMF (219 µl) was added into a mixture of (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (15.87 mg, 0.021 mmol) and (3R,5S,7R,9S)-methyl 9-((3aR,3a1R,4R,5S,5aR,10bR)-5-((3-(3-(((5-(azidomethyl)pyrimidin-2-yl)thio) methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (18.2 mg, 0.016 mmol). More DMF (219 µL) was added to dissolve both reactants. The vial was purged with nitrogen gas, capped, and sonicated for 5 mM. Then a freshly prepared solution of sodium ascorbate (100 mM in water, 32.9 µL, 3.29 µmol) in water (55 µL) was added, followed by the addition of a freshly prepared solution of copper sulfate pentahydrate (100 mM in water, 32.9 µL, 3.29 µmol) in water (55 µL). The vial was purged with nitrogen gas, capped, sonicated for 5 min, and agitated on a shaker at rt. A yellow suspension was formed. As the reaction proceeded, more solids went into the solution. After 2.5 h, LCMS showed mainly product. The reaction was stopped. The whole was dissolved with 1.5 mL of DMSO, and passed through an ISCO solid loading filter plug with an aid of a vacuum. For the residue, dissolved with ~0.5 mL of DMSO and passed through the same filter plug. The combined filtrate (2 mL) was purified by a reversed phase preparative HPLC. Using the 10 mM ammonium bicarbonate in water and MeCN mobile phases with gradient 1 for reverse phase preparative HPLC to obtain 6.15 mg, 20.2% yield of the title compound as a light yellow solid after lyophilizing 1.51 min LCMS using acidic mobile phase and method [polar_3 min_0_1500] (M+2)=1851.2, (M+2)/2=926.0, (M+3)/3=617.7, (M+4)/4=463.6. $^1$H NMR (400 MHz, DMSO-d$_6$) δ ppm 0.01-0.09 (m, 7H) 0.16 (s, 7H) 0.43-0.55 (m, 2H) 0.63 (br s, 1H) 0.70-0.88 (m, 7H) 1.09-1.37 (m, 7H) 1.38-1.66 (m, 5H) 1.81-2.09 (m, 6H) 2.16 (brd, J=7.07 Hz, 2H) 2.27-2.43 (m, 6H) 2.60-2.77 (m, 8H) 2.89 (brd, J=9.85 Hz, 2H) 3.01-3.22 (m, 15H) 3.43-3.57 (m, 18H) 3.71 (s, 5H) 3.83 (br d, J=5.81 Hz, 1H) 3.91-4.11 (m, 3H) 4.23 (br s, 1H) 4.43-4.55 (m, 4H) 5.52-5.73 (m, 5H) 6.19 (s, 1H) 6.44 (s, 1H) 6.54-6.70 (m, 3H) 6.86-7.05 (m, 5H) 7.26 (d, J=8.08 Hz, 1H) 7.37 (d, J=7.83 Hz, 1H) 7.63 (br d, J=8.34 Hz, 2H) 7.77 (br t, J=5.68 Hz, 1H) 7.89 (br s, 1H) 8.09 (br s, 1H) 8.20 (s, 1H) 8.48-8.73 (m, 4H) 9.33 (s, 1H). MS (ES+): m/z=(M+2)=1851.2, (M+2)/2=926.0, (M+3)/3=617.7, (M+4)/4=463.6. [M+H]$^+$; LCMS: t$_R$=1.51 min [polar_3 min_1500].

Methyl(3R,5S,7R,9S)-9-((3aR,3a1R,4R,5S,5aR,10bR)-5-((3-(3-(((5-(azidomethyl) pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate [Example 64]

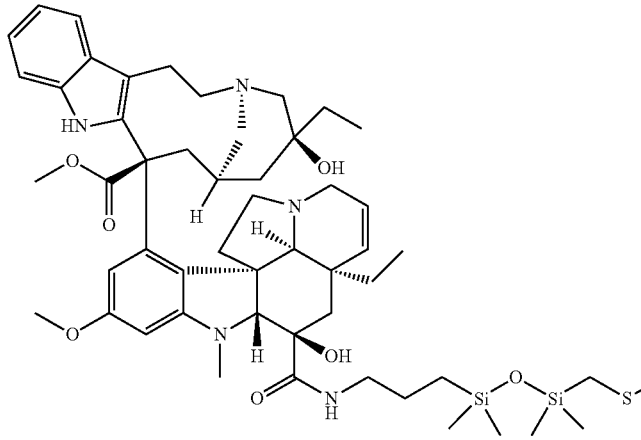

A solution of (3R,5S,7R,9S)-methyl 5-ethyl-9-((3aR,3a1R,4R,5S,5aR,10bR)-3a-ethyl-5-(hydrazinecarbonyl)-4,5-dihydroxy-8-methoxy-6-methyl-3a,3a1,4,5,5a,6,11,12-octahydro-1H-indolizino[8,1-cd]carbazol-9-yl)-5-hydroxy-2,4,5,6,7,8,9,10-octahydro-1H-3,7-methano[1]azacycloundecino[5,4-b]indole-9-carboxylate (200 mg, 0.260 mmol) in acetonitrile (3.34 ml) was cooled to −10° C. and charged with 1 M HCl in water (12.33 ml, 12.33 mmol) and maintained at −10° C. then charged with solid sodium nitrite (41.3 mg, 0.598 mmol) (Note: upon addition of NaNO$_2$ the color changed from pale yellow/colorless to a yellowish brown color) After 10 min the yellowish brown solution was adjusted to pH ~8.00 with dropwise addition of cold sat NaHCO$_3$ solution (~13.2 mL of NaHCO$_3$ added). The solution was extracted rapidly with DCM (5×10 mL) and the combined organic layers were washed with brine (1×20 mL) and dried over Na$_2$SO$_4$, filtered, and concentrated to ~8.00 mL-10 mL cooled to 0° C. and charged with a solution of 3-(3-(((5-(azidomethyl)pyrimidin-2-yl)thio)methyl)-1,1,3,3-tetramethyldisiloxanyl)propan-1-amine [Example 44] (96 mg, 0.260 mmol) in DCM (8.0 mL) and allowed to stir at 0° C. for 2 hr. The reaction mixture was concentrated in vacuo resulting in a light tan solid. The crude was further purified by chromatography on silica gel [ISCO CombiFlash, 12 g Gold cartridge, eluting with 0% of (10% 7N NH3 in MeOH) to 8% (10% 7N NH3 in MeOH) in DCM resulting in 127 mg, 44% yield of the title compound as a pale yellow foam solid. $^1$H NMR (CHLOROFORM-d, 400 MHz): δ (ppm) 9.47-9.59 (m, 1H), 8.49 (s, 2H), 8.04 (s, 1H), 7.54 (d, J=8.1 Hz, 1H), 7.15-7.21 (m, 3H), 7.08-7.14 (m, 1H), 6.61 (s, 1H), 6.08 (s, 1H), 5.84 (s, 2H), 4.34 (s, 2H), 4.19 (d, J=4.8 Hz, 1H), 3.92-4.03 (m, 1H), 3.78 (s, 3H), 3.63-3.74 (m, 1H), 3.61 (s, 3H), 3.38-3.45 (m, 2H), 3.07-3.37 (m, 8H), 2.83-2.89 (m, 1H), 2.79-2.83 (m, 5H), 2.62 (s, 1H), 2.60 (d, J=4.8 Hz, 1H), 2.37-2.50 (m, 4H), 2.24-2.33 (m, 1H), 1.98-2.10 (m, 1H), 1.68-1.83 (m, 2H), 1.52-1.60 (m, 4H), 1.45-1.51 (m, 1H), 1.37-1.45 (m, 1H), 1.21-1.36 (m, 4H), 0.87-1.00 (m, 7H), 0.85 (br d, J=6.1 Hz, 1H), 0.54-0.62 (m, 2H), 0.19-0.25 (m, 6H), 0.10 (s, 6H), MS (ES+): m/z=1107.61, 1108.56 [M+H]$^+$; LCMS: t$_R$=1.62 min [polar_3 min_1500].

Methyl(3R,5S,7R,9S)-9-03aR,3a1R,4R,5S,5aR,10bR)-5-((3-(3-(((5-(azidomethyl)pyrimidin-2-yl)thio)methyl)-1,1,3,3-tetramethyldisiloxanyl) propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate (3)

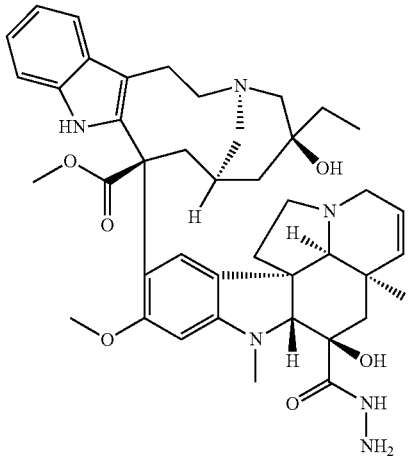

A solution of hydrazine (12.77 ml, 407 mmol) in Ethanol (15.03 ml) was charged with (3aR,3a1R,4R,5S,5aR,10bR)-methyl 4-acetoxy-3a-ethyl-9-((3R,5S,7R,9S)-5-ethyl-5-hydroxy-9-(methoxycarbonyl)-2,4,5,6,7,8,9,10-octahydro-1H-3,7-methano[1]azacycloundecino[5,4-b]indol-5-yl)-5-hydroxy-8-methoxy-6-methyl-3a,3a1,4,5,5a,6,11,12-octahydro-1H-indolizino[8,1-cd]carbazole-5-carboxylate, sulfuric acid salt (2.5 g, 2.75 mmol) and heated to 60° C. under a $N_2$ atmosphere. The reaction mixture was heated to 60° C. for 16 h then stirred at rt for an additional 6 hrs. The reaction mixture was poured into 90 mL of HPLC grade water and the aqueous was extracted with 5×90 mL of DCM and the combined organic fractions were washed with water 1×90 mL and brine 1×120 mL and dried over anhydrous $Na_2SO_4$, filtered and concentrated in vacuo resulting in crude product that was further purified by column chromatography on silica gel [ISCO Combiflash, 12 g gold catridge] eluting with a gradient of 100% DCM to 8% 7N NH3 in MeOH in DCM] resulting in 1.42 g, 67.1% yield of the title compound as an off-white solid. $^1$H NMR (DMSO-$d_6$, 400 MHz): δ (ppm) 9.31 (s, 1H), 8.87-9.03 (m, 1H), 8.81 (br s, 1H), 8.33 (s, 1H), 7.37 (d, J=7.8 Hz, 1H), 7.26 (d, J=8.1 Hz, 1H), 6.96-7.04 (m, 1H), 6.88-6.95 (m, 1H), 6.45 (s, 1H), 6.20 (s, 1H), 5.76 (s, 2H), 5.66-5.72 (m, 1H), 5.54-5.62 (m, 1H), 4.23 (br d, J=3.8 Hz, 2H), 4.12 (br d, J=3.5 Hz, 1H), 4.05 (br dd, J=15.2, 13.6 Hz, 1H), 3.90-3.97 (m, 2H), 3.82 (d, J=6.1 Hz, 1H), 3.65-3.78 (m, 4H), 3.54 (s, 3H), 3.36 (s, 1H), 3.26 (br d, J=14.1 Hz, 1H), 3.03-3.22 (m, 4H), 2.89 (br dd, J=14.4, 4.5 Hz, 1H), 2.61-2.77 (m, 6H), 2.28-2.42 (m, 2H), 1.97-2.05 (m, 1H), 1.88-1.97 (m, 1H), 1.74 (s, 2H), 1.51-1.66 (m, 2H), 1.25-1.38 (m, 2H), 1.12-1.21 (m, 3H), 0.71-0.85 (m, 6H), 0.56-0.67 (m, 1H), MS (ES+): m/z=769.40, 770.41 [M+H]$^+$; LCMS: $t_R$=132 min [polar_3 min_1500].

Compound 6

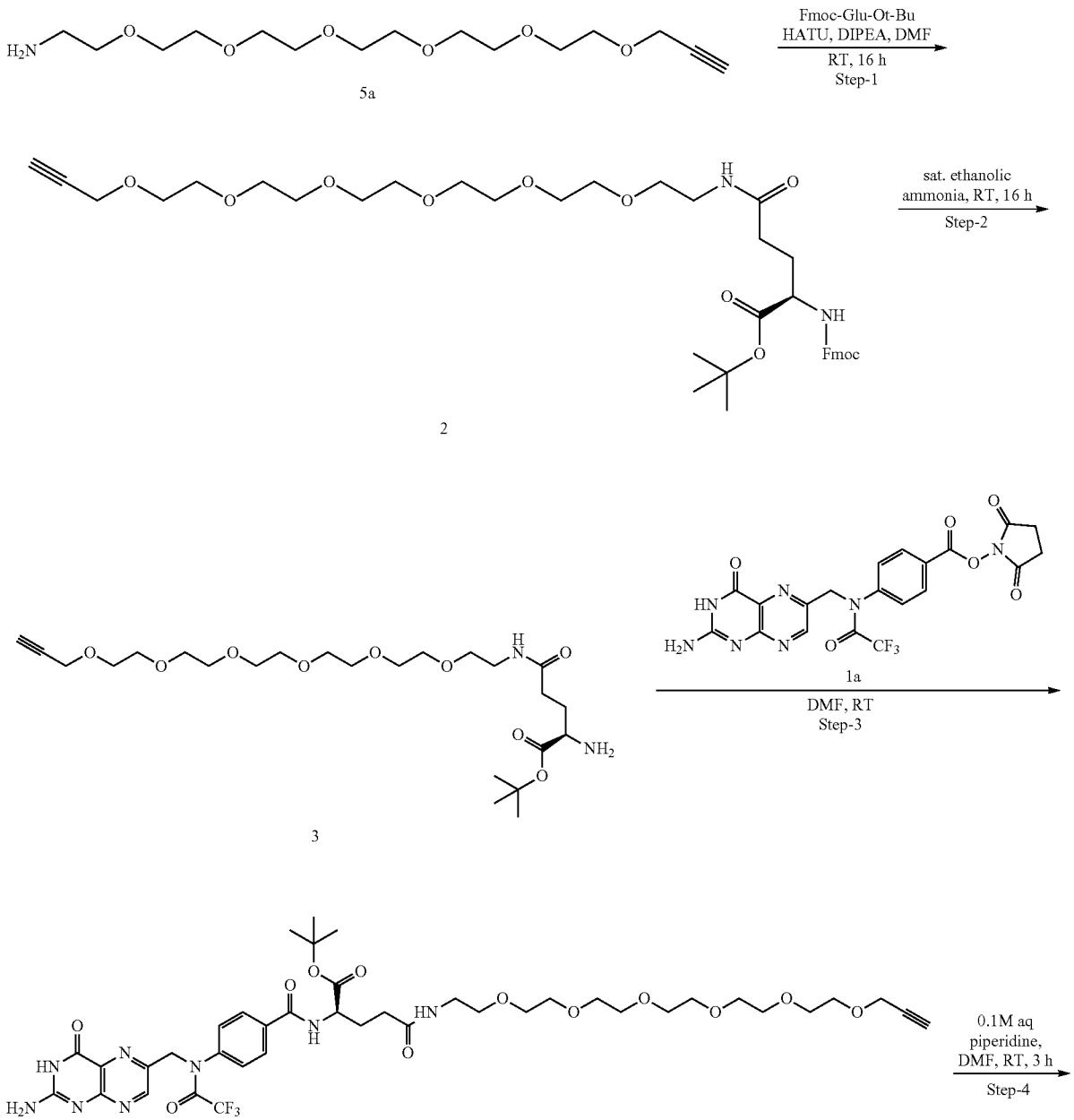

-continued

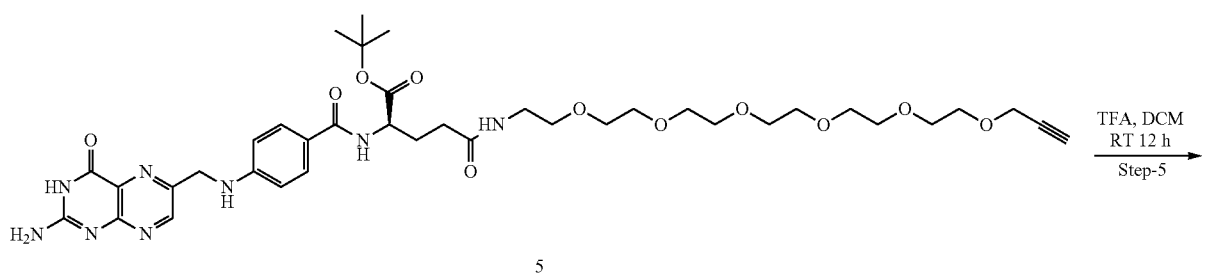

5

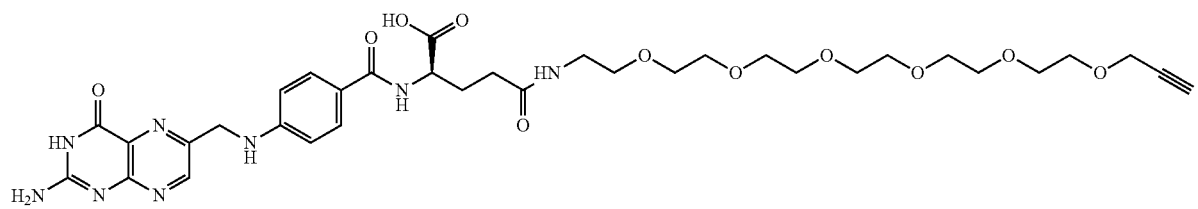 [SMILES: C#CCOCCOCCOCCOCCOCCOCCNC(=O)CC[C@@H](NC(=O)c1ccc(NCc2cnc3nc(N)[nH]c(=O)c3n2)cc1)C(=O)O]

6

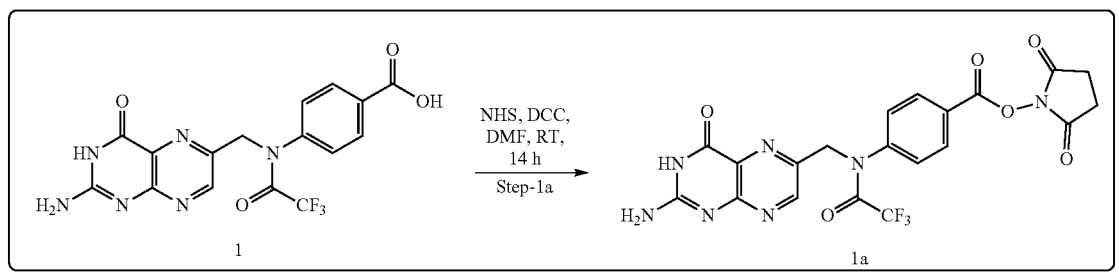

(R)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic Acid (6)

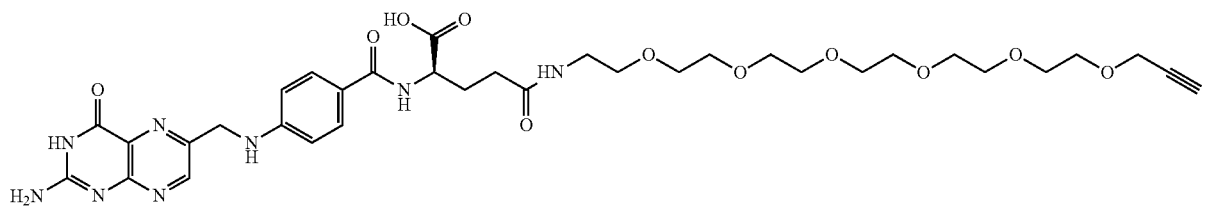

A solution of tert-butyl(R)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oate 5 (1.66 g, 2.080 mmol) in DCM (50 mL) was charged with trifluoroacetic acid (50 mL) and stirred at room temperature for 12 h. The reaction mixture was concentrated in vacuo resulting in the crude compound which was purified by reverse phase combiflash column chromatography (acetonitrile:water: 0.1% TFA) to afford 650 mg, 42% yield of the title compound as a yellow solid. $^1$H NMR (400 MHz, DMSO-$d_6$) δ=12.49 (s, 1H), 8.66 (s, 1H), 8.20 (d, J=7.34 Hz, 1H), 7.87-7.94 (m, 1H), 7.65 (d, J=8.31 Hz, 2H), 7.12 (br. s, 2H), 6.63 (d, J=8.31 Hz, 2H), 4.49 (s, 2H), 4.22-4.32 (m, 1H), 4.13 (d, J=2.45 Hz, 2H), 3.45-3.56 (m, 20H), 3.43 (t, J=2.20 Hz, 1H), 3.36 (t, J=5.87 Hz, 2H), 3.17 (q, J=5.87 Hz, 2H), 2.14-2.24 (m, 2H), 1.99-2.08 (m, 1H), 1.84-1.96 (m, 1H); MS (ES$^+$): m/z=743.41 [M+H]$^+$; LCMS: $t_R$=1.83 min.

tert-Butyl(R)-26-(4-(((2-amino-4-oxo-3,4-dihydropteridin-6-yl)methyl) amino) benzamido)-23-oxo-4,7,10,13,16,19-hexaoxa-22-azaheptacos-1-yn-27-oate (5)

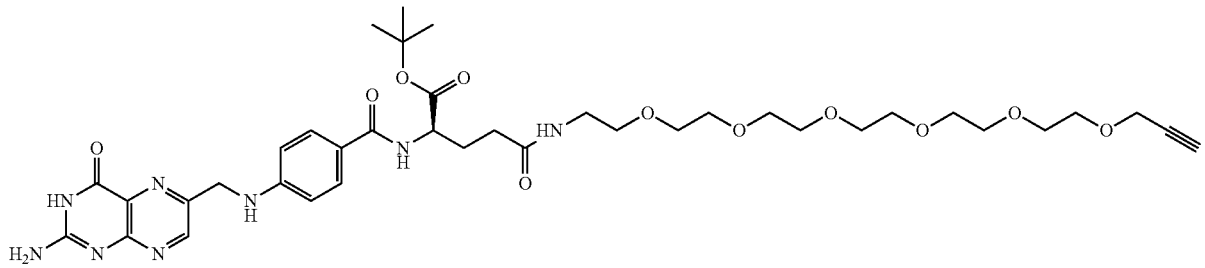 [SMILES: C#CCOCCOCCOCCOCCOCCOCCNC(=O)CC[C@@H](NC(=O)c1ccc(NCc2cnc3nc(N)[nH]c(=O)c3n2)cc1)C(=O)OC(C)(C)C]

A solution of tert-butyl(R)-26-(4-(N-((2-amino-4-oxo-3,4-dihydropteridin-6-yl)methyl)-2,2,2-trifluoroacetamido)benzamido)-23-oxo-4,7,10,13,16,19-hexaoxa-22-azaheptacos-1-yn-27-oate (2.0 g, 2.237 mmol) in DMF (40 mL) was charged with 0.1M solution of piperdine (40 mL) and stirred at room temperature for 3 h. The reaction mixture was concentrated in vacuo resulting in the crude compound. The crude compound was stirred in diethyl ether (40 mL) for 10 min and the solid was filtered and washed with diethyl ether (20 mL) and dried to afford 1.60 g (90% yield) of the title compound as yellow solid. $^1$H NMR (400 MHz, DMSO-$d_6$) δ=8.64 (s, 1H), 8.16-8.21 (m, 1H), 7.91 (t, J=5.62 Hz, 1H), 7.64 (d, J=8.31 Hz, 2H), 6.95 (t, J=5.87 Hz, 1H), 6.63 (d, J=8.80 Hz, 2H), 4.48 (d, J=5.38 Hz, 2H), 4.16-4.23 (m, 1H), 4.13 (d, J=1.96 Hz, 2H), 3.45-3.57 (m, 20H), 3.13-3.20 (m, 2H), 2.93-2.98 (m, 2H), 2.14-2.23 (m, 2H), 1.85-2.03 (m, 2H), 1.52-1.64 (m, 4H), 1.39 (s, 9H); MS (ES$^+$): m/z=799.40 [M+H]$^+$; LCMS: $t_R$=2.20 min.

tert-Butyl(R)-26-(4-(N-((2-amino-4-oxo-3,4-dihydropteridin-6-yl)methyl)-2,2,2-trifluoroacetamido)benzamido)-23-oxo-4,7,10,13,16,19-hexaoxa-22-azaheptacos-1-yn-27-oate (4)

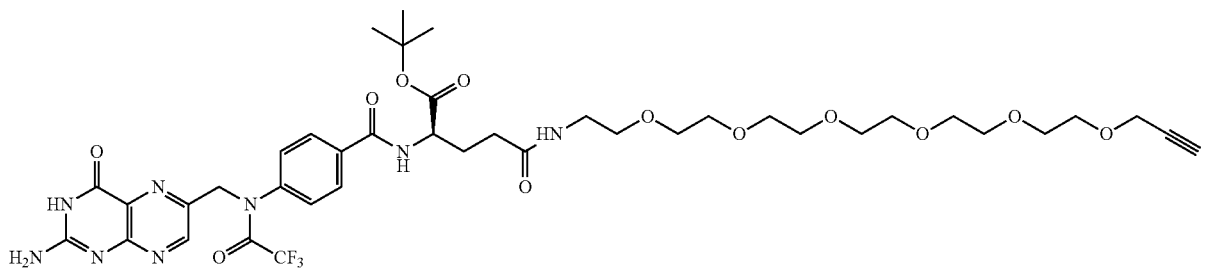 [SMILES: C#CCOCCOCCOCCOCCOCCOCCNC(=O)CC[C@@H](NC(=O)c1ccc(N(Cc2cnc3nc(N)[nH]c(=O)c3n2)C(=O)C(F)(F)F)cc1)C(=O)OC(C)(C)C]

A solution of 2,5-dioxopyrrolidin-1-yl 4-(N-((2-amino-4-oxo-3,4-dihydropteridin-6-yl)methyl)-2,2,2-trifluoroacetamido)benzoate (2.10 g, 4.158 mmol) and tert-butyl(R)-26-amino-23-oxo-4,7,10,13,16,19-hexaoxa-22-azaheptacos-1-yn-27-oate (2.09 g, 4.158 mmol) in DMF (40 mL) was added DIPEA (1.44 mL, 8.316 mmol) under nitrogen atmosphere for 4 h. The reaction mixture was concentrated in vacuo resulting in the crude compound. The crude compound was stirred in diethyl ether (250 mL) for 15 min and the solid precipitated was filtered and washed with diethyl ether (100 mL) and dried to afford 3.25 g, 87% yield of the title compound as off white solid. ¹H NMR (400 MHz, DMSO-d₆) δ=8.73-8.78 (m, 1H), 8.62 (s, 1H), 7.89 (d, J=7.34 Hz, 3H), 7.63 (d, J=7.83 Hz, 2H), 6.88 (s, 3H), 5.11 (br. s, 2H), 4.20-4.28 (m, 1H), 4.13 (s, 2H), 3.45-3.58 (m, 17H), 3.38 (dd, J=5.87, 12.23 Hz, 4H), 3.13-3.22 (m, 2H), 2.17-2.28 (m, 2H), 1.84-2.09 (m, 4H), 1.40 (s, 9H); MS (ES⁺): m/z=895.30 [M+H]⁺; LCMS: t$_R$=2.48 min.

tert-Butyl(R)-26-amino-23-oxo-4,7,10,13,16,19-hexaoxa-22-azaheptacos-1-yn-27-oate (3)

mmol) and DIPEA (4.2 mL, 32.91 mmol) and was stirred at room temperature for 16 h. The reaction mixture was diluted with water and extracted with ethyl acetate. The combined organic layers were dried over anhydrous Na₂SO₄, filtered and concentrated in vacuo resulting in a crude compound which was purified by column chromatography on combiflash eluting with 0-5% methanol in DCM to afford 9.2 g, 58% yield, of the title compound as an off white semisolid.

¹H NMR (400 MHz, CDCl₃) δ=7.77 (d, J=7.34 Hz, 2H), 7.59-7.64 (m, 2H), 7.38-7.43 (m, 2H), 7.29-7.35 (m, 2H), 6.57 (br. s, 1H), 5.78 (d, J=7.83 Hz, 1H), 4.39 (dq, J=7.34, 10.76 Hz, 2H), 4.22 (t, J=7.09 Hz, 2H), 4.19 (d, J=2.45 Hz, 2H), 3.59-3.70 (m, 20H), 3.53-3.57 (m, 2H), 3.41-3.47 (m,

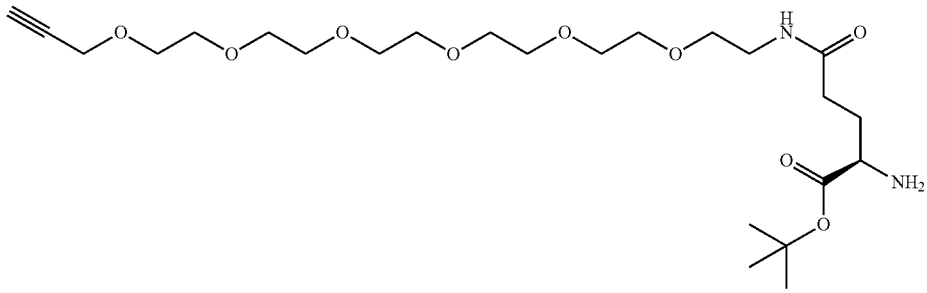 [SMILES: C#CCOCCOCCOCCOCCOCCOCCNC(=O)CC[C@@H](N)C(=O)OC(C)(C)C]

A solution of tert-butyl(R)-26-((((9H-fluoren-9-yl)methoxy)carbonyl)amino)-23-oxo-4,7,10,13,16,19-hexaoxa-22-azaheptacos-1-yn-27-oate (9 g, 12.39 mmol) in saturated ethanolic ammonia (50 mL) in a seal tube was stirred at room temperature for 16 h. The reaction mixture was concentrated in vacuo resulting in the crude compound which was purified by flash column chromatography eluting with 0-10% methanol in DCM to afford 4.68 g (75% yield) of the title compound as a colorless oil. ¹H NMR (400 MHz, DMSO-d₆) δ=6.65 (s, 1H), 6.08 (s, 2H), 4.21 (d, J=2.45 Hz, 2H), 3.59-3.72 (m, 19H), 3.54-3.57 (m, 2H), 3.42-3.48 (m, 2H), 3.34 (dd, J=4.65, 9.05 Hz, 1H), 2.42-2.46 (m, 1H), 2.31-2.37 (m, 2H), 2.05-2.15 (m, 1H), 1.73-1.83 (m, 2H), 1.46 (s, 9H); MS (ES⁺): m/z=505.00 [M+H]⁺; LCMS: t$_R$=2.46 min.

tert-Butyl(R)-26-((((9H-fluoren-9-yl)methoxy)carbonyl)amino)-23-oxo-4,7,10,13,16,19-hexaoxa-22-azaheptacos-1-yn-27-oate (2)

2H), 2.43 (t, J=2.45 Hz, 1H), 2.22-2.32 (m, 2H), 1.47 (s, 9H), 1.23-1.27 (m, 2H); MS (ES⁺): m/z=727.51 [M+H]⁺; LCMS: t$_R$=3.18 min.

2,5-Dioxopyrrolidin-1-yl 4-(N-((2-amino-4-oxo-3,4-dihydropteridin-6-yl)methyl)-2,2,2-trifluoroacetamido)benzoate (1a)

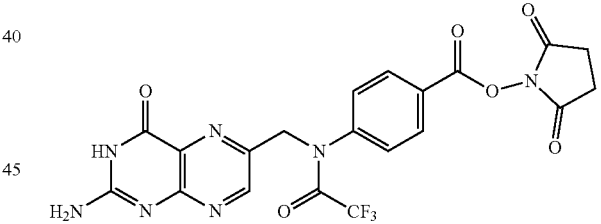

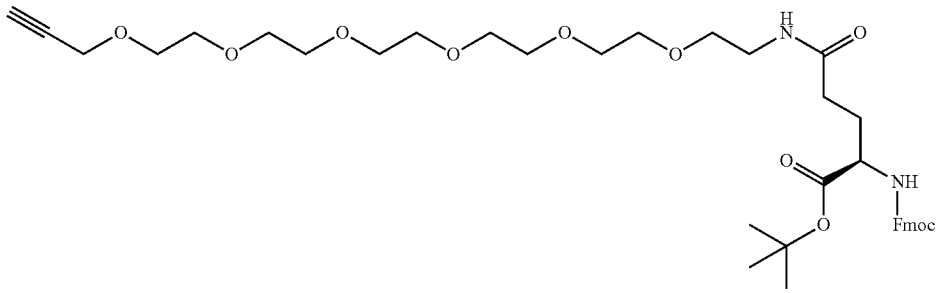

A solution of 3,6,9,12,15,18-hexaoxahenicos-20-yn-1-amine (7 g, 21.94 mmol) in DMF (25 mL) was charged with Fmoc-Glu-Ot-Bu (mg, 21.94 mmol), HATU (12.5 g, 32.91

A solution of 4-(N-((2-amino-4-oxo-3,4-dihydropteridin-6-yl)methyl)-2,2,2-trifluoroacetamido)benzoic acid (550 mg, 1.348 mmol) in DMF (20 mL) was charged with NHS (186 mg, 1.617 mmol), DCC (333 mg, 1.617 mmol) and was stirred at room temperature for 14 h. The reaction mixture was quenched with water (25 mL), filtered and washed with water (20 mL) and dried resulting in the crude compound (580 mg). The crude compound was stirred in methanol (25 mL) for 1 h at room temperature. The solid was filtered and washed with methanol (5 mL) and dried to afford 350 mg, 51% yield, of the title compound as an off white solid. ¹H NMR (400 MHz, DMSO-$d_6$) δ=11.47 (br. s, 1H), 8.65 (s, 1H), 8.16 (d, J=8.31 Hz, 2H), 7.80 (d, J=8.31 Hz, 2H), 5.57 (d, J=7.82 Hz, 2H), 2.89 (br. s, 2H), 1.68-1.76 (m, 2H), 1.57-1.66 (m, 2H); MS (ES$^+$): m/z=506.30 [M+H]$^+$; LCMS: $t_R$=2.22 min.

Example 65

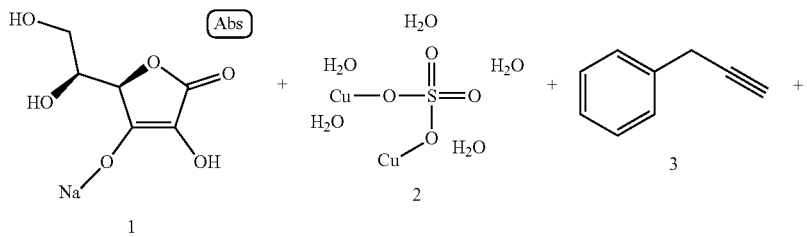

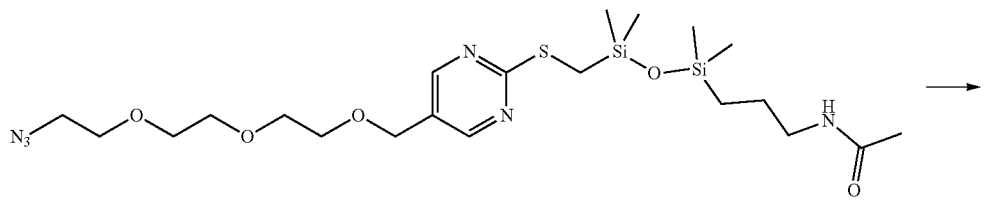

Example 58

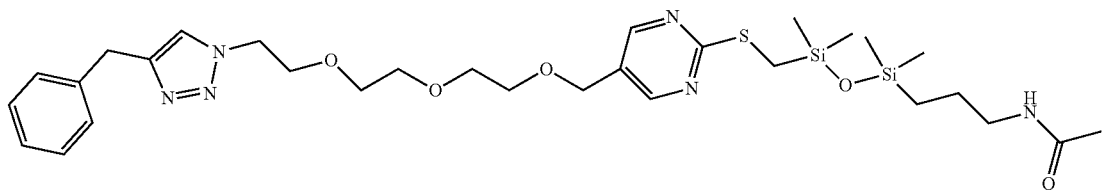

Example 65

N-(3-(3-(((5-((2-(2-(2-(4-benzyl-1H-1,2,3-triazol-1-yl)ethoxy)ethoxy)ethoxy)methyl) pyrimidin-2-yl)thio)methyl)-1,1,3,3-tetramethyldisiloxanyl)propyl) acetamide [Example 65]

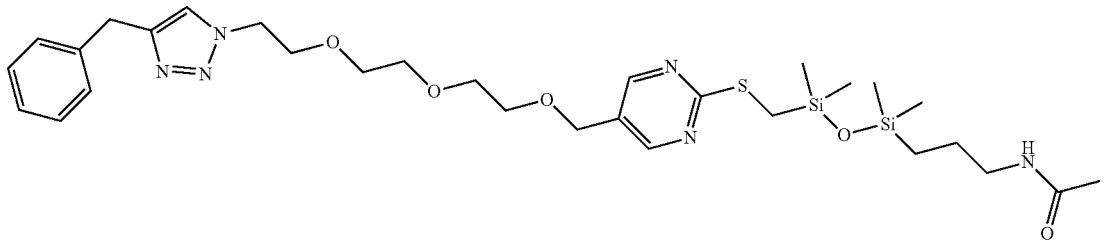 [SMILES: CC(=O)NCCC[Si](C)(C)O[Si](C)(C)CSc1ncc(COCCOCCOCCn2cc(Cc3ccccc3)nn2)cn1]

A solution of N-(3-(3-(((5-((2-(2-(2-azidoethoxy)ethoxy)ethoxy)methyl)pyrimidin-2-yl)thio)methyl)-1,1,3,3-tetramethyldisiloxanyl)propyl)acetamide [Example 58] (30 mg, 0.055 mmol) and prop-2-yn-1-ylbenzene (6.72 mg, 0.058 mmol) were dissolved in DMF (55.1 µl) and charged with sodium ascorbate (10.91 mg, 0.055 mmol) in water (55.1 µl) followed by the addition of copper sulfate pentahydrate (12.94 mg, 0.041 mmol) in water (55.1 µl) and allowed to stir for 30 min. The reaction mixture was partitioned between DCM and water and separated. The aqueous was extracted with DCM (3×) and the combined organic fractions were washed with brine (1×), dried over $Na_2SO_4$, filtered, and concentrated in vacuo resulting in 24 mg, 66% yield of the title compound as a pale yellow oil. 1HNMR (CHLOROFORM-d, 400 MHz): δ (ppm) 8.38 (s, 2H), 7.06-7.23 (m, 5H), 5.57 (br s, 1H), 4.32-4.44 (m, 4H), 3.98 (s, 2H), 3.74 (t, J=5.2 Hz, 2H), 3.42-3.53 (m, 8H), 3.07-3.18 (m, 2H), 2.31 (s, 2H), 1.84-1.93 (m, 3H), 1.36-1.47 (m, 2H), 0.38-0.50 (m, 2H), 0.09-0.14 (m, 6H), −0.06-0.02 (m, 6H), MS (ES+): m/z=661.41[M+H]$^+$; LCMS: $t_R$=2.17 min [polar_3 min_1500].

Example 66

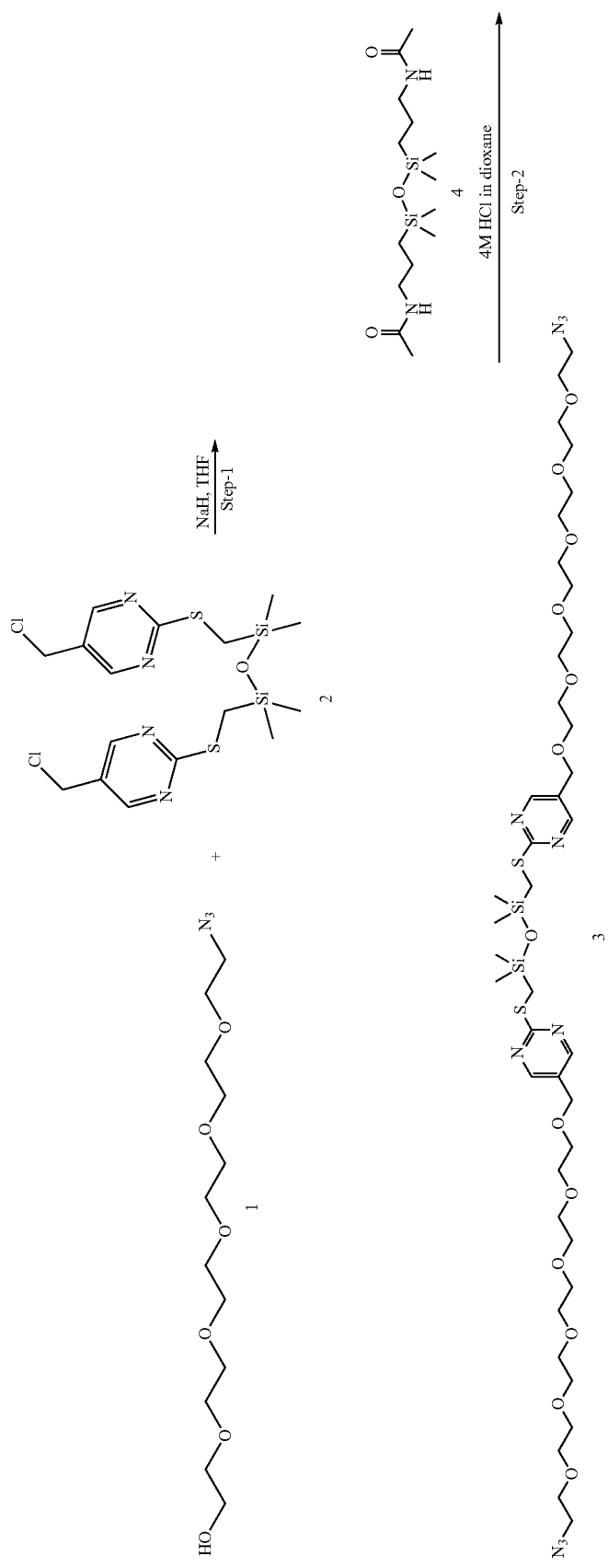

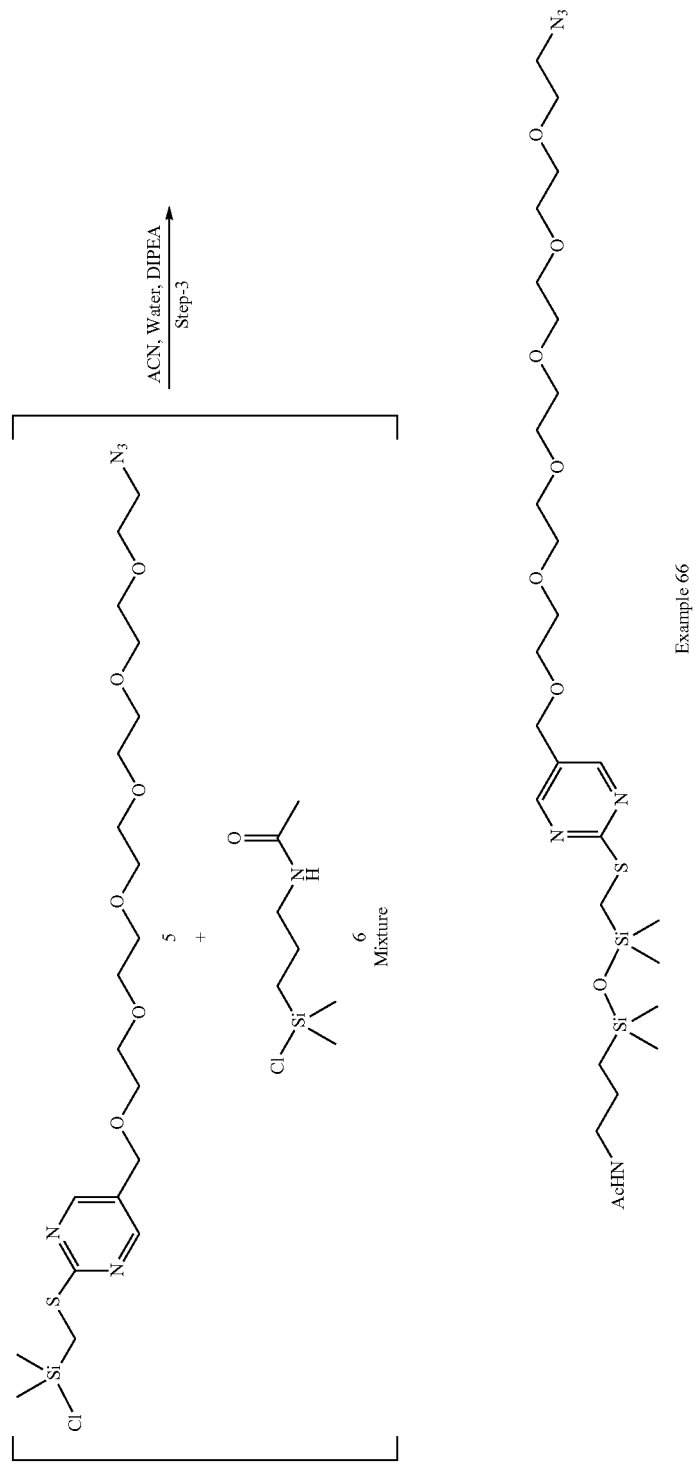

N-(3-(3-(((5-(19-azido-2,5,8,11,14,17-hexaoxanonadecyl)pyrimidin-2-yl)thio)methyl)-1,1,3,3-tetramethyldisiloxanyl)propyl)acetamide [Example 66]

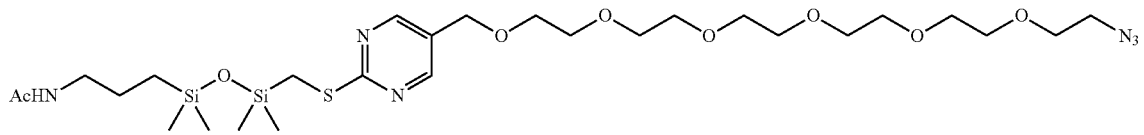 [SMILES: CC(=O)NCCC[Si](C)(C)O[Si](C)(C)CSc1ncc(COCCOCCOCCOCCOCCOCCN=[N+]=[N-])cn1]

A solution of 1,3-bis(((5-(19-azido-2,5,8,11,14,17-hexaoxanonadecyl)pyrimidin-2-yl)thio)methyl)-1,1,3,3-tetramethyldisiloxane (4.90 g, 4.799 mmol) and N,N-((1,1,3,3-tetramethyldisiloxane-1,3-diyl)bis(propane-3,1-diyl))diacetamide (3.30 g, 4.799 mmol) in 4M HCl in dioxane (100 mL) was stirred at room temperature for 1 h. The reaction mixture was concentrated in vacuo resulting in the crude intermediate 5 and 6. The intermediate 5 and 6 was dissolved in acetonitrile (250 mL) and followed by addition of water (250 mL) and DIPEA (4.90 mL, 28.79 mmol) and stirred at room temperature for another 1 h. The reaction mixture was concentrated in vacuo resulting in the crude compound which was purified by combiflash chromatography on silica gel eluting with 50-80% ethyl acetate in n-hexane to afford 3.56 g, 55% yield, of the title compound as a colorless oil. $^1$H NMR (400 MHz, DMSO-$d_6$) δ=8.60 (s, 2H), 7.76-7.82 (m, 1H), 4.47-4.51 (m, 2H), 3.49-3.64 (m, 22H), 3.37-3.42 (m, 2H), 2.94-3.02 (m, 2H), 2.36-2.42 (m, 2H), 1.78 (s, 3H), 1.34-1.45 (m, 2H), 0.44-0.53 (m, 2H), 0.18 (s, 6H), 0.07 (s, 6H); MS (ES$^+$): m/z=676.70 [M+H]$^+$; LCMS: $t_R$=3.27 min.

1,3-Bis(((5-(19-azido-2,5,8,11,14,17-hexaoxanonadecyl)pyrimidin-2-yl)thio)methyl)-1,1,3,3-tetramethyldisiloxane (3)

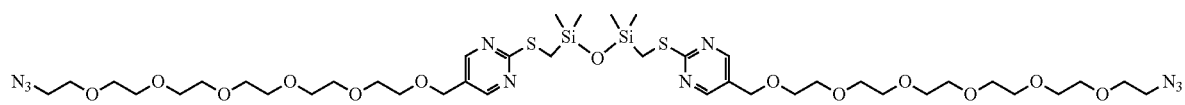 [SMILES: C[Si](C)(CSc1ncc(COCCOCCOCCOCCOCCOCCN=[N+]=[N-])cn1)O[Si](C)(C)CSc1ncc(COCCOCCOCCOCCOCCOCCN=[N+]=[N-])cn1]

A solution of 17-azido-3,6,9,12,15-pentaoxaheptadecan-1-ol (3 g, 9.771 mmol) in THF (250 mL) at 0° C. was charged with sodium hydride (502 mg, 14.65 mmol) and stirred at same temperature for 30 min. Followed by addition of 1,3-bis(((5-(chloromethyl)pyrimidin-2-yl)thio)methyl)-1,1,3,3-tetramethyldisiloxane (7 g, 14.65 mmol) to the resulting solution and was stirred at the same temperature for another 1 h. The reaction mixture was concentrated in vacuo resulting in the crude compound which was purified by combiflash column chromatography eluting with 0-5% methanol in DCM to afford 5.90 g, 60% yield, of the title compound as colorless oil. $^1$H NMR (400 MHz, DMSO-$d_6$) δ=8.60 (s, 1H), 8.57 (s, 3H), 4.46-4.49 (m, 4H), 3.49-3.63 (m, 45H), 3.36-3.43 (m, 6H), 2.39-2.42 (m, 4H), 0.18 (s, 9H); MS (ES$^+$): m/z=511.40 [M/2+H]$^+$; LCMS: $t_R$=3.53 min.

Example 67

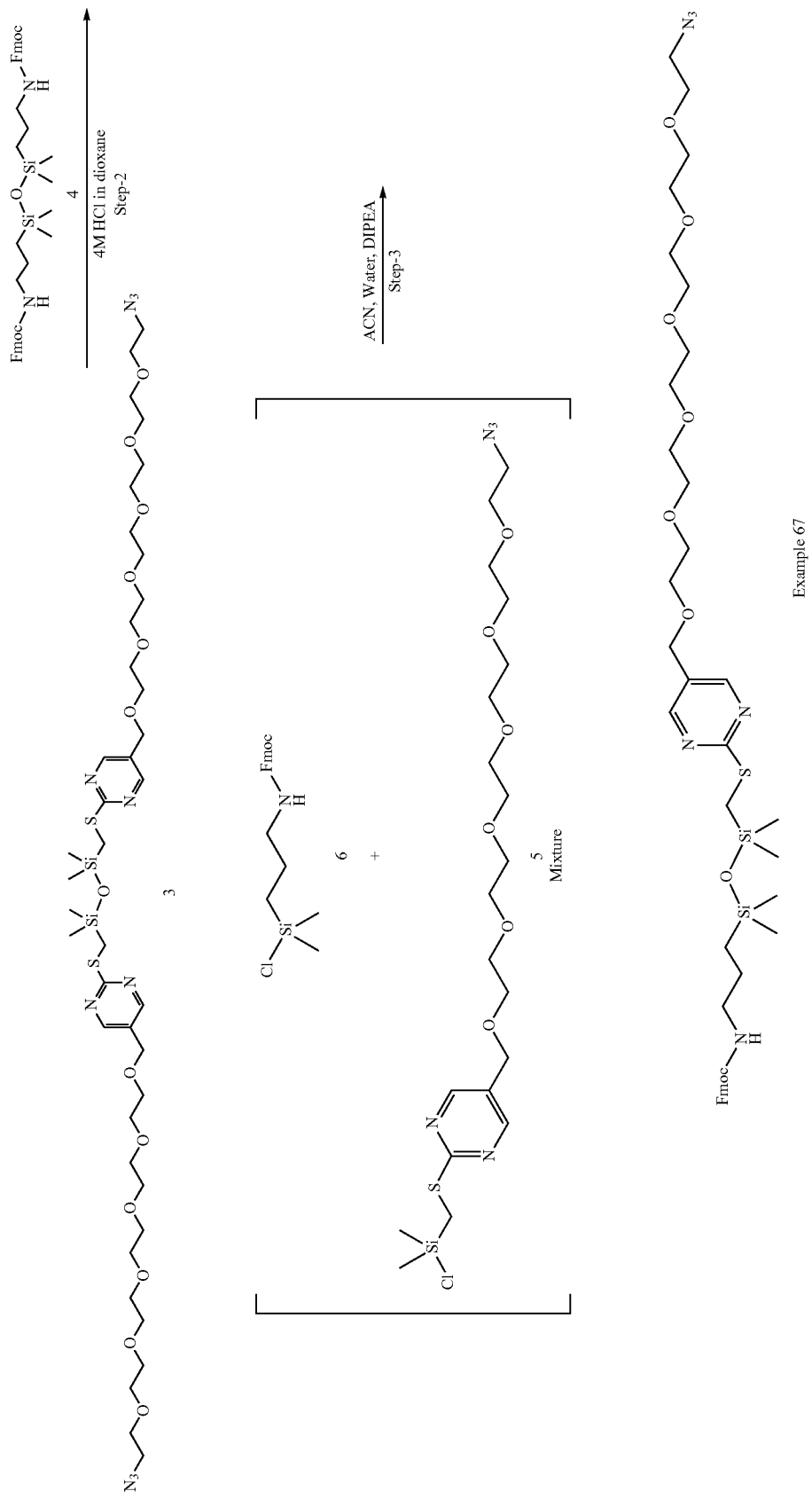

(9H-fluoren-9-yl)methyl(3-(3-(((5-(19-azido-2,5,8,11,14,17-hexaoxanonadecyl)pyrimidin-2-yl)thio)methyl)-1,1,3,3-tetramethyldisiloxanyl)propyl)carbamate [Example 67]

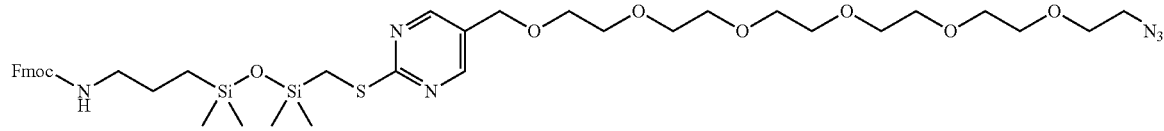

A solution of 1,3-bis(((5-(19-azido-2,5,8,11,14,17-hexaoxanonadecyl)pyrimidin-2-yl)thio)methyl)-1,1,3,3-tetramethyldisiloxane (1 g, 0.979 mmol) and bis((9H-fluoren-9-yl)methyl) ((1,1,3,3-tetramethyldisiloxane-1,3-diyl)bis(propane-3,1-diyl))dicarbamate (325 mg, 0.979 mmol) in 4M HCl in dioxane (30 mL) was stirred at room temperature for 1 h. The reaction mixture was concentrated in vacuo resulting in the crude intermediate 5 and 6. The mixture of intermediate 5 and 6 was dissolved in acetonitrile (50 mL) and followed by addition of water (0.07 mL, 3.917 mmol), DIPEA (1.01 mL, 5.876 mmol) and stirred at room temperature for 1 h. The reaction mixture was concentrated in vacuo resulting in the crude compound which was purified by combiflash column chromatography eluting with 50-80% ethyl acetate in n-hexane to afford 584 mg, 35% yield, of the title compound as a colorless oil. $^1$H NMR (400 MHz, DMSO-$d_6$) δ=8.54 (s, 2H), 7.85 (d, J=7.34 Hz, 2H), 7.64 (d, J=7.34 Hz, 2H), 7.34-7.40 (m, 2H), 7.25-7.31 (m, 3H), 4.43 (s, 2H), 4.25 (d, J=6.85 Hz, 2H), 4.13-4.19 (m, 1H), 3.45-3.57 (m, 20H), 3.34 (t, J=5.14 Hz, 2H), 3.28 (s, 2H), 2.91 (q, J=6.68 Hz, 2H), 2.35 (s, 2H), 1.33-1.44 (m, 2H), 0.41-0.47 (m, 2H), 0.13 (s, 6H), 0.02 (s, 6H); MS (ES$^+$): m/z=856.65 [M+H]$^+$; LCMS: $t_R$=4.07 min.

Example 68

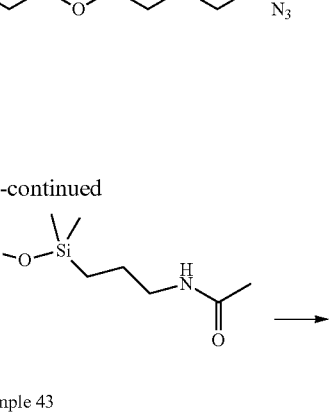

Example 43

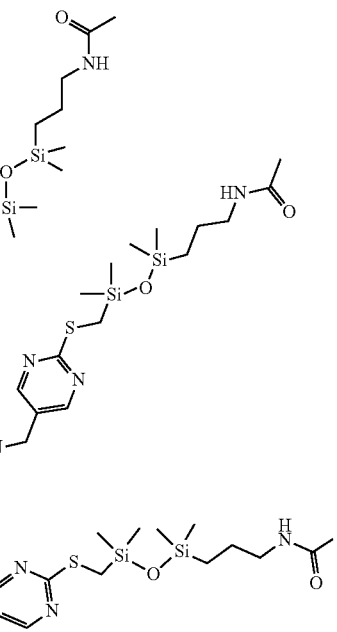

Example 68

A solution of tert-butyl(1,3-bis((4-ethynylbenzyl)oxy)-2-(((4-ethynylbenzyl) oxy)methyl) propan-2-yl)carbamate (10.00 mg, 0.018 mmol) and N-(3-(3-(((4-(azidomethyl)phenyl)thio) methyl)-1,1,3,3-tetramethyldisiloxanyl)propyl) acetamide (22.59 mg, 0.055 mmol) were dissolved in DMF (40.0 μl). The reaction mixture was charged with a solution of sodium ascorbate (1.757 mg, 8.87 μmol) in water (80 μl) followed by the addition of a solution of copper sulfate pentahydrate (2.78 mg, 8.87 μmol) in water (80 μl). After 5 min the reaction mixture was partitioned between DCM and

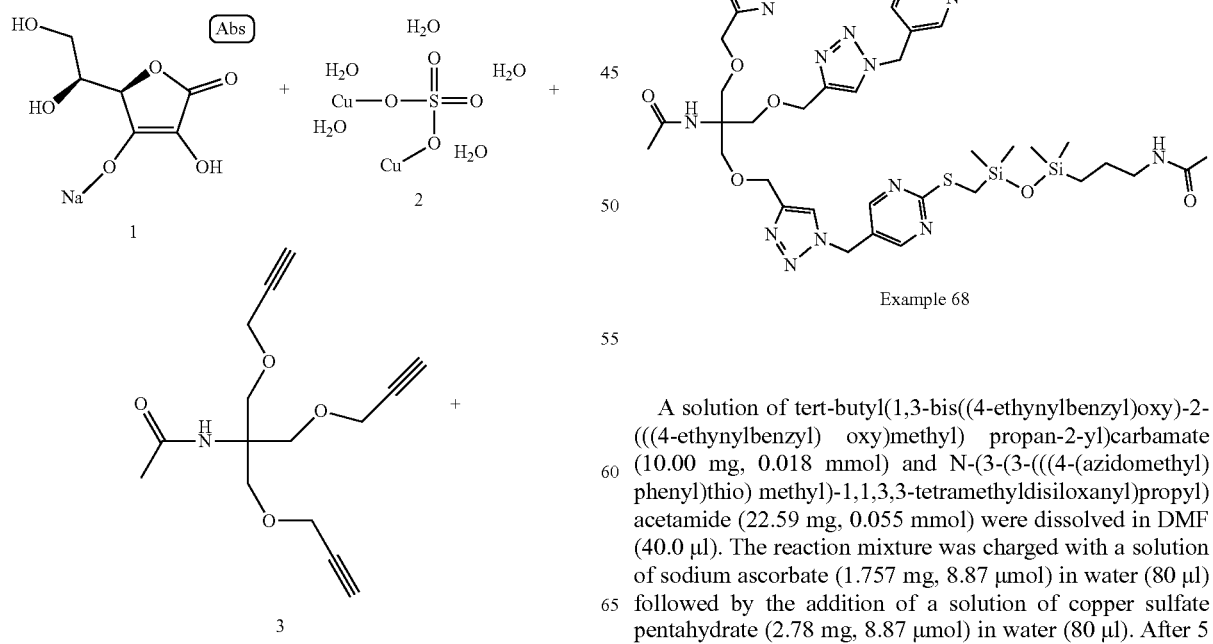

water and separated. The aqueous was extracted with DCM (3×) and the combined organic fractions dried over Na₂SO₄, filtered and concentrated in vacuo. The resulting in crude e material was purified by ISCO chromatography on silica gel [4 g cartridge, eluting with 0% of (10% NH₄OH in MeOH) in DCM to 8% of (10% NH₄OH in MeOH) in DCM] resulting in 11 mg, 20.13% yield of the title compound as a clear colorless oil. $^1$H NMR (CHLOROFORM-d, 400 MHz): δ (ppm) 8.55 (s, 6H), 7.69 (s, 3H), 5.96 (s, 1H), 5.65-5.82 (m, 3H), 5.52 (s, 6H), 4.58 (s, 6H), 3.76 (s, 6H), 3.14-3.25 (m, 7H), 2.40 (s, 6H), 1.96 (s, 9H), 1.91 (s, 3H), 1.71 (s, 7H), 1.46-1.56 (m, 7H), 0.49-0.55 (m, 6H), 0.20 (s, 18H), 0.08 (s, 18H), MS (ES⁺): m/z=1514.96, 1516.02 [M+H]⁺; LCMS: $t_R$=2.27 min [nonpolar_3 min].

Example 69

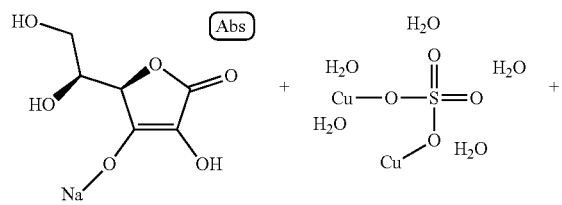

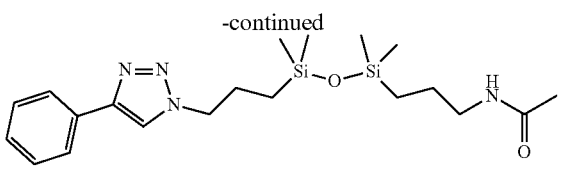

Example 69

N-(3-(1,1,3,3-tetramethyl-3-(3-(4-phenyl-1H-1,2,3-triazol-1-yl)propyl)disiloxanyl) propyl)acetamide
[Example 69]

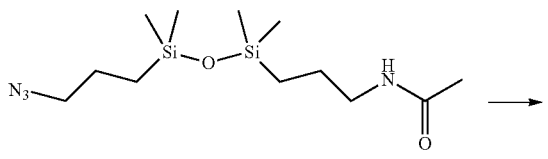

Example 53

Phenyl acetylene (5 μL, 0.046 mmol) and N-(3-(3-(3-azidopropyl)-1,1,3,3-tetramethyldisiloxanyl)propyl)acetamide (21.6 mg, 0.068 mmol) were dissolved with DMF (114 μL). Sodium ascorbate (2.71 mg, 0.014 mmol) in water (114 μL) was added, followed by copper sulfate pentahydrate (1.43 mg, 4.55 μmol) in water (114 μL). The vial was purged with nitrogen gas, capped, sonicated for 5 min, and agitated on a shaker at rt. The blue solution became a yellow solid in a minute. After 10 min, the reaction was quenched with water. The product was extracted with EtOAc. The organic layer was washed with brine, dried over Na₂SO₄, filtered, and concentrated in vacuo. The crude was purified by column chromatography (solid loading) on silica gel eluting with 50:50 to 30:70 Hex:EtOAc to afford 14 mg, 73.4% yield of the title compound as a clear film. $^1$H NMR (400 MHz, CHLOROFORM-d) δ ppm 0.04-0.06 (m, 6H) 0.07-0.09 (m, 6H) 0.43-0.62 (m, 4H) 1.40-1.57 (m, 2H) 1.92-2.08 (m, 5H) 3.14-3.31 (m, 2H) 4.39 (t, J=7.07 Hz, 2H) 7.31-7.38 (m, 1H) 7.41-7.48 (m, 2H) 7.79 (s, 1H) 7.82-7.88 (m, 2H), MS (ES⁺): m/z=419.36 [M+H]⁺; LCMS: $t_R$=2.22 min [polar_3 min_0_1500].

Example 70

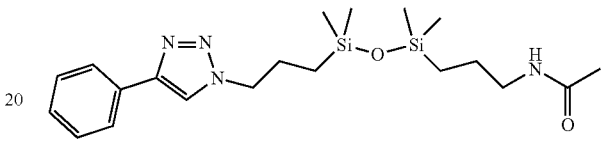

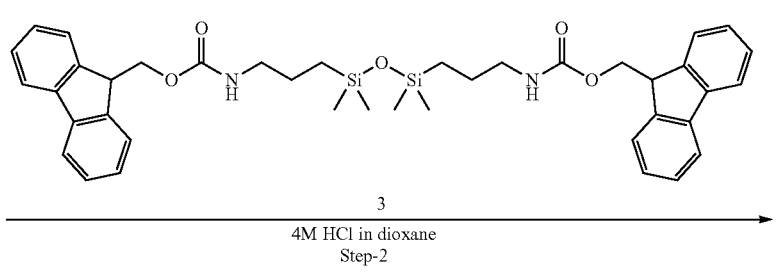

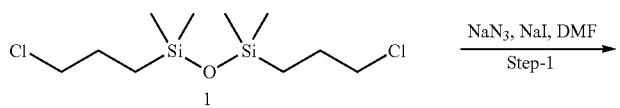

-continued

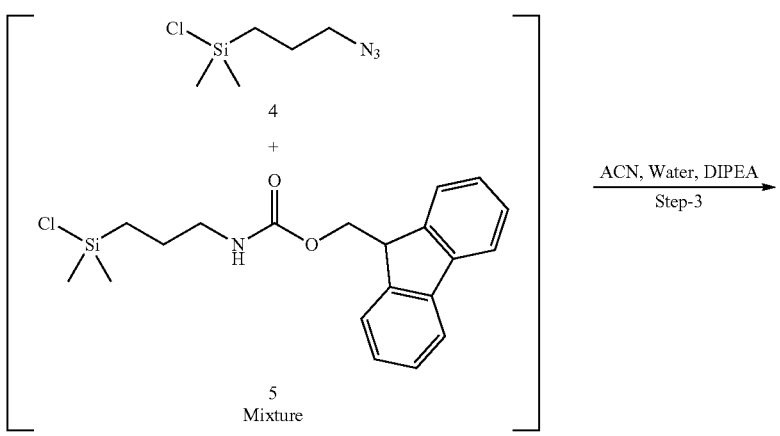

5
Mixture

ACN, Water, DIPEA
Step-3 →

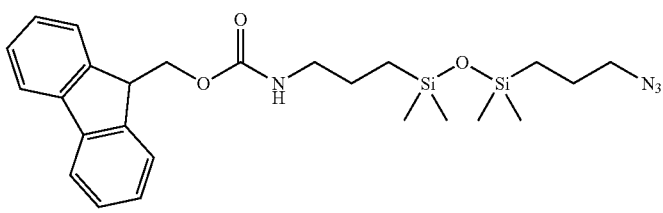

Example 70

(9H-fluoren-9-yl)methyl(3-(3-(3-azidopropyl)-1,1,3,3-tetramethyldisiloxanyl) propyl)carbamate [Example 70]

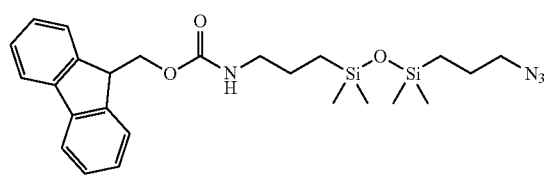 [SMILES: C[Si](C)(CCCN=[N+]=[N-])O[Si](C)(C)CCCNC(=O)OCC1c2ccccc2-c2ccccc21]

A solution of 1,3-bis(3-azidopropyl)-1,1,3,3-tetramethyldisiloxane (400 mg, 1.333 mmol) and bis((9H-fluoren-9-yl)methyl)((1,1,3,3-tetramethyldisiloxane-1,3-diyl)bis(propane-3,1-diyl))dicarbamate (923 mg, 1.333 mmol) in 4M HCl in dioxane (30 mL) was stirred at room temperature for 1 h. The reaction mixture was concentrated in vacuo resulting in the crude intermediate 4 and 5. The intermediate 4 and 5 was dissolved in acetonitrile (50 mL) and followed by addition of water (0.95 mL) and DIPEA (1.34 mL, 7.999 mmol) and stirred at room temperature for another 1 h. The reaction mixture was concentrated in vacuo resulting in the crude compound which was purified by combiflash column chromatography on silica gel eluting with 10-30% ethyl acetate in n-hexane to afford 541 mg, 41% yield, of the title compound as a white solid. $^1$H NMR (400 MHz, DMSO-$d_6$) δ=7.84-7.90 (m, 2H), 7.67 (d, J=7.34 Hz, 2H), 7.37-7.42 (m, 2H), 7.30 (t, J=7.58 Hz, 2H), 7.23-7.27 (m, 1H), 4.27 (d, J=6.85 Hz, 2H), 4.20 (d, J=6.36 Hz, 1H), 3.26 (t, J=6.85 Hz, 2H), 2.93 (q, J=6.52 Hz, 2H), 1.48-1.57 (m, 2H), 1.39 (td, J=7.64, 15.53 Hz, 2H), 0.49-0.55 (m, 2H), 0.41-0.48 (m, 2H), 0.04 (s, 6H), 0.03 (s, 6H); MS (ES$^+$): m/z=338 [M+H]$^+$ monomer; LCMS: $t_R$=4.39 min.

1,3-Bis(3-azidopropyl)-1,1,3,3-tetramethyldisiloxane (2)

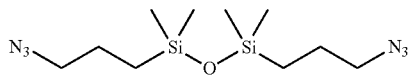 [SMILES: C[Si](C)(CCCN=[N+]=[N-])O[Si](C)(C)CCCN=[N+]=[N-]]

A solution of 1,3-bis(3-chloropropyl)-1,1,3,3-tetramethyldisiloxane (1 g, 3.484 mmol) in DMF (20 mL) was charged with sodium iodide (1.03 g, 6.912 mmol) and sodium azide (566 mg, 8.707 mmol) at room temperature. The reaction mixture was heated to 90° C. for 14 h. The reaction mixture was concentrated in vacuo, the residue was diluted with water and extracted with DCM (3×). The combined organic layers were dried over anhydrous Na$_2$SO$_4$, filtered and concentrated in vacuo to afford 810 mg, 78% yield, of the title compound as a colorless oil. $^1$H NMR (400 MHz, DMSO-$d_6$) δ=3.26-3.31 (m, 4H), 1.49-1.59 (m, 4H), 0.50-0.56 (m, 4H), 0.06 (s, 12H).

Example 71

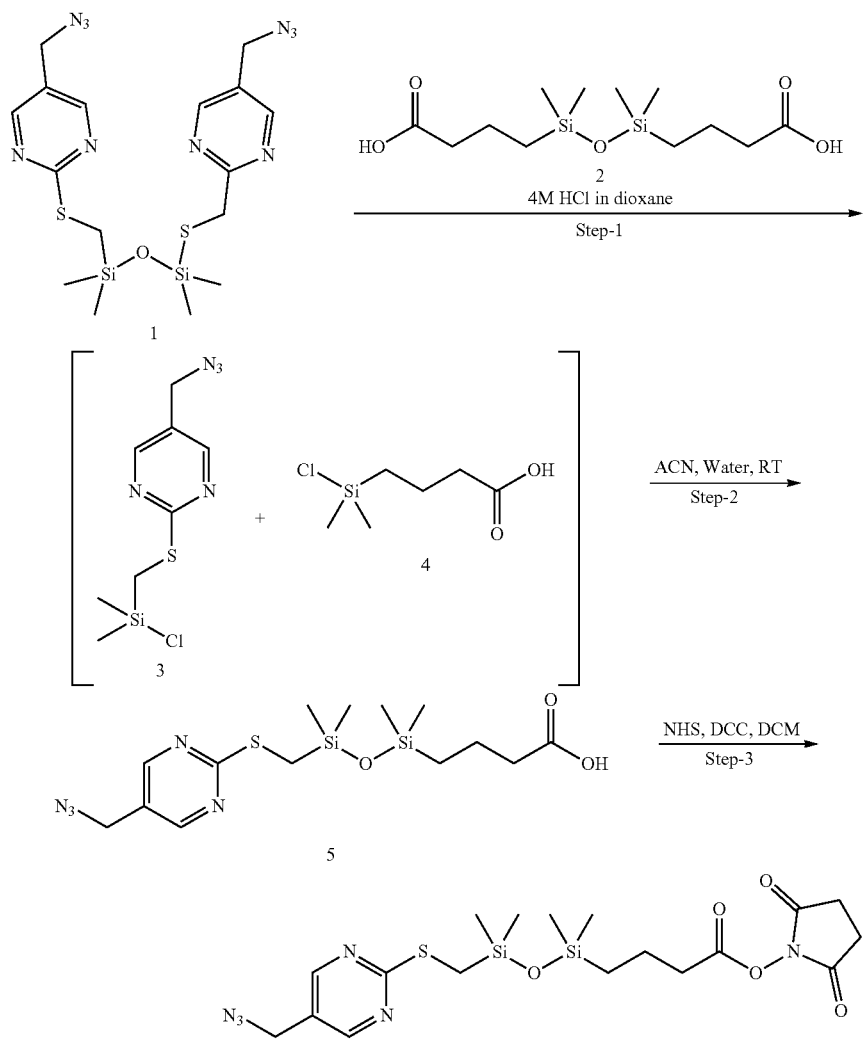

2,5-Dioxopyrrolidin-1-yl 4-(3-(((5-(azidomethyl)pyrimidin-2-yl)thio)methyl)-1,1,3,3-tetramethyldisiloxanyl)butanoate [Example 71]

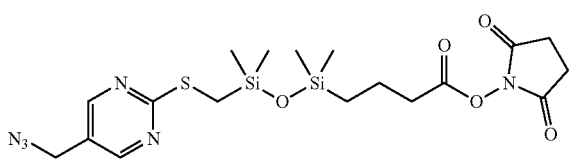 [SMILES: C[Si](C)(CCCC(=O)ON1C(=O)CCC1=O)O[Si](C)(C)CSc1ncc(CN=[N+]=[N-])cn1]

A solution of 4-(3-(((5-(azidomethyl)pyrimidin-2-yl)thio)methyl)-1,1,3,3-tetramethyldisiloxanyl)butanoic acid (1 g, 3.007 mmol) in DCM (20 mL) was charged with DCC (619 mg, 3.007 mmol) and N-hydroxysuccinimide (345 mg, 3.007 mmol) and stirred at room temperature for another 2 h. The reaction mixture was concentrated in vacuo, diluted with acetonitrile and re-concentrated. The slurry was cooled and the solid was filtered and washed. The filtrate was concentrated in vacuo, resulting in the crude compound which was purified by combiflash column chromatography eluting with 10-30% ethyl acetate in n-hexane to afford 1.2 g (81% yield) of the title compound as a colorless oil. $^1$H NMR (400 MHz, DMSO-$d_6$) δ=8.64 (s, 2H), 4.47 (s, 2H), 2.78 (s, 4H), 2.64 (t, J=6.85 Hz, 2H), 2.38 (s, 2H), 1.58-1.69 (m, 2H), 0.56-0.63 (m, 2H), 0.12-0.17 (m, 6H), 0.02-0.06 (m, 6H); MS (ES+): m/z=497.29; LCMS: $t_R$=3.58 min.

4-(3-(((5-(Azidomethyl)pyrimidin-2-yl)thio)methyl)-1,1,3,3-tetramethyldisiloxanyl) butanoic Acid (5)

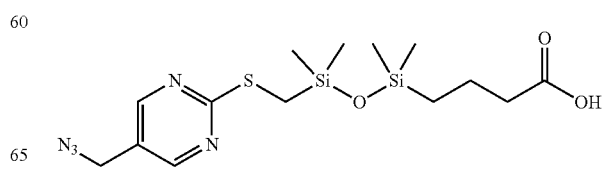

A solution of 1,3-bis(((5-(azidomethyl)pyrimidin-2-yl)thio)methyl)-1,1,3,3-tetramethyldisiloxane (1.5 g, 3.048 mmol) and 4,4'-(1,1,3,3-tetramethyldisiloxane-1,3-diyl)dibutyric acid (932 mg, 3.048 mmol) in 4M HCl in dioxane (30 mL) was stirred at room temperature for 1 h. The reaction mixture was concentrated in vacuo resulting in the crude intermediate 3 and 4. The intermediate 3 and 4 was dissolved in acetonitrile (200 mL) and followed by addition of water (0.11 mL, 6.097 mmol) and DIPEA (3.09 mL, 18.29 mmol) and stirred at room temperature for another 1 h. The reaction mixture was concentrated in vacuo resulting in the crude compound which was purified by combiflash column chromatography on silica gel eluting with 10-30% ethyl acetate in n-hexane to afford 1.2 g, 50% yield, of the title compound as a colorless oil. $^1$H NMR (400 MHz, DMSO-$d_6$) δ=11.95 (s, 1H), 8.67 (s, 2H), 4.50 (s, 2H), 2.39-2.44 (m, 2H), 2.22 (dt, J=3.67, 7.21 Hz, 2H), 1.48-1.60 (m, 2H), 0.52 (td, J=4.59, 12.35 Hz, 2H), 0.18 (s, 6H), 0.06 (s, 6H).

Example 72 and Example 82

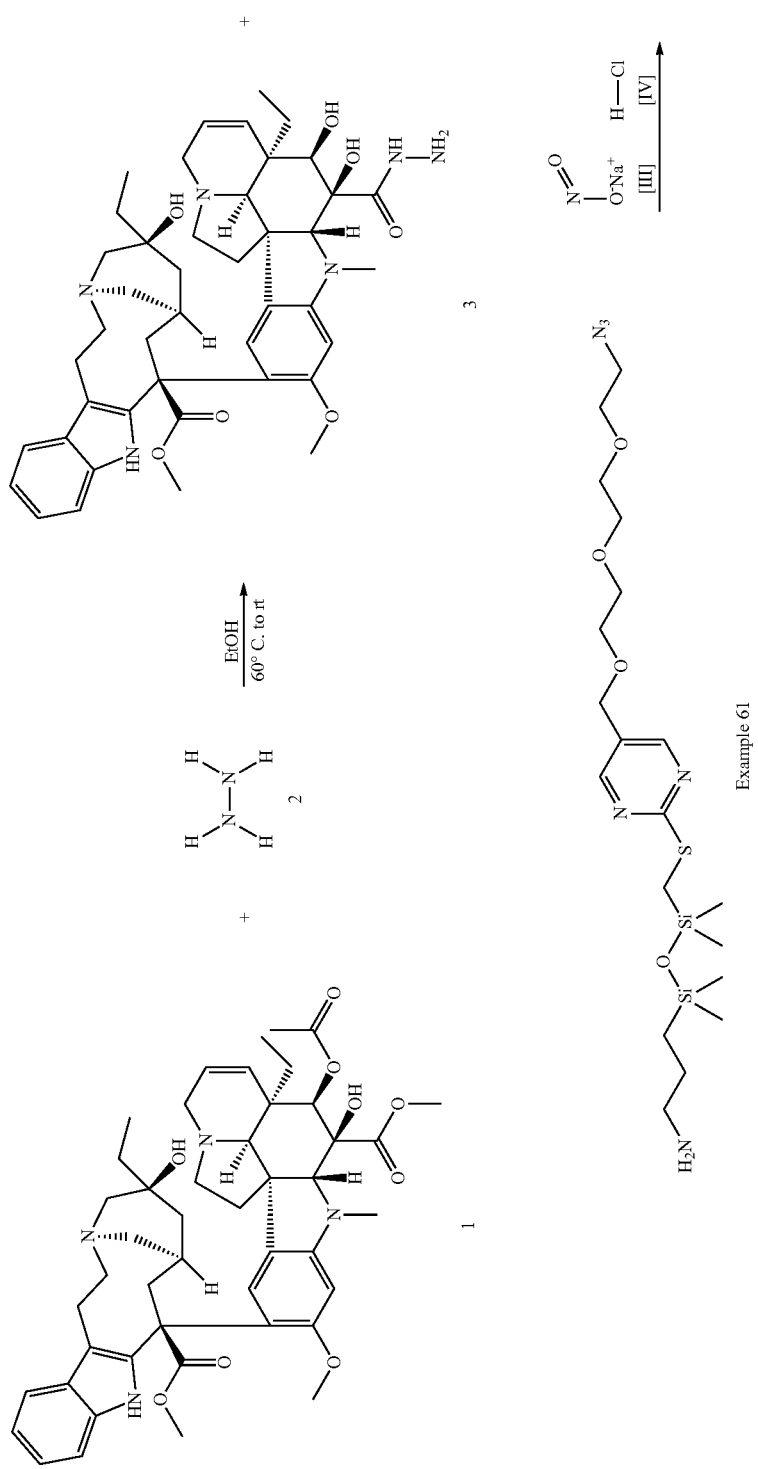

-continued
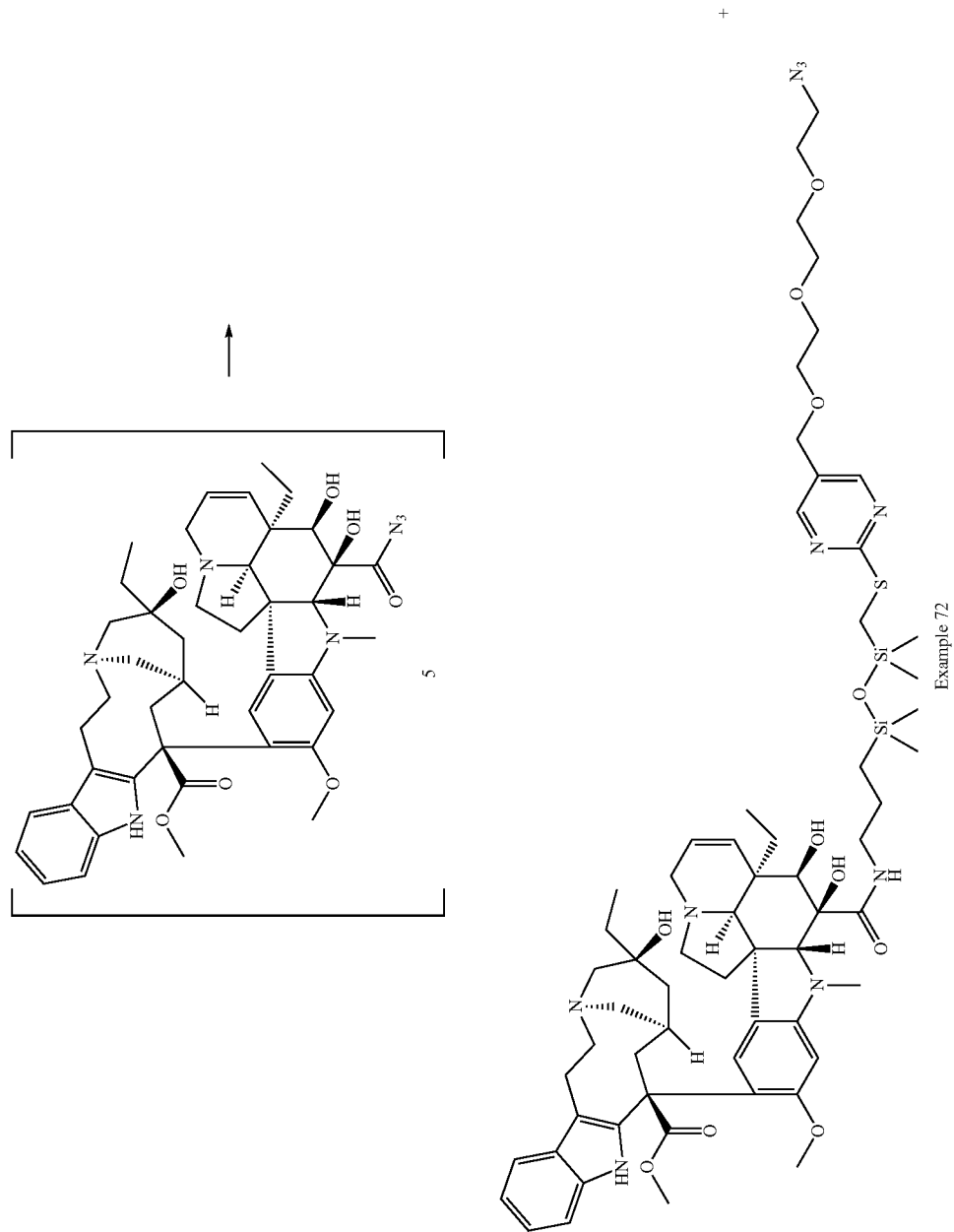
Example 72

-continued
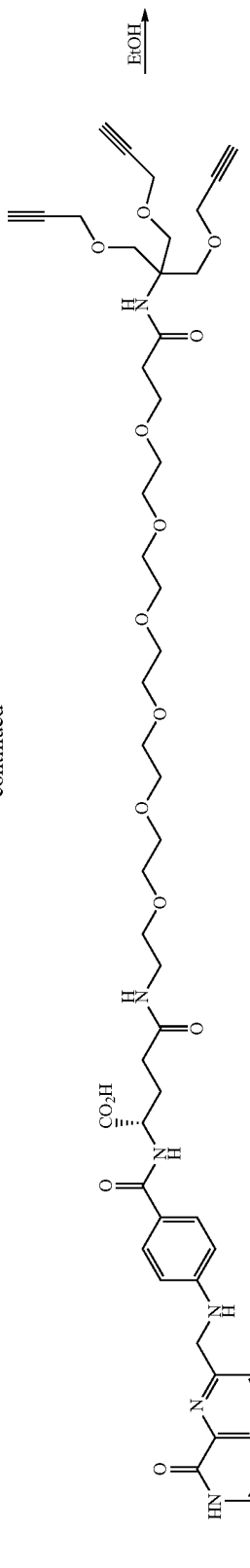
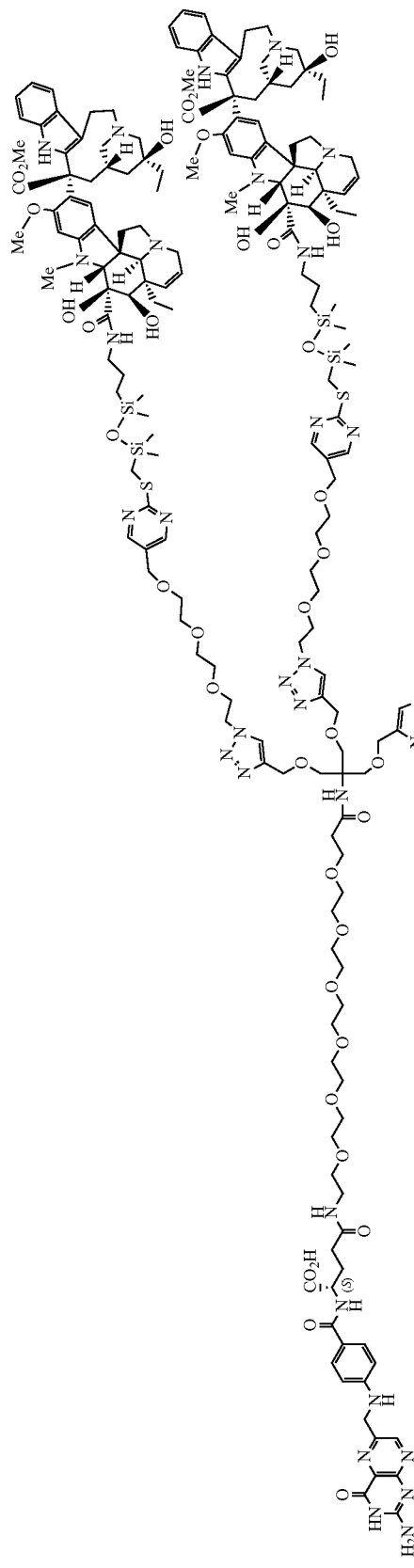
Example 82

Methyl(3R,5S,7R,9S)-9-((3aR,3a1R,4R,5S,5aR,
10bR)-5-((3-(3-(((5-((2-(2-(2-azidoethoxy)ethoxy)
ethoxy)methyl)pyrimidin-2-yl)thio)methyl)-1,1,3,3-
tetramethyldisiloxanyl)propyl)carbamoyl)-3a-ethyl-
4,5-dihydroxy-8-methoxy-6-methyl-3a,3a1,4,5,5a,6,
11,12-octahydro-1H-indolizino[8,1-cd]carbazol-9-
yl)-5-ethyl-5-hydroxy-1,4,5,6,7,8,9,10-octahydro-
2H-3,7-methano[1]azacycloundecino[5,4-b]indole-9-
carboxylate [Example 72]

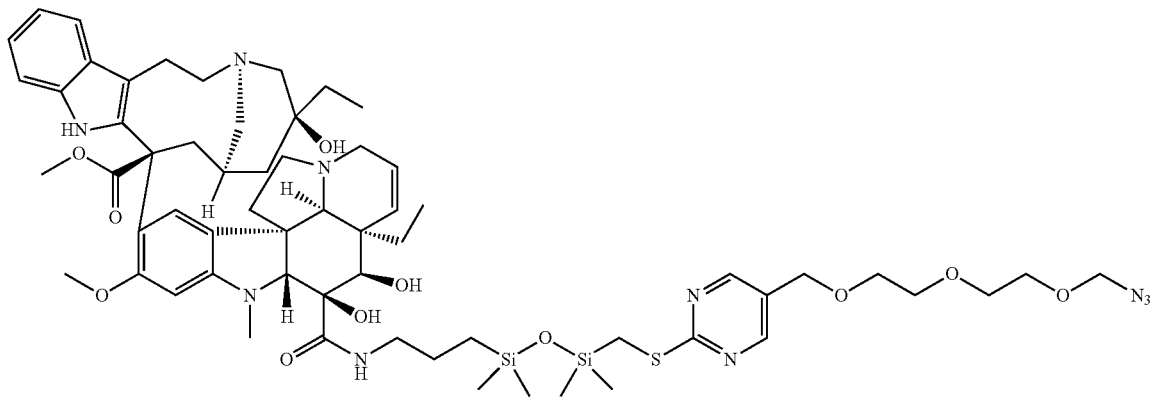

A solution of (3R,5S,7R,9S)-methyl 5-ethyl-9-((3aR,3a1R,4R,5S,5aR,10bR)-3a-ethyl-5-(hydrazinecarbonyl)-4,5-dihydroxy-8-methoxy-6-methyl-3a,3a1,4,5,5a,6,11,12-octahydro-1H-indolizino[8,1-cd]carbazol-9-yl)-5-hydroxy-2,4,5,6,7,8,9,10-octahydro-1H-3,7-methano[1]azacycloundecino[5,4-b]indole-9-carboxylate (100 mg, 0.130 mmol) in acetonitrile (1.67 ml) and 1 M HCl in water (6.16 ml, 6.16 mmol) cooled to −10° C. then charged with sodium nitrite (20.64 mg, 0.299 mmol). After 10 min the yellowish brown solution was adjusted to pH ~8.00 dropwise adding cold sat NaHCO$_3$ solution (~6.6 mL of NaHCO$_3$ added). The solution was extracted rapidly with DCM (5×5.0 mL) and the combined organic layers were washed with brine (1×10 mL) and dried over Na$_2$SO$_4$, filtered and concentrated to ~4.00 mL cooled to 0° C. in and charged with a solution of 3-(3-(((5-((2-(2-(2-azidoethoxy)ethoxy)ethoxy)methyl)pyrimidin-2-yl)thio)methyl)-1,1,3,3-tetramethyldisiloxanyl)propan-1-amine (65.4 mg, 0.130 mmol) in 4.0 mL of DCM and allowed to stir at 0° C. for 2 hr. The reaction mixture was concentrated in vacuo resulting in a light tan solid which was purified by chromatography on silica gel [ISCO CombiFlash, 12 g Gold cartridge, eluting with 0% of (10% 7N NH3 in MeOH) to 8% (10% 7N NH3 in MeOH) in DCM resulting in 65.5 mg, 41% yield of the title compound as a light yellow solid. $^1$H NMR (DMSO-d$_6$, 400 MHz): δ (ppm) 9.33 (s, 1H), 8.58 (s, 2H), 8.51 (s, 1H), 7.77 (br t, J=5.8 Hz, 1H), 7.37 (d, J=8.1 Hz, 1H), 7.26 (d, J=8.1 Hz, 1H), 7.00 (t, J=7.6 Hz, 1H), 6.88-6.95 (m, 1H), 6.44 (s, 1H), 6.19 (s, 1H), 5.69 (br dd, J=10.7, 5.4 Hz, 1H), 5.54-5.61 (m, 1H), 4.47 (s, 2H), 4.00-4.10 (m, 1H), 3.96 (s, 1H), 3.92 (s, 1H), 3.83 (d, J=5.8 Hz, 1H), 3.68-3.76 (m, 4H), 3.49-3.62 (m, 13H), 3.36-3.40 (m, 2H), 3.30-3.34 (m, 6H), 2.98-3.28 (m, 7H), 2.84-2.93 (m, 1H), 2.59-2.77 (m, 6H), 2.52-2.55 (m, 1H), 2.48-2.52 (m, 7H), 2.30-2.42 (m, 4H), 1.89-2.05 (m, 2H), 1.42-1.65 (m, 4H), 1.12-1.36 (m, 5H), 0.69-0.85 (m, 6H), 0.57-0.68 (m, 1H), 0.46-0.55 (m, 2H), 0.17 (s, 6H), 0.07 (s, 6H), MS (ES+): m/z=1240.00, 1240.90 [M+H]$^+$; LCMS: t$_R$=1.65 min [polar_3 min_1500].

(31S)-31-(4-(((2-Amino-4-oxo-3,4-dihydropteridin-
6-yl)methyl)amino)benzamido)-1-(1-(2-(2-(2-((2-
(((3-(3-((3aR,3a1R,4R,5S,5aR,10bR)-3a-ethyl-9-
((5S,7S,9S)-5-ethyl-5-hydroxy-9-
(methoxycarbonyl)-1,4,5,6,7,8,9,10-octahydro-2H-3,
7-methano[1]azacycloundecino[5,4-b]indol-9-yl)-4,
5-dihydroxy-8-methoxy-6-methyl-3a,3a1,4,5,5a,6,
11,12-octahydro-1H-indolizino[8,1-cd]carbazole-5-
carboxamido)propyl)-1,1,3,3-tetramethyldisiloxanyl)
methyl) thio)pyrimidin-5-yl)methoxy) ethoxy)
ethoxy) ethyl)-1H-1,2,3-triazol-4-yl)-4,4-bis(((1-(2-
(2-(2-(2-(((3-(3-((3aR,3a1R,4R,5S,5aR,10bR)-3a-
ethyl-9-((5S,7S,9S)-5-ethyl-5-hydroxy-9-(methoxy-
carbonyl)-1,4,5,6,7,8,9,10-octahydro-2H-3,7-
methano[1]azacycloundecino[5,4-b]indol-9-yl)-4,5-
dihydroxy-8-methoxy-6-methyl-3a,3a1,4,5,5a,6,11,
12-octahydro-1H-indolizino[8,1-cd]carbazole-5-
carboxamido)propyl)-1,1,3,3-tetramethyldisiloxanyl)
methyl)thio)pyrimidin-5-yl) methoxy)ethoxy)
ethoxy)ethyl)-1H-1,2,3-triazol-4-yl)methoxy)
methyl)-6,28-dioxo-2,9,12,15,18,21,24-heptaoxa-5,
27-diazadotriacontan-32-oic Acid [Example 82]

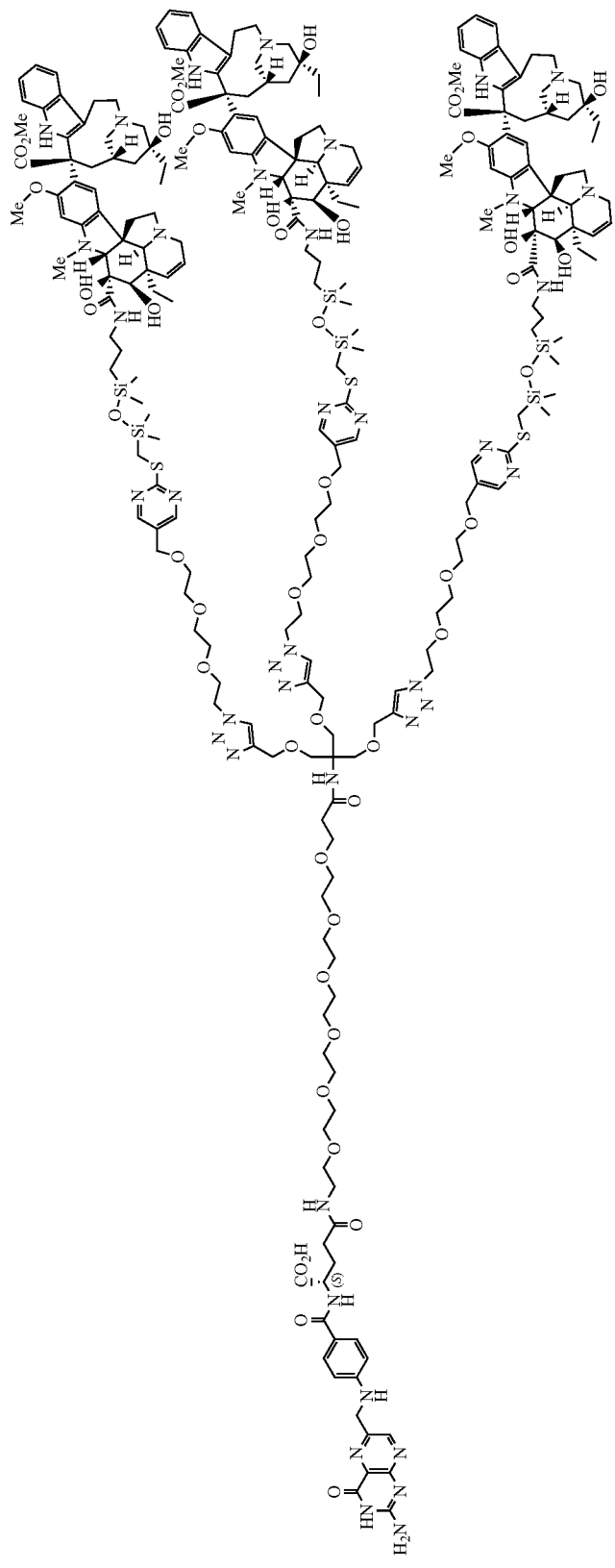

To an Eppendorf vial, DMF (134 μL) was added to a mixture of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (10 mg, 10.06 μmol) and (5S,7S,9S)-methyl 9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyl disiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (43.6 mg, 0.035 mmol). More DMF (134 μL) was added to dissolve both reactants. The whole was purged with nitrogen gas, capped, and sonicated for 5 min. Then a freshly prepared solution of sodium ascorbate (100 mM in water, 40.2 μL, 4.02 μmol) followed by the addition of a freshly prepared solution of copper sulfate pentahydrate (100 mM in water, 20.12 μL, 2.01 μmol). The whole was purged with nitrogen gas, capped, sonicated for 5 min, and agitated on a shaker at rt. After 1.5 h LCMS showed mainly both SMs but a lot of gummy solid adhered to the Eppendorf vial. More sodium ascorbate (100 mM in water, 80 μL, 8 μmol) and copper sulfate pentahydrate (100 mM in water, 40 μL, 4 μmol) were added. After 15 min, the reaction was stopped. The whole was passed through an ISCO solid loading filter plug with an aid of a vacuum. For the residue, dissolved with ~0.5 mL of DMSO and passed through the same filter plug. The combined filtrate (1.7 mL) was purified by a reversed phase preparative HPLC [Gradient 2] resulting in 2.12 mg, 4.47% yield of the title compound as a light yellow solid. $^1$H NMR (400 MHz, DMSO-$d_6$) δ ppm 9.32 (s, 1H) 8.63 (s, 1H) 8.56 (s, 2H) 7.98 (s, 2H) 7.69-7.85 (m, 1H) 7.61 (br d, J=8.08 Hz, 1H) 7.32-7.49 (m, 1H) 7.16-7.32 (m, 1H) 6.85-7.13 (m, 3H) 6.63 (br d, J=8.84 Hz, 1H) 6.44 (s, 1H) 6.19 (s, 1H) 5.76 (br s, 1H) 5.63-5.73 (m, 1H) 5.49-5.63 (m, 1H) 5.39 (br d, J=7.58 Hz, 1H) 4.37-4.67 (m, 9H) 3.87-4.15 (m, 7H) 3.74-3.87 (m, 6H) 3.71 (s, 5H) 3.63 (br s, 5H) 3.41-3.57 (m, 26H) 3.21-3.27 (m, 1H) 3.00-3.21 (m, 4H) 2.89 (br d, J=10.36 Hz, 1H) 2.70 (s, 4H) 2.63 (br d, J=14.15 Hz, 2H) 2.53-2.58 (m, 1H) 2.29-2.40 (m, 3H) 1.86-2.03 (m, 1H) 1.59 (br dd, J=13.39, 7.33 Hz, 1H) 1.47 (dt, J=15.85, 7.61 Hz, 2H) 1.20-1.36 (m, 3H) 1.16 (brd, J=7.83 Hz, 3H) 0.67-0.86 (m, 5H) 0.63 (br s, 1H) 0.45-0.58 (m, 2H) 0.16 (s, 5H) 0.00-0.11 (m, 7H). MS (ES+): m/z=(M+3)/3=1571.9, (M+4)/4=1179.4, (M+5)/5=943.7, (M+6)/6=786.6; LCMS: $t_R$=1.58 min [polar_3 min_1500].

Compound 6

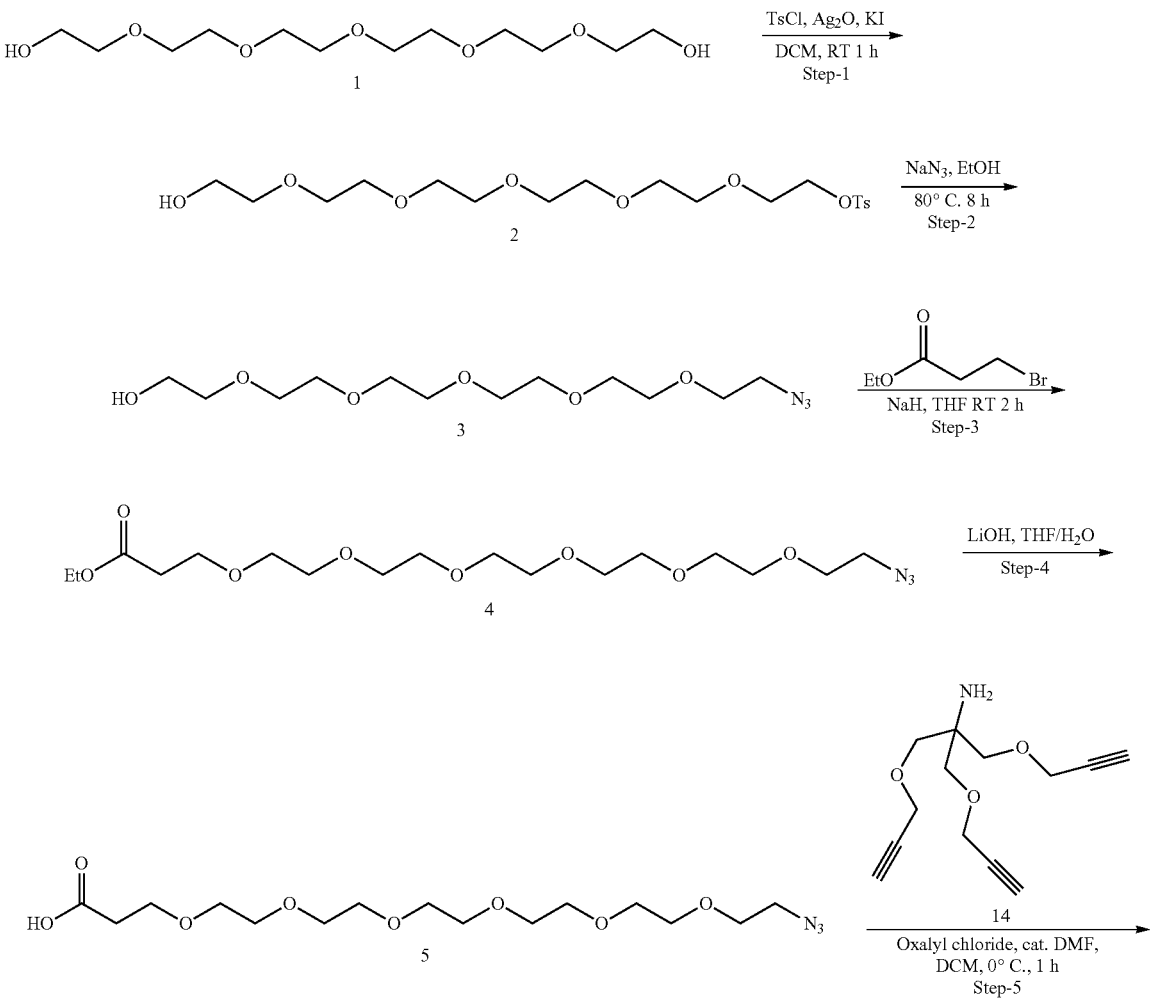

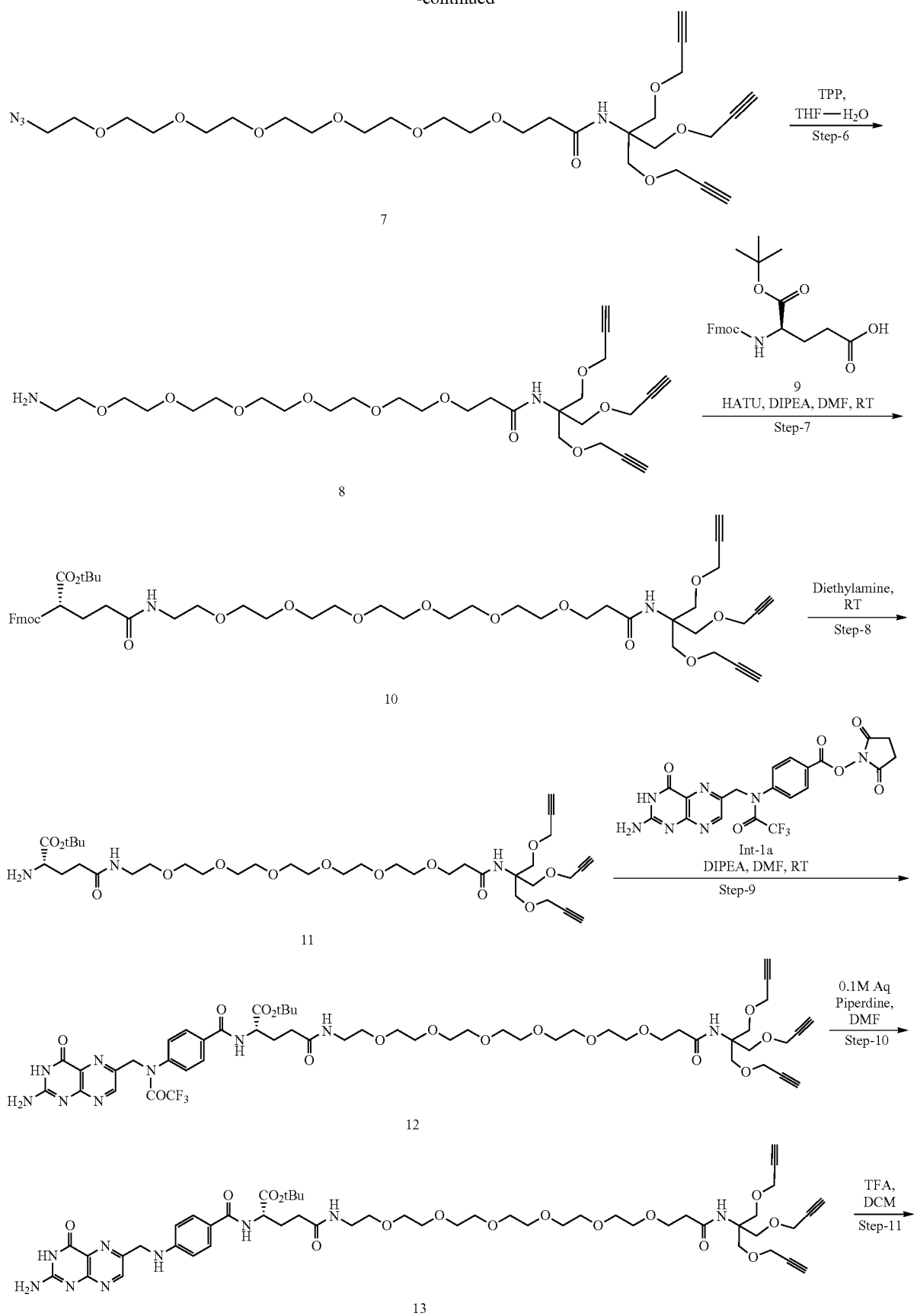

-continued

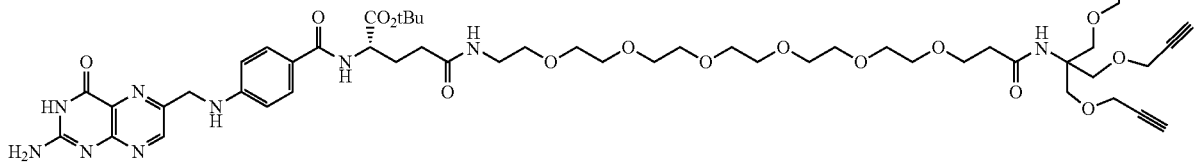

6

(S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic Acid
(6)

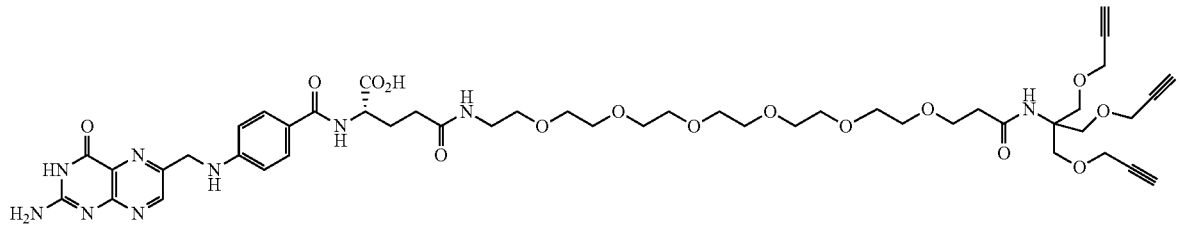 [SMILES: C#CCOCC(COCC#C)(COCC#C)NC(=O)CCOCCOCCOCCOCCOCCOCCNC(=O)CC[C@H](NC(=O)c1ccc(NCc2cnc3nc(N)[nH]c(=O)c3n2)cc1)C(=O)O]

A solution of tert-butyl(S)-33-(4-(((2-amino-4-oxo-3,4-dihydropteridin-6-yl)methyl) amino)benzamido)-8,30-dioxo-6,6-bis((prop-2-yn-1-yloxy)methyl)-4,11,14,17,20,23,26-heptaoxa-7,29-diazatetratriacont-1-yn-34-oate (2.2 g, 2.095 mmol) in DCM (25 mL) was charged with trifluoroacetic acid (25 mL) and stirred at room temperature for 12 h. The reaction mixture was concentrated in vacuo resulting in the crude compound. The crude compound was purified by reverse phase combiflash column chromatography (acetonitrile:water: 0.1% TFA) to afford 91 mg, 4% yield of the title compound as a yellow solid. $^1$H NMR (400 MHz, DMSO-$d_6$) δ=12.44 (br. s, 2H), 11.56 (br. s, 2H), 8.71 (s, 1H), 8.20 (br. s, 1H), 7.96 (br. s, 1H), 7.71 (d, J=8.31 Hz, 2H), 7.37 (br. s, 1H), 6.97-7.03 (m, 2H), 6.70 (d, J=8.31 Hz, 2H), 4.55 (d, J=5.38 Hz, 1H), 4.31 (br. s, 1H), 4.18 (br. s, 4H), 3.71 (s, 4H), 3.35-3.65 (m, 31H), 3.23 (d, J=5.38 Hz, 2H), 2.35-2.42 (m, 2H), 2.24 (d, J=6.36 Hz, 2H), 2.04-2.19 (m, 1H), 1.87-2.00 (m, 1H), MS (ES$^+$): m/z=994.55 [M+H]$^+$; LCMS: $t_R$=2.23 min.

tert-Butyl(S)-33-(4-(((2-amino-4-oxo-3,4-dihydropteridin-6-yl)methyl)amino) benzamido)-8,30-dioxo-6,6-bis((prop-2-yn-1-yloxy)methyl)-4,11,14,17,20,23,26-heptaoxa-7,29-diazatetratriacont-1-yn-34-oate
(13)

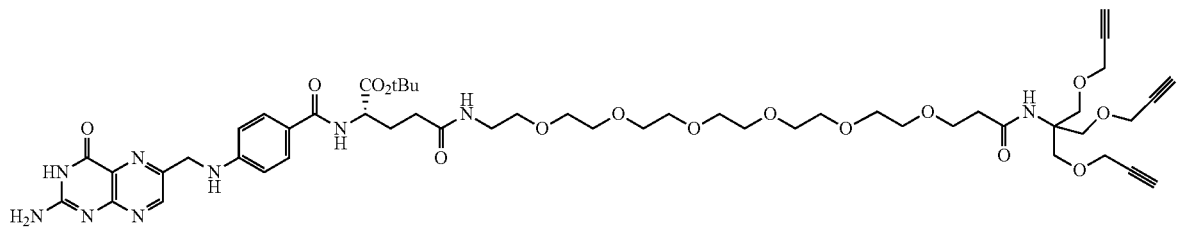 [SMILES: C#CCOCC(COCC#C)(COCC#C)NC(=O)CCOCCOCCOCCOCCOCCOCCNC(=O)CC[C@H](NC(=O)c1ccc(NCc2cnc3nc(N)[nH]c(=O)c3n2)cc1)C(=O)OC(C)(C)C]

A solution of tert-butyl(S)-33-(4-(N-((2-amino-4-oxo-3,4-dihydropteridin-6-yl)methyl)-2,2,2-trifluoroacetamido)benzamido)-8,30-dioxo-6,6-bis((prop-2-yn-1-yloxy)methyl)-4,11,14,17,20,23,26-heptaoxa-7,29-diazatetratriacont-1-yn-34-oate (2.9 g, 2.530 mmol) in DMF (25 mL) was charged with 0.1M solution of piperdine (50 mL) and stirred at room temperature for 3 h. The reaction mixture was concentrated in vacuo resulting in the crude compound. The crude compound was stirred in diethyl ether (40 mL) for 10 min and the solid was filtered and washed with diethyl ether (20 mL) and dried to afford 2.2 g, 83% yield of the title compound as a yellow solid. $^1$H NMR (400 MHz, DMSO-$d_6$) δ=8.64 (s, 1H), 8.17 (d, J=7.34 Hz, 1H), 7.95 (s, 2H), 7.89 (t, J=5.38 Hz, 1H), 7.64 (d, J=8.80 Hz, 2H), 7.30 (s, 1H), 6.89-6.94 (m, 2H), 6.64 (d, J=8.80 Hz, 2H), 4.48 (d, J=5.87 Hz, 2H), 4.17-4.23 (m, 1H), 4.11 (d, J=1.47 Hz, 4H), 3.65 (s, 4H), 3.55 (t, J=6.36 Hz, 2H), 3.35-3.51 (m, 27H), 3.14-3.21 (m, 2H), 2.32 (t, J=6.11 Hz, 2H), 2.19 (dd, J=7.09, 11.49 Hz, 2H), 1.81-2.03 (m, 2H), 1.44-1.61 (m, 2H), 1.39 (s, 9H); MS (ES+): m/z=1050.00 [M]$^+$; LCMS: $t_R$=1.90 min.

tert-Butyl(S)-33-(4-(N-((2-amino-4-oxo-3,4-dihydropteridin-6-yl)methyl)-2,2,2-trifluoroacetamido)benzamido)-8,30-dioxo-6,6-bis((prop-2-yn-1-yloxy)methyl)-4,11,14,17,20,23,26-heptaoxa-7,29-diazatetratriacont-1-yn-34-oate (12)

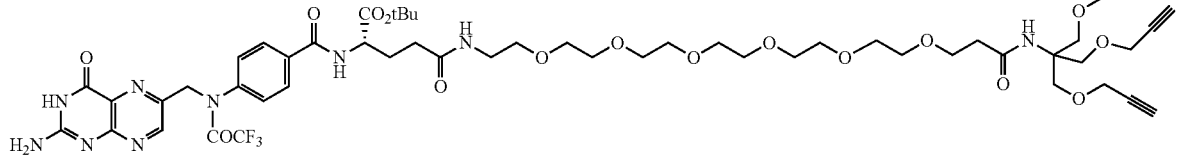

A solution of 2,5-dioxopyrrolidin-1-yl 4-(N-((2-amino-4-oxo-3,4-dihydropteridin-6-yl)methyl)-2,2,2-trifluoroacetamido)benzoate (1.5 g, 2.913 mmol) and tert-butyl(S)-33-amino-8,30-dioxo-6,6-bis((prop-2-yn-1-yloxy)methyl)-4,11,14,17,20,23,26-heptaoxa-7,29-diazatetratriacont-1-yn-34-oate (2.2 g, 2.913 mmol) in DMF (25 mL) was added DIPEA (1.01 mL, 5.826 mmol) under nitrogen atmosphere for 4 h. The reaction mixture was concentrated in vacuo resulting in the crude compound. The crude compound was stirred in diethyl ether (125 mL) for 15 min and the solid precipitated was filtered and washed with diethyl ether (50 mL) and dried to afford 3 g, 90% yield, of the title compound as a yellow semisolid. $^1$H NMR (400 MHz, DMSO-$d_6$) δ=11.42 (s, 2H), 8.76 (d, J=6.85 Hz, 1H), 8.62 (br. s, 1H), 7.89 (d, J=7.34 Hz, 2H), 7.63 (d, J=7.82 Hz, 2H), 7.25-7.32 (m, 1H), 6.79-7.08 (m, 2H), 4.20-4.30 (m, 1H), 4.04-4.14 (m, 6H), 3.65 (s, 4H), 3.55 (t, J=6.11 Hz, 3H), 3.38-3.51 (m, 20H), 3.09-3.22 (m, 8H), 2.32 (t, J=5.87 Hz, 2H), 2.21 (d, J=6.36 Hz, 2H), 1.99-2.11 (m, 2H), 1.91 (dd, J=6.60, 14.43 Hz, 2H), 1.40 (s, 9H); MS (ES$^+$): m/z=1146.63 [M+H]$^+$; LCMS: $t_R$=2.64 min.

tert-Butyl(S)-33-amino-8,30-dioxo-6,6-bis((prop-2-yn-1-yloxy)methyl)-4,11,14,17,20,23,26-heptaoxa-7,29-diazatetratriacont-1-yn-34-oate (11)

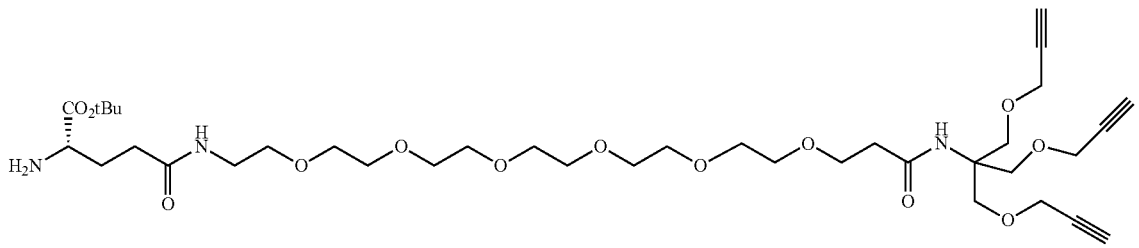 [SMILES: C#CCOCC(COCC#C)(COCC#C)NC(=O)CCOCCOCCOCCOCCOCCOCCNC(=O)CC[C@H](N)C(=O)OC(C)(C)C]

A solution of tert-butyl(S)-33-((((9H-fluoren-9-yl)methoxy)carbonyl)amino)-8,30-dioxo-6,6-bis((prop-2-yn-1-yloxy)methyl)-4,11,14,17,20,23,26-heptaoxa-7,29-diazatetratriacont-1-yn-34-oate (3.8 g, 3.885 mmol) in diethyl amine (50 mL) was stirred at room temperature under nitrogen atmosphere for 12 h. The reaction mixture was concentrated in vacuo resulting in the crude compound which was purified by flash column chromatography eluting with 0-15% methanol saturated with ammonia in DCM to afford 2.2 g, 75% yield, of the title compound as a colorless oil. $^1$H NMR (400 MHz, CDCl$_3$) δ=4.15 (d, J=2.45 Hz, 6H), 3.83 (s, 6H), 3.70-3.75 (m, 3H), 3.62-3.69 (m, 19H), 3.59 (t, J=5.14 Hz, 2H), 3.48-3.50 (m, 2H), 3.42-3.47 (m, 2H), 2.80 (s, 6H), 2.42-2.49 (m, 6H), 1.49 (s, 9H).

tert-Butyl(S)-33-((((9H-fluoren-9-yl)methoxy)carbonyl)amino)-8,30-dioxo-6,6-bis((prop-2-yn-1-yloxy)methyl)-4,11,14,17,20,23,26-heptaoxa-7,29-diazatetratriacont-1-yn-34-oate (10)

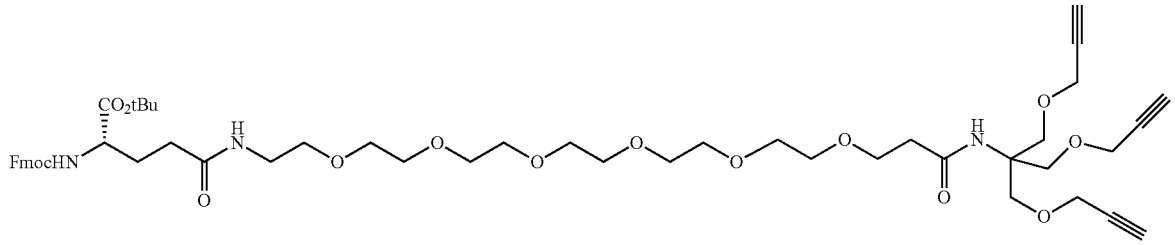

A solution of 1-amino-N-(1,3-bis(prop-2-yn-1-yloxy)-2-((prop-2-yn-1-yloxy)methyl)propan-2-yl)-3,6,9,12,15,18-hexaoxahenicosan-21-amide (1.71 g, 4.035 mmol) in DCM (50 mL) was charged with (R)-4-((((9H-fluoren-9-yl)methoxy)carbonyl)amino)-5-(tert-butoxy)-5-oxopentanoic acid (2.3 g, 4.035 mmol), HATU (2.3 g, 6.052 mmol) and DIPEA (1.4 mL, 8.070 mmol) and was stirred at room temperature for 16 h. The reaction mixture was diluted with water and extracted with ethyl acetate. The combined organic layers were dried over anhydrous Na$_2$SO$_4$, filtered and concentrated in vacuo resulting in a crude compound which was purified by column chromatography on combi-flash eluting with 0-5% methanol in DCM to afford 3.51 g, 89% yield, of the title compound as a yellow oil. $^1$H NMR (400 MHz, CDCl$_3$) δ=7.76 (d, J=7.82 Hz, 2H), 7.59-7.64 (m, 2H), 7.37-7.43 (m, 2H), 7.29-7.34 (m, 2H), 6.44 (br. s, 1H), 6.26 (br. s, 1H), 5.74 (d, J=7.82 Hz, 1H), 4.39 (t, J=7.09 Hz, 2H), 4.23 (t, J=6.85 Hz, 2H), 4.14 (d, J=1.96 Hz, 5H), 3.83 (s, 4H), 3.60-3.73 (m, 16H), 3.56 (t, J=4.89 Hz, 2H), 3.39-3.48 (m, 2H), 3.17 (q, J=7.34 Hz, 1H), 2.80 (s, 4H), 2.41-2.46 (m, 4H), 2.15-2.32 (m, 2H), 1.90-2.04 (m, 1H), 1.54-1.60 (m, 6H), 1.47 (s, 9H); MS (ES$^+$): m/z=978.58 [M+H]$^+$; LCMS: t$_R$=3.24 min.

1-Amino-N-(1,3-bis(prop-2-yn-1-yloxy)-2-((prop-2-yn-1-yloxy)methyl)propan-2-yl)-3,6,9,12,15,18-hexaoxahenicosan-21-amide (8)

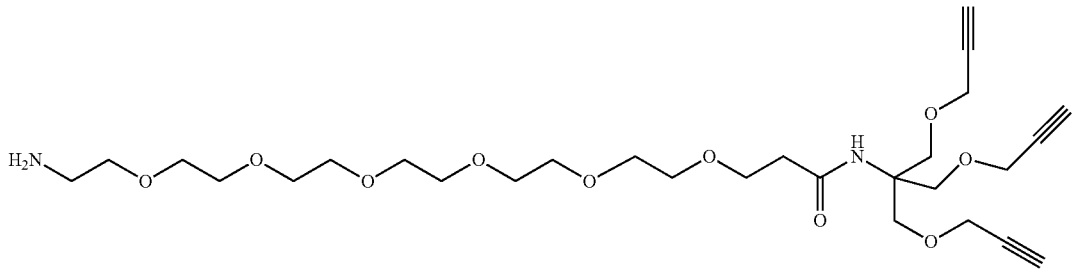 [SMILES: C#CCOCC(COCC#C)(COCC#C)NC(=O)CCOCCOCCOCCOCCOCCOCCN]

A solution of 1-azido-N-(1,3-bis(prop-2-yn-1-yloxy)-2-((prop-2-yn-1-yloxy)methyl)propan-2-yl)-3,6,9,12,15,18-hexaoxahenicosan-21-amide (3.2 g, 5.369 mmol) in THF:H$_2$O (4:1, 62.5 mL) was charged with TPP (4.22 g, 16.11 mmol) and was stirred at room temperature for 14 h. The reaction mixture was concentrated in vacuo resulting in the crude compound which was purified by column chromatography on silica gel eluting with 0-10% methanol in DCM to afford 2.35 g, 77% yield, of the title compound as light yellow oil. $^1$H NMR (400 MHz, CDCl$_3$) δ=6.37 (s, 1H), 4.13-4.17 (m, 6H), 3.84 (s, 6H), 3.71 (t, J=5.87 Hz, 2H), 3.61-3.68 (m, 23H), 3.48-3.53 (m, 2H), 2.86 (t, J=5.38 Hz, 2H), 2.43-2.46 (m, 4H).

1-Azido-N-(1,3-bis(prop-2-yn-1-yloxy)-2-((prop-2-yn-1-yloxy)methyl)propan-2-yl)-3,6,9,12,15,18-hexaoxahenicosan-21-amide (7)

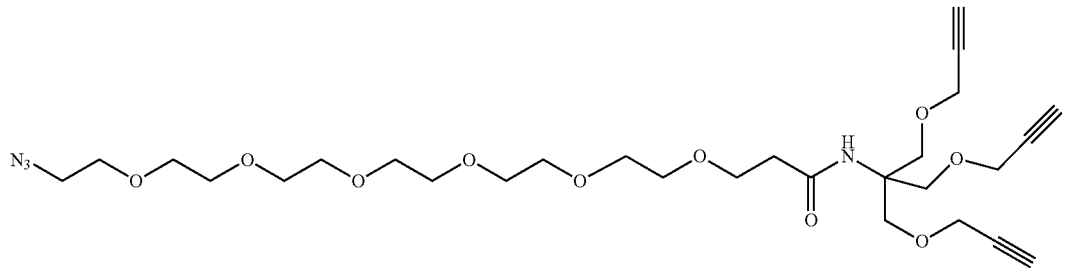 [SMILES: C#CCOCC(COCC#C)(COCC#C)NC(=O)CCOCCOCCOCCOCCOCCOCCN=[N+]=[N-]]

A solution of 1-azido-3,6,9,12,15,18-hexaoxahenicosan-21-oic acid (2.6 g, 6.860 mmol) in DCM (50 mL) was charged with oxalyl chloride (0.87 mL, 10.29 mmol) and catalytic DMF (3 drops) and stirred at room temperature for 1 h. The reaction mixture was concentrated in vacuo resulting in the crude intermediate acid chloride which was used directly without isolation for further reaction. To the resulting solution at 0° C. was added DIPEA (4.7 mL, 27.44 mmol) and 1,3-bis(prop-2-yn-1-yloxy)-2-((prop-2-yn-1-yloxy)methyl)propan-2-amine (2.28 g, 6.860 mmol) and was stirred at room temperature for 2 h. The reaction mixture was diluted with water and extracted with ethyl acetate. The combined organic layers were dried over anhydrous Na$_2$SO$_4$, filtered and concentrated in vacuo to afford 3.6 g, 88% yield, of the title compound as a light yellow solid. $^1$H NMR (400 MHz, CDCl$_3$) δ=6.59 (s, 1H), 4.13-4.19 (m, 6H), 3.82-3.89 (m, 6H), 3.61-3.71 (m, 25H), 3.39 (t, J=4.89 Hz, 2H), 2.43-2.48 (m, 2H), 1.47-1.52 (m, 2H).

1-Azido-3,6,9,12,15,18-hexaoxahenicosan-21-oic Acid (5)

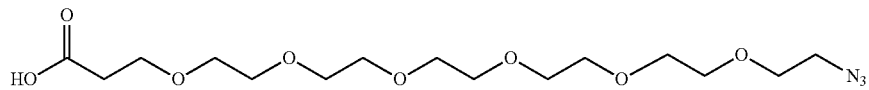

A solution of ethyl 1-azido-3,6,9,12,15,18-hexaoxahenicosan-21-oate (5 g, 12.27 mmol) in THF: H$_2$O (4:1, 40 mL) at 0° C. was charged with lithium hydroxide (1.47 g, 61.35 mmol) and stirred at room temperature for 2 h. The reaction mixture solvent was evaporated and the aqueous layer was washed with DCM. The separated aqueous layer was acidified with 2N HCl solution and extracted with 10% methanol in DCM. The combined organic layers were dried over anhydrous Na$_2$SO$_4$, filtered and concentrated in vacuo resulting in the crude compound which was purified by column chromatography on silica gel eluting with 1-10% methanol in DCM to afford 3.8 g, 80% yield, of the title compound as a colorless oil. $^1$H NMR (400 MHz, CDCl$_3$) δ=3.79 (t, J=5.87 Hz, 2H), 3.63-3.71 (m, 23H), 3.40 (t, J=4.89 Hz, 2H), 2.61 (t, J=5.87 Hz, 2H).

Ethyl 1-azido-3,6,9,12,15,18-hexaoxahenicosan-21-oate (4)

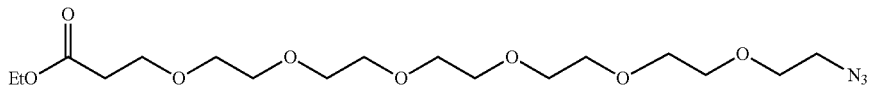 [SMILES: [N-]=[N+]=NCCOCCOCCOCCOCCOCCOCCC(=O)O]

A solution of 17-azido-3,6,9,12,15-pentaoxaheptadecan-1-ol (10 g, 32.57 mmol) in THF (100 mL) at 0° C. was charged with sodium hydride (1.94 g, 48.85 mmol) over a period of 30 min. Followed by addition of ethyl 3-bromopropanoate (5 mL, 39.08 mmol) at the same temperature and stirred for 2 h. The reaction mixture was quenched with ammonium chloride solution and extracted with ethyl acetate. The combined organic layers were dried over anhydrous $Na_2SO_4$, filtered and concentrated in vacuo resulting in the crude compound which was purified by silica gel column chromatography eluting with 1-3% methanol in DCM to afford 5.2 g, 40% yield, of the title compound as a colorless oil. 1H NMR (400 MHz, $CDCl_3$) δ=4.11-4.19 (m, 2H), 3.73-3.79 (m, 2H), 3.60-3.70 (m, 21H), 3.36-3.43 (m, 2H), 2.56-2.62 (m, 2H), 1.26 (t, J=7.09 Hz, 3H).

17-Azido-3,6,9,12,15-pentaoxaheptadecan-1-ol (3)

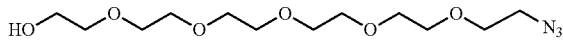

A solution of 17-hydroxy-3,6,9,12,15-pentaoxaheptadecyl 4-methylbenzenesulfonate (16 g, 36.69 mmol) in ethanol (200 mL) was charged with sodium azide (7.15 g, 110.1 mmol) and heated at 80° C. for 8 h. The reaction mixture was cooled to room temperature and the solvent was evaporated up to dryness. The residue obtained was stirred in ethyl acetate, filtered and the filtrate was concentrated in vacuo resulting in 11.6 g of the crude compound as yellow oil. The crude compound was used in the next step without further purification. $^1H$ NMR (400 MHz, $CDCl_3$) δ=3.59-3.77 (m, 23H), 3.37-3.41 (m, 2H).

17-Hydroxy-3,6,9,12,15-pentaoxaheptadecyl 4-methylbenzenesulfonate (2)

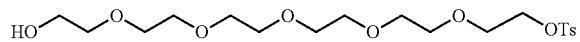 [SMILES: Cc1ccc(S(=O)(=O)OCCOCCOCCOCCOCCOCCO)cc1]

A solution of 3,6,9,12,15-pentaoxaheptadecane-1,17-diol (25 g, 88.59 mmol) in DCM (900 mL) at 0° C. was charged with silver oxide (30.5 g, 132.88 mmol), potassium iodide (2.94 g, 17.71 mmol) and tosyl chloride (18.51 g, 97.44 mmol) and stirred at 0° C. for 1 h. The reaction mixture was filtered, washed with DCM and the filtrate was concentrated in vacuo resulting in the crude compound which was purified by column chromatography on silica gel eluting with 1-3% methanol in DCM to afford 16 g, 41% yield of the title compound as a pale yellow oil. $^1H$ NMR (400 MHz, $CDCl_3$) δ=7.80 (d, J=7.83 Hz, 2H), 7.34 (d, J=7.83 Hz, 2H), 4.14-4.18 (m, 2H), 3.57-3.75 (m, 23H), 2.45 (s, 3H).

Example 73

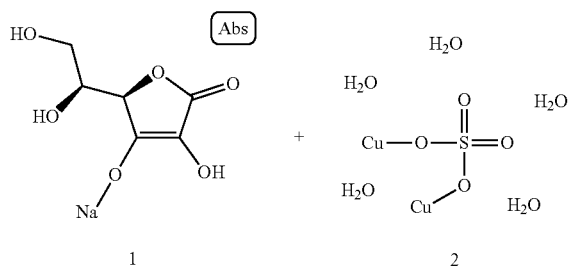

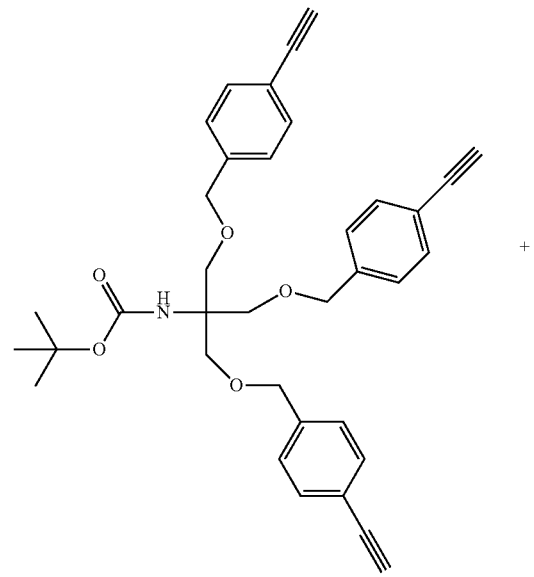

-continued
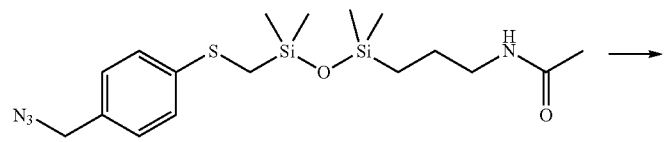
Example 43
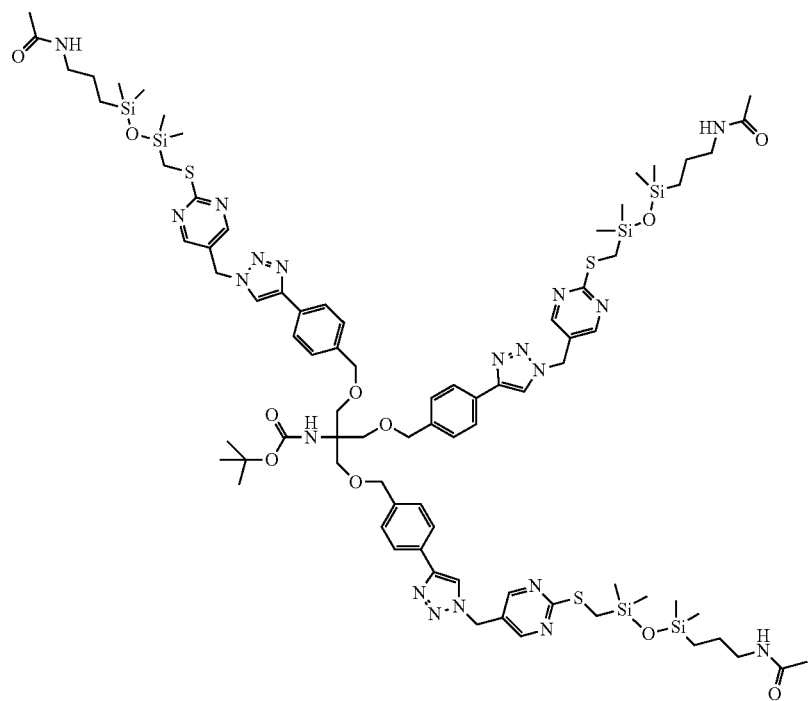
Example 73 tert-butyl(1,3-bis((4-(1-((2-(((3-(3-acetamidopropyl)-1,1,3,3-tetramethyldisiloxanyl) methyl)thio) pyrimidin-5-yl)methyl)-1H-1,2,3-triazol-4-yl)benzyl)oxy)-2-(((4-(1-((2-(((3-(3-acetamidopropyl)-1,1,3,3-tetramethyldisiloxanyl)methyl)thio)pyrimidin-5-yl)methyl)-1H-1,2,3-triazol-4-yl)benzyl)oxy)methyl) propan-2-yl)carbamate [Example 73]

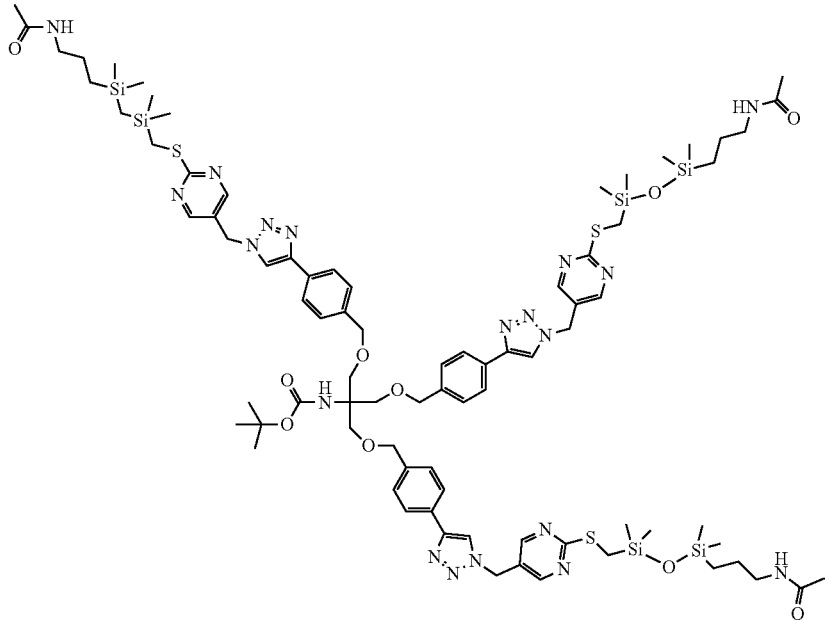 [SMILES: CC(=O)NCCC[Si](C)(C)C[Si](C)(C)CSc1ncc(Cn2cc(-c3ccc(COCC(COCc4ccc(-c5cn(Cc6cnc(SC[Si](C)(C)O[Si](C)(C)CCCNC(C)=O)nc6)nn5)cc4)(COCc4ccc(-c5cn(Cc6cnc(SC[Si](C)(C)O[Si](C)(C)CCCNC(C)=O)nc6)nn5)cc4)NC(=O)OC(C)(C)C)cc3)nn2)cn1]

A solution of tert-butyl(1,3-bis((4-ethynylbenzyl)oxy)-2-(((4-ethynylbenzyl) oxy)methyl) propan-2-yl)carbamate (10.00 mg, 0.018 mmol) and N-(3-(3-(((4-(azidomethyl) phenyl)thio) methyl)-1,1,3,3-tetramethyldisiloxanyl)propyl) acetamide (22.59 mg, 0.055 mmol) were dissolved in DMF (40.0 µl). The reaction mixture was charged with a solution of sodium ascorbate (1.757 mg, 8.87 µmol) in Water (80 µl) followed by the addition of a solution of copper sulfate pentahydrate (2.78 mg, 8.87 µmol) in Water (80 µl). (NOTE: the reaction mixture formed turned brown upon addition of copper sulfate then turned into a yellow gel precipitate). After 5 min the reaction mixture was checked by LCMS and found to have a mass consistent with desired product. The reaction mixture was partitioned between DCM and water and separated. The aqueous was extracted with DCM (3×) and the combined organic fractions were checked by LCMS and this showed a peak consistent with product mass and a peak consistent with sm azide. The crude1 was purified by ISCO chromatography on silica gel [4 g cartridge, eluting with 0% of (10% NH$_4$OH in MeOH) in DCM to 8% of (10% NH$_4$OH in MeOH) in DCM] resulting in 12 mg, 37.5% yield of the title compound as a clear colorless oil. $^1$H NMR (CHLOROFORM-d, 400 MHz): δ (ppm) 8.59 (s, 6H), 7.90 (s, 3H), 7.65-7.70 (m, 6H), 7.26-7.27 (m, 3H), 7.23-7.26 (m, 3H), 5.64-5.72 (m, 2H), 5.55 (s, 6H), 4.49-4.53 (m, 6H), 3.75-3.81 (m, 6H), 3.16-3.23 (m, 6H), 2.40 (s, 6H), 1.96 (s, 9H), 1.58 (s, 17H), 1.46-1.56 (m, 6H), 1.43 (s, 9H), 0.47-0.57 (m, 5H), 0.21 (s, 18H), 0.08 (s, 18H), MS (ES$^+$): 1802.66 m/z=[M+H]$^+$; LCMS: t$_R$=2.55 min [polar_3 min_0_1500].

Compound 3

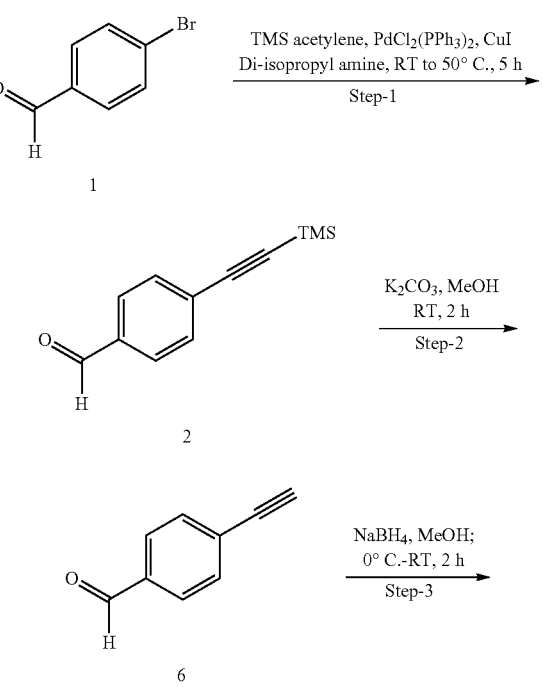

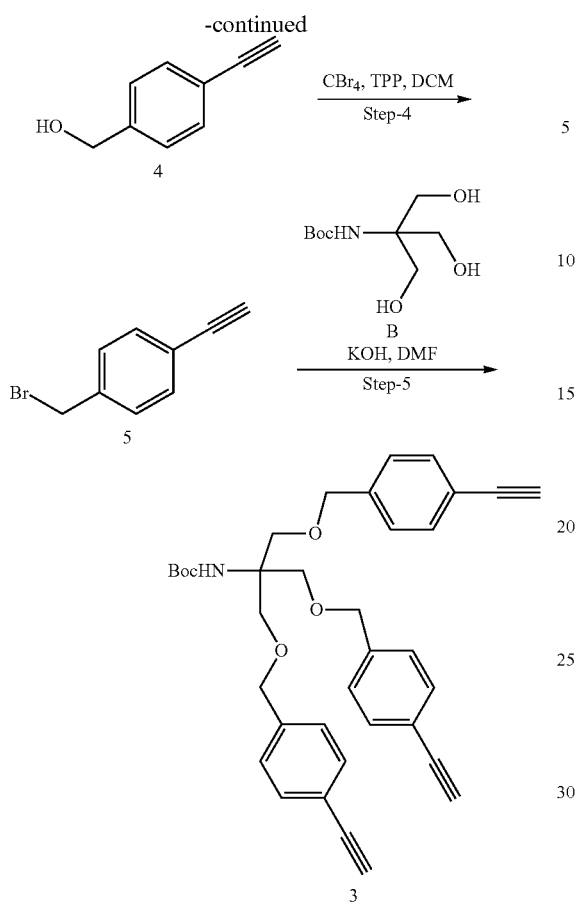

tert-butyl(1,3-bis((4-ethynylbenzyl)oxy)-2-(((4-ethynylbenzyl)oxy)methyl)propan-2-yl)carbamate (3)

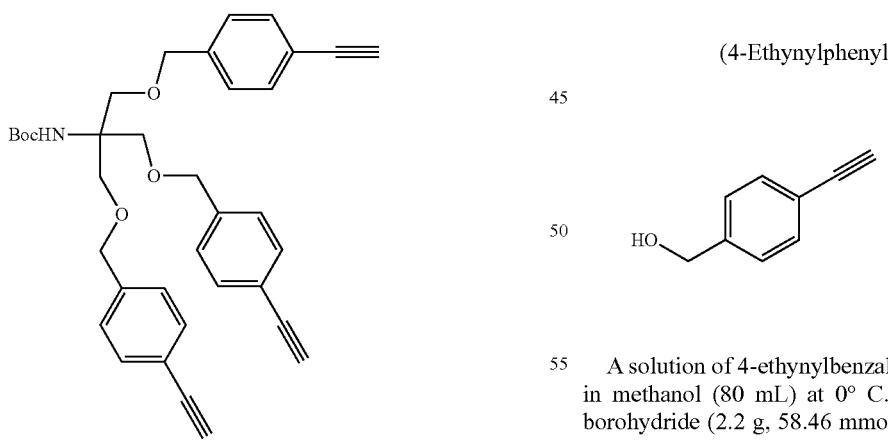

A solution of tert-butyl(1,3-dihydroxy-2-(hydroxymethyl)propan-2-yl)carbamate (800 mg, 3.619 mmol) in DMF (5 mL) at 0° C. was charged with 1-(bromomethyl)-4-ethynylbenzene 5 (4.21 g, 21.71 mmol) and powdered potassium hydroxide (1.18 g, 21.71 mmol) portionwise over a period of 30 min. The reaction mixture was allowed to attain room temperature and stirred for 14 h. The reaction mixture was diluted with water was extracted with DCM. The combined organic layers were dried over anhydrous $Na_2SO_4$, filtered and concentrated in vacuo resulting in the crude compound which was purified by column chromatography on silica gel eluting with 0-5% methanol in DCM to afford 1.52 g, 75% yield, of the title compound as colorless oil. $^1$H NMR (400 MHz, $CDCl_3$) δ=7.44 (d, J=7.82 Hz, 6H), 7.21 (d, J=7.82 Hz, 6H), 4.96 (s, 1H), 4.47-4.50 (m, 6H), 3.76 (s, 6H), 3.07 (s, 3H), 1.41 (s, 9H); MS (ES$^+$): m/z=564.55 [M+H]$^+$; LCMS: $t_R$=3.94 min.

1-(Bromomethyl)-4-ethynylbenzene (5)

A solution of triphenyl phosphine (11.8 g, 45.45 mmol) in DCM (100 mL) at 0° C. was charged with a solution of (4-ethynylphenyl)methanol (3 g, 22.72 mmol), carbon tetrabromide (15 g, 45.45 mmol) and 2,6 lutidine (13.2 mL, 113.5 mmol) in DCM (mL). The reaction mixture allowed to attain room temperature and stirred for 16 h. The reaction mixture was concentrated in vacuo, diluted with diethyl ether and stirred for 15 min. The solid precipitated out was filtered and the filtrate was washed with 2N HCl solution and water. The separated organic layers were dried over anhydrous $Na_2SO_4$, filtered and concentrated in vacuo resulting in the crude compound which was purified by column chromatography on combiflash eluting with 0-5% ethyl acetate in n-hexane to afford 3 g (70% yield) of the title compound as yellow oil. $^1$H NMR (400 MHz, $CDCl_3$) δ=7.46 (d, J=8.31 Hz, 2H), 7.35 (d, J=7.83 Hz, 2H), 4.47 (s, 2H), 3.10 (s, 1H).

(4-Ethynylphenyl)methanol (4)

A solution of 4-ethynylbenzaldehyde (3.8 g, 29.23 mmol) in methanol (80 mL) at 0° C. was charged with sodium borohydride (2.2 g, 58.46 mmol) portionwise. The reaction mixture allowed to attain room temperature and stirred for 2 h. The reaction mixture was concentrated in vacuo, quenched with saturated ammonium chloride solution and extracted with ethyl acetate The combined organic layers were dried over anhydrous $Na_2SO_4$, filtered and concentrated in vacuo to afford 3.47 g, 90% yield, of the title compound as light yellow oil.

$^1$H NMR (400 MHz, $CDCl_3$) δ=7.49 (d, J=7.83 Hz, 2H), 7.33 (d, J=7.82 Hz, 2H), 4.71 (s, 2H), 3.07 (s, 1H).

4-Ethynylbenzaldehyde (6)

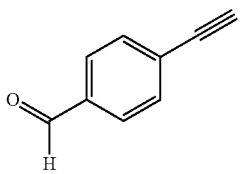

A solution of 4-(((trimethylsilyl)ethynyl)benzaldehyde (7.5 g, 37.12 mmol) in methanol (100 mL) was charged with potassium carbonate (512 mg, 3.712 mmol) and stirred at room temperature for 1 h. The reaction mixture was concentrated in vacuo, diluted with ethyl acetate and separated organic layer was washed with water. The separated organic layers were dried over anhydrous $Na_2SO_4$, filtered and concentrated in vacuo resulting in the crude compound which was purified by column chromatography on silica gel eluting with 0-20% ethyl acetate in n-hexane to afford 1.2 g, 81% yield, of the title compound as light yellow solid. $^1$H NMR (400 MHz, CDCl$_3$) δ=10.02 (s, 1H), 7.85 (d, J=7.83 Hz, 2H), 7.64 (d, J=8.31 Hz, 2H), 3.30 (s, 1H).

4-((Trimethylsilyl)ethynyl)benzaldehyde (2)

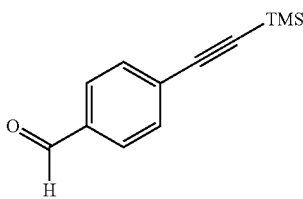 [SMILES: C[Si](C)(C)C#Cc1ccc(C=O)cc1]

A solution of 4-bromobenzaldehyde (10 g, 54.64 mmol) in diisopropyl amine (500 mL) was charged with bis(triphenylphosphine)palladium(II) dichloride (380 mg, 0.546 mmol) and copper iodide (205 mg, 1.09 mmol) and degassed for 20 min. The reaction mixture was cooled to 0° C. and followed by dropwise addition of trimethyl silyl acetylene (11.2 mL, 81.06 mmol) for a period of 30 min. The reaction mixture was allowed to attain room temperature and further refluxed for 3 h. The reaction mixture was cooled to room temperature and HBr salt formed was filtered. The filtrate was concentrated in vacuo, diluted with ethyl acetate and washed with 1N HCl solution followed by saturated sodium bicarbonate and water. The separated organic layers were dried over anhydrous $Na_2SO_4$, filtered and concentrated in vacuo resulting in the crude compound which was purified by column chromatography on silica gel eluting with 0-5% ethyl acetate in n-hexane to afford 7.7 g, 70% yield, of the title compound as an off white solid. $^1$H NMR (400 MHz, CDCl$_3$) δ=10.00 (s, 1H), 7.82 (d, J=8.31 Hz, 2H), 7.60 (d, J=7.83 Hz, 2H), 0.27 (s, 9H); MS (ES+): m/z=244.16 [M+H]$^+$; LCMS: $t_R$=3.58 min.

tert-Butyl(1,3-dihydroxy-2-(hydroxymethyl)propan-2-yl)carbamate (B)

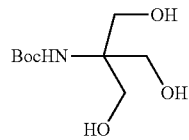

A solution of Boc anhydride (81.2 mL, 619.0 mmol) in tert-butanol (150 mL) was charged with a solution of 2-amino-2-(hydroxymethyl)propane-1,3-diol A (50 g, 413.00 mmol) in mixture of tert-butanol:methanol (1:1, 250 mL) and stirred at room temperature for 24 h. The reaction mixture was concentrated in vacuo, resulting in the crude residue as white powder which was purified by recrystallisation in ethanol to afford 45.6 g, 50% yield of the title compound as a white solid. $^1$H NMR (400 MHz, DMSO-d$_6$) δ=5.74 (s, 1H), 4.45-4.51 (m, 3H), 3.52 (d, J=5.87 Hz, 6H), 1.37 (s, 9H).

Example 74

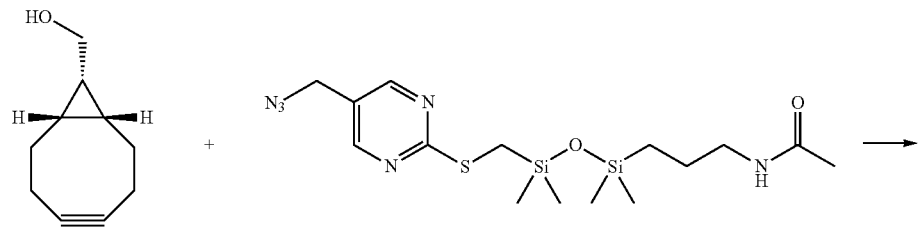

1        Example 43

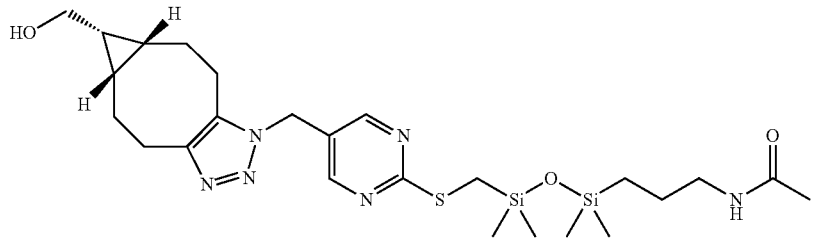

Example 74

A solution of N-(3-(3-(((5-(azidomethyl)pyrimidin-2-yl)thio)methyl)-1,1,3,3-tetra methyl disiloxanyl)propyl)acetamide (15.93 mg, 0.039 mmol) in 0.766 mL of a 3:1 mixture of acetonitrile/water was charged with (1R,8S,9s)-bicyclo[6.1.0]non-4-yn-9-ylmethanol (5.8 mg, 0.039 mmol) and stirred overnight at rt. The crude reaction mixture was concentrated in vacuo then purified by chromatography on silica gel, ISCO, 4 g gold cartridge [eluting with 100% DCM to 5% (10% 7N NH3 in MeOH) in DCM] resulting in 13.7 mg, 63% yield of the title compound as a thick clear colorless oil. $^1$H NMR (CHLOROFORM-d, 400 MHz): δ (ppm) 8.38 (s, 2H), 5.60 (br s, 1H), 5.41 (s, 2H), 3.61-3.82 (m, 2H), 3.18-3.24 (m, 2H), 3.09-3.17 (m, 1H), 2.80-2.97 (m, 2H), 2.63 (ddd, J=16.1, 10.5, 3.4 Hz, 1H), 2.39 (s, 2H), 2.11-2.30 (m, 2H), 1.97 (s, 3H), 1.46-1.60 (m, 4H), 1.41 (br s, 1H), 1.26 (s, 1H), 1.20 (dt, J=16.5, 8.4 Hz, 1H), 1.04 (dtd, J=10.8, 8.9, 5.1 Hz, 1H), 0.76-0.97 (m, 2H), 0.49-0.58 (m, 2H), 0.20 (s, 6H), 0.08 (s, 6H), MS (ES+): m/z=563.45 [M+H]$^+$; LCMS: t$_R$=1.93 min [polar_3 min_1500].

Example 75

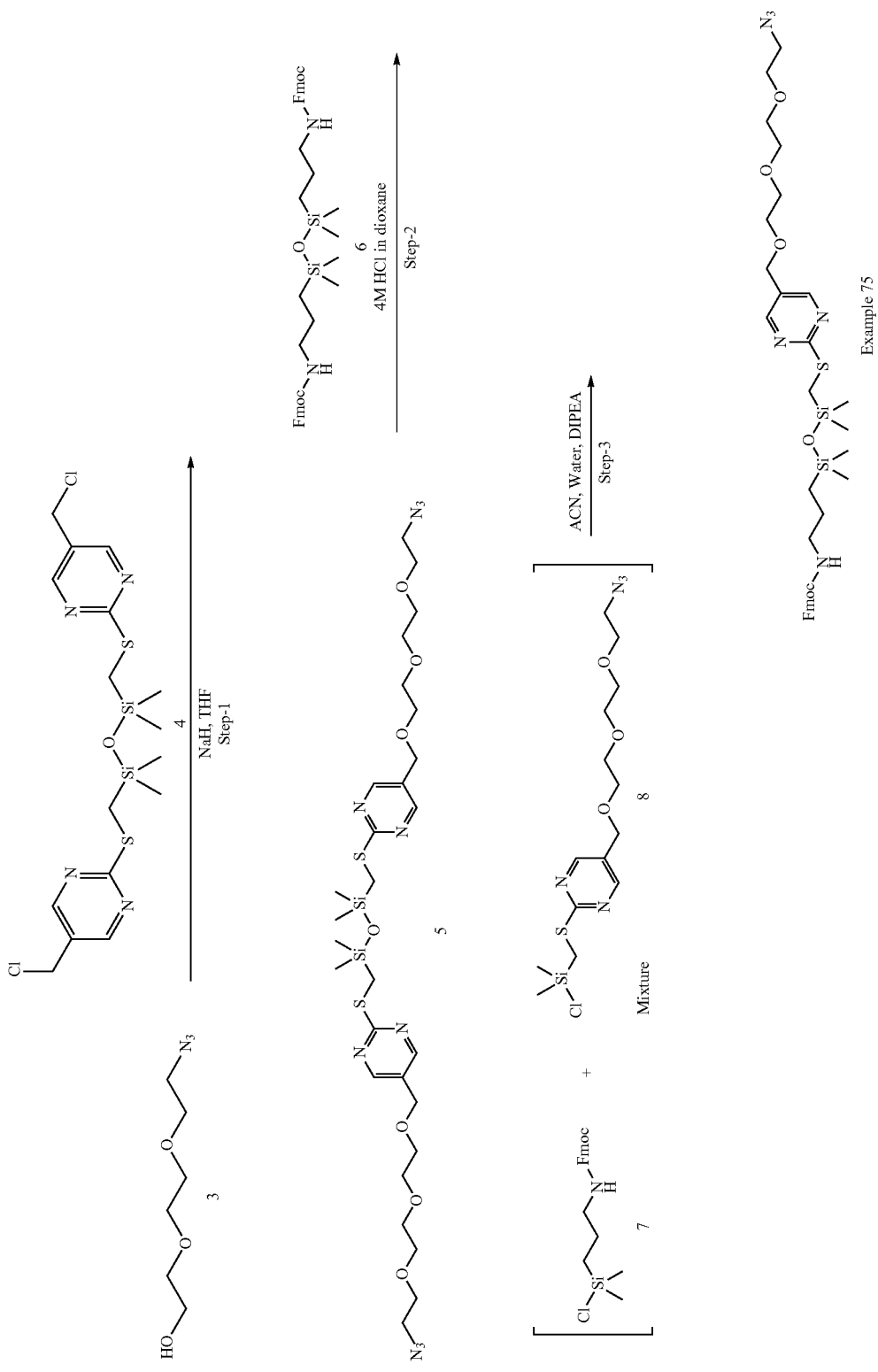

(9H-fluoren-9-yl)methyl(3-(3-(((5-((2-(2-(2-azido-ethoxy)ethoxy) ethoxy) methyl)pyrimidin-2-yl)thio)methyl)-1,1,3,3-tetramethyldisiloxanyl)propyl)carbamate [Example 75]

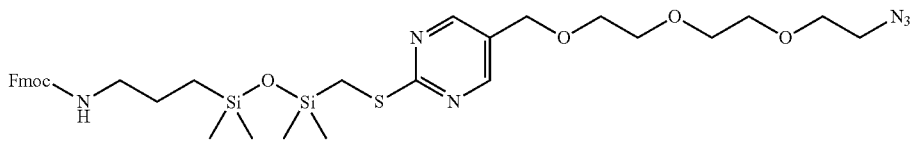

A solution of mixture of 1,3-bis(((5-((2-(2-(2-azidoethoxy)ethoxy)ethoxy)methyl)pyrimidin-2-yl)thio)methyl)-1,1,3,3-tetramethyldisiloxane (4.89 g, 6.459 mmol) and bis((9H-fluoren-9-yl)methyl) ((1,1,3,3-tetramethyldisiloxane-1,3-diyl)bis(propane-3,1-diyl))dicarbamate (4.30 g, 6.459 mmol) in 4M HCl in dioxane (50 mL) was stirred at room temperature for 1 h. The reaction mixture was concentrated in vacuo resulting in the crude intermediate 7 and 8. The mixture of intermediate 7 and 8 was dissolved in acetonitrile (150 mL) and followed by addition of water (0.114 mL, 6.459 mmol), DIPEA (3.3 mL, 19.37 mmol) and stirred at room temperature for 1 h. The reaction mixture was concentrated in vacuo resulting in the crude compound which was purified by combiflash column chromatography on silica gel eluting with 70-100% ethyl acetate in n-hexane to afford 3.69 g, 82% yield, of the title compound as a colorless oil. $^1$H NMR (400 MHz, DMSO-$d_6$) δ=8.56 (s, 2H), 7.88 (d, J=7.34 Hz, 2H), 7.67 (d, J=7.34 Hz, 2H), 7.36-7.43 (m, 2H), 7.31 (t, J=7.34 Hz, 2H), 7.27 (br. s, 1H), 4.45 (s, 2H), 4.27 (d, J=6.85 Hz, 2H), 4.20 (d, J=6.36 Hz, 1H), 3.51-3.60 (m, 10H), 3.34-3.39 (m, 2H), 2.90-2.98 (m, 2H), 2.38 (s, 2H), 1.34-1.45 (m, 2H), 0.43-0.50 (m, 2H), 0.15 (s, 6H), 0.05 (s, 6H); MS (ES$^+$): m/z=725.51 [M+H]$^+$; LCMS: $t_R$=3.97 min.

1,3-Bis(((5-((2-(2-(2-azidoethoxy)ethoxy)ethoxy)methyl)pyrimidin-2-yl)thio)methyl)-1,1,3,3-tetramethyldisiloxane (5)

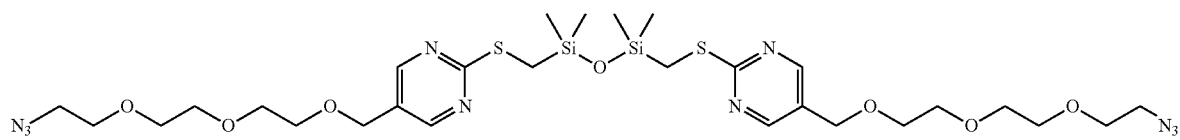 [SMILES: C[Si](C)(CSc1ncc(COCCOCCOCCN=[N+]=[N-])cn1)O[Si](C)(C)CSc1ncc(COCCOCCOCCN=[N+]=[N-])cn1]

A solution of 2-(2-(2-azidoethoxy)ethoxy)ethan-1-ol (2.3 g, 13.14 mmol) in THF (500 mL) at 0° C. was charged with sodium hydride (1.62 g, 39.42 mmol) and stirred at the same temperature for 30 min. The reaction was then charged with 1,3-bis(((5-(chloromethyl)pyrimidin-2-yl)thio)methyl)-1,1,3,3-tetramethyldisiloxane (6.5 g, 13.14 mmol) and stirred at 0° C. 1 h. The reaction mixture was concentrated in vacuo resulting in the crude compound which was purified by combiflash column chromatography on silica gel eluting with 0-5% methanol in DCM to afford 5.94 g, 60% yield, of the title compound as a colorless oil. $^1$H NMR (400 MHz, DMSO-$d_6$) δ=8.57 (s, 4H), 4.57 (t, J=5.62 Hz, 2H), 4.47 (s, 4H), 3.46-3.63 (m, 22H), 2.41 (s, 4H), 0.18 (s, 12H); MS (ES$^+$): m/z=380.00 [M/2+H]$^+$; LCMS: $t_R$=3.66 min.

Example 76
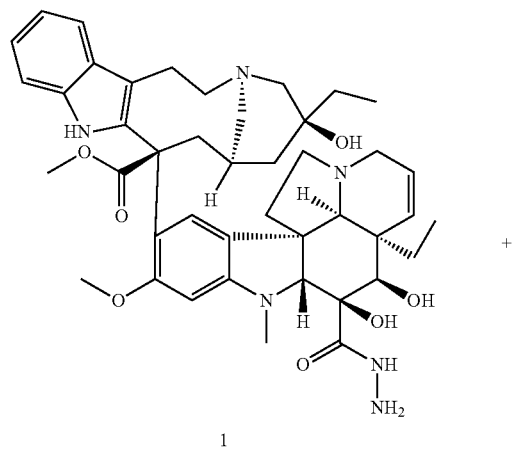
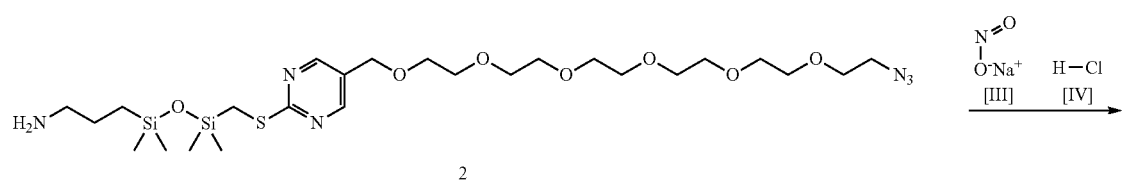
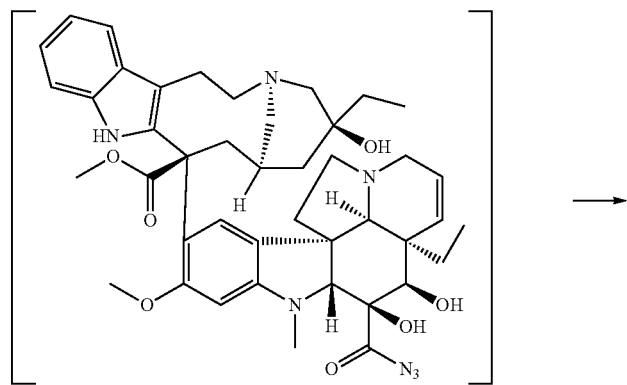
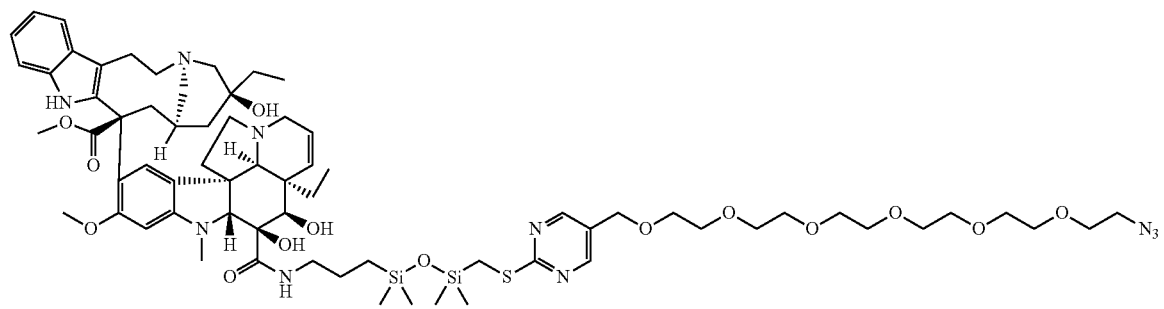
Example 76

Methyl(3R,5S,7R,9S)-9-03aR,3a1R,4R,5S,5aR,10bR)-5-((3-(3-(((5-(19-azido-2,5,8,11,14,17-hexaoxanonadecyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-1,4,5,6,7,8,9,10-octahydro-2H-3,7-methano[1]azacycloundecino[5,4-b]indole-9-carboxylate [Example 76]

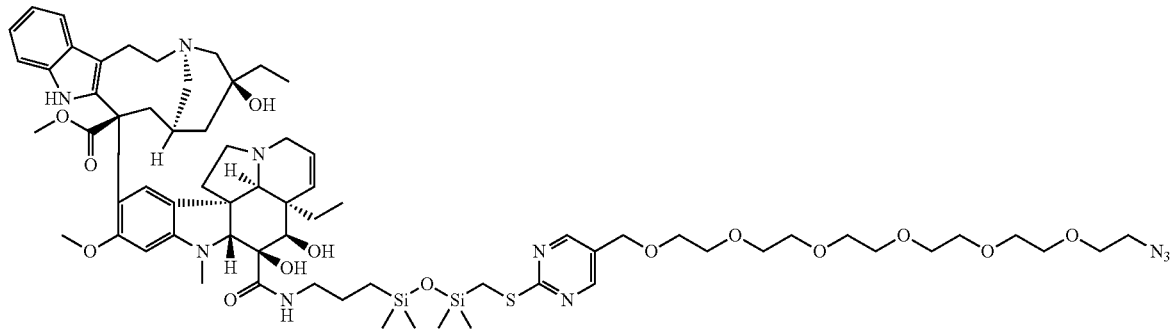

A solution of (3R,5S,7R,9S)-methyl 5-ethyl-9-((3aR,3a1R,4R,5S,5aR,10bR)-3a-ethyl-5-(hydrazinecarbonyl)-4,5-dihydroxy-8-methoxy-6-methyl-3a,3a1,4,5,5a,6,11,12-octahydro-1H-indolizino[8,1-cd]carbazol-9-yl)-5-hydroxy-2,4,5,6,7,8,9,10-octahydro-1H-3,7-methano[1]azacycloundecino[5,4-b]indole-9-carboxylate (200 mg, 0.260 mmol) in Acetonitrile (3.34 ml) and 1 M HCl in water (12.33 ml, 12.33 mmol) cooled to −10° C. then charged with solid sodium nitrite (41.3 mg, 0.598 mmol). After 10 min the yellowish brown solution was adjusted to pH ~8.00 drop-wise adding cold sat NaHCO₃ solution (~13.2 mL of NaHCO₃ added). The solution was extracted rapidly with DCM (5×10 mL) and the combined organic layers were washed with brine (1×20 mL) and dried over Na₂SO₄, filtered and concentrated to ~8.00 mL-10 mL cooled to 0° C. in and charged with a solution of 3-(3-(((5-(19-azido-2,5,8,11,14,17-hexaoxanonadecyl)pyrimidin-2-yl)thio)methyl)-1,1,3,3-tetramethyldisiloxanyl)propan-1-amine (165 mg, 0.260 mmol) in 8.0 mL of DCM and allowed to stir at 0° C. for 2 hr. The reaction mixture was concentrated in vacuo resulting in a light tan solid. The crude was purified by chromatography on silica gel [ISCO CombiFlash, 12 g Gold cartridge, eluting with 0% of (10% 7N NH3 in MeOH) to 8% (10% 7N NH3 in MeOH) in DCM resulting in 137 mg, 38.4% yield of the title compound as a light orange foam solid. ¹H NMR (CHLOROFORM-d, 400 MHz): δ (ppm) 9.54 (s, 1H), 8.50 (s, 2H), 8.04 (br s, 1H), 7.54 (d, J=8.1 Hz, 1H), 7.15-7.23 (m, 3H), 7.06-7.13 (m, 1H), 6.61 (s, 1H), 6.08 (s, 1H), 5.83 (s, 2H), 4.51 (s, 2H), 4.18 (d, J=4.8 Hz, 1H), 3.90-4.03 (m, 1H), 3.76-3.81 (m, 3H), 3.64-3.72 (m, 24H), 3.57-3.63 (m, 4H), 3.37-3.41 (m, 3H), 3.18-3.35 (m, 6H), 3.09-3.16 (m, 2H), 2.79-2.90 (m, 6H), 2.58-2.64 (m, 2H), 2.37-2.49 (m, 4H), 2.22-2.32 (m, 1H), 1.97-2.11 (m, 1H), 1.69-1.83 (m, 2H), 1.17-1.66 (m, 13H), 0.86-1.00 (m, 7H), 0.84 (br d, J=6.1 Hz, 1H), 0.53-0.62 (m, 2H), 0.17-0.24 (m, 6H), 0.10 (s, 6H), MS (ES+): m/z=1371.50, 1372.57 [M+H]⁺; LCMS: $t_R$=1.63 min [polar_3 min_1500].

Example 77

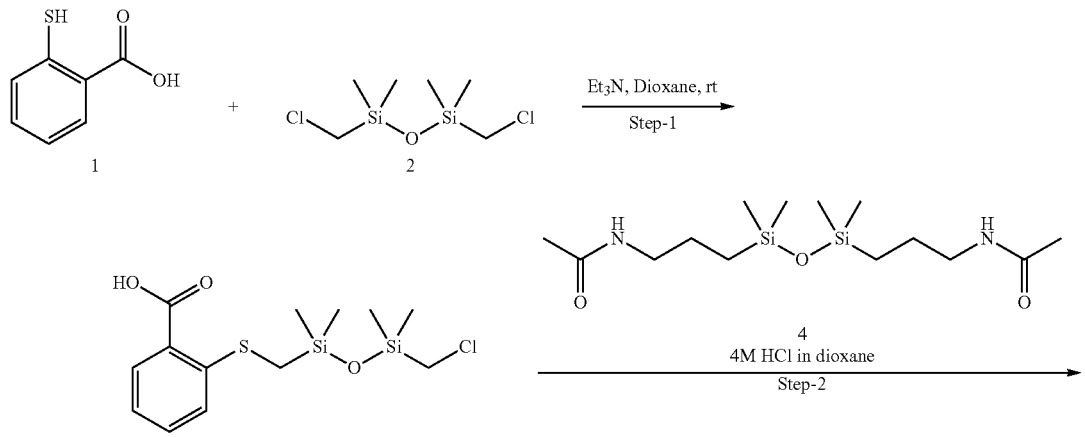

Example 92

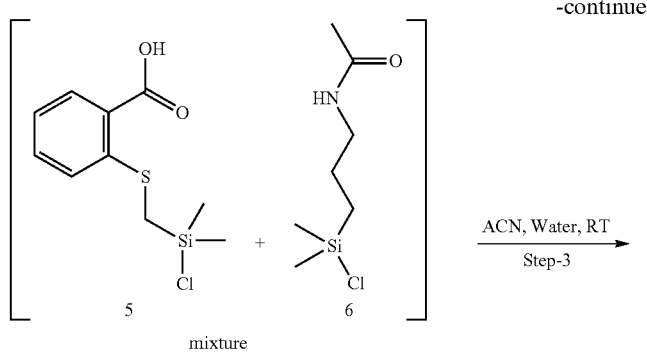

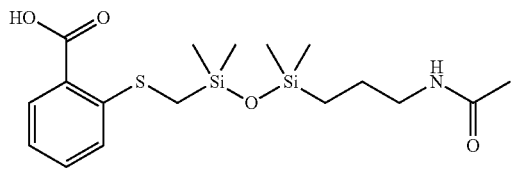

Example 78

2-(((3-(3-Acetamidopropyl)-1,1,3,3-tetramethyldisiloxanyl)methyl)thio)benzoic Acid [Example 78]

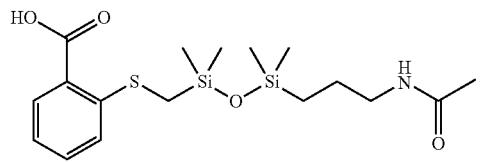 [SMILES: CC(=O)NCCC[Si](C)(C)O[Si](C)(C)CSc1ccccc1C(=O)O]

A solution of mixture of 2-(((3-(chloromethyl)-1,1,3,3-tetramethyldisiloxanyl)methyl)thio)benzoic acid (1 g, 2.873 mmol) and N,N'-((1,1,3,3-tetramethyldisiloxane-1,3-diyl) bis(propane-3,1-diyl)) diacetamide (954 mg, 2.873 mmol) in 4M HCl in dioxane (50 mL) was stirred at room temperature for 1 h. The reaction mixture was concentrated in vacuo resulting in the crude intermediates 5 and 6. The mixture of intermediate 5 and 6 was dissolved in acetonitrile (20 mL) and followed by addition of water (0.21 mL, 11.78 mmol) and DIPEA (3.1 mL, 17.24 mmol) and stirred at room temperature for 1 h. The reaction mixture was concentrated in vacuo resulting in the crude compound which was purified by Combi Flash chromatography on silica gel eluting with 0-10% methanol in DCM to afford 917 mg, 40% yield, of the title compound as a colorless oil. $^1$H NMR (400 MHz, DMSO-$d_6$) δ=12.86 (s, 1H), 7.83 (d, J=7.82 Hz, 1H), 7.74 (s, 1H), 7.43-7.53 (m, 2H), 7.13-7.18 (m, 1H), 2.92-2.99 (m, 2H), 2.10 (s, 2H), 1.74 (s, 3H), 1.33-1.42 (m, 2H), 0.45-0.51 (m, 2H), 0.18 (s, 6H), 0.06 (s, 6H), MS (ES$^+$): m/z=400.10 [M+H]$^+$; LCMS: $t_R$=3.19 min.

2-(((3-(Chloromethyl)-1,1,3,3-tetramethyldisiloxanyl)methyl)thio)benzoic Acid [Example 92]

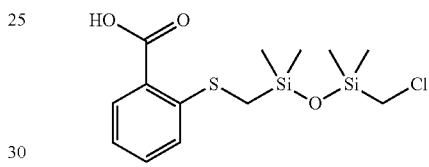

To a solution of 2-mercaptobenzoic acid (2 g, 12.98 mmol) in 1,4 dioxane (50 mL) was added triethyl amine (3.3 mL, 25.97 mmol) and 1,3-bis(chloromethyl)-1,1,3,3-tetramethyldisiloxane (5.9 g, 25.89 mmol) and stirred at room temperature for 4 h. The reaction mixture was concentrated in vacuo resulting in the crude compound which was purified by Combi Flash column chromatography on silica gel eluting with 0-10% methanol in DCM to afford 1.80 g, 41% yield, of the title compound as a white solid. $^1$H NMR (400 MHz, DMSO-$d_6$) δ=12.92 (s, 1H), 7.88 (d, J=7.83 Hz, 1H), 7.47-7.58 (m, 2H), 7.20 (t, J=7.34 Hz, 1H), 2.92 (s, 2H), 2.18 (s, 2H), 0.25 (s, 6H), 0.21 (s, 6H), MS (ES$^+$): m/z=224.95 monomer [M+H]$^+$; LCMS: $t_R$=3.74 min.

Example 79

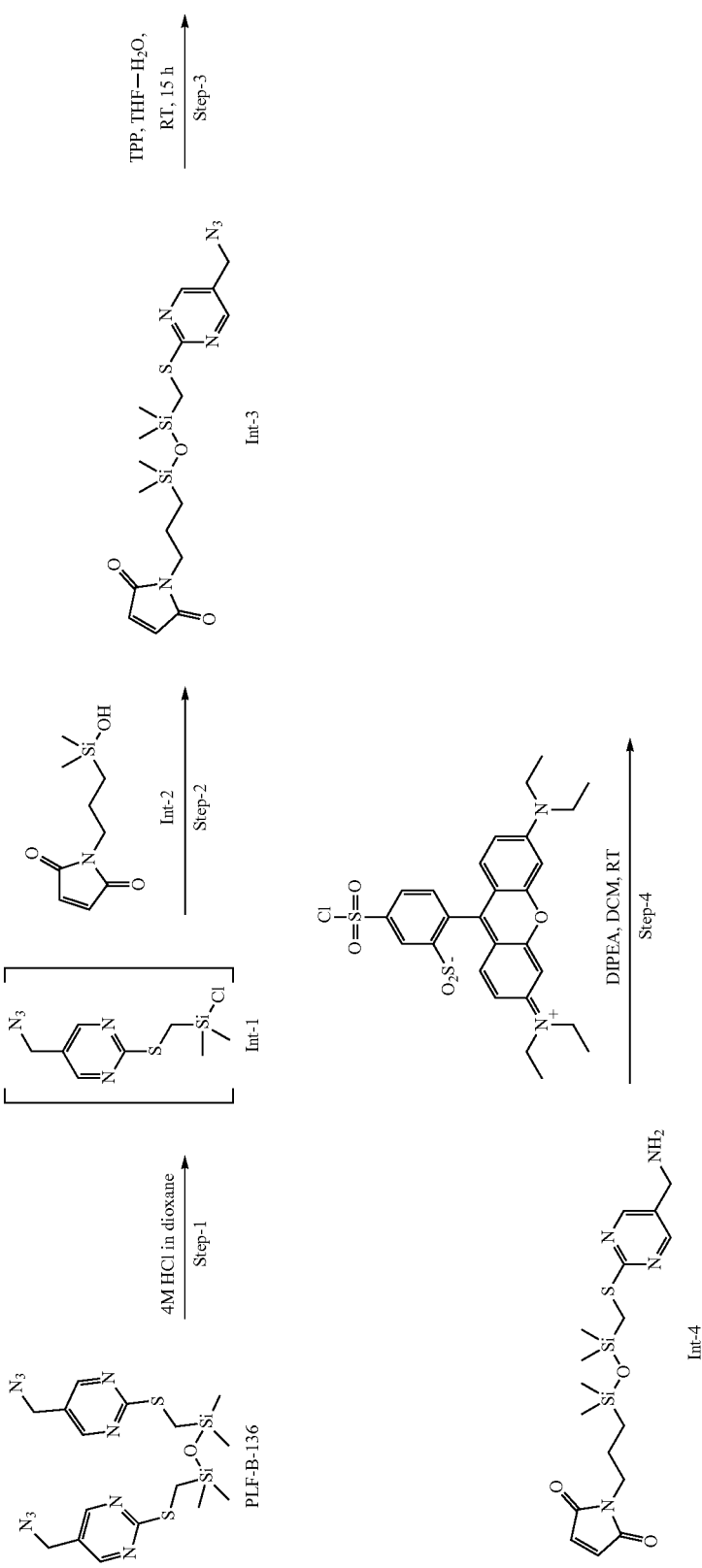

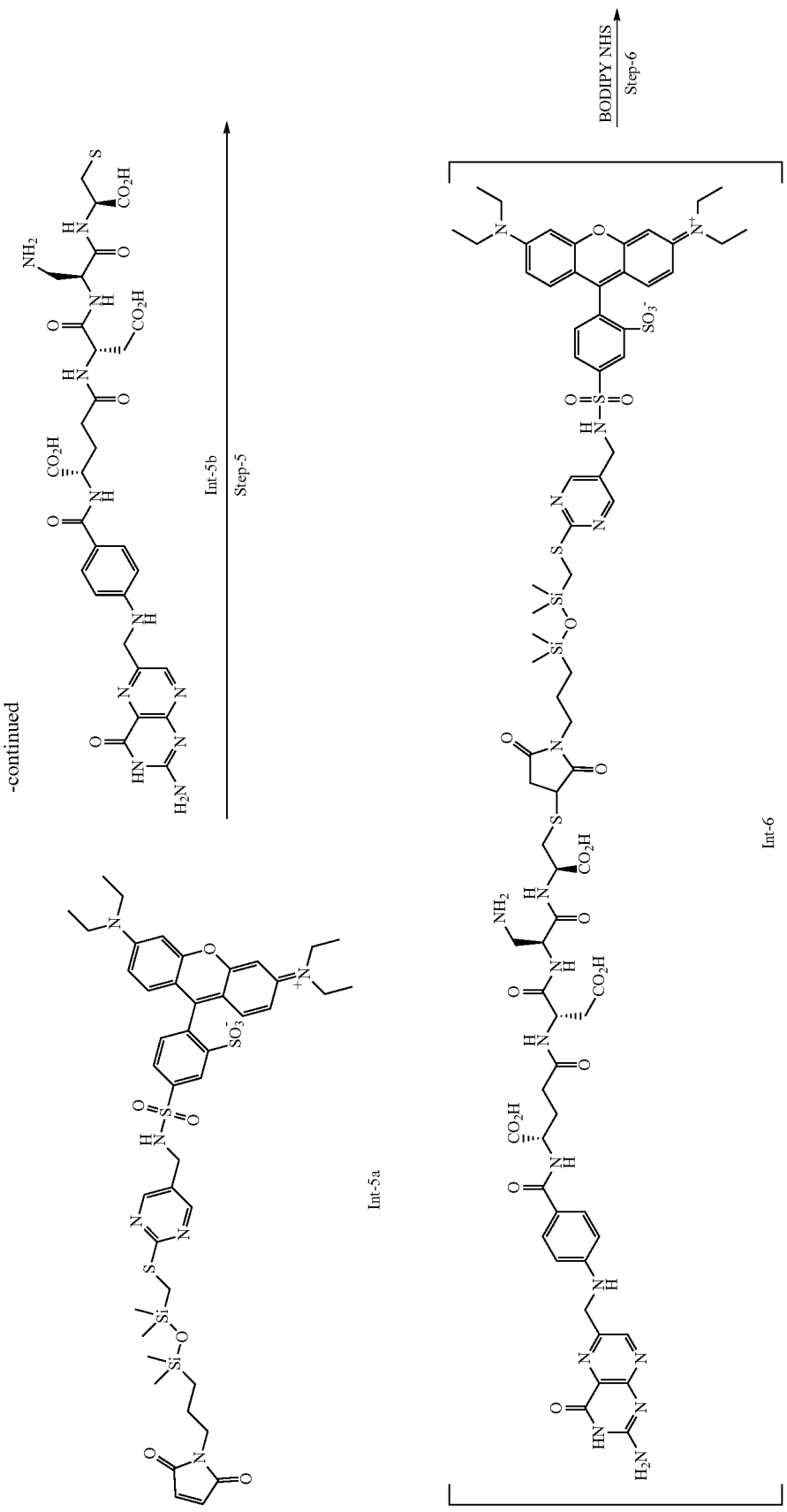

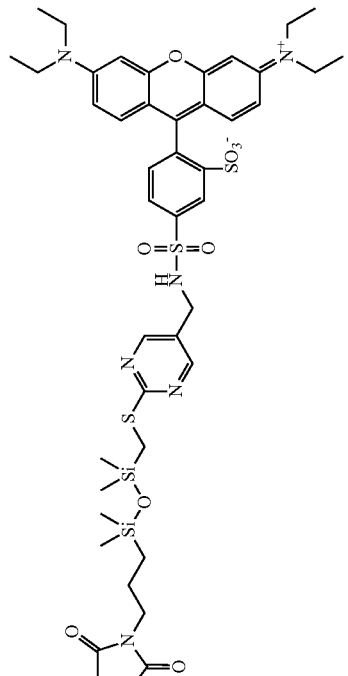
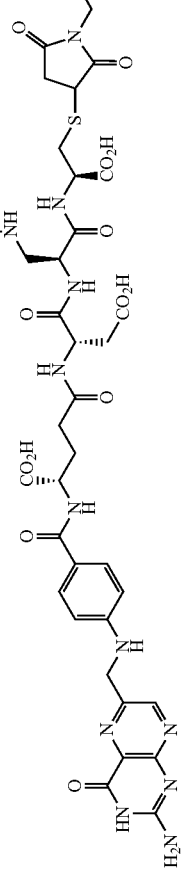
Example 79

5-(N-((2-(((3-(3-(3-(((3S,8S,11S,14R)-1-(4-(((2-amino-4-oxo-3,4-dihydropteridin-6-yl)methyl)amino)phenyl)-3,14-dicarboxy-8-(carboxymethyl)-11-((3-(5,5-difluoro-7,9-dimethyl-5H-4l4,5l4-dipyrrolo[1,2-c:2',1'-f][1,3,2]diazaborinin-3-yl)propanamido)methyl)-1,6,9,12-tetraoxo-2,7,10,13-tetraazapentadecan-15-yl)thio)-2,5-dioxopyrrolidin-1-yl)propyl)-1,1,3,3-tetramethyldisiloxanyl)methyl)thio)pyrimidin-5-yl)methyl)sulfamoyl)-2-(6-(diethylamino)-3-(diethyliminio)-3H-xanthen-9-yl)benzenesulfonate [Example 79]

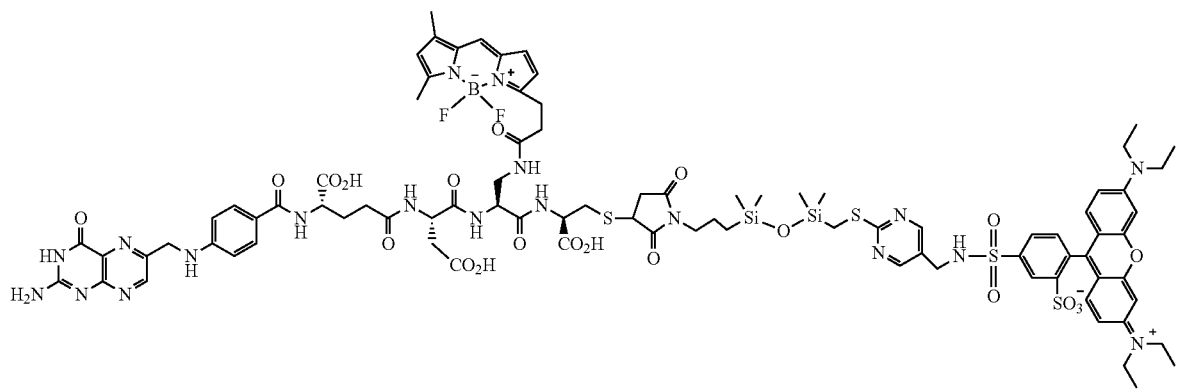

A solution of 5-(N-((2-(((3-(3-(3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)propyl)-1,1,3,3-tetramethyldisiloxanyl)methyl)thio)pyrimidin-5-yl)methyl)sulfamoyl)-2-(6-(diethylamino)-3-(diethyliminio)-3H-xanthen-9-yl)benzenesulfonate (17.62 mg, 10.30 mmol) in DMF was added Bodipy NHS ester stirred at room temperature for 1 h. The TLC showed consumption of starting material. The reaction mixture was concentrated in vacuo resulting in the crude intermediate and purified by triturating in acetonitrile to afford 35 mg (crude) of the title compound as violet solid. $^1$H NMR (400 MHz, DMSO-$d_6$) δ=12.98 (s, 1H), 12.45 (s, 1H), 12.28 (s, 1H), 11.38 (s, 1H), 8.62 (br. s, 1H), 8.55 (s, 1H), 8.44 (br. s, 2H), 8.26 (s, 2H), 8.20 (d, J=6.36 Hz, 1H), 8.16 (d, J=6.36 Hz, 1H), 8.01 (s, 2H), 7.85 (d, J=7.83 Hz, 2H), 7.60-7.68 (m, 4H), 7.40 (d, J=7.34 Hz, 1H), 6.85-7.06 (m, 8H), 6.61 (d, J=7.34 Hz, 2H), 6.28 (d, J=19.56 Hz, 2H), 4.45 (br. s, 4H), 4.25-4.38 (m, 4H), 4.13 (br. s, 2H), 3.98 (d, J=16.63 Hz, 2H), 3.55-3.70 (m, 8H), 3.02-3.07 (m, 2H), 2.84-2.89 (m, 2H), 2.65 (br. s, 3H), 2.32 (d, J=10.27 Hz, 4H), 2.22 (br. s, 6H), 1.82-2.11 (m, 8H), 1.42-1.46 (m, 2H), 1.12-1.27 (m, 12H), 0.10 (br. s, 6H), 0.03 (br. s, 6H); MS (ES$^+$): m/z=993.40 [M+H]$^+$; LCMS: $t_R$=3.07 min.

5-(N-((2-(((3-(3-(3-(((3S,8S,11S,14R)-1-(4-(((2-amino-4-oxo-3,4-dihydropteridin-6-yl)methyl)amino)phenyl)-11-(aminomethyl)-3,14-dicarboxy-8-(carboxymethyl)-1,6,9,12-tetraoxo-2,7,10,13-tetraazapentadecan-15-yl)thio)-2,5-dioxopyrrolidin-1-yl)propyl)-1,1,3,3-tetramethyldisiloxanyl)methyl)thio)pyrimidin-5-yl)methyl)sulfamoyl)-2-(6-(diethylamino)-3-(diethyliminio)-3H-xanthen-9-yl)benzenesulfonate (6)

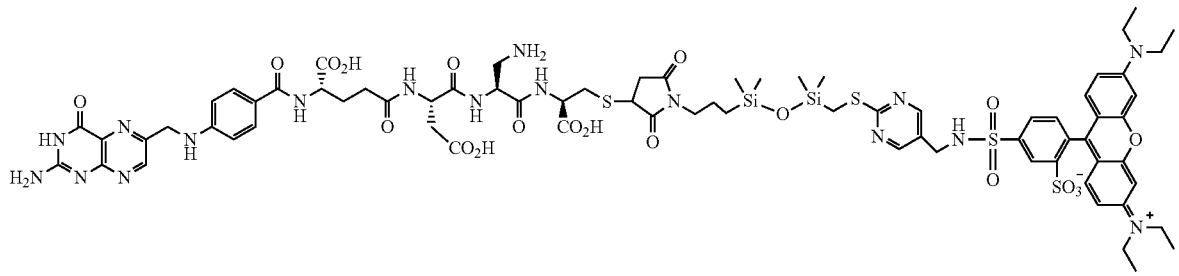

To a solution of 2-(6-(diethylamino)-3-(diethyliminio)-3H-xanthen-9-yl)-5-(N-((2-(((3-(3-(2,5-dioxo-2,5-dihydro-1H-pyrrol-1-yl)propyl)-1,1,3,3-tetramethyl disiloxanyl)methyl)thio) pyrimidin-5-yl)methyl)sulfamoyl)benzenesulfonate (10 mg, 0.01 mmol) and N5-((S)-1-(((S)-3-amino-1-(((R)-1-carboxy-2-(l1-sulfanyl)ethyl)amino)-1-oxopropan-2-yl)amino)-3-carboxy-1-oxopropan-2-yl)-N2-(4-(((2-amino-4-oxo-3,4-dihydropteridin-6-yl)methyl)amino)benzoyl)-L-glutamine (7.7 mg, 0.01 mmol) in DMF (1 mL) was added DIPEA (0.01 mL, 0.04 mmol) at room temperature and stirred for 1 h. The reaction was monitored by LCMS (showed 80% desired product 6). The reaction mixture was used as such in the next step without work-up. MS (ES$^+$): m/z=857.15 [M/2+H]$^+$; LCMS: $t_R$=2.47 min.

2-(6-(Diethylamino)-3-(diethyliminio)-3H-xanthen-9-yl)-5-(N-((2-(((3-(3-(2,5-dioxo-2,5-dihydro-1H-pyrrol-1-yl)propyl)-1,1,3,3-tetramethyldisiloxanyl)methyl)thio)pyrimidin-5-yl)methyl)sulfamoyl)benzenesulfonate (5a)

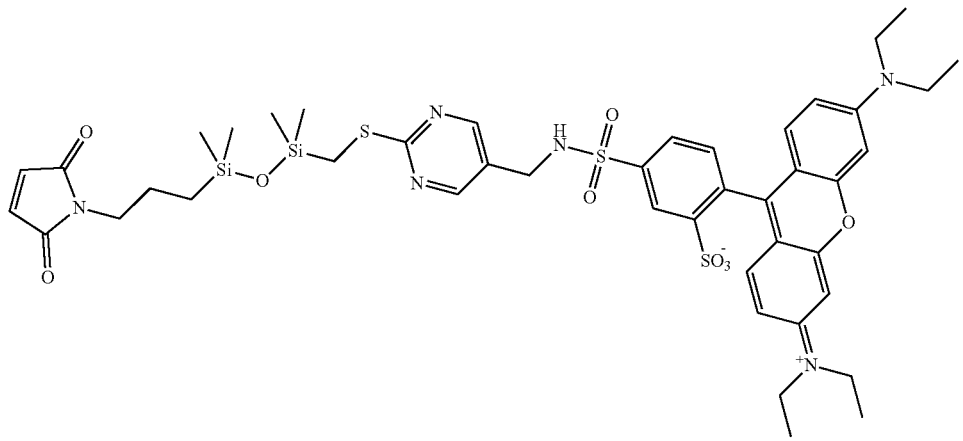

A solution of 1-(3-(3-(((5-(aminomethyl)pyrimidin-2-yl)thio)methyl)-1,1,3,3-tetramethyldisiloxanyl)propyl)-1H-pyrrole-2,5-dione (300 mg, 0.707 mmol) in THF (10 mL) was added DIPEA (0.24 mL, 1.41 mmol) and 5-(chlorosulfonyl)-2-(6-(diethylamino)-3-(diethyliminio)-3H-xanthen-9-yl)benzenesulfonate (408 mg, 0.707 mmol) at room temperature and stirred for 1 h. The completion of reaction was monitored by TLC. The reaction mixture was concentrated in vacuo resulting in the crude compound which was purified column chromatography on silica gel eluting with 0-10% methanol in DCM to afford 150 mg, 22% yield of the title compound as dark pink solid. MS (ES$^+$): m/z=965.20 [M+H]$^+$, 483.40 [M/2+H]$^+$; LCMS: $t_R$=3.47 min.

1-(3-(3-(((5-(aminomethyl)pyrimidin-2-yl)thio)methyl)-1,1,3,3-tetramethyl disiloxanyl) propyl)-1H-pyrrole-2,5-dione (4)

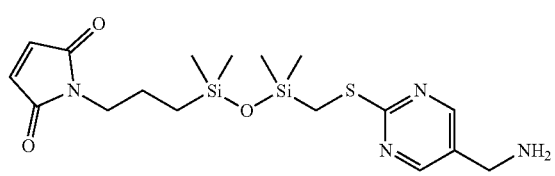 [SMILES: C[Si](C)(CCCN1C(=O)C=CC1=O)O[Si](C)(C)CSc1ncc(CN)cn1]

A solution of 1-(3-(3-(((5-(azidomethyl)pyrimidin-2-yl)thio)methyl)-1,1,3,3-tetramethyldisiloxanyl)propyl)-1H-pyrrole-2,5-dione (750 mg, 1.66 mmol) in THF: H$_2$O (2.25: 0.75 mL) was added TPP (1.3 g, 4.99 mmol) and stirred at room temperature for 10 h. The completion of reaction was monitored by TLC. The reaction mixture was concentrated in vacuo resulting in the crude compound which was purified by column chromatography on silica gel eluting with 0-10% methanol in DCM to afford 300 mg, 42% yield of the title compound as colorless oil. MS (ES$^+$): m/z=424.67 [M+H]$^+$ 1-(3-(3-(((5-(azidomethyl)pyrimidin-2-yl)thio)methyl)-1,1,3,3-tetramethyldisiloxanyl) propyl)-1H-pyrrole-2,5-dione (3)

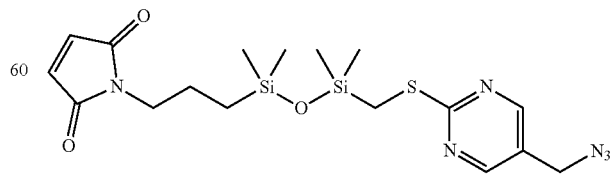

A solution of 1,3-bis(((5-(azidomethyl)pyrimidin-2-yl)thio)methyl)-1,1,3,3-tetramethyldisiloxane (1 g, 2.03 mmol)

in 4M HCl in dioxane (20 mL) was stirred at room temperature for 1 h. The reaction mixture was concentrated in vacuo resulting in the crude intermediate Int-1. The crude intermediate Int-1 (1.1 g, 4.02 mmol) was dissolved in acetonitrile (20 mL) and was added 1-(3-(hydroxydimethylsilyl)propyl)-1H-pyrrole-2,5-dione 2 (865 mg, 4.06 mmol) was added triethyl amine (1.09 mL, 8.05 mmol) and stirred at room temperature for 1 h. The reaction mixture was concentrated in vacuo resulting in the crude compound which was purified by column chromatography on silica gel eluting with 0-40% ethyl acetate in n-hexane to afford 750 mg, 82% yield of the title compound as a colorless oil. MS (ES$^+$): m/z=450.66 [M+H]$^+$.

Example 81

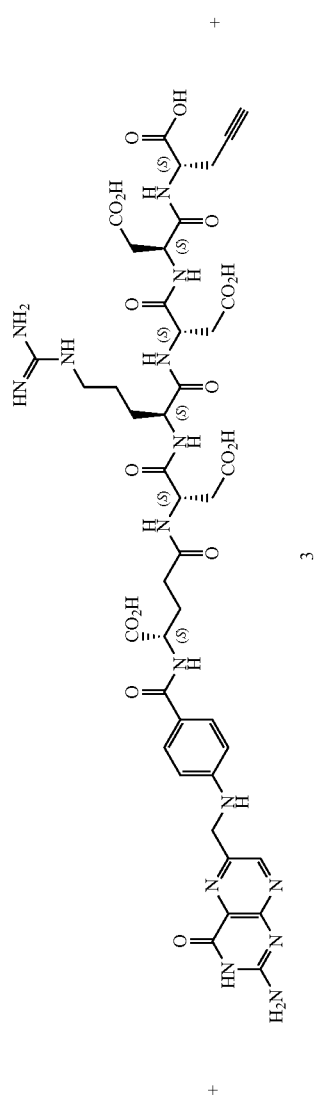
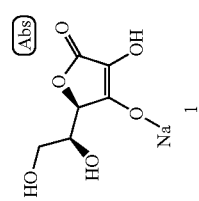
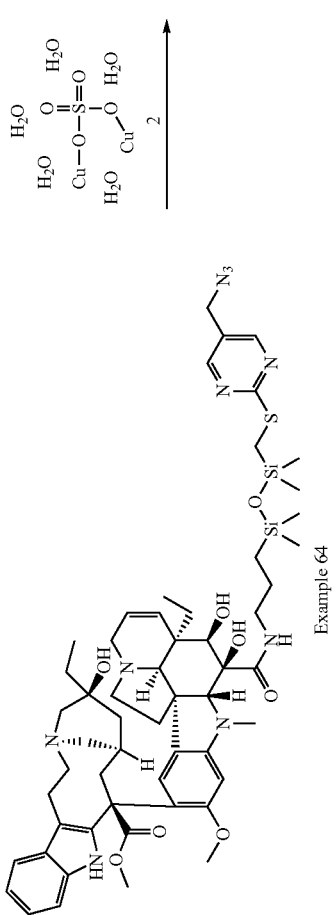

-continued
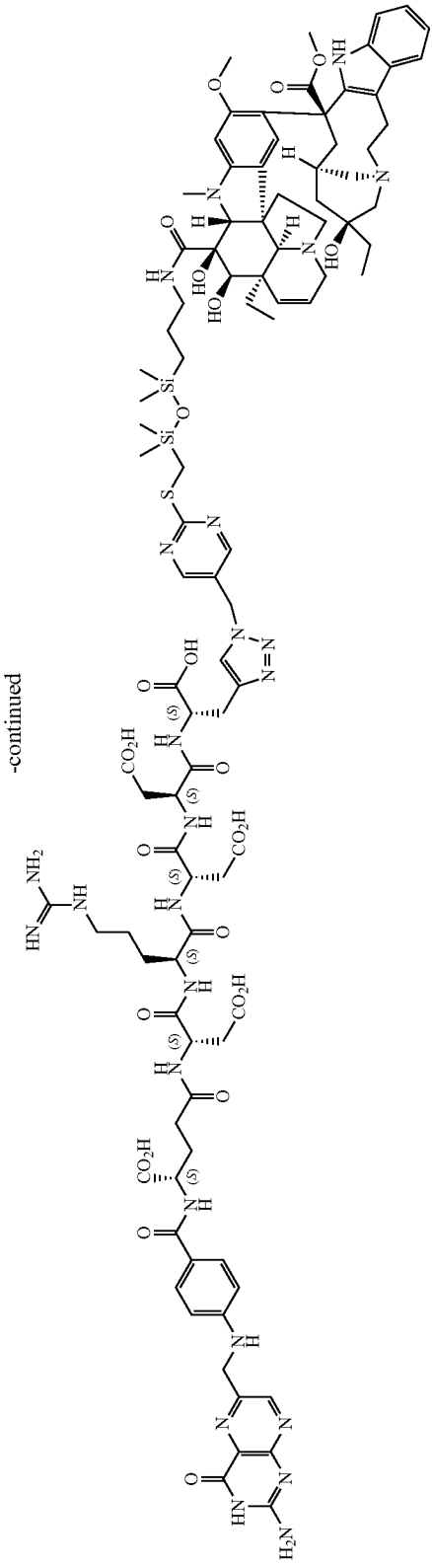
Example 81

(2S,5S,8S,11S,14S,19S)-19-(4-(((2-amino-4-oxo-3,4-dihydropteridin-6-yl)methyl)amino)benzamido)-5,8,14-tris(carboxymethyl)-2-((1-((2-(((3-(3-((3aR,3a1R,4R,5S,5aR,10bR)-3a-ethyl-9-03S,5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methyl)-1H-1,2,3-triazol-4-yl)methyl)-11-(3-guanidinopropyl)-4,7,10,13,16-pentaoxo-3,6,9,12,15-pentaazaicosane-1,20-dioic Acid [Example 81]

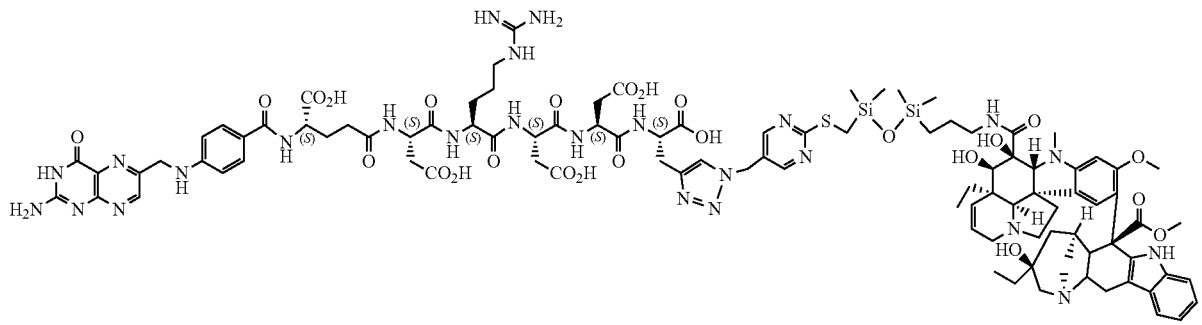

To an Eppendorf vial, DMSO (1 mL) was added to a mixture of (2S,5S,8S,11S,14S,19S)-19-(4-(((2-amino-4-oxo-3,4-dihydropteridin-6-yl)methyl)amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosane-1,20-dioic acid (17.0 mg, 0.016 mmol) and (3R,5S,7R,9S)-methyl-9-((3aR,3a1R,4R,5S,5aR,10bR)-5-((3-(3-(((5-(azidomethyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (18.14 mg, 0.016 mmol) at rt. The vial was purged with nitrogen gas, capped, and sonicated for 5 min. Then a freshly prepared solution of sodium ascorbate (100 mM in water 32.8 μL, 3.28 μmol) was added, followed by the addition of a freshly prepared solution of copper sulfate pentahydrate (100 mM in water, 32.8 μL, 3.28 μmol). The whole was purged with nitrogen gas, capped, sonicated for 5 min, and agitated on a shaker at rt. After 1 h, LCMS showed mainly product. The reaction was stopped. The whole was passed through an ISCO solid loading filter plug with an aid of a vacuum. For the residue, dissolved with ~0.5 mL of DMSO and passed through the same filter plug. The combined filtrate (2 mL) was purified by a reversed phase preparative HPLC [gradient 1] resulting in 10.3 mg, 29.3% yield of the title compound as a light yellow solid after lyophilizing. $^1$H NMR (400 MHz, DMSO-$d_6$) δ ppm 8.52-8.70 (m, 4H) 8.45 (br s, 1H) 8.25 (br d, J=6.32 Hz, 1H) 8.17 (br s, 1H) 7.98 (s, 1H) 7.72-7.90 (m, 2H) 7.63 (m, J=8.84 Hz, 2H) 7.54 (br s, 1H) 7.35-7.43 (m, 1H) 7.12-7.33 (m, 2H) 6.85-7.11 (m, 6H) 6.62 (m, J=8.84 Hz, 2H) 6.43 (s, 1H) 6.20 (s, 1H) 5.68 (br dd, J=10.36, 5.56 Hz, 1H) 5.48-5.61 (m, 3H) 4.53-4.79 (m, 2H) 4.42-4.53 (m, 3H) 4.25-4.41 (m, 3H) 4.16 (br d, J=5.31 Hz, 2H) 3.94-4.10 (m, 3H) 3.89 (br s, 1H) 3.74-3.85 (m, 3H) 3.62-3.74 (m, 5H) 3.51-3.62 (m, 7H) 3.03-3.33 (m, 36H) 2.93 (br s, 4H) 2.64-2.78 (m, 7H) 2.53-2.64 (m, 2H) 2.21-2.47 (m, 10H) 1.80-2.05 (m, 5H) 1.39-1.65 (m, 7H) 1.13-1.39 (m, 6H) 0.64-0.86 (m, 7H) 0.44-0.61 (m, 2H) 0.16 (s, 6H) −0.03-0.14 (m, 8H), MS (ES$^+$): m/z=[M+2]=1073.3, [M+3]/3=716.1, [M+4]/4=537.4; LCMS: $t_R$=1.74 min [polar_3 min_0_1500].

(2S,5S,8S,11S,14S,19S)-19-(4-(((2-amino-4-oxo-3,4-dihydropteridin-6-yl)methyl) amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosanedioic Acid (3)

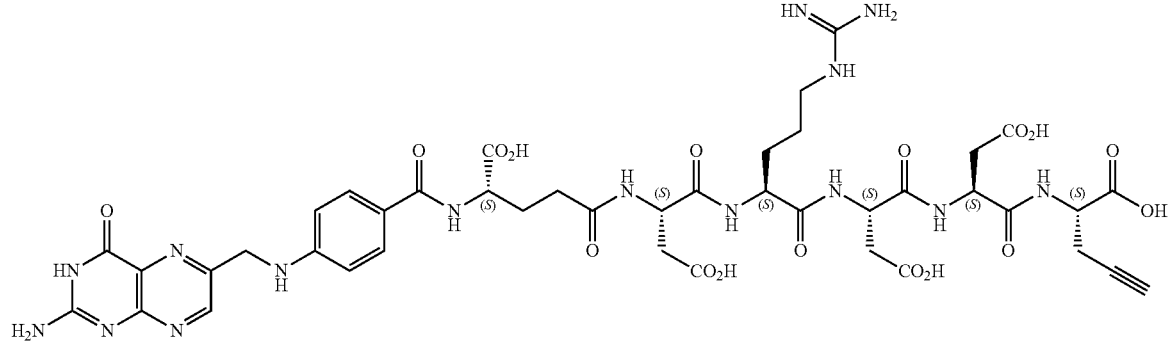

The title compound was prepared by a similar solid phase synthetic route using L-propargyl lysine as described in these publications: (1) Vlahov, Iontcho R., et al. "Design and regioselective synthesis of a new generation of targeted chemotherapeutics. Part 1: EC145, a folic acid conjugate of desacetylvinblastine monohydrazide." *Bioorganic & medicinal chemistry letters* 16.19 (2006): 5093-5096. (2) Vlahov, Iontcho R., et al. "Design and regioselective synthesis of a new generation of targeted chemotherapeutics. Part II: Folic acid conjugates of tubulysins and their hydrazides:" *Bioorganic & medicinal chemistry letters* 18.16 (2008): 4558-4561, $^1$H NMR (400 MHz, DMSO-d$_6$) δ ppm 8.65 (s, 1H) 8.25 (br d, J=7.33 Hz, 1H) 8.04-8.18 (m, 4H) 7.95 (d, J=7.58 Hz, 1H) 7.82 (br d, J=7.83 Hz, 1H) 7.67 (d, J=8.84 Hz, 2H) 7.35 (br s, 1H) 6.96 (br s, 3H) 6.65 (d, J=8.84 Hz, 3H) 4.45-4.66 (m, 6H) 4.15-4.36 (m, 4H) 3.04 (br d, J=6.57 Hz, 4H) 2.83-2.90 (m, 1H) 2.65-2.80 (m, 4H) 2.54-2.64 (m, 4H) 2.31 (br t, J=7.96 Hz, 3H) 1.80-2.08 (m, 3H) 1.63-1.78 (m, 2H) 1.38-1.59 (m, 4H). $^{19}$F NMR (400 MHz, DMSO-d$_6$) δ ppm −73.74. MS (ES$^+$): m/z=1038.3 [M+H]$^+$, 520.0 [M+2H]$^+$/2; LCMS: t$_R$=1.19 min [polar_3 min_1500].

Example 83

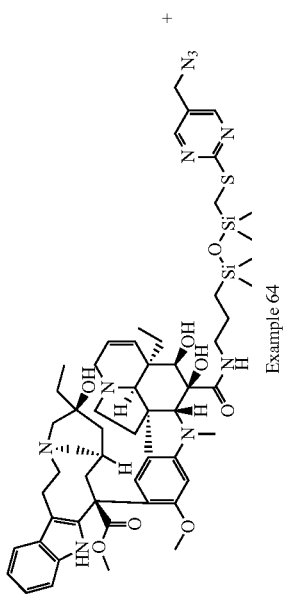
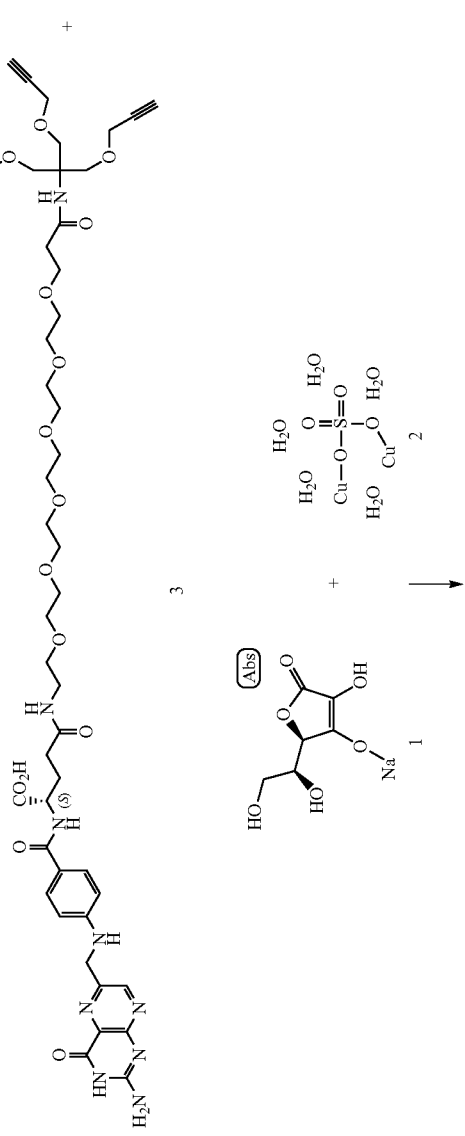

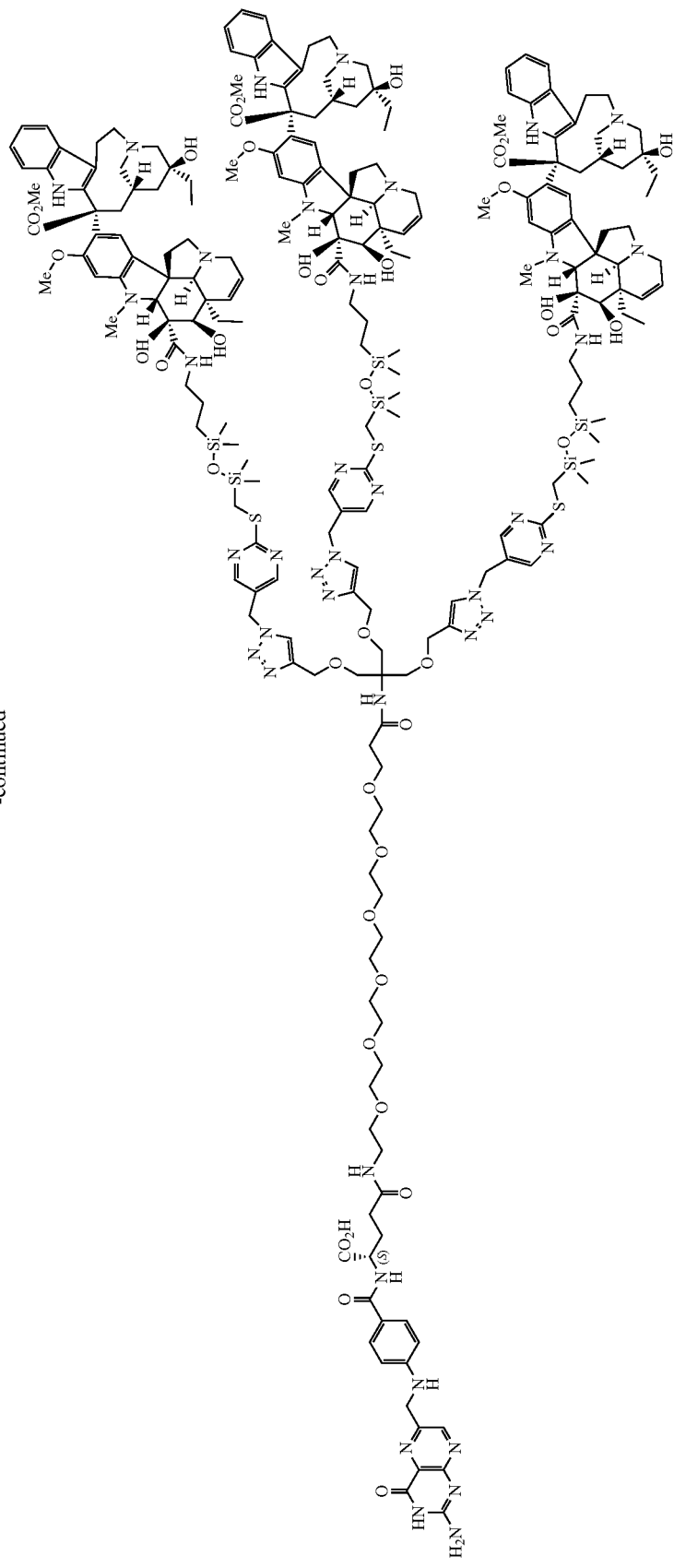
Example 83

(31S)-31-(4-(((2-Amino-4-oxo-3,4-dihydropteridin-6-yl)methyl)amino)benzamido)-1-(1-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methyl)-1H-1,2,3-triazol-4-yl)-4,4-bis(((1-((2-(((3-(3-((3aR,3a1R,4R,5S,5aR,10bR)-3a-ethyl-9-((5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methyl)thio)pyrimidin-5-yl)methyl)-1H-1,2,3-triazol-4-yl)methoxy)methyl)-6,28-dioxo-2,9,12,15,18,21,24-heptaoxa-5,27-diazadotriacontan-32-oic acid [Example 83]

The whole was purged with nitrogen gas, capped, and sonicated for 5 min. Then a freshly prepared solution of sodium ascorbate (100 mM in water, 26.2 µL, 2.62 µmol) followed by the addition of a freshly prepared solution of copper sulfate pentahydrate (100 mM in water, 13.08 µL, 1.308 µmol). The whole was purged with nitrogen gas, capped, sonicated for 5 min, and agitated on a shaker at rt for 1.5 h. The reaction was incomplete therefore additional sodium ascorbate (100 mM in water, 4.02 µL, 0.402 µmol) and copper sulfate pentahydrate (100 mM in water, 2.012 µL, 0.201 µmol) were added to the reaction mixture and agitated on a shaker for 1 h. The whole was diluted with 1 mL DMSO and passed through an ISCO solid loading filter plug with an aid of a vacuum. The residue was dissolved with ~0.3 mL of DMSO and passed through the same filter plug and the combined filtrate (1-2 mL) was purified by a reversed phase preparative HPLC [gradient 2] resulting in 1.94 mg, 6.87% yield of the title compound as a light yellow solid. $^1$H NMR (400 MHz, DMSO-$d_6$) δ ppm 9.33 (s, 2H) 8.61-8.71 (m, 7H) 8.52 (br s, 2H) 8.16 (s, 3H) 7.97 (br s, 1H) 7.77 (s, 3H) 7.57 (br s, 2H) 7.36 (br d, J=7.58 Hz, 3H) 7.26 (br d, J=7.83 Hz, 3H) 6.84-7.04 (m, 7H) 6.63 (d, J=8.59 Hz,

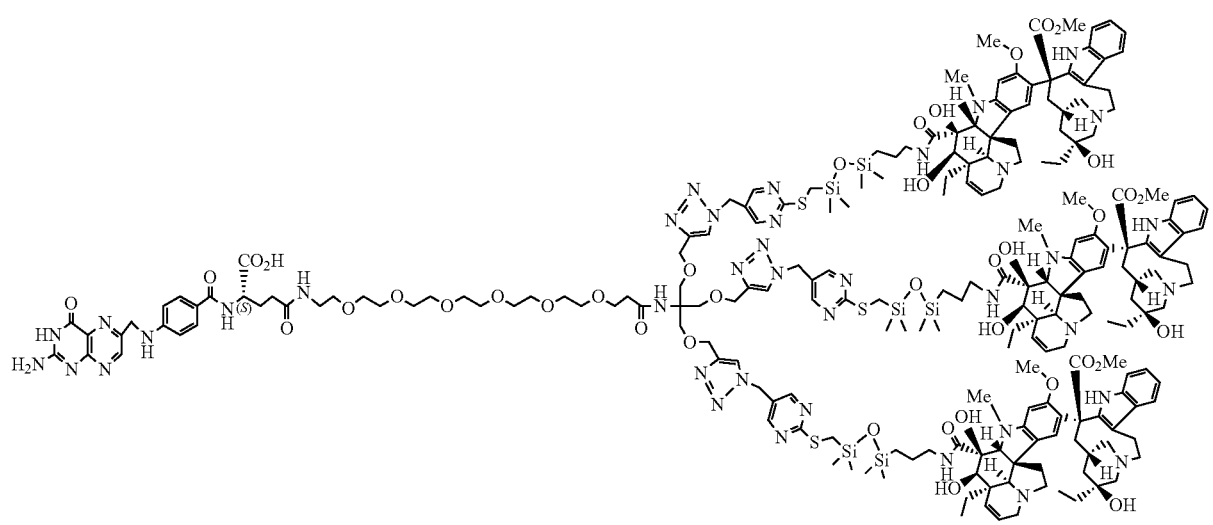

To an Eppendorf vial, DMF (87 µL) was added to a mixture of (S)-33-(4-(((2-amino-4-oxo-3,4-dihydropteridin-6-yl)methyl)amino)benzamido)-8,30-dioxo-6,6-bis((prop-2-yn-1-yloxy)methyl)-4,11,14,17,20,23,26-heptaoxa-7,29-diazatetratriacont-1-yn-34-oic acid (6.50 mg, 6.54 µmol) and (3R,5S,7R,9S)-methyl 9-((3aR,3a1R,4R,5S,5aR,10bR)-5-((3-(3-(((5-(azidomethyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,5,6,7,8,9,10-octahydro-1H-3,7-methano[1]azacycloundecino[5,4-b]indole-9-carboxylate (25.3 mg, 0.023 mmol). More DMF (87 µL) to dissolve both reactants.

1H) 6.53-6.71 (m, 1H) 6.56 (s, 1H) 6.44 (s, 2H) 6.19 (s, 2H) 5.50-5.80 (m, 11H) 4.40-4.52 (m, 8H) 3.91-4.11 (m, 11H) 3.82 (br d, J=5.81 Hz, 2H) 3.71 (s, 15H) 3.38-3.62 (m, 61H) 2.96-3.22 (m, 21H) 2.88 (br d, J=10.61 Hz, 4H) 2.59-2.77 (m, 17H) 2.22-2.41 (m, 11H) 1.86-2.14 (m, 7H) 1.39-1.64 (m, 12H) 1.10-1.37 (m, 28H) 0.67-0.90 (m, 21H) 0.63 (br s, 3H) 0.42-0.54 (m, 6H) 0.15 (s, 18H) −0.02-0.08 (m, 21H), MS (ES$^+$): m/z=[M+3]/3=1439.3, [M+4]/4=1080.4, [M+5]/5=864.4, [M+6]/6=720.5; LCMS: $t_R$=1.52 min [polar_3 min_0_1500]

Example 84

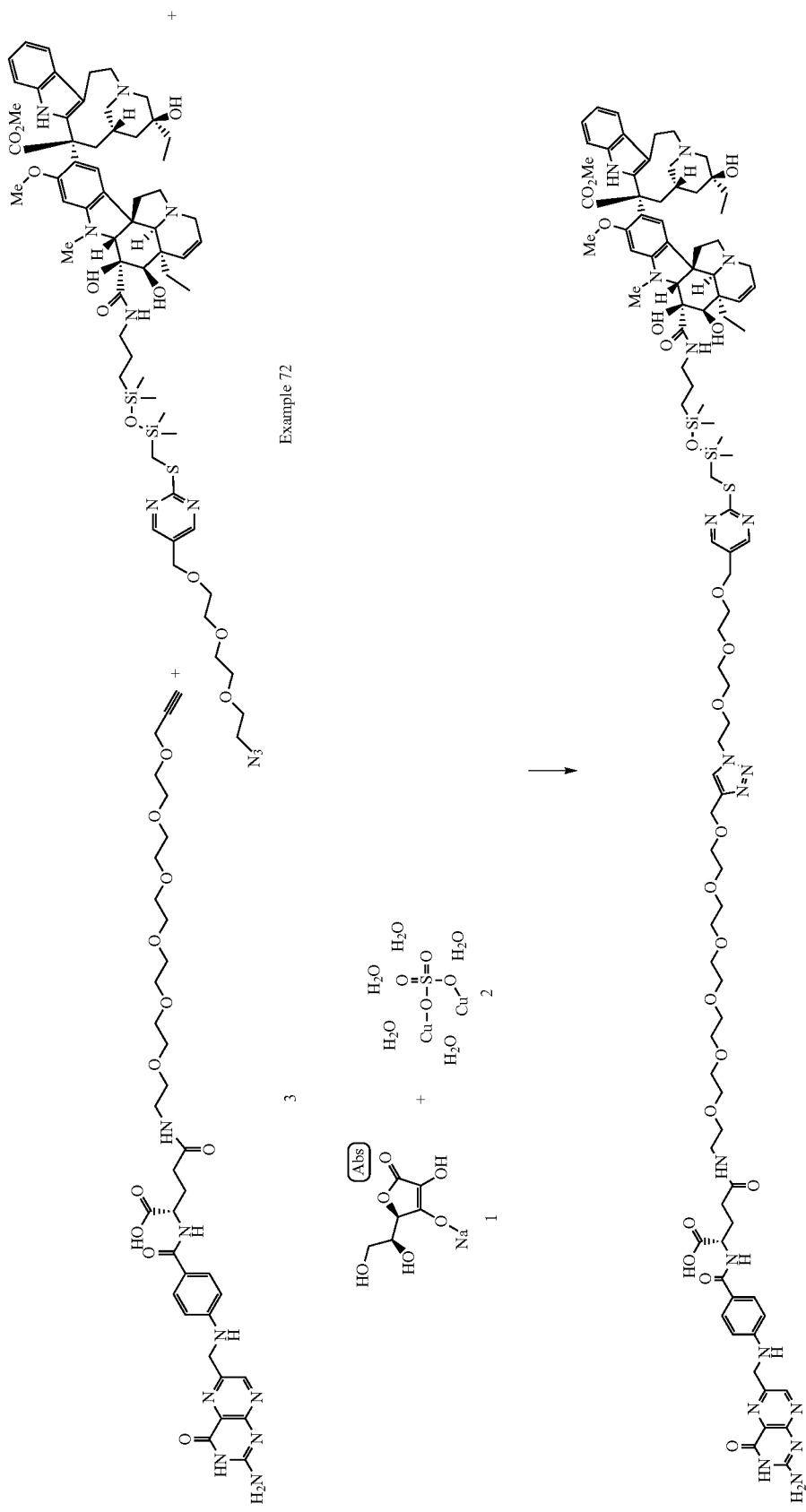

(24S)-24-(4-(((2-Amino-4-oxo-3,4-dihydropteridin-6-yl)methyl)amino)benzamido)-1-(1-(2-(2-(2-((2-(((3-(3-((3aR,3a1R,4R,5S,5aR,10bR)-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl) methyl)thio)pyrimidin-5-yl)methoxy)ethoxy)ethoxy)ethyl)-1H-1,2,3-triazol-4-yl)-21-oxo-2,5,8,11,14,17-hexaoxa-20-azapentacosan-25-oic Acid
[Example 84]

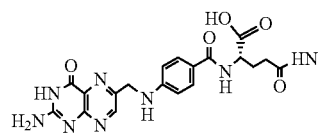
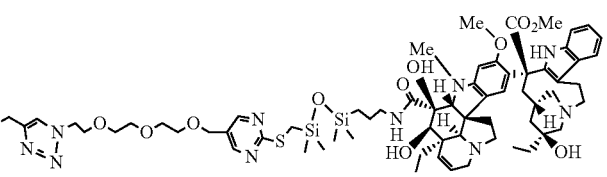

Using a similar procedure as for Example 80, Example 84 was synthesized using, DMF (26 μL), (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (2 mg, 2.69 μmol), (5S,7S,9S)-methyl9-((3aR,3a1R,4R,5S,5aR,10bR)-5-((3-(3-(((5-((2-(2-(2-azidoethoxy)ethoxy)ethoxy)methyl)pyrimidin-2-yl)thio)methyl)-1,1,3,3-tetramethyldisiloxanyl)propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (5.01 mg, 4.04 μmol), sodium ascorbate (freshly prepared 100 mM in water, 5.39 μl, 0.539 μmol), water (13.46 μL), copper sulfate pentahydrate (freshly prepared 100 mM in water, 2.69 μl, 0.269 μmol), and water (13.46 μL). The sample was purified by reverse phase HPLC [gradient 1] resulting in 1.29 mg, 24.2% yield of the title compound as a light yellow solid after lyophilization. LCMS using acidic mobile phase and method polar_3 min_0_1500 (0.8 mL/min flow) showed 98.0% pure (retention time=1.56 min) and confirmed title compound. $^1$H NMR (400 MHz, DMSO-$d_6$) δ ppm 9.33 (s, 1H) 8.47-8.73 (m, 4H) 8.04 (s, 1H) 7.95 (br s, 1H) 7.78 (s, 1H) 7.59 (br d, J=8.08 Hz, 2H) 7.37 (d, J=7.83 Hz, 1H) 7.26 (d, J=8.34 Hz, 1H) 6.86-7.08 (m, 4H) 6.56-6.73 (m, 3H) 6.44 (s, 1H) 6.19 (s, 1H) 5.50-5.78 (m, 2H) 4.39-4.58 (m, 9H) 3.67-4.03 (m, 13H) 3.42-3.62 (m, 30H) 2.99-3.19 (m, 1H) 2.94-3.22 (m, 6H) 2.89 (br d, J=10.61 Hz, 1H) 2.58-2.79 (m, 6H) 2.28-2.42 (m, 4H) 1.77-2.20 (m, 5H) 1.07-1.66 (m, 10H) 0.58-0.89 (m, 7H) 0.52 (br d, J=7.58 Hz, 2H) 0.17 (s, 6H) 0.06 (s, 8H), MS (ES$^+$): m/z=. [M+2]/2=992.2, [M+3]/3=661.8; LCMS: $t_R$=1.52 min [polar_3 min_0_1500]

Example 85

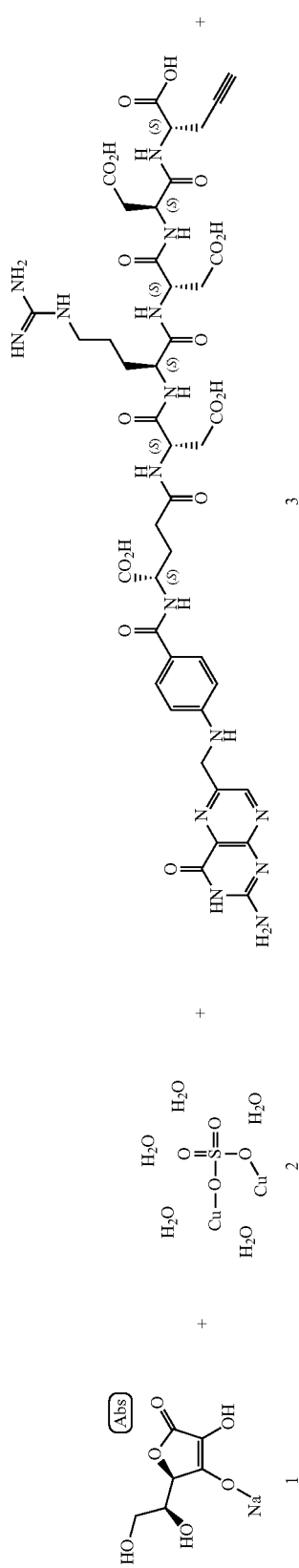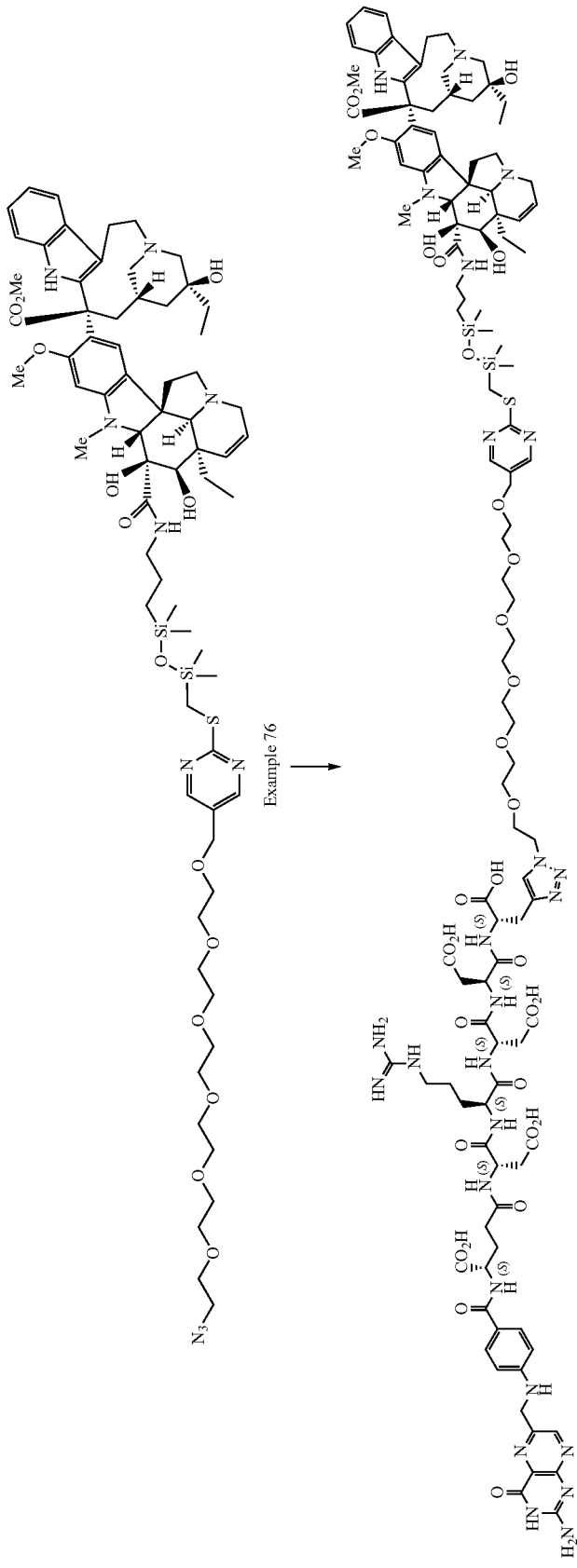

(2S,5S,8S,11S,14S,19S)-19-(4-(((2-Amino-4-oxo-3,
4-dihydropteridin-6-yl)methyl)amino)benzamido)-5,
8,14-tris(carboxymethyl)-2-((1-(1-(2-(((3-(3-((3aR,
3a1R,4R,5S,5aR,10bR)-3a-ethyl-9-05S,7S,9S)-5-
ethyl-5-hydroxy-9-(methoxycarbonyl)-2,4,5,6,7,8,9,
10-octahydro-1H-3,7-methano[1]azacycloundecino
[5,4-b]indol-9-yl)-4,5-dihydroxy-8-methoxy-6-
methyl-3a,3a1,4,5,5a,6,11,12-octahydro-1H-
indolizino[8,1-cd]carbazole-5-carboxamido)propyl)-
1,1,3,3-tetramethyldisiloxanyl) methyl)thio)
pyrimidin-5-yl)-2,5,8,11,14,17-hexaoxanonadecan-
19-yl)-1H-1,2,3-triazol-4-yl)methyl)-11-(3-
guanidinopropyl)-4,7,10,13,16-pentaoxo-3,6,9,12,
15-pentaazaicosane-1,20-dioic Acid [Example 85]

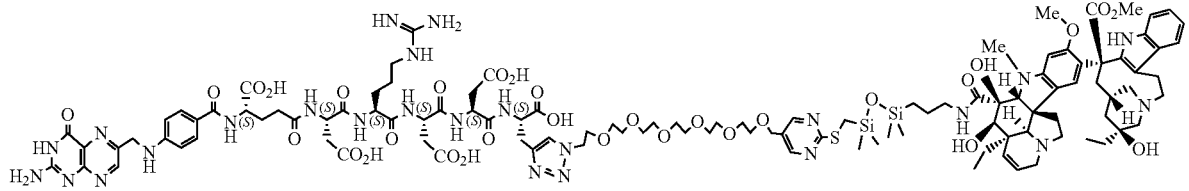

To an Eppendorf vial, DMSO (377 µL) was added to a mixture of (2S,5S,8S,11S,14S,19S)-19-(4-(((2-amino-4-oxo-3,4-dihydropteridin-6-yl)methyl)amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosane-1,20-dioic acid (15.66 mg, 0.015 mmol), and (5S,7S,9S)-methyl 9-((3aR,3a1R,4R,5S,5aR,10bR)-5-((3-(3-(((5-(19-azido-2,5,8,11,14,17-hexaoxanonadecyl)pyrimidin-2-yl)thio)methyl)-1,1,3,3-tetramethyldisiloxanyl) propyl)carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (20.7 mg, 0.015 mmol) at rt Immediately, solids precipitated out the solution and the reaction mixture became green. The whole was purged with nitrogen gas, capped, and sonicated for 5 min. Then a freshly prepared solution of sodium ascorbate (100 mM in water, 30.2 µL, 3.02 µmol) followed by a freshly prepared solution of copper sulfate pentahydrate (100 mM in water, 15.09 µL, 1.509 µmol). The whole was purged with nitrogen gas, capped, sonicated for 5 min, and agitated on a shaker at rt. A dark brown homogenous solution was formed. After 1 h, more sodium ascorbate (100 mM in water, 30.2 µL, 3.02 µmol) followed by copper sulfate pentahydrate (100 mM in water, 15.09 µL, 1.509 µmol). The reaction was incomplete therefore more alkyne SM (8 mg), sodium ascorbate (100 mM in water, 30.2 µL, 3.02 µmol), and copper sulfate pentahydrate (100 mM in water, 15.09 µL, 1.51 µmol) were added and agitated for another 1 h. The reaction was stopped and the whole was diluted with 1 mL DMSO and passed through an ISCO solid loading filter plug with an aid of a vacuum. The remaining residue was dissolved with ~0.3 mL of DMSO and passed through the same filter plug and the combined filtrate (2 mL) was purified by a reversed phase preparative HPLC [gradient 1] resulting in 9.55 mg, 26.3% yield of the title compound as a light yellow solid after lyophilization. $^1$H NMR (400 MHz, DMSO-$d_6$) δ ppm 10.08 (br s, 1H) 9.34 (s, 1H) 8.55-8.68 (m, 3H) 8.15-8.54 (m, 5H) 7.73-7.94 (m, 2H) 7.64 (br d, J=7.33 Hz, 2H) 7.51 (br s, 1H) 7.37 (br d, J=7.83 Hz, 1H) 7.26 (d, J=8.08 Hz, 1H) 6.87-7.18 (m, 5H) 6.62 (br d, J=8.08 Hz, 2H) 6.44 (s, 1H) 6.19 (s, 1H) 5.65-5.74 (m, 1H) 5.57 (br d, J=10.36 Hz, 1H) 4.25-4.65 (m, 10H) 3.92-4.20 (m, 2H) 3.67-3.89 (m, 11H) 2.83-3.63 (m, 91H) 2.58-2.78 (m, 9H) 2.19-2.43 (m, 13H) 1.73-2.10 (m, 9H) 1.10-1.66 (m, 16H) 0.59-0.85 (m, 7H) 0.45-0.56 (m, 2H) 0.17 (s, 6H) 0.06 (s, 6H), MS (ES$^+$): m/z=[M+2]/2=1206.4, [M+3]/3=804.2; LCMS: $t_R$=1.50 min [polar_3 min_0_1500]

Example 86

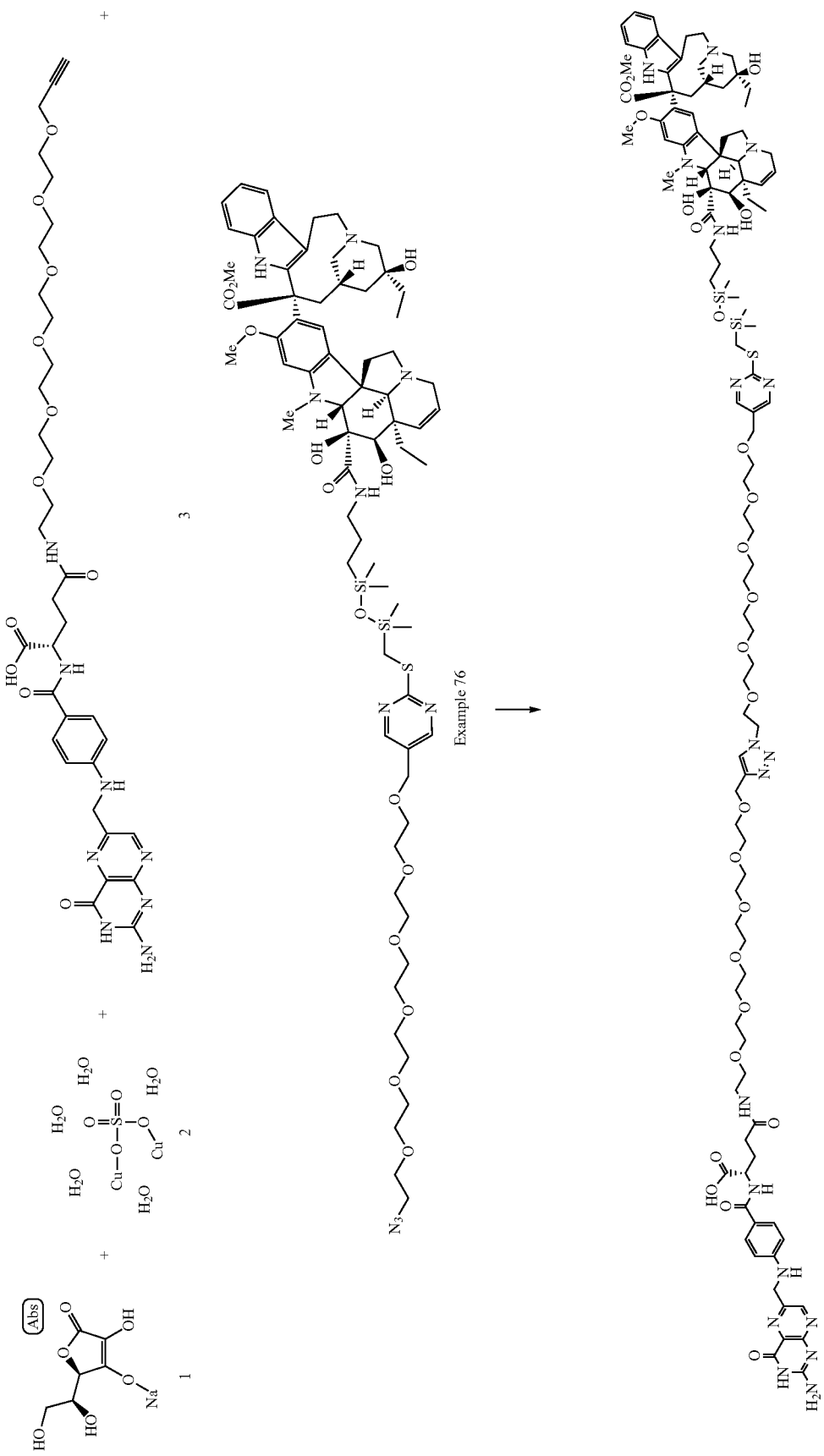

(24S)-24-(4-(((2-Amino-4-oxo-3,4-dihydropteridin-6-yl)methyl)amino)benzamido)-1-(1-(1-(2-(((3-(3-((3aR,3a1R,4R,5S,5aR,10bR)-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-4,5-dihydroxy-8-methoxy-6-methyl-3a,3a1,4,5,5a,6,11,12-octahydro-1H-indolizino[8,1-cd]carbazole-5-carboxamido)propyl)-1,1,3,3-tetramethyldisiloxanyl)methy)thio)pyrimidin-5-yl)-2,5,8,11,14,17-hexaoxanonadecan-19-yl)-1H-1,2,3-triazol-4-yl)-21-oxo-2,5,8,11,14,17-hexaoxa-20-azapentacosan-25-oic acid [Example 86]

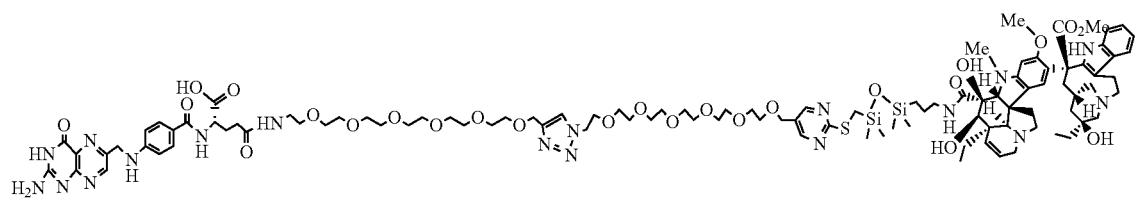

To an Eppendorf vial, DMSO (359 μL) was added into a mixture of (S)-26-(4-(((2-amino-4-oxo-3,4-dihydropteridin-6-yl)methyl)amino)benzamido)-23-oxo-4,7,10,13,16,19-hexaoxa-22-azaheptacos-1-yn-27-oic acid (12.0 mg, 0.016 mmol) and (5S,7S,9S)-methyl 9-((3aR,3a1R,4R,5S,5aR,10bR)-5-((3-(3-(((5-(19-azido-2,5,8,11,14,17-hexaoxanonadecyl) pyrimidin-2-yl)thio)methyl)-1,1,3,3-tetramethyldisiloxanyl) propyl) carbamoyl)-3a-ethyl-4,5-dihydroxy-8-methoxy-6-methyl-3a,3a1,4,5,5a,6,11,12-octahydro-1H-indolizino[8,1-cd]carbazol-9-yl)-5-ethyl-5-hydroxy-2,4,5,6,7,8,9,10-octahydro-1H-3,7-methano[1]azacycloundecino[5,4-b]indole-9-carboxylate (22.2 mg, 0.016 mmol). The whole was purged with nitrogen gas, capped, and sonicated for 5 min. Then a freshly prepared solution of sodium ascorbate (100 mM in water, 32.3 μL, 3.23 μmol) followed by a freshly prepared solution of addition of copper sulfate pentahydrate (100 mM in water, 16.2 μL, 1.62 μmol). A dark brown homogenous solution was formed. The whole was purged with nitrogen gas, capped, sonicated for 5 min, and agitated on a shaker at rt. After 1 h, more sodium ascorbate (100 mM in water, 32.3 μL, 3.23 μmol) and copper sulfate pentahydrate (100 mM in water, 16.2 μL, 1.62 μmol) were added. After 1 h, the reaction was stopped. The whole was diluted with 2.5 mL DMSO and passed through an ISCO solid loading filter plug with an aid of a vacuum and the residue was dissolved with ~0.3 mL of DMSO and passed through the same filter plug. The combined filtrate (3 mL) was purified by a reversed phase preparative HPLC [gradient 1] resulting in 9.55 mg, 28.0% yield, of the title compound as a light yellow solid after lyophilization. $^1$H NMR (400 MHz, DMSO-$d_6$) δ ppm 8.64 (s, 1H) 8.58 (s, 2H) 8.04 (s, 1H) 7.64 (br d, J=8.34 Hz, 1H) 7.37 (d, J=8.08 Hz, 1H) 7.26 (d, J=7.83 Hz, 1H) 6.87-7.03 (m, 4H) 6.64 (br d, J=8.59 Hz, 2H) 5.66-5.71 (m, 1H) 4.44-4.52 (m, 8H) 3.89-4.09 (m, 3H) 3.69-3.84 (m, 8H) 3.65 (brd, J=9.09 Hz, 1H) 3.42-3.56 (m, 49H) 3.01-3.26 (m, 6H) 2.90 (br d, J=17.18 Hz, 2H) 2.61-2.78 (m, 6H) 2.30-2.46 (m, 4H) 2.17 (br s, 2H) 1.85-2.07 (m, 4H) 1.54-1.63 (m, 2H) 1.48 (br dd, J=15.66, 7.83 Hz, 2H) 1.21-1.35 (m, 2H) 1.13-1.21 (m, 3H) 0.70-0.84 (m, 6H) 0.64 (br s, 1H) 0.46-0.54 (m, 2H) 0.17 (s, 6H) 0.06 (s, 7H), MS (ES$^+$): m/z=[M+2]/2=1058.1, [M+3]/3=705.8; LCMS: $t_R$=1.57 min [polar_3 min_0_1500].

Example 87

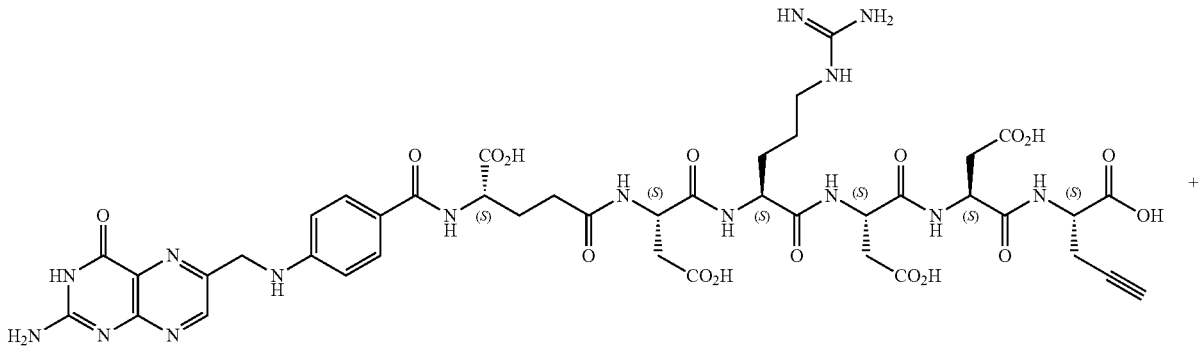

-continued

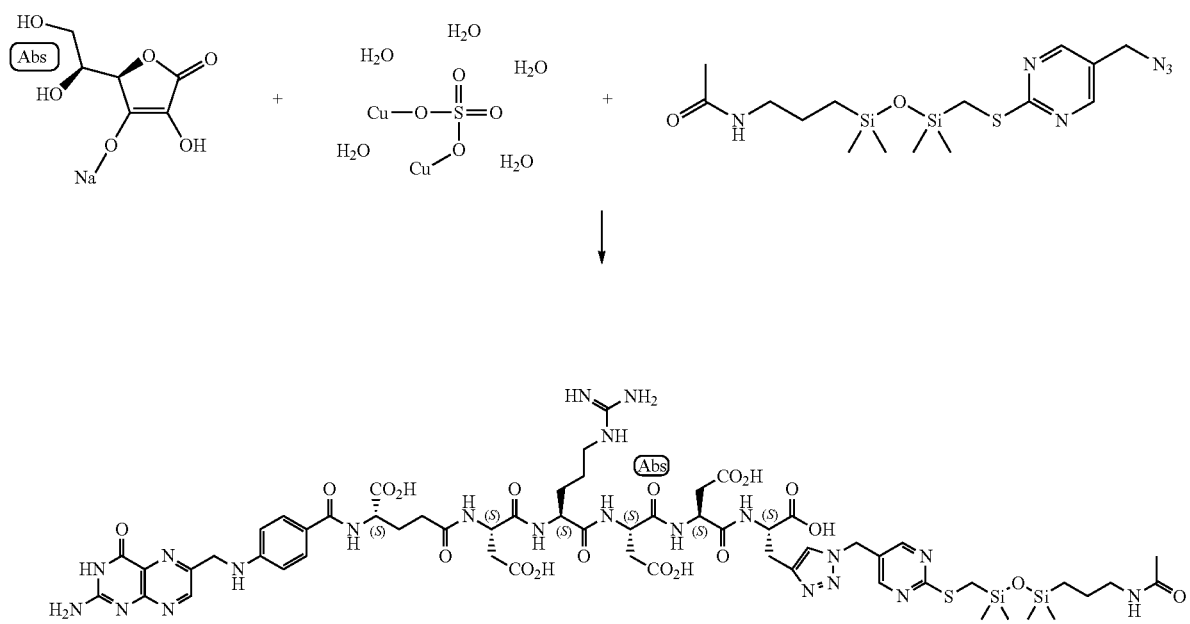

(2S,5S,8S,11S,14S,19S)-2-((1-((2-(((3-(3-Acetamidopropyl)-1,1,3,3-tetramethyldisiloxanyl)methyl)thio)pyrimidin-5-yl)methyl)-1H-1,2,3-triazol-4-yl)methyl)-19-(4-(((2-amino-4-oxo-3,4-dihydropteridin-6-yl)methyl)amino)benzamido)-5,8,14-tris(carboxymethyl)-11-(3-guanidinopropyl)-4,7,10,13,16-pentaoxo-3,6,9,12,15-pentaazaicosane-1,20-dioic acid [Example 87]

water (55 μL) followed by the addition of copper sulfate pentahydrate (100 mM in water, 48.5 μL, 4.85 μmol) in water (55 μL). The whole was purged with nitrogen gas, capped, sonicated for 5 min, and agitated on a shaker at rt. As the reaction proceeded, more solids went into solution. After 2.5 h, the reaction was stopped. The whole was diluted with 1.5 mL DMSO and passed through an ISCO solid loading filter plug with an aid of a vacuum. The residue was dissolved with ~0.5 mL of DMSO and passed through the

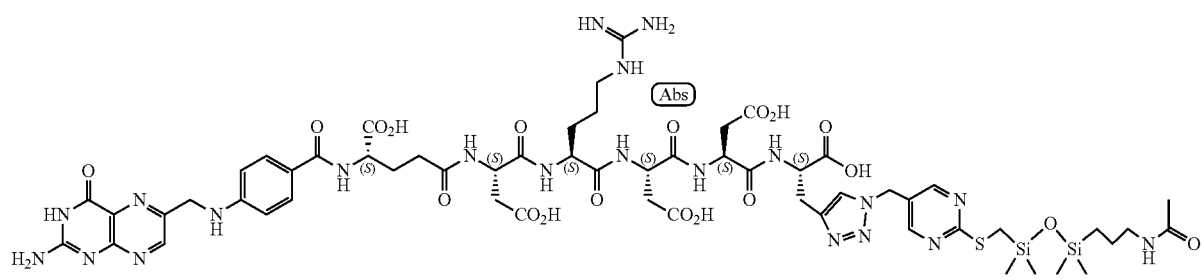

To an Eppendorf vial, DMF (323 μL) was added into a mixture of (2S,5S,8S,11S,14S,19S)-19-(4-(((2-amino-4-oxo-3,4-dihydropteridin-6-yl)methyl)amino)benzamido)-5,8,14-tris(carboxymethyl)-11-(3-guanidinopropyl)-4,7,10,13,16-pentaoxo-2-(prop-2-yn-1-yl)-3,6,9,12,15-pentaazaicosane-1,20-dioic acid (32.7 mg, 0.032 mmol) and N-(3-(3-(((5-(azidomethyl)pyrimidin-2-yl)thio)methyl)-1,1,3,3-tetramethyldisiloxanyl)propyl)acetamide (10 mg, 0.024 mmol). More DMF (323 μL) was added to dissolve alkyne SM. The whole was purged with nitrogen gas, capped, and sonicated for 5 min. Then a freshly prepared solution of sodium ascorbate (100 mM in water, 48.5 μl, 4.85 μmol) in same filter plug and the combined filtrate (2 mL) was purified by a reversed phase preparative HPLC [gradient 1] resulting in 6 mg, 17.1% yield, of the title compound as a light yellow solid after lyophilization. $^1$H NMR (400 MHz, DMSO-$d_6$) δ ppm 0.04 (s, 6H) 0.15 (s, 6H) 0.36-0.58 (m, 2H) 1.25-1.53 (m, 3H) 1.92 (br s, 2H) 2.22-2.42 (m, 3H) 2.88-3.05 (m, 3H) 4.24-4.70 (m, 6H) 5.55 (br s, 2H) 6.62 (br s, 2H) 6.86-7.30 (m, 4H) 7.35-7.72 (m, 3H) 7.75-8.09 (m, 3H) 8.13-8.52 (m, 2H) 8.62 (br s, 4H) 10.07 (br s, 1H). ($C_{57}H_{79}N_{21}O_{19}SSi_2$- calculated: 79 Hs, observed: 52 Hs, some may be hidden in water peak or exchanging with water), MS (ES$^+$): m/z=1451.3 [M+2], 726.3 [M+2]/2; LCMS: $t_R$=1.53 min [polar_3 min_0_1500].

Example 88

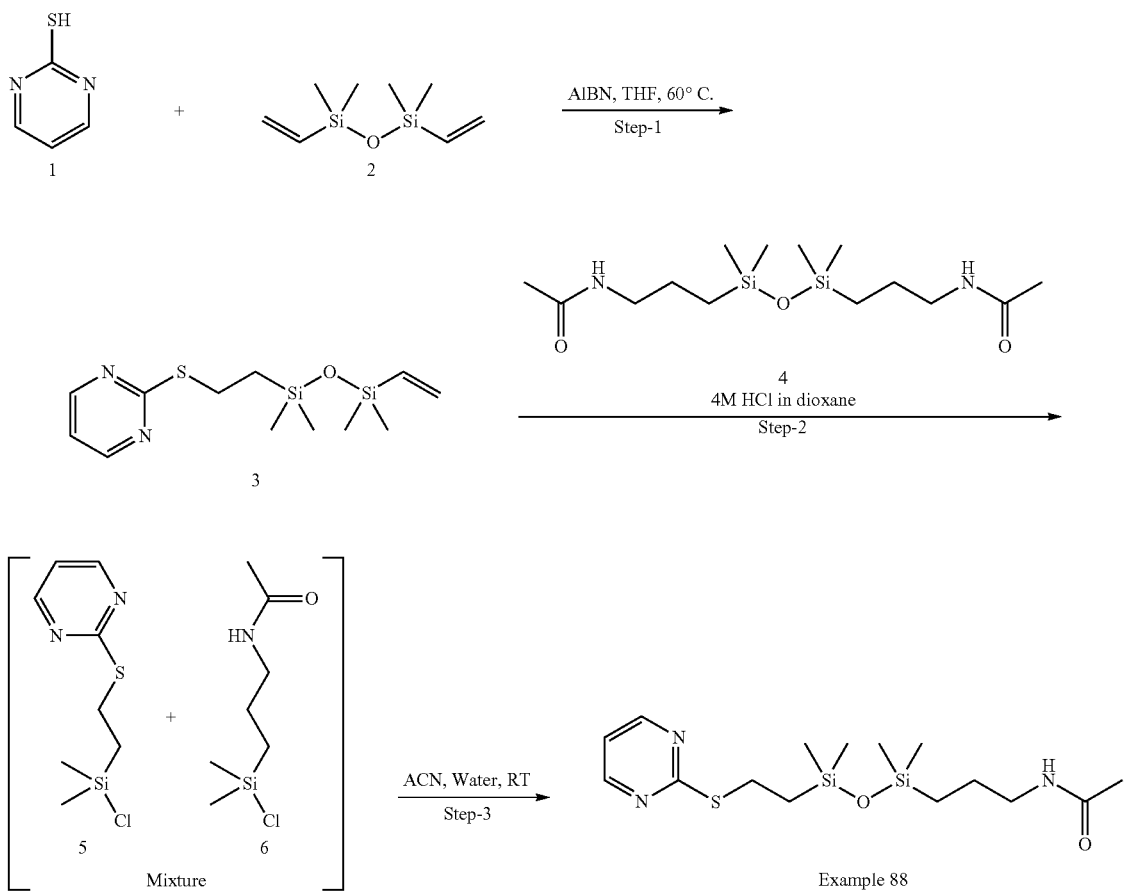

N-(3-(1,1,3,3-Tetramethyl-3-(2-(pyrimidin-2-ylthio)ethyl)disiloxanyl)propyl)acetamide [Example 88]

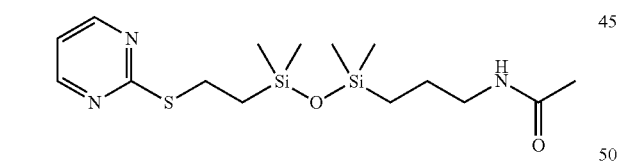

A solution of mixture of 2-((2-(1,1,3,3-tetramethyl-3-vinyldisiloxanyl)ethyl)thio)pyrimidine (500 mg, 1.677 mmol) and N,N-((1,1,3,3-tetramethyldisiloxane-1,3-diyl)bis(propane-3,1-diyl))diacetamide (570 mg, 1.677 mmol) in 4M HCl in dioxane (25 mL) was stirred at room temperature for 1 h. The reaction mixture was concentrated in vacuo resulting in the crude intermediate 5 and 6. The mixture of intermediate 5 and 6 was dissolved in acetonitrile (20 mL) and followed by addition of water (0.12 mL, 6.711 mmol) and DIPEA (1.85 mL, 10.06 mmol) and stirred at room temperature for 1 h. The reaction mixture was concentrated in vacuo resulting in the crude compound which was purified by Combi Flash chromatography on silica gel eluting with 0-10% methanol in DCM to afford 510 mg, 41% yield, of the title compound as a light yellow oil. $^1$H NMR (400 MHz, DMSO-$d_6$) δ=8.55 (d, J=4.89 Hz, 2H), 7.72 (br. s, 1H), 7.09-7.15 (m, 1H), 3.04-3.11 (m, 2H), 2.88-2.96 (m, 2H), 1.72 (s, 3H), 1.27-1.38 (m, 2H), 0.89-0.97 (m, 2H), 0.39-0.46 (m, 2H), 0.05 (s, 6H), 0.00 (s, 6H); MS (ES$^+$): m/z=372.10 [M+H]$^+$; LCMS: $t_R$=3.20 min.

2-((2-(1,1,3,3-Tetramethyl-3-vinyldisiloxanyl)ethyl)thio)pyrimidine (3)

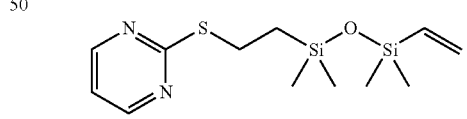

A solution of pyrimidine-2-thiol (1 g, 8.928 mmol) and 1,1,3,3-tetramethyl-1,3-divinyldisiloxane (3.32 g, 17.85 mmol) in THF (50 mL) was added AIBN (146 mg, 0.892 mmol) and silica (100 mg, 10% w/w) at room temperature. The resulting solution was heated to reflux at 60° C. for 4 h. The reaction mixture was concentrated in vacuo resulting in the crude compound which was purified by Combi Flash chromatography on silica gel eluting with 0-100% ethyl acetate in n-hexane to afford 1 g, 40% yield, of the title compound as a colorless oil. MS (ES$^+$): m/z=299.05 [M+H]$^+$; LCMS: $t_R$=3.71, 3.87 and 3.97 min.

Example 89 and Example 94

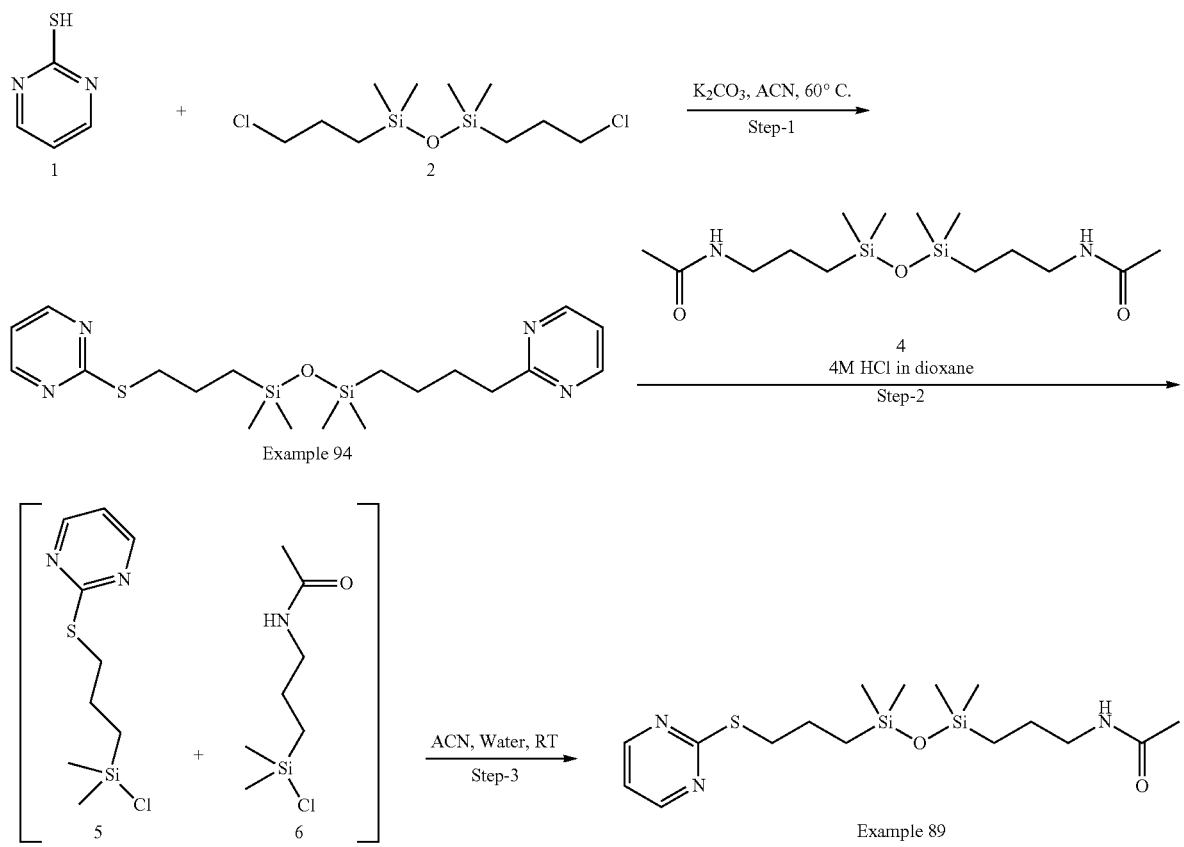

N-(3-(1,1,3,3-Tetramethyl-3-(3-(pyrimidin-2-ylthio) propyl)disiloxanyl)propyl)acetamide [Example 89]

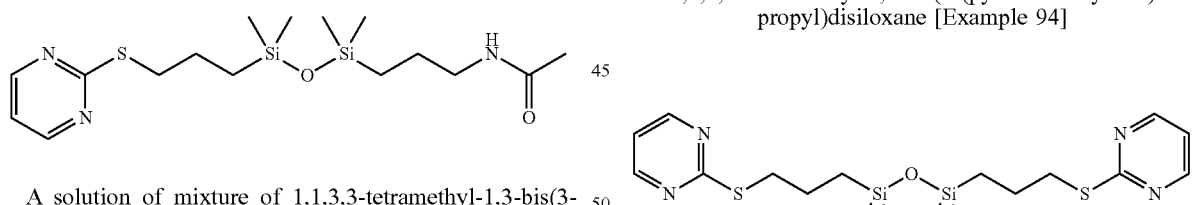

A solution of mixture of 1,1,3,3-tetramethyl-1,3-bis(3-(pyrimidin-2-ylthio)propyl)disiloxane (1 g, 2.283 mmol) and N,N'-((1,1,3,3-tetramethyldisiloxane-1,3-diyl)bis(propane-3,1-diyl))diacetamide (757 mg, 2.283 mmol) in 4M HCl in dioxane (50 mL) was stirred at room temperature for 1 h. The reaction mixture was concentrated in vacuo resulting in the crude intermediate 5 and 6. The mixture of intermediate 5 and 6 was dissolved in acetonitrile (50 mL) and followed by addition of water (0.16 mL, 9.132 mmol) and DIPEA (2.4 mL, 13.69 mmol) and stirred at room temperature for 1 h. The reaction mixture was concentrated in vacuo resulting in the crude compound which was purified by Combi Flash chromatography on silica gel eluting with 0-10% methanol in DCM to afford 788 mg, 45% yield, of the title compound as a light yellow oil. $^1$H NMR (400 MHz, DMSO-$d_6$) δ=8.61 (d, J=4.89 Hz, 2H), 7.78 (br. s, 1H), 7.19 (t, J=4.89 Hz, 1H), 3.10 (t, J=7.09 Hz, 2H), 2.95 (q, J=6.85 Hz, 2H), 1.77 (s, 3H), 1.63-1.73 (m, 2H), 1.29-1.40 (m, 2H), 0.60-0.68 (m, 2H), 0.40-0.47 (m, 2H), 0.04 (s, 6H), 0.00 (s, 6H); MS (ES$^+$): m/z=386.10 [M+H]$^+$; LCMS: $t_R$=3.34 min.

1,1,3,3-Tetramethyl-1,3-bis(3-(pyrimidin-2-ylthio) propyl)disiloxane [Example 94]

A solution of pyrimidine-2-thiol (2 g, 17.85 mmol) in acetonitrile (50 mL) was added potassium carbonate (7.39 g, 53.57 mmol) and 1,3-bis(3-chloropropyl)-1,1,3,3-tetramethyldisiloxane (2.3 g, 8.035 mmol) at room temperature and further heated to 60° C. for 4 h. The reaction mixture was concentrated in vacuo, diluted with DCM and the inorganic material was filtered. The filtrate was concentrated in vacuo resulting in the crude compound which was purified by Combi Flash chromatography on silica gel eluting with 0-20% ethyl acetate in n-hexane to afford 2.3 g, 30% yield, of the title compound as a colorless oil. $^1$H NMR (400 MHz, DMSO-$d_6$) δ=8.59 (d, J=4.89 Hz, 4H), 7.17 (t, J=4.89 Hz, 2H), 3.06 (t, J=7.09 Hz, 4H), 1.60-1.70 (m, 4H), 0.58-0.65 (m, 4H), 0.01 (s, 12H), MS (ES$^+$): m/z=439.15 [M+H]$^+$; LCMS: $t_R$=4.13 min.

Example 90 and Example 93

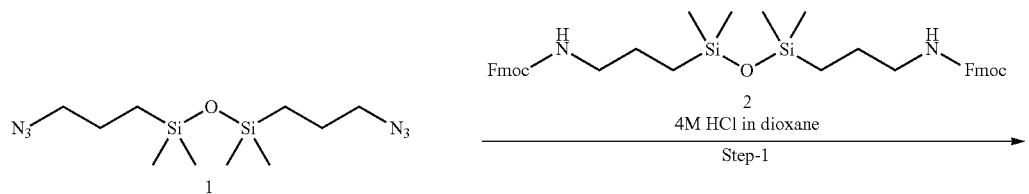

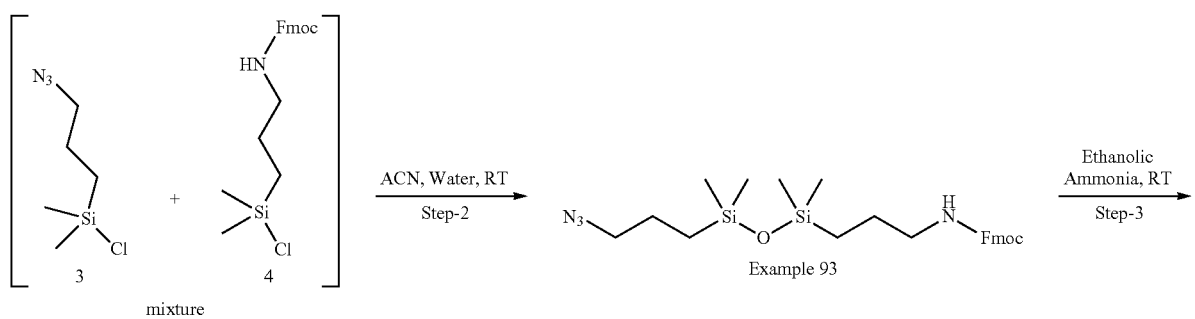

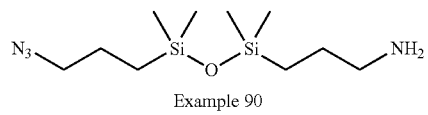

3-(3-(3-Azidopropyl)-1,1,3,3-tetramethyldisiloxanyl) propan-1-amine [Example 90]

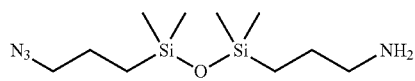

A solution of (9H-fluoren-9-yl)methyl(3-(3-(3-azidopropyl)-1,1,3,3-tetramethyldisiloxanyl) propyl)carbamate (1 g, 2.016 mmol) in saturated ethanolic ammonia (50 mL) was stirred at room temperature for 14 h. The reaction mixture was concentrated in vacuo and the crude compound was purified by Combi Flash chromatography on silica gel eluting with 0-10% methanol saturated with ammonia in DCM to afford 375 mg, 68% yield, of the title compound as a light yellow oil. $^1$H NMR (400 MHz, CDCl$_3$) δ=3.24 (t, J=6.85 Hz, 2H), 2.67 (t, J=7.09 Hz, 2H), 1.57-1.66 (m, 2H), 1.40-1.49 (m, 4H), 0.48-0.59 (m, 4H), 0.07 (s, 6H), 0.06 (s, 6H); MS (ES$^+$): m/z=275.00 [M+H]$^+$; LCMS: t$_R$=5.55 min.

(9H-Fluoren-9-yl) methyl(3-(3-(3-azidopropyl)-1,1,3,3-tetramethyldisilonxanyl) propyl)carbamate [Example 93]

A mixture of 1,3-bis(3-azidopropyl)-1,1,3,3-tetramethyldisiloxane (1 g, 3.333 mmol) and bis((9H-fluoren-9-yl) methyl)((1,1,3,3-tetramethyldisiloxane-1,3-diyl)bis(propane-3,1-diyl))dicarbamate (2.3 g, 3.333 mmol) in 4M HCl in dioxane (50 mL) was stirred at room temperature for 1 h. The reaction mixture was concentrated in vacuo resulting in the crude intermediate 3 and 4. The mixture of intermediate 3 and 4 was dissolved in acetonitrile (20 mL) and followed by addition of water (0.24 mL, 13.33 mmol) and DIPEA (3.7 mL, 19.99 mmol) and stirred at room temperature for 1 h. The reaction mixture was concentrated in vacuo resulting in the crude compound which was purified by Combi Flash chromatography on silica gel eluting with 0-70% ethyl acetate in n-hexane to afford 1.48 g, 45% yield, of the title compound as a white solid. $^1$H NMR (400 MHz, DMSO-d$_6$) δ=7.88 (d, J=7.34 Hz, 2H), 7.67 (d, J=7.34 Hz, 2H), 7.37-7.45 (m, 2H), 7.24-7.35 (m, 3H), 4.28 (d, J=6.85 Hz, 2H), 4.20 (d, J=6.85 Hz, 1H), 3.26 (t, J=6.85 Hz, 2H), 2.94 (q, J=6.68 Hz, 2H), 1.48-1.57 (m, 2H), 1.39 (td, J=7.64, 15.53 Hz, 2H), 0.42-0.56 (m, 4H), 0.04 (s, 6H), 0.03 (s, 6H); MS (ES$^+$): m/z=497.00 [M+H]$^+$; LCMS: t$_R$=4.58 min.

Example 95 temperature for another 1 h. The reaction mixture was concentrated in vacuo resulting in the crude compound which was purified by Combi Flash column chromatography on silica gel eluting with 0-5% methanol in DCM to afford 129 mg, 30% yield, of the title compound as a colorless oil. $^1$H NMR (400 MHz, DMSO-d$_6$) δ=12.45 (s, 1H), 7.82 (br. s, 1H), 7.47-7.51 (m, 1H), 7.32-7.37 (m, 1H), 7.07-7.13 (m, 2H), 2.99 (q, J=6.85 Hz, 2H), 2.57 (s, 2H), 1.78 (s, 3H), 1.36-1.46 (m, 2H), 0.48-0.54 (m, 2H), 0.20 (s, 6H), 0.09 (s, 6H); MS (ES$^+$): m/z=239.00 monomer [M+H]$^+$; LCMS: t$_R$=1.65 min.

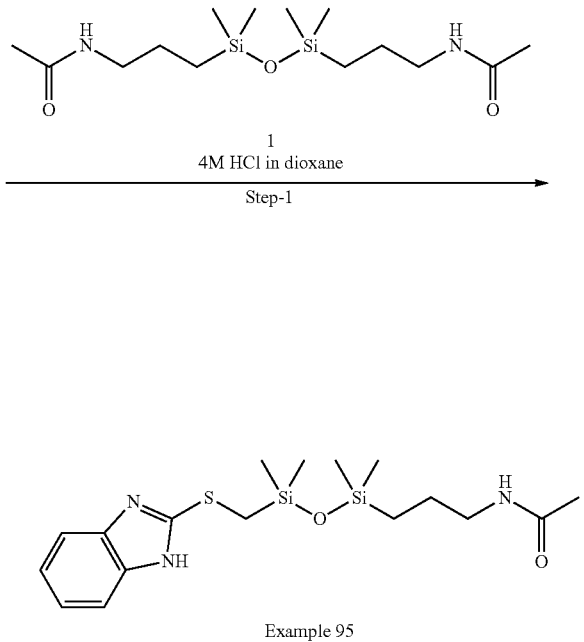

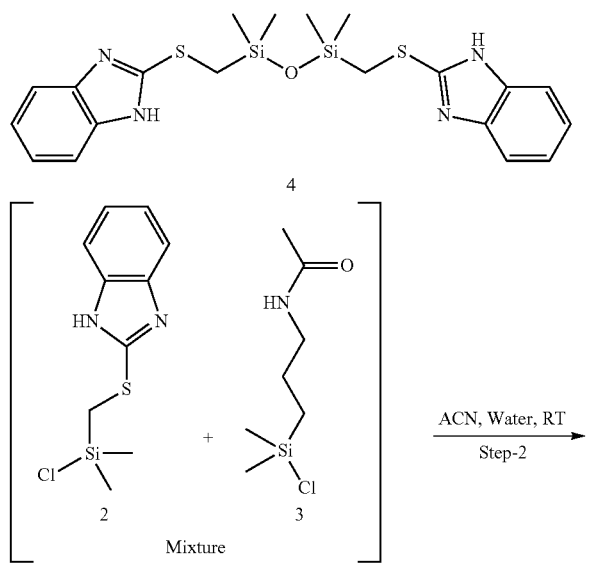

N-(3-(3-(((1H-Benzo[d]imidazol-2-yl)thio)methyl)-1,1,3,3-tetramethyldisiloxanyl) propyl)acetamide [Example 95]

Example 96

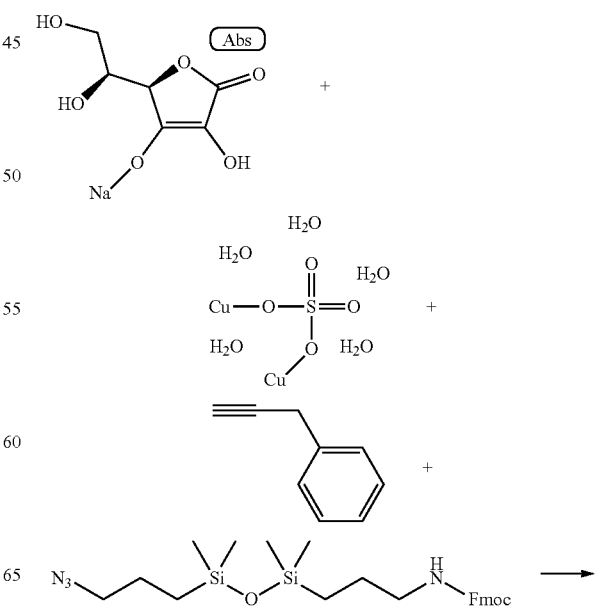

A solution of 1,3-bis(((1H-benzo[d]imidazol-2-yl)thio) methyl)-1,1,3,3-tetramethyldisiloxane (250 mg, 0.545 mmol) and N,N'-((1,1,3,3-tetramethyldisiloxane-1,3-diyl) bis(propane-3,1-diyl))diacetamide 1 (181 mg, 0.545 mmol) in 4M HCl in dioxane (20 mL) was stirred at room temperature for 1 h. The reaction mixture was concentrated in vacuo resulting in the crude intermediate 2 and 3. The mixture of intermediate 2 and 3 was dissolved in acetonitrile (30 mL) and followed by addition of water (0.4 mL, 2.183 mmol) and DIPEA (0.6 mL, 3.275 mmol) and stirred at room

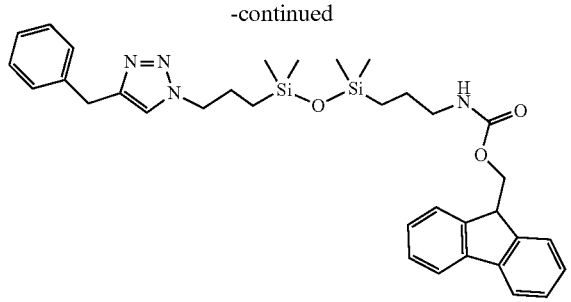

Example 96

(9H-Fluoren-9-yl)methyl(3-(3-(3-(4-benzyl-1H-1,2,3-triazol-1-yl)propyl)-1,1,3,3-tetramethyldisiloxanyl)propyl)carbamate [Example 96]

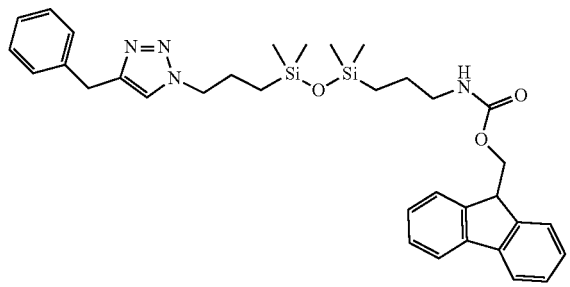 [SMILES: C[Si](C)(CCCNC(=O)OCC1c2ccccc2-c2ccccc21)O[Si](C)(C)CCCn1cc(Cc2ccccc2)nn1]

To an Eppendorf vial, DMF (171 µL) was added to a mixture of (9H-fluoren-9-yl)methyl(3-(3-(3-azidopropyl)-1,1,3,3-tetramethyldisiloxanyl)propyl)carbamate (17 mg, 0.034 mmol) and 3-phenyl-1-propyne (5.11 mL, 0.041 mmol). More DMF (171 mL) was added to dissolve both reactants. The vial was purged with nitrogen gas, capped, and sonicated for 5 min Sodium ascorbate (100 mM in water, 68.4 µL, 6.84 µmol) in water (171 µL) was added followed by the addition of copper sulfate pentahydrate (100 mM in water, 34.2 µL, 3.42 µmol) in water (171 µL). The vial was purged with nitrogen gas, capped, sonicated for 5 min, and agitated on a shaker at rt. A yellow suspension was formed and after 5 min, the reaction was quenched with water. The product was extracted with EtOAc (3×15 mL) and combined organic layers were dried over $Na_2SO_4$, filtered through a plug of glass wool, and concentrated in vacuo. The crude was purification by column chromatography (solid loading) on silica gel [ISCO Combi-Flash, 4 g cartridge] eluting with 70:30 to 30:70 Hex:EtOAc afforded 8 mg, 38.1% yield, of the title compound as a colorless oil. LCMS (ESI+), 3 min run, 20-90% gradient, retention time=2.45 m/z=613.51 [M+1]+. $^1$H NMR (400 MHz, CHLOROFORM-d) δ ppm 0.05 (d, J=2.78 Hz, 10H) 0.19 (br d, J=2.53 Hz, 1H) 0.44-0.55 (m, 4H) 0.80-0.97 (m, 1H) 1.13-1.38 (m, 2H) 1.40-1.54 (m, 2H) 1.58 (s, 6H) 1.71-1.97 (m, 3H) 2.06 (s, 1H) 3.16 (q, J=6.57 Hz, 2H) 4.09 (s, 2H) 4.17-4.32 (m, 3H) 4.40 (d, J=7.07 Hz, 2H) 5.06 (br s, 1H) 7.14 (s, 1H) 7.19-7.34 (m, 7H) 7.40 (t, J=7.33 Hz, 2H) 7.53-7.68 (m, 2H) 7.77 (d, J=7.58 Hz, 2H), MS (ES+): m/z=[M+2]/2=1058.1, [M+3]/3=705.8; LCMS: $t_R$=1.57 min [polar_3 min_0_1500].

Example 97: Synthesis of Conjugates

Conjugates are synthesized as exemplified in Schemes 1 and 2, below. Scheme 1 depicts a route where first a targeting moiety, folic acid, is activated by reaction with DCC and N-hydroxysuccinimide and then reacted with a protected siloxane or silylether core to form a targeting moiety-core conjugate.

Scheme 1.

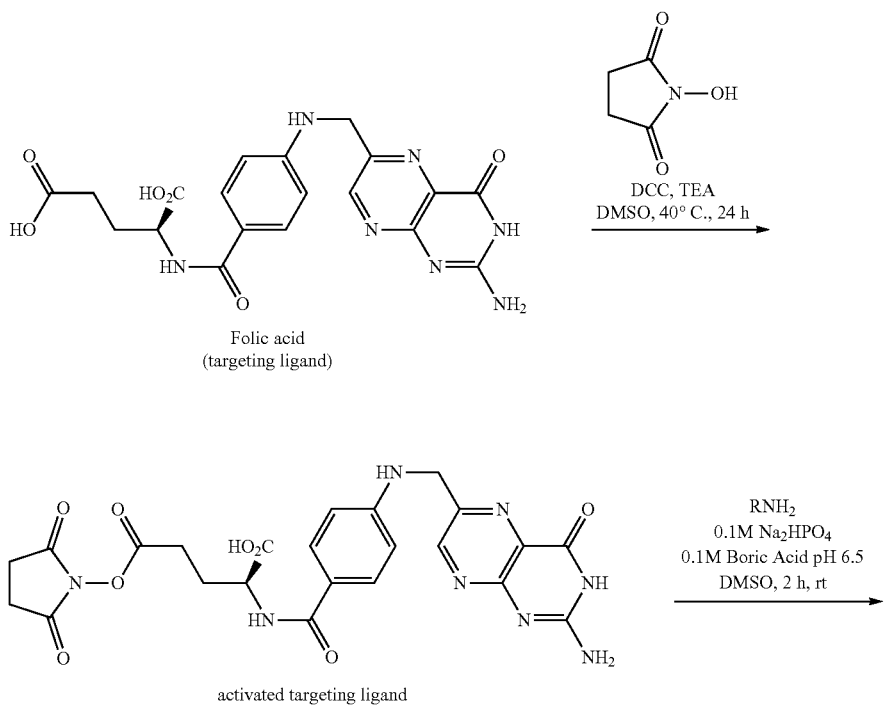

-continued
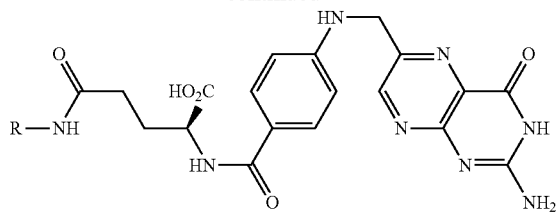
targeting ligand-core conjugate
RHN$_2$ =
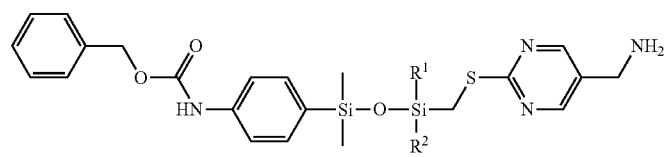
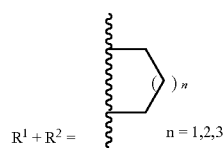
$R^1 + R^2 =$  n = 1,2,3
$R^1 = R^2 =$ Me, i-Pr, t-Bu
$R^1 =$ Me, $R^2 =$ i-Pr
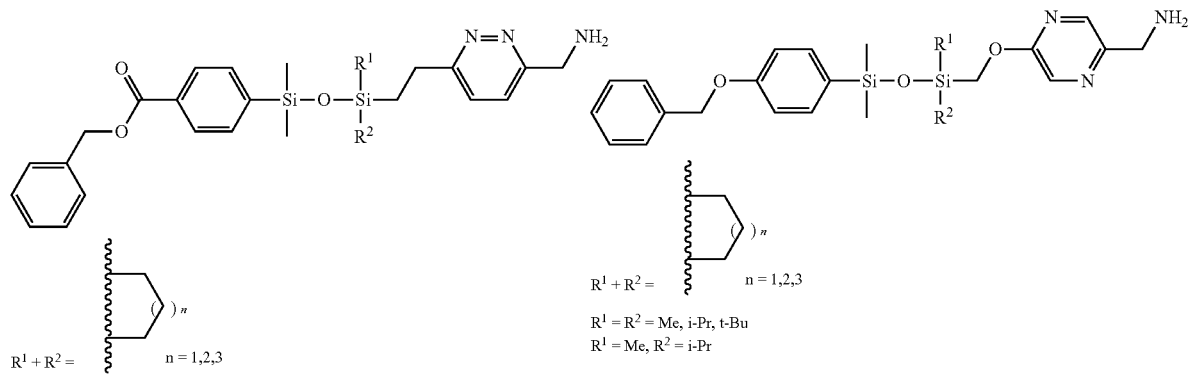
Scheme 2, below, shows an alternate route where a protected targeting moiety-core conjugate is reacted with an activated payload to form a targeting moiety-core-payload conjugate.
Scheme 2.
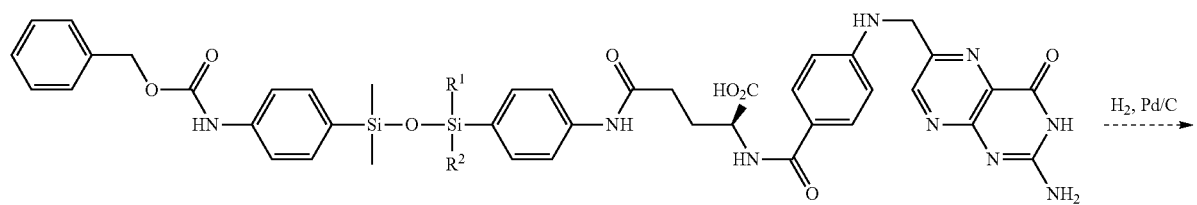
protecting targeting ligand-core conjugate

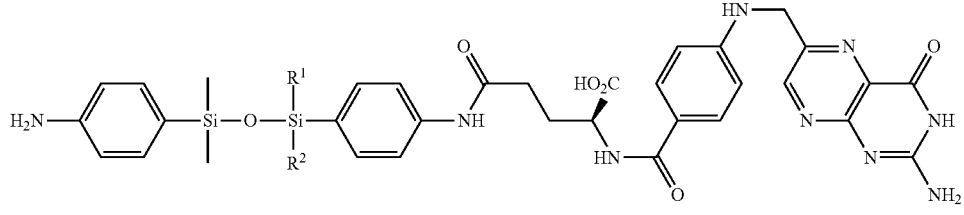
targeting ligand-core conjugate
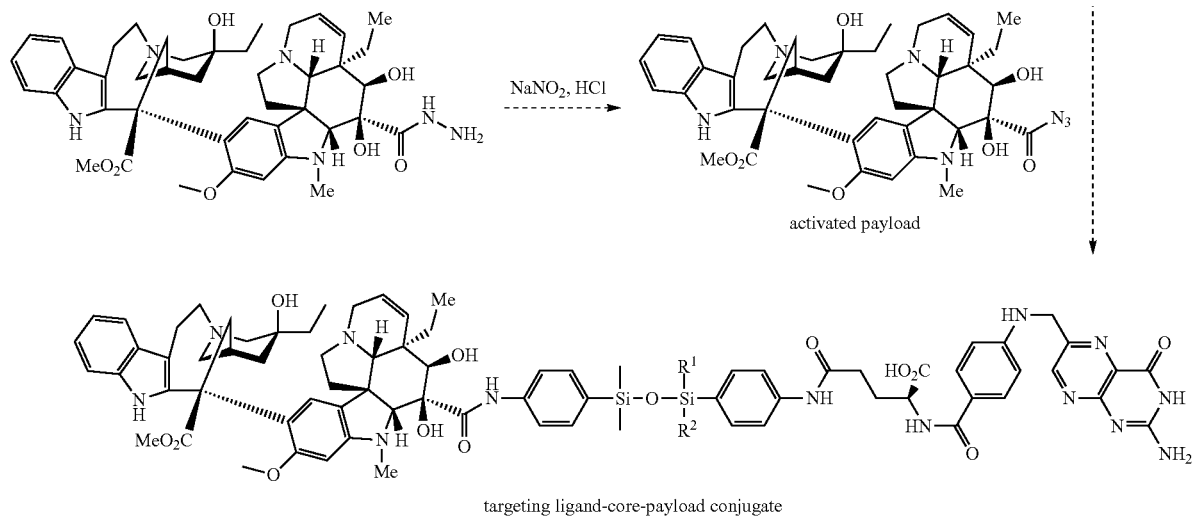
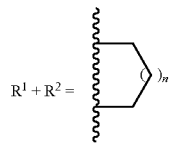
n = 1, 2, 3
$R^1 = R^2 =$ Me, i-Pr, t-Bu
$R^1 =$ Me, $R^2 =$ i-Pr
Example 98: Vinblastine-Folic Acid Conjugates
Siloxane conjugates with a vinblastine payload and a folic acid targeting moiety are synthesized following a route as described in Example 97.
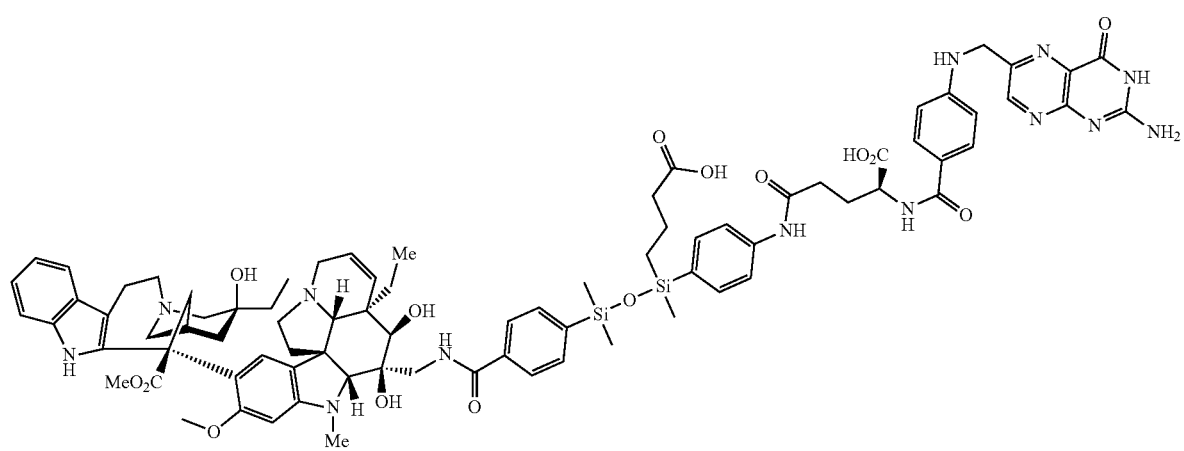

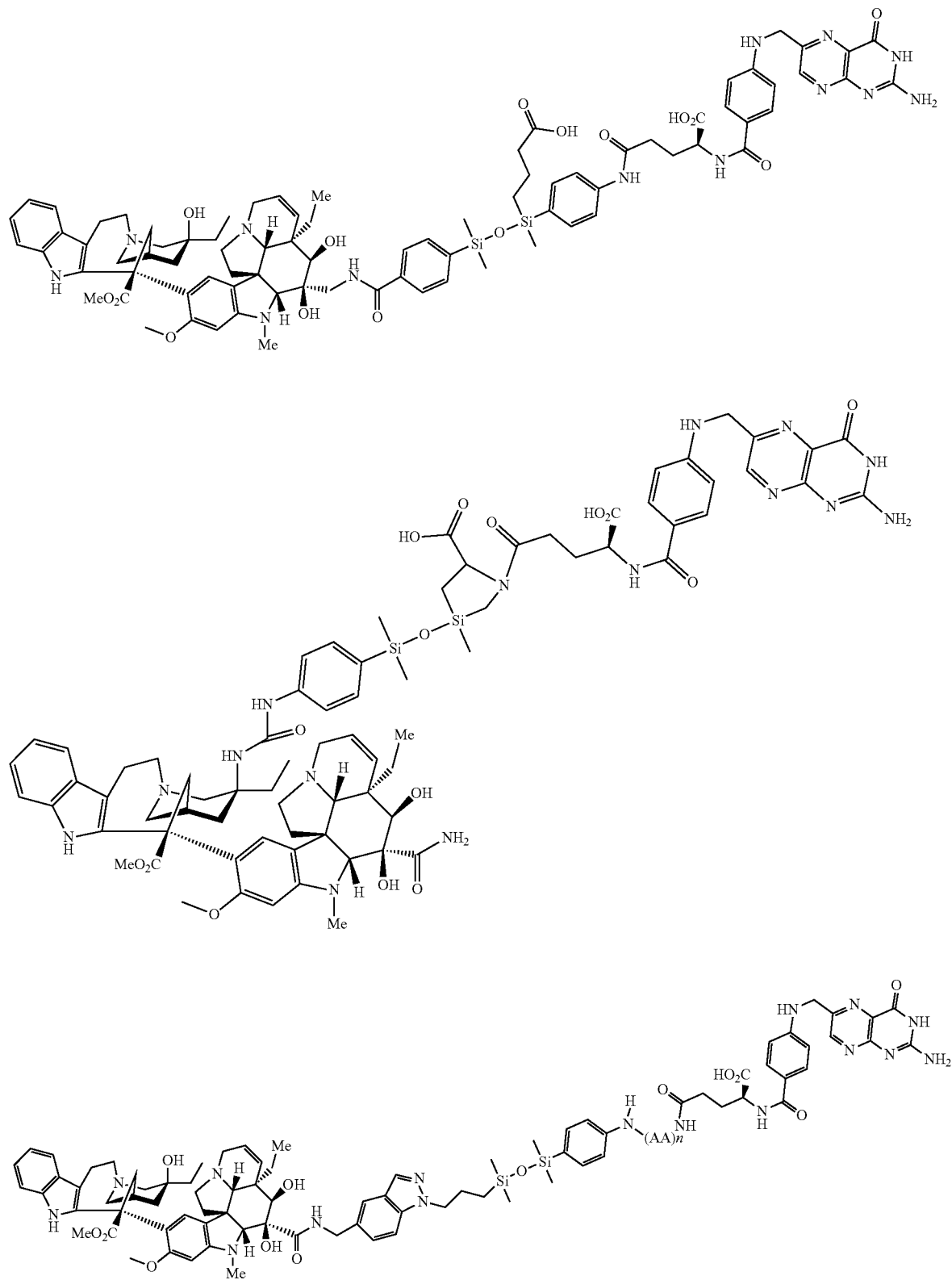
AA = amino acids (natural, unatural)

Example 99: Vinblastine-Arginylglycylaspartic Acid (Vinblastine-RGD) Conjugate Siloxane conjugates with vinblastine payload and a RGD targeting moiety are synthesized following a route as described in Example 97.

cyclo-diketopiperazine-RGD-disiloxane vinblastine construct

Example 100: Vinblastine-2-[3-(1,3-dicarboxypropyl)ureido]pentanedioic Acid (Vinblastine-DUPA) Conjugates Siloxane conjugates with vinblastine payload and DUPA targeting moiety are synthesized following a route as described in Example 97.

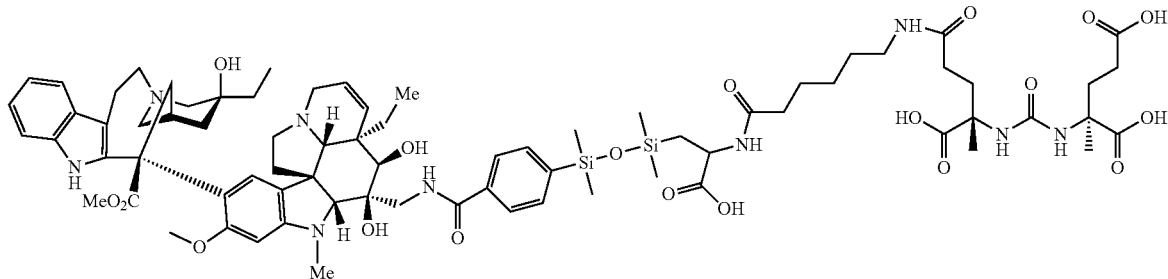

DUPA-disiloxane vinblastine construct

Example 101: Camptothecin-Folic Acid Conjugates

Siloxane conjugates with camptothecin payload and folic acid-targeting moiety are synthesized following a route as described in Example 97.

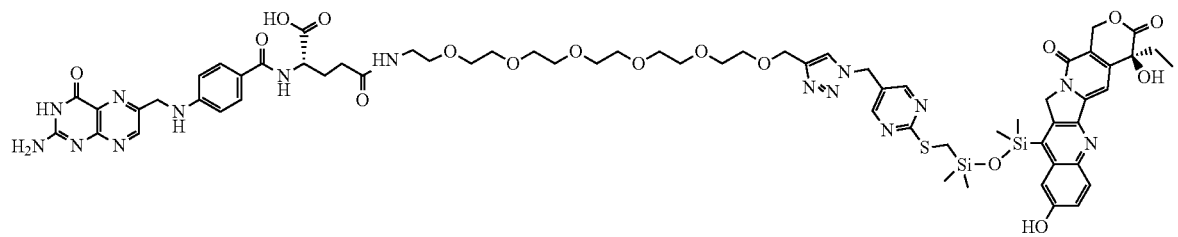

FA-PEG-SiLinker-SilaCampothecin

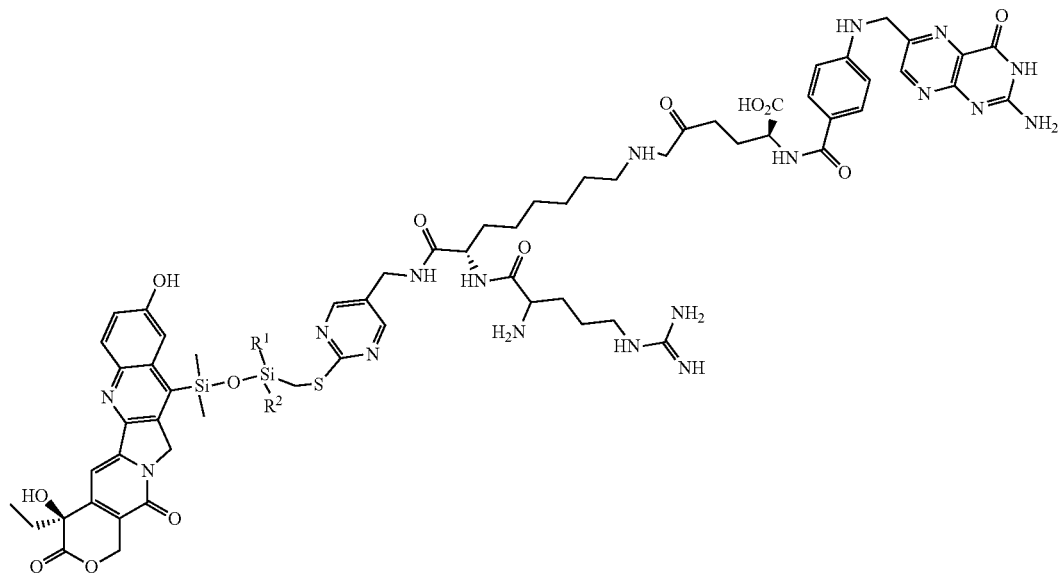

-continued

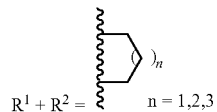

$R^1 + R^2 =$    $n = 1,2,3$ $R^1, R^2$ = independently selected: Me, i-Pr, t-Bu, (CH2)n-carboxylic acid, (CH2)n-amino acid, (CH2)n-amine (optionally further substituted)

Example 102: Platinum(II)-Folic Acid and Platinum(IV)-DUPA Acid Conjugates

Siloxane conjugates with platinum (II) and platinum (IV) payload and DUPA targeting moieties are synthesized following a route as described in Example 97. These conjugates are pictured below.

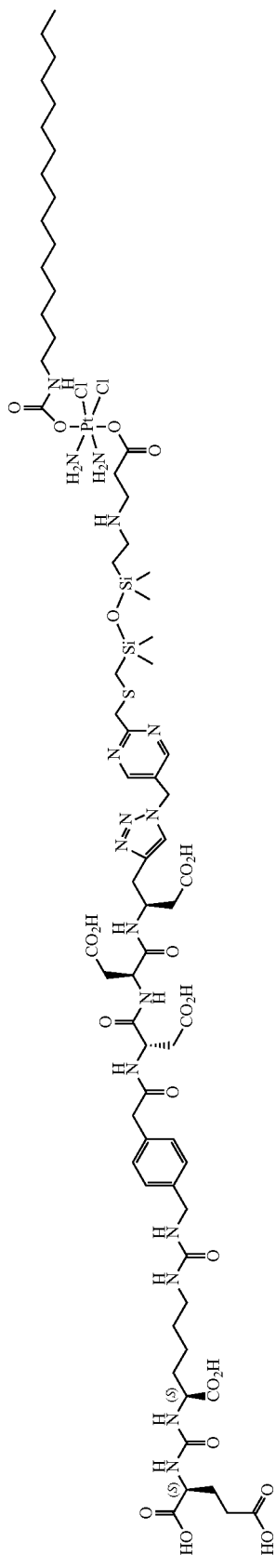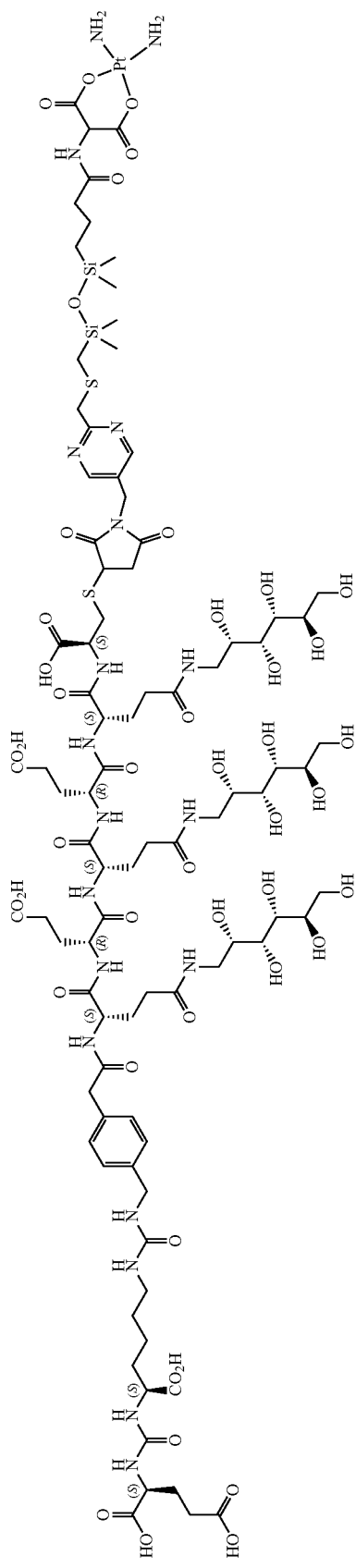

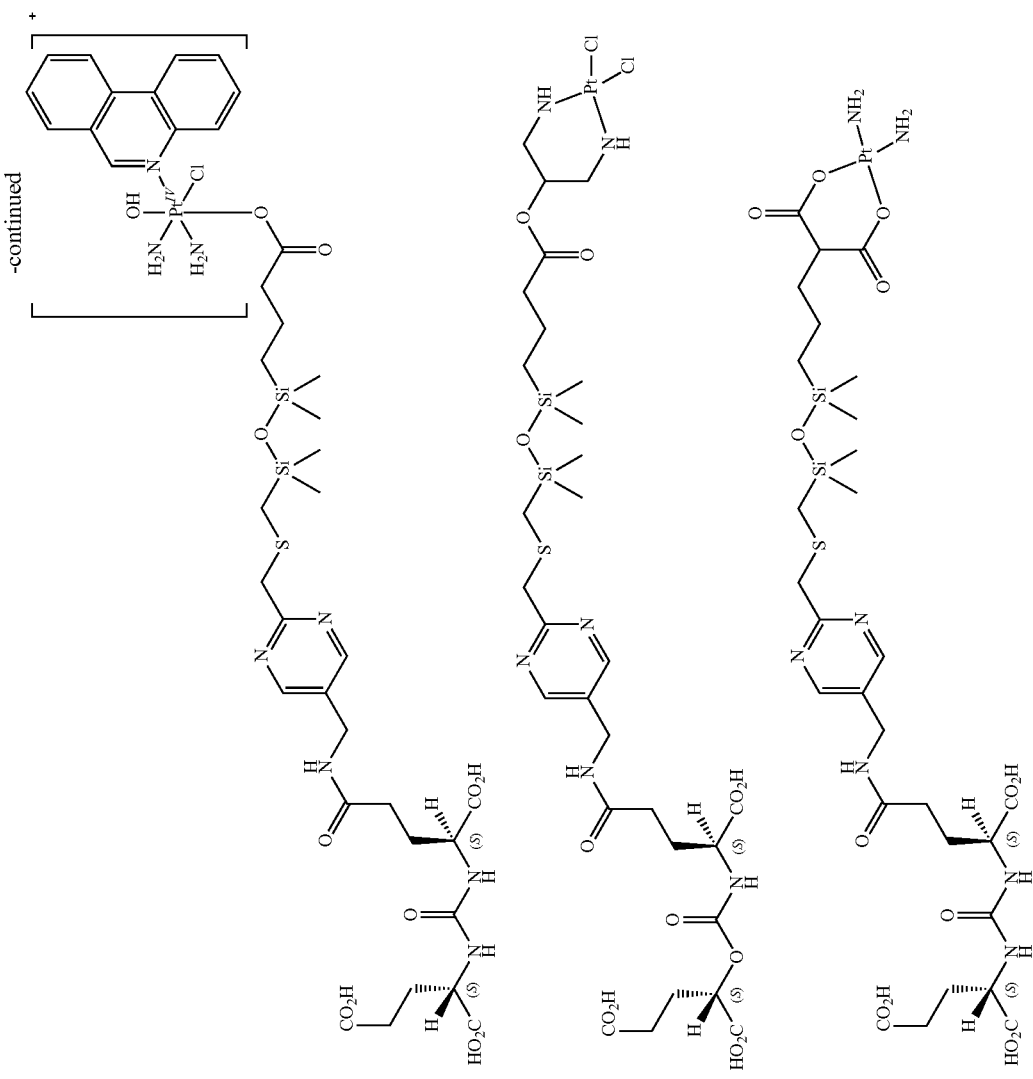

Example 103: Fluorophore/Quencher-Folic Acid Conjugates

Siloxane conjugates with a fluorophor/quencher payload and folic acid-targeting moieties are synthesized following a route as described in Example 97. These conjugates are pictured below.

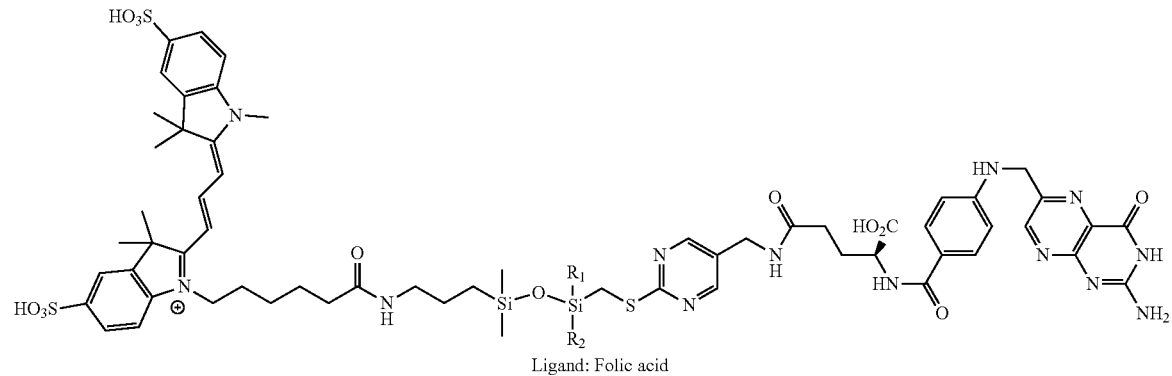

Ligand: Folic acid

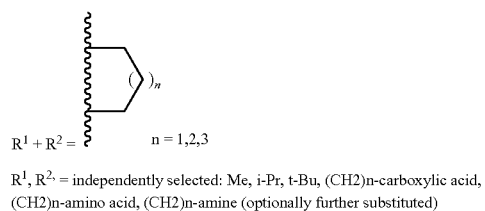

$R^1, R^{2,}$ = independently selected: Me, i-Pr, t-Bu, (CH2)n-carboxylic acid, (CH2)n-amino acid, (CH2)n-amine (optionally further substituted)

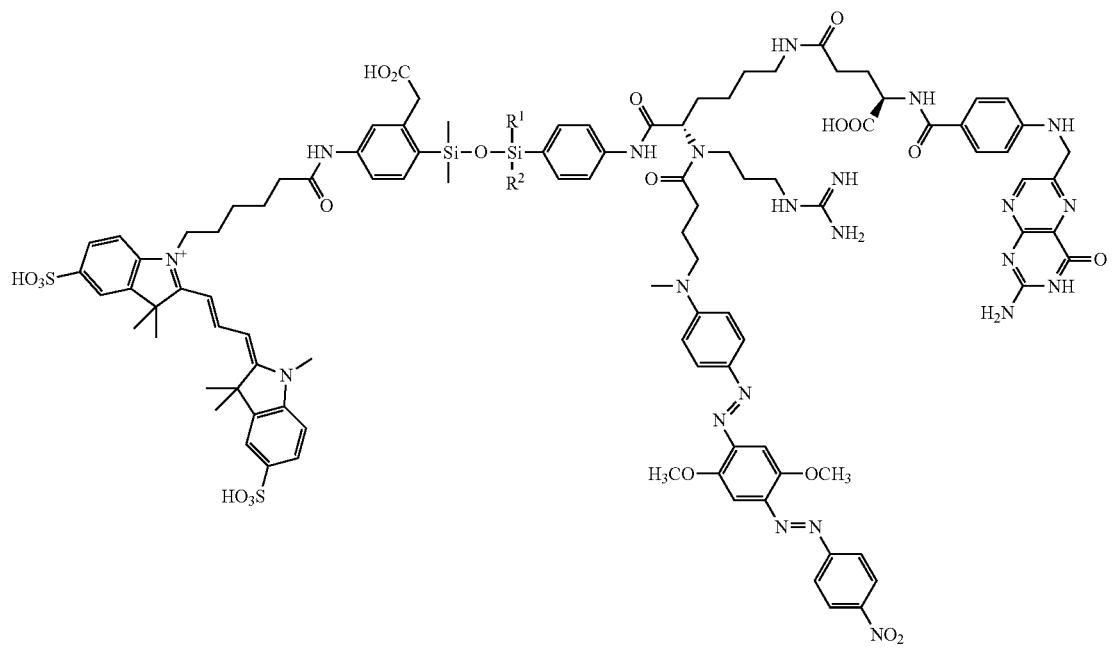

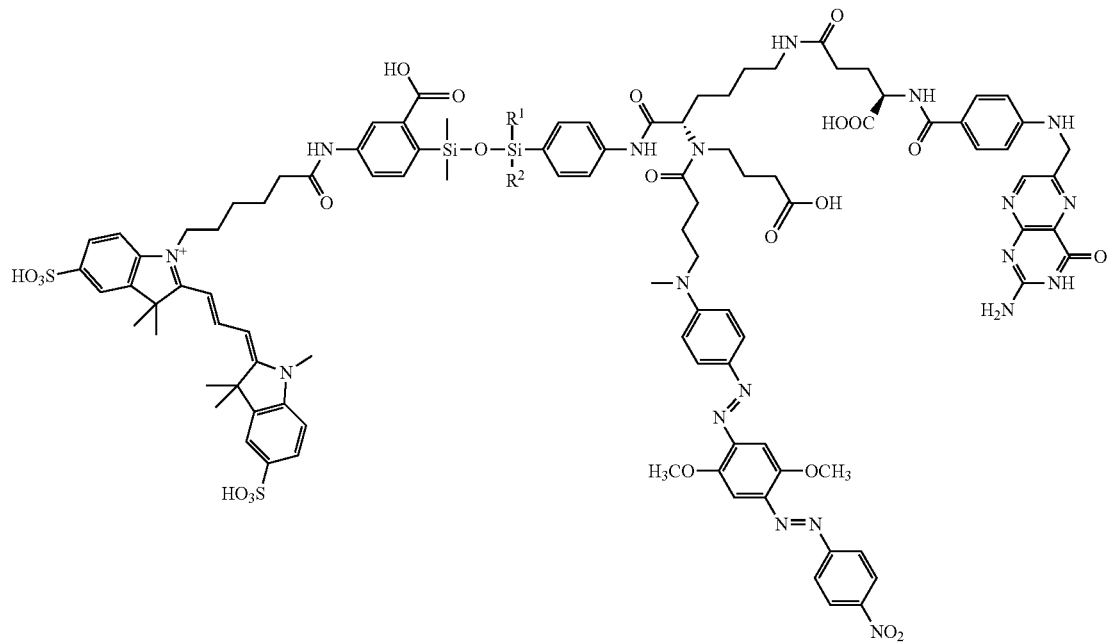
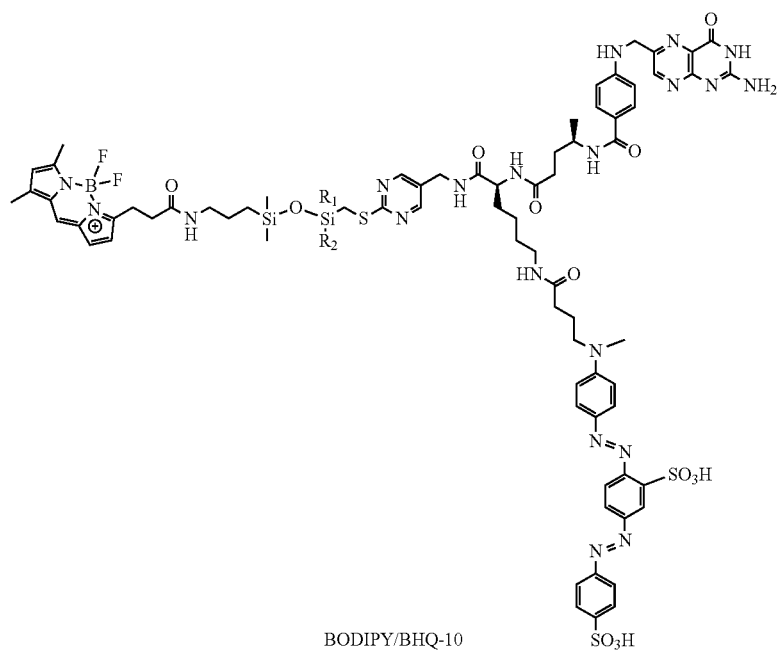
BODIPY/BHQ-10

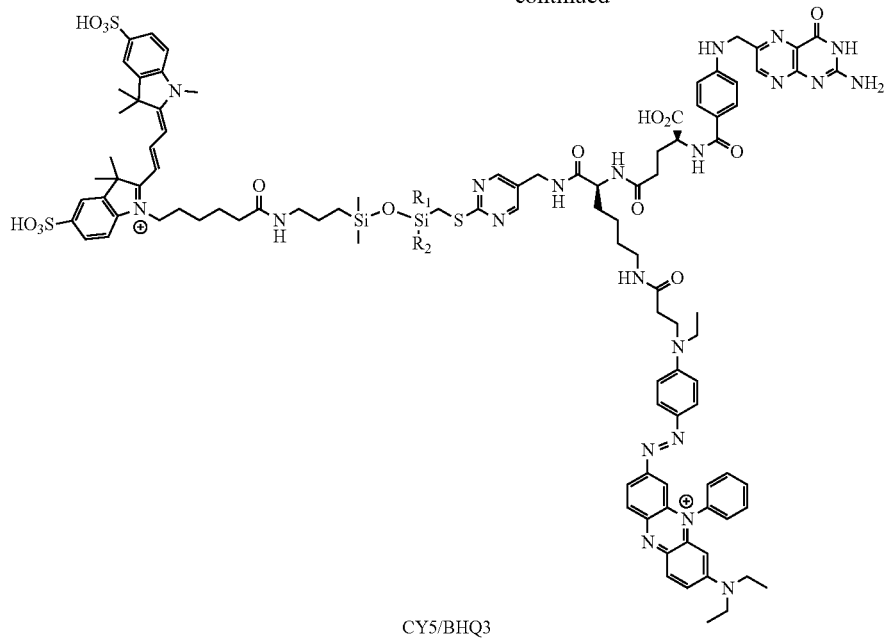

CY5/BHQ3

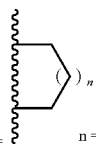    n = 1,2,3

R$^1$ + R$^2$ =

R$^1$, R$^{2,}$ = independently selected: Me, i-Pr, t-Bu, (CH2)n-carboxylic acid, (CH2)n-amino acid, (CH2)n-amine (optionally further substituted)

Example 104: Fluorescein-Folic Acid Conjugates

Siloxane conjugates with a fluorescein payload and folic acid targeting moieties are synthesized following a route as described in Example 97. These conjugates are pictured below.

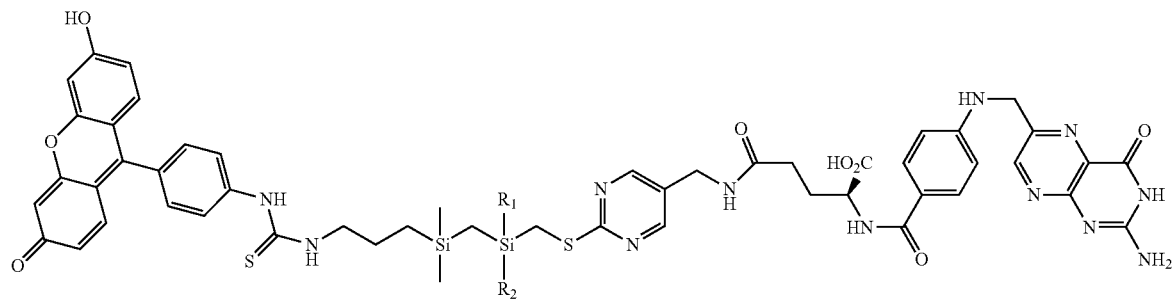

Ligand: Folic acid

R$^1$ + R$^2$ = 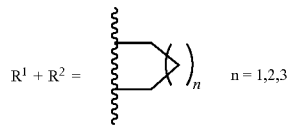    n = 1,2,3

R$^1$, R$^{2,}$ = independently selected: Me, i-Pr, t-Bu, (CH2)n-carboxylic acid, (CH2)n-amino acid, (CH2)n-amino (optionally further substituted)

Example 105: Silyldiether and Silylmonoether Conjugates

Silyldiether and silylmonoether conjugates with a payload and a targeting moiety are synthesized following a route as described in Example 97. These conjugates are pictured below.

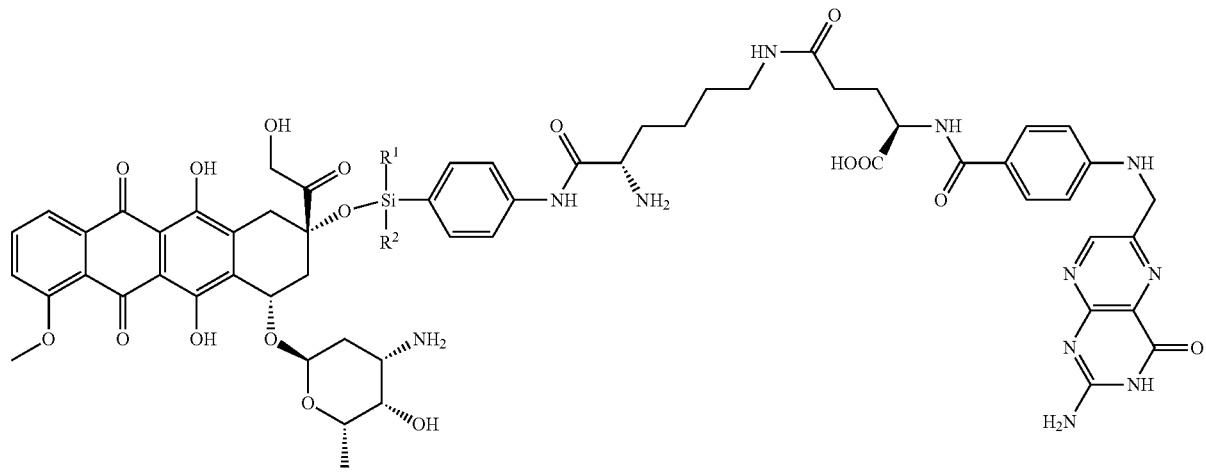

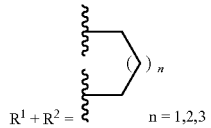

$R^1 + R^2 =$   n = 1,2,3

$R^1$, $R^2$, = independently selected: Me, i-Pr, t-Bu, (CH2)n-carboxylic acid, (CH2)n-amino acid, (CH2)n-amine (optionally further substituted)

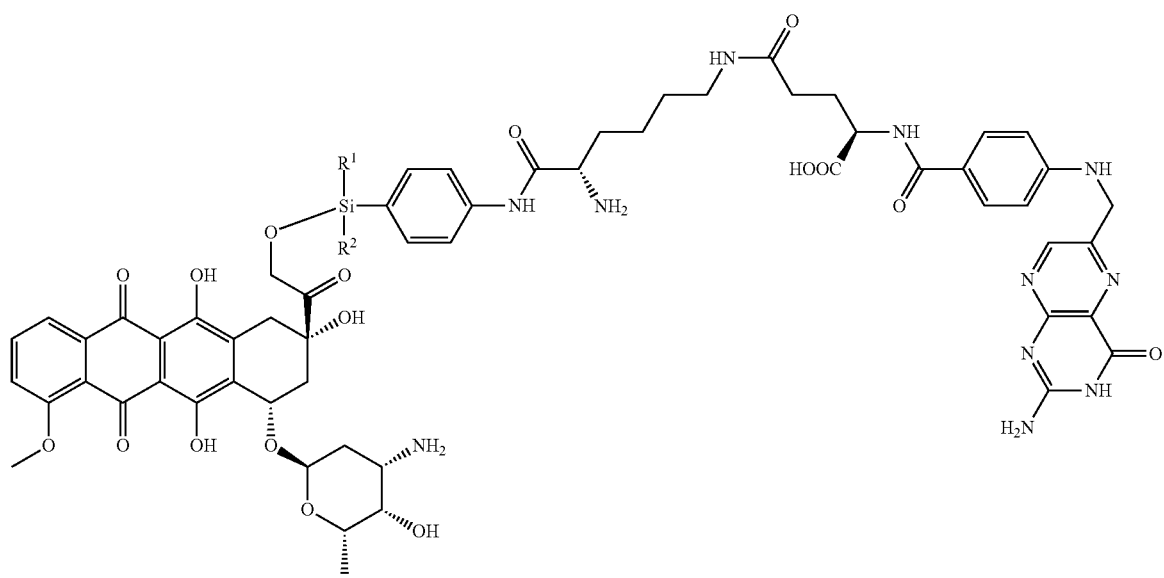

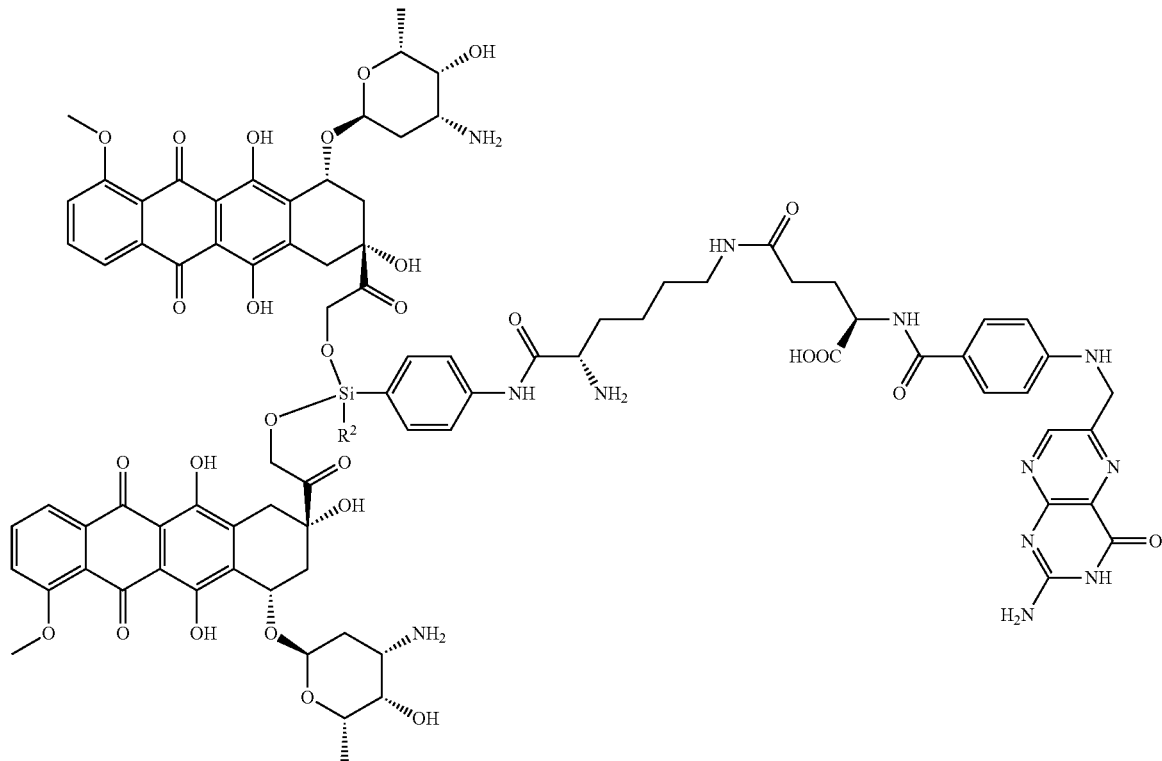
Example 106: Paclitaxel-Folic Acid Conjugates
Siloxane conjugates with a paclitaxel payload and folic acid targeting moiety are synthesized following a route as described in Example 97. These conjugates are pictured below.
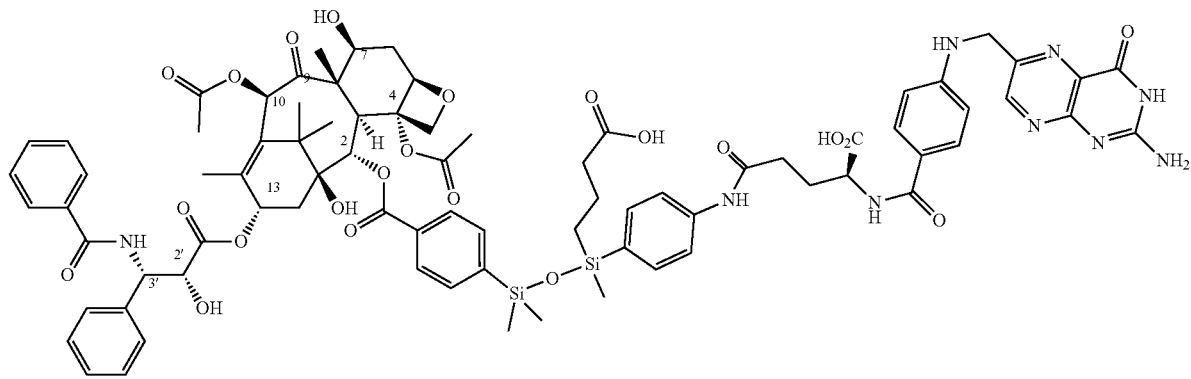
(attachment at paclitaxel C2 position)

323
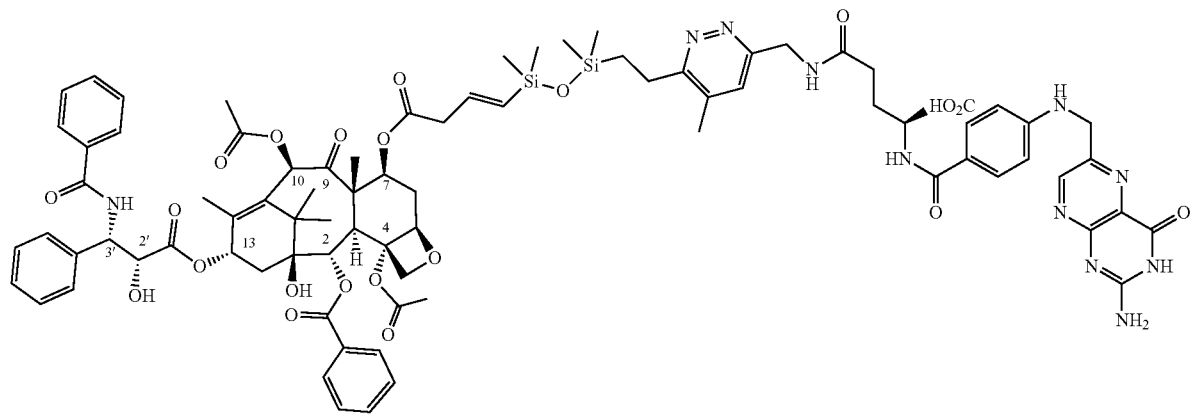
(attachment at paclitaxel C7 position)
324
-continued
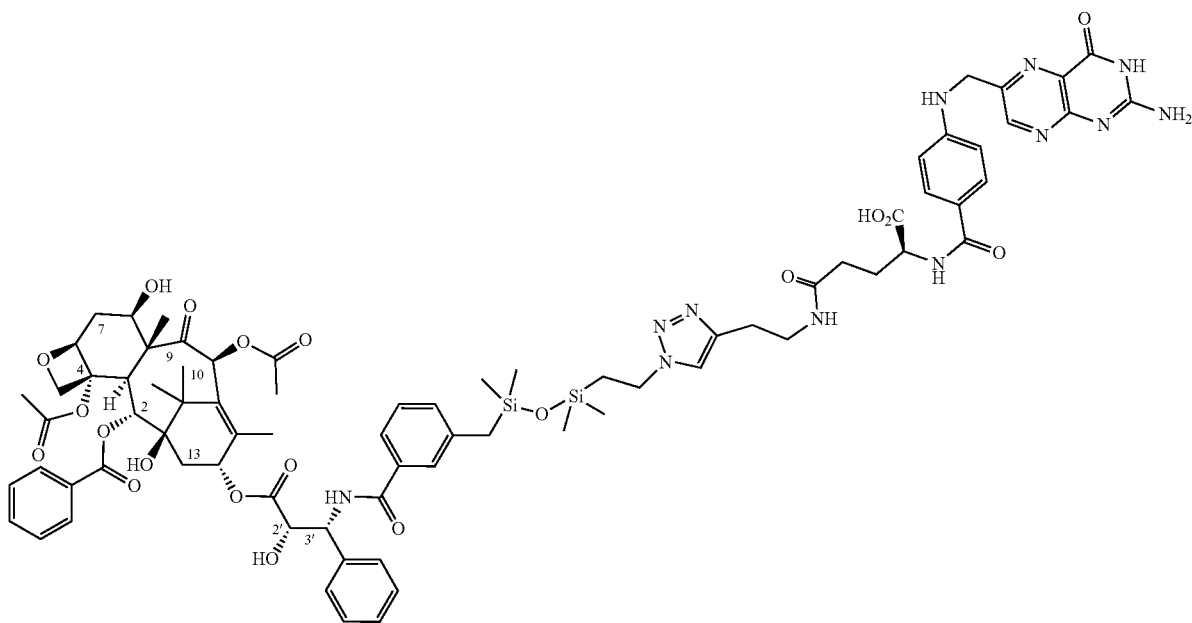
(attachment at paclitaxel C3' position)

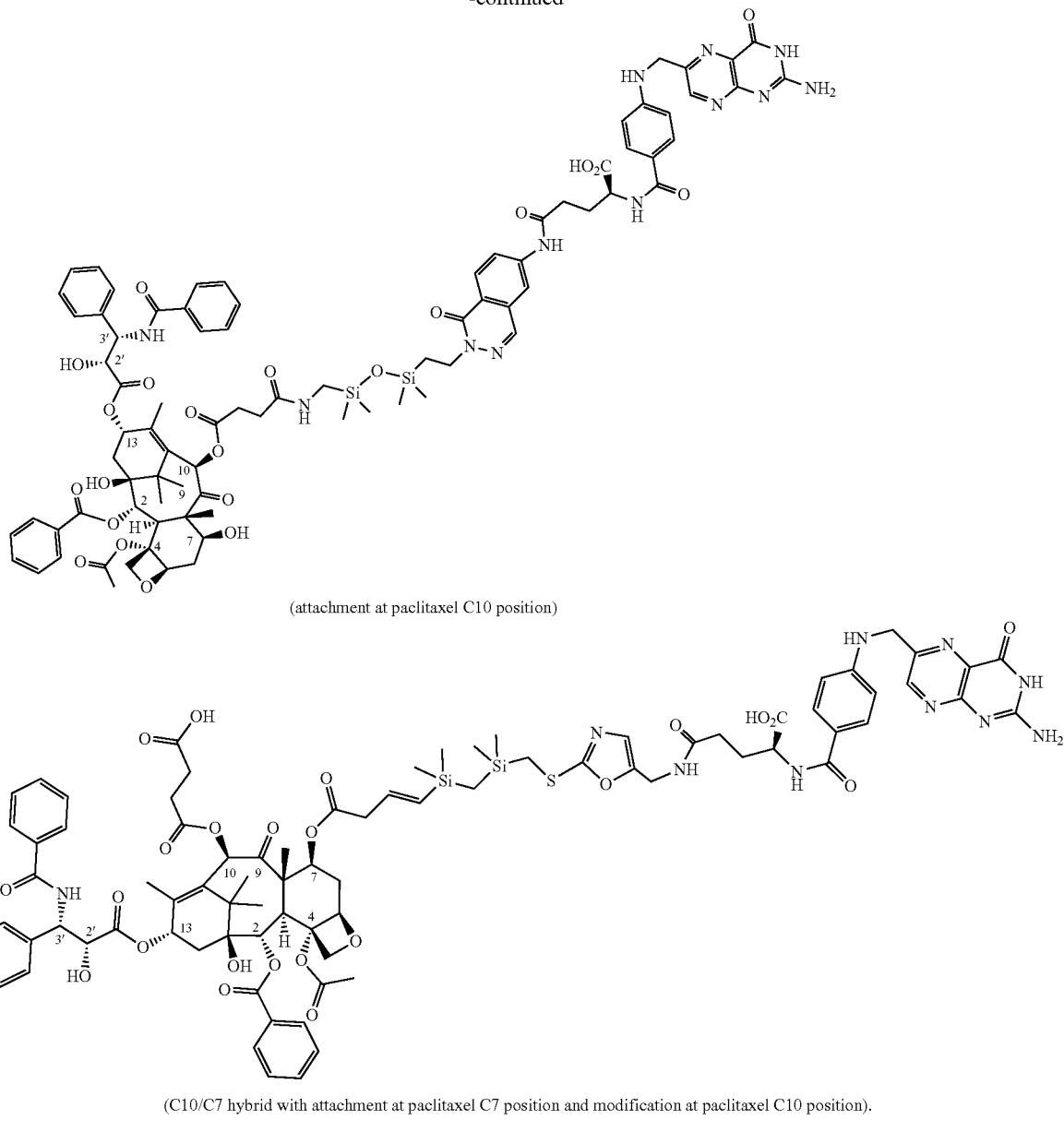

(attachment at paclitaxel C10 position)

(C10/C7 hybrid with attachment at paclitaxel C7 position and modification at paclitaxel C10 position).

Example 107: Hydrolysis Studies

Table 1 shows representative hydrolysis data of silicon-linker constructs and conjugates.

TABLE 1

| Compound | T1/2 at pH 7.4 (min) | T1/2 at pH 5.0 (min) | Comments |
|---|---|---|---|
| Example 1 | >1440 | 100 | a |
| Example 7 | >1440 | 20 | a |
| Example 8 | 1440 | 5 | a |
| Example 9 | 2400 | 25 | a |
| Example 10 | 35 | 35 | a |
| Example 15 | >240 | 25 | a |
| Example 27 | >120 | 12 | a |
| Example 28 | ND | >120 | a |
| Example 31 | ND | 30 | a |
| Example 34 | >120 | 2 | a |

TABLE 1-continued

| Compound | T1/2 at pH 7.4 (min) | T1/2 at pH 5.0 (min) | Comments |
|---|---|---|---|
| Example 79 | >1080 | 100 | a |
| Example 62 | >180 | 20 | b |
| Example 63 | >1080 | 60 | b |
| Example 69 | >360 | 240 | b |
| Example 73 | >1080 | 1080 | b |
| Example 80 | 1440 | 45 | b |
| Example 81 | 1440 | 35 | b |
| Example 82 | >1440 | 60 | a |
| Example 83 | >1440 | NA | a |

[a] experiment performed at 37° C. in HEPES buffer with 2% DMSO using water UPLC/MS.
[b] experiment performed at 20° C. in HEPES buffer with 2% DMSO using water UPLC/MS.

Example 108: Imaging Study Demonstrating Endocytosis and Si—O Cleavage

Example 79 as shown above contains a folate receptor targeting ligand, a spacer moiety, a siloxane core and two different fluorescent dyes (BODIPY and rhodamine) positioned on either side of the siloxane core. Folate receptor alpha expressing KB cells were grown in folic acid free media. The cells were incubated for 30 minutes on ice with 50 nM of Example 79, washed with fresh culture medium and then incubated in media at 37° C. for the desired length of time. The fate of both dyes was simultaneously monitored using confocal microscopy using Zeiss LSM 780 laser scanning microscope. Imaging studies revealed that at t=0 the intact Example 79 was bound to the folate receptor on the cell surface as visualized by colocalization of red and green signals and overlap of fluorescent dyes on the cell surface, thereby showing Folate Receptors-specific binding of the silicon based conjugate. At t=30 min, endocytosis of intact Example 79 into the cell was observed as visualized by BODIPY and rhodamine fluorescent signals and overlap of dyes inside the cells (i.e., inside the endosomes). At t=30 min, cleavage of the siloxane core was observed as visualized by color separation of the two fluorescent dyes.

Example 109: Cellular Data

KB cells in culture were seeded in white clear bottom 96-well tissue culture plate at a density of 5,000 cells per well in a folate free RPMI media with 10% FBS a day prior to compound addition. Cells were counted visually with a hemocytometer and diluted accordingly to obtain the desired density. Cells were allowed to incubate for 24 hours in a humidified $CO_2$ atmosphere in an incubator at 37° C. The spent media was aspirated and replenished with 100 µL of fresh media containing a 3-fold serial dilution of compound with concentrations ranging from 0.3 to 2000 nM and with a final DMSO concentration of 0.1%. Blank wells without compound were also treated with media containing 0.1% DMSO. Cells were incubated for 2 h and washed 4 times with fresh media. The plates were incubated for an additional 70 h in an incubator at 37° C. in 100 uL fresh folate free RPMI. At the end of 70 h, the spent media was removed and cells were washed once with fresh media and then suspended 100 µL of PBS. 100 µL of constituted Cell titer-glo reagent was added to each well and luminescence was recorded with a VICTOR plate reader according to manufacturers' protocol.

Table 2 shows EC50 values of siloxane based conjugates.

TABLE 2

| Compound | EC50 |
| --- | --- |
| Example 80 | ~265 nM |
| Example 81 | ~156 nM |
| Example 82 | ~193 nM |

Table 3 shows percent cell kill with silicon based conjugates at 48 h.

TABLE 3

| Compound | % Kill (48 h) |
| --- | --- |
| Example 80 | 84 |
| Example 81 | 86 |
| Example 82 | 80 |

Example 110: Synthetic Lethal Payload Combinations

Silicon based conjugates for treating VHL clear cell renal carcinoma via delivery of synthetic lethal payload combinations include:

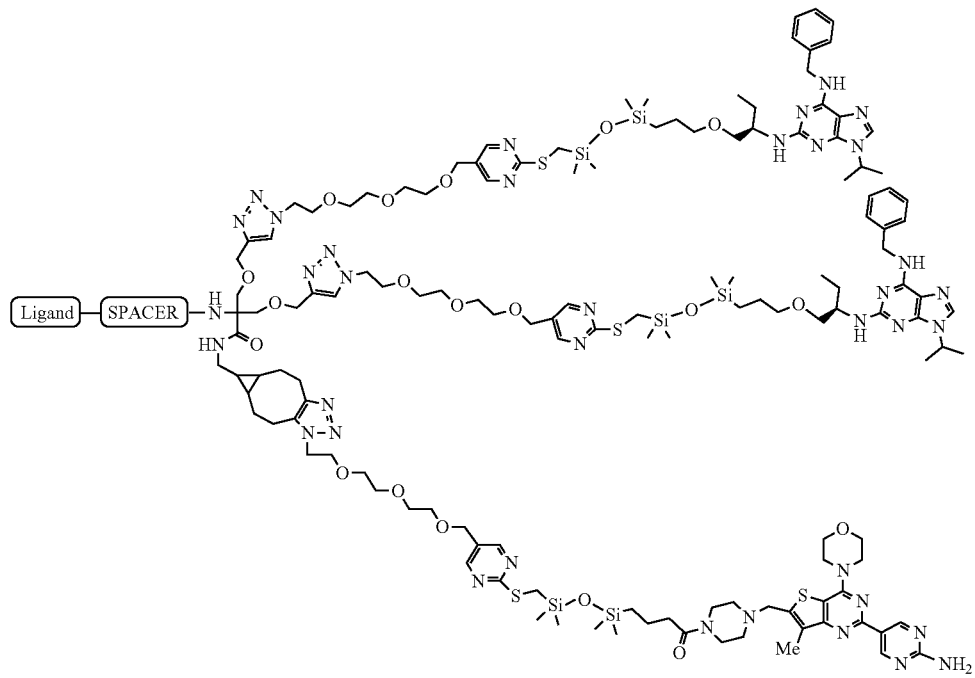

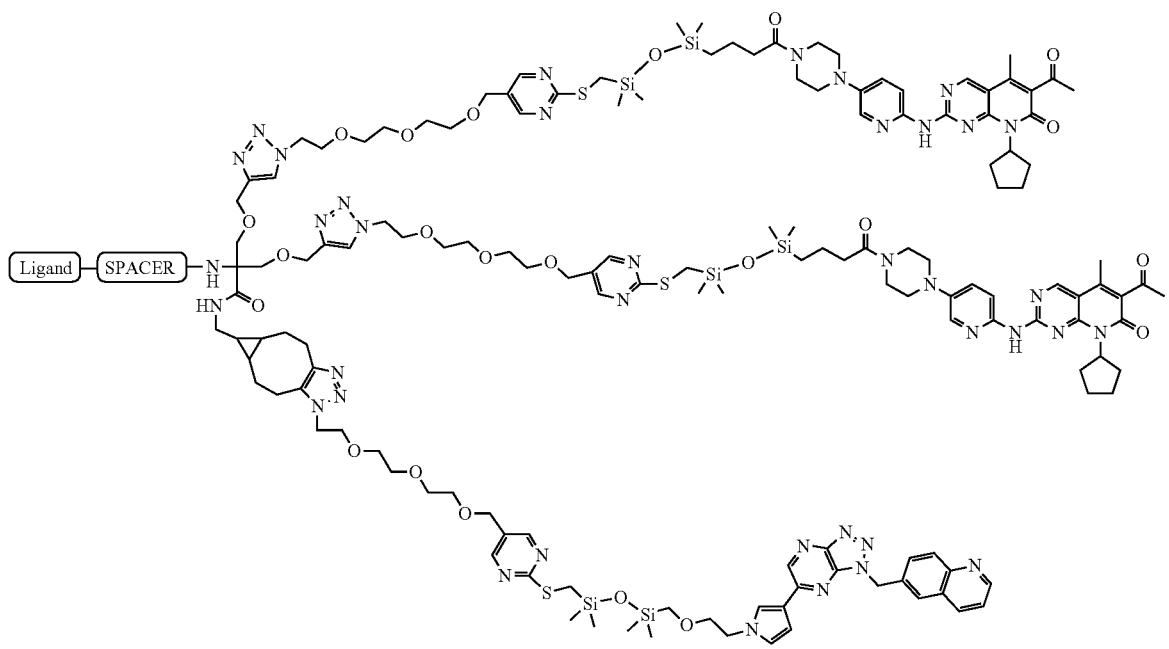
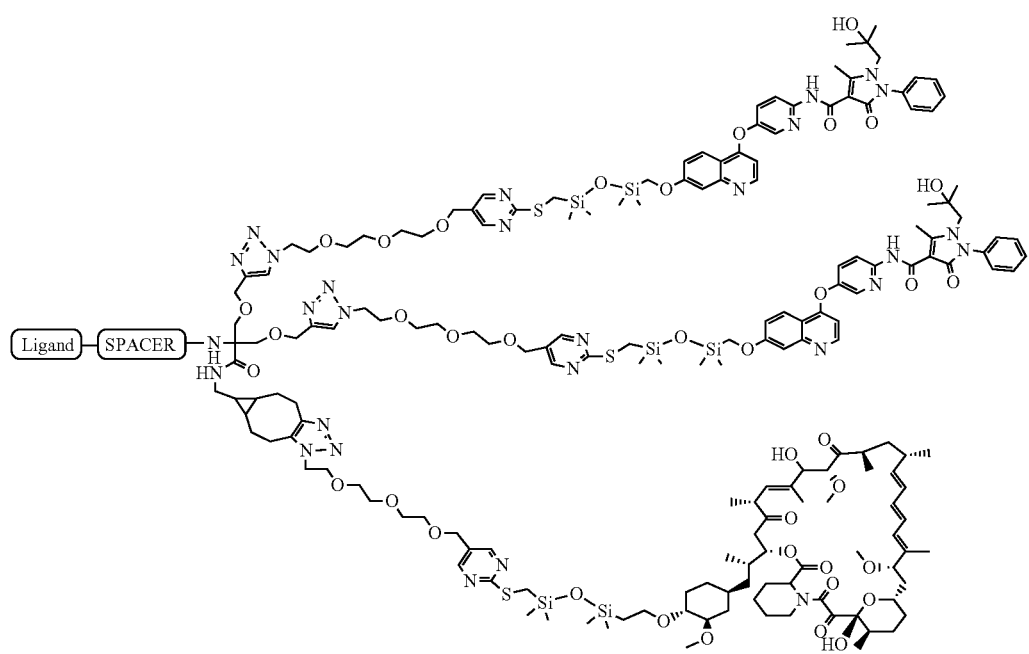

Silicon based conjugates for treating triple negative breast cancer via delivery of synthetic lethal payload combinations using, for example folic acid as a targeting ligand include:
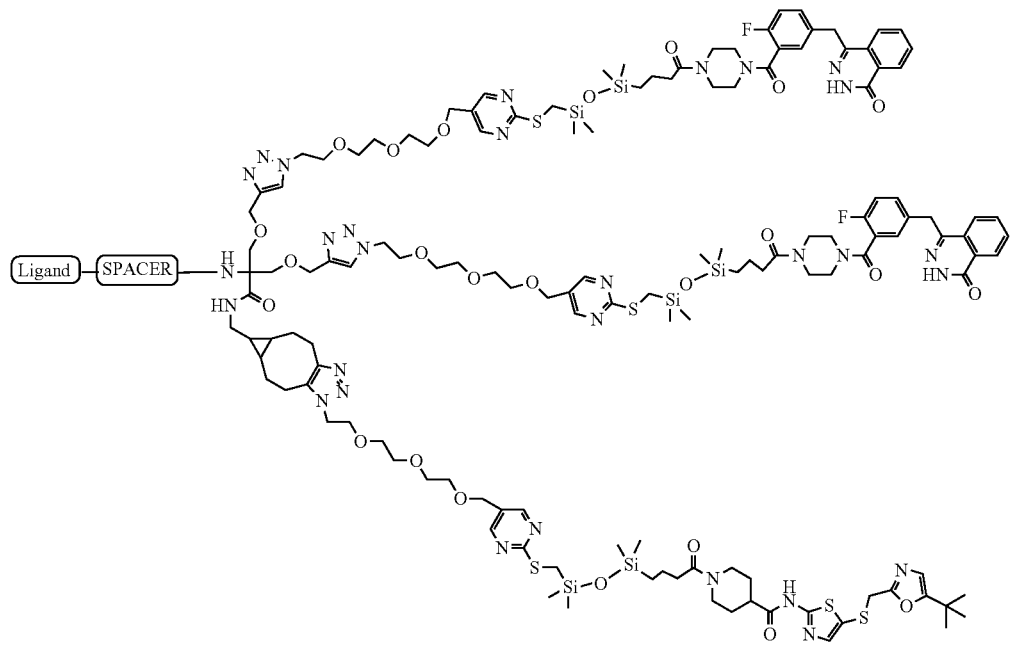
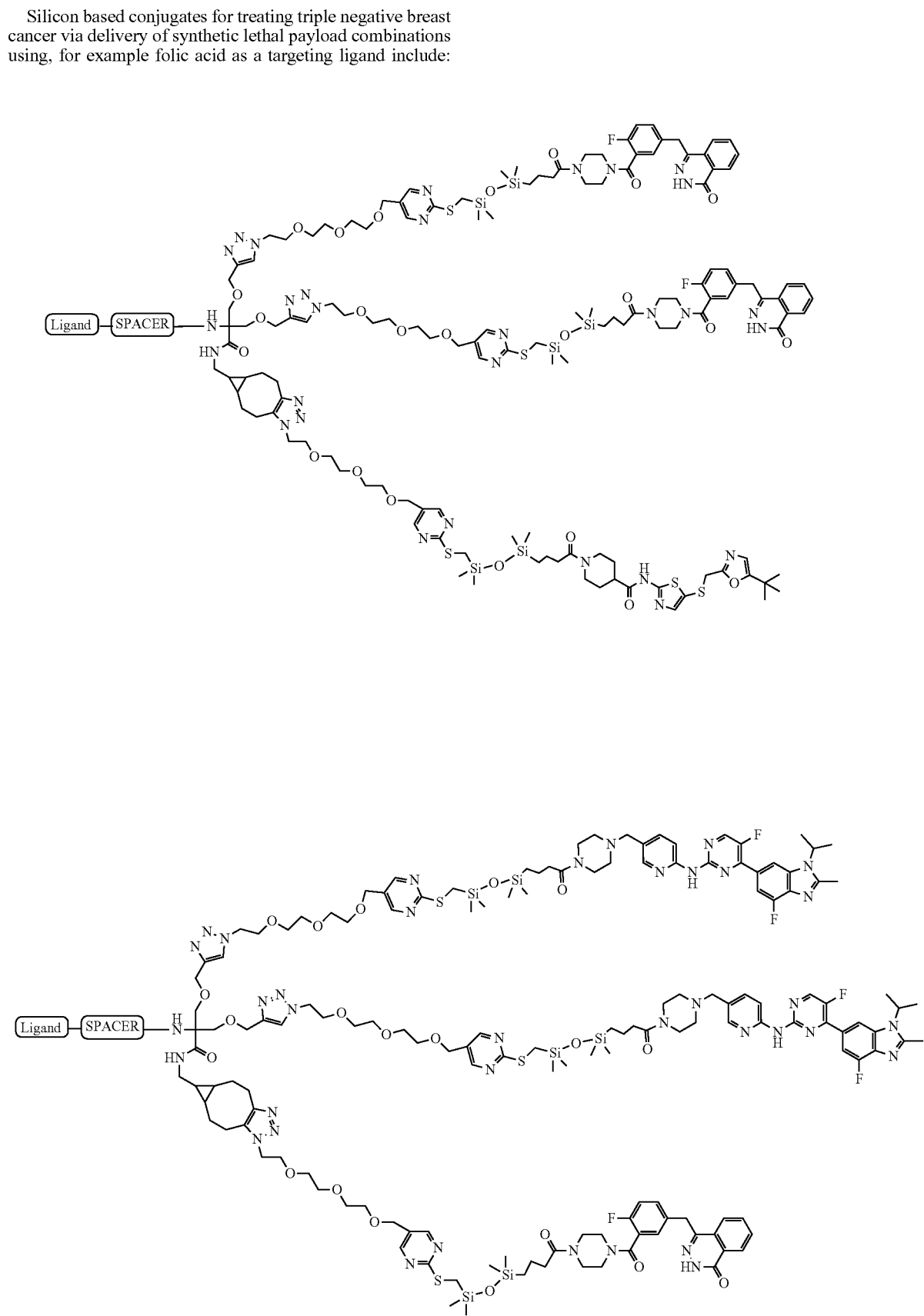

Silicon based conjugates for treating mutant KRAS cancers via, for example, an EGFR-targeting approach include:

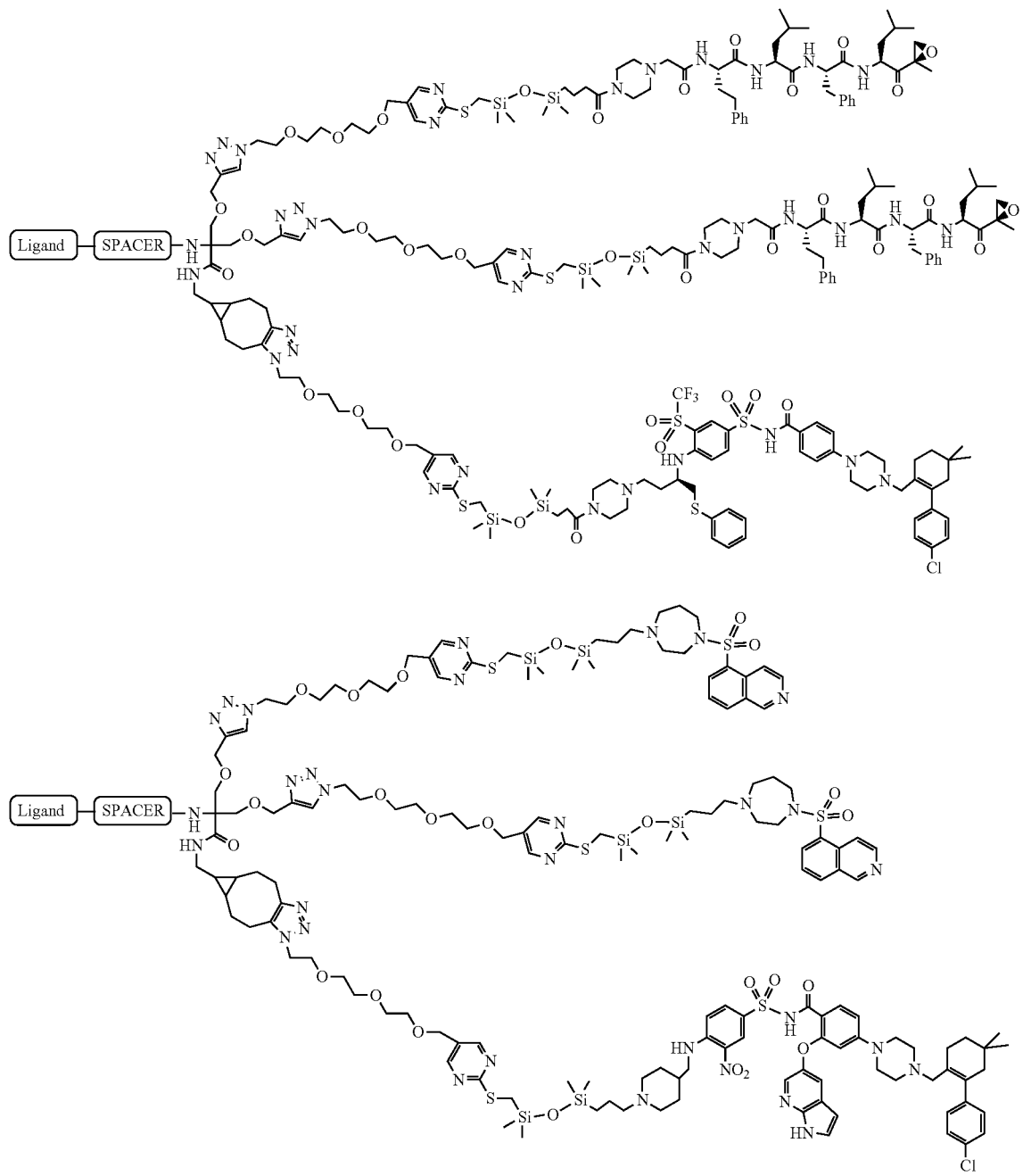

Example 111: Multiple Targeting Moieties

As described above, contemplated silicon based conjugates of the disclosure may contain multiple targeting moieties to increase avidity by increasing the number of targeting moieties for binding to a cell surface receptor. Targeting moieties are targeted toward cells, tissues, and organs shown in column 1 of Table 4. Targeting moieties are bound to receptors shown in column 2 of Table 4 with bound targeting moieties shown in brackets.

TABLE 4

| Cells/Tissues/Organs | Receptor [Ligand] |
| --- | --- |
| Brain | Transporter at BBB [Chlorotoxin], transporter at BBB [(PhPro)4] (SEQ ID NO: 1), LRP1 [AngioPep], |
| Kidney | Folic acid receptor a [folate], megalin [(KKEEE)3K] (SEQ ID NO: 2), megalin [lysozyme], |
| Liver | Asialoglycoprotein receptor ASGPR [Tris-GalNAc], LDLR [LDL] |
| Bone | Hydroxyapatite [bisphosphonate], |
| Lung | Delta-like protein-3 DLL3 receptor [DDL3 antibody] |

TABLE 4-continued

| Cells/Tissues/Organs | Receptor [Ligand] |
|---|---|
| Bladder | SLITRK6 (SLITRK6-antibody) |
| Intestine | Orally dosed silicon based conjugates are cleaved in the gut to give silanols that travel to intestines where they are absorbed and are active. Intestinal targets can be periphery restricted µ-opiod receptors [opiod PEG-silanols], chloride ion-channel, guanidine cyclase receptor [guanidine cyclase silanol] |
| Cancer | Folic acid receptor α [folate], prostate specific membrane antigen PSMA [DUPA], integrin $α_vβ_3$ receptor [RGD], receptor dystroglycan [laminin, agrin, pikachurin, biglycan], cholescystokinin receptor CCKR [chloescystokinin antagonist], carbonic anhydrase IX (CAIX) [ carbonic anhydrase inhibitors], androgen receptor [androgen antagonist], estrogen receptor [estrogen antagonist, estradiol], CD206 [humanized CD206 antibody], CD44 [hyaluronic acid, humanized CD44 antibody], CD22 [anti-CD22 single chain variable fragment scFv], CD33 [humanized anti-CD33 antibody], cMET receptor [cMET inhibitor], surface antigen in leukemia SAIL [SAIL antibody], Her-2 receptor [Herceptin], transferrin receptor TfR [transferrin mAb], glycoprotein NMB gpNMB [humanized anti-gpNMB monoclonal antibody], Trop-2 [anti-Trop-2-antibody], luteinizing hormone-releasing hormone receptor [lutenizing hormone-releasing hormone], matrix metalloproteinase-2 receptor MMP-2 [chlorotoxin CTX], HSP90 [HSP90 inhibitor], somatostatin receptor (subtypes 2, 3 5) [somatostatin analogs: octreotide, lanreotide] |
| Joints/Synovial Fluid | Folic acid receptor a [folate], [albumin], CD44 [hyaluronic acid, humanized CD44 antibody], |
| Macrophages | CD206 [CD206 antibody, Manocept], CD44 [hyaluronic acid, humanized CD44 antibody], |
| Dendritic cells | NY-ESO-1 antigen [DEC205 mAb], |
| Lymphatic system | CD206 [CD206 antibody, Lymphoseek], |
| Muscular System | OCTN2 transporters |

Silicon based conjugates that bind to an integrin receptor include:

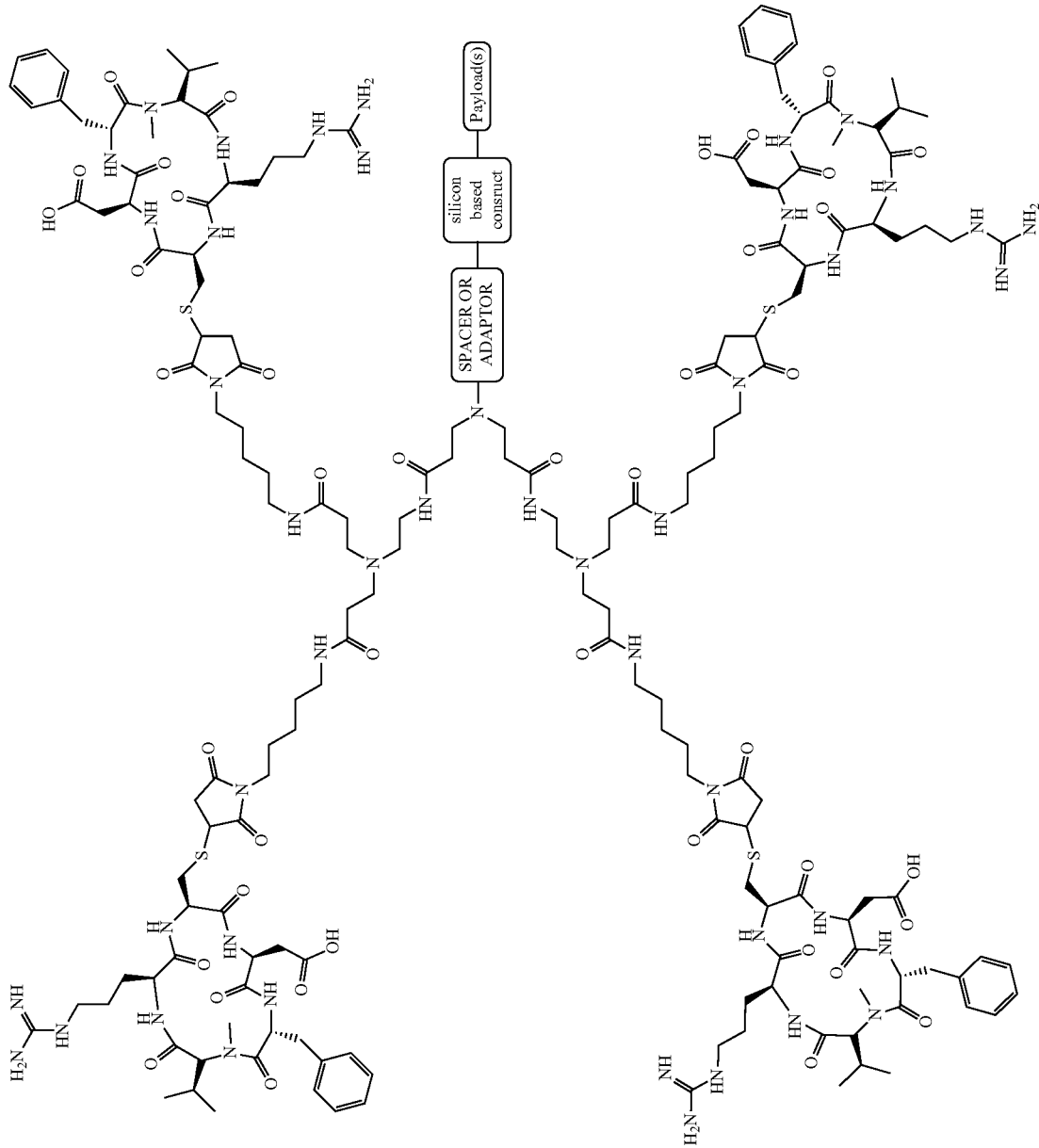

-continued
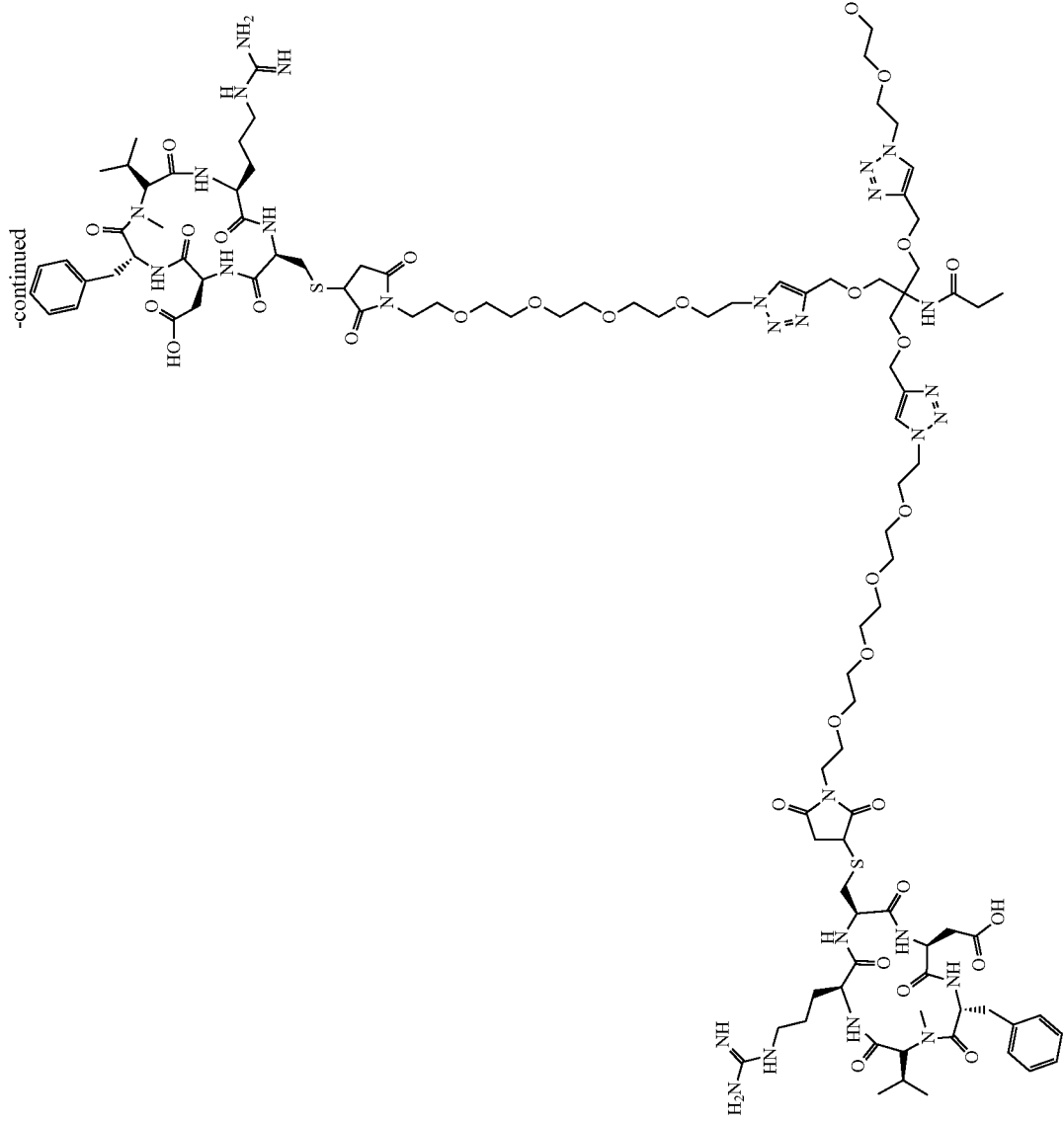

-continued
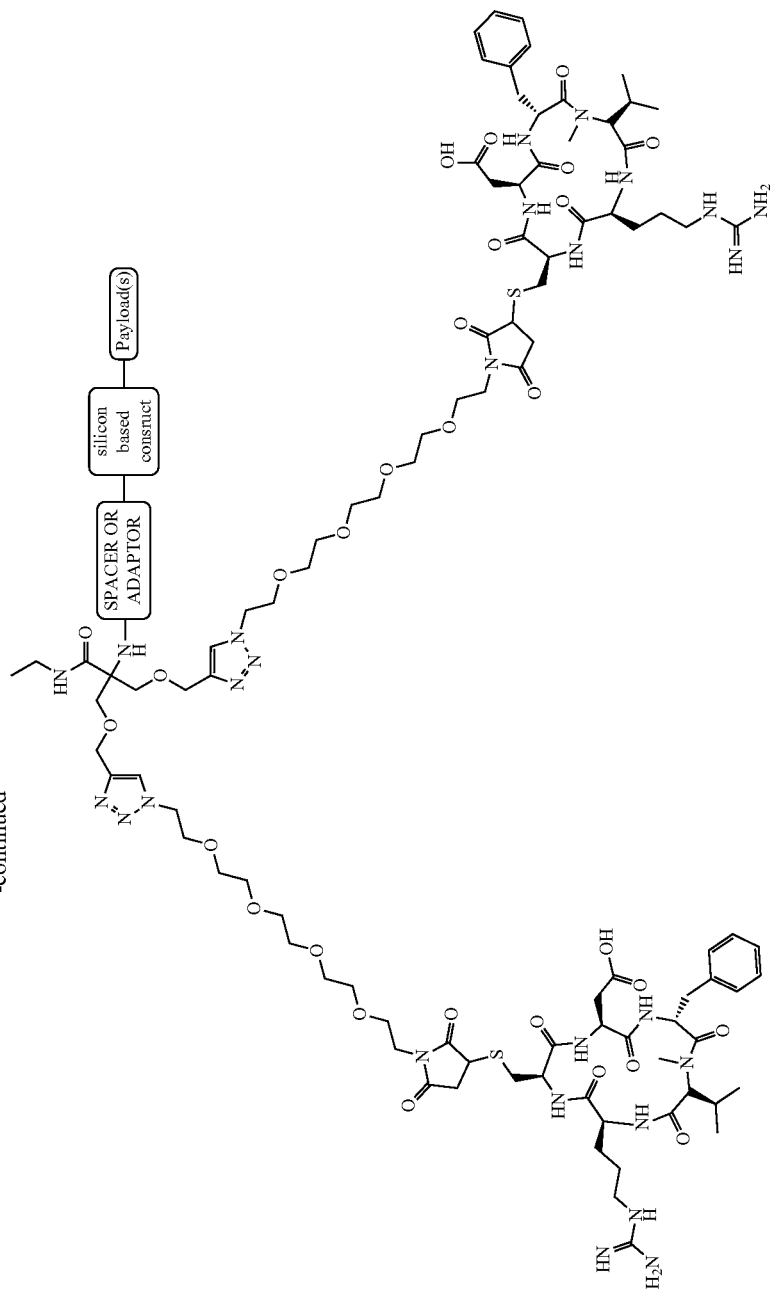

Silicon based conjugates having Tris-BPC-NeuAcα2-6Galβ1-4GlcNAc targeting moieties that bind to CD22 receptor (Siglec-2), a regulator of BCR signaling, include:
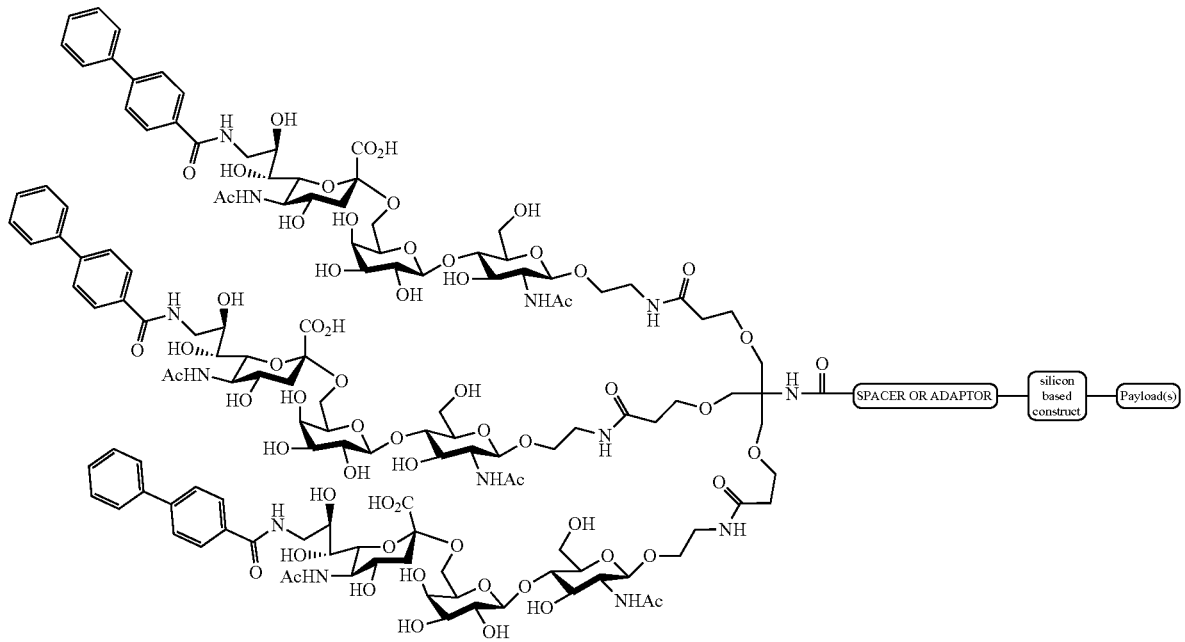
Silicon based conjugates having oligomeric saccharide of hyaluronic acid targeting moieties that bind to CD44

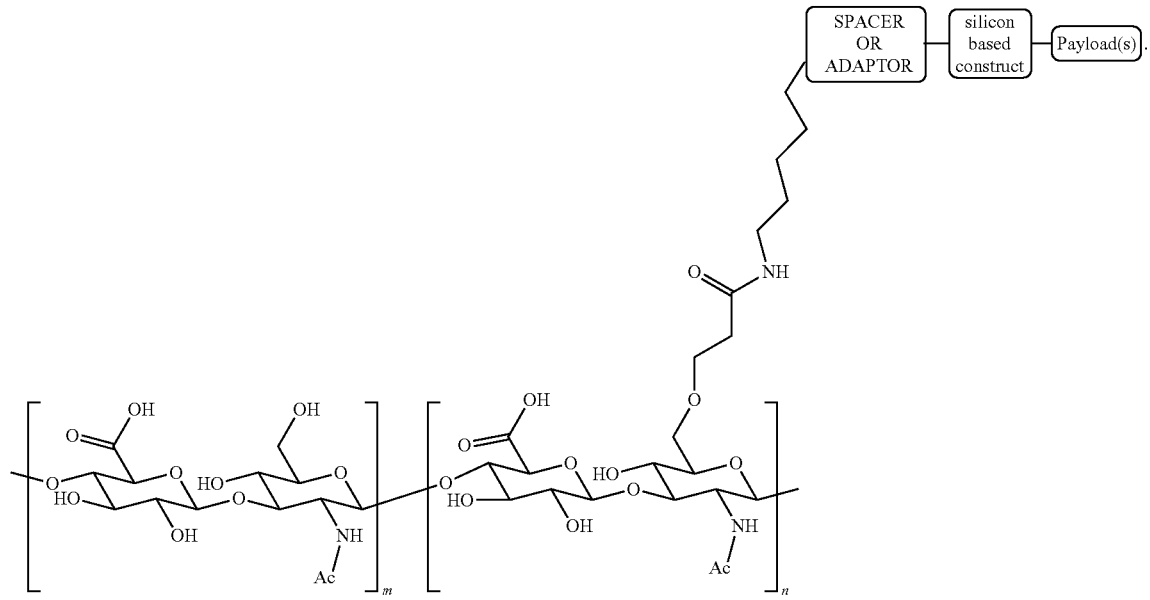
Disaccharide Unit of Hyaluronic Acid
Silicon based conjugates having folate targeting moieties that bind to folate receptor include:
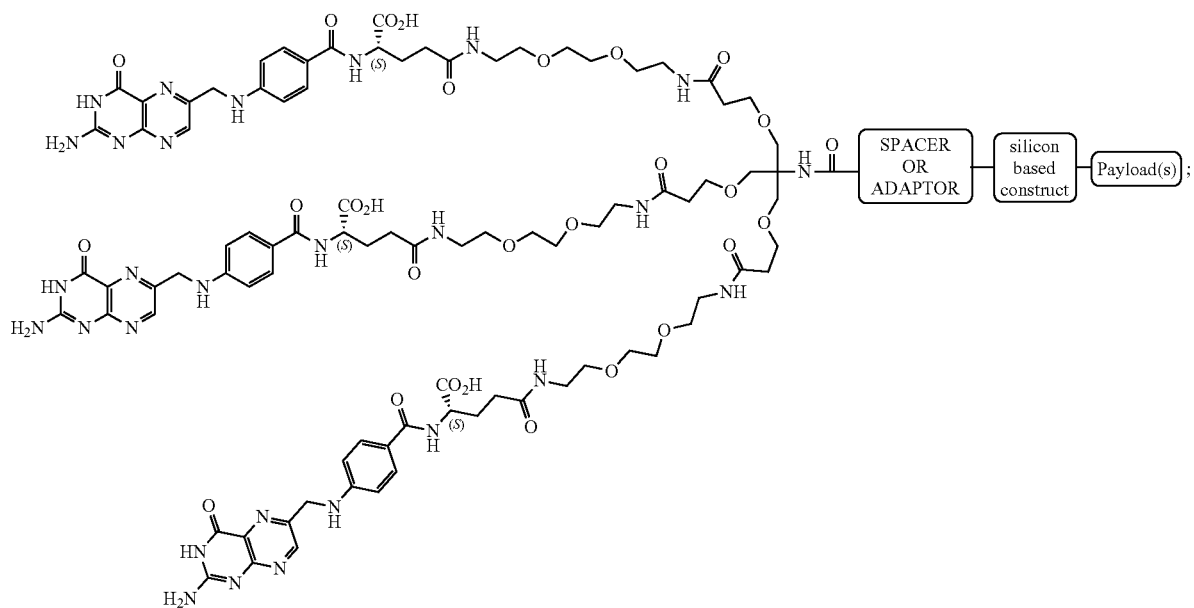

-continued
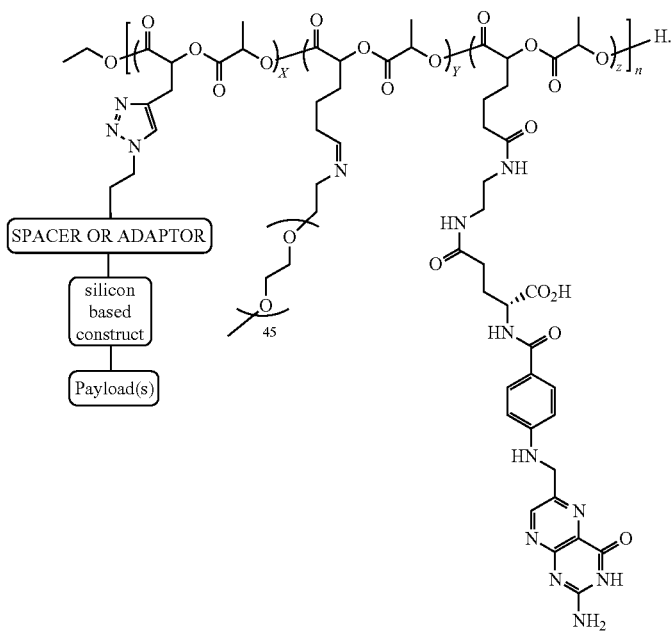
Silicon based conjugates having urea-based DUPA targeting moieties that bind to PSMA (prostate specific membrane antigen) include:
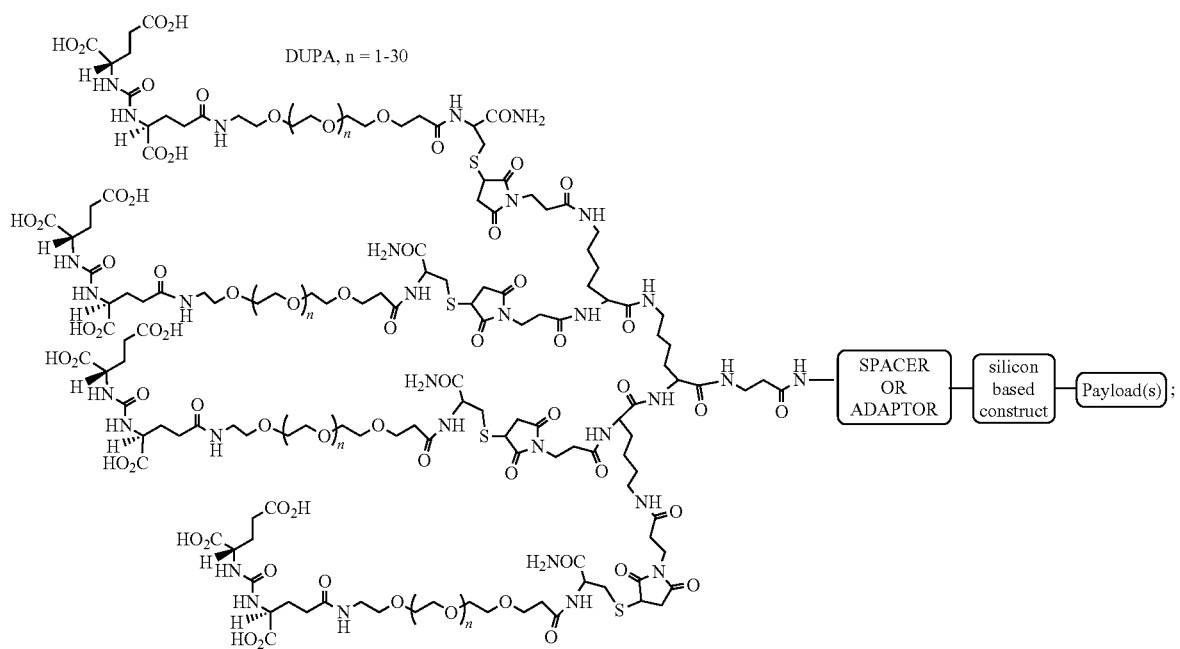

-continued

Silicon based conjugates having Neurotensin (NT) triazole analogs that bind to low density receptor-related protein 1 (LRP1) include:

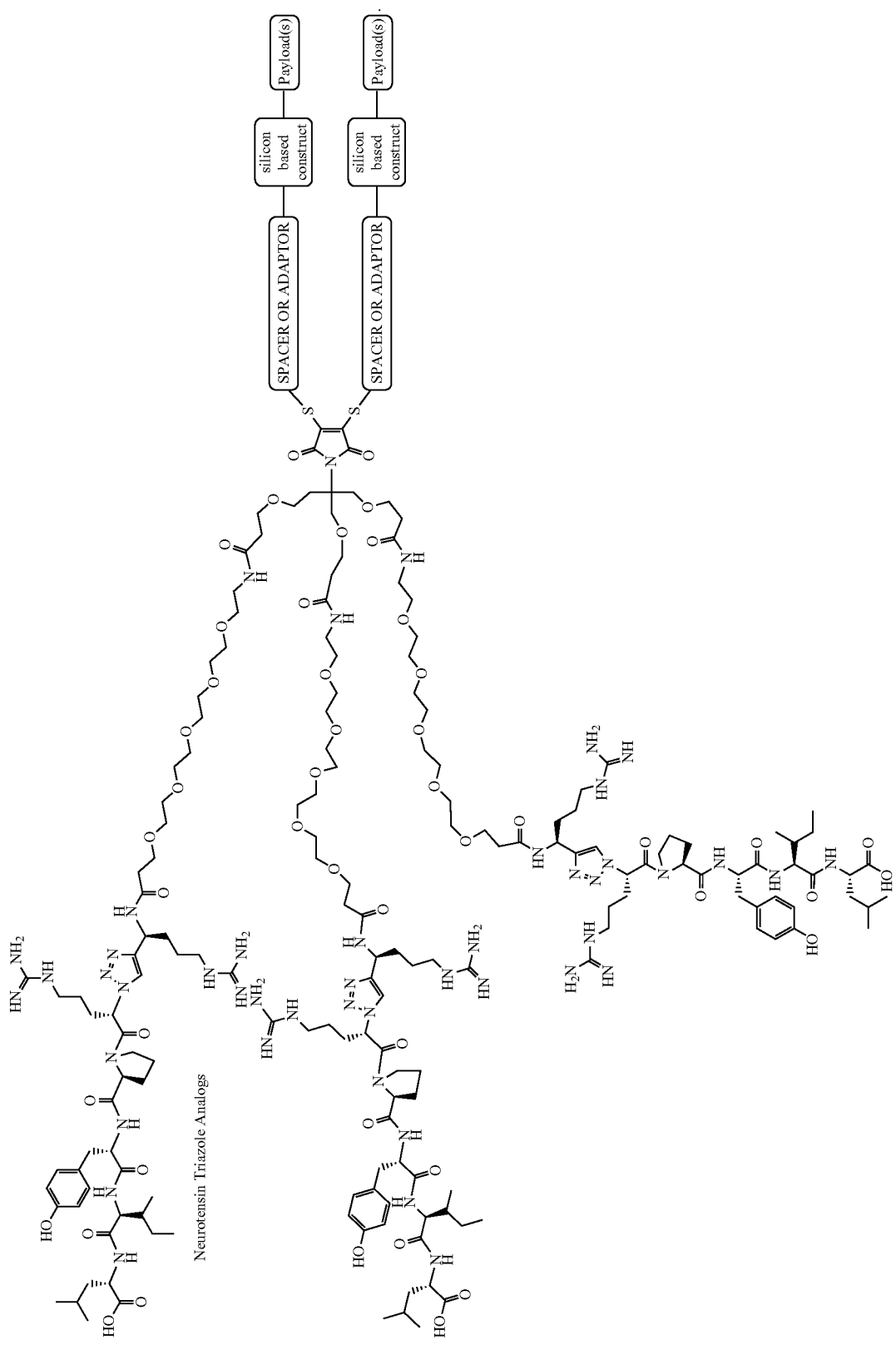

Silicon based conjugates having Carbonic anhydrase IX targeting moieties that bind to Carbonic anhydrase IX (CALX) receptor include:
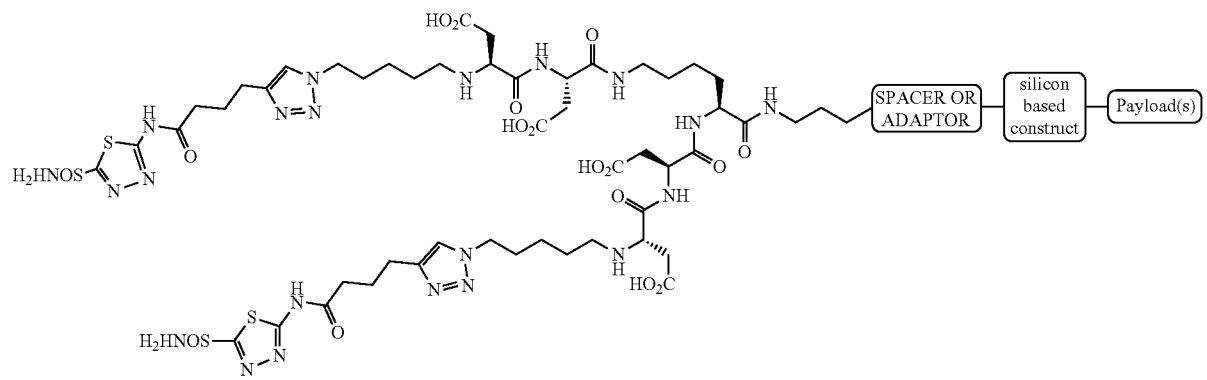
Carbonic anhydrase IX inhibitor
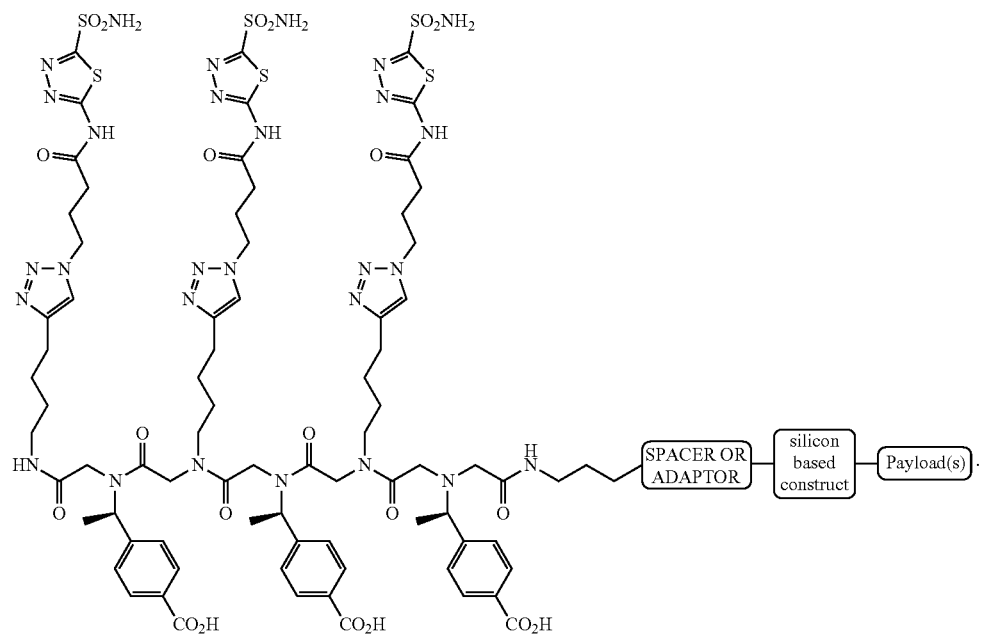
Peptoid Backbone Silicon based conjugates having GalNAc (N-Acetyl-D-galactosamine) targeting moieties as homing agents for asialoglycoprotein-receptor in liver cells include:
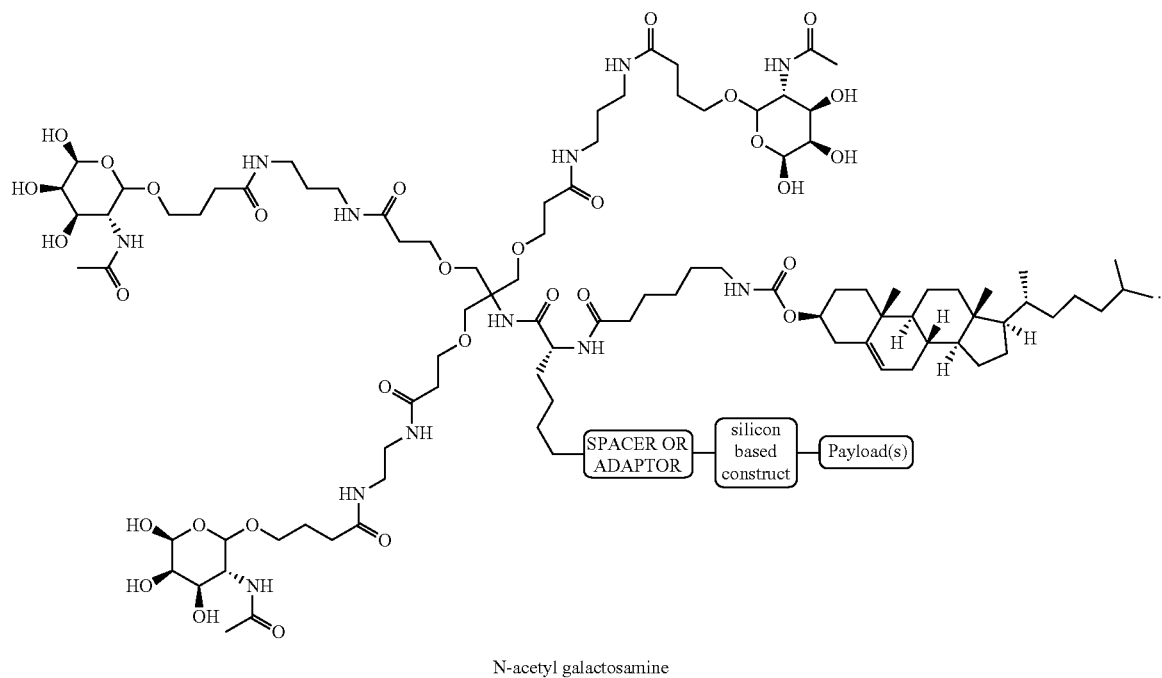
N-acetyl galactosamine
Silicon based conjugates having bisphosphonate targeting moieties that target bone hydroxyapatite without receptor mediated endocytosis include:
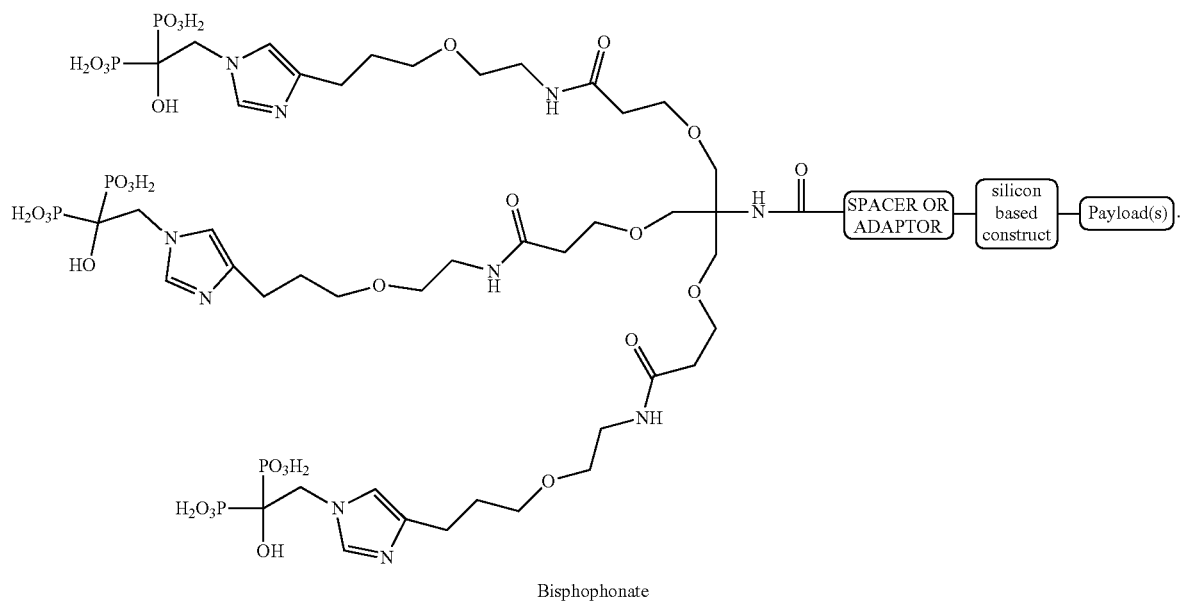
Bisphophonate Silicon based conjugates having mannose targeting moieties that bind to CD206 that is associated with positive disease-associated macrophages include:
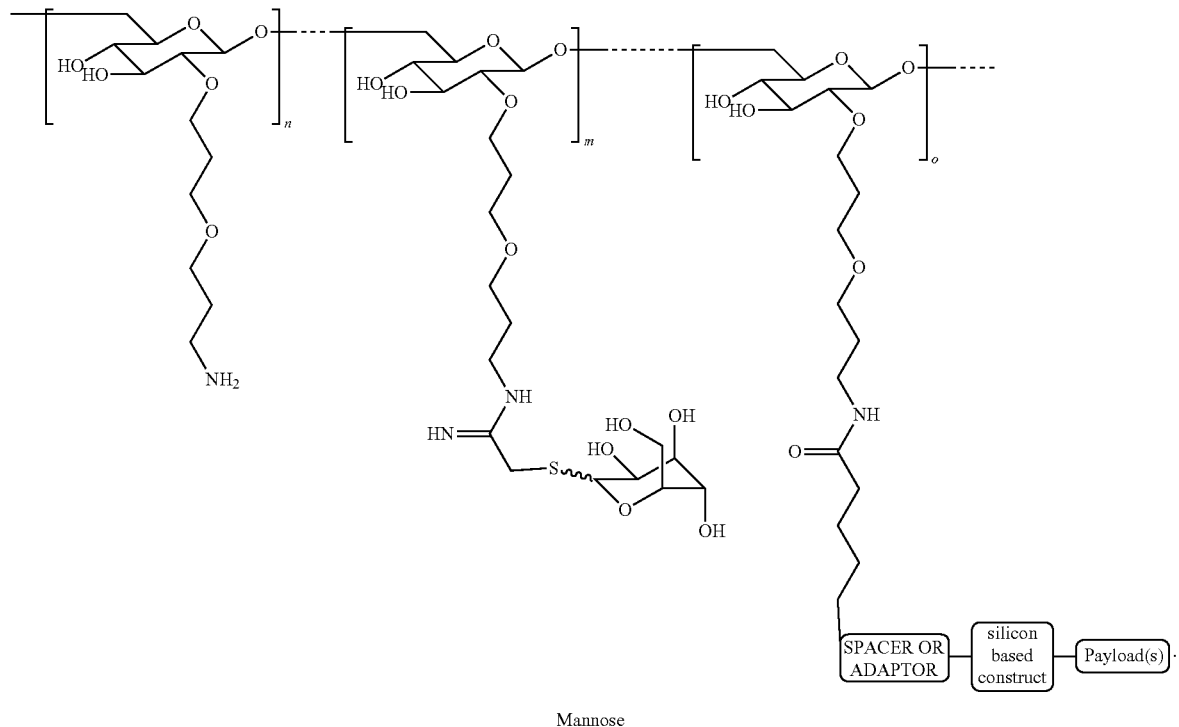
Mannose
Silicon based conjugates having mixed CCKRb ligand and folate targeting moieties that bind to CCKRb and folate receptors include:

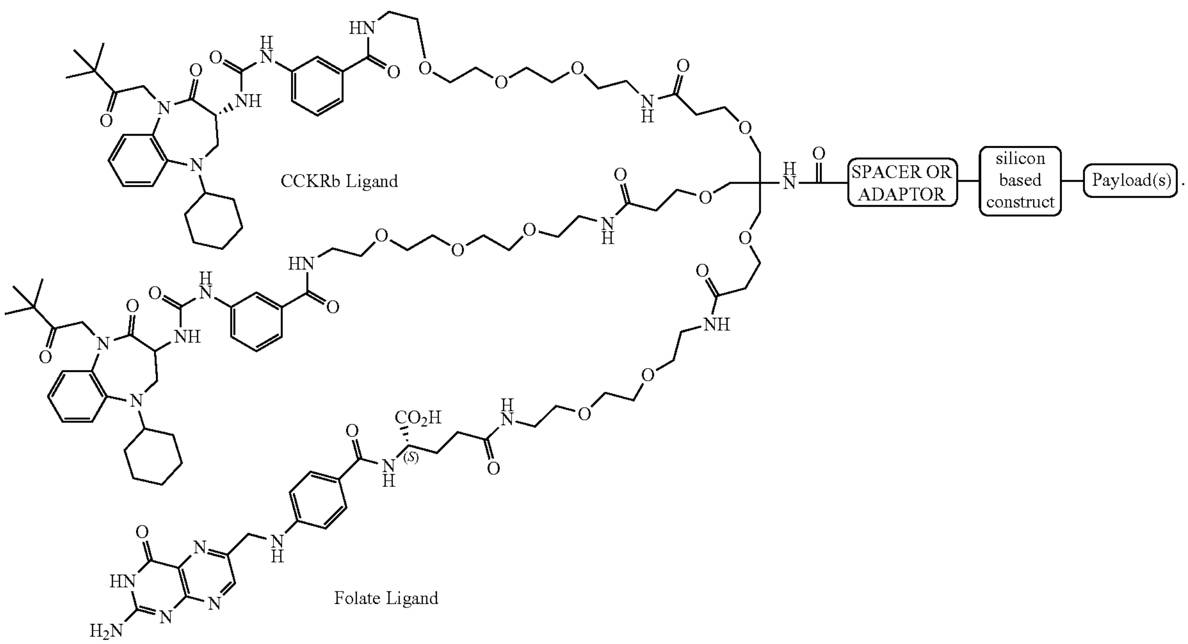

Silicon based conjugates having mixed folate and anti-CD33 antibody targeting moieties that bind to folate and CD33 receptors include:
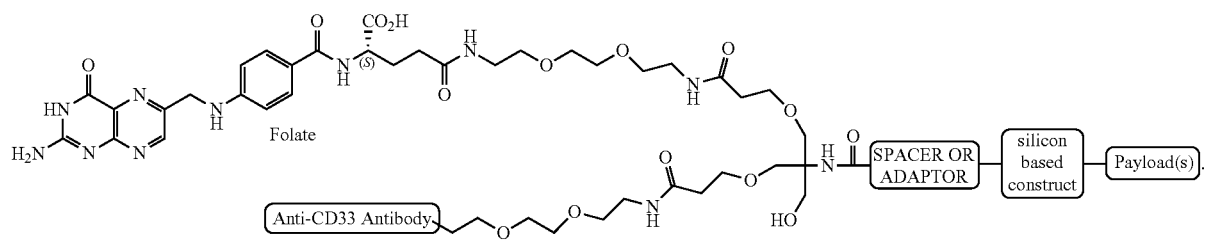
Silicon based conjugates having mixed folate and RGD targeting moieties that bind to folate and integrin receptors include:
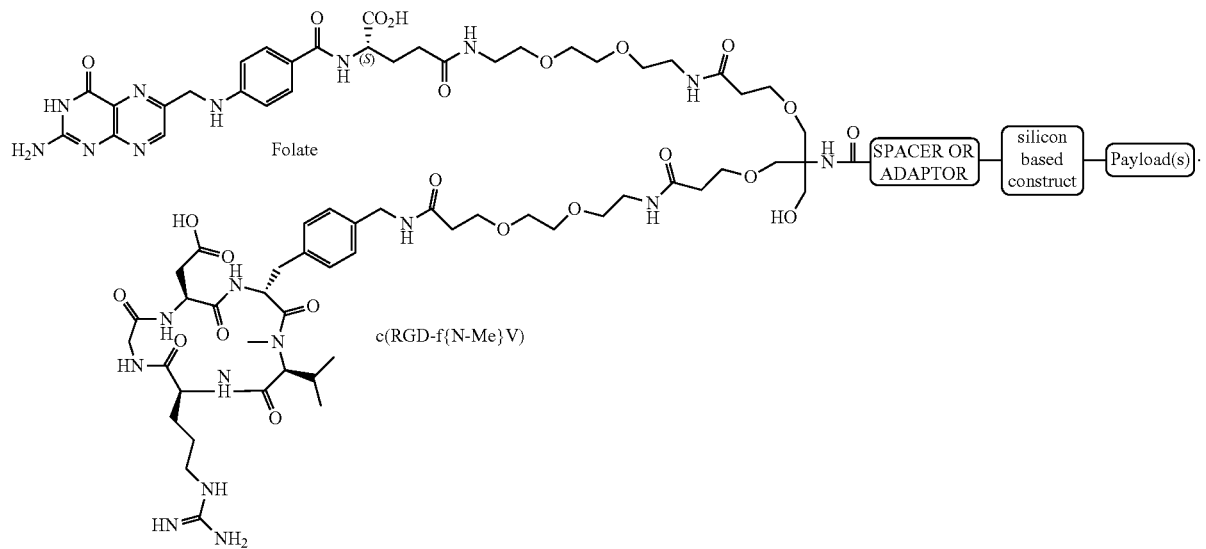

Silicon based conjugates having mixed somatostatin and anti-CD33 antibody targeting moieties that bind G protein-coupled somatostatin and CD33 receptors include:

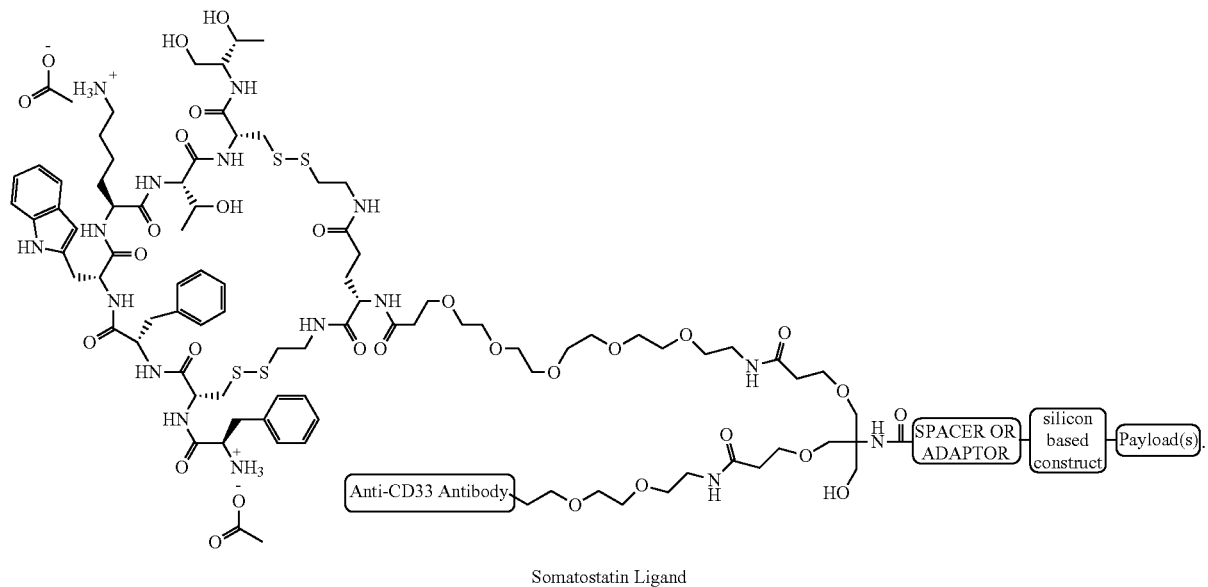

Somatostatin Ligand

Example 112: Catalytic Moieties

As described above, contemplated silicon based conjugates of the disclosure may contain one or more optional catalytic moieties covalently bound directly or indirectly to the silicon-heteroatom core (e.g., a siloxane). In an embodiment, a disclosed catalytic moiety may be divalent. In certain embodiments, a disclosed catalytic moiety or moieties may be selected to optimize bond cleavage of a Si—O bond of a siloxane such that the payload moiety is released into the target cell or tissue. For example, a disclosed catalytic moiety or moieties may be selected to facilitate a pH-sensitive release of the payload moiety from the conjugate at pH less than about 7 or greater than about 7.5. Exemplary catalytic moieties may include, but are not limited to, monocyclic or bicyclic heteroaryl systems, for example, optionally substituted pyrroles, furans, thiophenes, imidazoles, pyrazoles, oxazoles, isoxazoles, thiazoles, isothiazoles, pyridines, pyrimidines, triazoles, tetrazoles, etc. For example, catalytic moieties may include, but are not limited to:

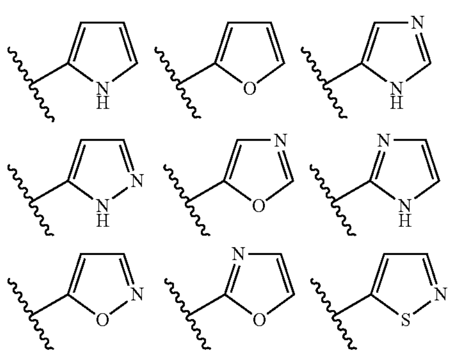

-continued

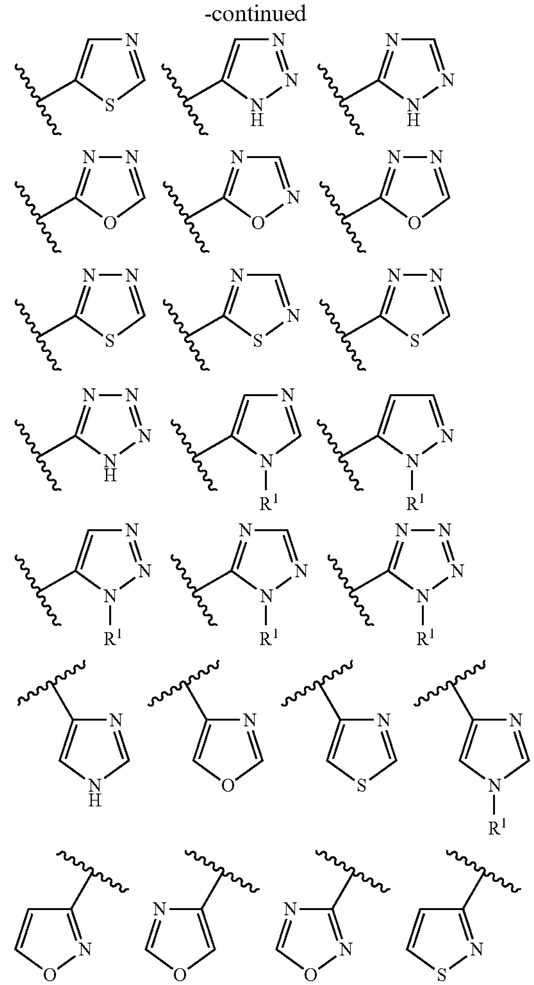

363
-continued
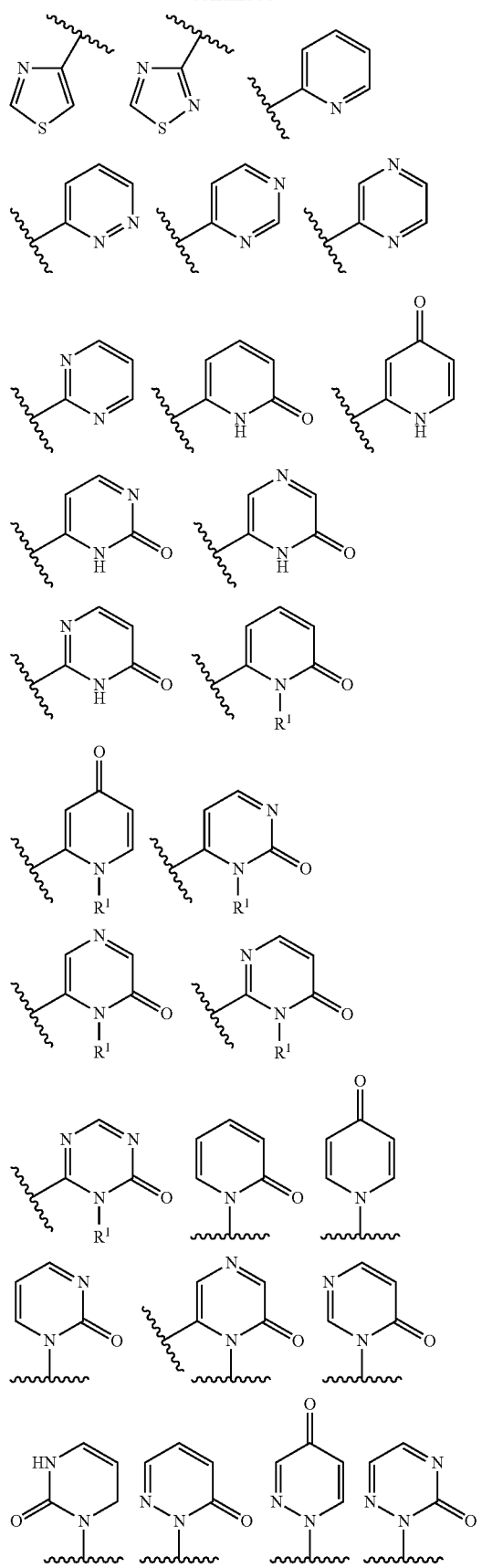
364
-continued
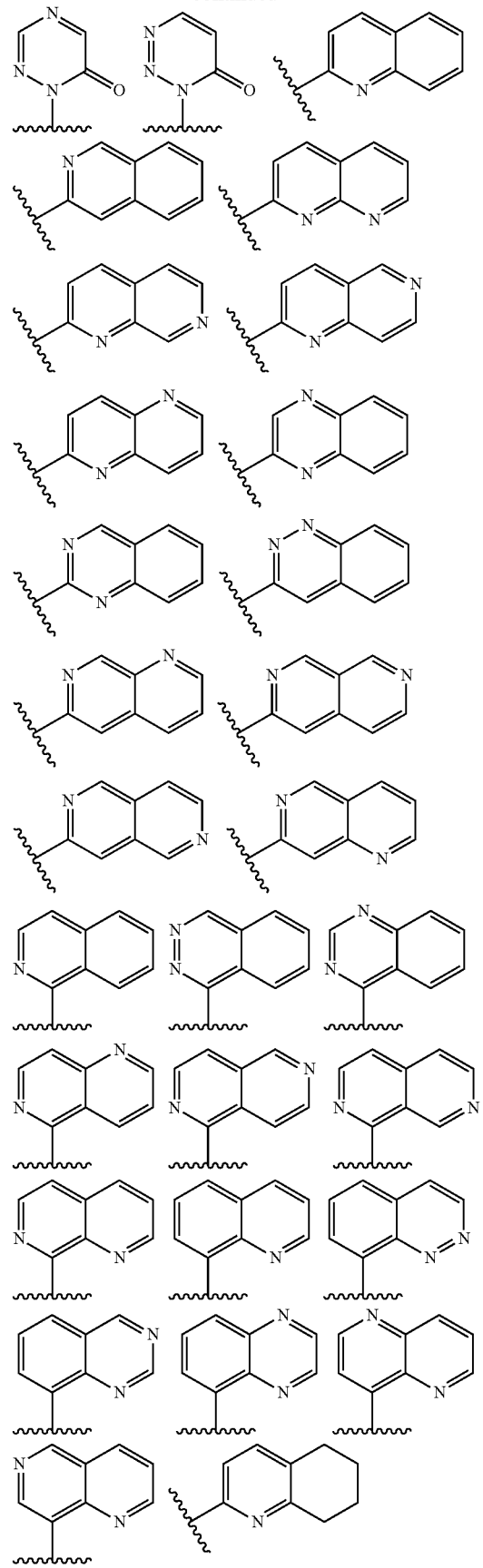

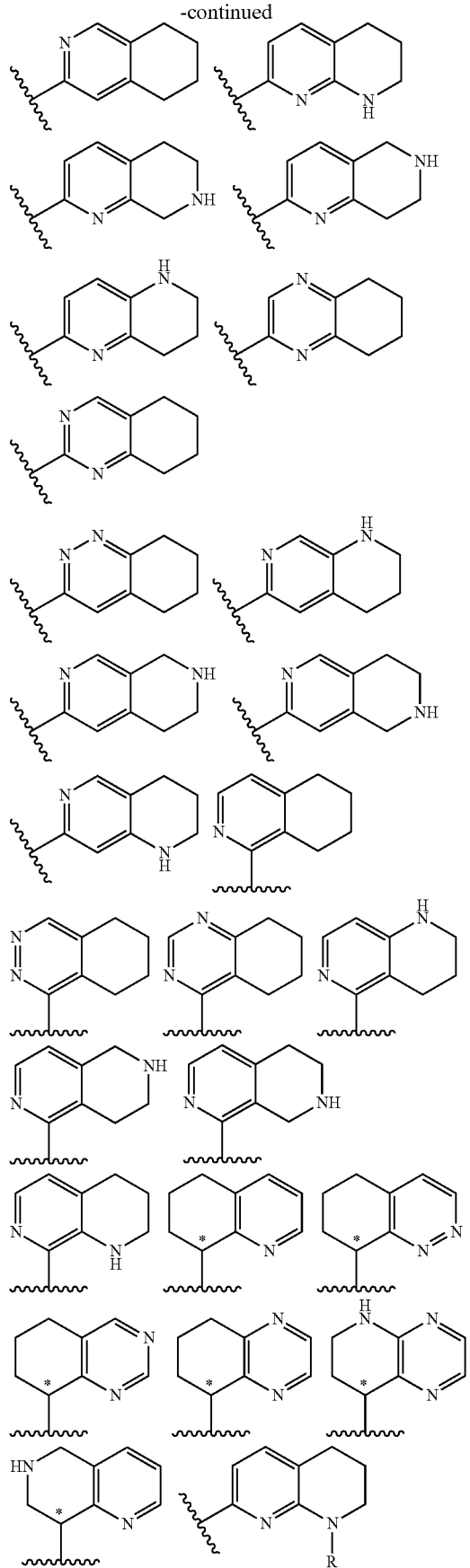
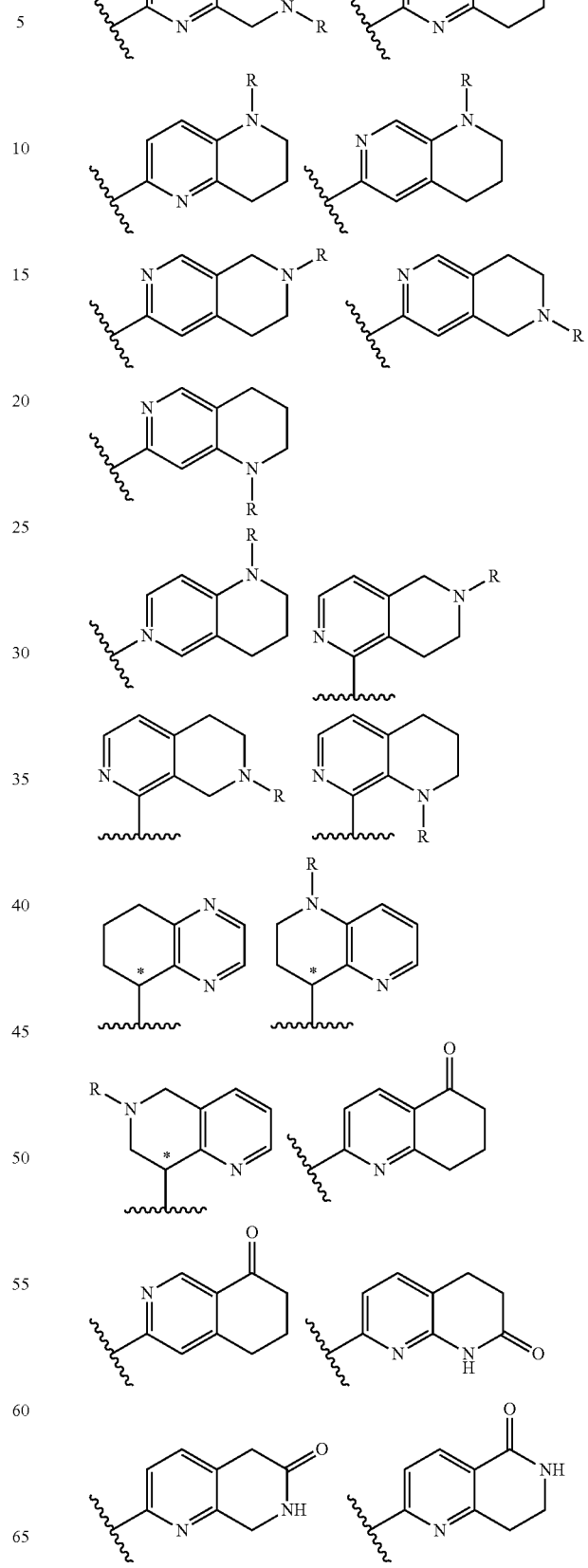

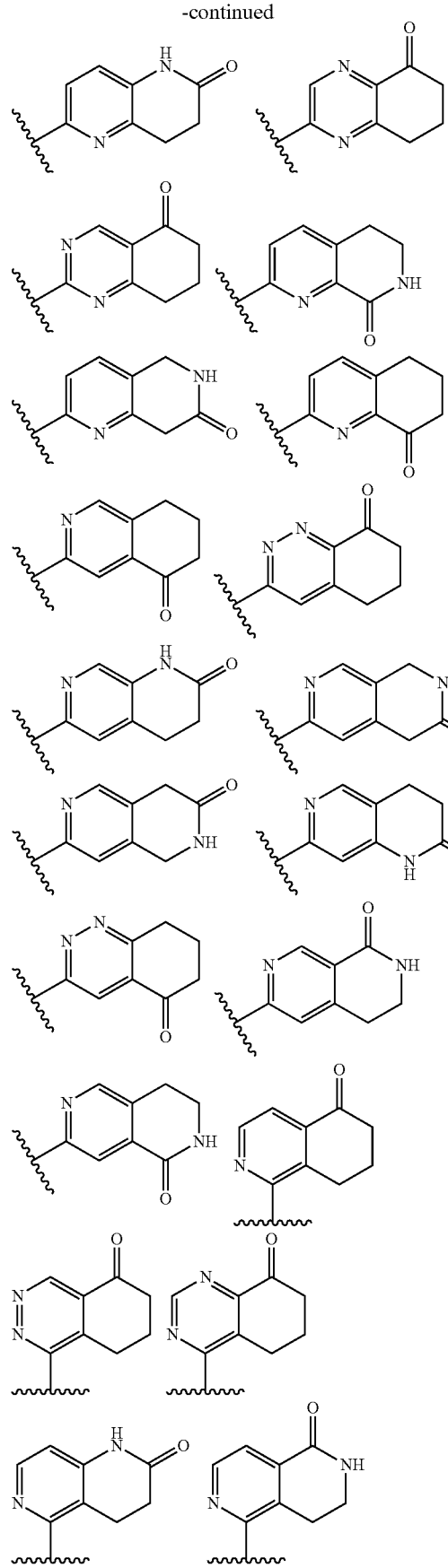
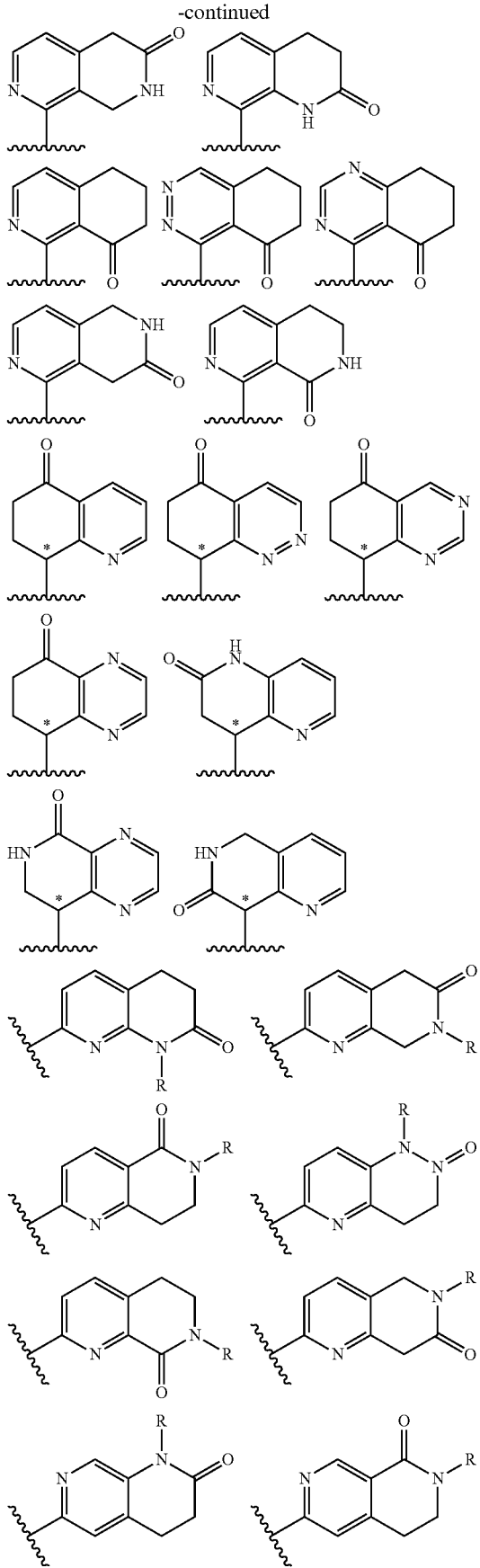

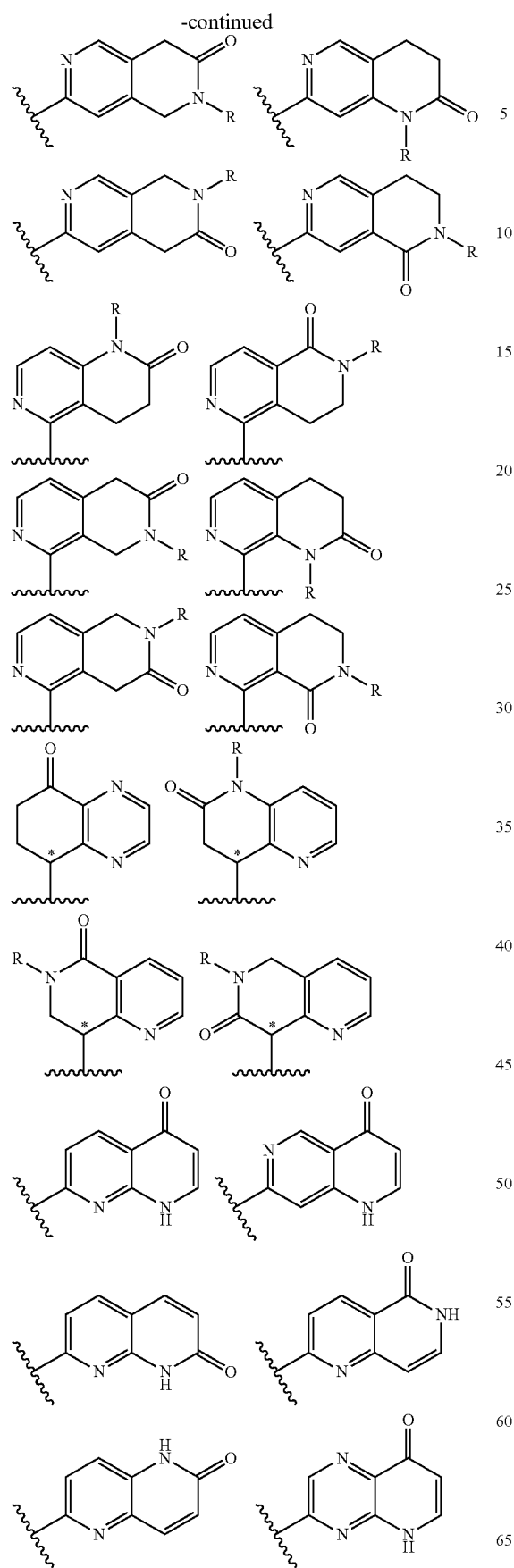
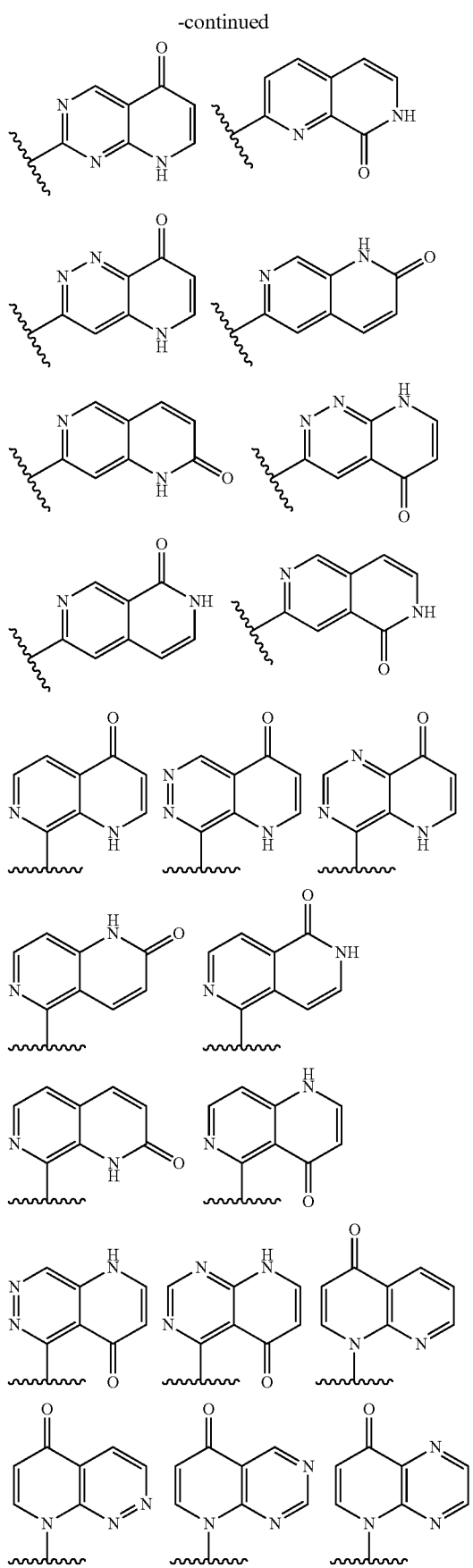

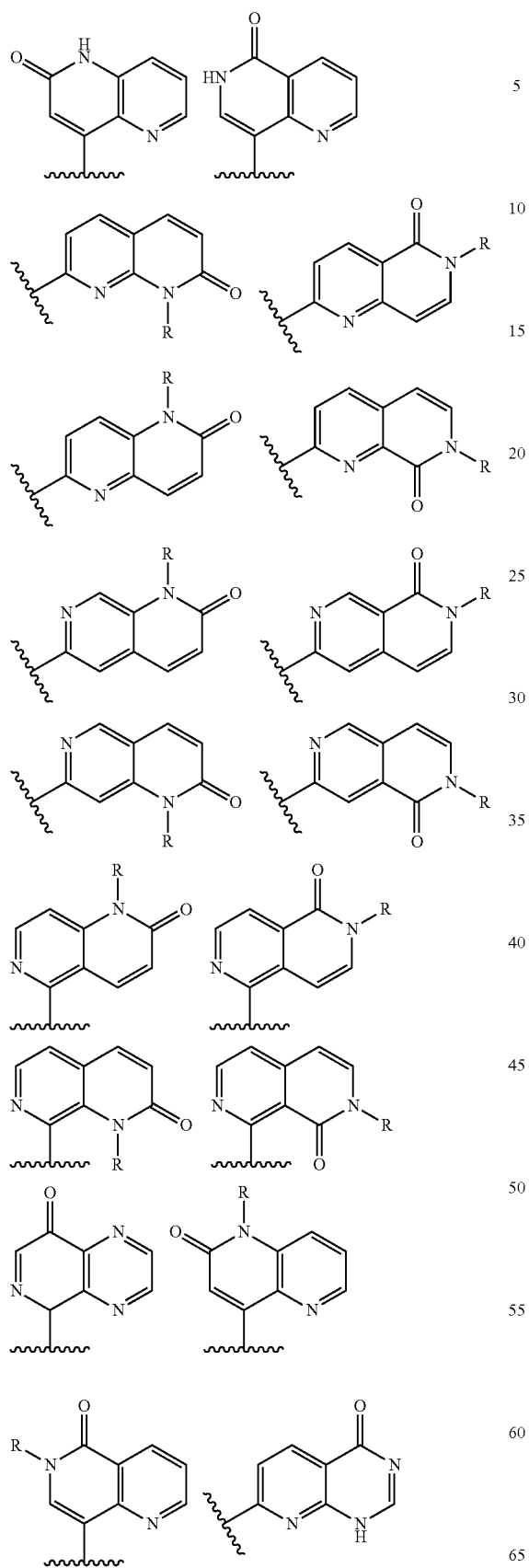
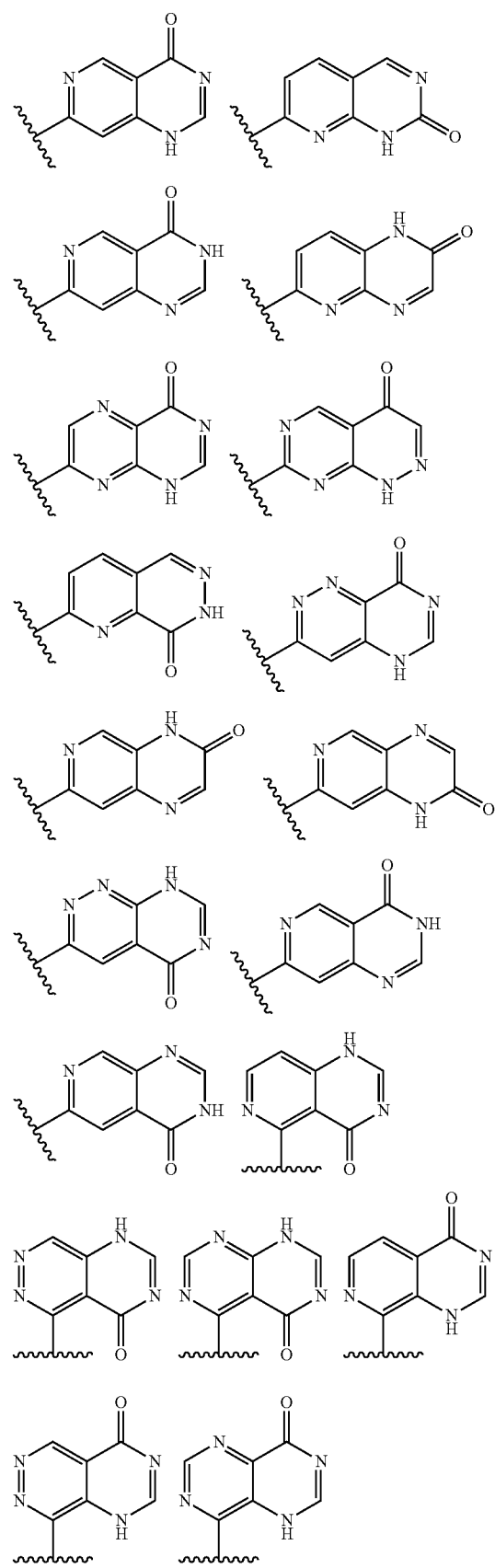

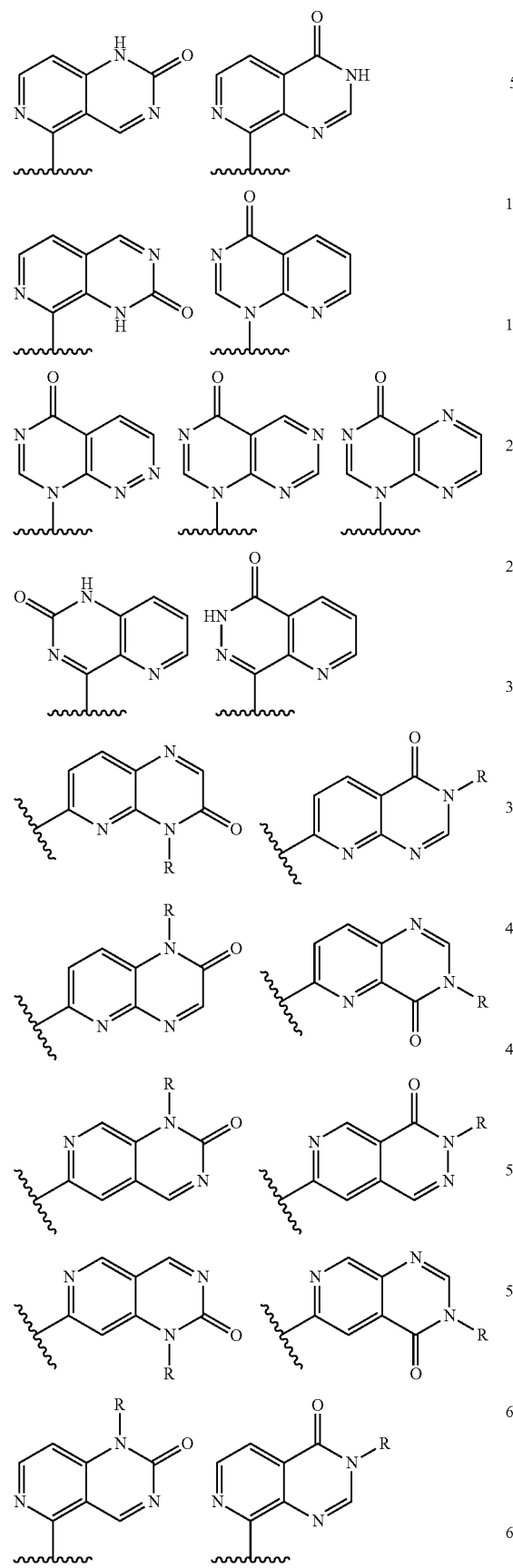
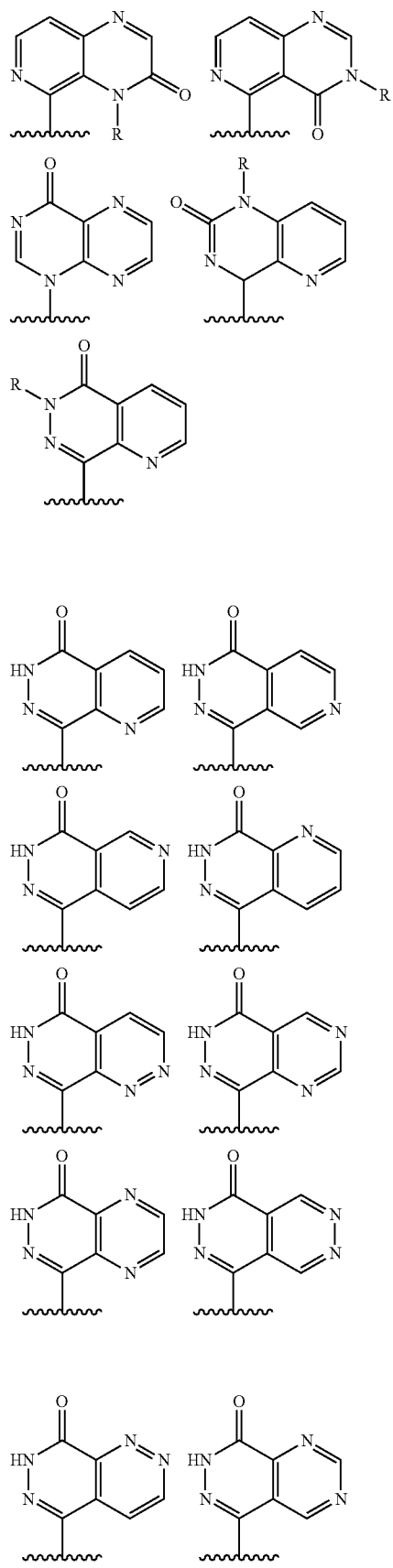

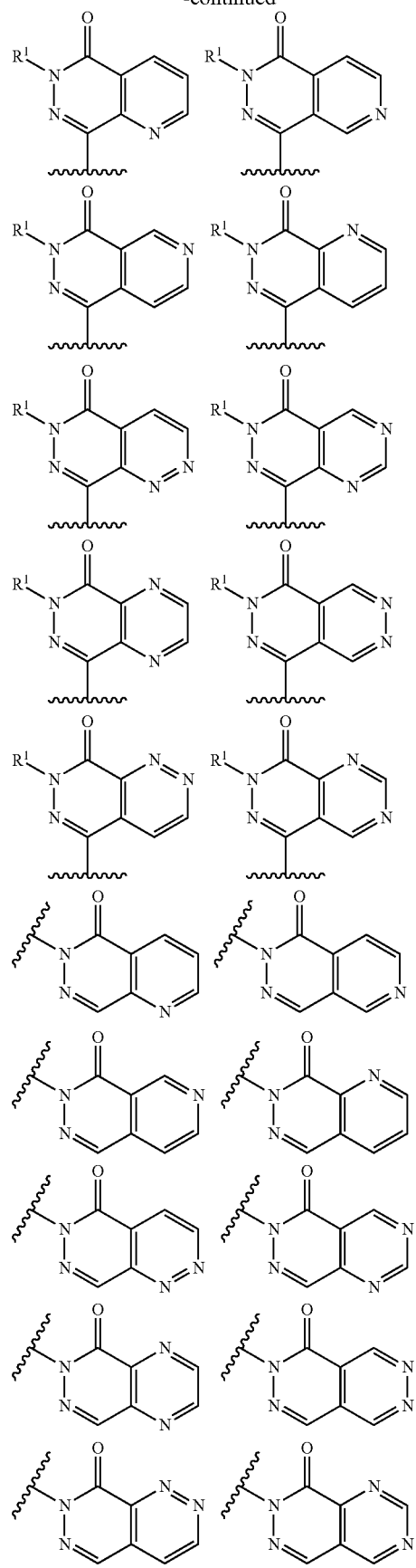
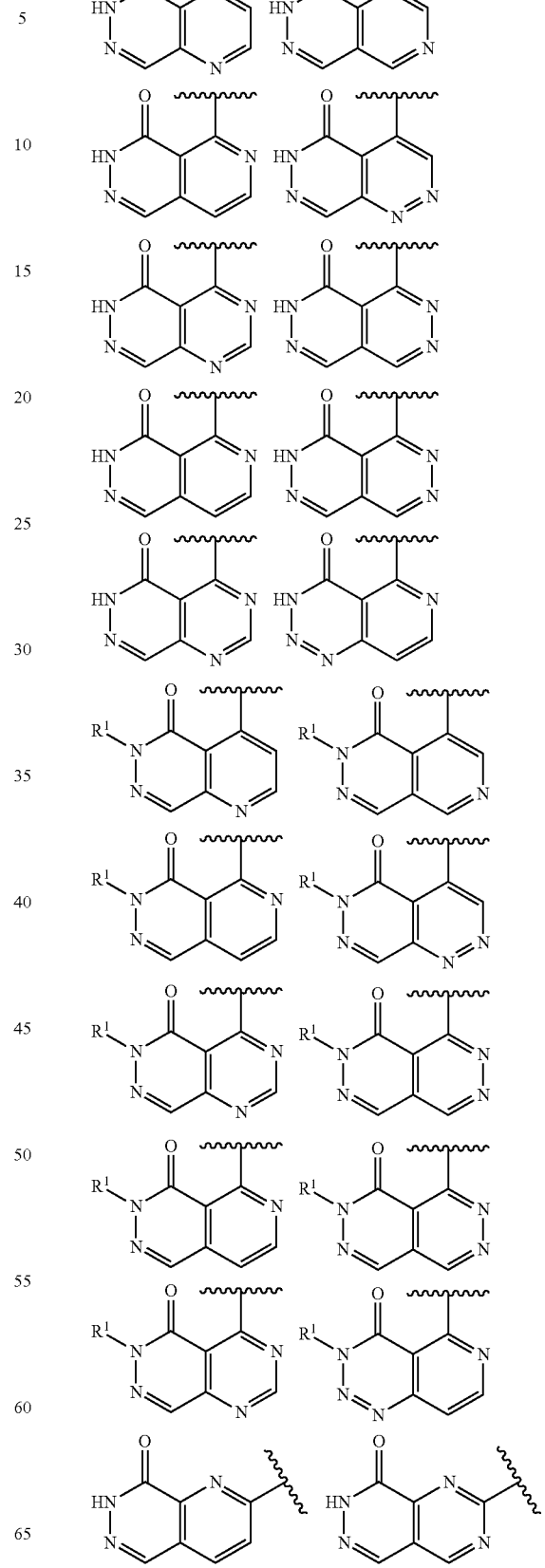

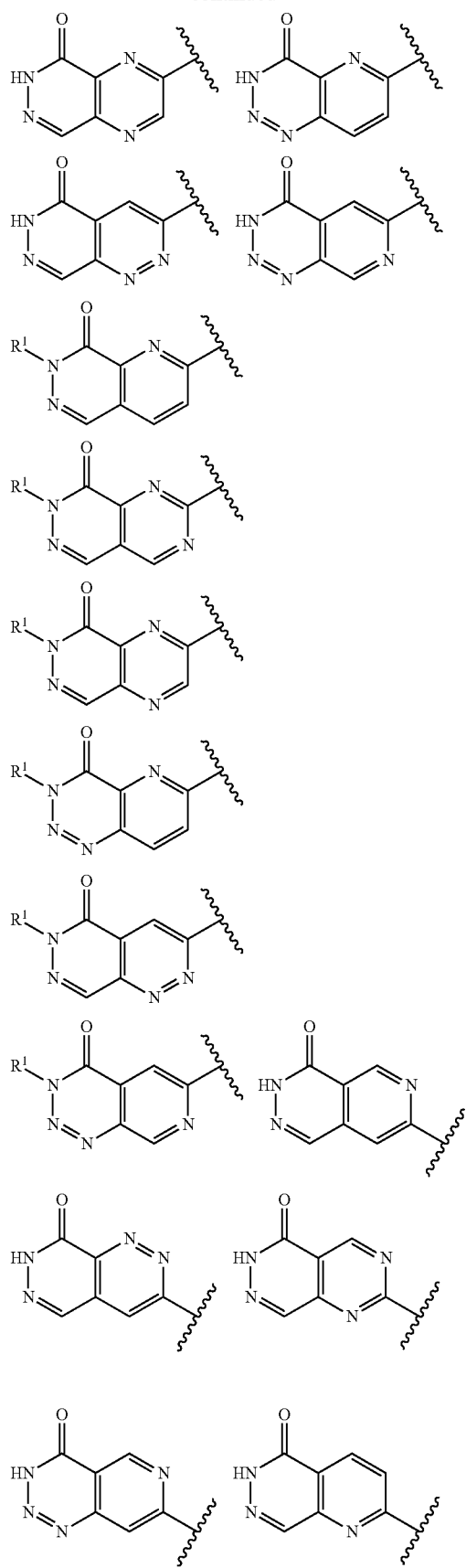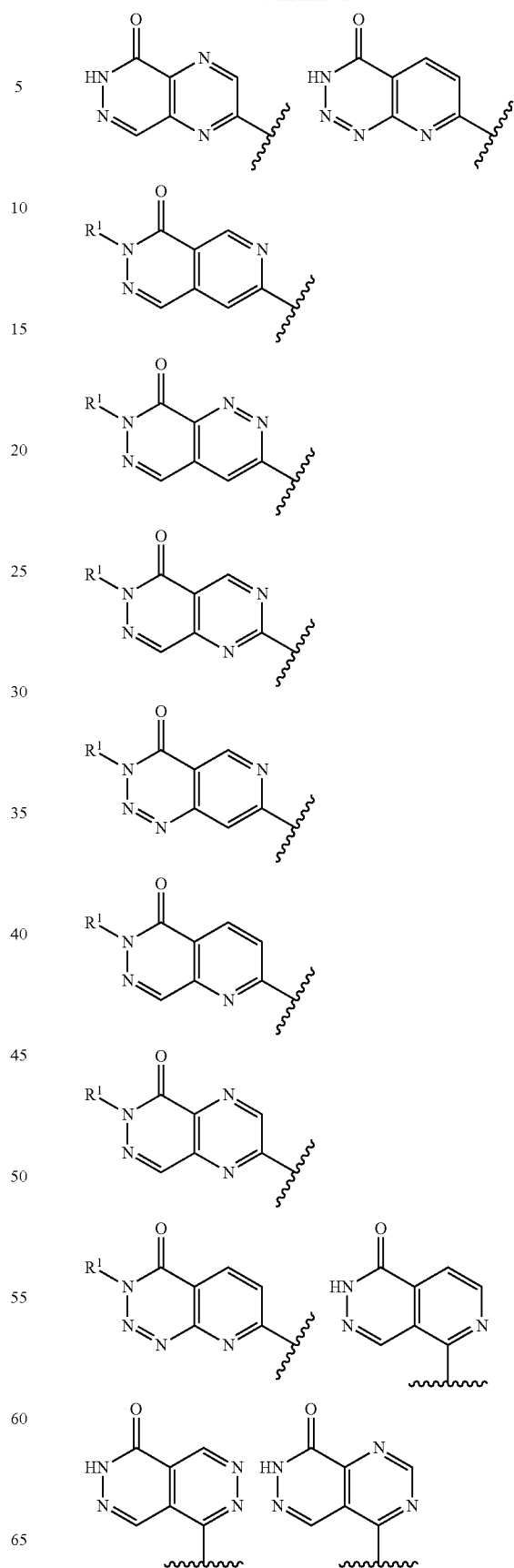

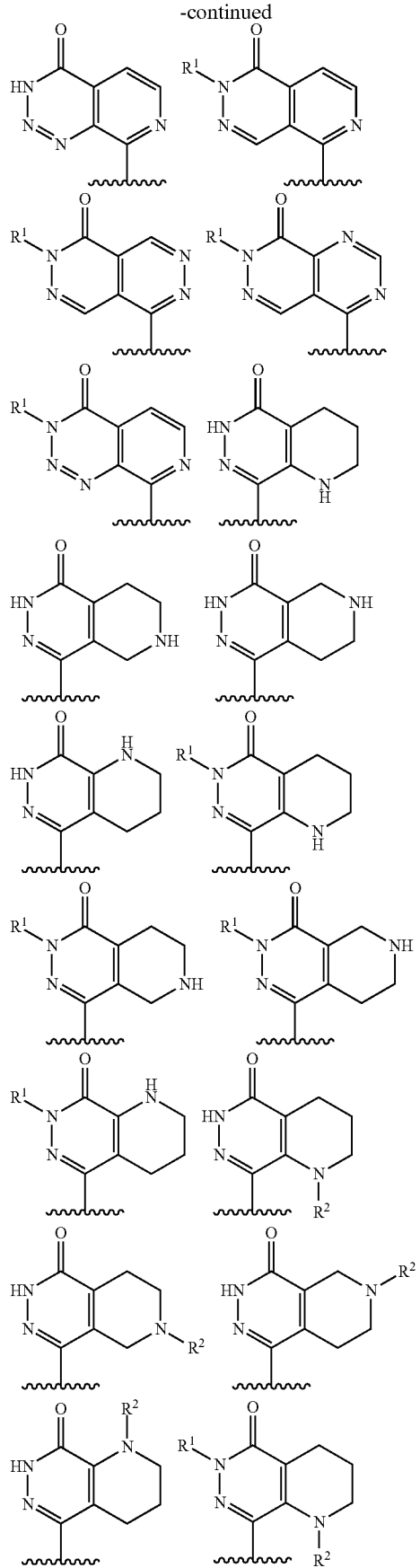
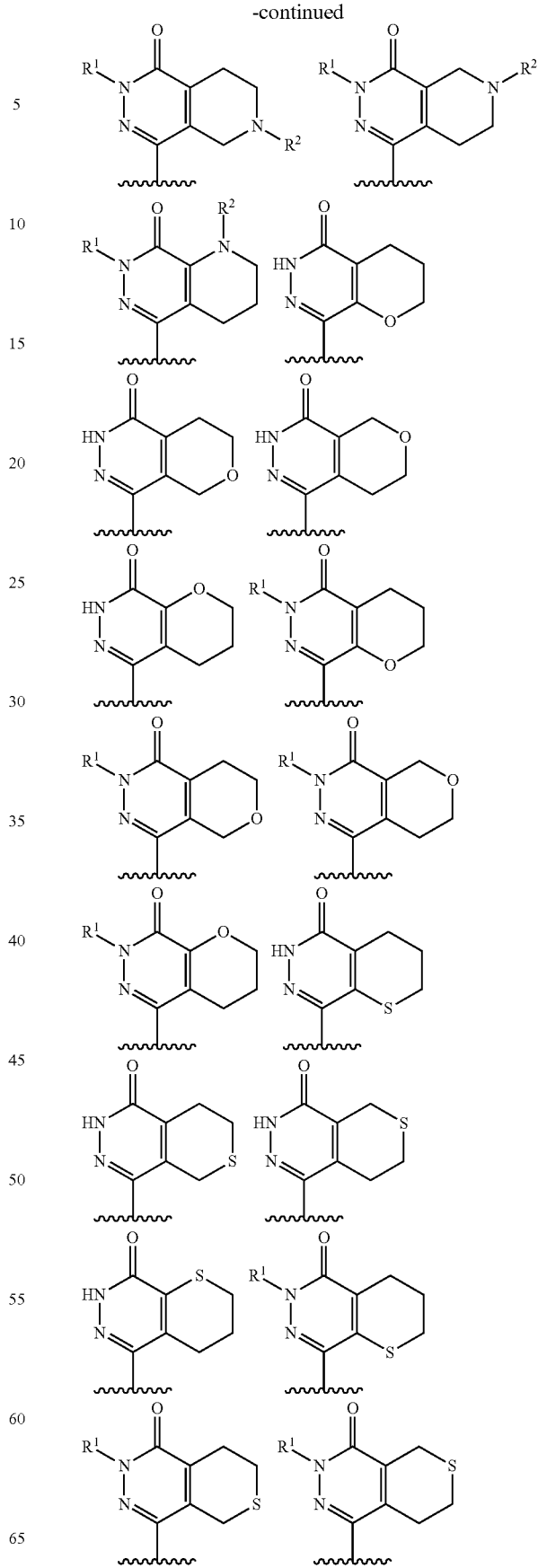

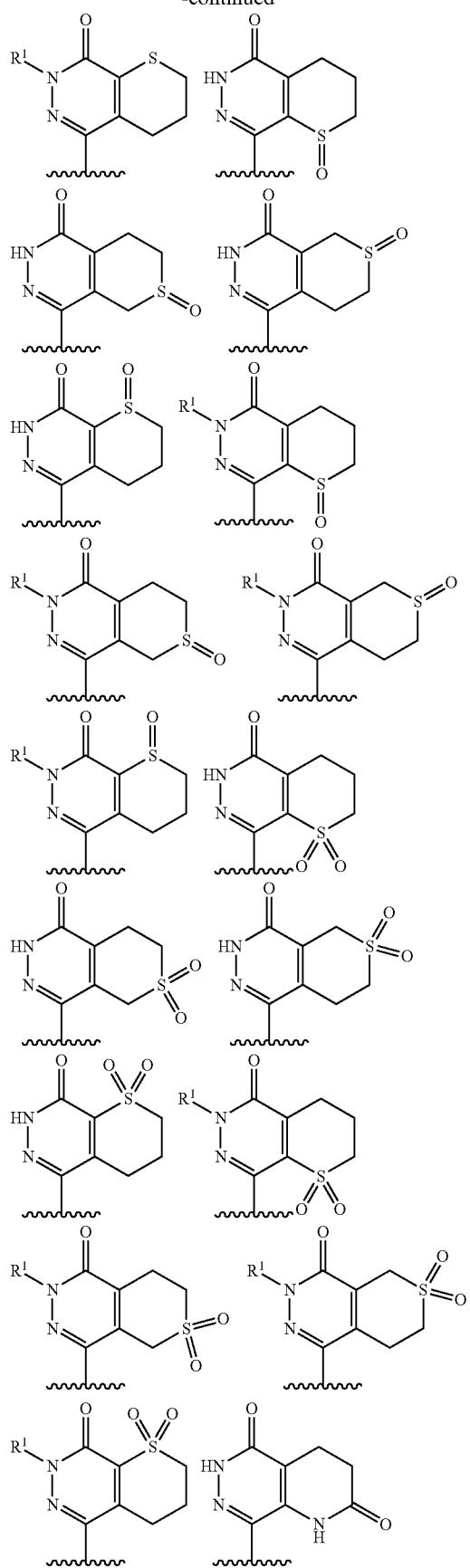
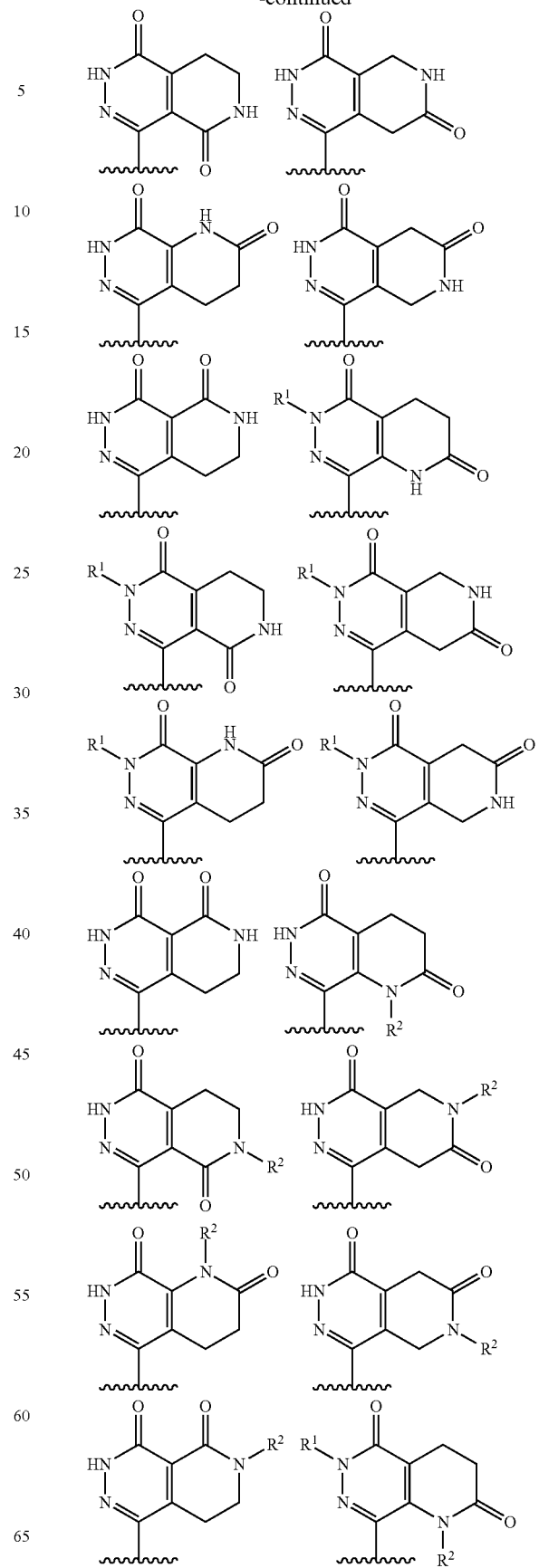

383
-continued
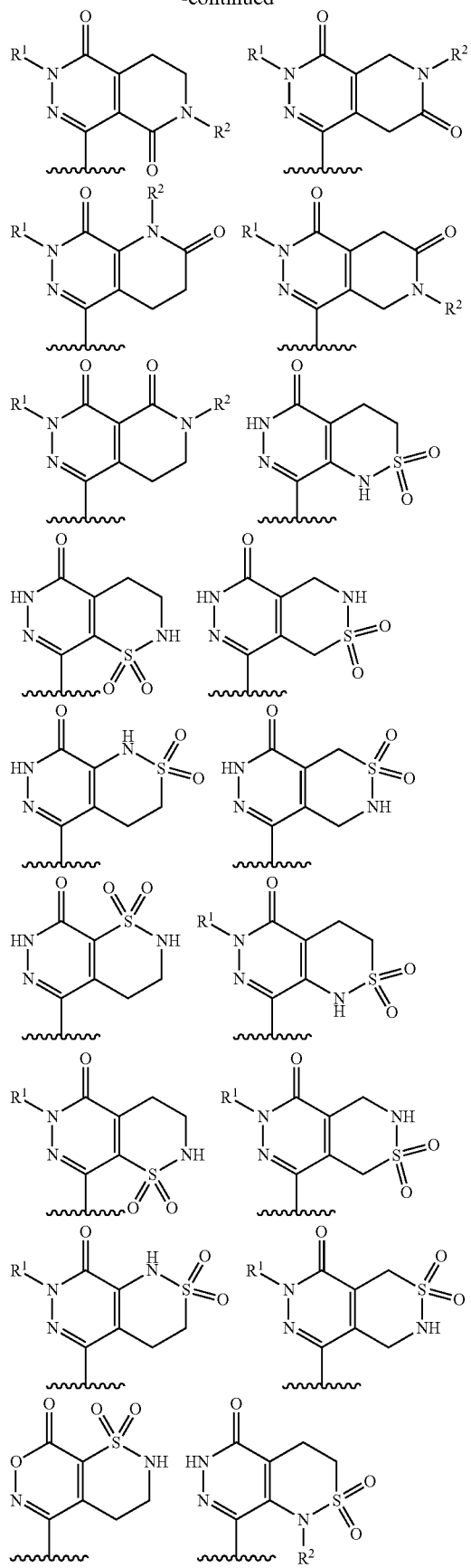
384
-continued
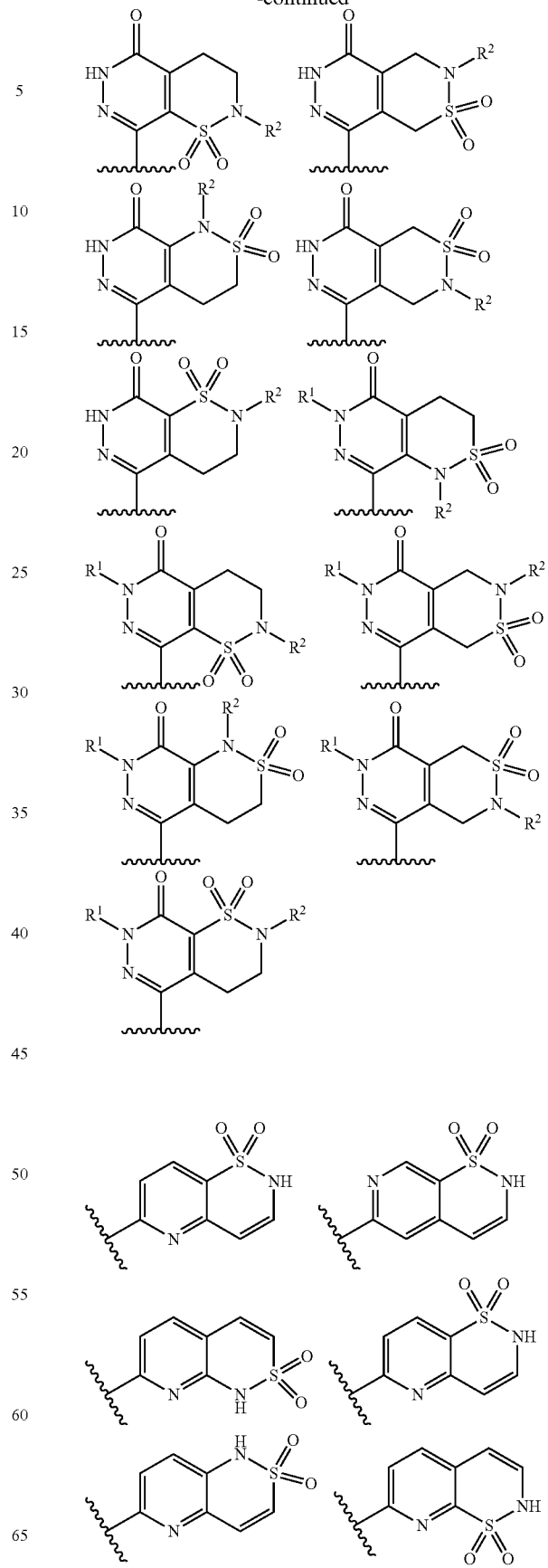

385
-continued
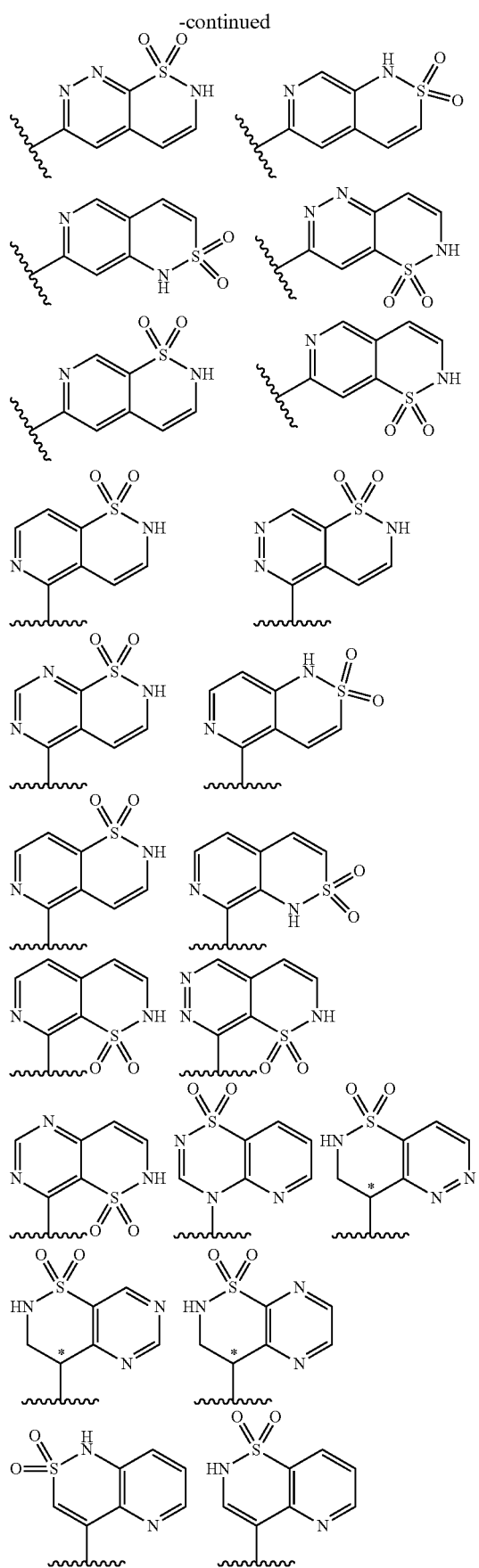
386
-continued
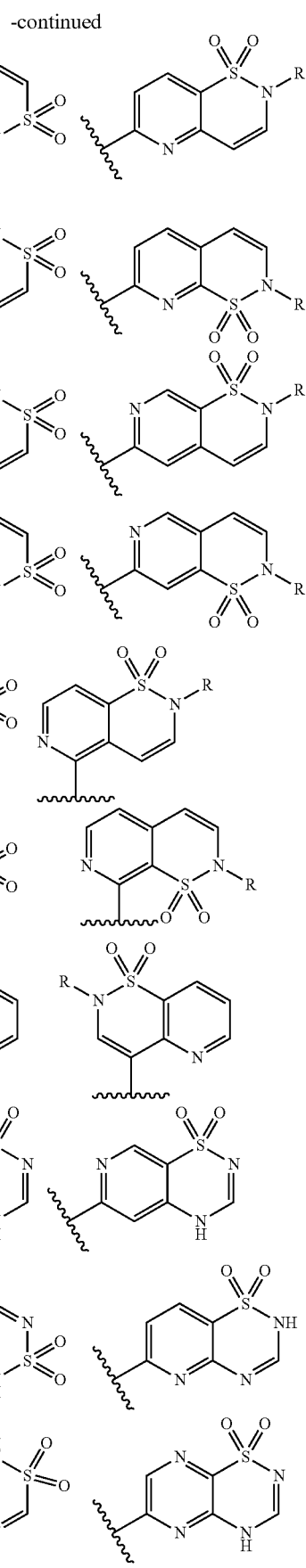

387
-continued
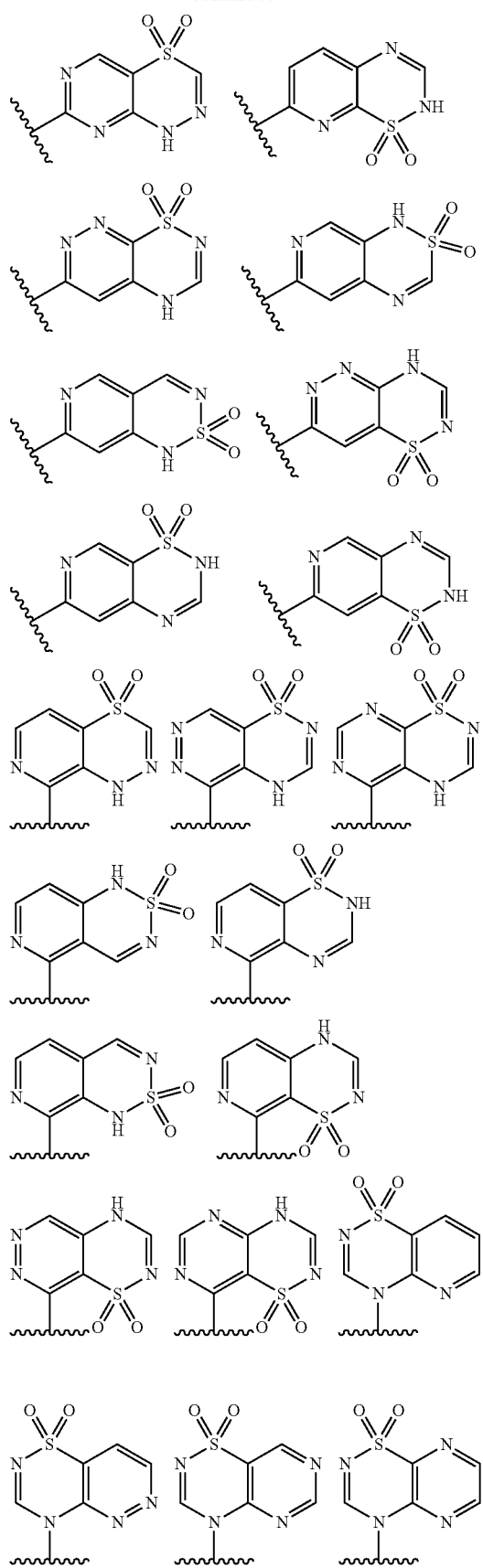
388
-continued
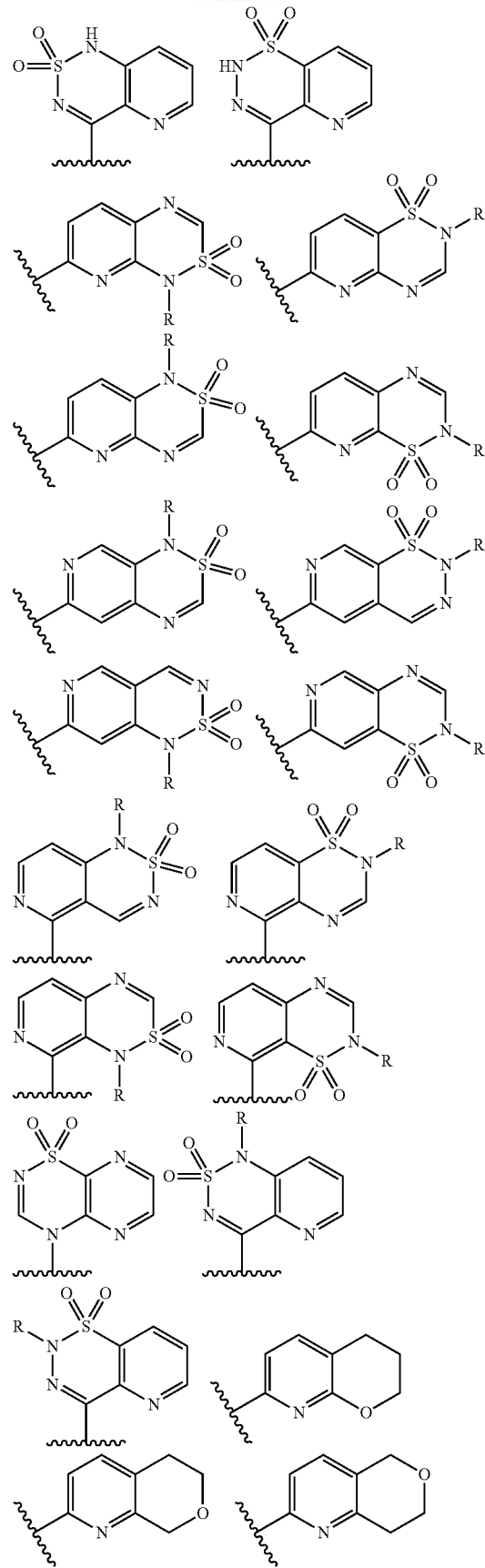

389
-continued
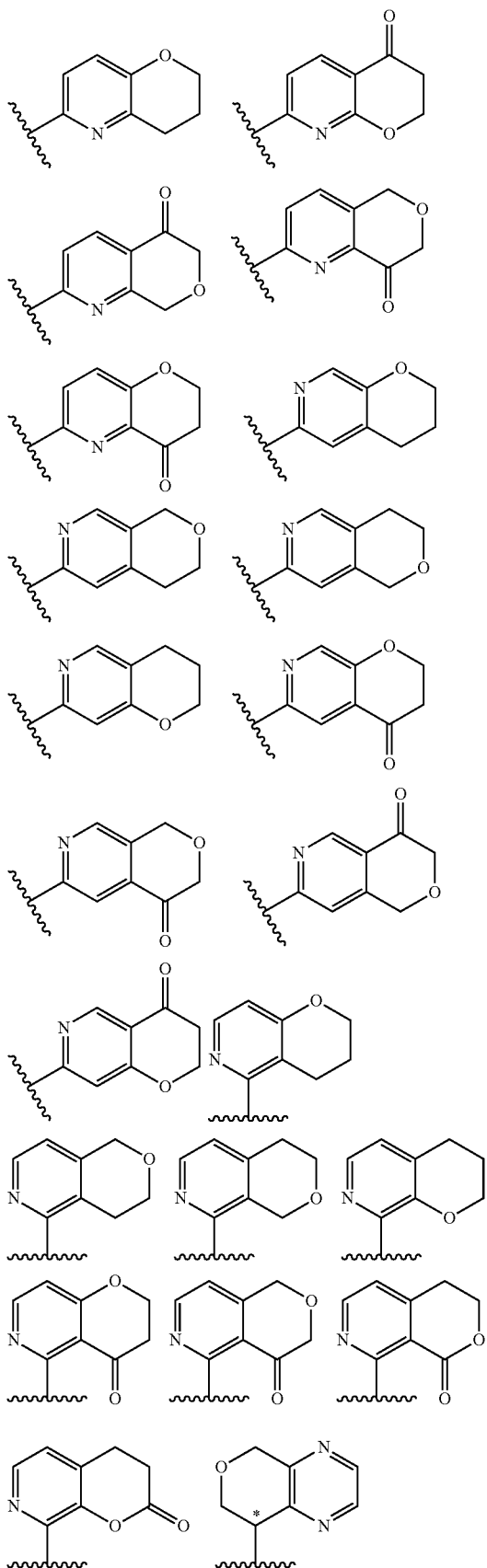
390
-continued
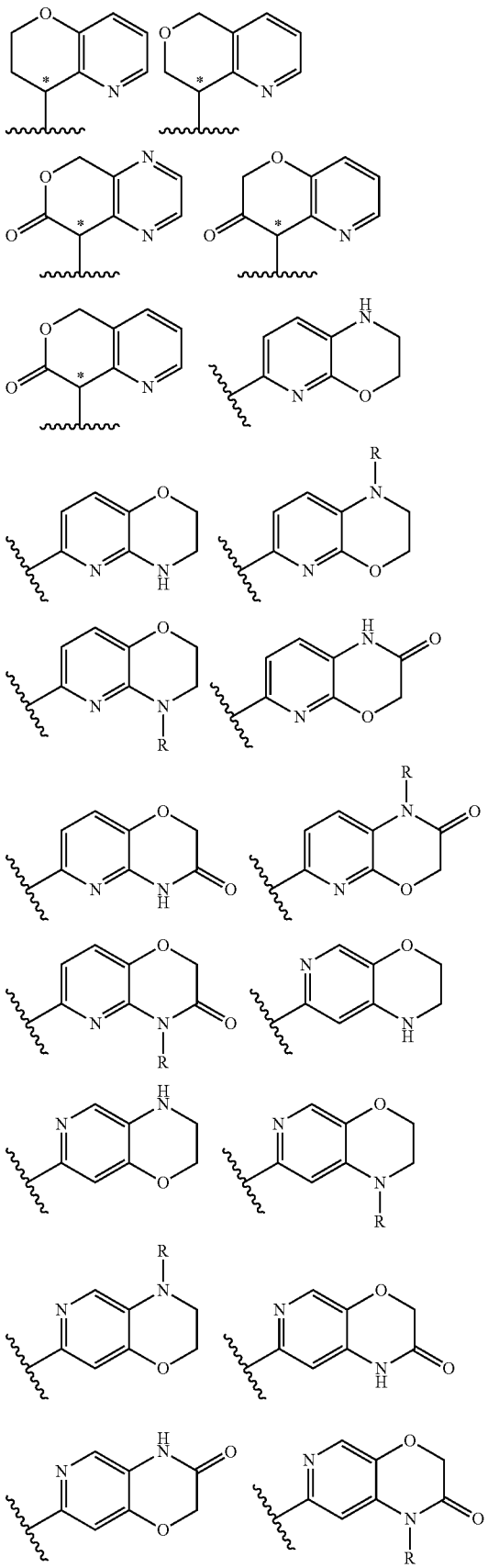

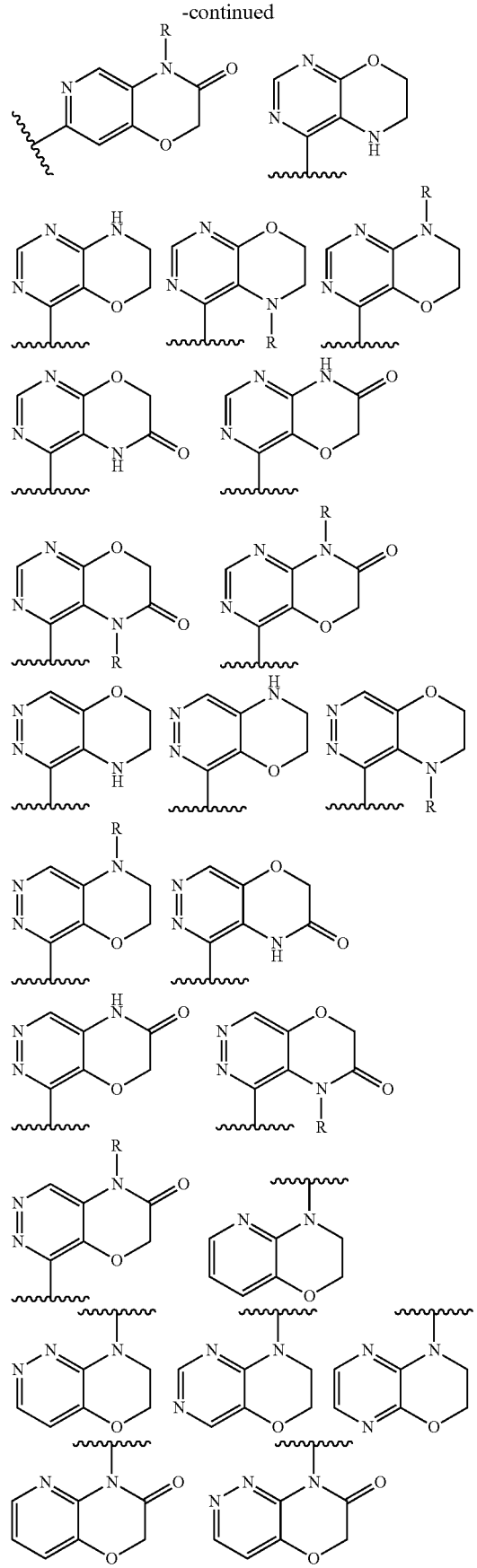
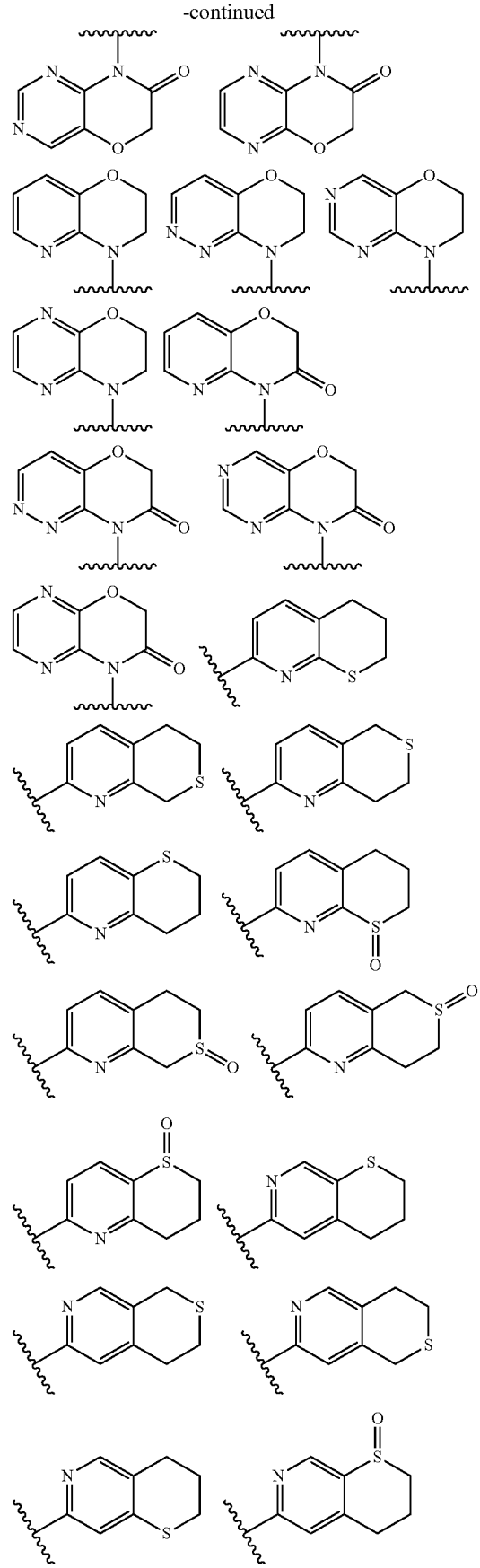

393
-continued
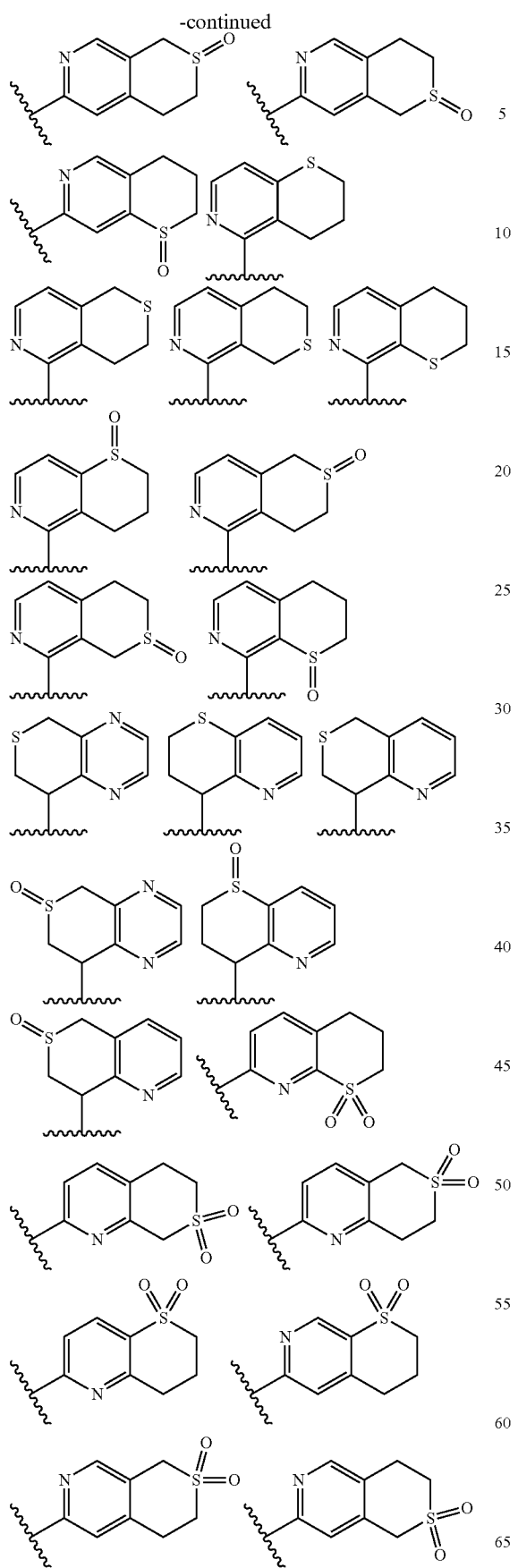
394
-continued
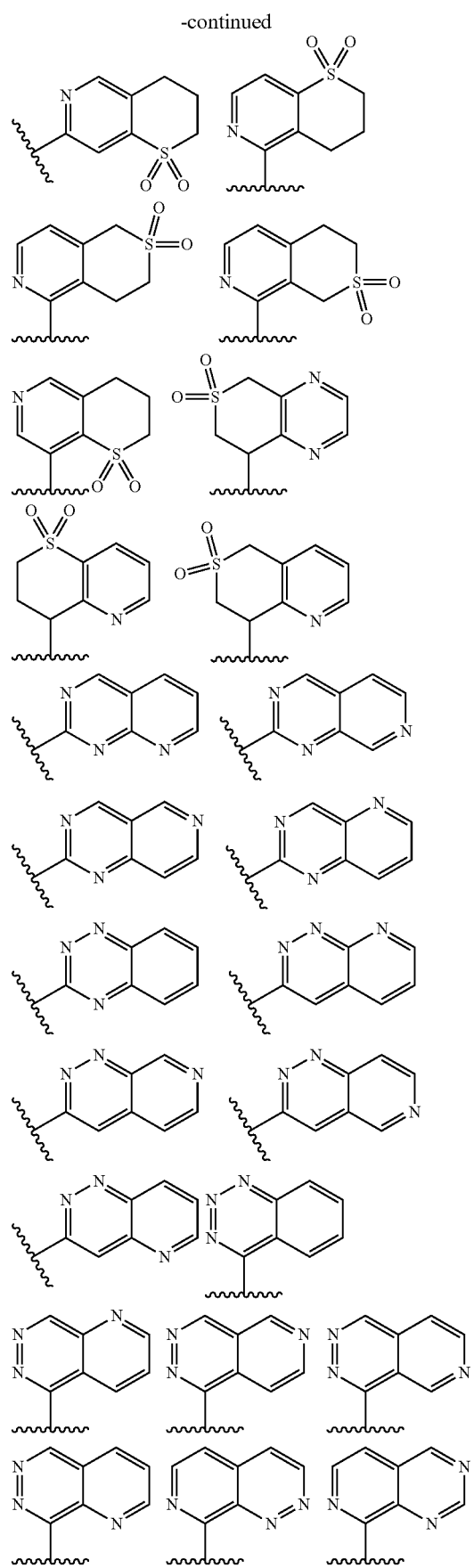

395
-continued
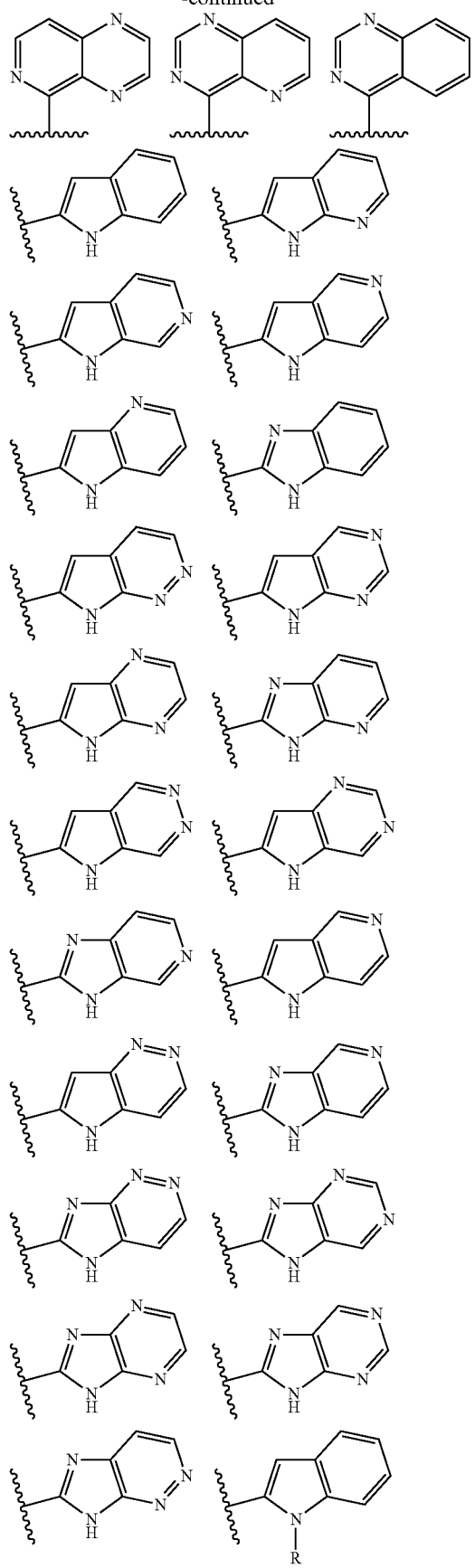
396
-continued
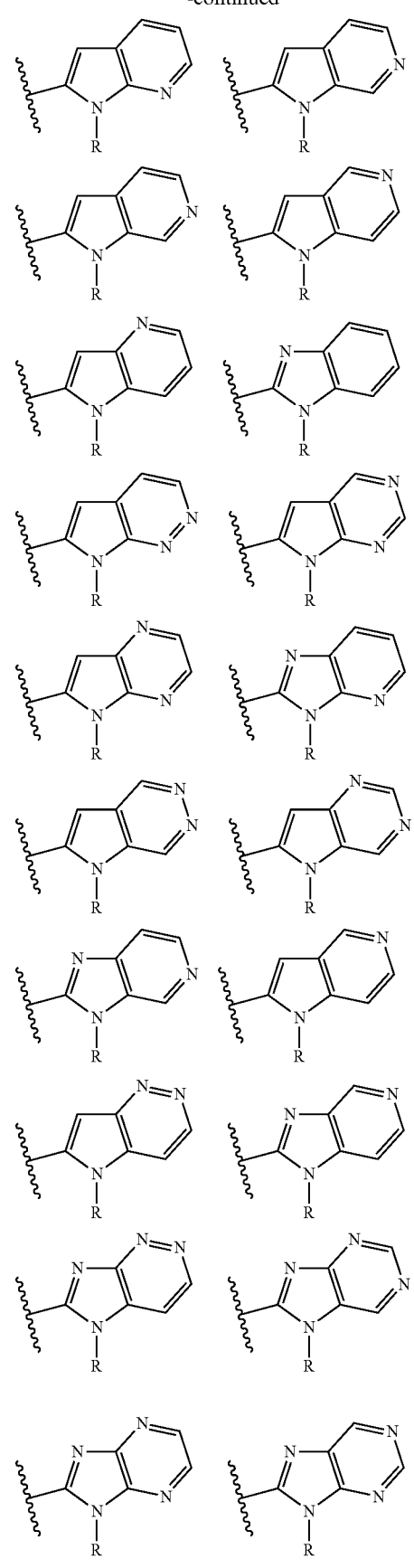

397
-continued
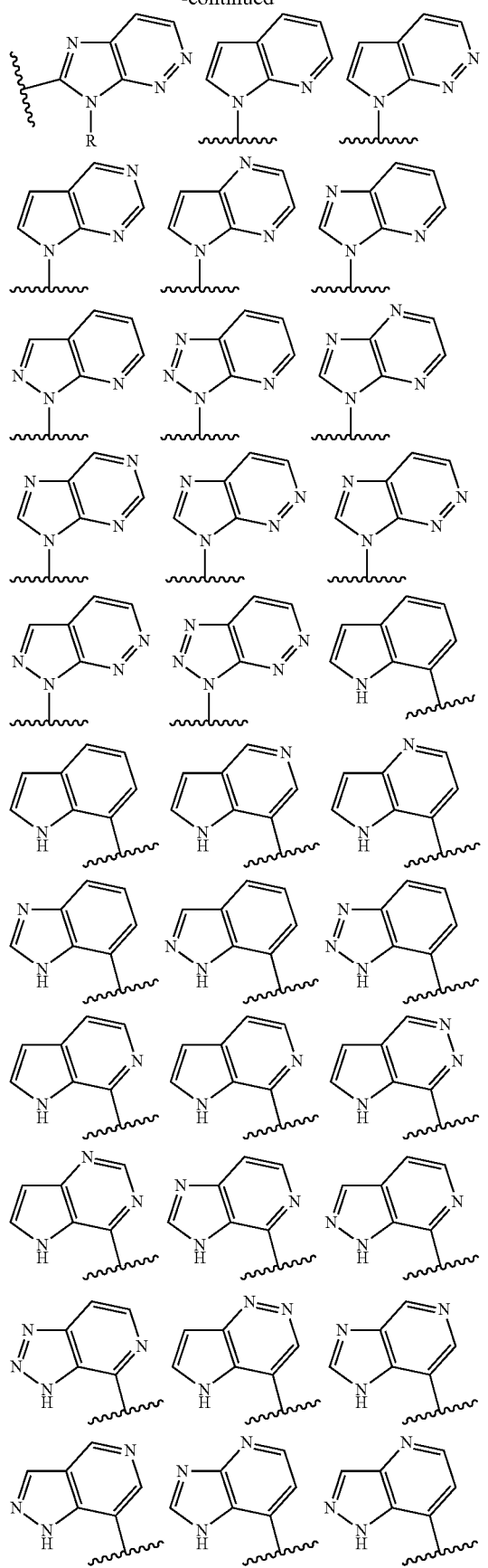
398
-continued
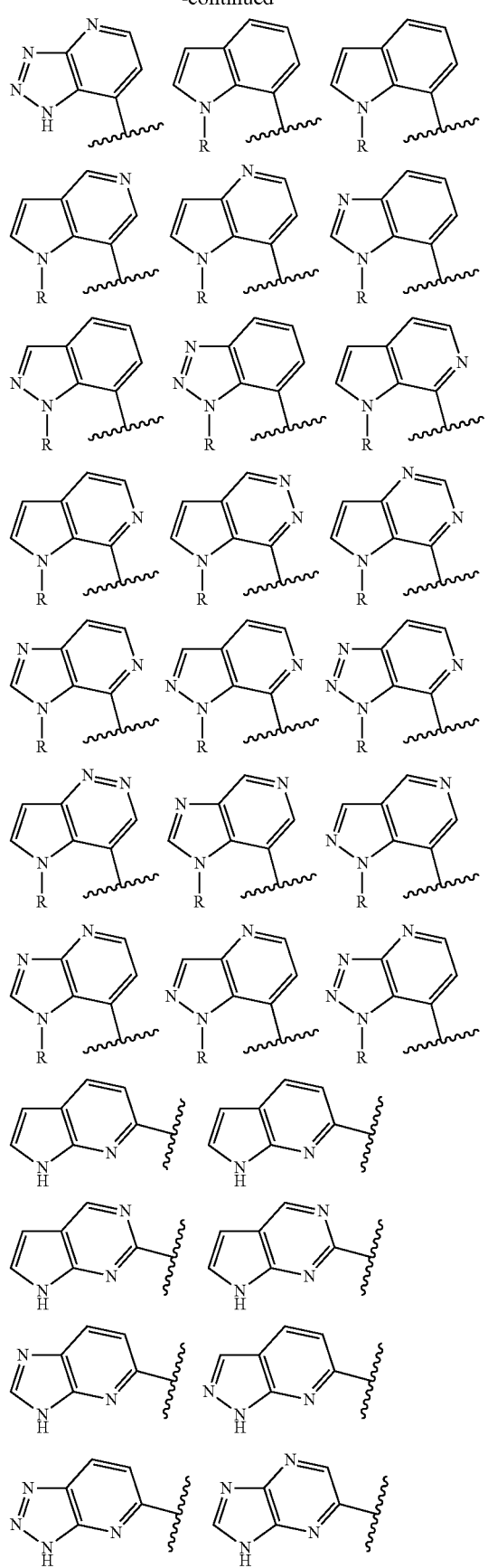

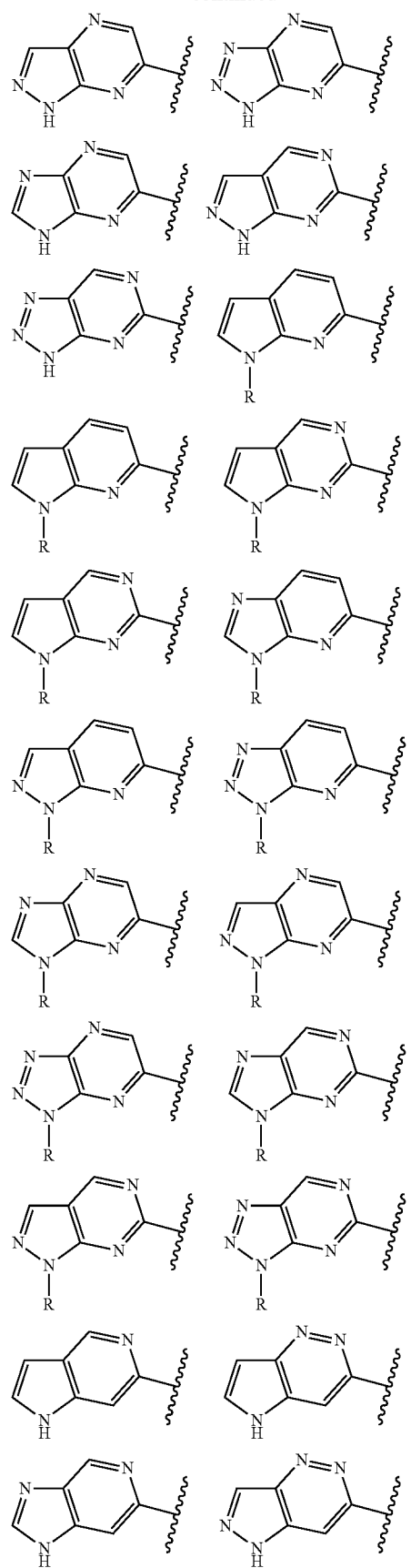
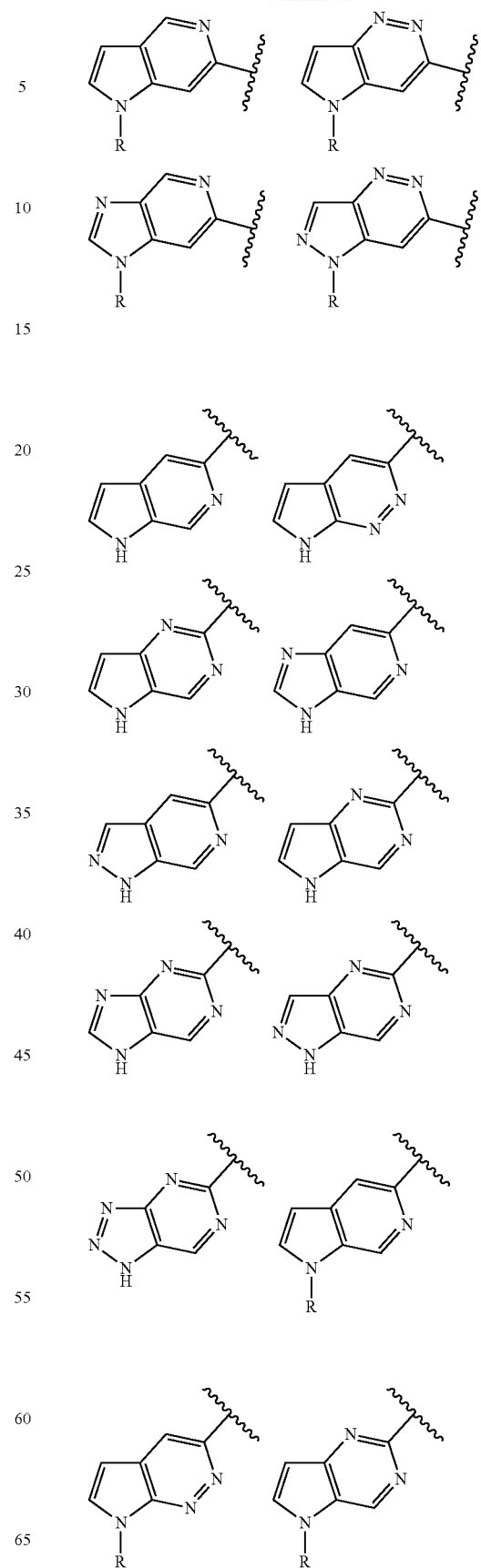

401
-continued
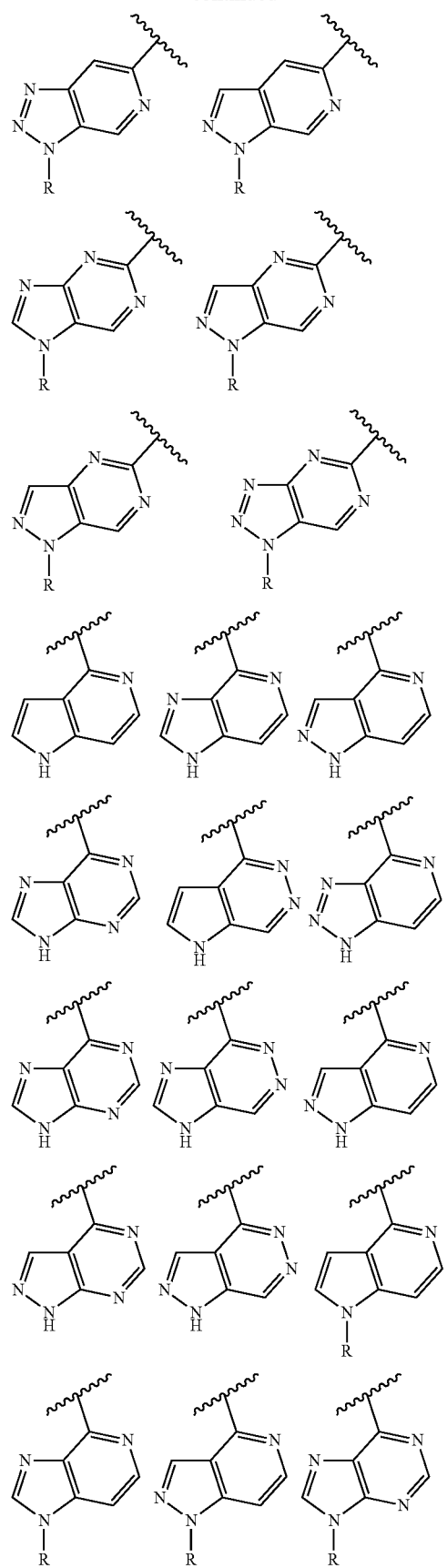
402
-continued
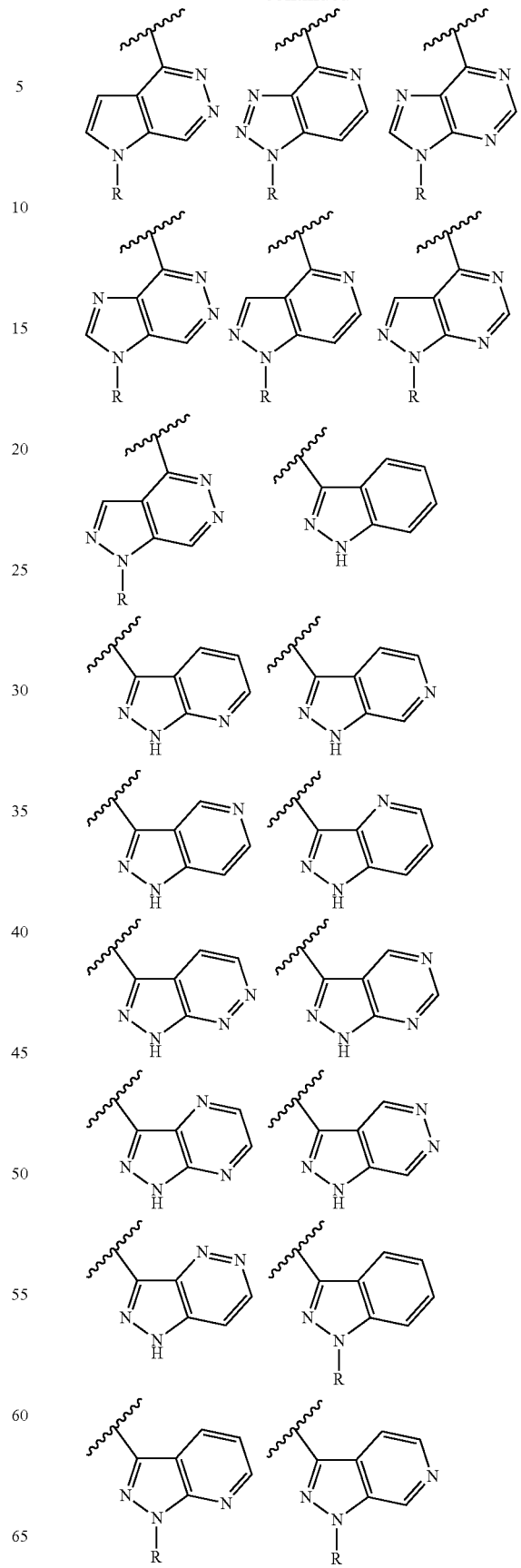

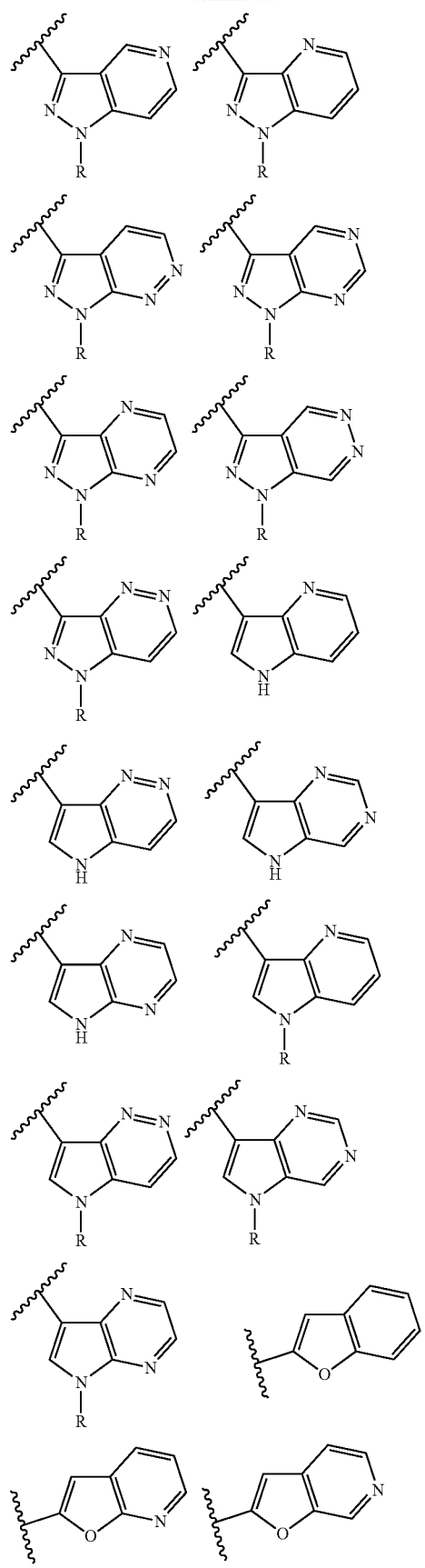
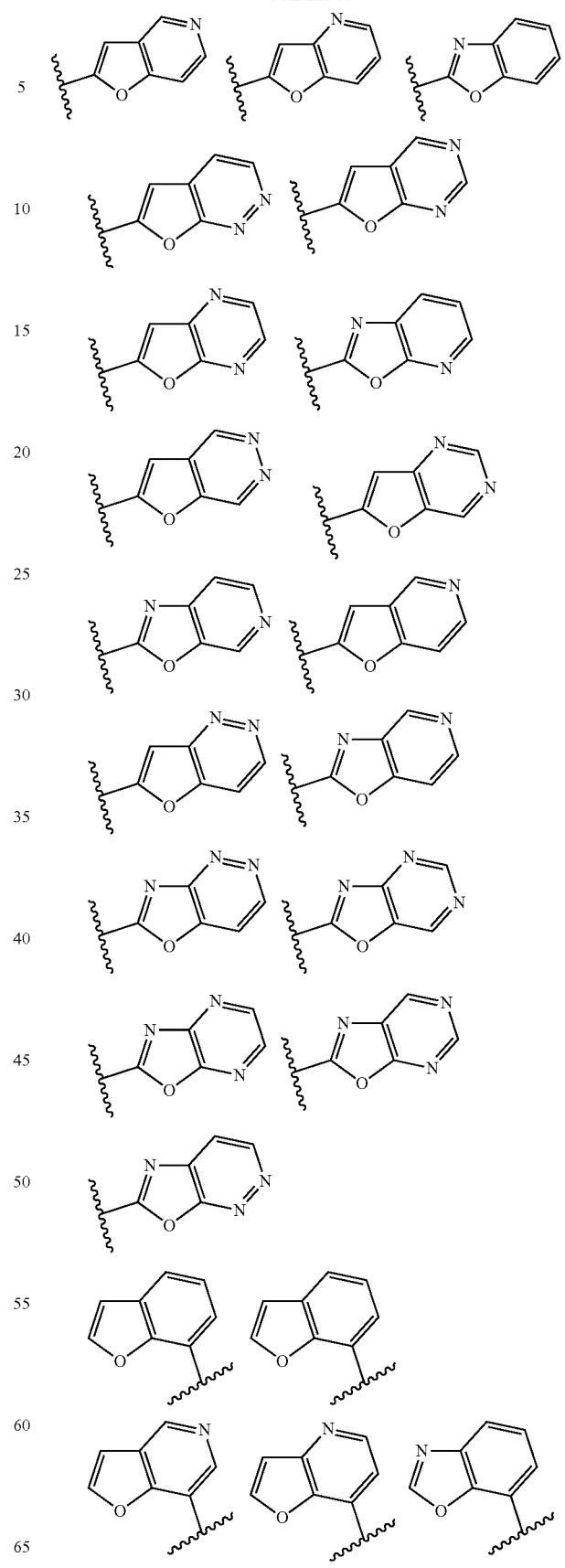

405
-continued
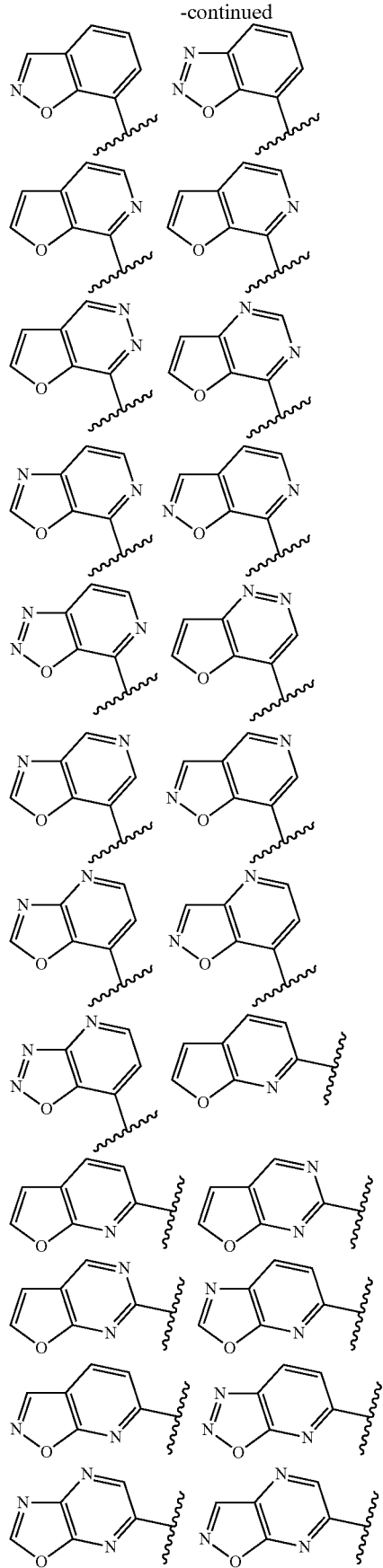
406
-continued
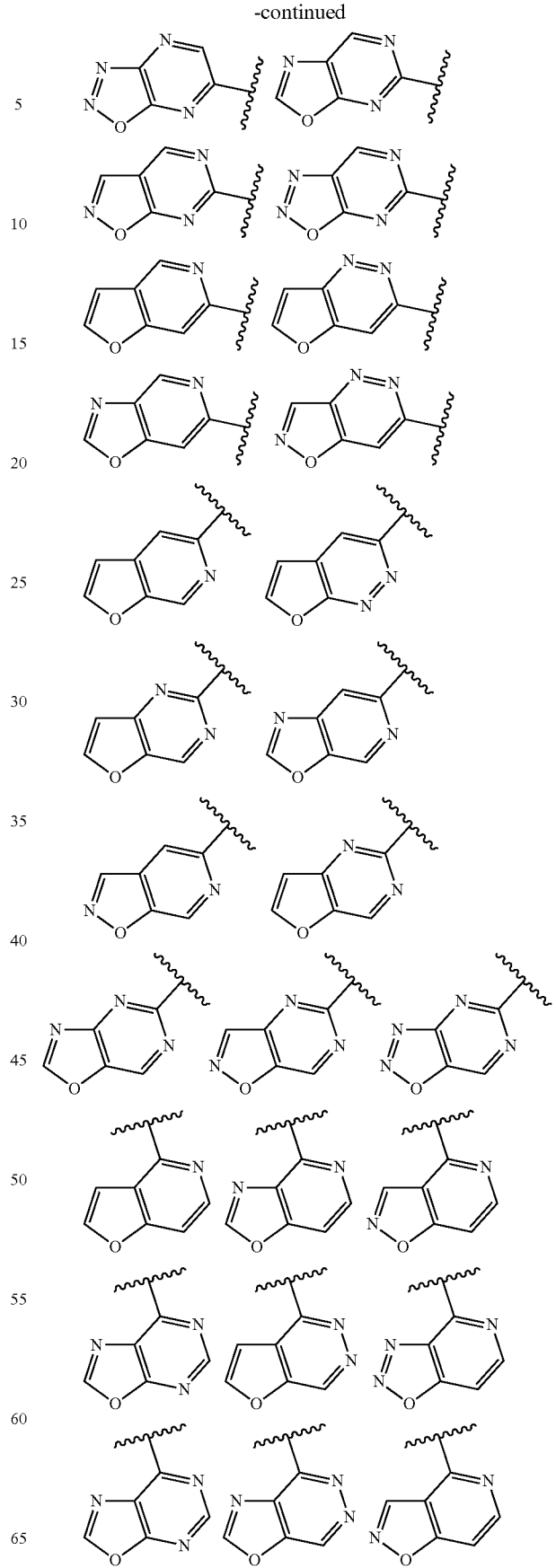

407
-continued
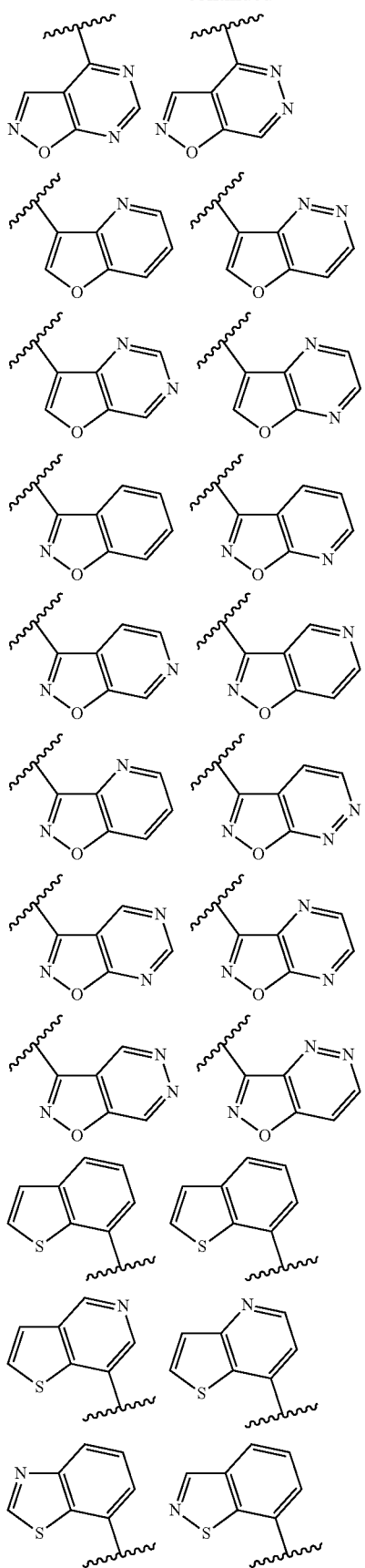
408
-continued
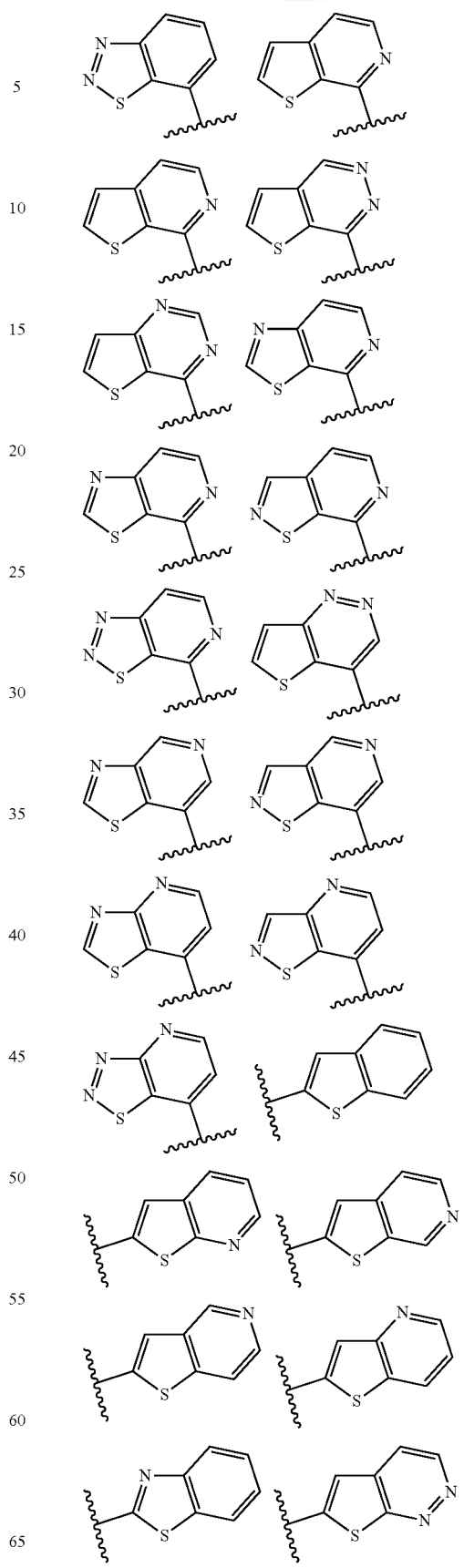

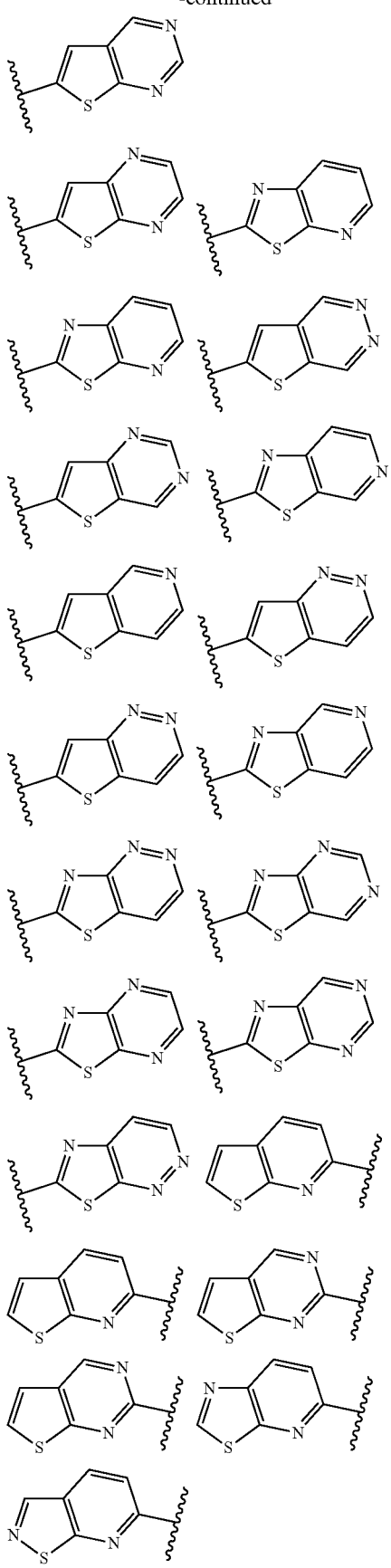
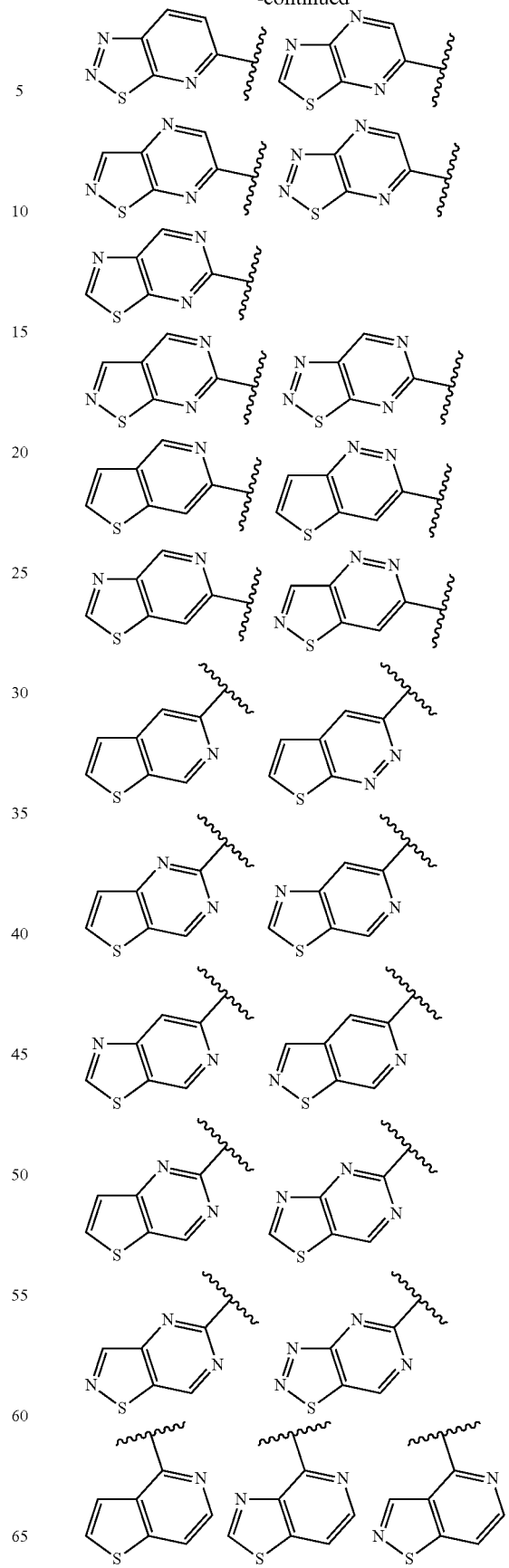

411
-continued
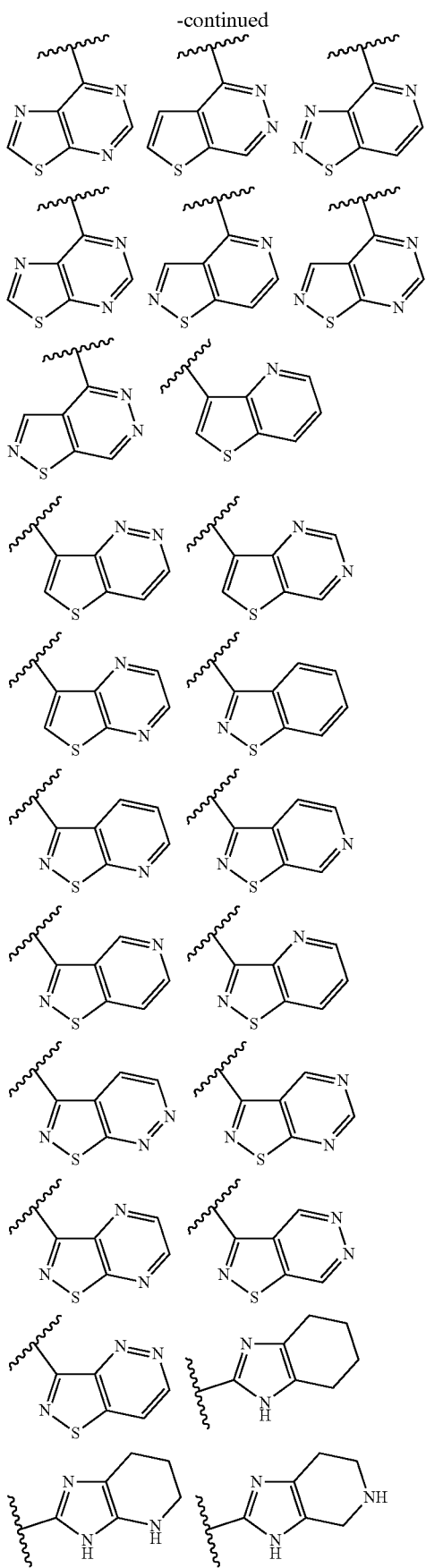
412
-continued
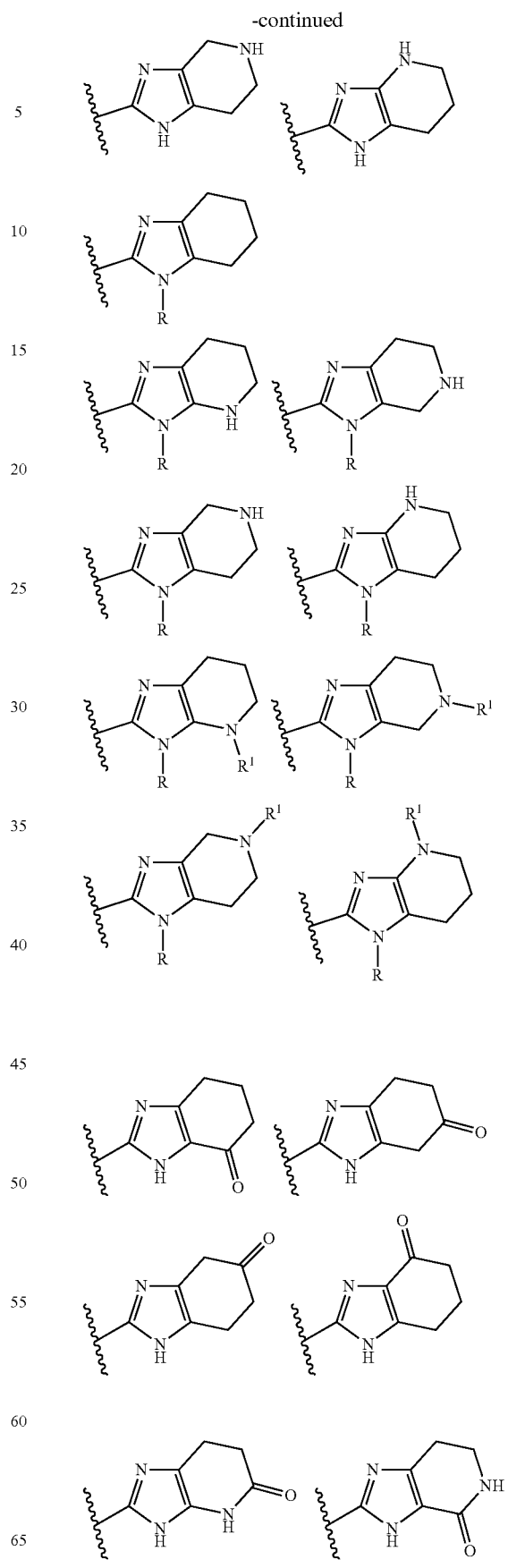

413
-continued
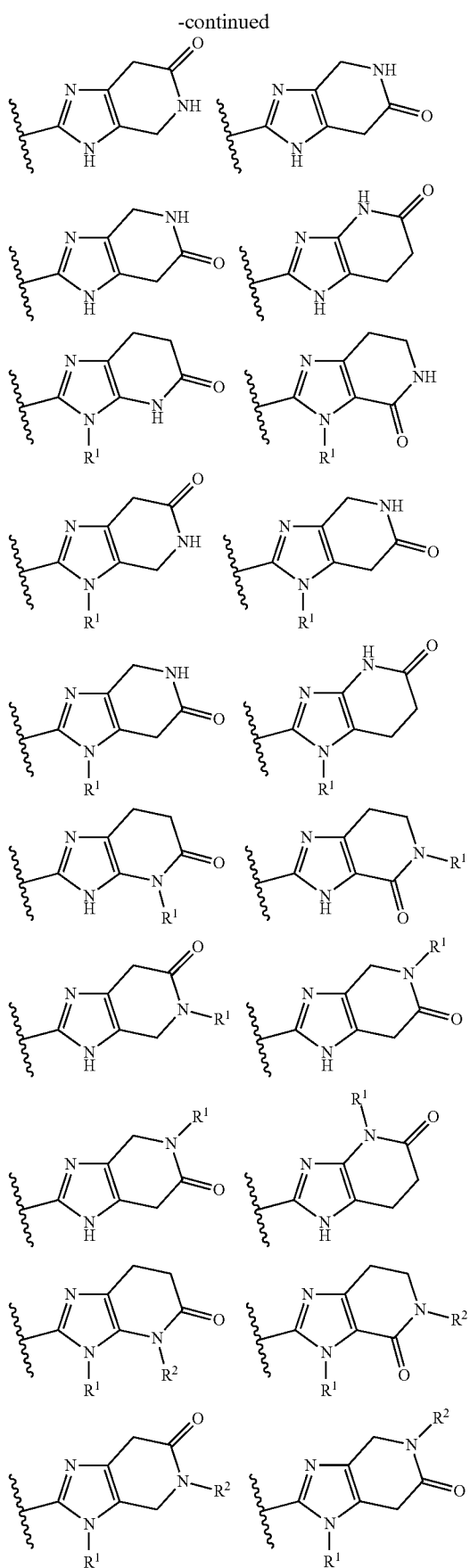
414
-continued
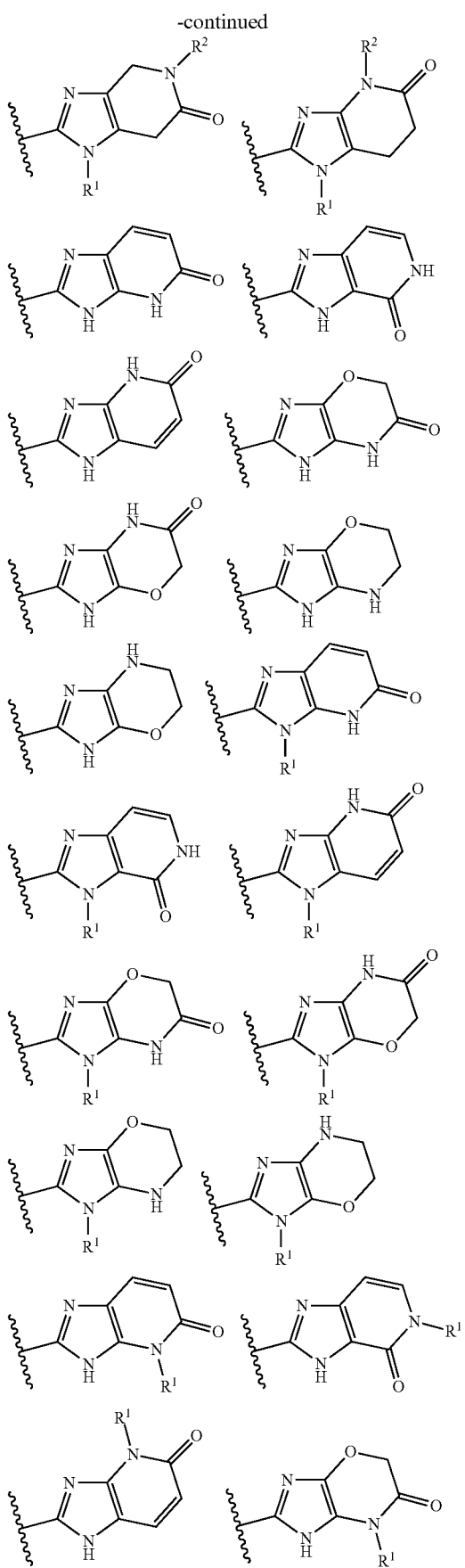

415
-continued
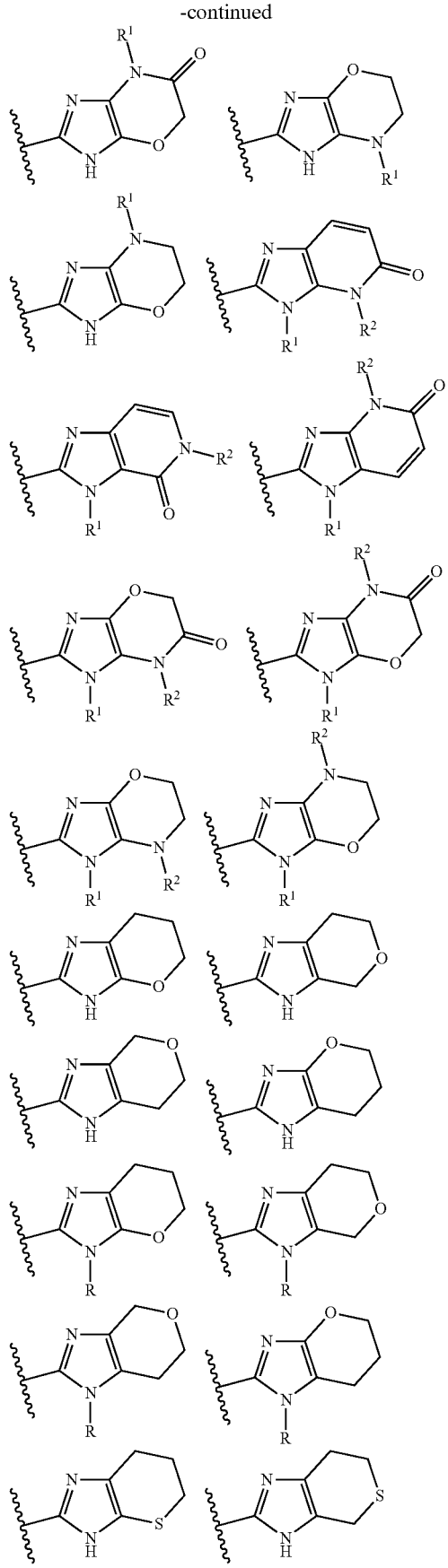
416
-continued
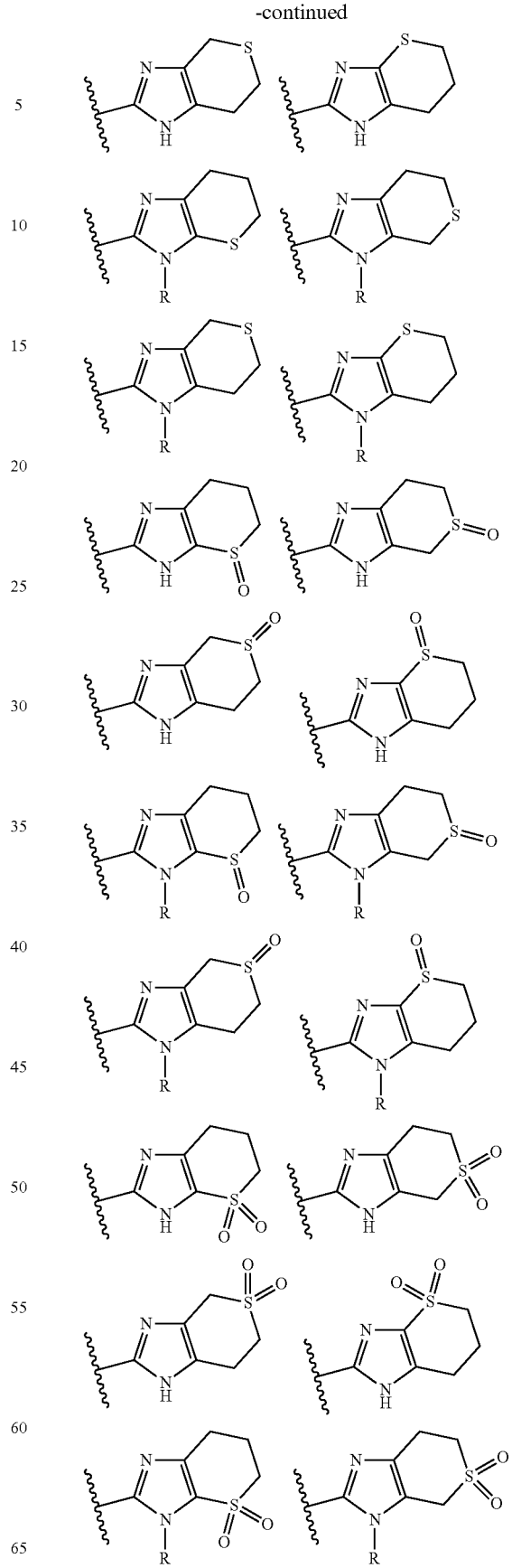

-continued
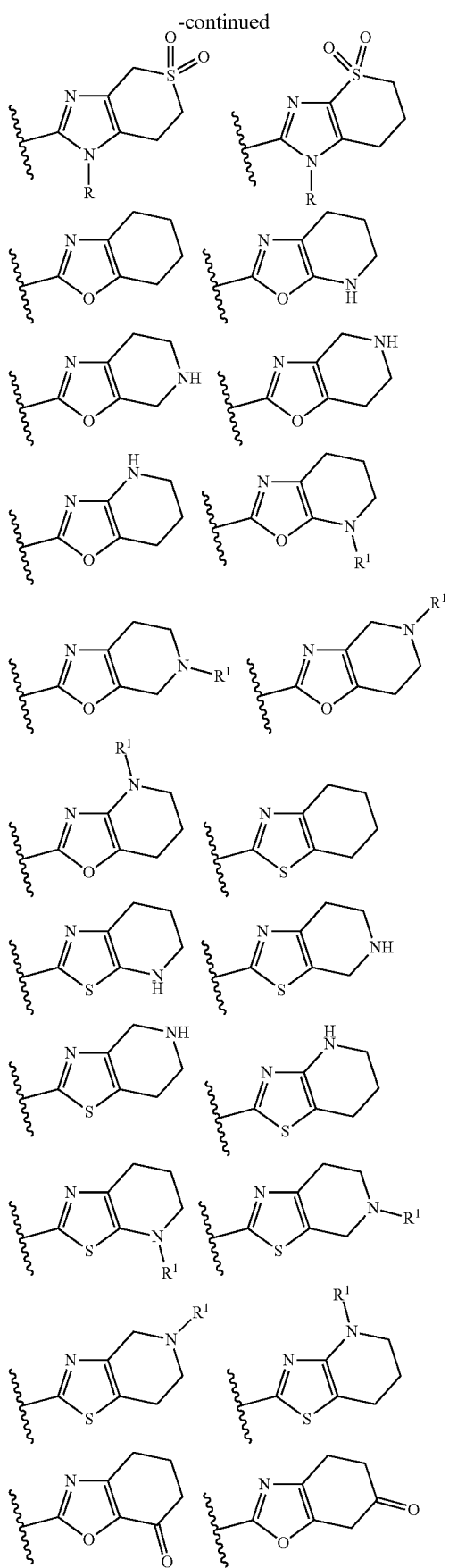
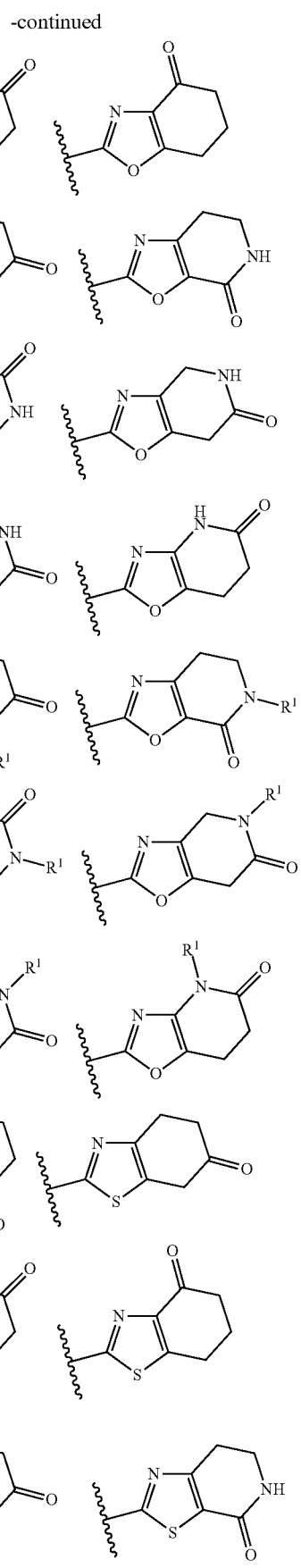

419
-continued
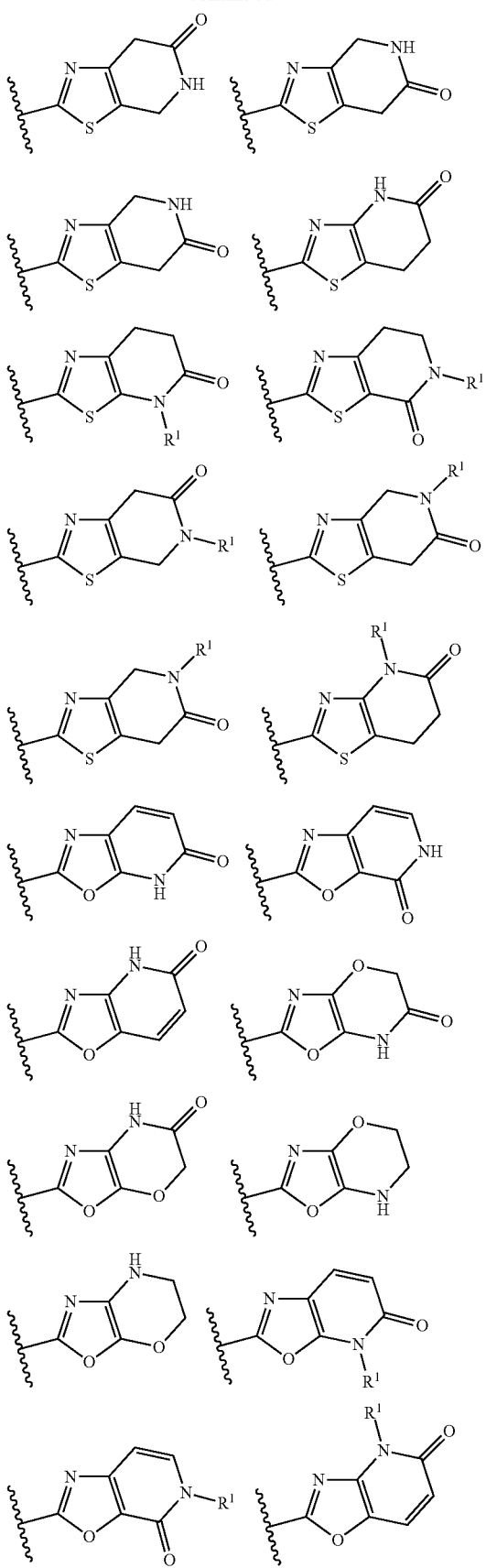
420
-continued
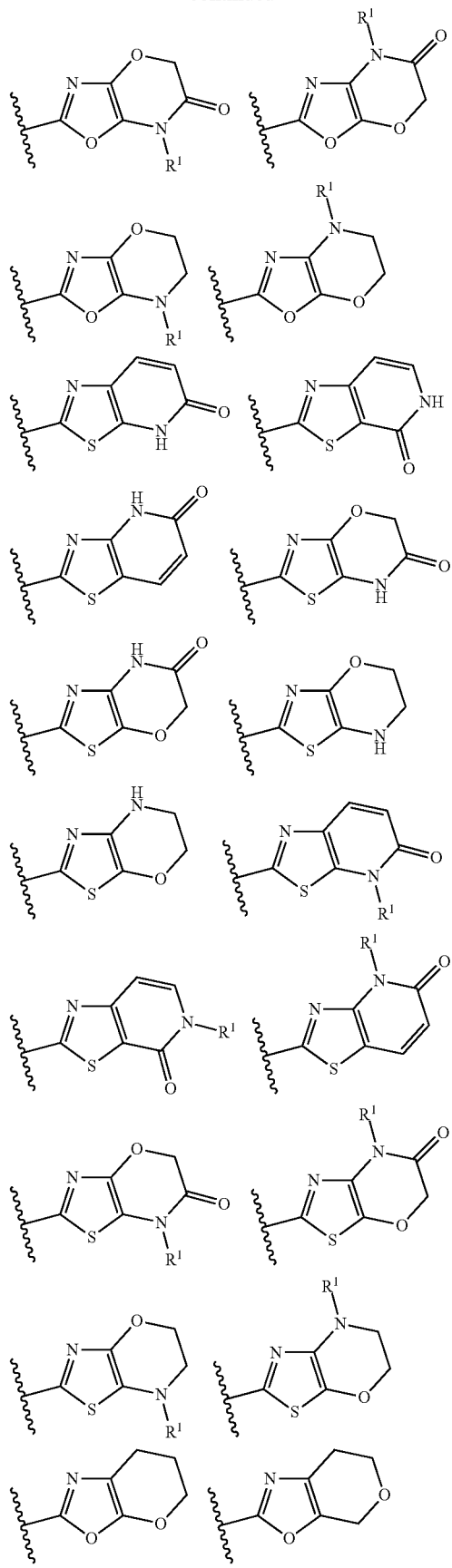

421
-continued
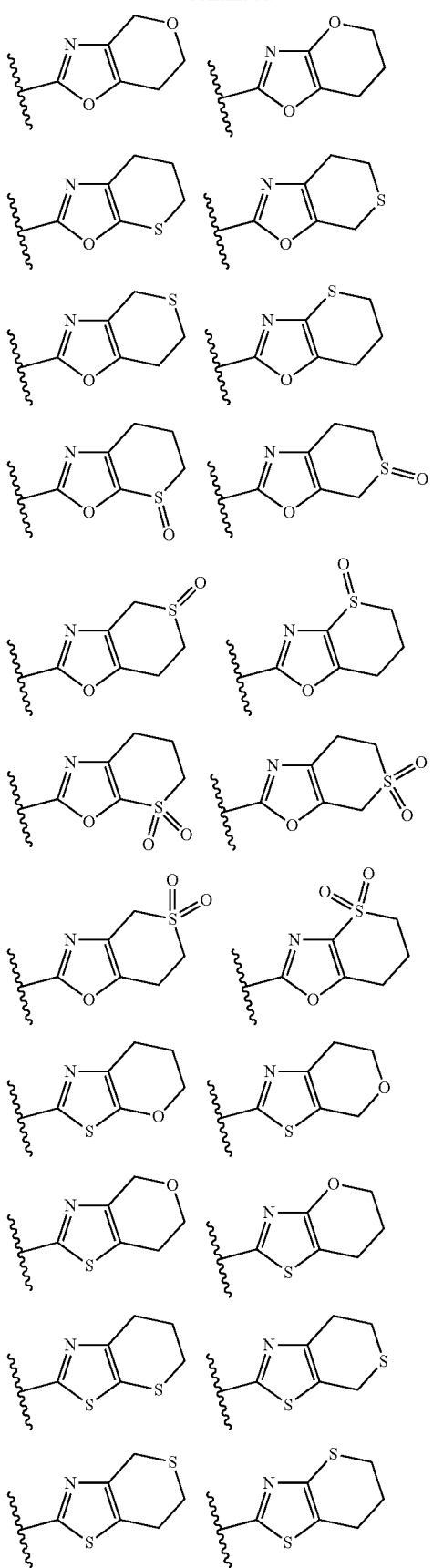
422
-continued
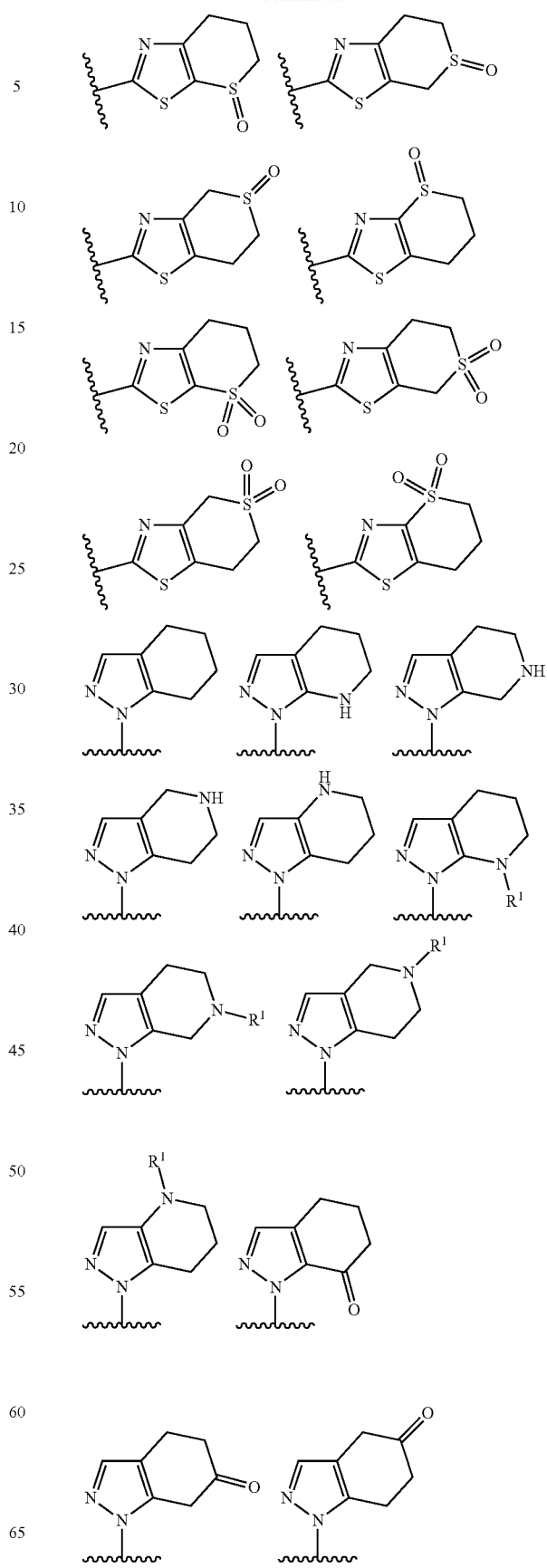

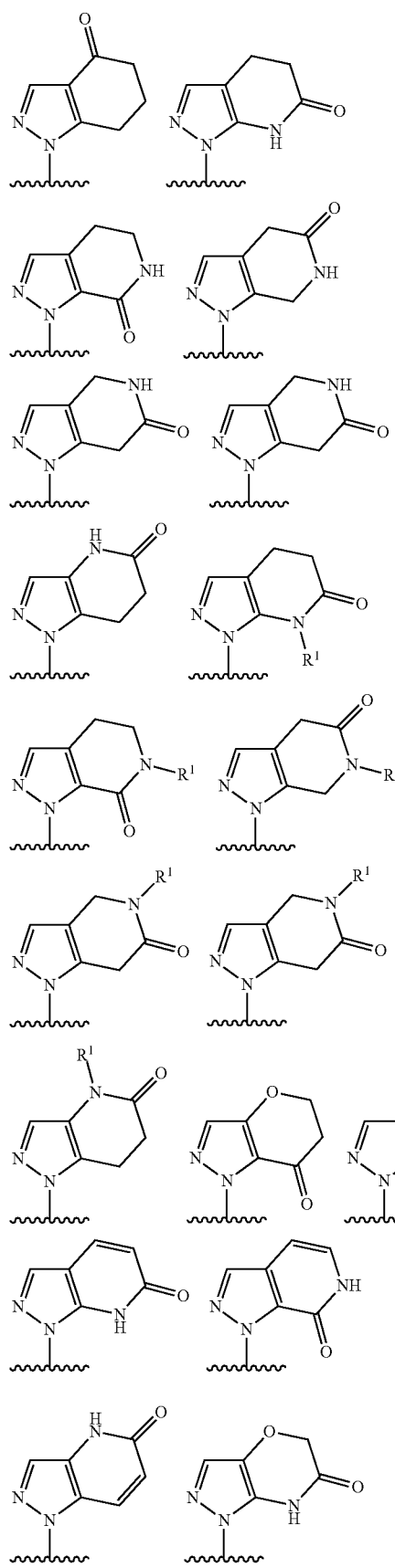
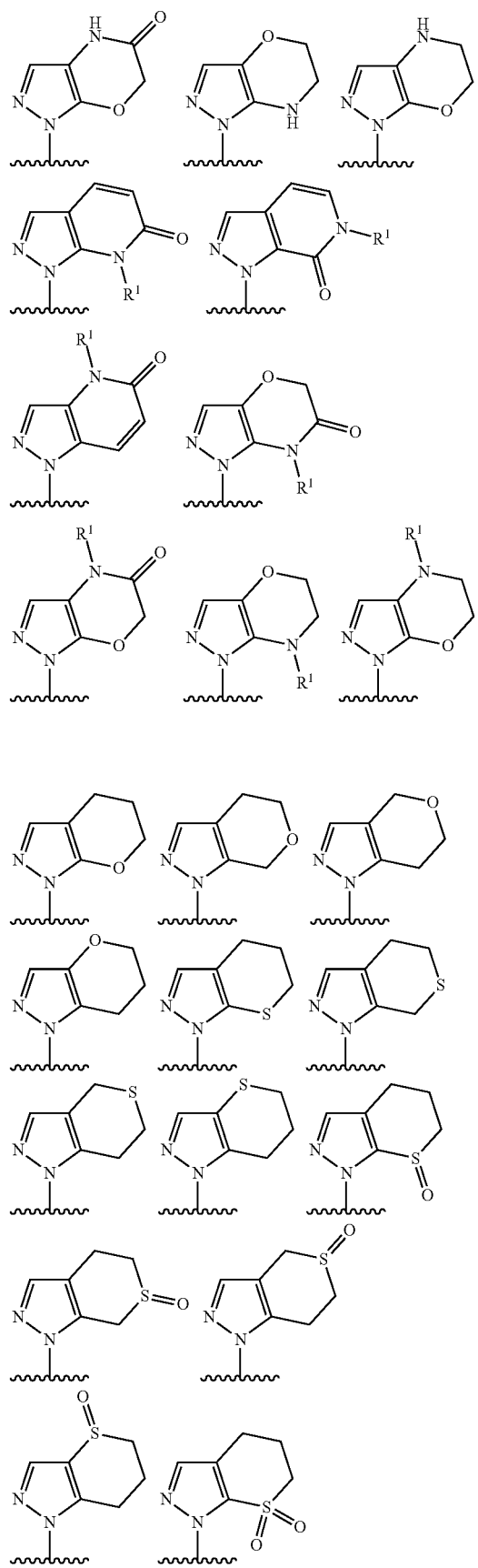

425
-continued
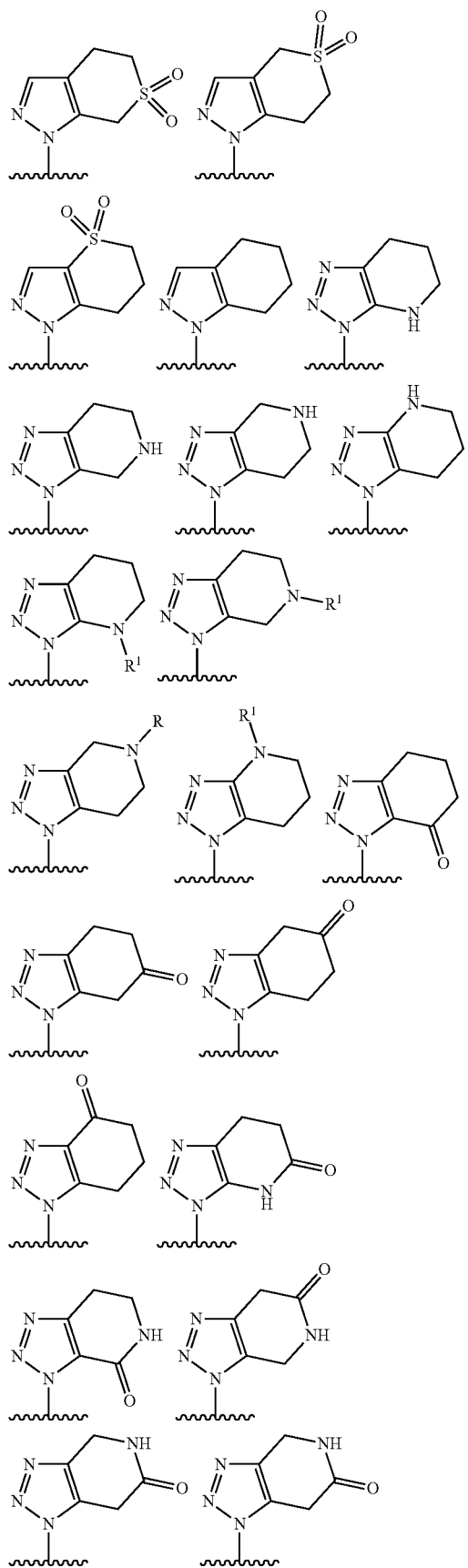
426
-continued
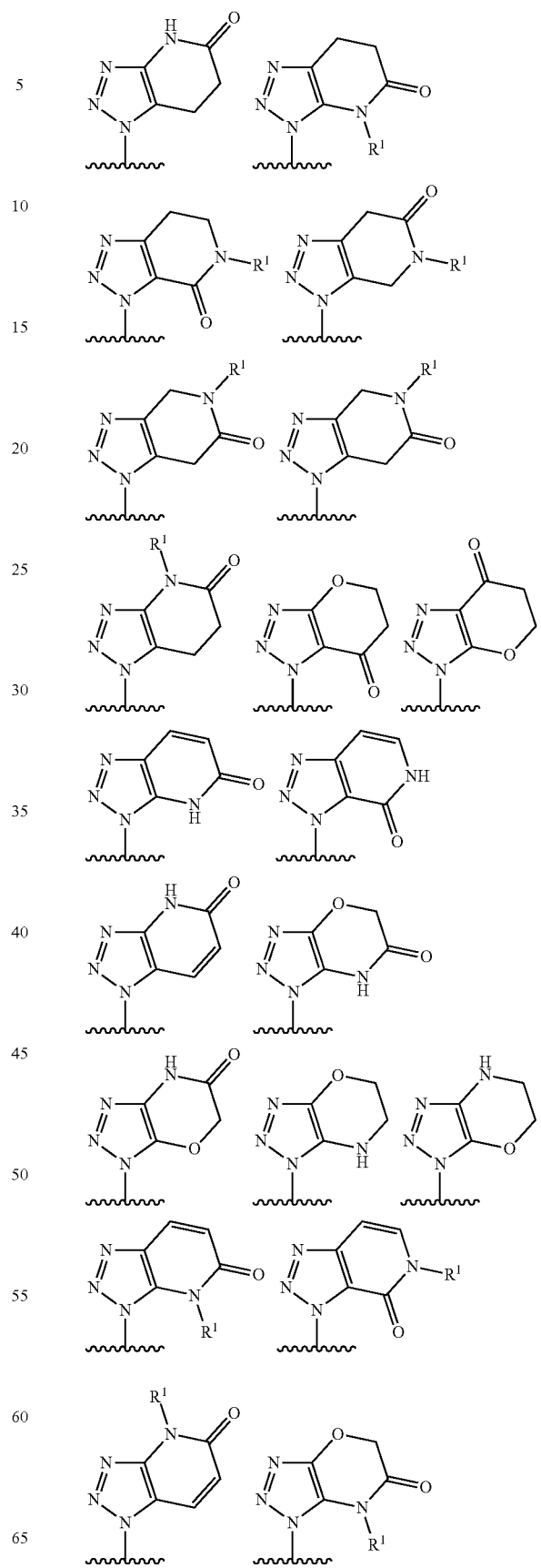

427
-continued
428
-continued
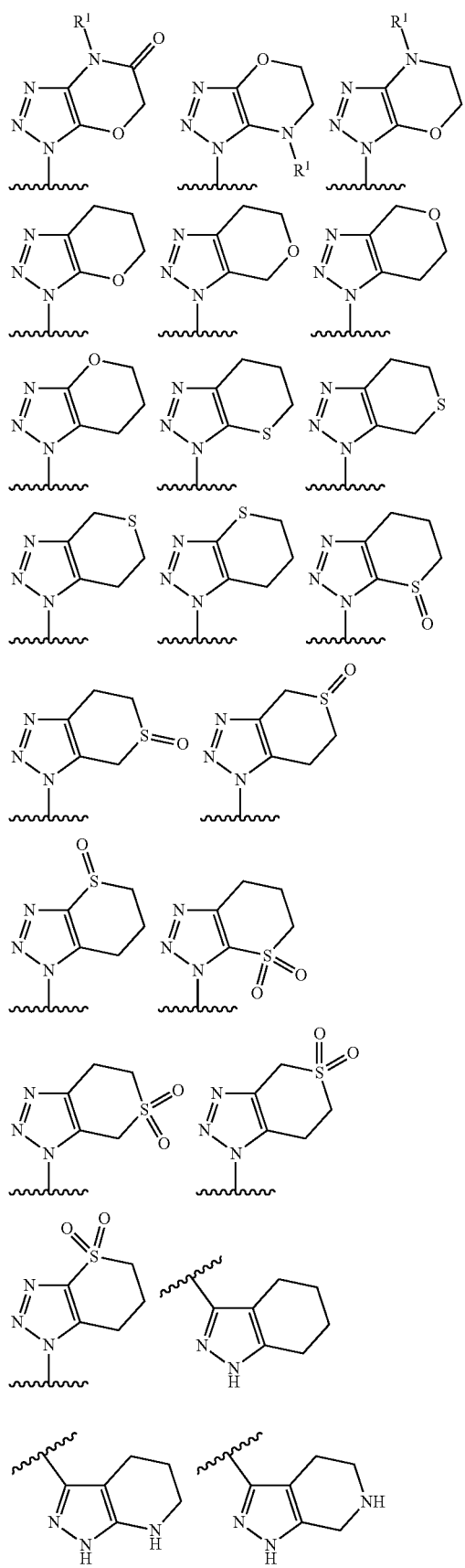
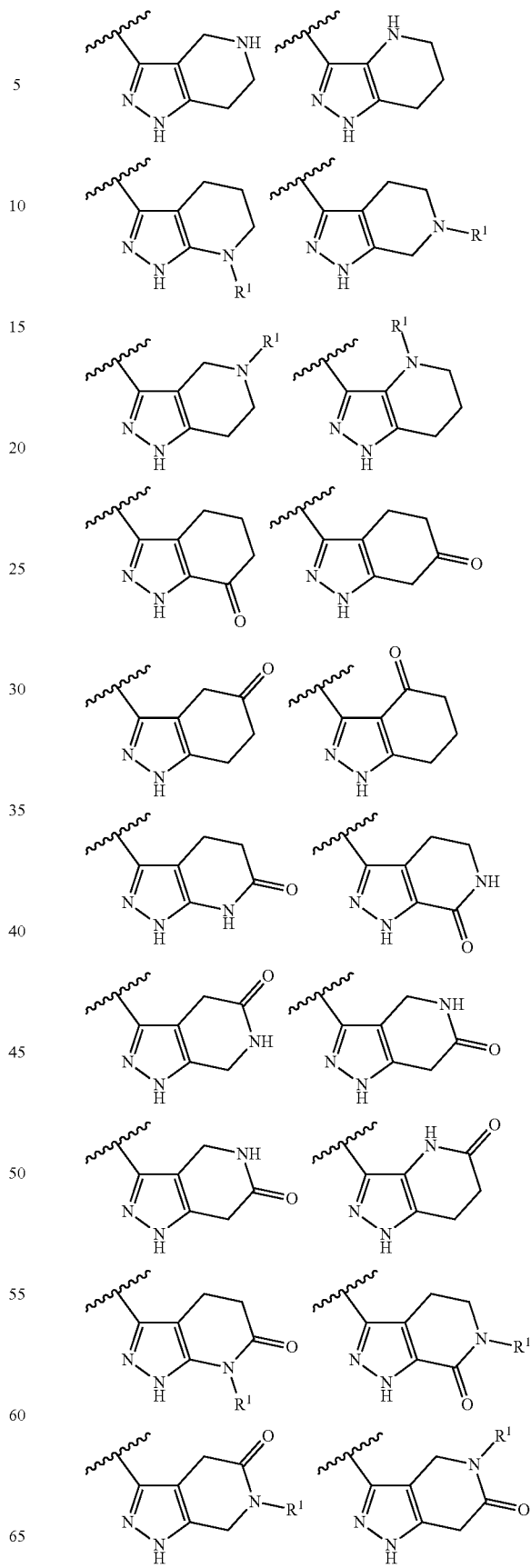

-continued
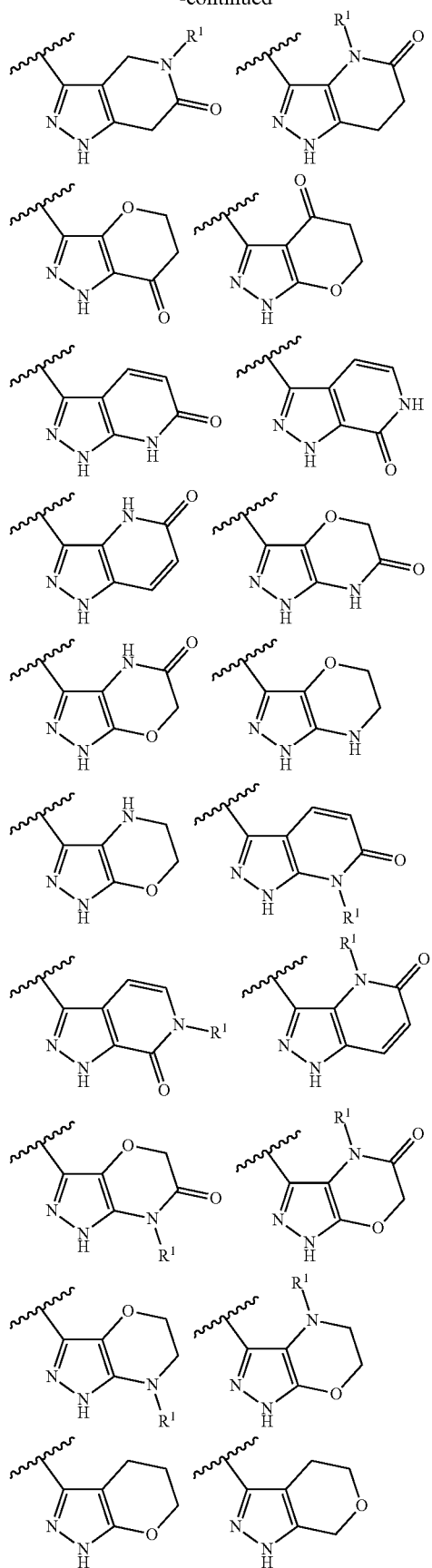
-continued
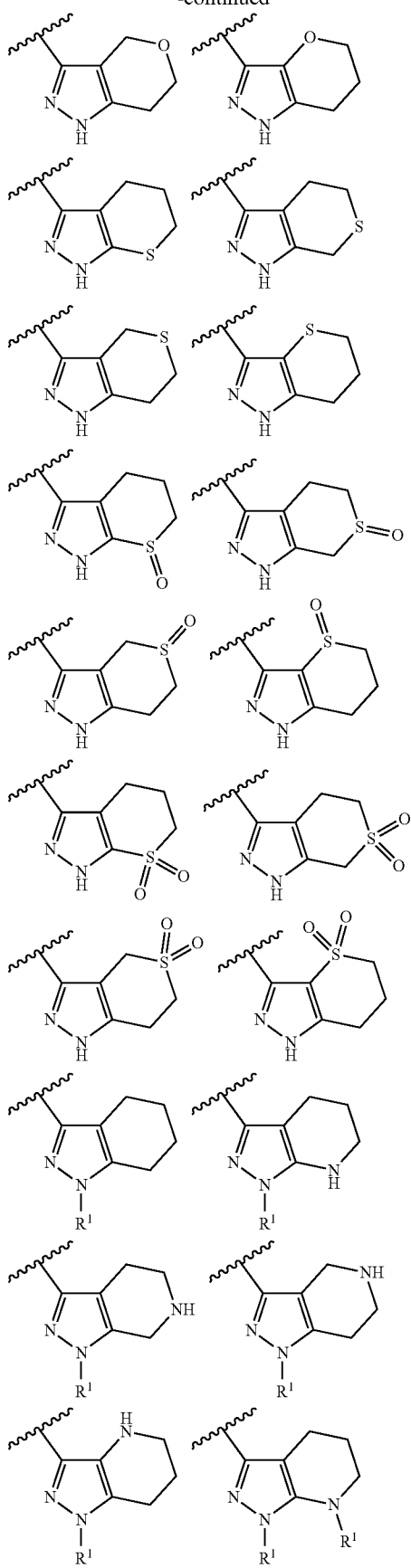

431
-continued
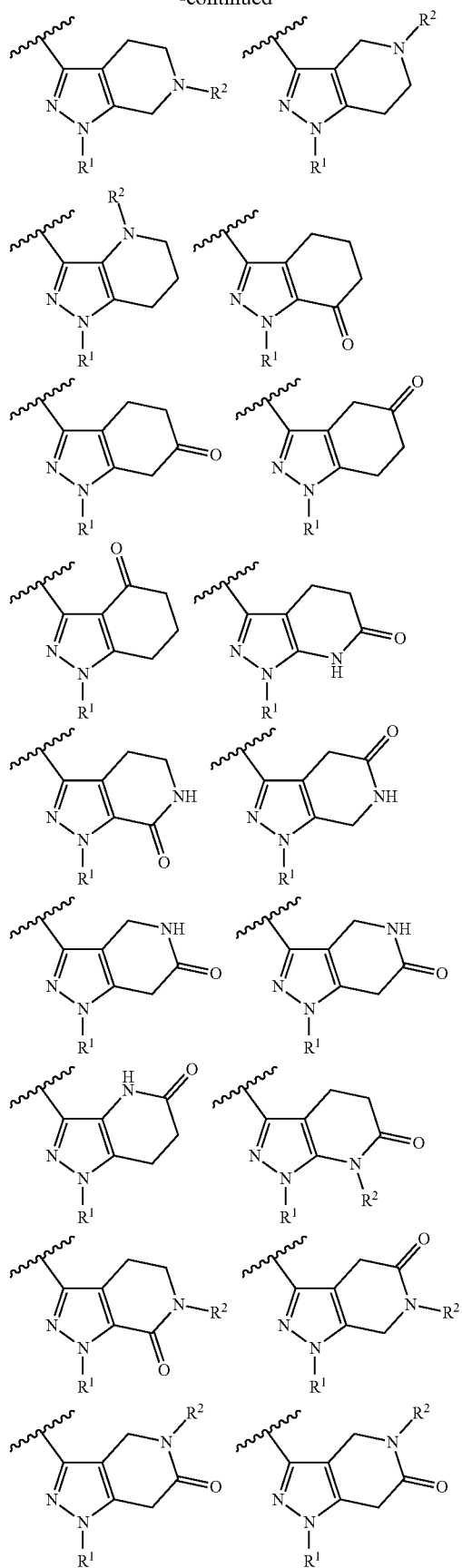
432
-continued
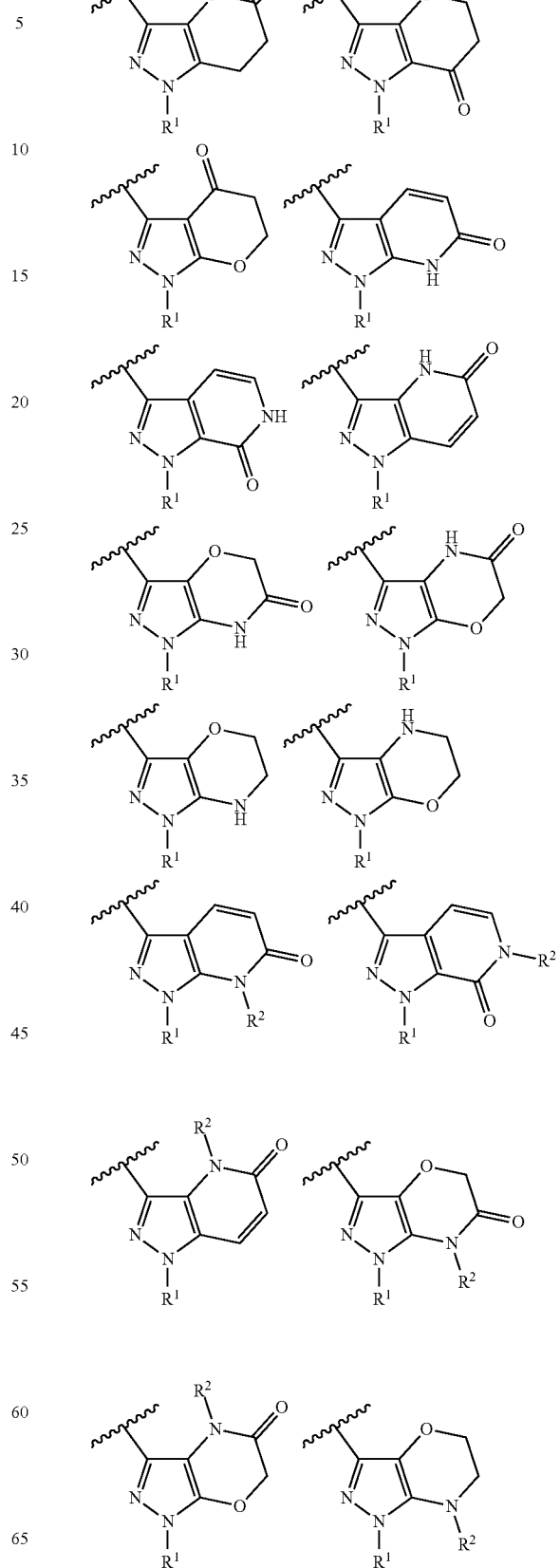

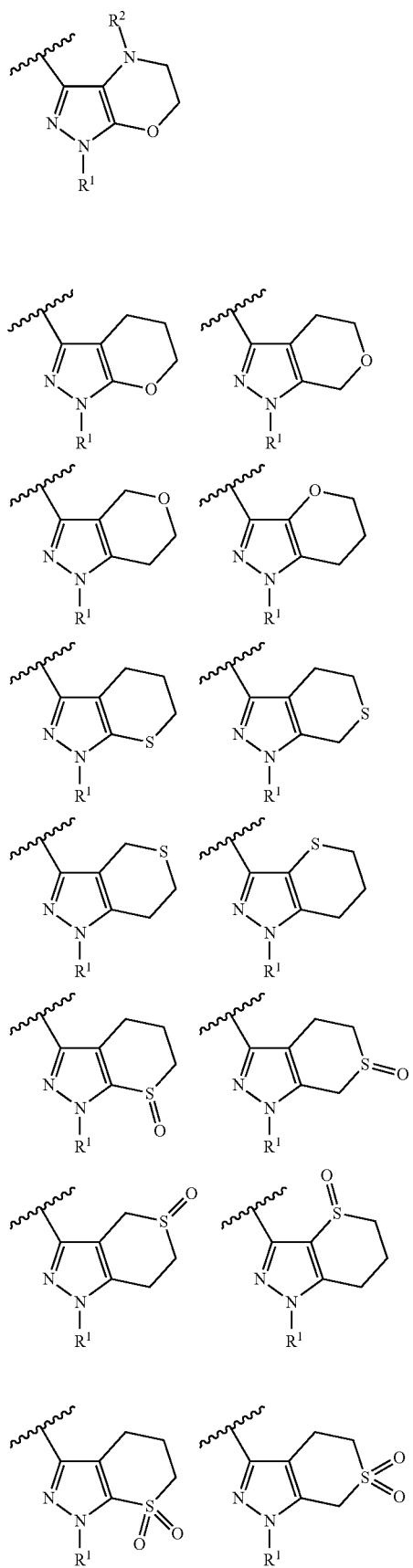
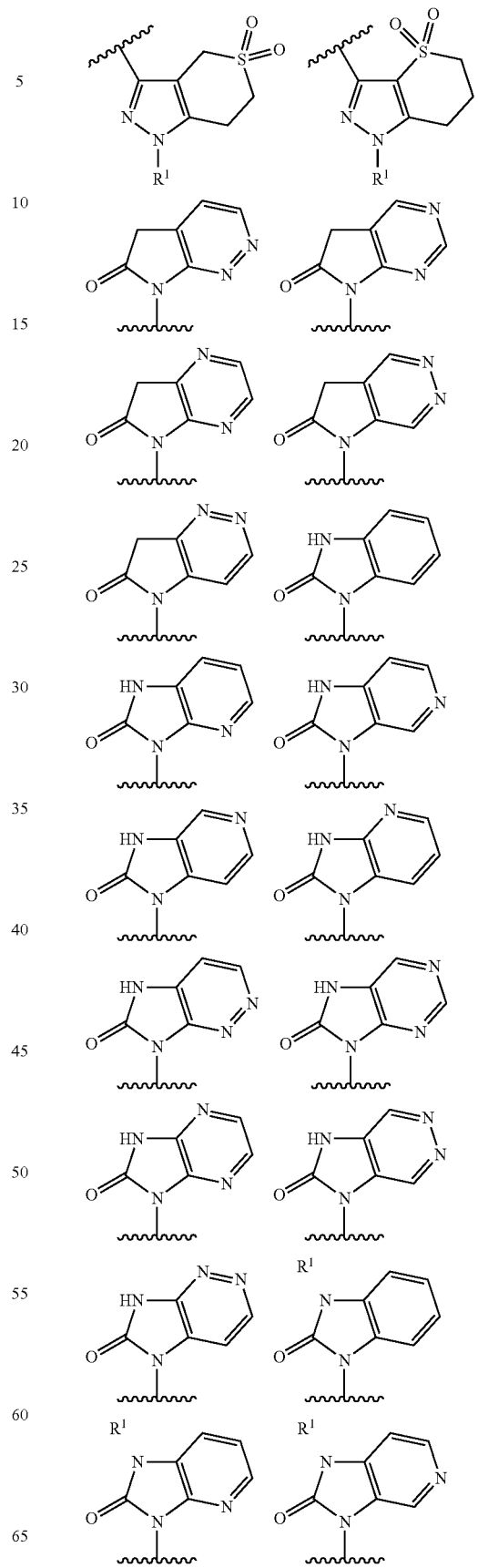

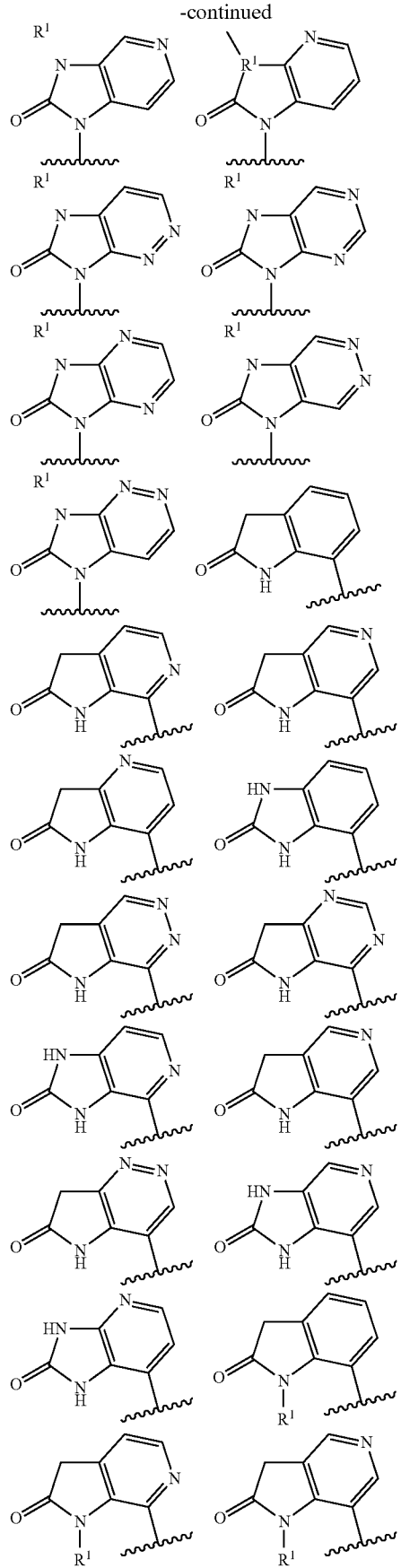
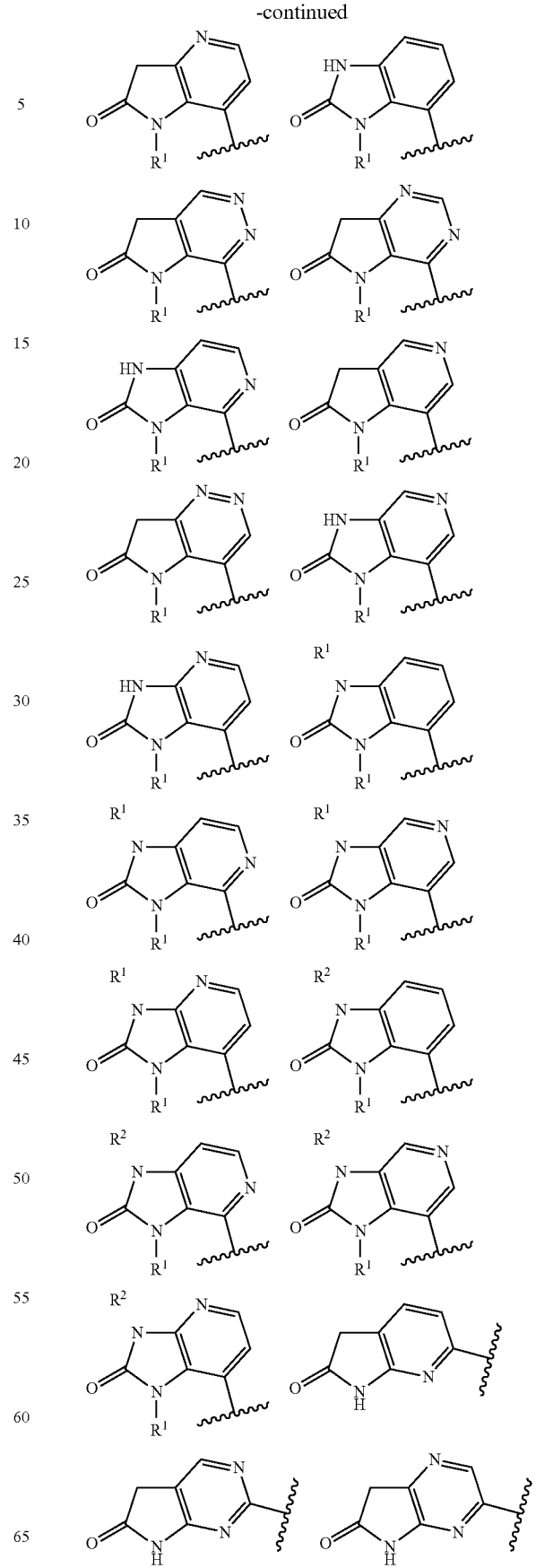

437
-continued
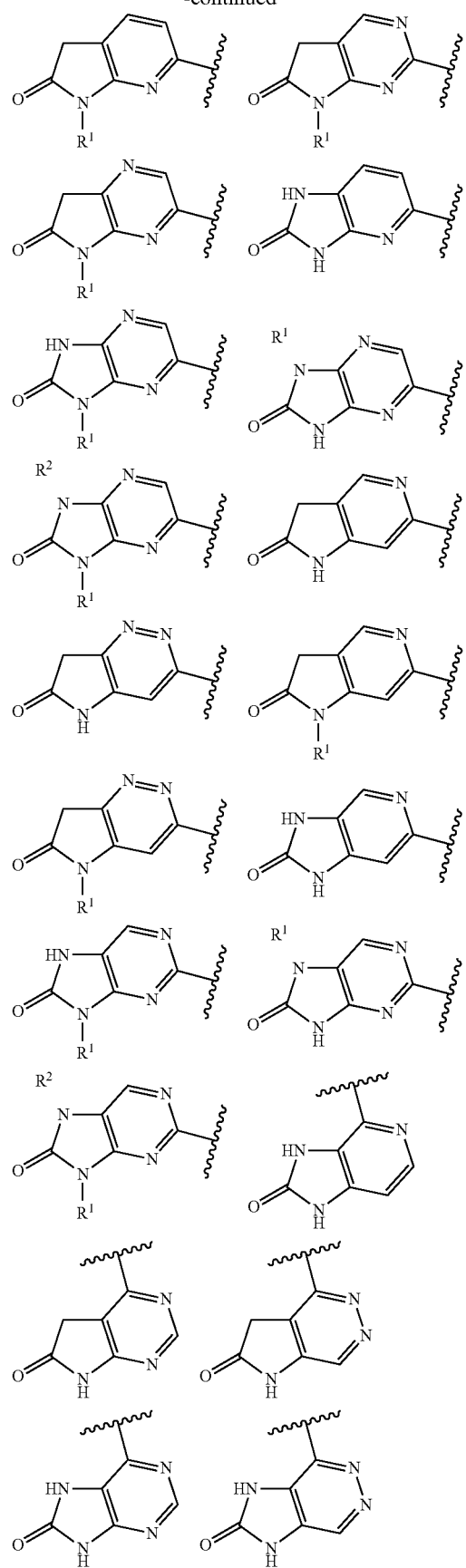
438
-continued
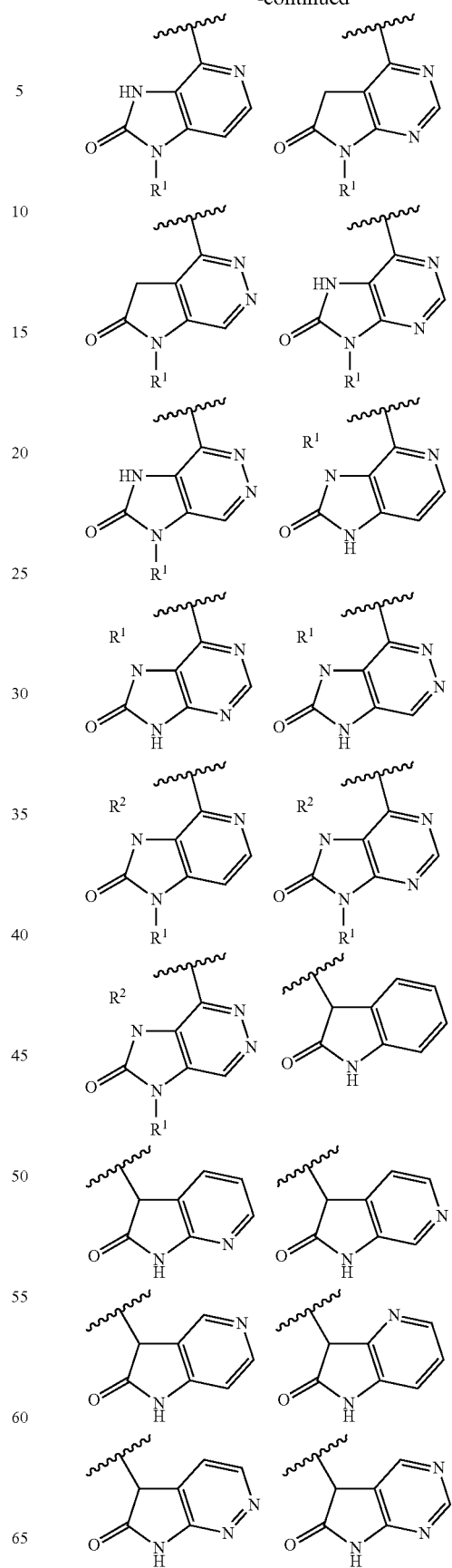

439
-continued
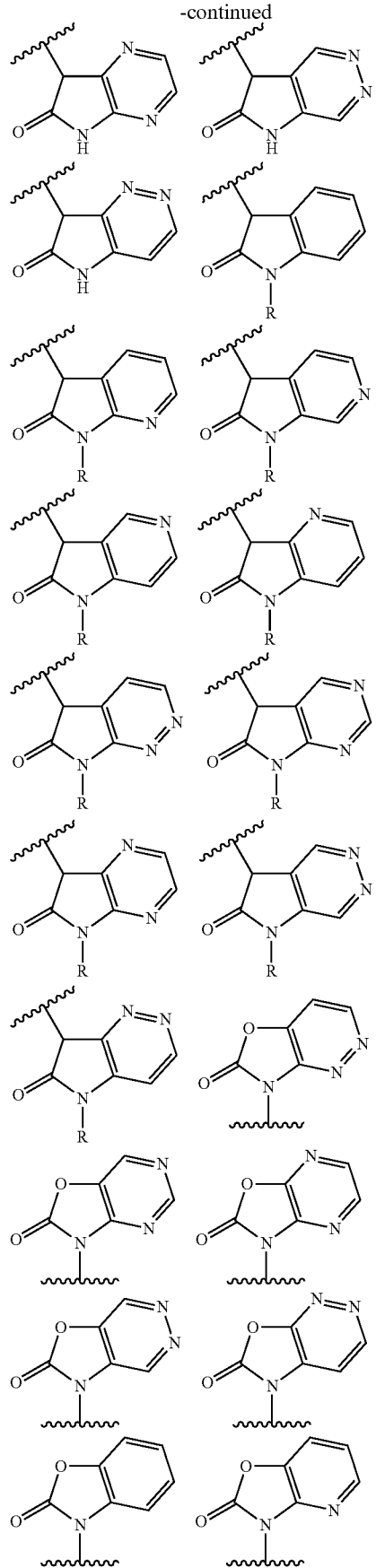
440
-continued
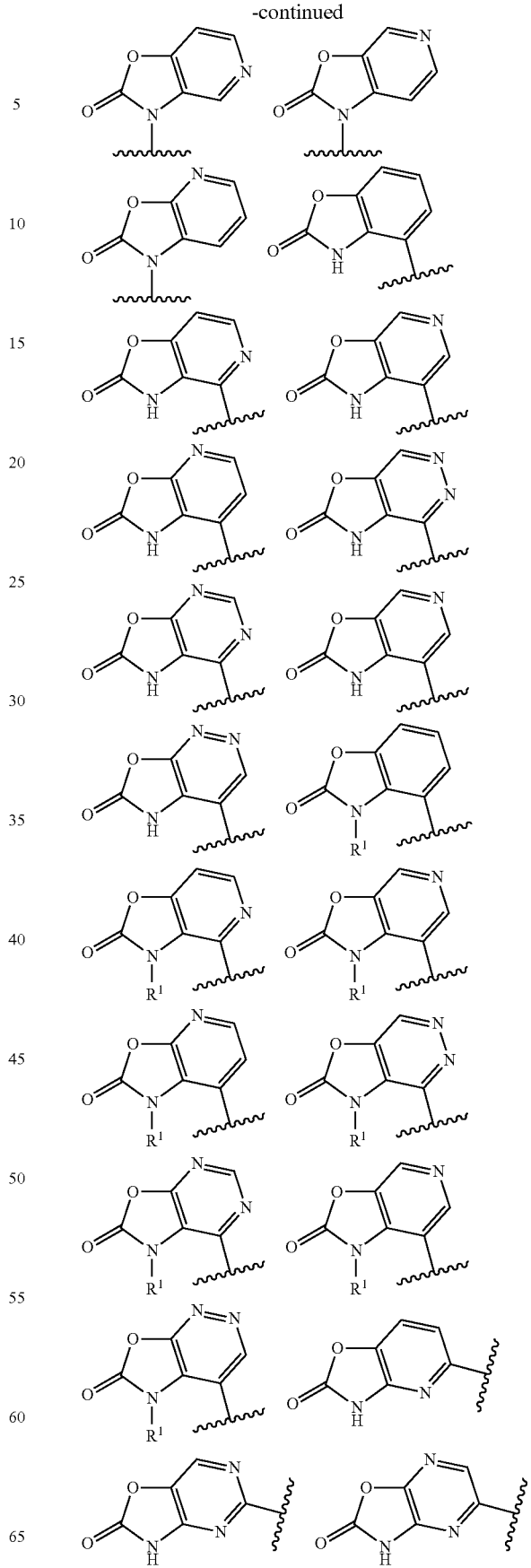

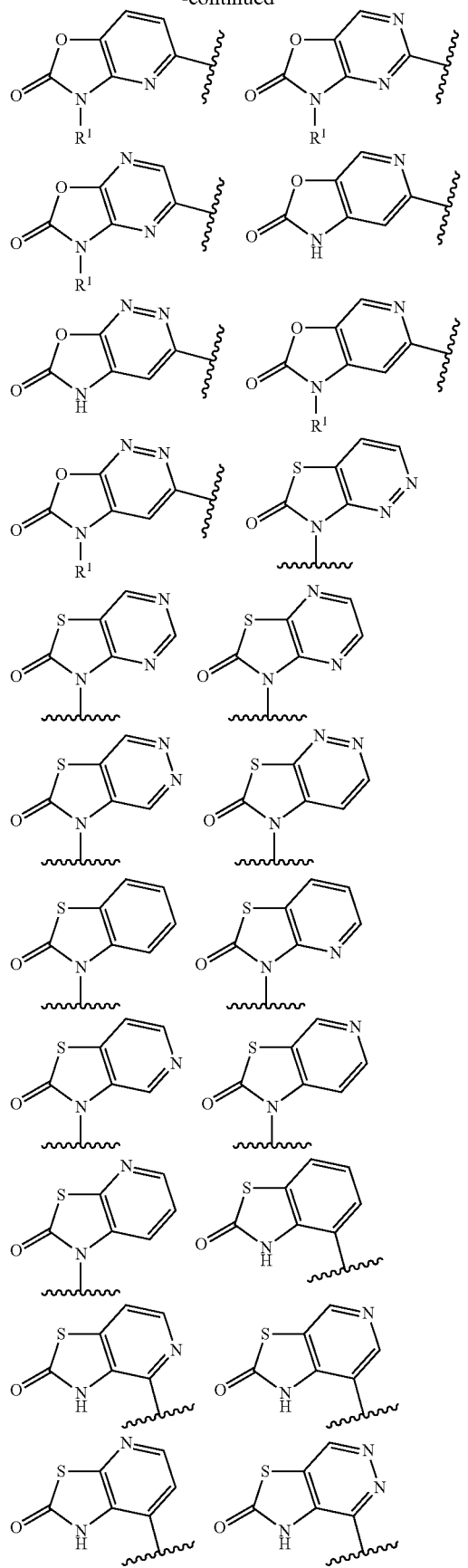
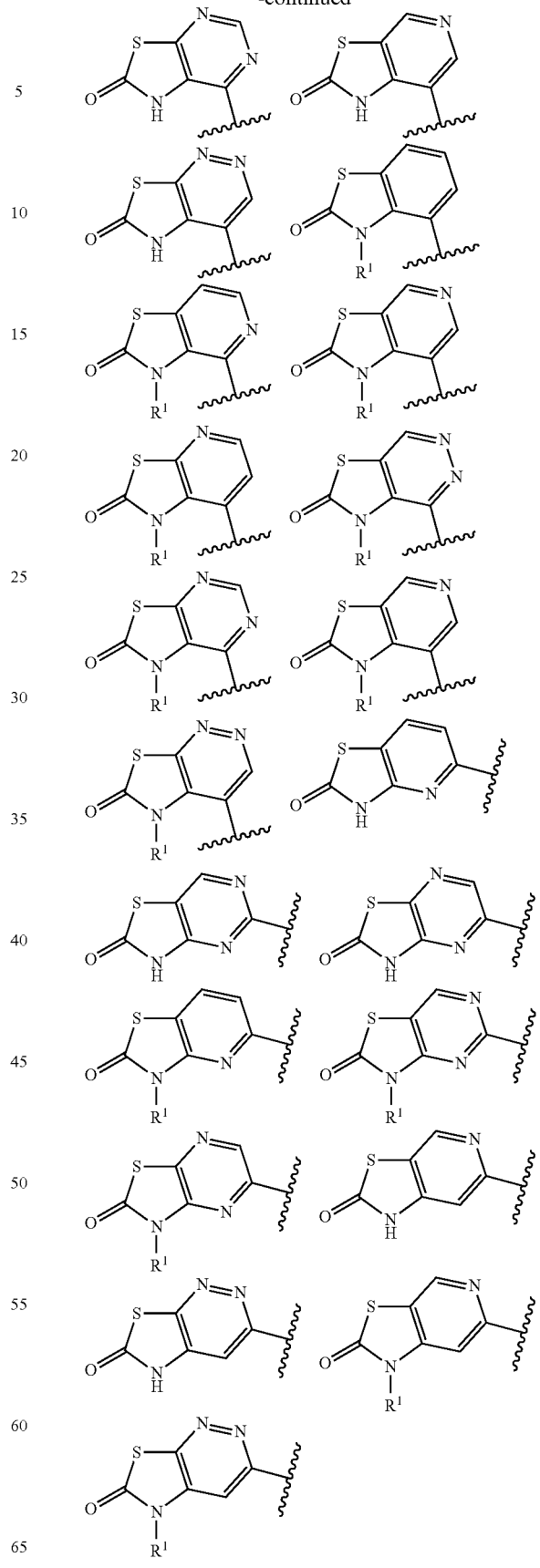

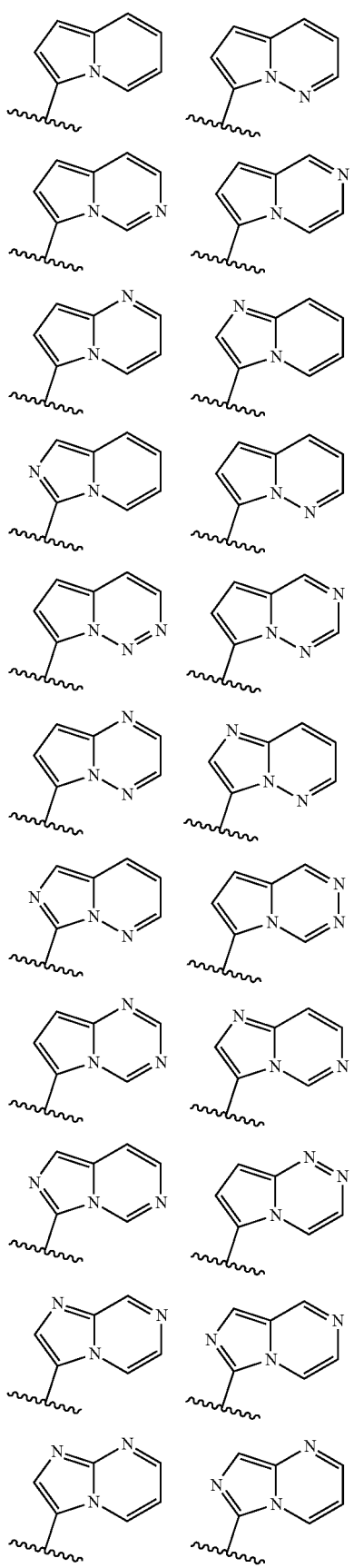
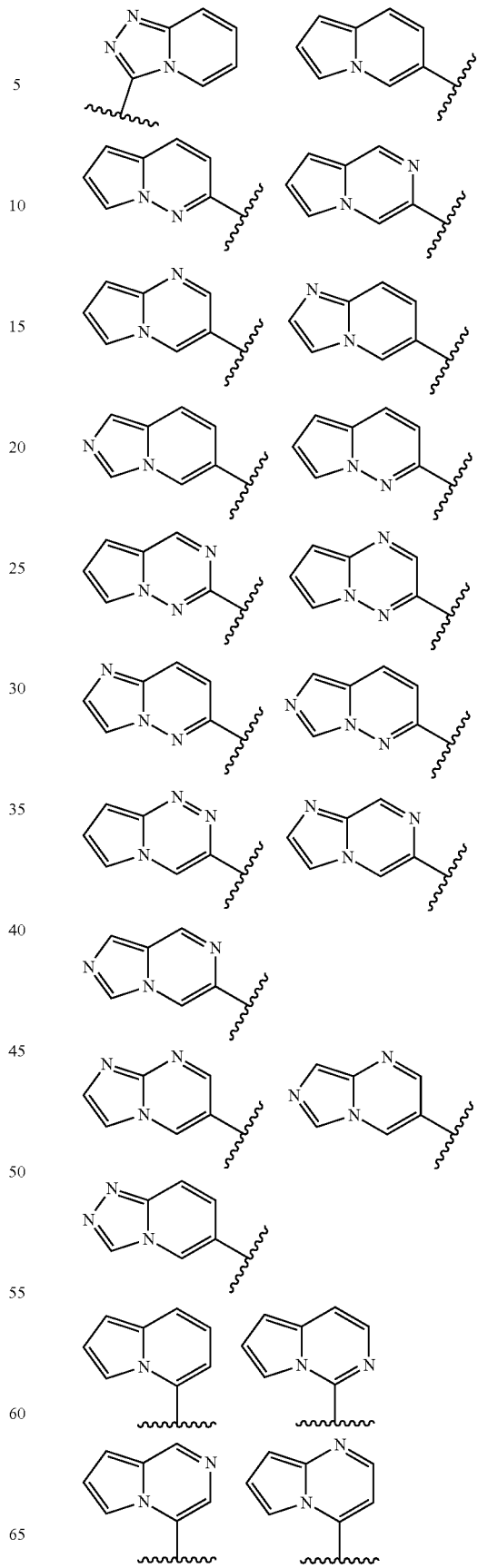

445
-continued
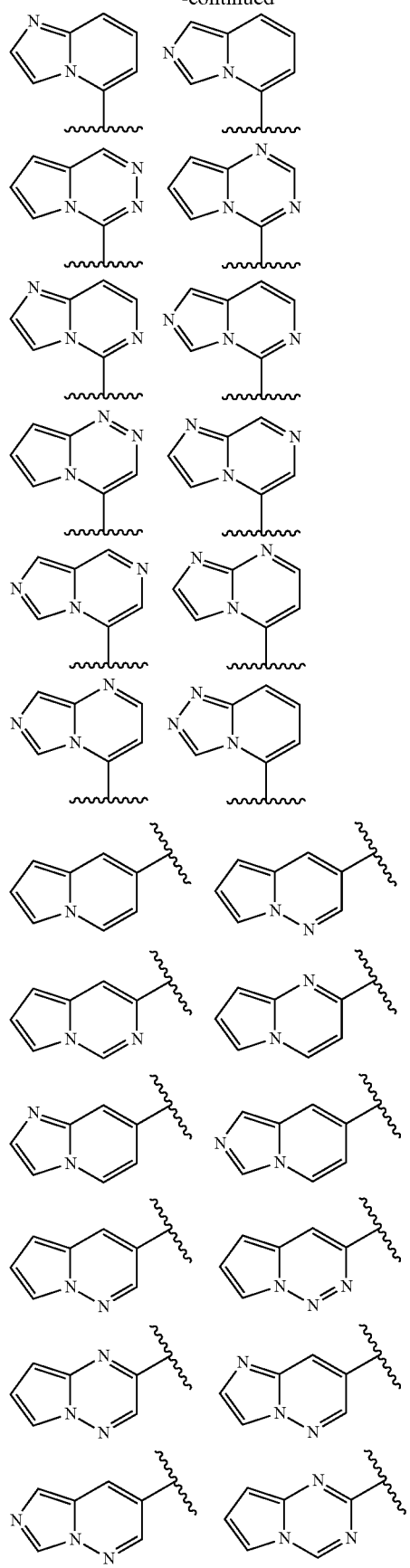
446
-continued
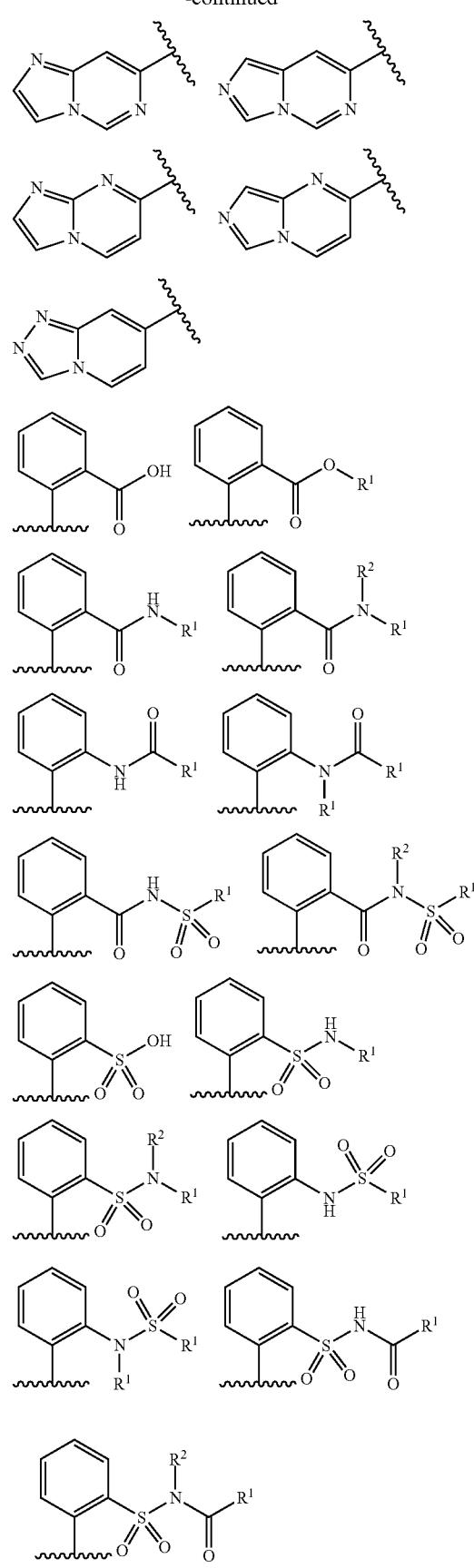

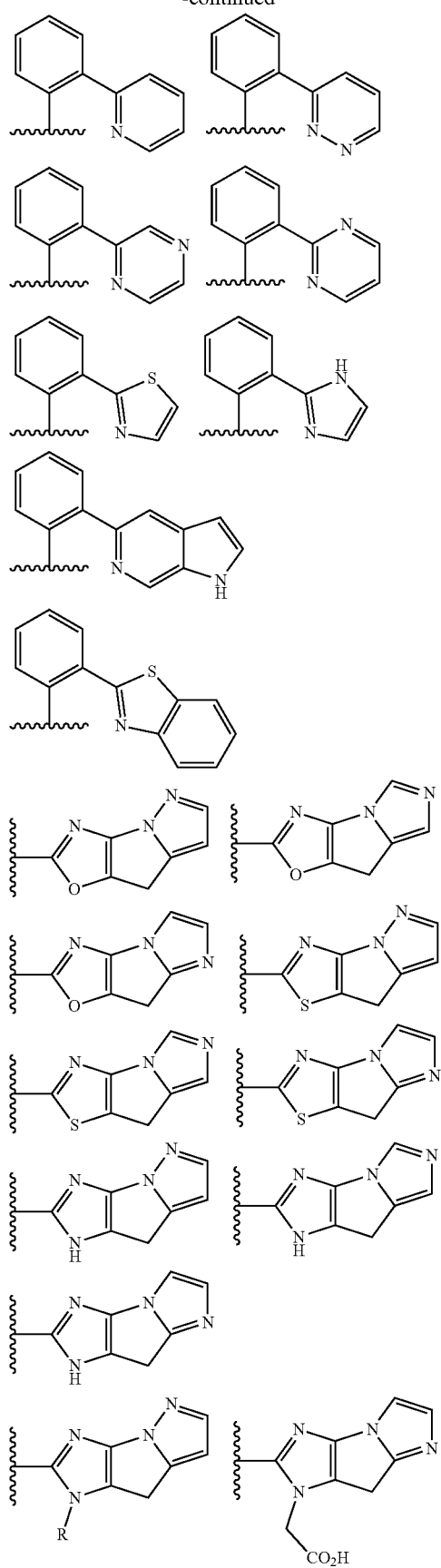
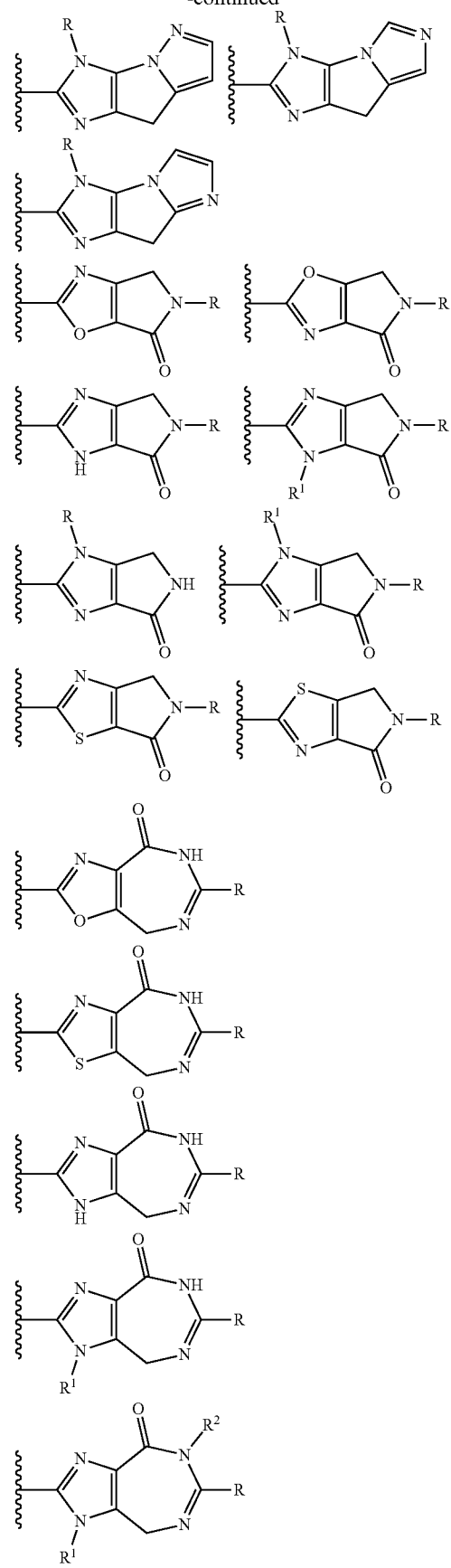

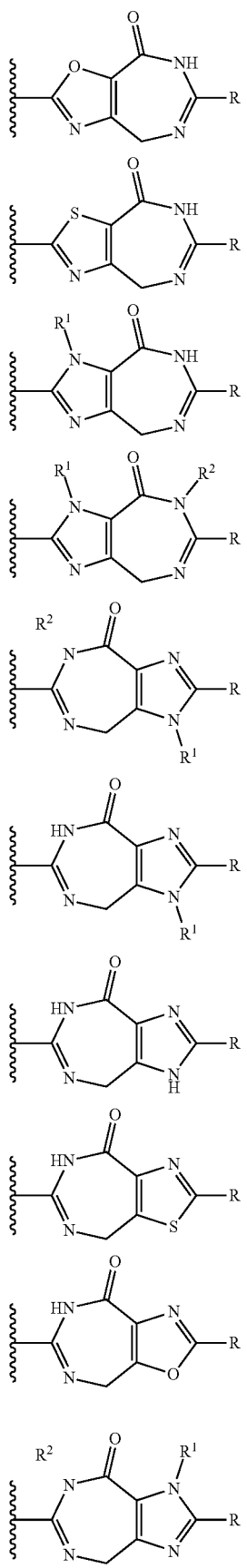
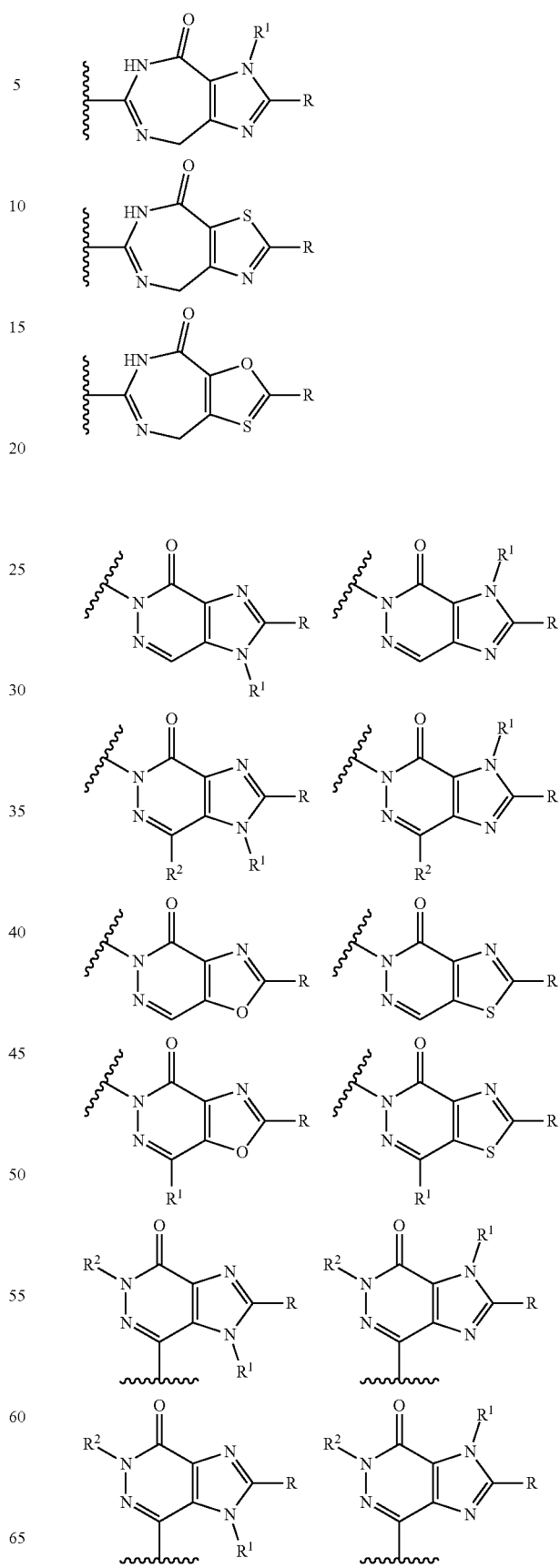

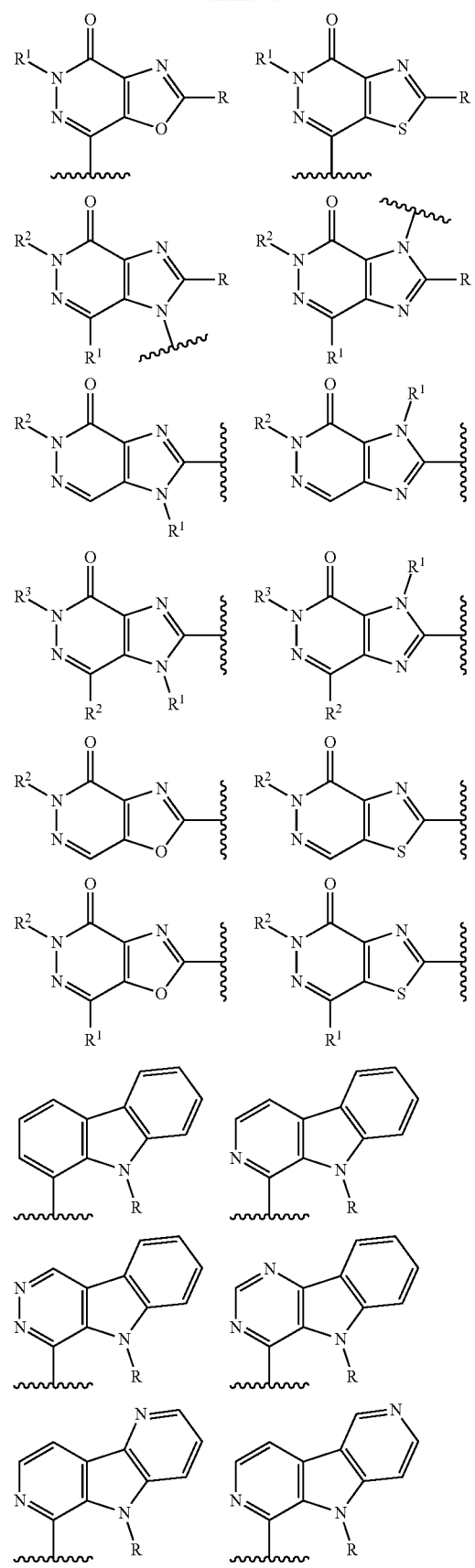
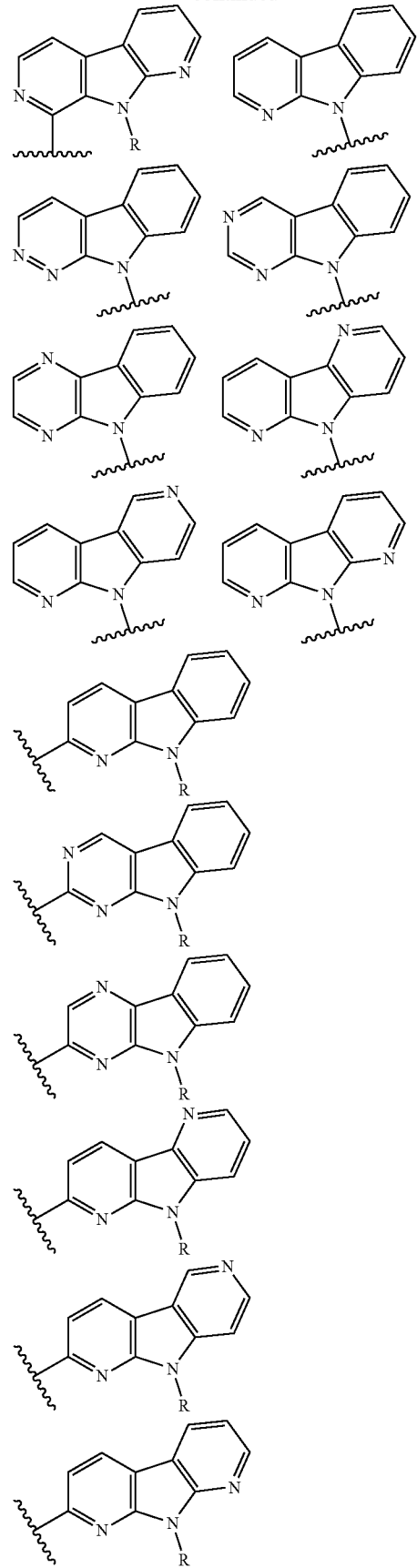

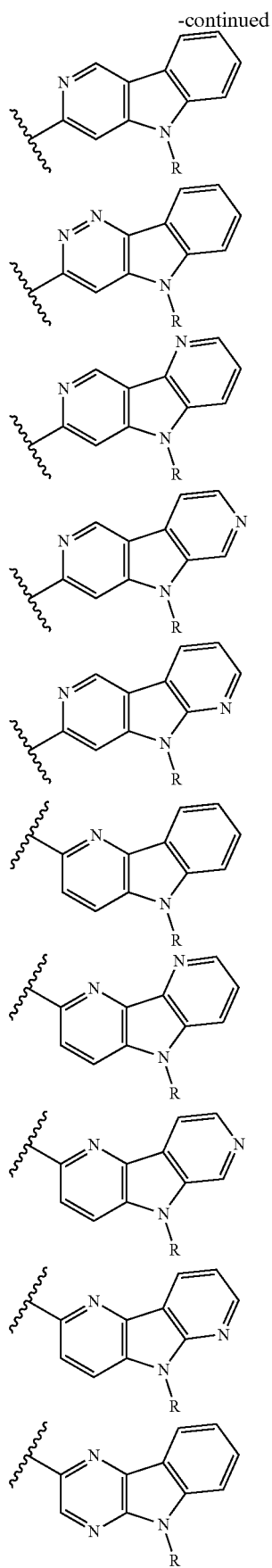
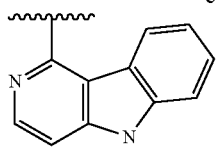
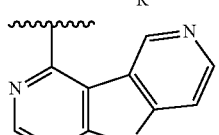
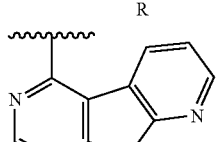
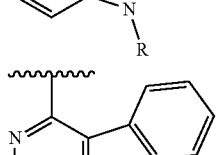
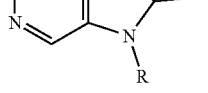
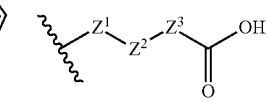
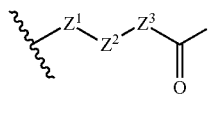
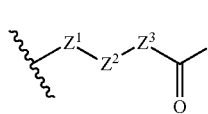
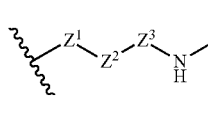
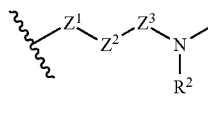
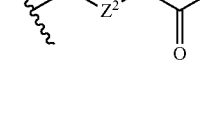
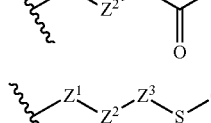
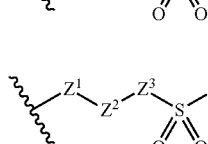

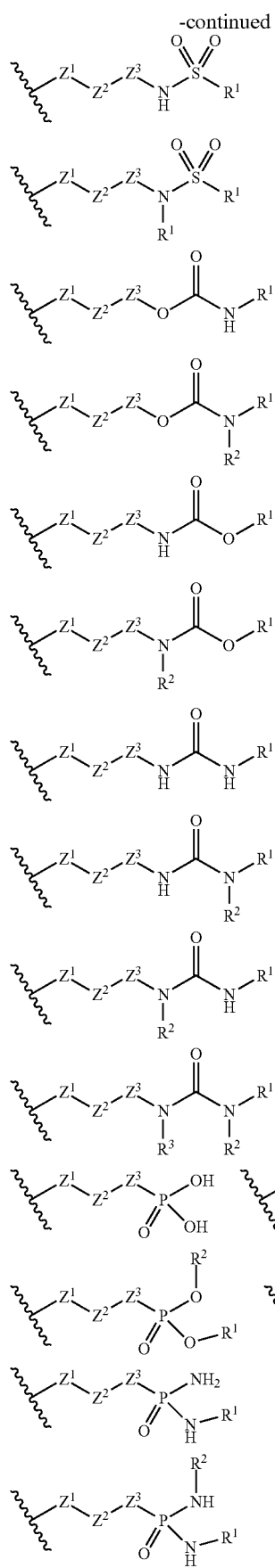
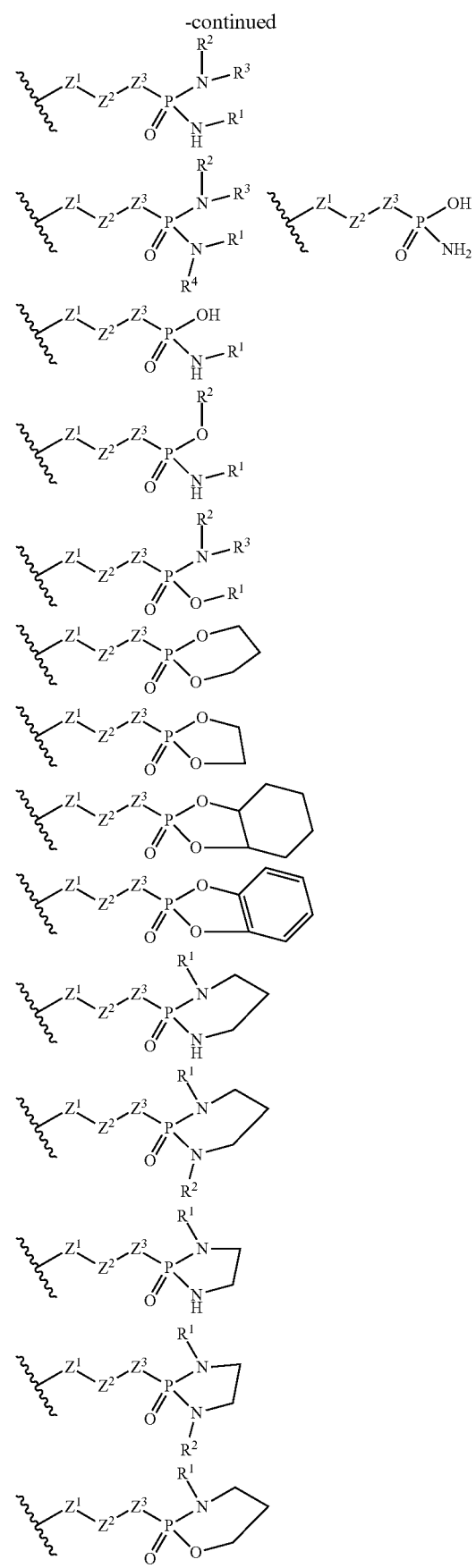

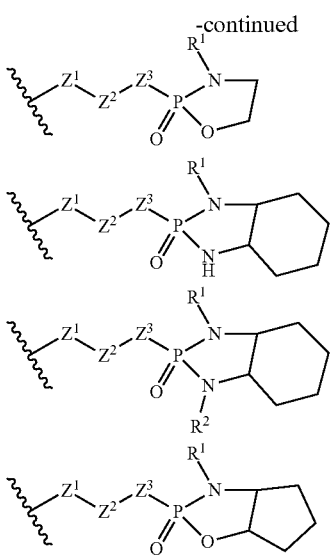

wherein R, $R^1$, $R^2$, $R^3$ and $R^4$ may be independently selected, for each occurrence, from the group consisting of hydrogen, $C_{1-6}$alkyl, $C_{2-6}$alkenyl, and phenyl (or $R^1$ and $R^4$, or $R^3$ and $R^2$, taken together form a heterocycle; and $Z^1$, $Z^2$ and $Z^3$ may be independently selected, for each occurrence, from the group consisting of a bond, $C_{1-6}$alkyl, $C_{2-6}$alkenyl, and phenyl; and wherein $C_{1-6}$alkyl, $C_{2-6}$alkenyl, and phenyl may be optionally substituted.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments have been discussed, the above specification is illustrative and not restrictive. Many variations will become apparent to those skilled in the art upon review of this specification. The full scope of the embodiments should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. A silicon based conjugate having the formula:

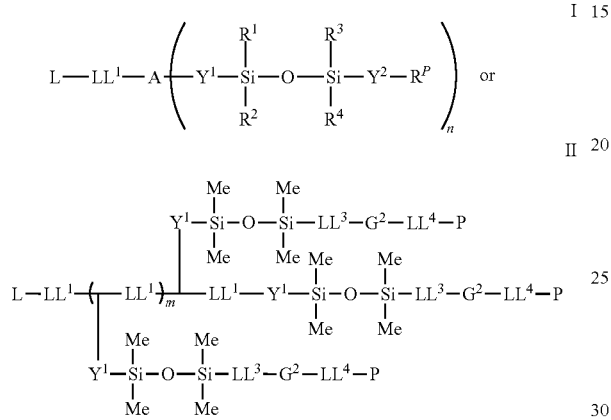

and pharmaceutically acceptable salts thereof, wherein:

L is a targeting moiety that permits selective accumulation of the conjugate within a target cell or tissue;

A is an adaptor moiety selected from the group consisting of a carbon atom, a nitrogen atom, $C_{3-6}$cycloalkyl, $C_{3-6}$cycloalkenyl, phenyl, heteroaryl, and mono or bicyclic heterocyclyl;

P is a payload moiety;

$R^P$ is P;

$Y^1$ is represented by the formula:

$-LL^2-G^1-LL^3-$;

$Y^2$ is represented by the formula:

$-LL^4-G^2-LL^5-$ n is an integer from 2 to 15;

m is an integer from 1 to 12;

at least one of $G^1$ and $G^2$ is a catalytic moiety, where at least one $G^1$ or $G^2$ is a heteroaryl;

$G^1$ and $G^2$ are independently selected for each occurrence from the group consisting of a bond, -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkyl, C$_{1-6}$alkoxy, —COOH, —C(O)—O—C$_{1-6}$alkyl, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl;

$LL^1$, $LL^2$, $LL^3$, $LL^4$ and $LL^5$ are spacer moieties each independently selected for each occurrence from the group consisting of a bond and C$_{1-20}$alkylene, wherein one, two, three or four methylene units of C$_{1-20}$alkylene are optionally and independently replaced by C$_{3-8}$cycloalkylene, C$_{2-10}$alkenylene C$_{2-10}$alkynylene, aryl, heteroaryl, NR$^{1Y}$—, —N(R$^{1Y}$)C(O)—, —C(O)N(R$^{1Y}$)—, —O—, —C(O)—, —OC(O)—, —C(O)O—, —S—, —SO—, —SO$_2$—, —C(=S)—, —C(=NR$^{1Y}$)—, —NR$^{1Y}$—C$_{1-15}$alkyl-NR$^{1Y}$—C(O)—; —(CH$_2$—CH$_2$—O)$_s$—, —(O—CH$_2$—CH$_2$)$_s$—, —NR$^{1Y}$—(CH$_2$—CH$_2$—O)$_s$—C$_{1-6}$alkyl-NR$^{1Y}$—C(O)—; —(O—CH$_2$—CH$_2$)$_s$—NR$^{1Y}$—C(O)—; —S—C$_{0-6}$alkyl-; —NR$^{1Y}$—C$_{1-6}$alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—NR$^{1Y}$—C$_{0-6}$alkyl-; —N(R$^{1Y}$)SO$_2$—C$_{0-6}$alkyl-; —SO$_2$-heterocyclyl-C$_{0-6}$alkyl-; -heterocyclyl-C(O)—; -heterocyclyl-C$_{0-6}$alkyl-NR$^{1Y}$—C(O)—; —NR$^{1Y}$—C$_{0-6}$alkylene-heterocyclyl-C(O)—; —O—C$_{1-6}$alkylene-C(O)—; —O—C$_{1-15}$alkylene-NR$^{1Y}$—C(O)—; —O—C$_{1-15}$alkylene-C(O)—NR$^{1Y}$—; —O—C$_{1-6}$alkylene-;

wherein, independently for each occurrence, $R^{1Y}$ is selected from the group consisting of H, C$_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;

s is an integer from 1-15;

$R^1$, $R^2$, $R^3$, $R^4$ are each methyl; and $R^a$ and $R^b$ are independently selected, for each occurrence, from the group consisting of hydrogen, C$_{1-6}$alkyl, C$_{2-6}$alkenyl, and phenyl; wherein C$_{1-6}$alkyl, C$_{2-6}$alkenyl, and phenyl may be optionally substituted;

or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted.

2. The silicon based conjugate of claim 1, wherein A is a carbon atom and n is 3.

3. A silicon based conjugate represented by the formula:

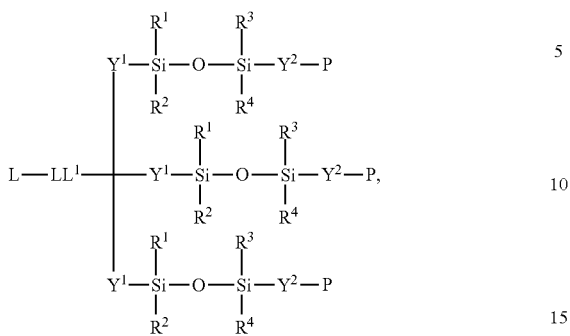

and pharmaceutically acceptable salts thereof, wherein:
L is a targeting moiety that permits selective accumulation of the conjugate within a target cell or tissue;
P is a payload moiety;
$Y^1$ is represented by the formula:

-LL²-G¹-LL³-;

$Y^2$ is represented by the formula:

-LL⁴-G²-LL⁵- at least one of $G^1$ and $G^2$ is a catalytic moiety, where at least one $G^1$ or $G^2$ is a heteroaryl;
$G^1$ and $G^2$ are independently selected for each occurrence from the group consisting of a bond, -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, —C(O)—C$_{0-6}$alkyl-, —C(O)—O—C$_{0-6}$alkyl-, —O—C(O)—C$_{0-6}$alkyl-, —NR$^a$—C(O)—C$_{0-6}$alkyl-, —C(O)—NR$^a$—C$_{0-6}$alkyl-, and —NR$^a$—C$_{0-6}$alkyl-; wherein -heteroaryl-, —O-heteroaryl-, —NR$^a$-heteroaryl-, —S(O)$_w$-heteroaryl- (wherein w is 0, 1, or 2), —NR$^a$—SO$_2$-heteroaryl-, —SO$_2$—NR$^a$-heteroaryl-, -phenyl-, —O-phenyl-, —NR$^a$-phenyl-, —S(O)$_w$-phenyl- (wherein w is 0, 1, or 2), —NR$^a$—SO$_2$-phenyl-, —SO$_2$—NR$^a$-phenyl-, may optionally be substituted by one or more substituents selected from the group consisting of halogen, hydroxyl, cyano, C$_{1-6}$alkyl, C$_{1-6}$alkoxy, —COOH, —C(O)—O—C$_{1-6}$alkyl, —C(O)—NR$^a$R$^b$, —NR$^a$—C(O)—C$_{1-6}$alkyl, —C(O)—NR$^a$—SO$_2$—C$_{1-6}$alkyl, —SO$_3$H, —SO$_2$—NR$^a$R$^b$, —NR$^a$—SO$_2$—C$_{1-6}$alkyl, and —SO$_2$—NR$^a$—C$_{1-6}$alkyl;
$LL^1$, $LL^2$, $LL^3$, $LL^4$ and $LL^5$ are spacer moieties each independently selected for each occurrence from the group consisting of a bond and C$_{1-20}$alkylene, wherein one, two, three or four methylene units of C$_{1-20}$alkylene are optionally and independently replaced by C$_{3-8}$cycloalkylene, C$_{2-10}$alkenylene C$_{2-10}$alkynylene, aryl, heteroaryl, NR$^{1Y}$, —N(R$^{1Y}$)C(O)—, —C(O)N(R$^{1Y}$)—, —O—, —C(O)—, —OC(O)—, —C(O)O—, —S—, —SO—, —SO$_2$—, —C(=S)—, —C(=NR$^{1Y}$)—, —NR$^{1Y}$—C$_{1-15}$alkyl-NR$^{1Y}$—C(O)—, —(CH$_2$—CH$_2$—O)$_s$—, —NR$^{1Y}$—(CH$_2$—O)$_s$—C$_{1-6}$alkyl-NR$^{Y1}$—C(O)—; —(O—CH$_2$—CH$_2$)$_s$—NR$^{1Y}$—C(O)—; —S—C$_{0-6}$alkyl-; —NR$^{1Y}$—C$_{1-6}$alkyl-; —N(C$_{1-3}$alkyl)-C$_{1-6}$alkyl-NH—C(O)—; —NH—C$_{1-6}$alkyl-N(C$_{1-3}$alkyl)-C(O)—; —SO$_2$—NR$^{1Y}$—C$_{0-6}$alkyl-; —N(R$^{1Y}$)SO$_2$—C$_{0-6}$alkyl-; —SO$_2$-heterocyclyl-C$_{0-6}$alkyl-; -heterocyclyl-C(O)—; -heterocyclyl-C$_{0-6}$alkyl-NR$^{1Y}$—C(O)—; —NR$^{1Y}$—C$_{0-6}$alkylene-heterocyclyl-C(O)—; —O—C$_{1-6}$alkylene-C(O)—; —O—C$_{1-15}$alkylene-NR$^{1Y}$—C(O)—; —O—C$_{1-15}$alkylene-C(O)—NR$^{1Y}$—; —O—C$_{1-6}$alkylene-;
wherein, independently for each occurrence, $R^{1Y}$ is selected from the group consisting of H, C$_{1-6}$alkyl, cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic, wherein the cycloalkyl, haloalkyl, halocycloalkyl, heteroalkyl, heterocycloalkyl, heterohaloalkyl, heterohalocycloalkyl, aryl, biaryl, heteroaryl, heterobiaryl, mono or bicyclic heterocyclic are optionally substituted with one or more substituents selected from —COOH, urea, amidine, guanidine, sulfonamide, acylsulfonamide, and sulfonyl amide;
s is an integer from 1-15;
$R^1$, $R^2$, $R^3$, $R^4$ are each methyl; and
$R^a$ and $R^b$ are independently selected, for each occurrence, from the group consisting of hydrogen, C$_{1-6}$alkyl, C$_{2-6}$alkenyl, and phenyl; wherein C$_{1-6}$alkyl, C$_{2-6}$alkenyl, and phenyl may be optionally substituted;
or $R^a$ and $R^b$, together with the nitrogen to which they are attached, form a 4-7 membered heterocyclic ring, optionally containing an additional heteroatom selected from O, S, or N; wherein the 4-7 membered heterocyclic ring is optionally substituted.

4. The silicon based conjugate of claim 1, represented by the formula:

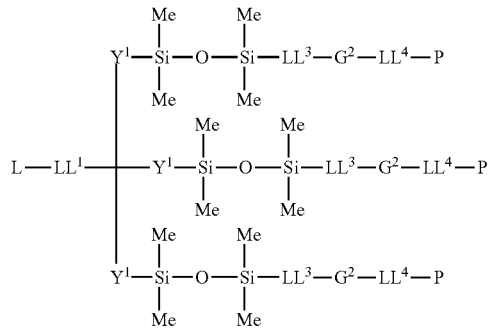

wherein G2 is a heteroaryl.

5. The silicon based conjugate of claim 1, wherein P is selected independently for each occurrence to provide a synthetic lethal drug combination capable of effecting death of a target cell having one or more gene mutations but not of a cell in which the one or more gene mutations are absent.

6. The silicon based conjugate of claim 1, wherein P is selected independently for each occurrence to provide a synthetic lethal drug combination capable of effecting death of a diseased target tissue comprised of cells having one or more gene mutations, but not of a tissue comprised of cells in which the one or more gene mutations are absent.

7. The silicon based conjugate of claim 5, wherein the one or more mutations are associated with a cancer selected from the group consisting of renal carcinoma, mutant KRAS cancer, and triple negative breast cancer.

8. The silicon based conjugate of claim 1, wherein the targeting moiety is capable of binding to at least one of: an overexpressed intracellular target, a cell surface receptor, a cognate ligand of a cell surface receptor, or a cell wall.

9. The silicon based conjugate of claim 8, wherein the cognate ligand of a cell surface receptor is a viral coat protein.

10. The silicon based conjugate of claim 1, wherein the targeting moiety is selected from the group consisting of a small-molecule, a protein, a nucleic acid, a lipid, an oligomer, a polysaccharide, a nanoparticle, an antibody, and an antibody fragment.

11. The silicon based conjugate of claim 1, wherein the payload moiety is selected from the group consisting of a therapeutic agent, a diagnostic agent, an imaging agent, a photosensitizer, and a radiosensitizer.

\* \* \* \* \*